United States Patent
Kirsebom et al.

(10) Patent No.: US 11,130,741 B2
(45) Date of Patent: Sep. 28, 2021

(54) ANTI-INFECTIVE HETEROCYCLIC COMPOUNDS AND USES THEREOF

(71) Applicant: Bioimics AB, Uppsala (SE)

(72) Inventors: Leif Kirsebom, Uppsala (SE); Ram Shankar Upadhayaya, Uppsala (SE); Raghava Reddy Kethiri, Bangalore (IN); Anders Virtanen, Uppsala (SE)

(73) Assignee: Bioimics AB, Uppsala (SE)

( * ) Notice: Subject to any disclaimer, the term of this patent is extended or adjusted under 35 U.S.C. 154(b) by 0 days.

(21) Appl. No.: 16/312,627

(22) PCT Filed: Jun. 22, 2017

(86) PCT No.: PCT/SE2017/050697
§ 371 (c)(1),
(2) Date: Dec. 21, 2018

(87) PCT Pub. No.: WO2017/222466
PCT Pub. Date: Dec. 28, 2017

(65) Prior Publication Data
US 2019/0233384 A1 Aug. 1, 2019

(30) Foreign Application Priority Data
Jun. 23, 2016 (SE) .................... 1650906-9

(51) Int. Cl.
| | |
|---|---|
| *C07D 279/28* | (2006.01) |
| *C07D 417/12* | (2006.01) |
| *C07D 417/14* | (2006.01) |
| *C07D 279/20* | (2006.01) |
| *C07D 513/04* | (2006.01) |
| *C07D 513/06* | (2006.01) |
| *A61P 33/00* | (2006.01) |
| *A61P 31/04* | (2006.01) |
| *A61P 31/10* | (2006.01) |
| *C07D 241/46* | (2006.01) |
| *C07D 265/38* | (2006.01) |
| *C07D 413/12* | (2006.01) |
| *C07D 417/04* | (2006.01) |
| *C07D 417/06* | (2006.01) |

(52) U.S. Cl.
CPC .......... *C07D 279/28* (2013.01); *A61P 31/04* (2018.01); *A61P 31/10* (2018.01); *A61P 33/00* (2018.01); *C07D 241/46* (2013.01); *C07D 265/38* (2013.01); *C07D 279/20* (2013.01); *C07D 413/12* (2013.01); *C07D 417/04* (2013.01); *C07D 417/06* (2013.01); *C07D 417/12* (2013.01); *C07D 417/14* (2013.01); *C07D 513/04* (2013.01); *C07D 513/06* (2013.01)

(58) Field of Classification Search
CPC . C07D 279/20; C07D 279/28; A61K 31/5415
See application file for complete search history.

(56) References Cited

U.S. PATENT DOCUMENTS

| | | | |
|---|---|---|---|
| 3,040,043 A | 6/1962 | Schuler et al. | |
| 3,082,210 A | 3/1963 | Jacob et al. | |

FOREIGN PATENT DOCUMENTS

| | | | |
|---|---|---|---|
| DE | 2214699 A1 | 9/1973 | |
| GB | 857546 A | 12/1960 | |
| JP | 2014521678 A | 8/2014 | |
| WO | WO-03/062388 A2 | 7/2003 | |
| WO | WO-2005/105145 A1 | 11/2005 | |
| WO | WO 2011/137447 | * 11/2011 | |
| WO | WO-2013/017637 A1 | 2/2013 | |

OTHER PUBLICATIONS

Bosseray et al., PubMed Abstract (Pathol Biol (Paris) 50(8): 483-92), 2002.*
Razonable et al., PubMed Abstract (Herpes 10(3): 60-5), 2003.*
Goff, PubMed Abstract (J Gene Med 3(6): 517-28), 2001.*
Douglas, Jr., Introduction to Viral Diseases, Cecil Textbook of Medicine, 20th Edition, vol. 2, pp. 1739-1747 (1996).*
Craig et al., Chemical constitution and anthelmintic activity—IV. Substituted phenothiazines, J. Med. Pharm. Chem., 2(6):659-68 (1960).
Gautam et al., Antioxidant and antimicrobial assessment of synthesized and spectrally characterized new nitrophenothiazines and their sulfone analogues, Phosporous, Sulfur, and Silicon, 190:528-36 (2015).
Gautam et al., Synthesis and biological activity of substituted 3-fluoro/3-trifluoromethyl 10H-phenothiazines, its ribofuranosides and sulfones, J. Fluorine Chem., 132(6):420-6 (2011).
Gautam et al., Synthesis and evaluation of antimicrobial and anthelmintic activity of novel fluorinated 7-ethyl-10H-phenothiazines, their sulphones and ribofuranosides, J. Chem. Sci., 126(1):197-204 (2014).
Gautam et al., Synthesis of 3-bromo-1-methylphenothiazines by smiles rearrangement, Heterocyclic Comm., 6(4):369-74 (2000).
Gross et al., 2-chlor-4-azaphenthiazine synthese und pharmakologische eigenschaften von cloxypendyl, Arzneimittelforschung, 18(4): 435-42 (1968). [English abstract].

(Continued)

*Primary Examiner* — Deepak R Rao
(74) *Attorney, Agent, or Firm* — Marshall, Gerstein & Borun LLP

(57) ABSTRACT

The present invention relates to heterocyclic compounds of Formula I useful as anti-infective agents. The present invention further relates to a method of treating an infection by administering such compounds, and to pharmaceutical compositions comprising such compounds.

(I)

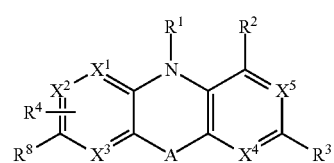

20 Claims, 20 Drawing Sheets

(56) References Cited

OTHER PUBLICATIONS

Gupta et al., Synthesis of 6-chloro-9-methyl-/7-methoxyphenothiazines via smiles rearrangement, Heterocylcic Comm., 8(3):265-40 (2002).
International Application No. PCT/SE2017/050697, International Preliminary Report on Patentability, dated Dec. 25, 2018.
International Application No. PCT/SE2017/050697, International Search Report and Written Opinion, dated Oct. 23, 2017.
Jadhav et al., Synthesis of 10-{(P-methyl anilino)-methyl}-7,8,9-substituted-1-carboxyl and 7/3-substituted-2/8-chloro phenothiazines as potential antimicrobial agents, Am. J. Pharmtech Res., 5(4): 11 pp. (2015).
Kachhee et al., Synthesis of 7-ethoxy- and 7-fluoro-phenothiazines, Phosphorus, Sulfur and Silicon and the Related Elements, 178(12):2671-8 (2003).
Kumar et al., Synthesis of 1- and 3-chloro-phenothiazines, Heterocyclic Comm., 8(5):447-50 (2002).
Kumar et al., Synthesis of sulfones of 4H-1,4-benzothiazines and phenothiazines, Phosphorus, Sulfur, and Silicon, 179:1941-8 (2004).
Madrid et al., Synthesis and antitubercular activity of phenothiazines with reduced binding to dopamine and serotonin receptors, Bioorg. Med. Chem. Lett., 17(11):3014-7 (2007).
Rathore et al., Synthesis of 7-chloro-9-trifluoromethyl-/7-fluorophenothiazines, Heteratom Chem., 18(1):81-6 (2007).
Sharma et al., Synthesis of phenothianines via smiles rearrangement, Heterocyclic Comm., 8(2):195-8 (2002).
Tang et al., One-Pot Synthesis of Pyrrolo[3,2,1-kl]phenothiazines through Copper-Catalyzed Tandem Coupling/Double Cyclization Reaction, J. Org. Chem., 80(21):11108-14 (Nov. 2015).
Thomas et al., Synthesis of 10H-phenothiazine and 4H-1,4-benzothiazine sulfones, Heterocyclic Comm., 8(3):293-8 (2002).
Yale et al., 10-(3-Dimethylaminopropyl)-2-(Trifluoromethyl)-phenothiazine Hydrochloride (VESPRIN) and Related Compounds. I, J. Am. Chem. Soc., 79(16):4375-9 (1957).
Russian Patent Application No. 2019101646, Office Action and Search Report, dated Jun. 30, 2020.
CAS Registry No. 1050508-95-6, STN Entry Date: Sep. 19, 2008, 10H-Phenothiazine-10-propanamine, N,N-diethyl-3-(trifluoromethyl)-, hydrochloride (1:1).
CAS Registry No. 735200-25-6, STN Entry Date: Aug. 29, 2004, 10H-Phenothiazine, 10-[3-(4-methyl-1-piperazinyl)propyl]-3-(trifluoromethyl).
Sharma et al., Synthesis of 7-Bromo/8,9-Dimethylphenothiazine Sulfones, Heterocyclic Comm., 8(6):549-52 (2002).

\* cited by examiner

Scheme II

Scheme III

Scheme IV

Scheme V

Scheme VI

Scheme VII

Scheme VIII

Scheme IX

Scheme X

Scheme XI

Scheme XII

Scheme XIII

Scheme XIV

Scheme XV

Scheme XVI

General Scheme XXIII

General Scheme XXIV

General Scheme XXV

General Scheme XXVI

General Scheme XXVII

General Scheme XXVIII

General Scheme XXIX

General Scheme XXXI

General Scheme XXXII

General Scheme XXXIII

ANTI-INFECTIVE HETEROCYCLIC COMPOUNDS AND USES THEREOF

FIELD OF THE INVENTION

The present invention relates to heterocyclic compounds useful as anti-infective agents. The present invention further relates to a method of treating an infection by administering such a compound. The present invention further relates to pharmaceutical compositions comprising such compounds.

BACKGROUND ART

Antimicrobial resistance is an increasingly serious threat to global public health. New resistance mechanisms emerge and spread globally, threatening the effective prevention and treatment of a range of infections caused by bacteria, parasites and fungi.

A number of examples can be provided to illustrate the threat posed. In 2013 there was approximately half a million new cases of multi-drug resistant tuberculosis. Resistance to artemisinin-based combination therapies, which are the best available treatment for *falciparum* malaria, has been detected in the Greater Mekong subregion. Highly resistant bacteria such as MRSA cause a high percentage of hospital-acquired infections. Patients with such drug-resistant infections have an increased risk of inferior clinical outcomes and death as compared to patients infected with non-resistant bacteria. Ten countries have reported cases where gonorrhoea was untreatable due to resistance to the treatments of last resort (3$^{rd}$ generation cephalosporins). Thus, gonorrhoea may soon become untreatable.

There is thus an increased and urgent need for new anti-infective agents for use in therapy.

SUMMARY OF THE INVENTION

The object of the invention is thus to provide compounds useful for the treatment or prevention of infection. A further object is to provide a method of treating an infection, such as a bacterial, fungal or parasitic infection.

These objects are achieved by compounds as disclosed by the appended claims.

The compounds have the Formula I:

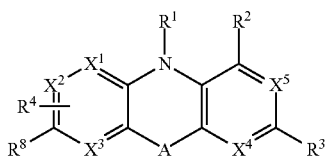

(I)

or a pharmaceutically acceptable salt thereof
wherein
A is selected from S and O;
each of $X^1$, $X^2$, $X^3$, $X^4$ and $X^5$ is independently selected from C and N;
$R^1$ is selected from the group consisting of
—H,
—$C_{1-6}$ alkyl,
—$C_{1-6}$ alkyl-amino wherein the amino group is optionally substituted with one or two $C_{1-6}$acyl or $C_{1-6}$alkyl groups,
and
—$C_{1-6}$ alkyl-heterocyclyl wherein the heterocyclyl group is a 5- or 6-membered aliphatic or aromatic heterocycle, optionally benzo-fused, and is optionally substituted with one or more $R^6$ groups;

$R^2$ is selected from the group consisting of —H, —$CF_3$, —$NO_2$, —$N(R^5)_2$, —$NHR^5$, —$N(R^5)C(O)R^5$, and —$N(R^5)C(S)N(R^5)_2$;
or
$R^1$ and $R^2$ together with the atoms to which they are bound form a 5- or 6-membered fused heterocyclic ring substituted with one or more $R^5$ groups;

$R^3$ is selected from —$CF_3$, —CN, —Cl, —$C_{1-6}$ alkyl, —$C_{3-6}$ cycloalkyl, —$C(O)NH_2$, —$C(O)NH$—$C_{1-6}$ alkyl, —NH-heterocyclyl, -phenyl, and -heterocyclyl, wherein the heterocyclyl group is a 5- or 6-membered aliphatic or aromatic optionally benzo-fused heterocycle, and wherein $R^3$ is optionally substituted with one of more $R^6$ groups;

each of $R^4$ and $R^8$ is selected from H, —CN, -halo, —$CF_3$, —$C_{1-6}$ alkoxy, —$CO_2$—$C_{1-6}$ alkyl, —$NO_2$, —$C_{1-6}$ alkyl-$NH_2$, -heterocyclyl, and —$CONH_m[(CH_2)_nNH_2]_{2-m}$, wherein the heterocyclyl group is a 5- or 6-membered aliphatic or aromatic optionally benzo-fused heterocycle;

each instance of $R^5$ is independently selected from the group consisting of
—H,
—$C_{1-6}$ alkyl optionally substituted with one or more $R^6$ groups,
—$C_{2-6}$ alkenyl optionally substituted with one or more $R^6$ groups,
—$C_{0-3}$ alkyl-$C_{3-6}$ cycloalkyl-$C_{0-3}$ alkyl optionally substituted with one or more $R^6$ groups,
-phenyl optionally substituted with one or more $R^6$ groups,
—C≡C-Ph optionally substituted with one or more $R^6$ groups,
and
—$C_{0-3}$ alkyl-heterocyclyl-$C_{0-3}$ alkyl optionally substituted with one or more $R^6$ groups, wherein the heterocyclyl group is a 5-, 6- or 7-membered aliphatic or aromatic optionally benzo-fused heterocycle;

each instance of $R^6$ is independently selected from the group consisting of -halo, —CN, —$C_{1-6}$ alkyl, —OH, —$C_{1-6}$ alkoxy, —$C_{1-6}$ alkyl-$NH_2$, —$NH_m[(CH_2)_nNH_2]_{2-m}$, —$NH_2$, —NH—$C_{1-6}$ alkyl, and —N—$C_{1-6}$dialkyl;

n and m are integers, wherein each instance of n is independently chosen from 2 or 3, and each instance of m is independently chosen from 0 or 1;

with the proviso that if $R^2$ is —H, then $R^1$ is not —H or —$C_{1-6}$ alkyl.

Compounds, or salts therefore, as defined by Formula I can be used in the treatment or prevention of infection, especially bacterial infection.

Without wishing to be bound by theory, it is thought that the compounds disclosed above achieve their antimicrobial effect at least in part by inhibition of RNase P. RNase P is a ribonucleoprotein complex present in all living cells. It catalyses the removal of 5'leader sequences from tRNA precursors and similar molecules. In bacteria, RNase P consists of one RNA subunit and a small basic protein, and it has been shown that the catalytic activity is associated with its RNA subunit. RNase P is potentially a good drug target since RNase P is indispensable for bacterial viability and the architecture of RNase P differs between bacteria and eukaryote. For example, the important P-15 loop in bacteria is a good target for antibacterial drug design.

The compounds of Formula I may belong to a subset of compounds having a Formula II:

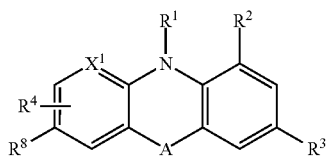

(II)

or a pharmaceutically acceptable salt thereof.

The compounds of Formula I or II may have a structure wherein:

A is selected from S and O;

$X^1$ is selected from C and N;

$R^1$ is selected from the group consisting of

—H,

—$C_{1-3}$ alkyl,

—$C_{1-3}$ alkyl-amino wherein the amino group is optionally substituted with one or two acetyl or $C_{1-3}$ alkyl groups, and —$C_{1-3}$ alkyl-heterocyclyl wherein the heterocyclyl group is selected from imidazolyl, piperazinyl and thiomorpholinyl and is optionally substituted with one or more $R^6$ groups;

$R^2$ is selected from the group consisting of —H, —$CF_3$, —$NO_2$, —$N(R^5)_2$, —$NHR^5$, —$N(R^5)C(O)R^5$, and —$N(R^5)C(S)N(R^5)_2$;

or $R^1$ and $R^2$ together with the atoms to which they are bound form a 5- or 6-membered fused heterocyclic ring substituted with one or more $R^5$ groups;

$R^3$ is selected from —$CF_3$, —CN, —Cl, —$C_{1-3}$ alkyl, —$C_{3-6}$ cycloalkyl, —$C(O)NH_2$, —$C(O)NH$—$C_{1-3}$ alkyl, —NH-piperazinyl, -phenyl, -pyridinyl, -indolyl, -benzimidazolyl, -benzothiazolyl, and -benzopyrazolyl, wherein $R^3$ is optionally substituted with one of more $R^6$ groups;

each of $R^4$ and $R^8$ is selected from H, —CN, —Cl, —F, —$CF_3$, —$C_{1-3}$ alkoxy, —$CO_2Me$, —$NO_2$, —$C_{1-3}$ alkyl-$NH_2$, -piperazinyl, -indolyl, and —$CONH_m[(CH_2)_nNH_2]_{2-m}$;

each instance of $R^5$ is independently selected from the group consisting of

—H,

—$C_{1-3}$ alkyl optionally substituted with one or more $R^6$ groups,

—$C_{2-3}$ alkenyl optionally substituted with one or more $R^6$ groups,

—$C_{0-3}$ alkyl-$C_{3-6}$ cycloalkyl-$C_{0-3}$ alkyl optionally substituted with one or more $R^6$ groups, -phenyl optionally substituted with one or more $R^6$ groups, —C≡C-Ph optionally substituted with one or more $R^6$ groups, and —$C_{0-3}$ alkyl-heterocyclyl-$C_{0-3}$ alkyl optionally substituted with one or more $R^6$ groups, wherein the heterocyclyl group is selected from azetidinyl, pyrrolidinyl, piperidinyl, piperazinyl, morpholinyl, azepanyl and indolyl;

each instance of $R^6$ is independently selected from the group consisting of —F, —Cl, —CN, —$C_{1-3}$ alkyl, —OH, —$C_{1-3}$ alkoxy, —$C_{1-3}$ alkyl-$NH_2$, —$NH_m[(CH_2)_nNH_2]_{2-n}$, —$NH_2$, —NHMe, and —$NMe_2$;

n and m are integers, wherein each instance of n is independently chosen from 2 or 3, and each instance of m is independently chosen from 0 or 1;

with the proviso that if $R^2$ is —H, then $R^1$ is not —H or —$C_{1-3}$ alkyl.

The compounds of Formula I or II may have a structure wherein $R^2$ is selected from the group consisting of —H, —$CF_3$, —$N(R^5)_2$, —$NHR^5$, —$N(R^5)C(O)R^5$, and —$N(R^5)C(S)N(R^5)_2$;

with the proviso that if $R^2$ is —H, then $R^1$ is not —H or —$C_{1-3}$ alkyl and $R^8$ is not H.

The compounds of Formula I or II may have a structure wherein $R^8$ is not H. Thus, the compounds of the invention may have substituents at the $R^1$, $R^3$ and $R^8$ positions, or alternatively at the $R^2$, $R^3$ and $R^8$. It has been found that thus substituted compounds are especially active in the treatment or prevention of infection.

The compounds of Formula I or II may have a structure wherein $X^1$, $X^2$, $X^3$, $X^4$ and $X^5$ are C.

The compounds of Formula I or II may have a structure wherein $R^1$ is H.

The compounds of Formula I or II may have a structure wherein $R^2$ is selected from the group consisting of —$NH_2$ and —$NHR^5$.

The compounds of Formula I or II may have a structure wherein $R^2$ is —$NHC(O)R^5$.

The compounds of Formula I or II may have a structure wherein $R^2$ is H.

The compounds of Formula I or II may have a structure wherein $R^4$ is H.

The compounds of Formula I or II may have a structure wherein A is S.

The compounds of Formula I or II may have a structure wherein $R^3$ is selected from the group consisting of —$CF_3$ and -indolyl.

According to another aspect of the present invention, the objects of the invention are achieved by a compound according to Formula I or II as disclosed above, for use in a method of treatment of the human or animal body by therapy. The therapy may be treatment or prevention of an infection. The infection may be a bacterial, fungal, or parasitic infection. The infection may be a bacterial infection caused or complicated by bacteria of a genus selected from *Staphylococcus, Enterococcus, Streptococcus, Pseudomonas, Legionella, Klebsiella, Haemophilus, Neisseria, Listeria, Escherichia* and *Mycobacterium*. The bacterial infection may be caused or complicated by a bacterial species selected from the group: *S. aureus, E. faecalis, E. faecium, S. pneumoniae, E. coli, K. pneumoniae, H. influenza, A. baumannii, P. aeruginosa, P. aeruginosa, N. gonorrhoeae*. The bacterial infection may be caused or complicated by a bacterial species selected from the group: *M. fortuitum, M. phlei, M. tuberculosis*.

According to a further aspect of the present invention, the objects of the invention are achieved by a method of treating an infection which comprises administering to a patient in need thereof a therapeutically effective amount of a compound as disclosed above. The infection may be a bacterial, fungal, or parasitic infection. The infection may be a bacterial infection caused or complicated by bacteria of a genus selected from *Staphylococcus, Enterococcus, Streptococcus, Pseudomonas, Legionella, Klebsiella, Haemophilus, Neisseria, Listeria, Escherichia* and *Mycobacterium*. The bacterial infection may be caused or complicated by a bacterial species selected from the group: *S. aureus, E. faecalis, E. faecium, S. pneumoniae, E. coli, K. pneumoniae, H. influenza, A. baumannii, P. aeruginosa, P. aeruginosa, N. gonorrhoeae*. The bacterial infection may be caused or complicated by a bacterial species selected from the group: *M. fortuitum, M. phlei, M. tuberculosis*.

According to yet another aspect of the present invention, the object of the invention is achieved by use of a compound as disclosed above, or a salt thereof, in inhibition of bacterial RNase P activity.

According to yet a further aspect of the present invention, the object of the invention is achieved by use of a compound as disclosed above, or a salt thereof, as a bactericide.

According to still a further aspect of the present invention, the object of the invention is achieved by a pharmaceutical composition comprising a compound as disclosed above, or a pharmaceutically acceptable salt thereof, in association with a pharmaceutically acceptable excipient, adjuvant, diluent and/or carrier.

Further aspects, objects and advantages are defined in the detailed description below with reference to the appended drawings.

BRIEF DESCRIPTION OF THE DRAWINGS

For the understanding of the present invention and further objects and advantages of it, the detailed description set out below can be read together with the accompanying drawings.

Fin 19 shows general synthetic scheme XXV for the synthesis of selected compounds according to the present invention

DETAILED DESCRIPTION

General Synthetic Methods

Figure 1:
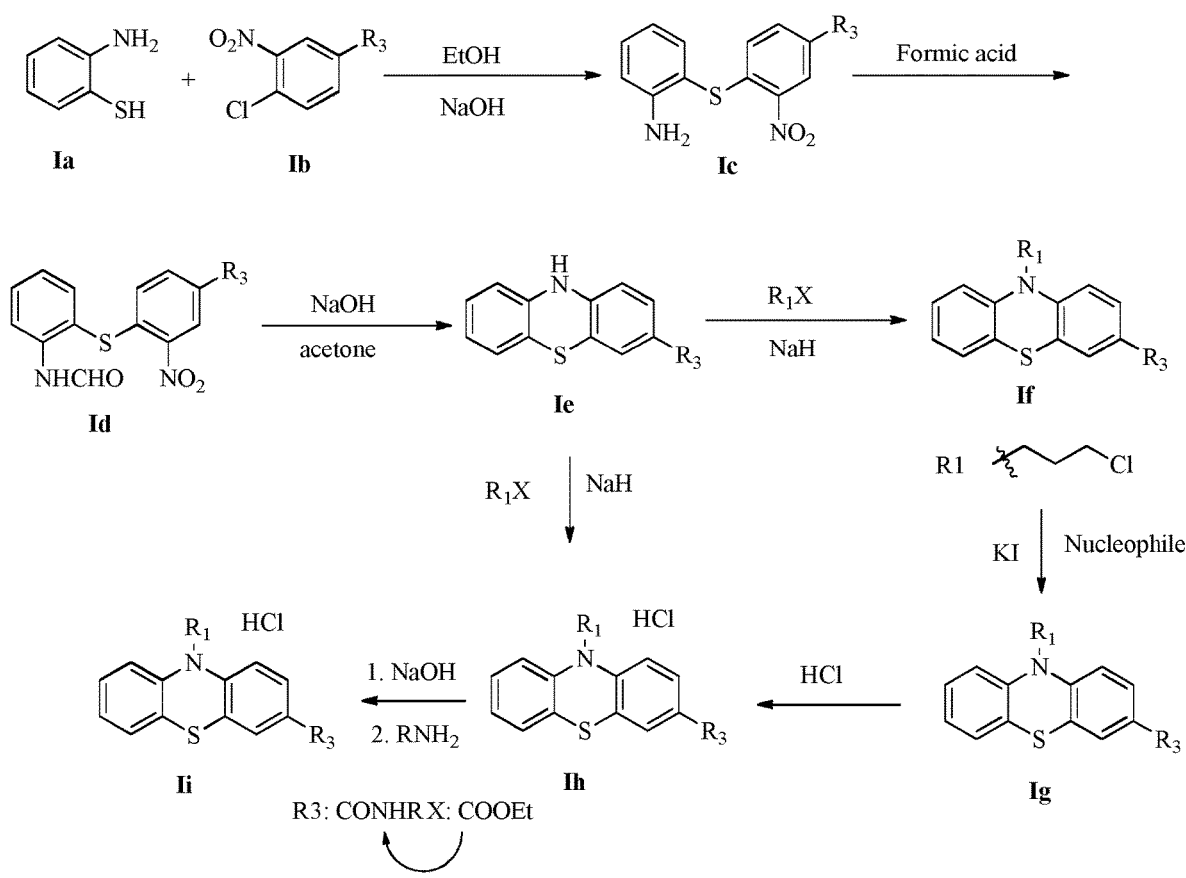
FIG. 1 shows general synthetic scheme I for the synthesis of selected compounds according to the present invention.

All reactions were carried out under dry nitrogen and or argon atmosphere unless otherwise specified. Unless otherwise stated, all the raw starting materials, solvents, and reagents were purchased from commercial sources (e.g., AVRA Chemicals, Apollo Scientific Limited, Bepharma Ltd., Combi-Blocks Inc., Sigma Aldrich Chemicals Pvt. Ltd., Ultra Labs, Toronto Research Chemicals Inc., Chemical House, RFCL Limited, Spectro Chem Pvt. Ltd., Leonid Chemicals, Loba Chemie, Changzhou Yangyuan, NeoSynth, Rankem, etc.) and used as such without further purification. Alternatively, reagents may be synthesized by procedures known in the literature.

The following abbreviations are used and have the indicated definitions: MHz is megahertz (frequency), m is multiplet, t is triplet, d is doublet, s is singlet, br is broad, $CDCl_3$ is deutero chloroform, calcd is calculated, min is minutes, h is hours, g is grams, mmol is millimoles, mL is milliliters, N is normality (concentration), M is molarity (concentration), μM is micromolar, ee is enantiomeric excess, de is diastercomeric excess, ° C. is degree centigrade, HPLC is High Performance Liquid Chromatography, LC-MS is Liquid Chromatography-Mass Spectroscopy, NMR is Nuclear Magnetic Resonance, TLC is Thin Layer Chromatography, THE is tetrahydrofuran, MeOH is methanol, DCM is dichloromethane, DEA is diethylamine, DMA is dimethylacetamide, DMF is N,N-dimethyl formamide, DMSO is dimethyl sulfoxide, EtOH is ethyl alcohol, EtOAc is ethyl acetate, RT is room temperature, HCl is hydrogen chloride or hydrochloric acid, TFA is trifluoroacetic acid, EtMgBr is ethyl magnesium bromide, n-BuLi is n-butyl lithium, NaHCO$_3$ is sodium bicarbonate, Na$_2$CO$_3$ is sodium carbonate, Na$_2$SO$_4$ is sodium sulfate, DCC is N,N-dicyclohexylcarbodiimide, DIPA is diisopropylamine, LDA is lithium diisopropylamine, HOBt is N-hydroxy-benzotriazole, NCS is N-chlorosuccinimide, and TBAB is tetrabutyl ammonium bromide.

Biotage Isolera® One and CombiFlash®(Teledyne Isco) Automated Flash Purification System were used for the purification of crude products using the eluent combination mentioned in the respective procedures. Flash Chromatography was performed using silica gel (60-100, 100-200 and 230-400 mesh) from ChemLabs, with nitrogen and/or compressed air. Preparative thin-layer chromatography was carried out using silica gel (GF 1500 μM 20×20 cm and GF 2000 μM 20×20 cm prep-scored plates from Analtech, Inc. Delaware, USA). Thin-layer chromatography was carried out using pre-coated silica gel sheets (Merck 60 F$_{254}$). Visual detection was performed with ultraviolet light, p-anisaldehyde stain, ninhydrin stain, dinitrophenyl hydrazine stain, potassium permanganate stain, or iodine. Reactions at lower temperature were performed by using cold baths, e.g., H$_2$O/ice at 0° C., and acetone/dry ice at −78° C. Melting points were determined by using a LabIndia MR-VIS visual melting range apparatus. $^1$H NMR spectra were recorded at 400 MHz with a Varian V400 spectrometer, Bruker 400 (unless otherwise noted) at ambient temperature, using tetramethylsilane as internal reference. The chemical shift values are quoted in δ (parts per million). Mass spectra of all the intermediates and final compounds were recorded using Acquity® UPLC-SQD (Waters) & Agilent 1290 Infinity® with 6150 SQD machines. HPLC spectra were recorded using Agilent 1290 Infinity® UHPLC and Alliance (Waters) systems. LCMS spectra were recorded using Agilent 1200® LCMS/Agilent 1290® UHPLC-SQD with diode array detector (DAD) detection LC-MS instruments using Kinetex C18 (50 mm×2.1 mm×2.7 mic) and/or X-terra MS C18 (50 mm×2.1 mm×3.0 micron) columns. The purity of each of the final compounds was detected using Waters® PDA with SQD or Aglient® DAD with 6150 SQD instrument.

The compounds according to Formulas I & II are prepared using conventional organic synthetic methods. A suitable synthetic route is depicted below in the following general reaction Schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Organic Synthesis*(4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

Description of Synthesis

FIG. 1 shows general synthetic scheme I for the synthesis of selected 3, N-10-disubstituted phenothiazenes. Nucleophilic substitution of 2-amino thiophenol (Ia) with aryl halides (Ib) resulted in the corresponding thioethers (Ic). N-formylation followed by Smiles rearrangement of thioethers (Ic) yielded 3-substituted phenothiazenes (Ie). N-alkylation of Ie with distinct alkyl halides using NaH as base yielded the corresponding N-10-alkylated phenothiazenes (If&Ih). The mono haloalkylated phenothiazenes (If) were reacted with nucleophiles (amines & alcohols) followed by salt preparations using HCl to give the corresponding salts (Ih). In case of ester analogues of Ih, ester hydrolysis followed by amide formation yielded the title compounds (Ii).

Figure 2:
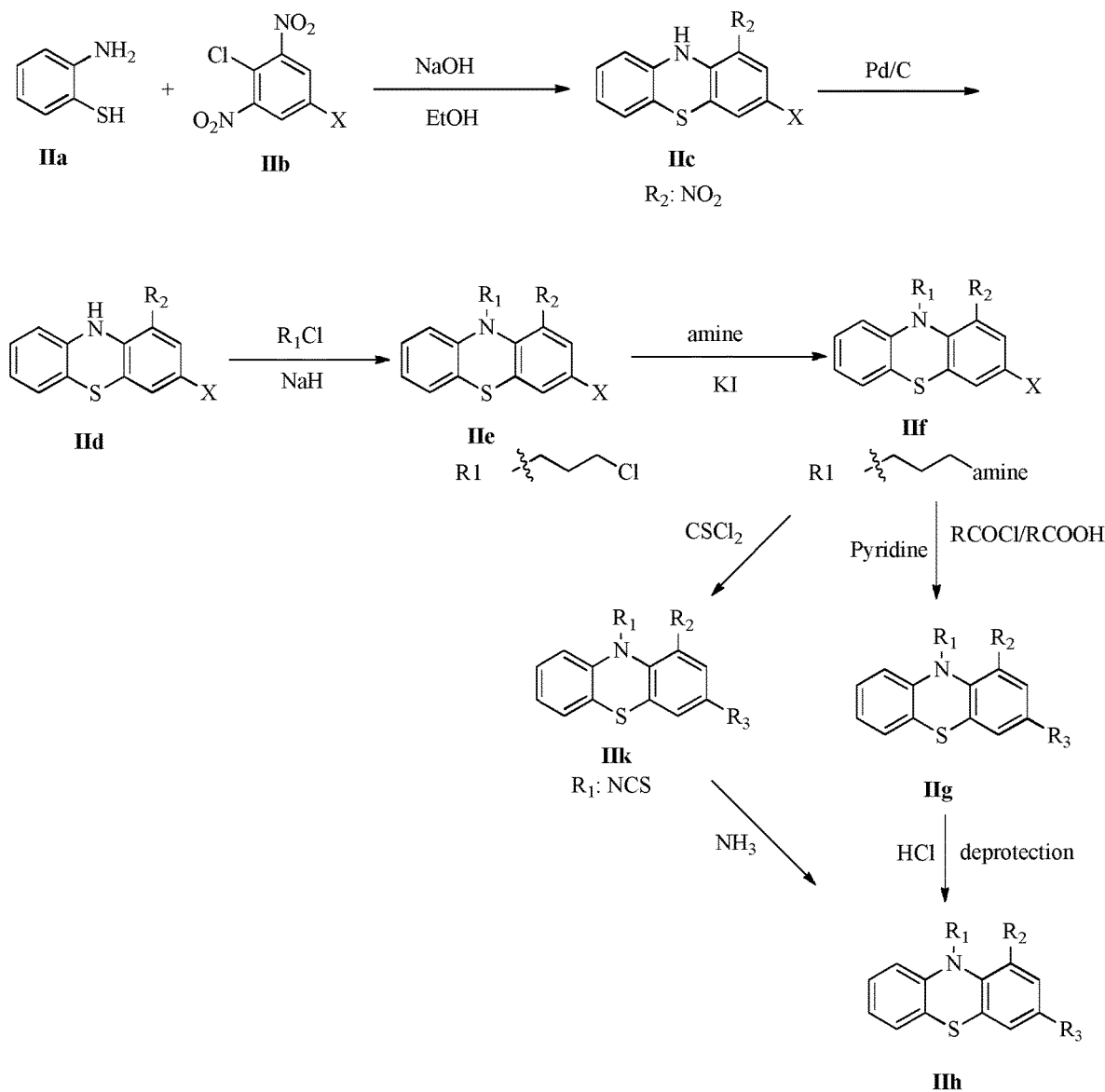
FIG. 2 shows general synthetic scheme II for the synthesis of selected compounds according to the present invention.

FIG. 2 shows general synthetic scheme II for the synthesis of selected 1, 3, N-10-trisubstituted phenothiazenes. Nucleophilic substitution of 2-amino thiophenol (IIa) with aryl halides (IIb) followed by insituSmiles rearrangement yielded 1,3-disubstituted phenothiazenes (IIc), which are reduce by Pd/C to yield the corresponding 1-amino substituted phenothiazenes (IId). The phenothiazenes (IId) were selectively alkylated at N-10 position with distinct alkyl halides using NaH as base yielded corresponding N-10-alkylated phenothiazines (IIe). The N-10-alkylated phenothiazenes (IIe) were reacted with amines yielded IIf. Amide formation of amines (IIf) by reacting with acid chlorides or acids yielded corresponding amide analogues (IIg). Deprotection of IIg using HCl resulted the title compounds IIh. If reaction with CSCl$_2$ followed by reaction with NH$_3$ resulted in title compounds IIh.

A detailed synthetic description of a compound synthesised by the method of Scheme II follows.

Compound 87: 1-(10-(3-(Dimethylamino)propyl)-3-(trifluoromethyl)-10H-phenothiazin-1-yl)thiourea

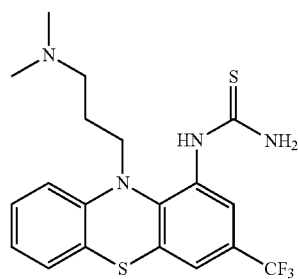

Step 1:
1-Nitro-3-(trifluoromethyl)-10H-phenothiazine

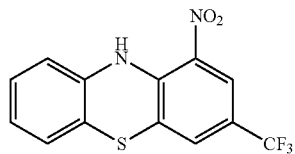

To a stirred solution of 2-chloro-1,3-dinitro-5-(trifluoromethyl)benzene (20 g, 74.0 mmol) in ethanol (300 mL) were added 2-aminobenzenethiol (8.0 mL, 74.0 mmol), sodium hydroxide (8.8 g, 222 mmol) and the reaction mixture was heated at 85° C. for 12 h. The reaction mixture was cooled to room temperature, concentrated, and the residue was washed with EtOH followed by H₂O to give the title compound as a brown solid (16.0 g, 70%): ¹H NMR (DMSO-d₆, 400 MHz) δ 6.97 (m, 1H), 7.02 (m, 1H), 7.09 (m, 2H), 7.65 (s, 1H), 8.01 (s, 1H), 9.84 (s, 1H); MS (ESI) m/z 311 (M−H)⁺.

Step 2:
3-(Trifluoromethyl)-10H-phenothiazin-1-amine

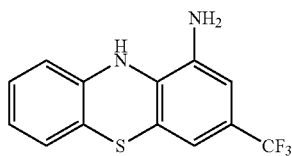

To a stirred solution of 1-nitro-3-(trifluoromethyl)-10H-phenothiazine (5.0 g, 16.2 mmol) in MeOH (30 mL) was added 10% Pd/C (50% wet, 0.4 g) and the reaction mixture was stirred at room temperature for 5 h. The reaction mixture was filtered through celite and filtrate was concentrated to give the title compound as a light pink solid (6.0 g, 66%): ¹H NMR (DMSO-d₆, 400 MHz) δ 5.44 (s, 2H), 6.49 (s, 1H), 6.73 (s, 1H), 6.81 (t, J=7.2 Hz, 1H), 6.92 (d, J=8 Hz, 1H), 6.92 (d, J=7.6 Hz, 1H), 7.01 (t, J=7.6 Hz, 1H), 7.81 (s, 1H); MS (ESI) m/z 281 (M−H)⁺.

Step 3: 10-(3-Iodopropyl)-3-(trifluoromethyl)-10H-phenothiazin-1-amine

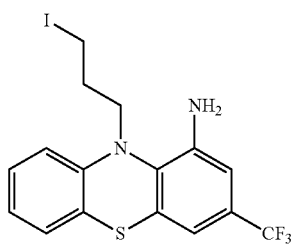 [SMILES: Nc1cc(C(F)(F)F)cc2c1N(CCCI)c1ccccc1S2]

To a stirred solution of 3-(trifluoromethyl)-10H-phenothiazin-1-amine (2.5 g, 8.86 mmol) in DMF (15 mL) at 0° C. under nitrogen atmosphere was added sodium hydride (0.5 g, 12.41 mmol) and stirred for 30 min. followed by the addition of 1,3-diiodopropane (1.2 mL, 10.63 mmol). The reaction mixture was stirred at room temperature for 30 min, quenched with saturated ammonium chloride solution, extracted with ethyl acetate and concentrated. The crude product was purified by column chromatography over silica gel using ethyl acetate/hexane (1:19) mixture as eluent to give the title compound (2.7 g, crude) as a blue solid: ¹H NMR (DMSO-d₆, 400 MHz) δ 3.11 (t, J=6.0 Hz, 2H), 4.81 (t, J=6.0 Hz, 2H), 6.87 (m, 2H), 6.97 (d, J=7.2 Hz, 1H), 7.06 (t, J=7.6 Hz, 1H), 7.17 (s, 1H), 7.29 (s, 1H), 7.96 (s, 1H), 9.66 (s, 1H); MS (ESI) m/z 451 (M+H)⁺.

Step 4: 10-(3-(Dimethylamino)propyl)-3-(trifluoromethyl)-10H-phenothiazin-1-amine

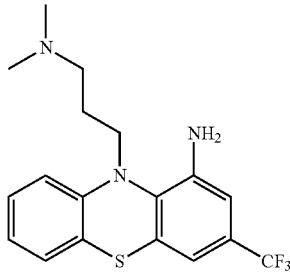 [SMILES: CN(C)CCCN1c2ccccc2Sc2cc(C(F)(F)F)cc(N)c21]

To a stirred solution of 10-(3-iodopropyl)-3-(trifluoromethyl)-10H-phenothiazin-1-amine (1.7 g, 3.77 mmol) in DMF (10 mL) were added potassium iodide (1.6 g, 11.33 mmol), dimethylamine in THF (0.25 mL, 5.66 mmol) and stirred at room temperature for 12 h. The reaction mixture was concentrated and the residue was purified by column chromatography over silica gel using methanol/dichloromethane (1:10) mixture as eluent to give the title compound as an green solid (0.26 g, 31%): ¹H NMR (DMSO-d₆, 400 MHz) δ 1.61 (m, 2H), 2.07 (s, 6H), 2.32 (m, 2H), 3.79 (m, 2H), 5.49 (s, 2H), 6.65 (s, 1H), 6.89 (s, 1H), 7.01 (t, J=6.8 Hz, 1H), 7.21 (m, 3H); MS (ESI) m/z 368 (M+H)⁺.

Step 5: 3-(1-Isothiocyanato-3-(trifluoromethyl)-10H-phenothiazin-10-yl)-N,N-dimethylpropan-1-amine

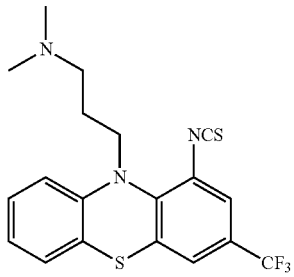

To a stirred solution of 10-(3-(dimethylamino)propyl)-3-(trifluoromethyl)-10H-phenothiazin-1-amine (0.1 g, 0.272 mmol) in chloroform (5 mL) and water (5 mL) was added sodium bicarbonate solution (0.025 g, 0.68 mmol) under cooling condition, the reaction mixture was stirred at same temperature for 1 h, thiophosgene (0.037 g, 0.326 mmol) was added, the reaction mixture was stirred at room temperature for 2 h. The reaction mixture was quenched with water, extracted with ethyl acetate, and concentrated. The crude product was purified by column chromatography over silica gel using methanol/dichloromethane (1:9) mixture as eluent to give the title compound (0.06 g, crude): MS (ESI) m/z 410.1 (M+H)⁺. The compound was used in next step without further purification.

Step 6: 1-(10-(3-(Dimethylamino)propyl)-3-(trifluoromethyl)-10H-phenothiazin-1-yl)thiourea

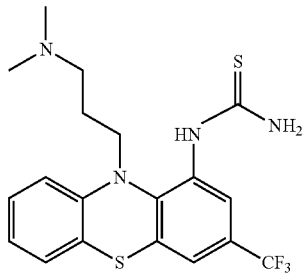 [SMILES: CN(C)CCCN1c2ccccc2Sc2cc(C(F)(F)F)cc(NC(N)=S)c21]

To a stirred solution of 3-(1-isothiocyanato-3-(trifluoromethyl)-10H-phenothiazin-10-yl)-N,N-dimethylpropan-1-amine (0.025 g, 0.61 mmol) in 1,4-dioxane (5 mL) was added aq.ammonia (0.2 mL) at 0° C. and the reaction mixture was stirred at room temperature for 3 h. The reaction mixture was concentrated and the residue was purified by column chromatography over silica gel using ethyl acetate/hexane (1:9) mixture as eluent to give the title compound as an off white solid (0.010 g, 16%): $^1$H NMR (DMSO-$d_6$, 400 MHz) δ 1.59-1.64 (m, 2H), 2.00-2.04 (m, 4H), 2.80-2.31 (m, 2H), 3.86 (t, J=6.8 Hz, 2H), 7.03 (t, J=7.6 Hz, 1H), 7.09 (d, J=8 Hz, 1H), 7.19 (d, J=7.2 Hz, 1H), 7.27 (t, J=7.2 Hz, 1H), 7.37 (s, 1H), 7.54 (s, 1H), 9.41 (s, 1H); MS (ESI) m/z 427 (M+H)$^+$; HPLC purity: 94.65%.

Table II lists examples of compounds synthesised by the method of Scheme 11.

TABLE II

| Cmpd # | R$^1$ = -nPr—R | R$^2$ = —NH—R | R$^3$ | A |
|---|---|---|---|---|
| 42 | dimethylaminomethyl | H | CF$_3$ | S |
| 44 | imidazolyl | H | CF$_3$ | S |
| 87 | dimethylaminomethyl | thioamide methyl | CF$_3$ | S |
| 83 | piperazinyl-NH | H | CF$_3$ | S |
| 88 | piperazinyl | H | CF$_3$ | S |
| 89 | dimethylaminomethyl | H | Cl | S |
| 90 | dimethylaminomethyl | —CO—CH(CH$_3$)—CH$_2$—NH$_2$ | CF$_3$ | S |

Figure 3:
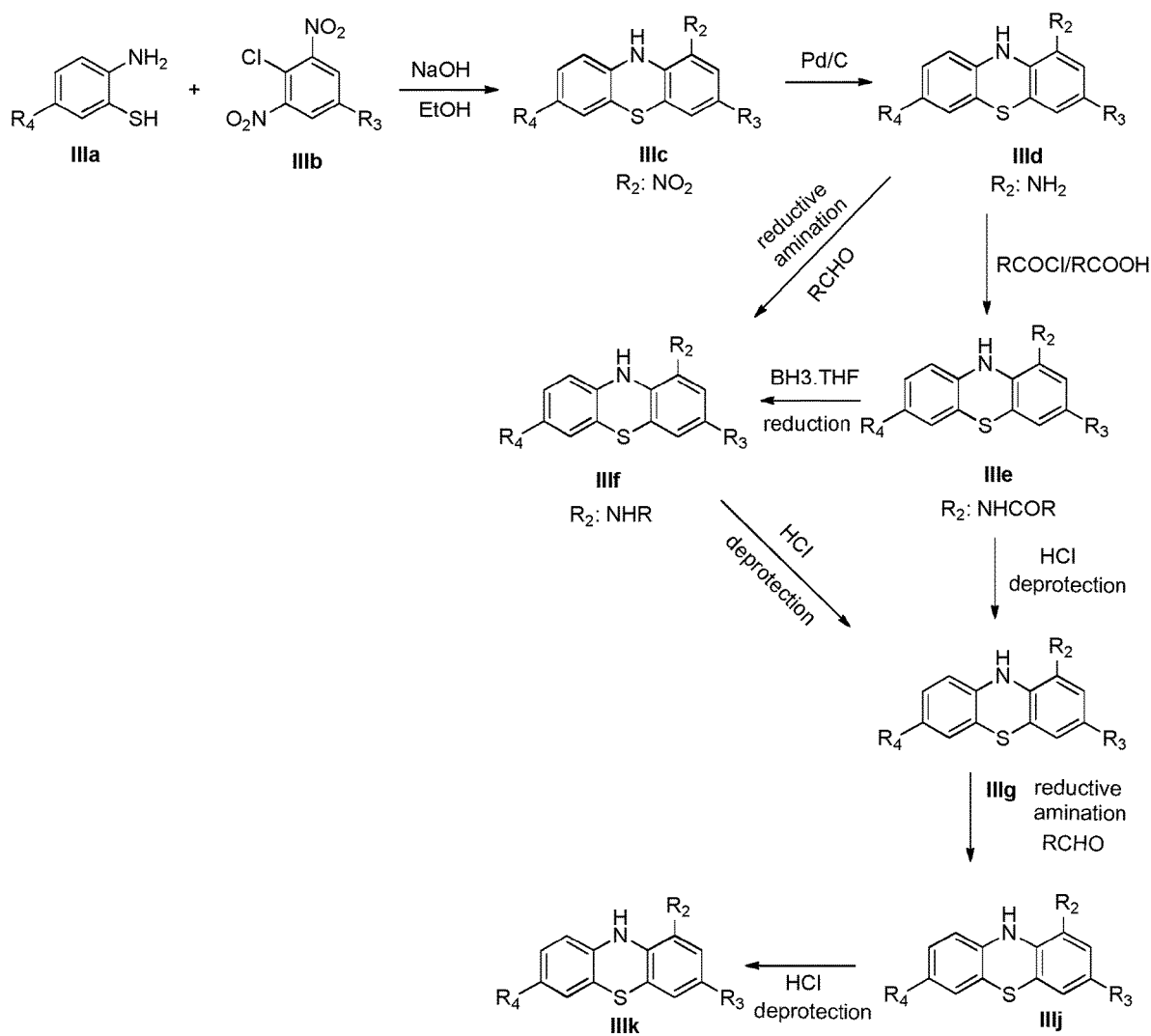
FIG. 3 shows general synthetic scheme III for the synthesis of selected compounds according to the present invention.

FIG. 3 shows general reaction scheme III for the synthesis of selected 1,3-disubstituted phenothiazenes. Nucleophilic substitution of 2-amino thiophenol/2-aminophenols (IIIa) with substituted aryl halides (IIIb) followed by insituSmiles rearrangement yielded substituted phenothiazene/substituted phenoxazines (IIIc). Compounds IIIc were reduced using Pd/C to yield the corresponding 1-amino phenothiazenes/1-amino phenoxazines (IIId). Compounds IIId were reacted with acid chlorides or acids to form corresponding amides IIIe, which further deprotected to yield corresponding title compounds IIIg. Reductive amination of compound IIId with various aldehydes yielded corresponding n-alkylated phenothiazines IIIf, which were further deprotected to give the corresponding title compounds IIIg. Further reductive amination of compound IIIg, followed by deprotection gave IIIk.

Detailed synthetic descriptions of some compounds synthesised by the method of Scheme III are provided below.

Compound 105: 3-Amino-N-(3-(trifluoromethyl)-10H-phenothiazin-1-yl)cyclohexanecarboxamide

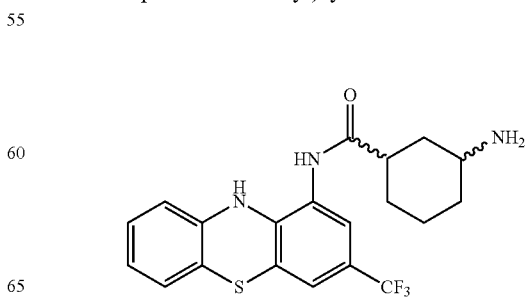

Step 1:
1-Nitro-3-(trifluoromethyl)-10H-phenothiazine

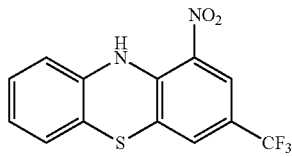

To a stirred solution of 2-chloro-1,3-dinitro-5-(trifluoromethyl)benzene (25 g, 92.5 mmol) in water (200 mL) were added 2-aminobenzenethiol (10.4 g, 83.3 mmol), sodium hydroxide (11.1 g, 277.5 mmol) and the reaction mixture was heated at 80° C. for 12 h. The reaction mixture was cooled to room temperature, filtered, and the solid obtained was washed with water followed by EtOH to give the title compound as a brown solid (25.0 g, 87%): $^1$H NMR (DMSO-$d_6$, 400 MHz) δ 6.97 (m, 1H), 7.02 (m, 1H), 7.09 (m, 2H), 7.65 (s, 1H), 8.01 (s, 1H), 9.84 (s, 1H); MS (ESI) m/z 312 (M+H)$^+$.

Step 2:
3-(Trifluoromethyl)-10H-phenothiazin-1-amine

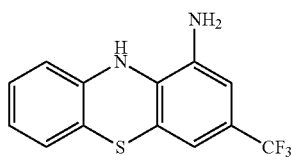

To a stirred solution of 1-nitro-3-(trifluoromethyl)-10H-phenothiazine (25 g, 801 mmol) in MeOH (250 mL) was added 10% Pd/C (50% wet, 5 g) and the reaction mixture was hydrogenated under $H_2$ gas (balloon) at room temperature for 16 h. The reaction mixture was filtered through celite and filtrate was concentrated to give the title compound as a light pink solid (20 g, 88%): $^1$H NMR (DMSO-$d_6$, 400 MHz) δ 5.44 (s, 2H), 6.49 (s, 1H), 6.73 (s, 1H), 6.81 (t, J=7.2 Hz, 1H), 6.92 (d, J=8 Hz, 1H), 6.92 (d, J=7.6 Hz, 1H), 7.01 (t, J=7.6 Hz, 1H), 7.81 (s, 1H); MS (ESI) m/z 283 (M+H)$^+$.

Step 3: Tert-butyl (3-((3-(trifluoromethyl)-10H-phenothiazin-1yl)carbamoyl)cyclohexyl)carbamate

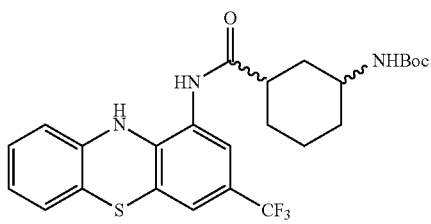 [SMILES: CC(C)(C)OC(=O)NC1CCCC(C(=O)Nc2cc(C(F)(F)F)cc3c2Nc2ccccc2S3)C1]

To a stirred solution of 3-((tert-butoxycarbonyl)amino)cyclohexanecarboxylic acid (10.3 g, 42.55 mmol) in pyridine (25 mL) was added $POCl_3$ (10 mL) at 0° C. and the reaction mixture was stirred for 15 min at 0° C. A solution of (3-(trifluoromethyl)-10H-phenothiazin-1-amine (10 g, 35.46 mmol) in pyridine (25 mL) was added to the reaction mixture and stirring continued at room temperature for 1 h. The reaction mixture was concentrated and the residue was purified by column chromatography over silica gel using 20% ethyl acetate/hexane mixture as eluant to give the title compound as a light yellow solid (6 g, 33%): $^1$H NMR (DMSO-$d_6$, 400 MHz) δ 1.09 (m, 1H), 1.18 (m, 4H), 1.30 (s, 9H), 1.37 (m, 2H), 1.97 (m, 2H), 3.35 (s, 2H), 3.55 (s, 2H), 4.45 (bs, 1H), 6.79 (m, 1H), 6.84 (d, J=6 Hz, 2H), 6.96 (t, J=7.2 Hz, 1H), 7.51 (d, J=8 Hz, 1H), 8.13 (s, 1H); MS (ESI) m/z 506 (M+H)$^-$.

Step 4: 3-Amino-N-(3-(trifluoromethyl)-10H-phenothiazin-1-yl)cyclohexanecarboxamide

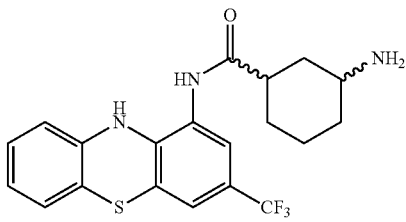

To a stirred solution of tert-butyl (3-((3-(trifluoromethyl)-10H-phenothiazin-1-yl)carbamoyl)cyclohexyl)carbamate (6.8 g, 13.4 mmol) in dichloromethane (60 mL) at 0° C. was added a solution of 4N HCl in dioxane (20 mL) and stirring continued at room temperature for 12 h. The reaction mixture was concentrated and the residue was triturated with diethyl ether and n-hexane to give the title compound as an off-white solid (2 g, 37%): $^1$H NMR (DMSO-$d_6$, 400 MHz) δ1.18-1.22 (m, 4H), 1.75-1.78 (m, 2H), 1.84-1.86 (m, 1H), 1.98-2.07 (d, J=12.4 Hz, 1H), 2.59 (s, 1H), 3.45-3.48 (m, 1H), 6.83-6.91 (m, 2H), 6.96 (d, J=6.8 Hz, 1H), 7.02 (t, J=7.6 Hz, 1H), 7.12 (s, 1H), 8.13 (s, 1H), 7.38 (s, 1H), 8.03 (s, 1H); MS (ESI) m/z 408 (M+H)$^+$; HPLC purity: 99.65%.

Compound 133: N-((3-Aminocyclohexyl)methyl)-3-(trifluoromethyl)-10H-phenothiazin-1-amine

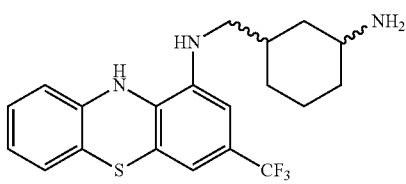

Step 1:
1-Nitro-3-(trifluoromethyl)-10H-phenothiazine

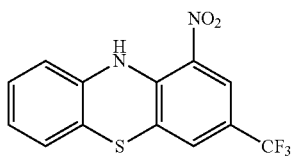

To a stirred solution of 2-chloro-1,3-dinitro-5-(trifluoromethyl)benzene (25 g, 92.5 mmol) in water (200 mL) were added 2-aminobenzenethiol (10.4 g, 83.3 mmol), sodium hydroxide (11.1 g, 277.5 mmol) and the reaction mixture was heated at 80° C. for 12 h. The reaction mixture was cooled to room temperature, filtered, and the solid obtained was washed with water followed by EtOH to give the title compound as a brown solid (25.0 g, 87%): $^1$H NMR (DMSO-$d_6$, 400 MHz) δ 6.97 (m, 1H), 7.02 (m, 1H), 7.09 (m, 2H), 7.65 (s, 1H), 8.01 (s, 1H), 9.84 (s, 1H); MS (ESI) m/z 312 (M+H)$^+$.

Step 2:
3-(Trifluoromethyl)-10H-phenothiazin-1-amine

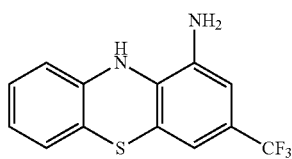

To a stirred solution of 1-nitro-3-(trifluoromethyl)-10H-phenothiazine (25 g, 80.1 mmol) in MeOH (250 mL) was added 10% Pd/C (50% wet, 5 g) and the reaction mixture was hydrogenated with $H_2$ gas (balloon) at room temperature for 16 h. The reaction mixture was filtered through celite and filtrate was concentrated to give the title compound as a light pink solid (20 g, 88%): $^1$H NMR (DMSO-$d_6$, 400 MHz) δ 5.44 (s, 2H), 6.49 (s, 1H), 6.73 (s, 1H), 6.81 (t, J=7.2 Hz, 1H), 6.92 (d, J=8 Hz, 1H), 6.92 (d, J=7.6 Hz, 1H), 7.01 (t, J=7.6 Hz, 1H), 7.81 (s, 1H); MS (ESI) m/z 283 (M+H)$^+$.

Step 3: Tert-butyl(3-(((3-(trifluoromethyl)-10H-phenothiazin-1-yl)amino)methyl)cyclohexyl)carbamate

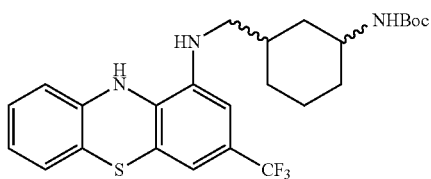

To a stirred solution of 3-(trifluoromethyl)-10H-phenothiazin-1-amine (10 g, 35.46 mmol), tert-butyl (3-formylcyclohexyl)carbamate (12 g, 54.05 mmol) in MeOH (100 mL) was added AcOH (2.5 mL) at 0° C. and the reaction was stirred for 1 h at 0° C. NaCNBH$_3$ (11 g, 177.3 mmol) was added to the reaction mixture at 0° C. and was stirred at room temperature for 12 h. The reaction mixture was evaporated, the residue was diluted with EtOAc, and washed with aq.NaHCO$_3$ solution. The organic layer was dried over anhydrous Na$_2$SO$_4$, concentrated, and the residue was purified by column chromatography over silica gel using 20% ethyl acetate/hexane as eluant to give the title compound as a light yellow solid (11 g, 62%): $^1$H NMR (DMSO-$d_6$, 400 MHz) δ 0.77-0.89 (m, 2H), 1.02-1.04 (m, 1H), 1.19-1.25 (m, 2H), 1.35 (s, 9H), 1.63-1.78 (m, 4H), 1.95-1.98 (m, 1H), 3.14-3.27 (m, 3H), 4.01-4.05 (m, 1H), 5.42 (bs, 1H), 6.50 (s, 1H), 6.53 (s, 1H), 6.72 (d, J=6.8 Hz, 1H), 6.81 (t, J=7.2 Hz, 1H), 6.87 (d, J=8 Hz, 1H), 6.93 (d, J=7.2 Hz, 1H), 7.02 (t, J=7.6 Hz, 1H), 7.99 (s, 1H); MS (ESI) m/z 494 (M+H)$^+$.

Step 4: N-((3-Aminocyclohexyl)methyl)-3-(trifluoromethyl)-10H-phenothiazin-1-amine

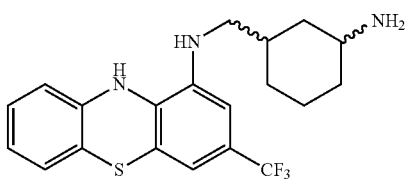 [SMILES: NC1CCCC(CNc2cc(C(F)(F)F)cc3c2Nc2ccccc2S3)C1]

To a stirred solution of tert-butyl (3-((3-(trifluoromethyl)-10H-phenothiazin-1-yl)carbamoyl)cyclohexyl)carbamate (10 g, 20.24 mmol) in dichloromethane (75 mL) at 0° C. was added a solution of 4N HCl in dioxane (15 mL) and was stirred at room temperature for 12 h. The reaction mixture was concentrated and the residue was triturated with diethyl ether followed by hexane. The crude product was diluted with water, basified with aq.NaHCO$_3$ solution, extracted with EtOAc, organic layer is dried over anhydrous Na$_2$SO$_4$, concentrated, and the crude product was triturated with acetonitrile to get the title compound as pale yellow solid (5 g, 63%): $^1$H NMR (DMSO-$d_6$, 400 MHz) δ 0.65-0.94 (m, 3H), 1.13-1.26 (m, 1H), 1.36-1.90 (m, 6H), 1.93-1.96 (m, 1H), 2.84-2.98 (m, 2H), 5.53 (s, 1H), 6.48 (s, 1H), 6.52 (s, 1H), 6.80 (t, J=7.6 Hz, 1H), 6.91 (q, J=7.6 Hz, 2H), 7.02 (t, J=7.6 Hz, 1H), 8.06 (s, 1H): MS (ESI) m/z 394 (M+H)$^+$; HPLC purity: 99.78%.

Compound 140: N-(1-(2-Aminoethyl)piperidin-4-yl)-3-(trifluoromethyl)-10H-phenothiazin-1-amine

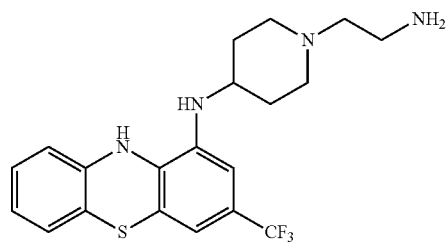

Step 1:
1-Nitro-3-(trifluoromethyl)-10H-phenothiazine

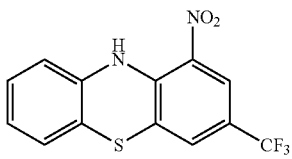

To a stirred solution of 2-chloro-1,3-dinitro-5-(trifluoromethyl)benzene (25 g, 92.5 mmol) in water (200 mL) were added 2-aminobenzenethiol (10.4 g, 83.3 mmol), sodium hydroxide (11.1 g, 277.5 mmol) and the reaction mixture was heated at 80° C. for 12 h. The reaction mixture was cooled to room temperature, filtered, and the solid obtained was washed with water followed by EtOH to give the title compound as a brown solid (25.0 g, 87%): $^1$H NMR (DMSO-$d_6$, 400 MHz) δ 6.97 (m, 1H), 7.02 (m, 1H), 7.09 (m, 2H), 7.65 (s, 1H), 8.01 (s, 1H), 9.84 (s, 1H); MS (ESI) m/z 312 (M+H)$^+$.

Step 2: 3-(Trifluoromethyl)-10H-phenothiazin-1-amine

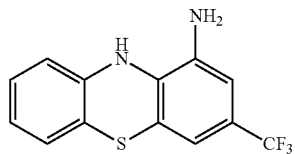

To a stirred solution of 1-nitro-3-(trifluoromethyl)-10H-phenothiazine (25 g, 80.1 mmol) in MeOH (250 mL) was added 10% Pd/C (50% wet, 5 g) and the reaction mixture was hydrogenated under $H_2$ gas (balloon) at room temperature for 16 h. The reaction mixture was filtered through celite and filtrate was concentrated to give the title compound as a light pink solid (20 g, 88%): $^1$H NMR (DMSO-$d_6$, 400 MHz) δ 5.44 (s, 2H), 6.49 (s, 1H), 6.73 (s, 1H), 6.81 (t, J=7.2 Hz, 1H), 6.92 (d, J=8 Hz, 1H), 6.92 (d, J=7.6 Hz, 1H), 7.01 (t, J=7.6 Hz, 1H), 7.81 (s, 1H); MS (ESI) m/z 283 (M+H)$^+$.

Step 3: Tert-butyl 4-((3-(trifluoromethyl)-10H-phenothiazin-1-yl)amino)piperidine-1 carboxylate

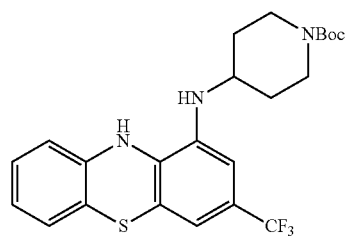 [SMILES: CC(C)(C)OC(=O)N1CCC(Nc2cc(C(F)(F)F)cc3c2Nc2ccccc2S3)CC1]

To a stirred solution of 3-(trifluoromethyl)-10H-phenothiazin-1-amine (10 g, 35.4 mmol) in DCE (250 mL) was added tert-butyl 4-oxopiperidine-1-carboxylate (8.4 g, 42.5 mmol) and the reaction mixture was stirred for 1 h at room temperature. Na(OAc)$_3$BH (11.26 g, 53.13 mmol) was added at room temperature and stirring was continued at room temperature for 16 h. The reaction mixture was diluted with aq.NaHCO$_3$ solution and extracted with DCM. The organic layer was dried over Na$_2$SO$_4$, concentrated, and the residue was as such take for the next step without further purification (13 g, crude): MS (ESI) m/z 466 (M+H)$^+$.

Step 4: N-(Piperidin-4-yl)-3-(trifluoromethyl)-10H-phenothiazin-1-amine

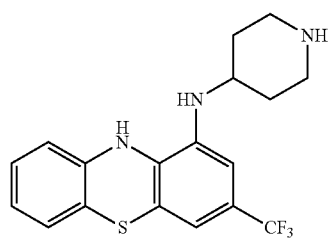 [SMILES: FC(F)(F)c1cc(NC2CCNCC2)c2c(c1)Sc1ccccc1N2]

To a stirred solution of tert-butyl 4-((3-(trifluoromethyl)-10H-phenothiazin-1-yl)amino)piperidine-1-carboxylate (13 g, 35.6 mmol) in dichloromethane (150 mL) was added 4N HCl in dioxane (20 mL) at 0° C. and stirred at room temperature for 5 h. The reaction mixture was concentrated, residue was diluted with aqueous sodium bicarbonate solution, extracted with dichloromethane, and concentrated. The residue was purified over silica gel using 8% MeOH/DCM as eluant to give the title compound as black solid (6.58 g, 66%); MS (ESI) m/z 366 (M+H)$^+$.

Step 5: Tert-butyl (2-(4-((3-(trifluoromethyl)-10H-phenothiazin-1-yl)amino)piperidin-1-yl)ethyl)carbamate

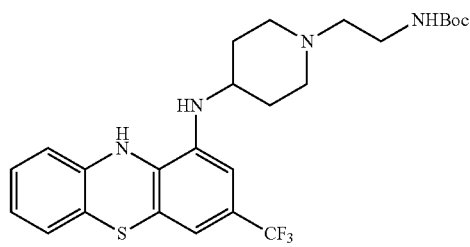 [SMILES: CC(C)(C)OC(=O)NCCN1CCC(Nc2cc(C(F)(F)F)cc3c2Nc2ccccc2S3)CC1]

To a stirred solution of N-(piperidin-4-yl)-3-(trifluoromethyl)-10H-phenothiazin-1-amine (5.58 g, 15.2 mmol) in acetonitrile (70 mL) were added tert-butyl (2-bromoethyl)carbamate (4.1 g, 18.3 mmol), potassium carbonate (6.3 g, 45.8 mmol) and was stirred at 70° C. for 16 h. The reaction mixture was concentrated, diluted with water, and extracted with ethyl acetate. The organic layer was washed with brine solution, dried over anhydrous sodium sulphate, and concentrated. The residue was purified by column chromatography over silica gel using 8% methanol/dichloromethane mixture as eluant to give the title compound as brown solid (4 g, 52%); MS (ESI) m/z 509 (M–H)$^+$.

Step 6: N-(1-(2-Aminoethyl)piperidin-4-yl)-3-(trifluoromethyl)-10H-phenothiazin-1-amine

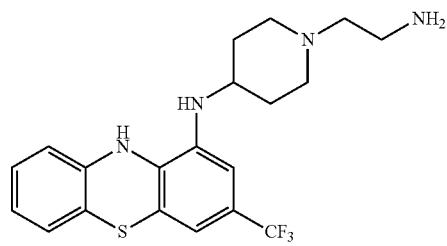

To a stirred solution of tert-butyl(2-(4-((3-(trifluoromethyl)-10H-phenothiazin-1-yl)amino)piperidin-1-yl)ethyl)carbamate (7.5 g, 14.7 mmol)) in dichloromethane (100 mL) at 0° C. was added 4M HCl in dioxane (10 mL) and the reaction was stirred at room temperature for 5 h. The reaction mixture was concentrated and washed with pentane. The crude product was dissolved in water, basified with aq.NaHCO$_3$ solution, filtered, and solid was triturated with diethyl ether followed by n-pentane to get the desired product N-(1-(2-aminoethyl)piperidin-4-yl)-3-(trifluoromethyl)-10H-phenothiazin-1-amine as brown solid (3.9 g, 65%): $^1$H NMR (DMSO-$d_6$, 400 MHz) δ 1.41-1.48 (m, 4H), 1.90-1.93 (d, J=12 Hz, 2H), 2.063 (t, J=12 Hz, 2H), 2.30 (t, J=4 Hz, 2H), 2.58-2.61 (m, 2H), 2.82-2.84 (d, J=8 Hz, 2H), 5.26-5.28 (d, J=8 Hz, 1H), 6.54 (s, 1H), 6.58 (s, 11H), 6.80-6.82 (m, 11H), 6.84-6.88 (m, 1H), 6.90-6.95 (m, 1H), 7.01-7.05 (m, 1H), 8.02 (s, 1H); MS (ESI) m/z 409 (M+H)$^+$; HPLC purity: 99.10%.

Table III lists examples of compounds synthesised by the method of Scheme III.

TABLE III

| Cmpd # | R² | A | R³ | R⁴ |
|---|---|---|---|---|
| 2 | NH₂ | S | CF₃ | H |
| 30 | (HN-C(=O)-CH₂-CH₂-NH₂) | S | CF₃ | H |
| 39 | (dimethylaminopropyl acrylamide) | S | CF₃ | H |
| 91 | (HN-C(=O)-piperidin-3-yl) | S | CF₃ | H |
| 95 | (HN-C(=O)-cyclohexyl-NH₂) | S | CF₃ | H |
| 98 | (HN-C(=S)-NH-CH₂CH₂-NH₂) | S | CF₃ | H |
| 101 | (HN-C(=O)-CH₂CH₂-piperazinyl) | S | CF₃ | H |
| 67 | (HN-C(=O)-CH(CH₃)-CH-NH₂) | S | CF₃ | H |
| 92 | (HN-C(=O)-CH=CH-4-fluorophenyl) | S | CF₃ | H |
| 97 | (HN-CH₂CH₂CH₂-NH₂) | S | CF₃ | H |
| 100 | (HN-C(=O)-piperidin-3-yl) | S | CF₃ | H |
| 105 | (HN-C(=O)-cyclohexyl-NH₂) | S | CF₃ | H |
| 108 | (HN-cyclohexyl-NH₂) | S | CF₃ | H |
| 118 | (HN-C(=O)-cyclohexyl-NH₂) | S | CF₃ | H |
| 106 | (HN-C(=O)-piperidin-3-yl) | S | CF₃ | H |
| 113 | (HN-C(=O)-cyclohexyl(NH₂)) | S | CF₃ | H |

TABLE III-continued

| Cmpd # | R² | A | R³ | R⁴ |
|---|---|---|---|---|
| 115 | 4,4-difluoro-1-hydroxycyclohexyl acetamide | S | CF₃ | H |
| 119 | 3-aminocyclohexyl carboxamide | S | CN | H |
| 125 | 3-aminocyclohexyl carboxamide (stereo) | S | CF₃ | H |
| 132 | 4,4-difluorocyclohexyl acetamide | S | CF₃ | H |
| 134 | 3-aminobenzamide | S | CF₃ | H |
| 140 | 4-(2-aminoethyl)piperidin-4-ylamino | S | CF₃ | H |
| 149 | 3-(aminomethyl)cyclohexyl carboxamide | S | CF₃ | H |
| 156 | 3-aminocyclohexyl carboxamide | O | CF₃ | H |
| 120 | 4-(aminomethyl)cyclohexyl carboxamide | S | CF₃ | H |
| 133 | 3-aminocyclohexyl methylamine | S | CF₃ | H |
| 139 | 6-aminopiperidin-3-yl carboxamide | S | CF₃ | H |
| 141 | piperidin-4-yl | S | CF₃ | H |
| 148 | 3-hydroxycyclohexyl carboxamide | S | CF₃ | H |
| 157 | 4-(2-aminoethyl)morpholin-3-yl carboxamide ·TFA | S | CF₃ | H |
| 159 | morpholin-3-yl carboxamide | S | CF₃ | H |
| 161 | 3-aminocyclohexyl carboxamide | S | Cl | H |

TABLE III-continued

| Cmpd # | R² | A | R³ | R⁴ |
|---|---|---|---|---|
| 163 | HN-C(=O)-cyclohexyl-NH-CH₂CH₂-NH₂ | S | CF₃ | H |
| 165 | HN-C(=O)-CH₂-cyclohexyl-NH₂ ·TFA | S | CF₃ | H |
| 158 | HN-CH₂-cyclohexyl-CH₂-NH₂ | S | CF₃ | H |
| 160 | HN-C(=O)-cyclohexyl-CH₂-NH₂ | O | CF₃ | H |
| 162 | HN-C(=O)-cyclohexyl-NH-CH₂CH₂CH₂-NH₂ | S | CF₃ | H |
| 164 | HN-CH₂-cyclohexyl-NH₂ | O | CF₃ | H |
| 167 | HN-C(=O)-CH₂-cyclohexyl-NH₂ | S | CF₃ | H |
| 170 | HN-C(=O)-cyclohexyl(-NH₂)(-NH₂) | S | CF₃ | H |
| 172 | HN-piperidinyl(NH) | S | CF₃ | H |
| 174 | HN-pyrrolidinyl(NH) | S | CF₃ | H |
| 178 | HN-CH(CH₂Cl)-CH₂-NH₂ | S | CF₃ | H |
| 180 | HN-cyclohexyl-NH₂ | S | CF₃ | H |
| 184 | HN-piperidinyl(NH) | S | Cl | H |
| 187 | HN-CH₂-cyclohexyl-NH₂ ·TFA | S | CF₃ | H |
| 169 | HN-piperidinyl(NH) | O | CF₃ | H |
| 171 | HN-CH₂-cyclohexyl-NH₂ | S | CF₃ | H |

TABLE III-continued

| Cmpd # | R² | A | R³ | R⁴ |
|---|---|---|---|---|
| 173 | HN-CH2-piperidine-NH | S | CF₃ | H |
| 175 | HN-C(O)-cyclobutyl-NH2 | S | CF₃ | H |
| 179 | HN-CH2-piperidine-N-CH2CH2NH2 | S | CF₃ | H |
| 182 | HN-CH2-cyclohexyl-NH2 | S | CF₃ | H |
| 185 | HN-piperidine | S | H | H |
| 188 | HN-C(O)-azetidine-NH | S | CF₃ | H |
| 190 | HN-cyclohexyl-NH2 | S | CF₃ | H |
| 193 | HN-azetidine-NH | S | CF₃ | H |
| 196 | HN-C(O)-azetidine-N-CH2CH2NH2 | S | CF₃ | H |
| 203 | HN-C(O)-piperidine-N-CH2CH2NH2 | S | CF₃ | H |
| 189 | HN-piperidine-CH2NH2 | S | CF₃ | H |
| 192 | HN-cyclohexyl-CH2OH | S | CF₃ | H |
| 199 | HN-C(O)-piperidine-N-CH2CH2NH2 | S | CF₃ | H |
| 204 | HN-cyclohexyl-NH2 | S | CF₃ | H |
| 207 | HN-C(O)-piperidine-NH | S | CF₃ | H |
| 228 | pyrrolidine-N-CH2CH2NH2, HN- | S | CF₃ | H |

TABLE III-continued

| Cmpd # | R² | A | R³ | R⁴ |
|---|---|---|---|---|
| 253 | (S)-2-amino-3-(1H-indol-3-yl)propanamide group | S | CF₃ | H |
| 215 | 4-((2-aminoethyl)piperidin-1-yl)amino | S | CN | H |
| 218 | 4-((2-aminoethyl)piperidin-1-yl)amino | S | CF₃ | H |
| 220 | 3-((2-aminoethyl)piperidin-1-yl)-NH- | S | CF₃ | H |
| 206 | 4-((2-aminoethyl)piperidin-1-yl)amino | O | CF₃ | H |
| 208 | 3-((2-aminoethyl)azetidin-1-yl)amino | S | CF₃ | H |
| 225 | 5-((2-aminoethyl)azepan-1-yl)amino | S | CF₃ | H |
| 234 | bis(2-aminoethyl)amino-ethyl-piperidinyl-amino | S | CF₃ | H |
| 214 | 4-((2-aminoethyl)piperidin-1-yl)amino | S | Cl | H |
| 215 | bis(2-aminoethyl)amino-ethyl-piperidinyl-amino TFA | S | CF₃ | H |
| 219 | 4-(2-((2-aminoethyl)amino)ethyl)piperidin-1-yl)amino | S | CF₃ | H |
| 221 | azepan-4-ylamino | S | CF₃ | H |
| 226 | 1-(2-aminoethyl)piperidine-4-carboxamide | S | CF₃ | Cl |

TABLE III-continued

| Cmpd # | R² | A | R³ | R⁴ |
|---|---|---|---|---|
| 223 | ![piperidine-4-carboxamide with methyl] | S | CF₃ | Cl |

Scheme IV: Synthesis of 3,N-10-disubstituted phenothiazenes

Figure 4:
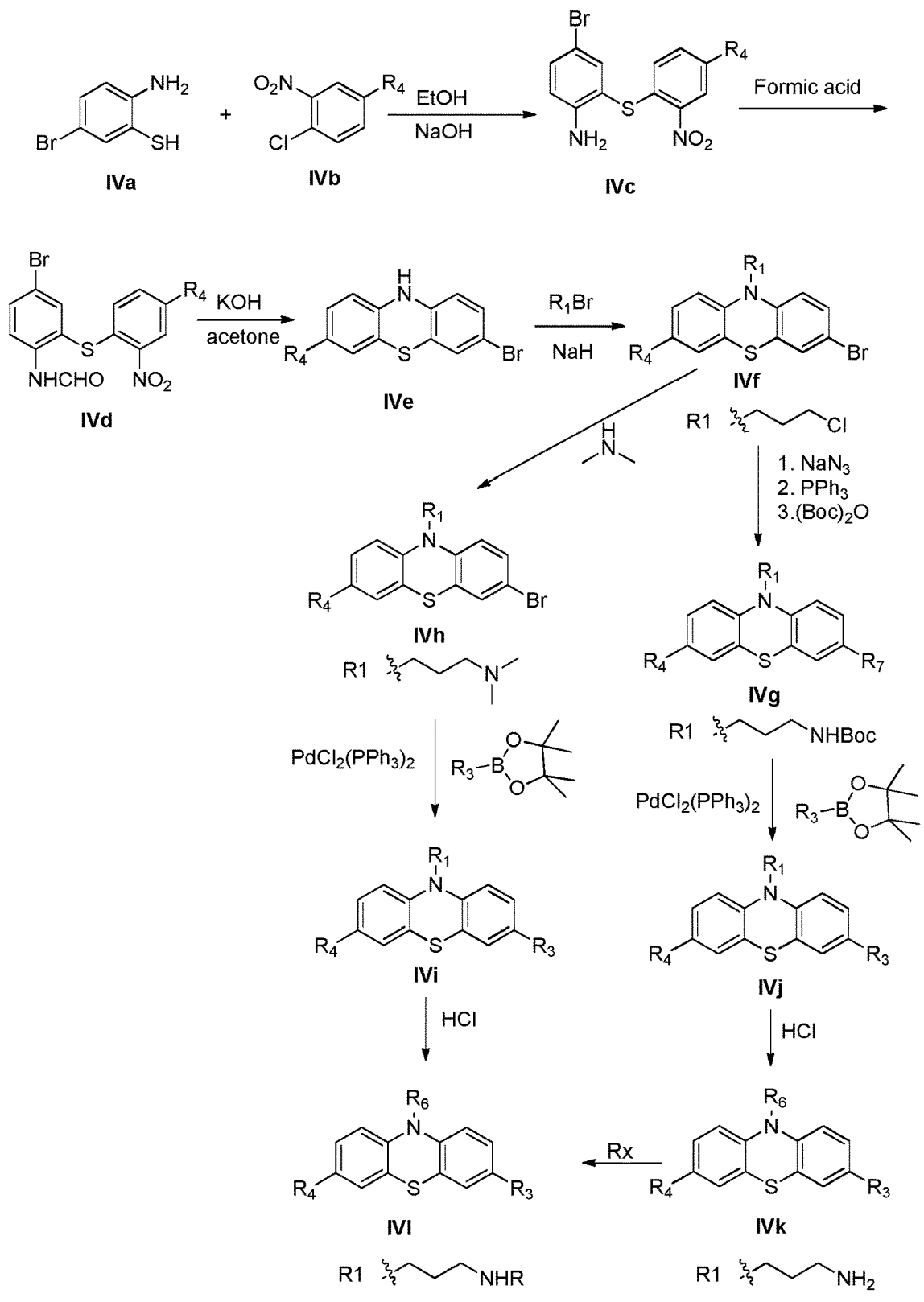
FIG. 4 shows general synthetic scheme IV for the synthesis of selected compounds according to the present invention.

FIG. 4 shows general synthetic scheme IV for the synthesis of selected 3,N-10-Disubstituted phenothiazenes. Nucleophilic substitution of 2-amino-5-bromobenzenethiol (IVa) with 1-chloro-2-nitrobenzene (IVb) resulted in compound IVc. N-Formylation followed by Smiles rearrangement of compound IVc yielded 3-bromo phenothiazene (IVe). N-alkylation of compound IVe with alkylbromides using NaH yielded N-10-alkylatedphenothiazene (IVf). Neucleophilic substitution of compound IVf followed by reduction, and protection of the resulting amine gave compound IVg. Parallelly, reaction with amines compound IVf resulted in compound IVh. Suzuki coupling of compounds IVg&IVh with arylborane compounds yielded corresponding 3-aryl phenothiazenes (IVj&IVi). Deprotection of compounds IVj&IVi gives title compounds IVl&IVk. Finally, reaction of IVk with acylchlorides or alkylhalides resulted in the corresponding title compounds IVl.

Detailed synthesis descriptions of some compounds synthesised by the method of Scheme IV is provided below.

Compound 111: 3-(3-(1H-Indol-2-yl)-10H-phenothiazin-10-yl)-N,N-dimethylpropan-1-amine

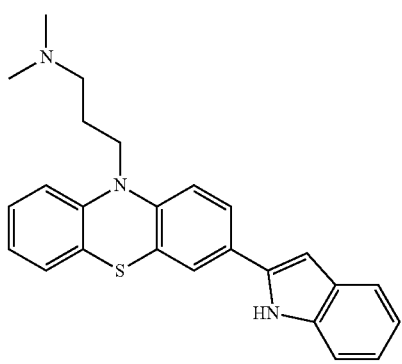 [SMILES: CN(C)CCCN1c2ccccc2Sc2cc(-c3cc4ccccc4[nH]3)ccc21]

Step 1: 2-((4-Bromo-2-nitrophenyl)thio)aniline

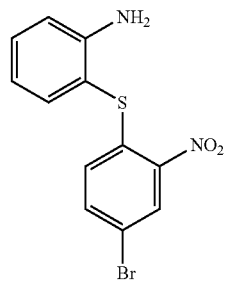 [SMILES: Nc1ccccc1Sc1ccc(Br)cc1[N+](=O)[O-]]

To a stirred solution of 1,4-dibromo-2-nitrobenzene (50 g, 179 mmol) in EtOH (500 mL) were added 2-aminobenzenethiol (23 mL, 215.16 mmol), KOH (8.6 g, 215.16 mmol) and the reaction was stirred at room temperature for 16 h. The precipitated solid was filtered, washed with n-hexane, dried under vacuum to give the title compound as yellow solid (65 g, quantitative): ¹H NMR (CDCl₃, 400 MHz) δ 5.53 (s, 2H), 6.59-6.67 (m, 2H), 6.80 (d, J=8.0 Hz, 1H), 7.23 (t, J=7.6.0 Hz, 1H), 7.31 (d, J=7.6 Hz, 1H), 7.73-7.75 (m, 1H), 8.35-8.36 (m, 1H).

Step 2: N-(2-((4-bromo-2-nitrophenyl)thio)phenyl)formamide

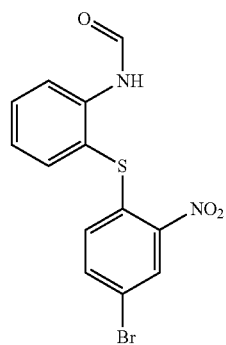 [SMILES: O=CNc1ccccc1Sc1ccc(Br)cc1[N+](=O)[O-]]

A mixture of 2-((4-bromo-2-nitrophenyl)thio)aniline (60 g) and formic acid (300 mL) was heated at 100° C. for 16 h. The reaction mixture was evaporated, the crude was poured on crushed ice, and the solid obtained was filtered, dried under vacuum to get the title compound as yellow solid (50 g, 92%): ¹H NMR (CDCl₃, 400 MHz) δ 6.52 (d, J=7.2 Hz, 1H), 7.257.29 (m, 1H), 7.58 (t, J=7.6 Hz, 1H), 7.67 (d, J=7.6 Hz, 1H), 7.73 (d, J=7.6 Hz, 1H), 8.15 (s, 1H), 8.33 (d, J=8 Hz, 1H), 8.40 (s, 1H), 9.72 (s, 1H).

Step 3: 3-Bromo-10H-phenothiazine

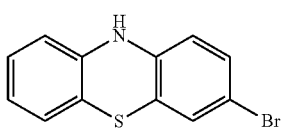

To a stirred solution of N-(2-((4-bromo-2-nitrophenyl)thio)phenyl)formamide (50 g, 142 mmol) in acetone (500 mL) was added KOH (25 g, 426 mmol) and the reaction mixture was stirred at 80° C. for 16 h. The reaction mixture was evaporated, the crude was suspended in water, and stirred for 5 h. The solid was filtered and dried under vacuum to get the title compound as light brown solid (40 g, quantitative): MS (ESI) m/z 278 (M+2H)+.

Step 4:
3-Bromo-10-(3-chloropropyl)-10H-phenothiazine

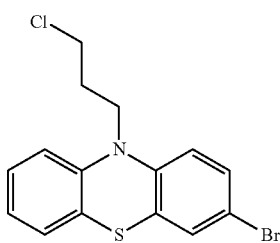

To a stirred solution of 3-bromo-10H-phenothiazine (18 g, 64.72 mmol) in DMF (100 mL) was added sodium hydride (3.8 g, 97.08 mmol) at 0° C. in small portions and the reaction mixture was stirred at 0° C. for 15 mins. To the reaction mixture was added 3-bromo chloropropane (12.2 g, 77.66 mmol) at 0° C. and stirring continued at room temperature for 1 h. The reaction was quenched with aq.NH$_4$Cl solution, extracted with EtOAc, organic layer is washed with brine, dried over anhydrous sodium sulphate, and concentrated. The crude product (20 g) was as such taken for the next step without further purification: MS (ESI) m/z 355 (M+2H)+.

Step 5:3-(3-Bromo-10Hphenothiazin-10-yl)-N,N-dimethylpropan-1-amine

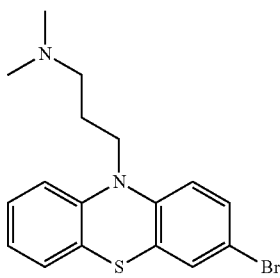 [SMILES: CN(C)CCCN1c2ccccc2Sc2cc(Br)ccc21]

To a stirred solution of 3-bromo-10-(3-chloropropyl)-10H-phenothiazine (15 g, 42.28 mmol) in DMF (150 mL) were added 2M solution of N,N-dimethyl amine in THF (4.7 mL, 84.57 mmol), potassium phosphate (26.9 g, 126.84 mmol) and the reaction mixture was stirred at 80° C. for 12 h. The reaction mixture was diluted with water, and extracted with EtOAc. The organic layer was washed with ice-cold water followed by brine solution, dried over sodium sulphate, and concentrated. The crude product was purified over silica gel using 5% MeOH/DCM as eluant to give title compound as brown liquid (8 g, 53%): $^1$H NMR (DMSO, 400 MHz) δ 1.69-1.76 (m, 2H), 2.05 (s, 6H), 2.23-2.26 (m, 2H), 3.83-3.86 (m, 2H), 6.91-6.94 (m, 2H), 7.0 (d, J=8 Hz, 1H), 7.12 (d, J=7.6 Hz, 1H), 7.18-7.20 (m, 1H), 7.30-7.33 (m, 2H); MS (ESI) m/z 365 (M+2H)+.

Step 6: Tert-butyl-2-(10-(3-(dimethylamino)propyl)-10H-phenothiazin-3-yl)-1H-indole-1-carboxylate

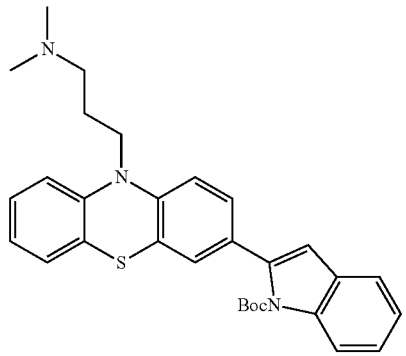 [SMILES: CN(C)CCCN1c2ccccc2Sc2cc(-c3cc4ccccc4n3C(=O)OC(C)(C)C)ccc21]

To a solution of 3-(3-bromo-10H-phenothiazin-10-yl)-N,N-dimethylpropan-1-amine (3 g, 8.25 mmol) in a mixture of DME/water (50/5 mL) were added potassium carbonate (3.4 g, 24.75 mmol), (1-(tert-butoxycarbonyl)-1H-indol-2-yl)boronic acid (3.2 g, 12.38 mmol) and reaction mixture was purged with nitrogen for 10 mins. To the reaction mixture was added bis(triphenylphosphine)palladium(II) dichloride (0.57 g, 0.82 mmol), was purged with nitrogen for 10 mins, and refluxed for 16 h. The reaction mixture was filtered through celite, filtrate was diluted with EtOAc, washed with water, dried over sodium sulphate, and concentrated. The crude product was purified over silica gel using 4% MeOH/DCM as eluant to get title compound as brown viscous liquid (2 g, 48%): $^1$H NMR (DMSO, 400 MHz) δ 1.28 (s, 9H), 1.71-1.81 (m, 2H), 2.09 (s, 6H), 2.29-2.33 (m, 2H), 3.91-3.95 (m, 2H), 6.67 (s, 1H), 6.93 (t, J=7.6 Hz, 1H), 7.05 (t, J=8.8 Hz, 2H), 7.13-7.30 (m, 6H), 7.56 (d, J=7.6 Hz, 1H), 8.04 (d, J=8.4 Hz, 1H); MS (ESI) m/z 500 (M+H)+.

Step 7: 3-(3-(1H-Indol-2-yl)-10H-phenothiazin-10-yl)-N,N-dimethylpropan-1-amine

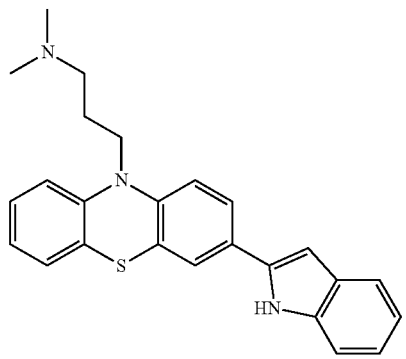 [SMILES: CN(C)CCCN1c2ccccc2Sc2cc(-c3cc4ccccc4[nH]3)ccc21]

To a solution of tert-butyl-2-(10-(3-(dimethylamino)propyl)-10H-phenothiazin-3-yl)-1H-indole-1-carboxylate (3 g, 6 mmol) in MeOH (30 mL) was added potassium carbonate (2.5 g, 18 mmol) and the reaction mixture was heated at 70° C. for 12 h. The reaction mixture was evaporated, residue was diluted with water, extracted with ethyl acetate, organic layer was dried over sodium sulphate, and concentrated. The crude product was purified over silica gel using 5% MeOH/DCM as eluant to afford 3-(3-(1H-indol-2-yl)-10H-phenothiazin-10-yl)-N,N-dimethylpropan-1-amine as off-white solid (1.3 g, 54%): $^1$H NMR (DMSO-$d_6$, 400 MHz) δ 1.94 (s, 6H), 2.31 (s, 2H), 2.66 (s, 2H), 3.96 (s, 2H), 6.80 (s, 1H), 6.96-6.97 (m, 2H), 7.04-7.08 (m, 2H), 7.12 (d, J=8.0 Hz, 1H), 7.19-7.24 (m, 2H), 7.35 (d, J=8.0 Hz, 1H), 7.48 (d, J=8.0 Hz, 1H), 7.66-7.69 (m, 2H), 11.40 9s, 1H); MS (ESI) m/z 400 (M+H)$^+$.

Example 150: 3-(3-(1H-Indol-2-yl)-10H-phenothiazin-10-yl)propan-1-amine

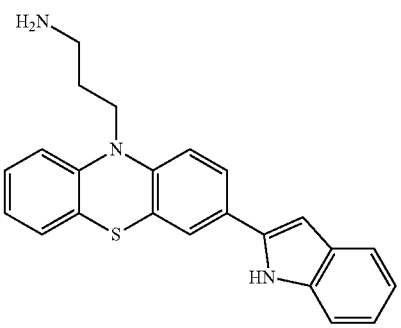 [SMILES: NCCCN1c2ccccc2Sc2cc(-c3cc4ccccc4[nH]3)ccc21]

Step 1: 2-((4-Bromo-2-nitrophenyl)thio)aniline

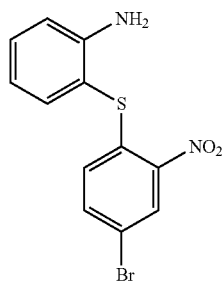 [SMILES: Nc1ccccc1Sc1ccc(Br)cc1[N+](=O)[O-]]

To a stirred solution of 1,4-dibromo-2-nitrobenzene (50 g, 179 mmol) in EtOH (500 mL) were added 2-aminobenzenethiol (23 mL, 215.16 mmol), NaOH (8.6 g, 215.16 mmol) and the reaction mixture was stirred at room temperature for 16 h. The precipitated solid was filtered, washed with n-hexane, and dried under vacuum to give the title compound as yellow solid (65 g, quantitative): $^1$H NMR (CDCl$_3$, 400 MHz) δ 5.53 (s, 2H), 6.59-6.67 (m, 2H), 6.80 (d, J=8.0 Hz, 1H), 7.23 (t, J=7.6.0 Hz, 1H), 7.31 (d, J=7.6 Hz, 1H), 7.73-7.75 (m, 1H), 8.35-8.36 (m, 1H).

Step 2: N-(2-((4-Bromo-2-nitrophenyl)thio)phenyl)formamide

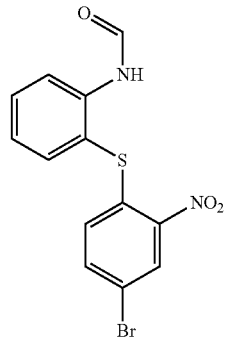 [SMILES: O=CNc1ccccc1Sc1ccc(Br)cc1[N+](=O)[O-]]

A mixture of 2-((4-bromo-2-nitrophenyl)thio)aniline (60 g, 185 mmol) and formic acid (300 mL) was heated at 100° C. for 16 h. The reaction mixture was evaporated, the crude was poured on crushed ice, precipitated solid was filtered, and dried to get the title compound as yellow solid (50 g, 92%): $^1$H NMR (CDCl$_3$, 400 MHz) δ 6.52 (d, J=7.2 Hz, 1H), 7.257.29 (m, 1H), 7.58 (t, J=7.6 Hz, 1H), 7.67 (d, J=7.6 Hz, 1H), 7.73 (d, J=7.6 Hz, 1H), 8.15 (s, 1H), 8.33 (d, J=8 Hz, 1H), 8.40 (s, 1H), 9.72 (s, 1H).

Step 3:3-Bromo-10H-phenothiazine

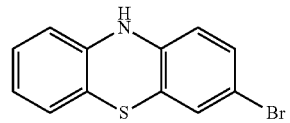 [SMILES: Brc1ccc2c(c1)Sc1ccccc1N2]

To a stirred solution of N-(2-((4-bromo-2-nitrophenyl)thio)phenyl)formamide (50 g, 142 mmol) in acetone (500 mL) was added KOH (25 g, 426 mmol) and the reaction mixture was stirred at 80° C. for 16 h. The reaction mixture was evaporated, the residue was suspended in water, and was stirred for 5 h. The precipitated solid was filtered, dried to get the title compound as light brown solid (40 g, quantitative): MS (ESI) m/z 278 (M+2H)$^+$.

Step 4:3-Bromo-10-(3-chloropropyl)-10H-phenothiazine

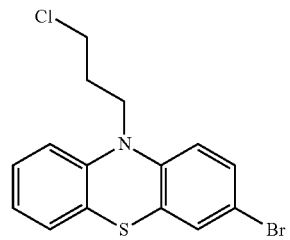 [SMILES: ClCCCN1c2ccccc2Sc2cc(Br)ccc21]

To a stirred solution of 3-bromo-10H-phenothiazine (18 g, 64.72 mmol) in DMF (100 mL) was added sodium hydride (3.8 g, 97.08 mmol) at 0° C. in small portions and the reaction mixture was stirred at 0° C. for 15 mins. To the reaction mixture was added 3-bromo chloropropane (12.2 g, 77.66 mmol) at 0° C. and stirring continued at room temperature for 1 h. The reaction mixture was quenched with aq.NH₄Cl solution, extracted with EtOAc, the organic layer was washed with brine, dried over anhydrous sodium sulphate, and concentrated. The crude product (20 g) was as such taken for the next step without further purification: MS (ESI) m/z 355 (M+2H)⁺.

Step 5:10-(3-Azidopropyl)-3-bromo-10H-phenothiazine

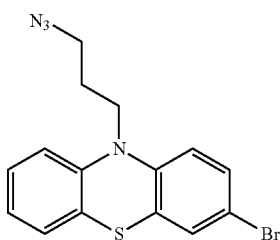 [SMILES: [N-]=[N+]=NCCCN1c2ccccc2Sc2cc(Br)ccc21]

To a stirred solution of 3-bromo-10-(3-chloropropyl)-10H-phenothiazine (10 g, 28.19 mmol) in DMSO (100 mL) was added sodium azide (10.9 g, 161.5 mmol) and the reaction mixture was stirred at room temperature for 16 h. The reaction mixture was quenched with ice, extracted with EtOAc, the organic layer was dried over sodium sulphate, and concentrated. The crude product was purified over silica gel using 100% hexane as eluent to give the desired product as viscous solid (9 g, 88%): ¹H NMR (DMSO, 400 MHz) δ 1.84-1.91 (m, 2H), 3.39-3.43 (m, 2H), 3.90-3.94 (m, 2H), 6.93-6.98 (m, 2H), 7.05 (d, J=8 Hz, 1H), 7.12-7.22 (m, 2H), 7.32-7.34 (m, 2H); MS (ESI) m/z 365 (M+2H)⁺.

Step 6:3-(3-Bromo-10H-phenothiazin-10-yl)propan-1-amine

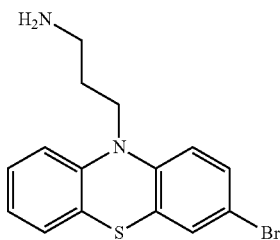 [SMILES: NCCCN1c2ccccc2Sc2cc(Br)ccc21]

To a stirred solution of 10-(3-azidopropyl)-3-bromo-10H-phenothiazine (9 g, 24.86 mmol) in a mixture of THF (100 mL) and H₂O (20 mL) was added triphenylphosphine (13 g, 49.72 mmol) and was stirred at room temperature for 16 h. The reaction mixture was diluted with water, extracted with ethyl acetate, the organic layer is dried over sodium sulphate, and concentrated to get the desired crude product which was taken for next step without further purification (9 g): MS (ESI) m/z 336 (M,M+2H)⁺.

Step 7: Tert-butyl (3-(3-bromo-10H-phenothiazin-10-yl)propyl)carbamate

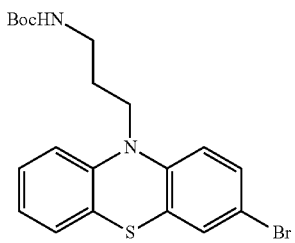

To a stirred solution of 3-(3-bromo-10H-phenothiazin-10-yl)propan-1-amine (9 g, 25.33 mmol) in dichloromethane (100 mL) were added Et₃N (7.4 mL, 50.6 mmol), (Boc)₂O (11.6 mL, 50.6 mmol) at 0° C. and was stirred at room temperature for 2 h. The reaction mixture was concentrated and the crude product was purified over silica gel using 40% EtOAc in hexane as eluant to get the desired product as brown viscous liquid (9 g, 78%): ¹H NMR (DMSO, 400 MHz) δ 1.74-1.78 (m, 2H), 2.99-3.01 (m, 2H), 3.80-3.84 (m, 2H), 6.79-6.85 (m, 1H), 6.90-7.02 (m, 3H), 7.12-7.19 (m, 2H), 7.30-7.34 (m, 2H); MS (ESI) m/z 436 (M+2)+.

Step 8: Tert-butyl 2-(10-(3-((tert-butoxycarbonyl)amino)propyl)-10H-phenothiazin-3-yl)-1H-indole-1-carboxylate

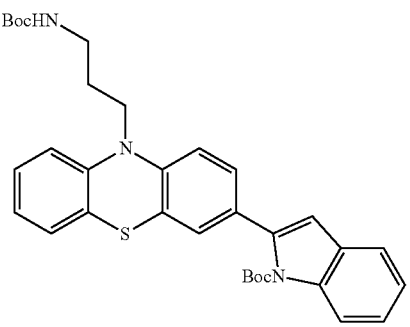 [SMILES: CC(C)(C)OC(=O)NCCCN1c2ccccc2Sc2cc(-c3cc4ccccc4n3C(=O)OC(C)(C)C)ccc21]

To a stirred solution of tert-butyl (3-(3-bromo-10H-phenothiazin-10-yl)propyl)carbamate (2 g, 4.39 mmol) and (1-(tert-butoxycarbonyl)-1H-indol-2-yl)boronic acid (1.3 g, 5.27 mmol) in a mixture of DME/Water (55/5 mL) was added potassium carbonate (0.9 g, 6.58 mmol) and reaction mixture was purged with nitrogen for 10 mins. To the reaction mixture was added bis(triphenylphosphine)palladium(II) dichloride (0.3 g, 0.43 mmol), was purged with nitrogen for 10 mins, and refluxed for 12 h. The reaction mixture was filtered through celite, filtrate was diluted with EtOAc, washed with water followed by brine. The organic layer was dried over sodium sulphate, and concentrated. The crude was purified over silica gel using 15% EtOAc/hexane as eluant to give title compound as brown viscous liquid (1.6 g, 63%): MS (ESI) m/z 572 (M+H)⁺.

Step 9: 3-(3-(1H-Indol-2-yl)-10H-phenothiazin-10-yl)propan-1-amine

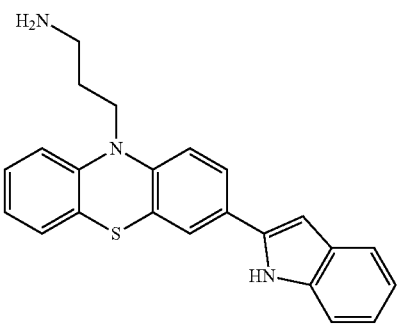 [SMILES: NCCCN1c2ccccc2Sc2cc(-c3cc4ccccc4[nH]3)ccc21]

To a stirred solution of tert-butyl 2-(10-(3-((tert-butoxycarbonyl)amino)propyl)-10H-phenothiazin-3-yl)-1H-indole-1-carboxylate (4 g, 70 mmol) in dichloromethane (60 mL) was added TFA (12 mL) at 0° C. and was stirred at room temperature for 16 h. The reaction mixture was concentrated, residue was basified with saturated sodium bicarbonate solution, extracted with dichloromethane, the organic layer was dried over sodium sulphate, and concentrated. The residue was washed with diethyl ether led to 3-(3-(1H-indol-2-yl)-10H-phenothiazin-10-yl)propan-1-amine as pale yellow solid (1.9 g, 73%): $^1$H NMR (DMSO-$d_6$, 400 MHz) δ 1.78-1.81 (m, 2H), 2.67-2.71 (m, 2H), 3.93-3.96 (m, 2H), 6.77 (s, 1H), 6.93-6.98 (m, 3H), 7.02-7.21 (m, 6H), 7.33 (d, J=8 Hz, 1H), 7.56 (d, J=7.6 Hz, 1H), 7.62-7.66 (m, 2H), 11.37 (s, 1H); MS (ESI) m/z 372 (M+H)$^+$; HPLC purity: 99.45%.

Table IV lists some examples of compounds synthesised by the method of Scheme IV.

TABLE IV

| Cmpd # | R$^3$ | R$^1$ | R$^4$ |
|---|---|---|---|
| 110 | phenyl | N,N-dimethylaminobutyl | H |
| 116 | cyclopropyl | N,N-dimethylaminobutyl | H |
| 121 | 1H-indol-5-yl | N,N-dimethylaminobutyl | H |
| 122 | 2-fluoropyridin-4-yl | N,N-dimethylaminobutyl | H |

TABLE IV-continued

| | | | |
|---|---|---|---|
| 136 | 2-(2-aminoethyl)-1H-indol-2-yl | N,N-dimethylaminobutyl | H |
| 144 | 5-methoxy-1H-indol-2-yl | N,N-dimethylaminobutyl | H |
| 151 | 5-cyano-1H-indol-2-yl · TFA | N,N-dimethylaminobutyl | H |
| 153 | 2-methoxypyridin-4-yl | N,N-dimethylaminobutyl | H |
| 130 | benzothiazol-5-yl | N,N-dimethylaminobutyl | H |
| 181 | 5-(aminomethyl)-1H-indol-2-yl | N,N-dimethylaminobutyl | H |
| 150 | 1H-indol-2-yl | 4-aminobutyl | H |

TABLE IV-continued
| | | | |
|---|---|---|---|
| 213 | 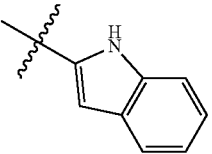 [SMILES: *c1cc2ccccc2[nH]1] | 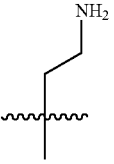 | H |
| 111 | 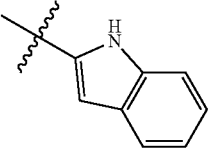 [SMILES: *c1cc2ccccc2[nH]1] | 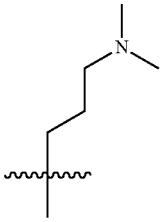 [SMILES: *CCCN(C)C] | H |
| 117 | 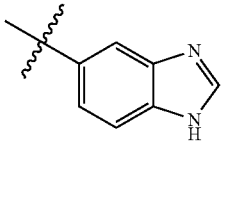 [SMILES: *c1ccc2[nH]cnc2c1] | 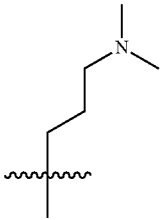 [SMILES: *CCCN(C)C] | H |
| 129 | 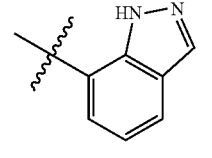 [SMILES: *c1cccc2cn[nH]c12] | 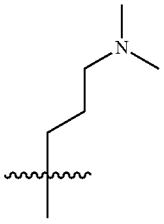 [SMILES: *CCCN(C)C] | H |
| 152 | 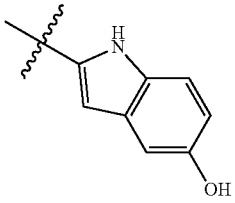 [SMILES: *c1cc2cc(O)ccc2[nH]1] | 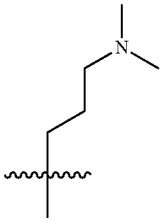 [SMILES: *CCCN(C)C] | H |
| 123 | 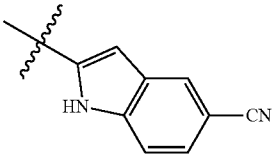 [SMILES: *c1cc2cc(C#N)ccc2[nH]1] | 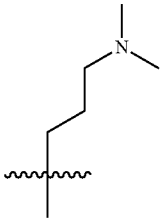 [SMILES: *CCCN(C)C] | H |
| 198 | 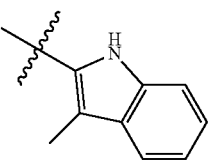 [SMILES: *c1[nH]c2ccccc2c1C] | 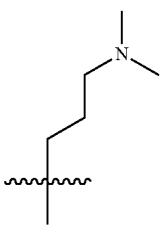 [SMILES: *CCCN(C)C] | H |

TABLE IV-continued
| Cmpd # | R³ | R¹ | R⁶ |
|---|---|---|---|
| 186 | 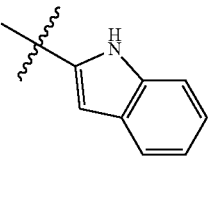 [SMILES: *c1cc2ccccc2[nH]1] | 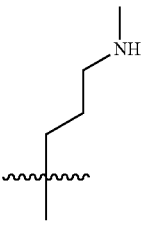 [SMILES: *CCCNC] | H |
| 197 | 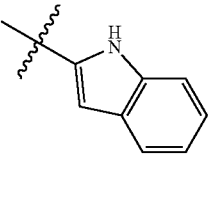 [SMILES: *c1cc2ccccc2[nH]1] | 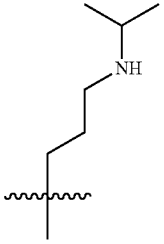 [SMILES: *CCCNC(C)C] | H |
| 241 | 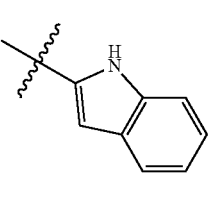 | 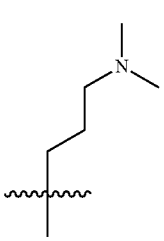 [SMILES: *CCCN(C)C] | NO₂ |
| 222 | 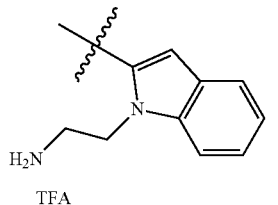 [SMILES: *c1cc2ccccc2n1CCN] | 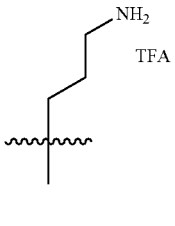 [SMILES: *CCCN] TFA | H |
| 245 | 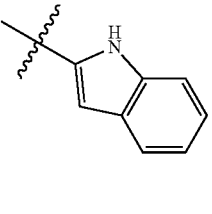 [SMILES: *c1cc2ccccc2[nH]1] | 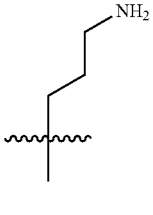 [SMILES: *CCCN] | CF₃ |
| 254 | 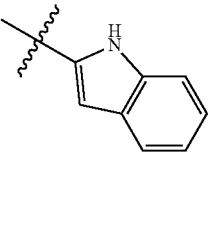 [SMILES: *c1cc2ccccc2[nH]1] | 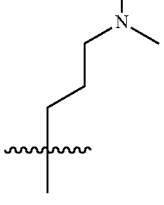 | OMe |
| Cmpd # | R³ | R¹ | R⁶ |
|---|---|---|---|
| 258 | 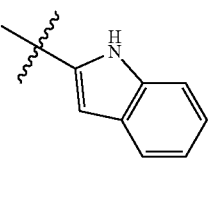 [SMILES: *c1cc2ccccc2[nH]1] | 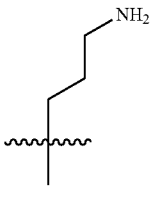 [SMILES: *CCCN] | 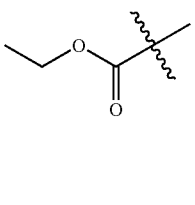 |

TABLE IV-continued
| 262 | 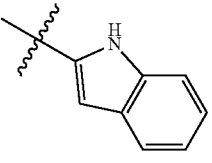 [SMILES: *c1cc2ccccc2[nH]1] | 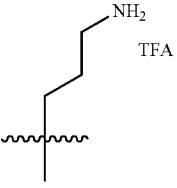 [SMILES: *CCCN] TFA | 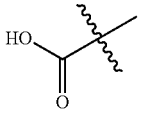 |
| --- | --- | --- | --- |
| 265 | CF3 | 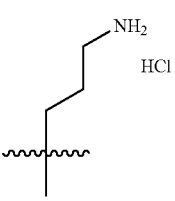 [SMILES: *CCCN ; Cl] HCl | 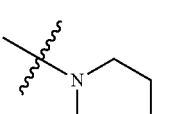 |
| 266 | CF3 | 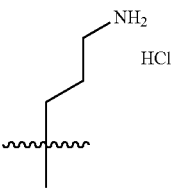 [SMILES: *CCCN ; Cl] HCl | 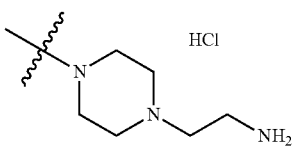 [SMILES: Cl ; *N1CCN(CCN)CC1] HCl |
| 278 | 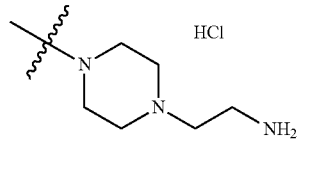 HCl | 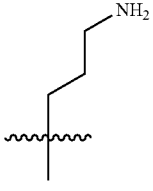 [SMILES: *CCCN] | Br |
| 271 | 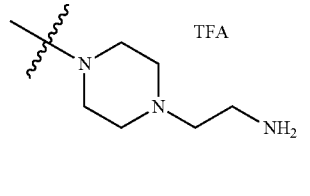 [SMILES: *N1CCN(CCN)CC1] TFA | 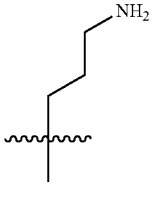 [SMILES: *CCCN] | 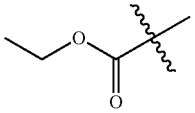 [SMILES: *C(=O)OCC] |
| 275 | 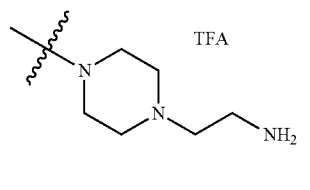 [SMILES: *N1CCN(CCN)CC1] TFA | 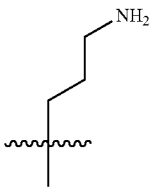 [SMILES: *CCCN] | 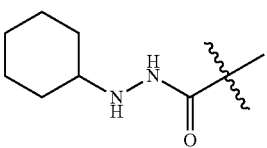 [SMILES: *C(=O)NNC1CCCCC1] |
| 276 | Br | 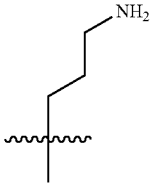 [SMILES: *CCCN] | 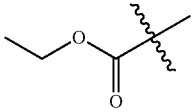 [SMILES: *C(=O)OCC] |

TABLE IV-continued

| | | | |
|---|---|---|---|
| 277 | 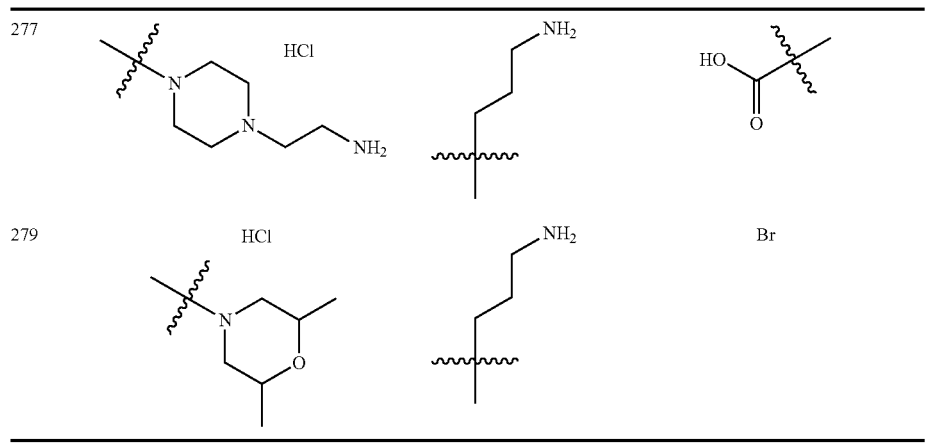 | | |
| 279 | | | |

Figure 5:
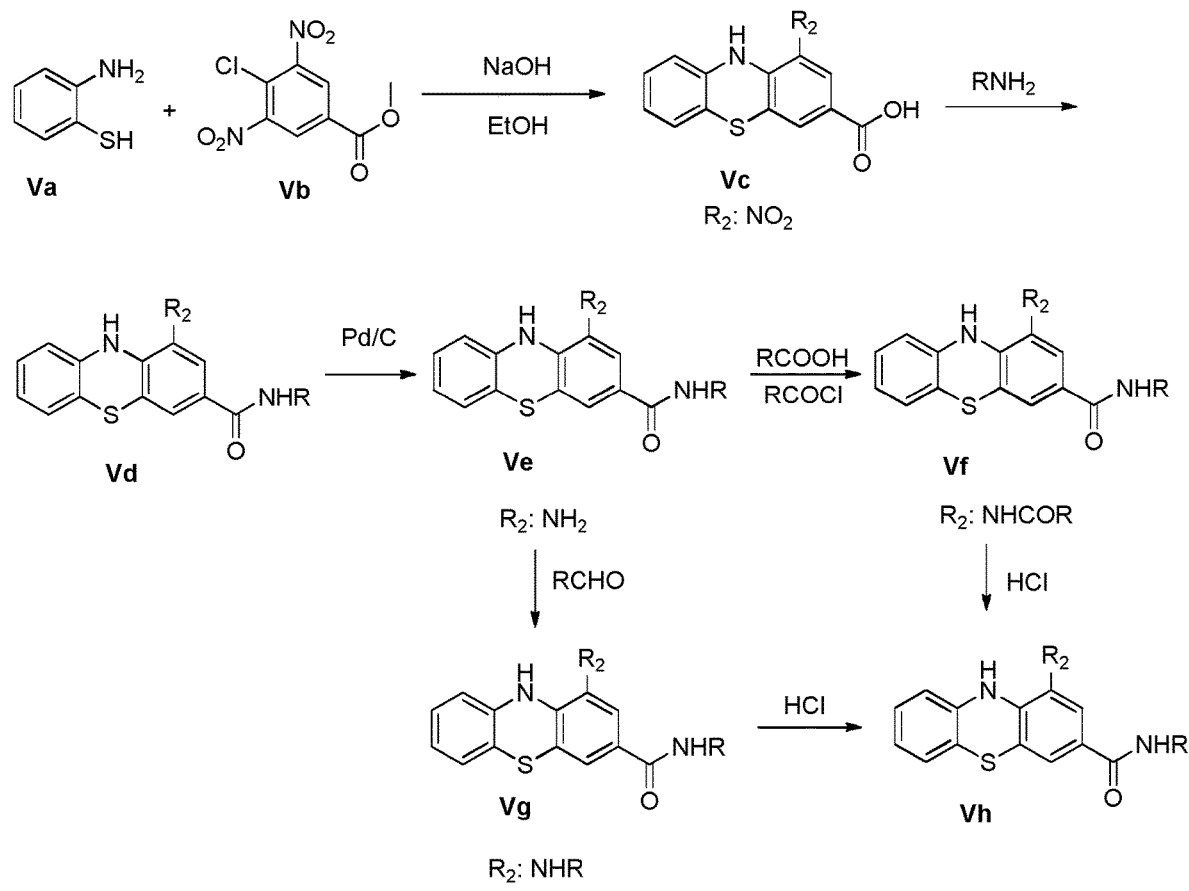
FIG. 5 shows general synthetic scheme V for the synthesis of selected compounds according to the present invention.

FIG. 5 shows general synthetic scheme V for the synthesis of selected 1,3-disubstituted phenothiazenes. Nucleophilic substitution of 2-aminothiophenol (Va) with aryl halides (Yb) followed by insituSmiles rearrangement using NaOH gives 1,3-disubstituted phenothiazene (Vc). Acid-amine coupling of compound Vc with distinct amines resulted in the corresponding amides Vd. Reducing the $NO_2$ group of Vd using Pd/C resulted in the corresponding amine compound Ye. Amide formation of compound Ye using corresponding acids or acid chlorides followed by deprotection of amine group resulted in title compounds Vh. Parallel, reductive amination of compound Ye with carbonyl compound followed by deprotection resulted in title compound Yh.

Some examples of compounds synthesised by the method of Scheme V are listed in Table V.

TABLE V

| Cmpd # | $R^3$ = CONH—R | $R^2$ |
|---|---|---|
| 210 | $NH_2$ | 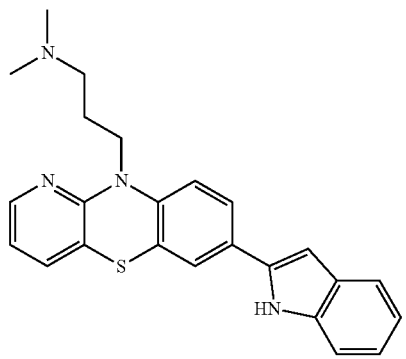 |
| 94 | 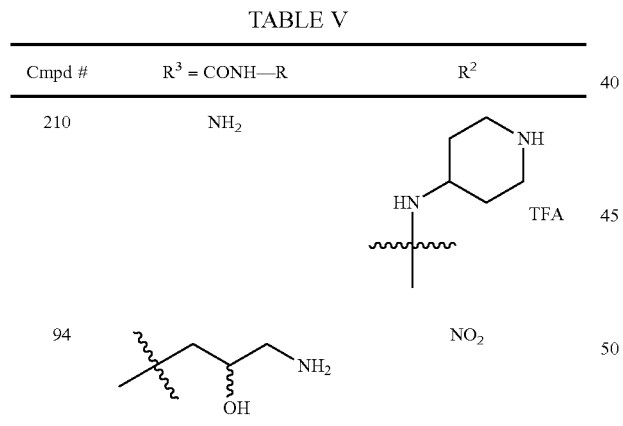 | $NO_2$ |

Figure 6:
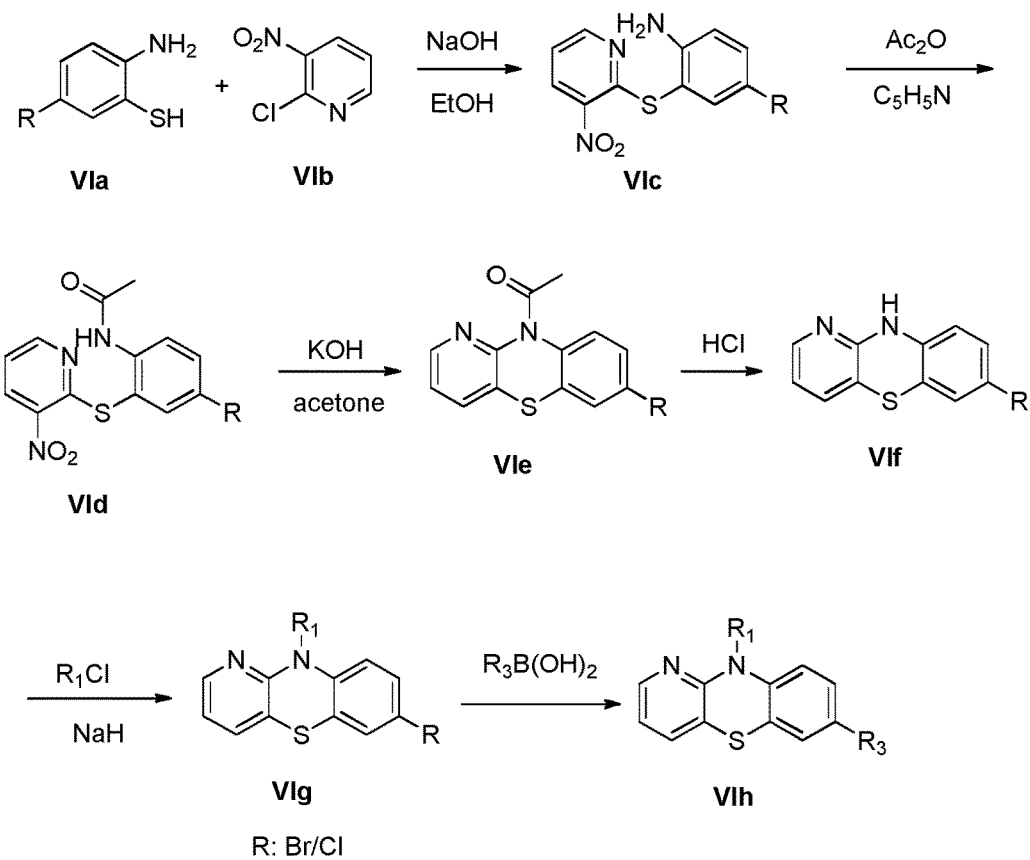
FIG. 6 shows general synthetic scheme VI for the synthesis of selected compounds according to the present invention.

FIG. 6 shows general synthetic scheme VI for the synthesis of selected 3, N-10-Disubstituted azaphenothiazenes. Nucleophilic substitution of substituted amino thiophenols (VIa) with 2-chloro-3-nitro pyridine (VIb) gives compound VIc. Acetylation followed by Smiles rearrangement of VIe yielded compound VIe. Deprotection of compound VIe using HCl gives 3-haloazaphenothiazenes VIf. Alkylation of compound VIf using alkyl chlorides/NaH followed by Suzuki coupling with arylboronic acid resulted title compounds VIh.

A detailed synthetic description of a compound synthesised by the method of Scheme VI is provided below.

Compound 135: 3-(7-(1H-Indol-2-yl)-10H-benzo[b]pyrido[2,3-e][1,4]thiazin-10-yl)-N,N-dimethylpropan-1-amine Step 1: 4-Bromo-2-((3-nitropyridin-2-yl)thio)aniline

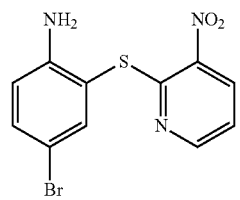 [SMILES: Nc1ccc(Br)cc1Sc1ncccc1[N+](=O)[O-]]

To a stirred solution of 4-bromo-2 amino-benzenethiol (2.0 g, 9.8 mmol) and 2-chloro3-nitro-pyridine (2.0 g, 12.7 mmol) in ethanol was added sodium hydroxide (1.2 g, 29.4 mmol) at r.t. and stirring continued at r.t for 4 h. Reaction mixture was filtered, solid was washed with DM water, and dried completely to offered the desired product as yellow solid (1.3 g, 42%): NMR (DMSO-$d_6$, 400 MHz) δ 5.55 (s, 2H), 6.68 (d, J=8.8 Hz, 1H) 7.27 (d, J=1.6 Hz, 1H), 7.29-7.42 (m, 2H), 8.59 (d, J=8.0 Hz, 2H); MS (ESI) m/z 326 (M+H)⁺.

Step 2: N-(4-Bromo-2-((3-nitropyridin-2-yl)thio)phenyl)acetamide

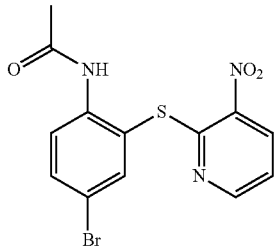 [SMILES: CC(=O)Nc1ccc(Br)cc1Sc1ncccc1[N+](=O)[O-]]

To a stirred solution of 4-bromo-2-((3-nitropyridin-2-yl)thio)aniline (1.8 g, 5.52 mmol) in pyridine (5 mL) was added acetic anhydride (2.8 mL, 27.6 mmol) at 0° C., and stirring continued at r.t for 3 h. Reaction mixture was concentrated, diluted with DM water (100 mL), extracted with EtOAc, dried the organic layer over sodium sulphate, and concentrated. Product was washed with ether to get the title compound as pale yellow solid (2 g, 97%): MS (ESI) m/z 368 (M+H)$^+$.

Step 3: 7-Bromo-10H-benzo[b]pyrido[2,3-e][1,4]thiazine

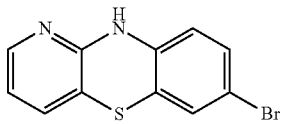 [SMILES: Brc1ccc2c(c1)Sc1cccnc1N2]

To a stirred solution of N-(4-bromo-2-((3-nitropyridin-2-yl)thio)phenyl)acetamide (2.0 g, 5.43 mmol) in acetone (40 mL) was added KOH (0.9 g, 16.3 mmol) and the reaction mixture was heated at 60° C. for 16 h. The reaction mixture was cooled to room temperature, concentrated, and the residue was purified by column chromatography over silica gel using 30% ethyl acetate/hexane mixture as eluant to give the title compound as an dark solid (1.4 g, 82%): MS (ESI) m/z 279 (M+H)$^+$.

Step 4: 3-(7-Bromo-10H-benzo[b]pyrido[2,3-e][1,4]thiazin-10-yl)-N,N-dimethylpropan-1-amine

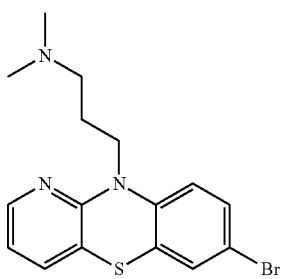 [SMILES: CN(C)CCCN1c2ccc(Br)cc2Sc2cccnc21]

To a stirred solution of sodium hydride (0.350 g, 7.16 mmol) in DMF (10 mL) at 0° C. was added a solution of 7-bromo-10H-benzo[b]pyrido[2,3-e][1,4]thiazine (1.0 g, 3.58 mmol) in DMF and stirring was continued for 20 min. To the reaction mixture 3-chloro-N,N-dimethylpropan-1-amine hydrochloride (0.1.12 g, 7.16 mmol) was added and the reaction mixture was heated at 65° C. for 16 h. The reaction mixture was cooled to room temperature, concentrated, and the residue was purified by column chromatography over silica gel using 5% methanol/dichloromethane mixture as eluant to afford title compound as gummy material (0.55 g, 45%): MS (ESI) m/z 364 (M+H)$^+$.

Step 5: Tert-butyl 2-(10-(3-(dimethylamino)propyl)-10H-benzo[b]pyrido[2,3-e][1,4]thiazin-7-yl)-1H-indole-1-carboxylate

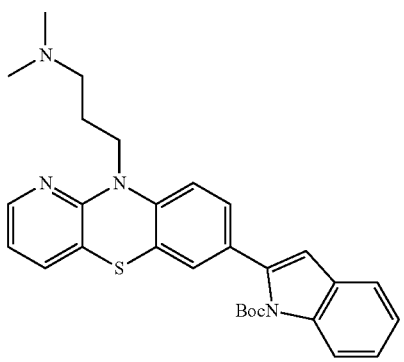 [SMILES: CN(C)CCCN1c2ccc(-c3cc4ccccc4n3C(=O)OC(C)(C)C)cc2Sc2cccnc21]

To a solution of 3-(7-bromo-10H-benzo[b]pyrido[2,3-e][1,4]thiazin-10-yl)-N,N-dimethylpropan-1-amine (0.30 g, 0.824 mmol) in DME/Water (6/2 mL) is added potassium carbonate (0.220 g, 1.64 mmol) and (1-(tert-butoxycarbonyl) 1H-indol-2-yl)boronic acid (0.320 g, 0.1.23 mmol) and purged with nitrogen for 10 min. followed by added bis(triphenylphosphine)palladium(II) dichloride (0.057 g, 0.082 mmol). Reaction mixture was again purged with nitrogen for 10 mins and refluxed for 12 h. The reaction mixture was filtered through diatomaceous earth. The filtrate is dried over sodium sulphate and concentrated. The crude product was purified on silica column using 5% methanol in dichloromethane as eluant to afford the title compound as gummy material (0.120 g, 30%): $^1$H NMR (DMSO-d$_6$, 400 MHz) δ 1.16 (s, 4H), 1.28 (s, 9H), 1.80-1.87 (m, 2H), 2.23 (s, 5H), 2.31-2.49 (m, 2H), 4.03-4.12 (m, 2H), 6.70 (s, 1H), 6.86-6.89 (m, 2H), 7.08 (d, J=8.8 Hz, 1H), 7.17 (d, J=2.0 Hz, 1H), 7.23-7.32 (m, 3H), 7.43-7.45 (m, 1H), 7.57 (d, J=7.2 Hz, 1H), 8.02-8.07 (m, 2H); MS (ESI) m/z 501 (M+H)$^+$.

Step 6: 3-(7-(1H-Indol-2-yl)-10H-benzo[b]pyrido[2,3-e][1,4]thiazin-10-yl)-N,N-dimethylpropan-1-amine

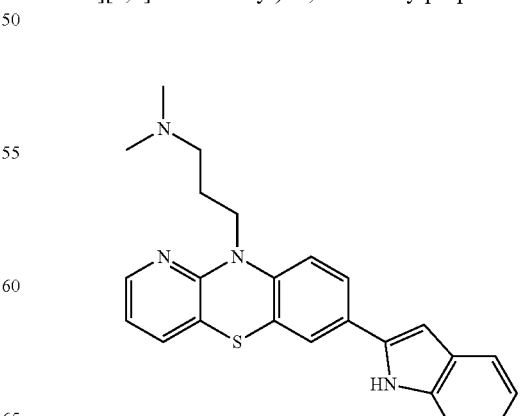

To a solution of tert-butyl 2-(10-(3-(dimethylamino)propyl)-10H-benzo[b]pyrido[2,3-e][1,4]thiazin-7-yl)-1H-indole-1-carboxylate (0.3 g, 0.599 mmol) in dichloromethane (10 mL) is added 4N HCl in dioxane (1.0 mL) and reaction mixture was stirred for 4 h at room temperature. Reaction mixture was basified with solid NaHCO$_3$, extracted with dichloromethane, organic layer is washed with saturated NaHCO$_3$ solution, dried over sodium sulphate, and concentrated. The crude product was purified by silica gel column chromatography using 10% methanol in dichloromethane as eluant to afford the title compound as brown solid (0.040 g, 44%): $^1$H NMR (DMSO-d$_6$, 400 MHz) δ0.84 (bs, H), 1.22 (s, 2H), 1.85-1.89 (m, 2H), 2.18 (s, 6H), 2.31-2.49 (m, 2H), 4.08 (t, J=7.2 Hz, 2H), 6.81 (s, 1H), 6.86-6.89 (m, 1H), 6.96 (t, J=7.6 Hz, 1H), 7.04-7.12 (m, 2H), 7.35 (d, J=8.4 Hz, 1H), 7.47 (t, J=8.0 Hz, 2H), 7.58 (s, 1H), 7.65 (d, J=8.8 Hz, 1H), 8.02 (d, J=3.6 Hz, 1H), 11.39 (s, 1H); MS (ESI) m/z 401.2 (M+H)$^-$; HPLC purity: 99.2%.

Some examples of compounds synthesised by the method of Scheme VI are listed in Table VI.

| Cmpd # | R$^1$ | R$^3$ |
|---|---|---|
| 126 | 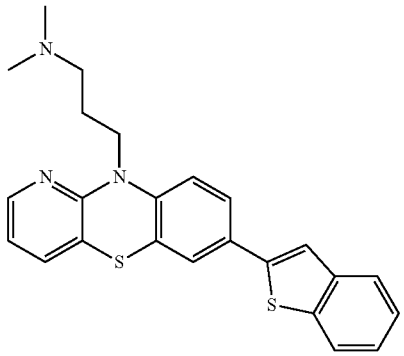 | Cl |
| 135 | | |

Figure 7:
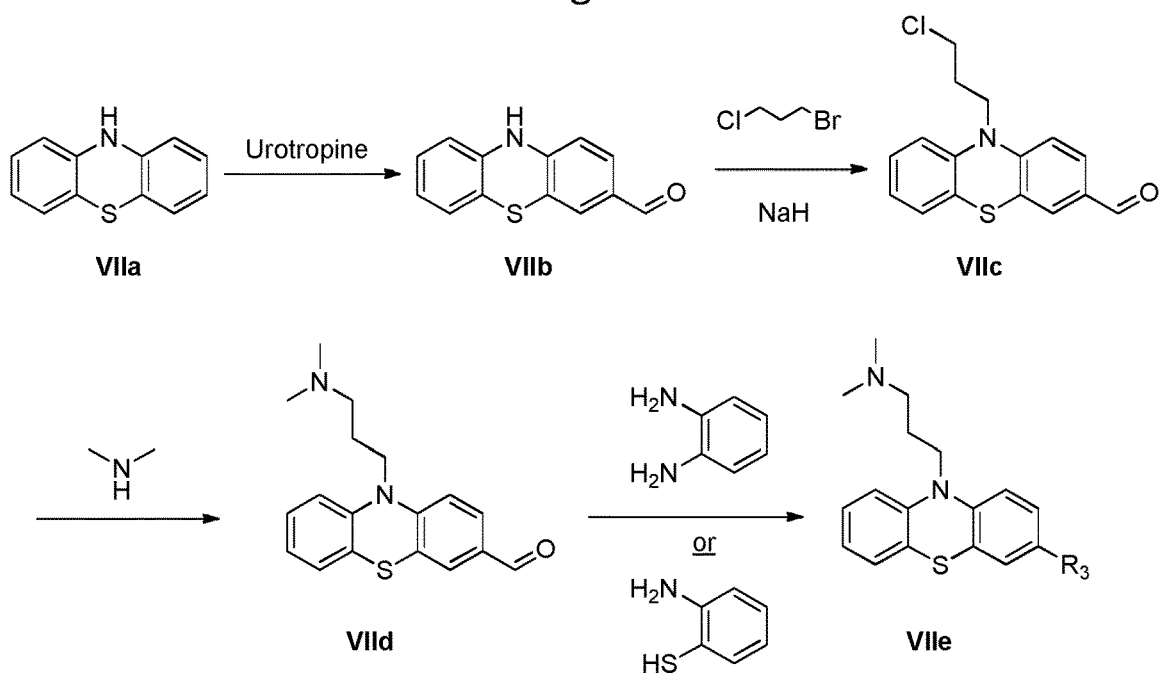
FIG. 7 shows general synthetic scheme VII for the synthesis of selected compounds according to the present invention.

FIG. 7 shows general synthetic scheme VII for the synthesis of selected 3. N-10-disubstituted phenothiazenes. Formylation of phenothiazene (VIIa) at C-3 position using urotropine yielded 3-formyl phenothiazene (VIIb). N-10 Alkylation of compound VIIb with alkyl bromide using NaH gives compound VIIc. Reaction of compound VIIc with amine resulted in compound VIId, which is further reacted with aryl diamine or aryl aminothiol to yield title compounds VIIe.

A detailed synthetic description of a compound synthesised by the method of Scheme VII is provided below.

Compound 143: 3-(3-(Benzo[d]thiazol-2-yl)-10H-phenothiazin-10-yl)-N,N-dimethylpropan-1-amine Step 1: 10H-Phenothiazine-3-carbaldehyde

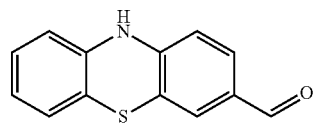 [SMILES: O=Cc1ccc2c(c1)Sc1ccccc1N2]

To a solution of 10H-phenothiazine (3.0 g, 15.06 mmol) in acetic acid (25 mL) was added hexamethylenetetramine (3.15 g, 22.59 mmol) in a microwave vial and subjected to microwave irradiation. Reaction mixture was poured into water, neutralized with Na$_2$CO$_3$, extracted with EtOAc. Organic layer was dried over sodium sulphate and concentrated. The crude product was purified by biotage purifier with 40% ethyl acetate in hexane as eluent to afford the desired product as a yellow solid (0.33 g, 10%): $^1$H NMR (CDCl$_3$, 400 MHz) δ 6.07 (s, 1H), 6.52-6.57 (m, 2H), 6.84-6.88 (m, 1H), 6.94 (4, J=7.6 Hz, 1H), 6.99 (t, J=7.6 Hz, 1H), 7.44 (s, 1H), 7.47 (d, J=8.0 Hz, 1H), 9.71 (s, 1H); MS (ESI) m/z 228 (M+H)$^+$.

Step 2: 10-(3-Chloropropyl)-10H-phenothiazine-3-carbaldehyde

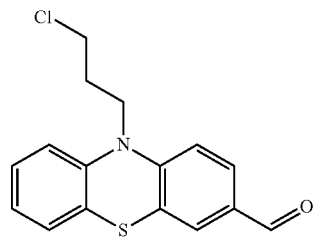 [SMILES: O=Cc1ccc2c(c1)Sc1ccccc1N2CCCCl]

To a solution of NaH (0.078 g, 1.95 mmol) in N,N-dimethyl formamide (8.0 mL) was added 10H-phenothiazine-3-carbaldehyde (0.3 g, 1.31 mmol) at 0° C. and reaction mixture was stirred for 0.5 h at room temperature. To the reaction mixture was added 1-bromo-3-chloro-propane (0.247 g, 1.57 mmol) at 0° C. and stirring continued at room temperature for 3 h. The reaction mixture was quenched with ice and extracted with EtOAc. Organic layer was washed with water, saturated NaHCO$_3$ solution, brine, dried over sodium sulphate, and concentrated. The crude product was purified by biotage purifier with 3% ethyl acetate in hexane as eluent to afford the title compound as a viscous liquid (0.15 g, 40%): $^1$H NMR (DMSO-d$_6$, 400 MHz) δ 1.11-1.14 (m, 2H), 3.72-3.75 (m, 2H), 4.10-4.13 (m, 2H), 7.02 (t, J=7.6 Hz, 1H), 7.14 (d, J=7.6 Hz, 1H), 7.19 (d, J=7.6 Hz, 1H), 7.24 (t, J=8.0 Hz, 2H), 7.62 (s, 1H), 7.73 (d, J=8.4 Hz, 1H), 9.79 (s, 1H); MS (ESI) m/z 304 (M+H)$^+$.

Step 3: 10-(3-(Dimethylamino)propyl)-10H-phenothiazine-3-carbaldehyde

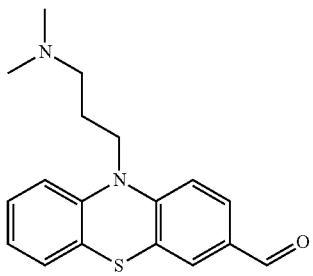 [SMILES: CN(C)CCCN1c2ccccc2Sc2cc(C=O)ccc21]

To a stirred solution of 10-(3-chloropropyl)-10H-phenothiazine-3-carbaldehyde (0.15 g, 0.495 mmol) in DMF (7.0 mL) were added potassium phosphate (0.314 g, 1.48 mmol), 2M solution of dimethylamine (0.5 mL, 0.990 mmol) and the reaction mixture was heated at 80° C. for 12 h. The reaction mixture was quenched with ice and extracted with EtOAc. Organic layer was washed with water, saturated NaHCO$_3$ solution, brine, dried over sodium sulphate, and concentrated. The crude product was purified by biotage purifier with 7% methanol in dichloromethane as eluent to afford the title compound as a viscous liquid (0.1 g, 67%): $^1$H NMR (DMSO-d$_6$, 400 MHz) δ 1.79 (t, J=7.2 Hz, 2H), 2.08 (s, 6H), 2.31 (t, J=6.4 Hz, 2H), 3.98 (t, J=6.8 Hz, 2H), 6.99 (t, J=8.0 Hz, 1H), 7.09 (d, J=8.0 Hz, 1H), 7.15-7.24 (m, 3H), 7.59 (d, J=1.6 Hz, 1H), 7.71 (dd, J=8.4 Hz, 1.6 Hz, 1H), 9.78 (s, 1H); MS (ESI) m/z 313 (M+H)$^+$.

Step 4: 3-(3-(Benzo[d]thiazol-2-yl)-10H-phenothiazin-10-yl)-N,N-dimethylpropan-1-amine

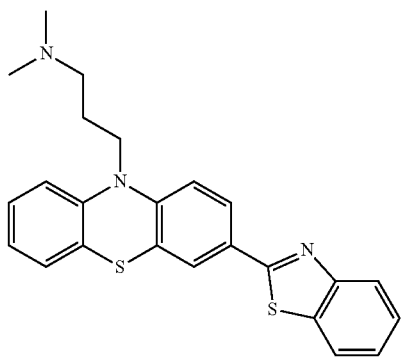 [SMILES: CN(C)CCCN1c2ccccc2Sc2cc(-c3nc4ccccc4s3)ccc21]

A solution of 10-(3-(dimethylamino)propyl)-10H-phenothiazine-3-carbaldehyde (0.05 g, 0.16 mmol) and 2-amino-benzenethiol (0.024 g, 0.192 mmol) in DMSO (5.0 mL) was heated at 150° C. for 12 h. The reaction mixture is quenched with ice, and extracted with EtOAc. Organic layer was washed with water, saturated NaHCO$_3$ solution, brine, dried over sodium sulphate, and concentrated. The crude product was purified by biotage purifier with 7% methanol in dichloromethane as eluent to afford the title compound as a green solid (0.012 g, 18%): $^1$H NMR (DMSO-d$_6$, 400 MHz) δ 1.78-1.85 (m, 2H), 2.08 (s, 6H), 2.32 (t, J=7.2 Hz, 21H), 3.97 (t, J=6.8 Hz, 2H), 6.98 (t, J=7.6 Hz, 1H), 7.08 (d, J=8.0 Hz, 1H), 7.16-7.18 (m, 2H), 7.23 (t, J=7.6 Hz, 1H), 7.42 (t, J=7.6 Hz, 1H), 7.51 (d, J=7.2 Hz, 1H), 7.79 (d, J=2.4 Hz, 1H), 7.87-7.89 (m, 1H), 7.99 (d, J=8.0 Hz, 1H), 8.09 (d, J=8.0 Hz, 2H); MS (ESI) m/z 418 (M+H)$^+$; HPLC purity: 99.38%.

Some examples of compounds synthesised by the method of Scheme VII are provided in Table VII.

| Cmpd # | R$^3$ |
|---|---|
| 137 | ![benzimidazole] |
| 143 | ![benzothiazole] |

Figure 8:
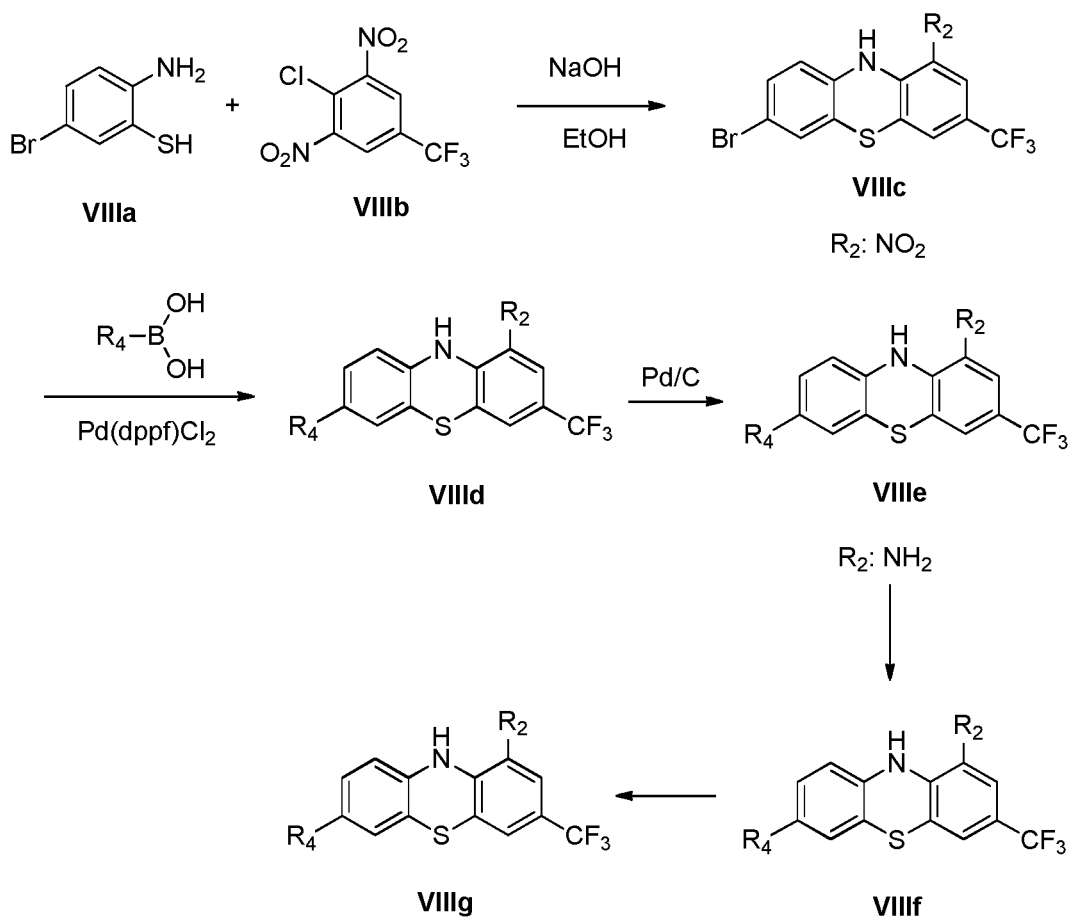
FIG. 8 shows general synthetic scheme VIII for the synthesis of selected compounds according to the present invention.

FIG. 8 shows general synthetic scheme VIII for the synthesis of selected 1,3,7-trisubstituted phenothiazenes. Neucleophilic substitution of substituted arylamino thiol (VIIIa) with aryl halide (VIIIb) followed by insituSmiles rearrangement gave trisubstituted phenothiazines (VIIIc). Suzuki coupling of VIIIc with arylboronic acid followed by reduction of nitro group with Pd/C gives compound VIIIe. Reductive amination of VIIIe with cyclic ketones followed by deprotection using HCl gave title compounds VIIIg.

Detailed synthetic descriptions of some compounds synthesised by the method of Scheme VIII are provided below.

Compound 212: 7-(1H-indol-2-yl)-N-(piperidin-4-yl)-3-(trifluoromethyl)-10H-phenothiazin-1-amine trifluoroacetic Acid Salt

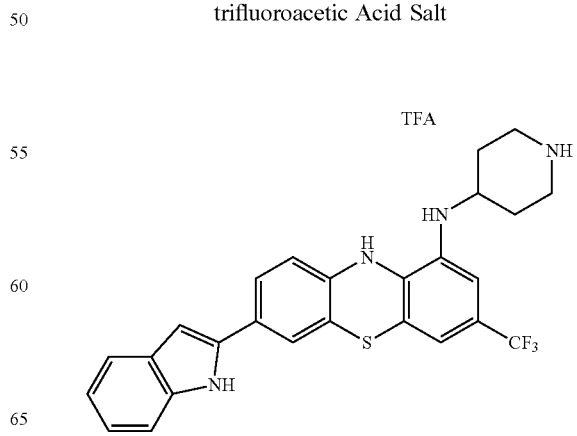

Step 1: 7-Bromo-1-nitro-3-(trifluoromethyl)-10H-phenothiazine

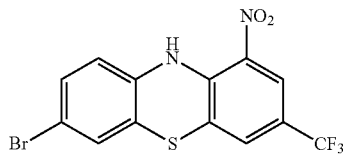

To a stirred solution of 2-amino-5-bromobenzenethiol (0.9 g, 4.411 mmol) in ethanol (30 mL) was added 2-chloro-1,3-dinitro-5-(trifluoromethyl)benzene (1.07 g, 3.369 mmol) and stirred for 20 min. To the reaction mixture was added sodium hydroxide (0.52 g, 13.233 mmol) at 0° C. and was stirred for 16 h. The reaction mixture was filtered and dried under vacuum to give the title compound as a black colour solid (0.9 g, 52%): $^1$H NMR (DMSO-$d_6$, 400 MHz) δ 7.05 (d, J=8.4 Hz, 1H), 7.27-7.24 (m, 1H), 7.30 (d, J=2 Hz, 1H), 7.67 (s, 1H), 8.0 (s, 1H); MS (ESI) m/z 389.0 (M−H)$^+$.

Step 2: 7-(1H-Indol-2-yl)-1-nitro-3-(trifluoromethyl)-10H-phenothiazine

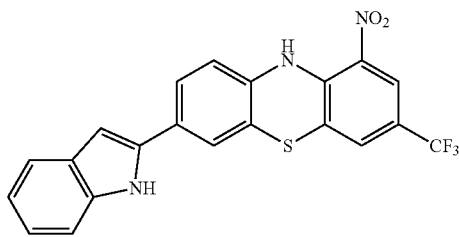

To a stirred solution of 7-bromo-1-nitro-3-(trifluoromethyl)-10H-phenothiazine (0.7 g, 1.789 mmol)) in 1,4-dioxane/water (2:1) were added (1-(tert-butoxycarbonyl)-1H-indol-2-yl)boronic acid (0.7 g, 2.684 mmol) and potassium carbonate (0.74 g, 5.367 mmol) and the reaction mixture was purged with argon gas for 15 min. To the reaction mixture Pd(dppf)Cl$_2$.DCM (0.073 g, 0.0894 mmol) was added and was stirred at 100° C. for 12 h in seal tube. The reaction mixture was washed with water, extracted with ethyl acetate, the combined organic phase was dried over Na$_2$SO$_4$, concentrated, and the residue was purified by column chromatography over silica gel using ethyl acetate/hexane (1:2.3) mixture as eluent to give the title compound as a light brown solid (0.15 g, 20%): MS (ESI) m/z 428.1 (M+H)$^+$.

Step 3: 7-(1H-Indol-2-yl)-3-(trifluoromethyl)-10H-phenothiazin-1-amine

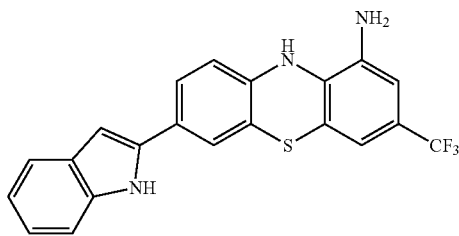

To a stirred solution of 7-(1H-indol-2-yl)-1-nitro-3-(trifluoromethyl)-10H-phenothiazine (0.15 g, 0.351 mmol) in methanol (10 mL) was added 10% Pd/C and stirred for 16 h under hydrogen atmosphere at room temperature. The reaction mixture was filtered, filtrate was concentrated, and the residue was purified by column chromatography over silica gel using ethyl acetate/hexane (1:2.3) mixture as eluent to give the title compound as a light green solid (0.01 g, 7%): $^1$H NMR (DMSO-$d_6$, 400 MHz) δ 5.43 (s, 2H), 6.52 (s, 1H), 6.72 (d, J=5.2 Hz, 2H), 6.88 (d, J=8.4 Hz, 1H), 6.94 (t, J=7.6 Hz, 1H), 7.02 (t, J=7.6 Hz, 1H), 7.31 (d, J=8.0 Hz, 1H), 7.43 (d, J=4H, 1H), 7.45 (s, 1H), 7.49 (d, J=8.4 Hz, 1H), 7.92 (s, 1H), 11.3 (s, 1H); MS (ESI) m/z 398.3 (M+H)$^+$; HPLC purity: 95.09%.

Step 4: Tert-butyl 2-(9-((1-(tert-butoxycarbonyl)piperidin-4-yl)amino)-7-(trifluoromethyl)10H-phenothiazin-3-yl)-1H-indole-1-carboxylate

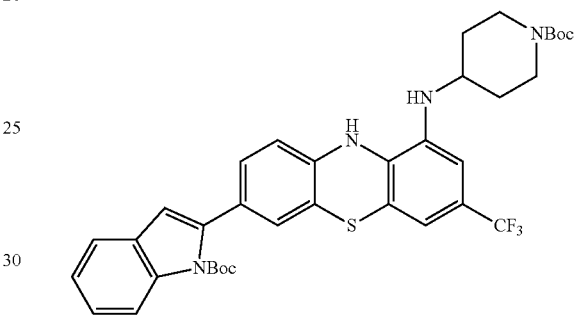

To a stirred solution of 7-(1H-indol-2-yl)-3-(trifluoromethyl)-10H-phenothiazin-1-amine (0.11 g, 0.22 mmol) in MeOH (10 mL) were added tert-butyl 4-oxopiperidine-1-carboxylate (8.4 g, 42.5 mmol), AcOH (0.1 mL), and the reaction mixture was stirred for 2 h at 70° C. The reaction mixture is cooled to room temperature, NaCNBH$_3$ (0.069 g, 1.105 mmol) was added and stirring continued at 70° C. for 12 h. The reaction mixture was evaporated, diluted with aq.NaHCO$_3$ solution, and extracted with DCM. The organic layer was dried over Na$_2$SO$_4$, concentrated, and the residue was purified on silica gel using 10% ethyl acetate in hexane eluant to afford title compound (0.02 g, 16%): MS (ESI) m/z 681 (M+H)$^+$.

Step 5: 7-(1H-Indol-2-yl)-N-(piperidin-4-yl)-3-(trifluoromethyl)-10H-phenothiazin-1-amine trifluoroacetic Acid Salt

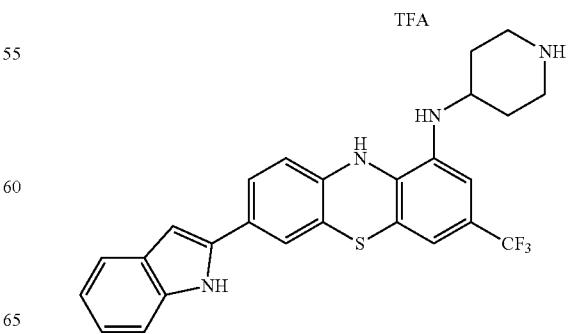

To a stirred solution of tert-butyl 2-(9-((1-(tert-butoxycarbonyl)piperidin-4-yl)amino)-7-(trifluoromethyl)-10H-phenothiazin-3-yl)-1H-indole-1-carboxylate (0.02 g, 0.029 mmol) in dichloromethane (5 mL) at 0° C. was added trifluoroacetic acid (0.5 mL) and stirred for 1 h. The reaction mixture was concentrated, neutralized with sodium bicarbonate solution, extracted with 10% methanol in dichloromethane, the combined organic phase was dried over Na$_2$SO$_4$, concentrated, and the residue was purified by preparative HPLC using 0.01% TFA in water/acetonitrile as eluent to give the title compound as a light black solid (0.004 g, 23%): $^1$H NMR (DMSO-d$_6$, 400 MHz) δ 5.43 (s, 2H), 6.52 (s, 1H), 6.72 (d, J=5.2 Hz, 2H), 6.88 (d, J=8.4 Hz, 1H), 6.94 (t, J=7.6 Hz, 1H), 7.02 (t, J=7.6 Hz, 1H), 7.31 (d, J=8.0 Hz, 1H), 7.43 (d, J=4 Hz, 1H), 7.45 (s, 1H), 7.49 (d, J=8.4 Hz, 1H), 7.92 (s, 1H), 11.3 (s, 1H): MS (ESI) m/z 481 (M, free base+H)$^+$; HPLC purity: 89.9%.

Compound 242: N-(7-(1H-Indol-2-yl)-3-(trifluoromethyl)-10H-phenothiazin-1-yl)-3-aminocyclohexanecarboxamide

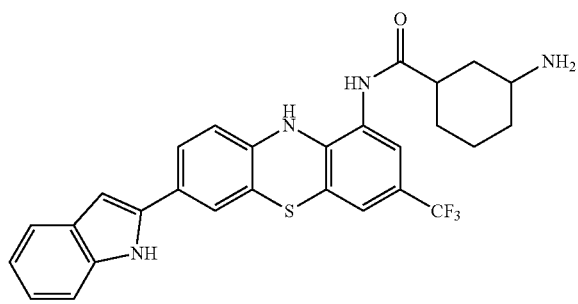 [SMILES: NC1CCCC(C(=O)Nc2cc(C(F)(F)F)cc3c2Nc2ccc(-c4cc5ccccc5[nH]4)cc2S3)C1]

Step 1: 7-Bromo-1-nitro-3-(trifluoromethyl)-10H-phenothiazine

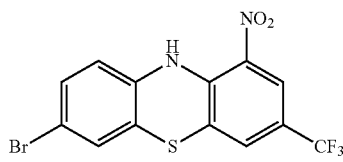 [SMILES: O=[N+]([O-])c1cc(C(F)(F)F)cc2c1Nc1ccc(Br)cc1S2]

To a stirred solution of 2-amino-5-bromobenzenethiol (5 g, 24.50 mmol)) in ethanol (100 mL) was added 2-chloro-1,3-dinitro-5-(trifluoromethyl)benzene (5.95 g, 22.058 mmol) and stirred for 20 min. To the reaction mixture was added sodium hydroxide (2.94 g, 73.527 mmol) at 0° C. and stirred for 16 h at room temperature. The reaction mixture was filtered and dried under vacuum to give the title compound as a black color solid (5 g, 52%): $^1$H NMR (DMSO-d$_6$, 400 MHz) δ 9.83 (s, 1H), 8.01 (s, 1H), 7.67 (s, 1H), 7.30 (d, J=2.4 Hz, 1H), 7.27-7.24 (m, 1H), 7.05 (d, J=8.4 Hz, 1H); MS (ESI) m/z 388.9 (M–H)$^+$.

Step 2: 7-(1H-Indol-2-yl)-1-nitro-3-(trifluoromethyl)-10H-phenothiazine

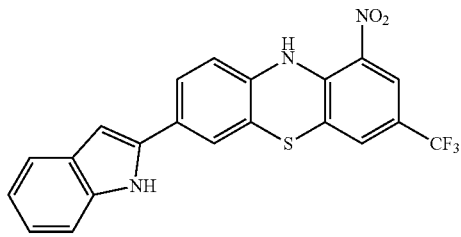 [SMILES: O=[N+]([O-])c1cc(C(F)(F)F)cc2c1Nc1ccc(-c3cc4ccccc4[nH]3)cc1S2]

To a stirred solution of 7-bromo-1-nitro-3-(trifluoromethyl)-10H-phenothiazine (1 g, 2.55 mmol)) in 1,4-dioxane/water (2:1)(15 mL) were added (1-(tert-butoxycarbonyl)-1H-indol-2-yl)boronic acid (1 g, 3.86 mmol) and potassium carbonate (1.05 g, 7.66 mmol) and the reaction mixture was purged with argon gas for 15 min. To the reaction mixture was added Pd(dppf)Cl$_2$.CH$_2$Cl$_2$ (0.1 g, 0.12 mmol) and stirring continued at 100° C. for 12 h in a seal tube. The reaction mixture was washed with water, extracted with ethyl acetate, the combined organic phase was dried over Na$_2$SO$_4$, concentrated, and the residue was purified by column chromatography over silica gel using ethyl acetate/hexane mixture as eluent to give the title compound as a block color solid (0.25 g, 23%): MS (ESI) m/z 426.0 (M–H)$^+$.

Step 3: 7-(1H-Indol-2-yl)-3-(trifluoromethyl)-10H-phenothiazin-1-amine

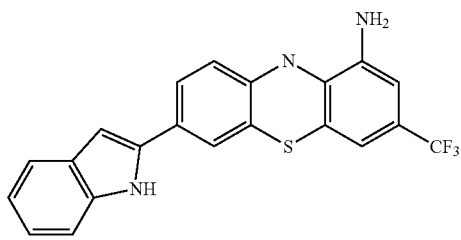 [SMILES: Nc1cc(C(F)(F)F)cc2c1Nc1ccc(-c3cc4ccccc4[nH]3)cc1S2]

To a stirred solution of 7-(1H-indol-2-yl)-1-nitro-3-(trifluoromethyl)-10H-phenothiazine (0.25 g, 0.351 mmol) in methanol (10 mL) was added 10% Pd/C and stirred for 3 h under hydrogen atmosphere at room temperature. The reaction mixture was filtered, concentrated, and the residue was purified by column chromatography over silica gel using ethyl acetate/hexane (1:2.3) mixture as eluent to give the title compound as a light green solid (0.07 g, 30%): $^1$H NMR (DMSO-d$_6$, 400 MHz) δ 5.43 (s, 2H), 6.52 (s, 1H), 6.72 (d, J=4.8 Hz, 2H), 6.88 (d, J=8.4 Hz, 1H), 6.94 (t, J=7.2 Hz, 1H), 7.02 (t, J=7.2 Hz, 1H), 7.31 (d, J=8.0 Hz, 1H), 7.48-7.42 (m, 2H), 7.50 (d, J=1.5 Hz, 1H), 7.92 (s, 1H), 11.3 (s, 1H); MS (ESI) m/z 398.0 (M+H)$^+$.

Step 4: Tert-butyl (3-((7-(1H-indol-2-yl)-3-(trifluoromethyl)-10H-phenothiazin-1-yl)carbamoyl)cyclohexyl)carbamate

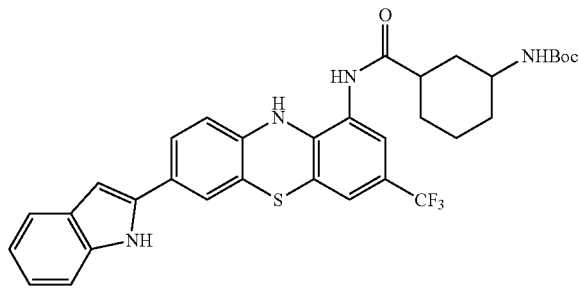 [SMILES: CC(C)(C)OC(=O)NC1CCCC(C(=O)Nc2cc(C(F)(F)F)cc3c2Nc2ccc(-c4cc5ccccc5[nH]4)cc2S3)C1]

To a stirred solution of 7-(1H-indol-2-yl)-3-(trifluoromethyl)-10H-phenothiazin-1-amine (0.07 g, 0.176 mmol)) in pyridine (3 mL) were added POCl₃ (0.5 mL) and 3-((tert-butoxycarbonyl)amino)cyclohexanecarboxylic acid (0.064 g, 0.264 mmol) and stirring continued for 2 h at room temperature. The reaction mixture was washed with water, extracted with ethyl acetate, the combined organic phase was dried over Na₂SO₄, concentrated, and the residue was purified by column chromatography over silica gel using ethyl acetate/hexane mixture as eluent to give the title compound as a light brown solid (0.02 g, 22%): MS (ESI) m/z 624 (M+H)⁺.

Step 5: N-(7-(1H-Indol-2-yl)-3-(trifluoromethyl)-10H-phenothiazin-1-yl)-3-aminocyclohexanecarboxamide

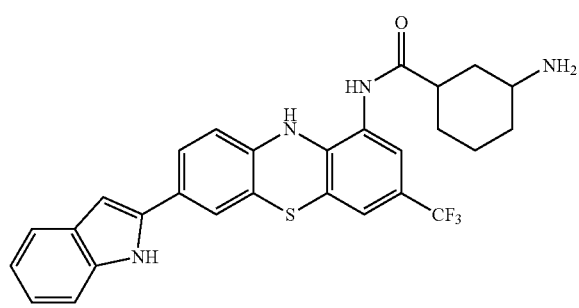 [SMILES: NC1CCCC(C(=O)Nc2cc(C(F)(F)F)cc3c2Nc2ccc(-c4cc5ccccc5[nH]4)cc2S3)C1]

To a stirred solution of tert-butyl (3-((7-(1H-indol-2-yl)-3-(trifluoromethyl)-10H-phenothiazin-1-yl)carbamoyl)cyclohexyl)carbamate (0.02 g, 0.0321 mmol)) in DCM (5 mL) was added trifluoro acetic acid (0.5 ml) at 0° C. and stirring continued for 2 h at room temperature. The reaction mixture concentrated, basified with sodium bicarbonate solution, extracted with ethyl acetate, the combined organic phase was dried over Na₂SO₄, concentrated, and the residue was recrystallised by using n-pentane-diethylether to give the title compound as a light green solid (0.001 g, 63%): ¹H NMR (DMSO-d₆, 400 MHz) δ 1.21 (s, 2H), 1.75 (s, 4H), 1.87 (s, 2H), 1.98 (s, 2H), 6.75 (s, 1H), 6.94 (t, J=7.2 Hz, 1H), 6.95 (d, J=7.6 Hz, 2H), 7.05-7.02 (m, 1H), 7.48-7.42 (m, 2H), 7.16 (s, 1H), 7.32 (d, J=8 Hz, 1H), 7.36 (s, 1H), 7.45 (d, J=8 Hz, 2H), 7.52 (d, J=8.4 Hz, 1H), 8.09 (s, 1H), 11.33 (s, 1H); MS (ESI) m/z 523.2 (M+H)⁺; HPLC Purity; 98.42%.

Some examples of compounds synthesised by the method of Scheme VIII are provided in Table VIII.

TABLE VIII

| Cmpd # | R⁴ | R² |
|---|---|---|
| 205 | indol-2-yl | NH₂ |
| 242 | indol-2-yl | cyclohexanecarboxamide |
| 212 | indol-2-yl | piperidin-4-ylamine · TFA |
| 243 | indol-2-yl | piperidin-4-ylamine |

Figure 9:
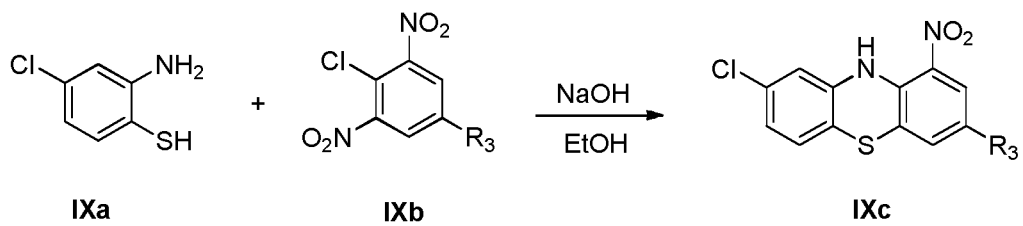
FIG. 9 shows general synthetic scheme IX for the synthesis of selected compounds according to the present invention.

FIG. 9 shows general synthetic scheme IX for the synthesis of selected 1,3,8-trisubstituted phenothiazenes. Nucleophilic substitution reaction of substituted 2-amino thiophenol (IXa) with aryl halides (IXb) followed by insituSmiles rearrangement gave title compounds IXc.

Figure 10:
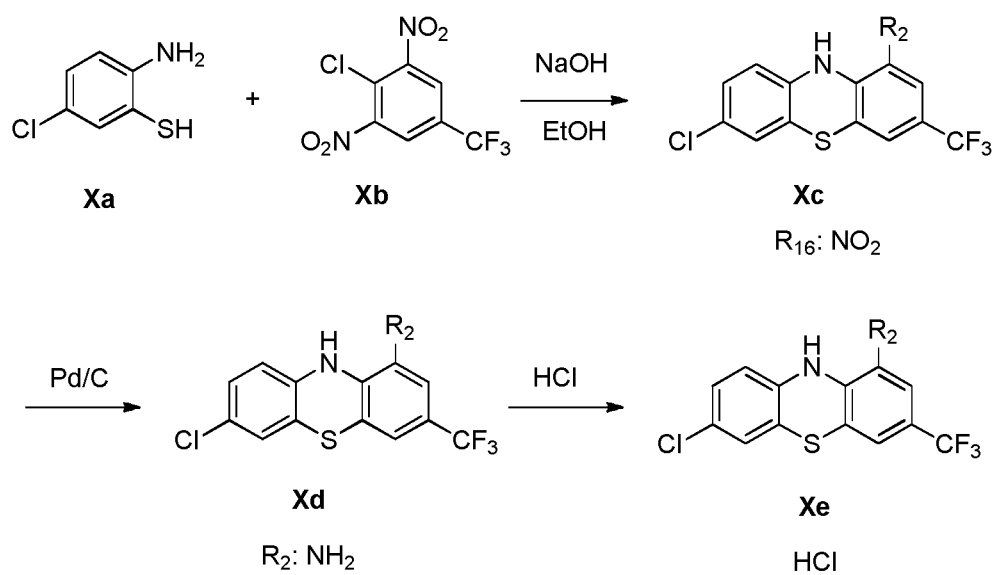
FIG. 10 shows general synthetic scheme X for the synthesis of selected compounds according to the present invention.

FIG. 10 shows general synthetic scheme X for the synthesis of selected 1,3,7-trisubstituted phenothiazenes. Nucleophilic substitution reaction of substituted 2-amino thiophenol (Xa) with aryl halides (Xb) followed by in situSmiles rearrangement gave title compounds Xc. Reduction of compound Xc using Pd/C followed by salt preparation resulted title compound Xe.

Figure 11:
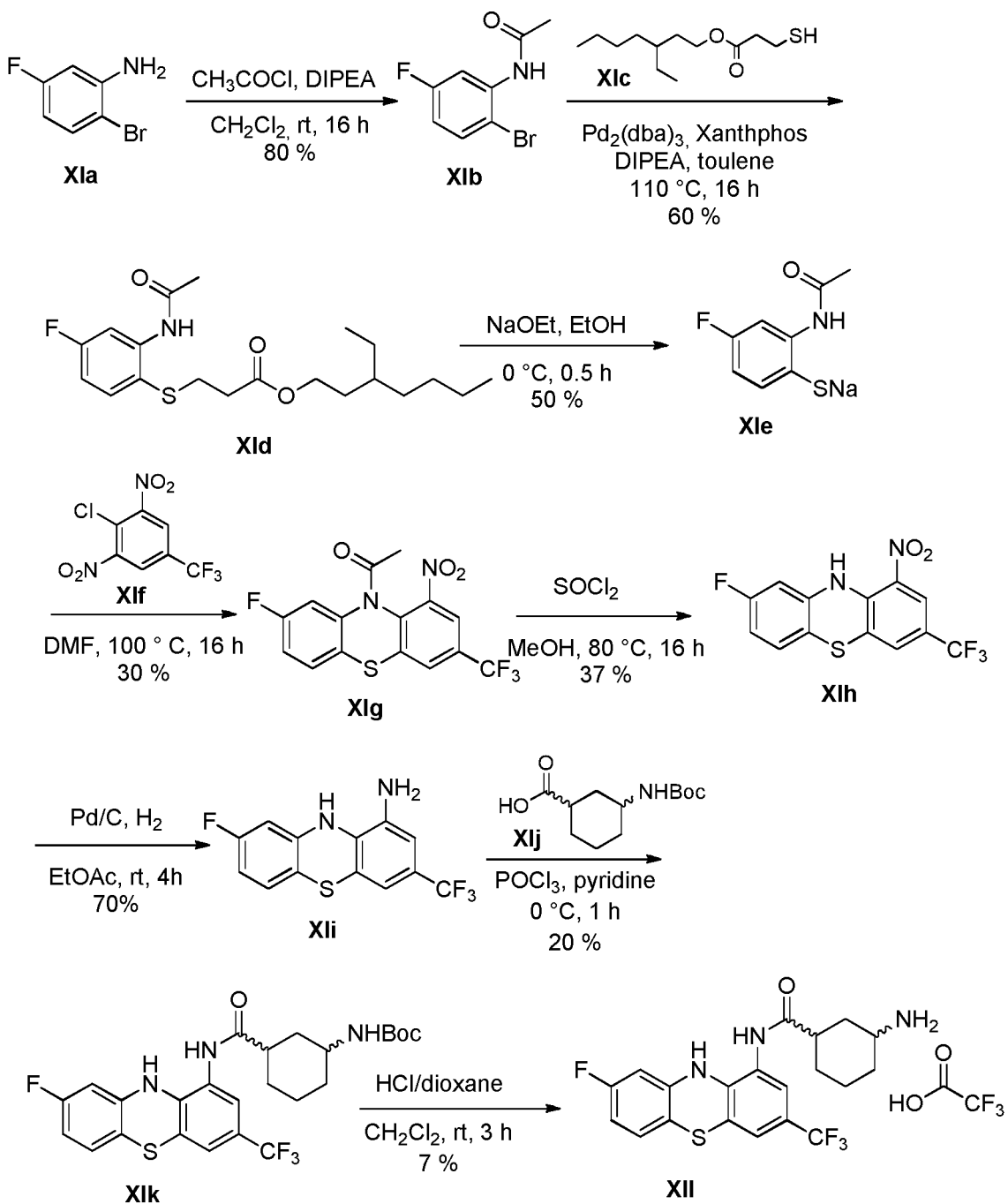
FIG. 11 shows general synthetic scheme XI for the synthesis of selected compounds according to the present invention.

FIG. 11 shows general synthetic scheme XI for the synthesis of a selected 1, 3, 8-trisubstituted phenothiazine. N-Acylation of 2-bromo-5-fluoroaniline (XIa) followed by nucleophilic substitution reaction with a thiol surrogate yielded compound XId. Deprotection of alkyl chain using NaOEt followed by nucleophilic substitution and Smiles rearrangement give compound XIg. Deprotection of compound XIg using SOCl₂ followed by reduction using Pd/C resulted compound XIi. Acid-amine coupling of XIi with XIj followed by deprotection using HCl yielded the title compound XIl.

A detailed synthetic description of a compound synthesised by the method of Scheme XI is provided below.

Compound 124: 3-Amino-N-(8-fluoro-3-(trifluoromethyl)-10H-phenothiazin-1-yl)cyclohexane carboxamide. TFA Salt

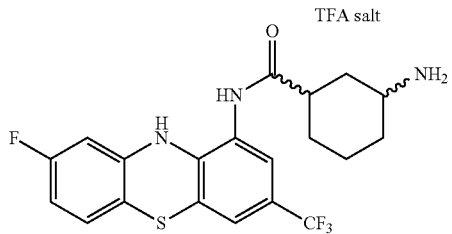 [SMILES: NC1CCCC(C(=O)Nc2cc(C(F)(F)F)cc3c2Nc2cc(F)ccc2S3)C1]

Step 1: N-(2-bromo-5-fluorophenyl) acetamide

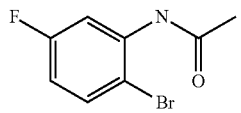

To a stirred solution of 2-bromo-5-fluoroaniline (3.0 g, 15.95 mmol) in dichloromethane (50 mL) was added di isopropyl ethylamine (5.5 mL, 31.9 mmol)) followed by acetyl chloride (1.7 mL, 23.9 mmol) at 0° C. and starred at room temperature for 16 h. The reaction mixture was washed with saturated sodium bicarbonate solution (50 mL), extracted the compound with dichloromethane, dried over sodium sulphate, filtered and concentrated. The crude product was purified on biotage with 6% ethyl acetate/n-hexane as eluant to get desired product 142a as off white solid. (3.0 g, 96%). MS (ESI) m/z 233 (M+H)$^+$.

Step 2: 3-Ethylheptyl 3-((2-acetamido-4-fluorophenyl)thio) propanoate

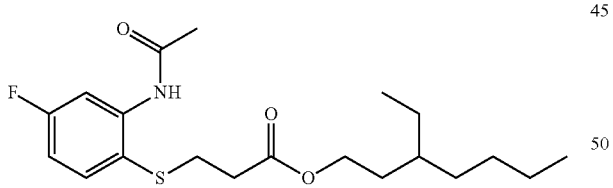

To a stirred solution of N-(2-bromo-5-fluorophenyl) acetamide (2.0 g, 0.086 mol) and 2-ethylhexyl 3-mercaptopropanoate in toluene (20 mL) was added DIPEA (4.6 mL 0.258 mol,) followed by Xanthpos (0.04 g, 0.086 mmol) at room temperature. Then purged with N$_2$ for 10 min, then added Pd$_2$(dba)$_3$ (0.078 g, 0.86 mol), then purged with N$_2$ for 10 min. Reaction mixture was stirred at 110° C. for 4 h. The reaction mixture was filtered through celite, concentrated under reduced pressure. Obtained crude product was purified on biotage with 20% Ethyl acetate/hexane as eluant to give the desired product as as off white solid (0.1.7 g, 55%): $^1$H NMR (CDCl$_3$, 400 MHz) δ 0.86-0.96.05 (m, 7H), 1.26-1.36 (m, 6H), 1.38-1.39 (m, 2H), 1.54 (s, 1H), 2.25 (s, 3H), 2.53 (t, J=13.2 Hz, 2H), 2.93 (t, J=6.8 Hz, 2H), 4.03-4.04 (m, 2H), 6.72-6.77 (m, 1H), 7.22-7.27 (m, 1H), 7.50 (t, J=6.4 Hz, 1H), 8.32 (t, J=11.1 Hz, 1H), 8.77 (s, 1H). MS (ESI) m/z 370 (M+H)$^+$.

Step 3: Sodium 2-acetamido-4-fluorobenzenethiolate

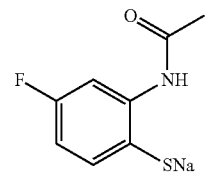

To a stirred sol of 3-ethylheptyl 3-((2-acetamido-4-fluorophenyl)thio) propanoate (0.7 g, 0.00189 mol) in ethanol (10 mL) was added sodium ethoxide solution in ethanol (1 mL) at 0° C., then stirred at 0° C. for 2 h, evaporated the solvent under reduced pressure. The crude (1.0 g) obtained was forwarded to the next step.

Step 4: 1-(8-Fluoro-1-nitro-3-(trifluoromethyl)-10H-phenothiazin-10-yl) ethanone

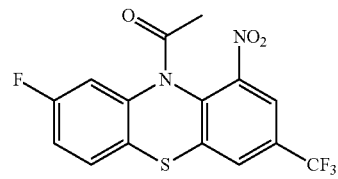 [SMILES: CC(=O)N1c2cc(F)ccc2Sc2cc(C(F)(F)F)cc([N+](=O)[O-])c21]

A stirred suspension of sodium 2-acetamido-4-fluorobenzenethiolate (1.0 g, 1.89 mmol) in DMF (5 mL) was heated at 100° C. for 14 h. To this added 50 mL of ice cold water, extracted the compound into EtOAc, dried the organic layer over sodium sulphate, filtered and concentrated. Obtained crude was purified on biotage with 30% EtOAc/hexane as eluant to give the product (0.8 g, 80%), MS (ESI), m/z 373 (M+H)$^+$.

Step 5: 8-Fluoro-1-nitro-3-(trifluoromethyl)-10H-phenothiazine

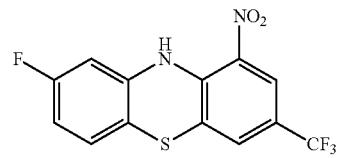

To a stirred solution of 1-(8-fluoro-1-nitro-3-(trifluoromethyl)-10H-phenothiazin-10-yl) ethanone (0.8 g, 0.00215 mol) in methanol (30 mL) was added thionyl chloride (6 mL) at 0° C. and starred at 70° for 18 h. The reaction mixture was concentrated under reduced pressure, quenched the reaction mixture with bicarbonate solution extracted the compound into EtOAc, dried the organic layer over sodium sulphate, filtered and concentrated. Obtained crude was purified on biotage with 20% EtOAc/hexane as eluant to to give the product (0.3 g, 42%), MS (ESI), m/z 329 (M−H)+.

Step 6: 8-Fluoro-3-(trifluoromethyl)-10H-phenothiazin-1-amine

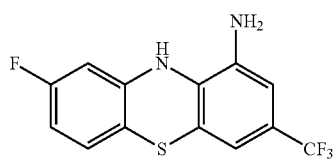 [SMILES: O=[N+]([O-])c1cc(C(F)(F)F)cc2c1Nc1cc(F)ccc1S2]

To a stirred solution of 8-fluoro-1-nitro-3-(trifluoromethyl)-10H-phenothiazine (142e, 0.3 g, 0.90 mmol) in ethyl acetate (20 mL) was added a solution of pd/C (50%, water wet, 0.2 g), and stirred at room temperature for 4 h. The reaction mixture was filtered through celite and concentrated to offer the title compound. (0.3 g crude). MS (ESI), m/z 301 (M+H)+.

Step 7: Tert-butyl(3-((8-fluoro-3-(trifluoromethyl)-10H-phenothiazin-1-yl)carbamoyl)cyclohexyl) carbamate

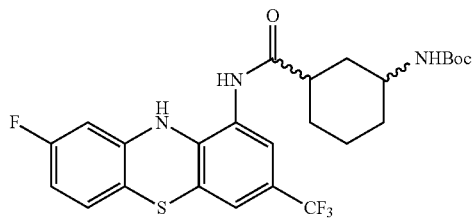

To a stirred solution of 8-fluoro-3-(trifluoromethyl)-10H-phenothiazin-1-amine (142f, 0.2 g, 0.6 mmol) and 3-((tert-butoxycarbonyl)amino)cyclohexanecarboxylic acid (0.2 g, 0.82 mmol) in pyridine (3 mL) was added a solution POCl₃ (0.3 mL) at 0° C. and starred at room temperature for 1 h. The reaction mixture was concentrated under reduced pressure, added 20 mL of DM water, extracted compound with EtOAc, dried the organic layer over sodium sulphate filtered and concentrated. The crude was purified on biotage with 30% EtOAc/hexane as eluant to get title compound 142 as off white solid (0.060 g, 17%). MS (ESI), m/z 524 (M−H)+.

Step 8: 3-Amino-N-(8-fluoro-3-(trifluoromethyl)-10H-phenothiazin-1-yl)cyclohexanecarboxamide. TFA Salt

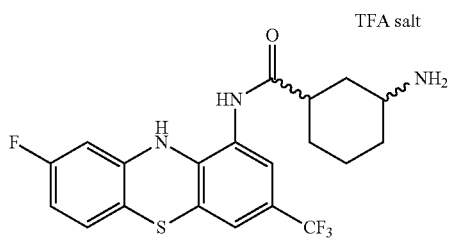 [SMILES: NC1CCCC(C(=O)Nc2cc(C(F)(F)F)cc3c2Nc2cc(F)ccc2S3)C1]

To a stirred solution of tert-butyl(3-((8-fluoro-3-(trifluoromethyl)-10H-phenothiazin-1-yl)carbamoyl)cyclohexyl) carbamate (0.060 g, 0.11 mmol) in dichloromethane (6 mL) was added a solution of HCl/dioxane (20%, 0.5 mL) at 0° C. and starred at room temperature for 1 h. The reaction mixture was concentrated under reduced pressure, dissolved in saturated sodium bicarbonate solution, extracted with dichloromethane, and concentrated. The crude was purified by prep TLC to get the title compound (0.020 g, 41%). ¹H NMR (DMSO-d₆, 400 MHz) δ 1.36-1.49 (m, 3H), 1.80-2.01 (m, 5H), 2.11-2.31 (m, 1H), 3.089 (bs, 1H), 6.70-6.77 (m, 2H), 7.00-7.04 (m, 1H), 7.20 (s, 1H), 7.30 (s, 1H), 7.77 (bs, 3H), 8.18 (s, 1H), 9.04 (s, 1H): MS (ESI) m/z 426.1 (M+H)⁻; HPLC purity: 99.1%.

Figure 12:
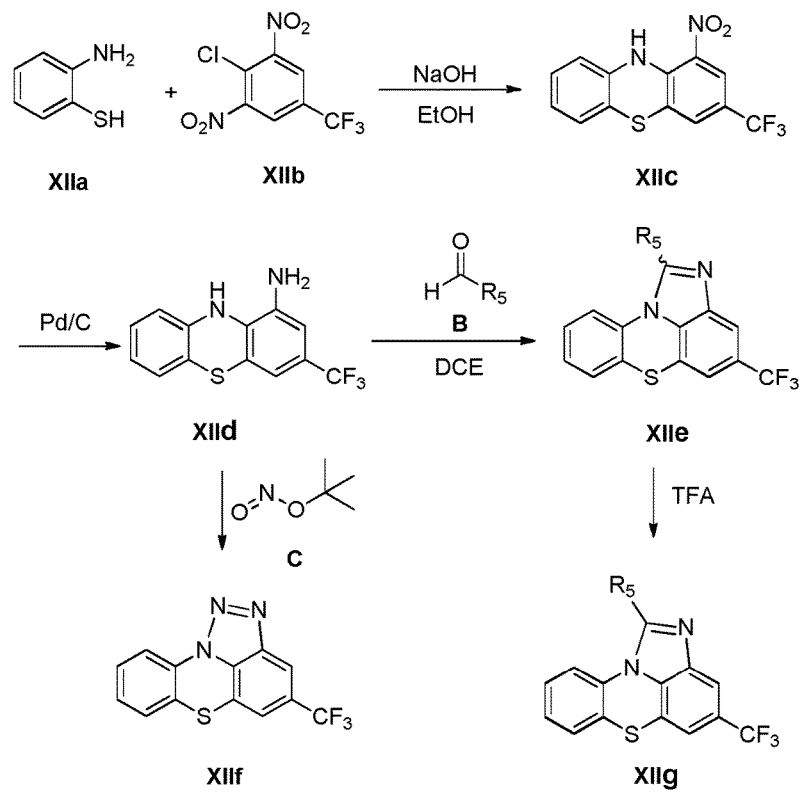
FIG. 12 shows general synthetic scheme XII for the synthesis of selected compounds according to the present invention.

FIG. 12 shows general synthetic scheme XII for the synthesis of selected triazolo phenothiazenes and imidazolo phenothiazenes. Nucleophilic substitution of 2-amino thiophenol (XIIa) with aryl halides (XIIb) followed by in situSmiles rearrangement give compound XIIc. Reduction of compound XIIc using Pd/C resulted compound XIId. Cyclization of compound XIId with aldehydes (B) followed by deprotection resulted imidazolo phenothiazenes (XIIg). Parallely, cyclization of compound XIId with nitroso compound (C) yielded triazolo phenothiazene (XIIf).

A detailed synthetic description of a compound synthesised by the method of Scheme XII is provided below.

Compound 239: 2-(4-(4-(Trifluoromethyl)imidazo[4,5,1-kl]phenothiazin-1-yl)piperidin-1-yl)ethanamine

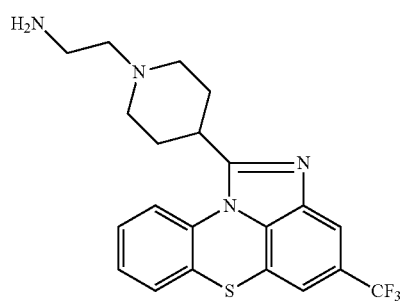 [SMILES: NCCN1CCC(c2nc3cc(C(F)(F)F)cc4c3n2-c2ccccc2S4)CC1]

Step 1:1-Nitro-3-(trifluoromethyl)-10H-phenothiazine

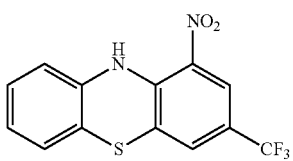

To a stirred solution of 2-chloro-1,3-dinitro-5-(trifluoromethyl)benzene (20 g, 74.07 mmol) in water (200 mL) were added 2-aminobenzenethiol (7.9 mL, 74.07 mmol), sodium hydroxide (8.8 g, 222 mmol) and the reaction mixture was heated at 100° C. for 16 h. The reaction mixture was cooled to room temperature, the residue was filtered, and washed with EtOH followed by H₂O to give the title compound as a brown solid (20 g, 86%). The product spot was matched with auenthetic in TLC.

Step 2:
3-(Trifluoromethyl)-10H-phenothiazin-1-amine

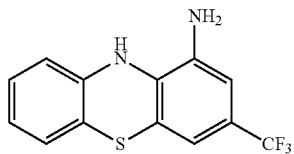

To a stirred solution of 1-nitro-3-(trifluoromethyl)-10H-phenothiazine (25 g, 18.128 mmol) in MeOH (300 mL) was added 10% Pd/C (50% wet, 5.0 g) and the reaction mixture was stirred at room temperature for 24 h under $H_2$ atmosphere. The reaction mixture was filtered through celite and filtrate was concentrated to give the title compound as a light brown solid (15 g, 67%): $^1$H NMR (DMSO-$d_6$, 400 MHz) δ 5.42 (s, 2H), 6.48 (s, 1H), 6.72 (s, 1H), 6.77 (t, J=7.2 Hz, 1H), 6.83 (d, J=8 Hz, 1H), 6.92 (d, J=8 Hz, 1H), 7.02 (t, J=7.6 Hz, 1H), 7.79 (s, 1H); MS (ESI) m/z 283 (M+H)$^+$.

Step 3: Tert-butyl 4-(4-(trifluoromethyl)imidazo[4,5,1-kl]phenothiazin-1-yl)piperidine-1-carboxylate

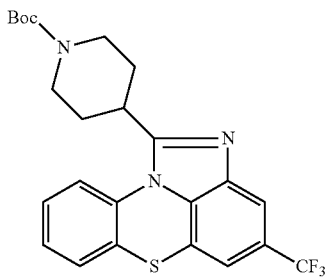

To a stirred solution of 3-(trifluoromethyl)-10H-phenothiazin-1-amine (0.8 g, 2.836 mmol)) in ethanol (30 mL) and pyrrolidine (0.23 mL, 2.836 mmol) was added tert-butyl 4-formylpiperidine-1-carboxylate (0.54 mL, 2.836 mmol) and stirring continued for 12 h at 70° C. The reaction mixture was concentrated, diluted with water, extracted with ethyl acetate, the combined organic phase was dried over $Na_2SO_4$, concentrated, and the residue was purified by column chromatography over silica gel using 10% ethyl acetate/hexane mixture as eluent to give the crude compound as a light brown liquid (0.3 g, crude): MS (ESI) m/z 476.1 (M+H)$^+$.

Step 4: 1-(Piperidin-4-yl)-4-(trifluoromethyl)imidazo[4,5,1-kl]phenothiazine

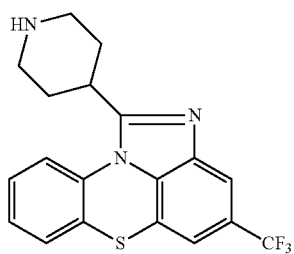 [SMILES: FC(F)(F)c1cc2c3c(c1)nc(C1CCNCC1)n3-c1ccccc1S2]

To a stirred solution of tert-butyl 4-(4-(trifluoromethyl)imidazo[4,5,1-kl]phenothiazin-1-yl)piperidine-1-carboxylate (0.3 g, crude) in dichloromethane (15 mL) at 0° C. was added 4N HCl in 1,4-dioxane (1 mL) and stirring continued for 16 h at room temperature. The reaction mixture was concentrated washed with sodium bicarbonate solution, extracted with ethyl acetate, the combined organic phase was dried over $Na_2SO_4$, concentrated, and the residue residue was purified by column chromatography over silica gel using 10% MeOH-DCM solvent system as eluent to give the compound as a off white solid (0.035 g, 15%): $^1$H NMR (DMSO-$d_6$, 400 MHz) δ 1.76 (t, J=10.8 Hz, 2H), 1.99 (d, J=12.8 Hz, 2H), 2.71 (t, J=12 Hz, 2H), 3.02 (d, J=11.6 Hz, 2H), 3.51 (s, 1H), 7.17 (t, J=7.6 Hz, 1H), 7.23 (s, 1H), 7.31 (s, 2H), 7.56 (s, 1H), 7.66 (s, J=8.4 Hz, 1H); MS (ESI) m/z 376.1 (M+H)$^+$.

Step 5: Tert-butyl(2-(4-(4-(trifluoromethyl)imidazo[4,5,1-kl]phenothiazin-1-yl)piperidin-1-yl)ethyl)carbamate

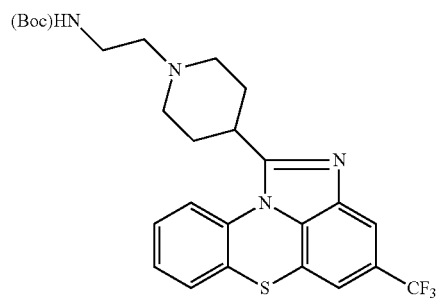

To a stirred solution of 1-(piperidin-4-yl)-4-(trifluoromethyl)imidazo[4,5,1-kl]phenothiazine (0.15 g, 0.4 mmol)) in acetonitrile (10 mL) were added potassium carbonate (0.16 g, 1.2 mmol), tert-butyl (2-bromoethyl)carbamate (0.13 g, 0.6 mmol) and stirring continued for 16 h at 80° C. The reaction mixture was diluted with water, extracted with ethyl acetate, the combined organic phase was dried over $Na_2SO_4$, concentrated, and the residue was purified by column chromatography over silica gel using 100% ethyl acetate mixture as eluent to give the title compound as a off white solid (0.17 g, 85%): $^1$H NMR (CDCl$_3$, 400 MHz) δ 1.46 (s, 9H), 2.17 (d, J=6.8 Hz, 4H), 2.4 (m, 1H), 2.53 (s, 2H), 3.07 (s, 2H), 3.25 (s, 4H), 6.94 (s, 1H), 7.23 (s, 1H), 7.09 (t, J=7.6 Hz, 1H), 7.17 (t, J=6.8 Hz, 2H), 7.45 (d, J=8 Hz, 2H), 7.54 (s, 1H); MS (ESI) m/z 519.1 (M+H)$^+$.

Step 6: 2-(4-(4-(Trifluoromethyl)imidazo[4,5,1-kl]phenothiazin-1-yl)piperidin-1-yl)ethanamine

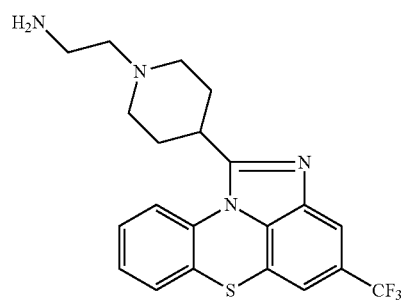 [SMILES: NCCN1CCC(c2nc3cc(C(F)(F)F)cc4c3n2-c2ccccc2S4)CC1]

To a stirred solution of tert-butyl (2-(4-(4-(trifluoromethyl)imidazo[4,5,1-kl]phenothiazin-1-yl)piperidin-1-yl)ethyl)carbamate (0.15 g, 0.289 mmol) in dichloromethane (10 mL) at 0° C. was added TFA (1 mL) and stirring continued for 5 h at room temperature. The reaction mixture was concentrated, washed with sodium bicarbonate solution, extracted with ethyl acetate, the combined organic phase was dried over Na$_2$SO$_4$, concentrated, and the residue was recrystallised by using diethyl ether and pentane to give the title compound as a off white solid (0.03 g, 25%): $^1$H NMR (DMSO-d$_6$, 400 MHz) δ 1.91-1.83 (m, 2H), 2.05 (d, J=11.6 Hz, 2H), 2.16 (t, J=11.2 Hz, 2H), 2.35-2.30 (m, 2H), 3.51 (s, 1H), 2.62 (t, J=6.8 Hz, 2H), 2.92 (d, J=11.2 Hz, 2H), 3.39 (d, J=11.6 Hz, 1H), 7.17 (t, J=7.2 Hz, 1H), 7.23 (s, 1H), 7.31 (t, J=7.6 Hz, 2H), 7.56 (s, 1H), 7.64 (d, J=8.4 Hz, 1H); MS (ESI) m/z 419.2 (M+H)$^+$; HPLC purity: 99.48%.

Some examples of compounds synthesised by the method of Scheme XII are provided in Table XII.

TABLE XII

| Cmpd # | R$^5$ |
|---|---|
| 232 | 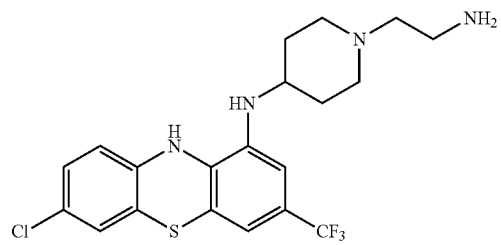 |
| 239 | |
| 191 | |

Figure 13:
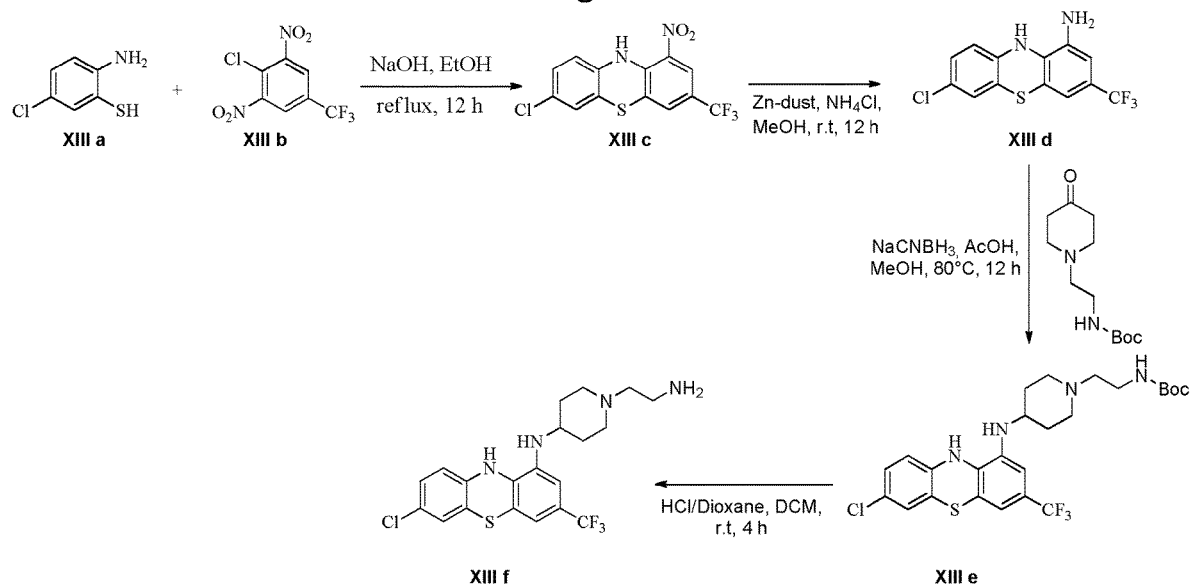
FIG. 13 shows general synthetic scheme XIII for the synthesis of selected compounds according to the present invention.

FIG. 13 shows general reaction scheme XIII for the synthesis of a selected trisubstituted phenothiazine. Nucleophilic substitution reaction of substituted amino thiols XIIIa with substituted dinitro aryl halides XIIIb, followed bu insituSmiles rearrangement resulted in the formation of trisubstituted phenothiazenes XIIIc. Nitro group reduction with Pd/C gave compound XIIId, which on reductive amination with an appropriate ketone resulted in corresponding amine compound (XIIIe), followed by deprotection resulted in title compound XIIIf.

A detailed synthetic description for a compound synthesised by the method of Scheme XIII is provided below.

Compound 226: N-(1-(2-Aminoethyl)piperidin-4-yl)-7-chloro-3-(trifluoromethyl)-10H-phenothiazin-1-amine Step 1: 7-Chloro-1-nitro-3-(trifluoromethyl)-10H-phenothiazine

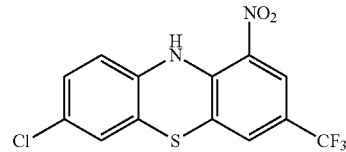

To a stirred solution of 2-amino-5-chlorobenzenethiol (5 g, 31.32 mmol) in EtOH (50 mL) were added 2-chloro-1,3-dinitro-5-(trifluoromethyl)benzene (8.4 g, 31.32 mmol), NaOH (2.5 g, 62.64 mmol) and the reaction mixture was heated at 85° C. for 12 h. The reaction mixture was cooled to room temperature, concentrated, and the residue was purified by column chromatography over silica gel using dichloromethane/hexane (2%) mixture as eluent to give the title compound as a black solid (3 g, 46%): $^1$H NMR (DMSO-d$_6$, 400 MHz) δ 7.10-7.14 (m, 2H), 7.18 (s, 1H), 7.67 (s, 1H), 8.00 (s, 1H), 8.71 (bs, 1H); MS (ESI) m/z 345 (M−H)$^+$.

Step 2: 7-Chloro-3-(trifluoromethyl)-10H-phenothiazin-1-amine

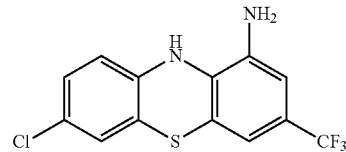 [SMILES: Nc1cc(C(F)(F)F)cc2c1Nc1ccc(Cl)cc1S2]

To a stirred solution of 7-chloro-1-nitro-3-(trifluoromethyl)-10H-phenothiazine (1 g, 2.88 mmol) in MeOH (50 mL) were added Zn powder (1 g, 15.78 mmol), ammonium chloride (0.2 g, 4.154 mmol) and stirring continued at room temperature for 12 h. The reaction mixture was filtered through celite, concentrated to give the title compound as a black solid (1 g, crude): $^1$H NMR (DMSO-d$_6$, 400 MHz) δ 5.41 (bs, 2H), 6.49 (s, 1H), 6.73 (s, 1H), 6.81 (d, J=8.4 Hz, 1H), 7.02-7.06 (m, 2H), 7.91 (bs, 1H); MS (ESI) m/z 316 (M+H)$^+$.

Step 3: Tert-butyl (2-(4-((7-chloro-3-(trifluoromethyl)-10H-phenothiazin-1-yl)amino)piperidin-1-yl)ethyl)carbamate

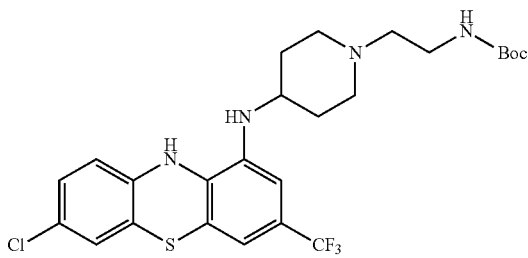

To a stirred solution of 7-chloro-3-(trifluoromethyl)-10H-phenothiazin-1-amine (0.5 g, 1.57 mmol) and tert-butyl (2-(4-oxopiperidin-1-yl)ethyl)carbamate (0.75 g, 3.14 mmol) in methanol (50 mL) was added acetic acid (0.47 mL) and stirring continued for 1 h at room temperature. To the reaction mixture was added NaCNBH$_3$ (0.49 g, 7.89 mmol) and was heated to 80° C. for 12 h. The reaction mixture was concentrated and washed with sodium bicarbonate solution, extracted with ethyl acetate, the combined organic phase was dried over Na$_2$SO$_4$, concentrated, and the residue was purified by column chromatography over silica gel using MeOH/DCM (3%) mixture as eluent to give the title compound as a black solid (0.1 g, 11%): MS (ESI) m/z 545 (M–H)$^+$.

Step 4: N-(1-(2-Aminoethyl)piperidin-4-yl)-7-chloro-3-(trifluoromethyl)-10H-phenothiazin-1-amine

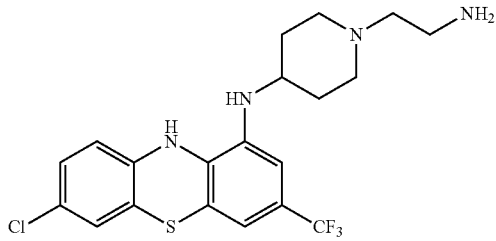 [SMILES: NCCN1CCC(Nc2cc(C(F)(F)F)cc3c2Nc2ccc(Cl)cc2S3)CC1]

To a stirred solution of tert-butyl (2-(4-((7-chloro-3-(trifluoromethyl)-10H-phenothiazin-1-yl)amino)piperidin-1-yl)ethyl)carbamate (0.1 g, 0.18 mmol) in dichloromethane (10 mL) at 0° C. was added 4N HCl in dioxane (0.5 mL) and stirring continued for 4 h at room temperature. The reaction mixture was neutralised with sodium bicarbonate solution, solid was filtered, and dried under vacuum to gave title compound as a off white solid (0.006 g, 8%): NMR (DMSO-d$_6$, 400 MHz) δ 1.39-1.47 (m, 2H), 1.88-1.91 (m, 2H), 1.96-1.98 (m, 2H), 2.06-2.09 (m, 2H), 2.23-2.27 (m, 2H), 2.61-2.65 (m, 2H), 2.81-2.84 (m, 2H), 6.56 (d, J=15.2 Hz, 2H), 6.86 (d, J=8.4 Hz, 1H), 7.04 (s, 1H), 8.11 (s, 1H); MS (ESI) m/z 443.1 (M+H)$^+$; HPLC purity: 99.14%.

Figure 14:
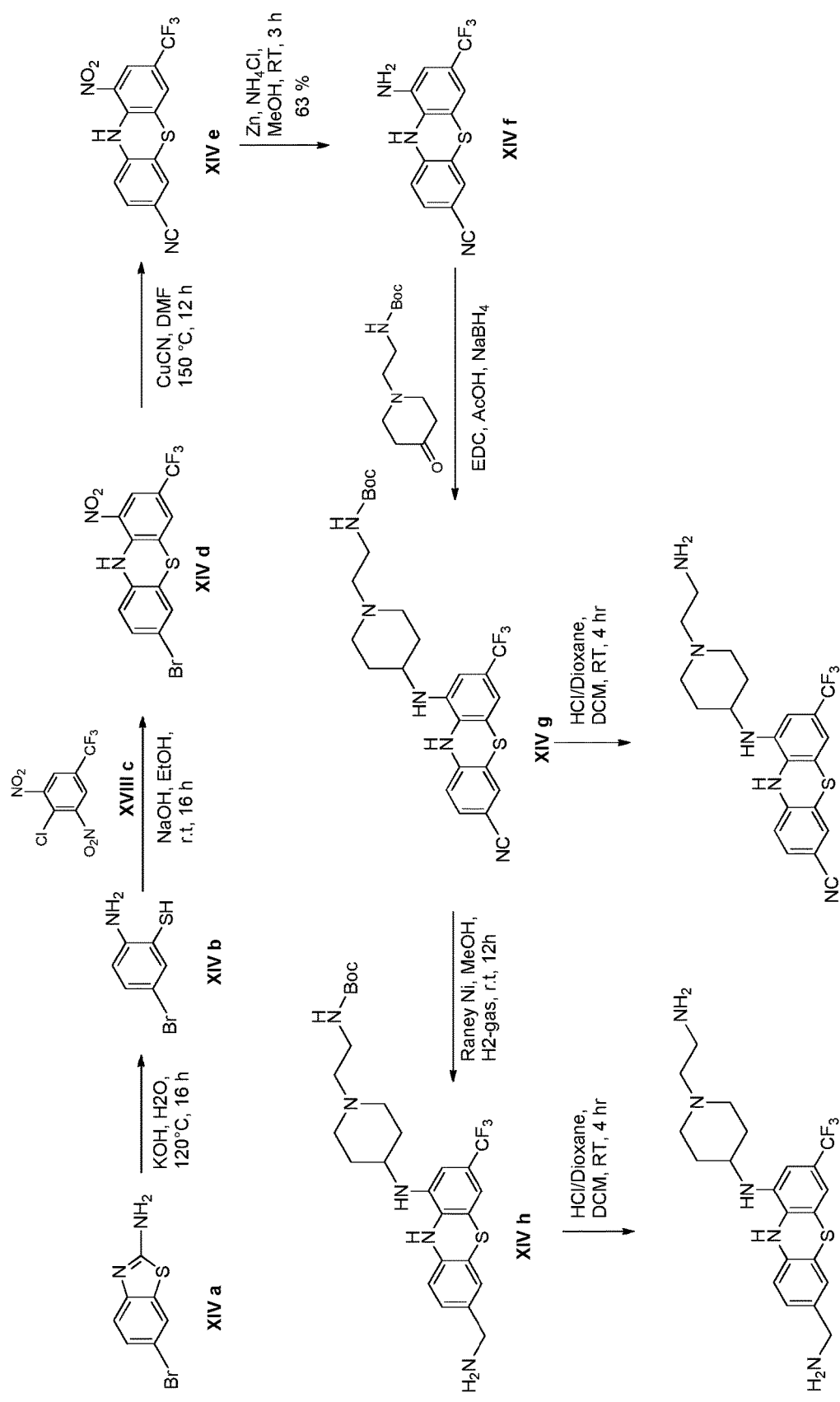
FIG. 14 shows general synthetic scheme XIV for the synthesis of selected compounds according to the present invention.

FIG. 14 shows general synthetic scheme XIV for the synthesis of selected trisubstituted phenothiazenes. Aqueous hydrolysis of compound XIVa, gave substituted amino thiols XIVb, which on nucleophilic substitution reaction with substituted dinitro arylhalides XIVc, followed bu insi-tuSmiles rearrangement resulted in the formation of trisubstituted phemothiaxzenes XIVd. Nitro group reduction with Pd/C gave compound XIVf, Reductive amination of XIVf with an appropriate ketone resulted in compound XIVfg, followed by deprotection resulted compound XIVj. Alternatively, compound XIVfg was reduced by Rany-Ni to the corresponding amine, followed by deprotection gave the title compound XIVi.

Detailed synthetic descriptions for some compounds synthesised by the method of Scheme XIV are provided below.

Compound 227: N-(1-(2-Aminoethyl)piperidin-4-yl)-7-(aminomethyl)-3-(trifluoromethyl)-10H-phenothiazin-1-amine bis(2,2,2-trifluoroacetate)

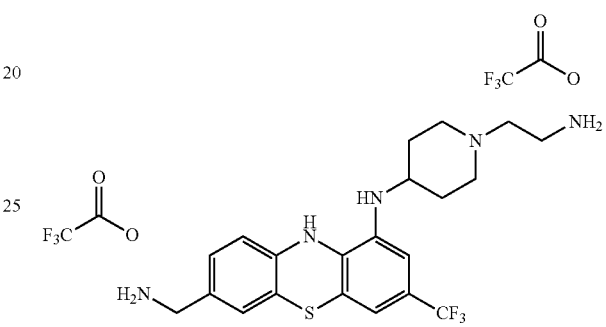

Step 1: 2-Amino-5-bromobenzenethiol

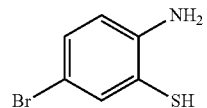

To a stirred solution of 6-bromobenzo[d]thiazol-2-amine (1 g, 4.364 mmol) in water (20 mL) was added KOH (7.34 g, 130.947 mmol) at 0° C., reaction mixture was heated at 120° C. for 16 h. The reaction mixture was acidified with glacial acetic acid (up to pH~6) at 0° C., solid was filtered, and dried under vacuum to give crude title compound as a light green solid (0.95 g, crude); MS (ESI) m/z 201 (M–H)$^+$.

Step 2: 7-Bromo-1-nitro-3-(trifluoromethyl)-10H-phenothiazine

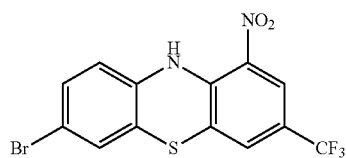

To a stirred solution of 2-amino-5-bromobenzenethiol (0.9 g, 4.411 mmol) in ethanol (30 mL) was added NaOH (0.52 g, 13.23 mmol) at 0° C. and stirring continued for 20 min at 0° C. To the reaction mixture was added 2-chloro-3-nitro-5-(trifluoromethyl)aniline (1.07 g, 3.969 mmol) and stirring continued at room temperature for 16 h. The reaction mixture was filtered and solid was washed with H₂O to gave the title compound as a brown solid (0.9 g, 52%): ¹H NMR (DMSO-d₆, 400 MHz) δ 7.05 (d, J=7.8 Hz, 1H), 7.27-7.24 (m, 1H), 7.30 (d, J=2 Hz, 1H), 7.67 (s, 1H), 8.00 (s, 1H), 9.83 (s, 1H); MS (EST) m/z 389.0 (M−H)⁺.

Step 3: 9-Nitro-7-(trifluoromethyl)-10H-phenothiazine-3-carbonitrile

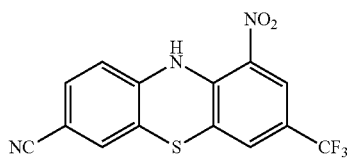

To a stirred solution of 7-bromo-1-nitro-3-(trifluoromethyl)-10H-phenothiazine (0.8 g, 2.04 mmol)) in DMF (15 mL) was added CuCN (0.36 g, 4.09 mmol) and reaction mixture was heated at 150° C. for 16 h. The reaction mixture was washed with water, extracted with ethyl acetate, the combined organic phase was dried over Na₂SO₄, concentrated, and the residue was purified by column chromatography over silica gel using ethyl acetate/hexane (1:2.3) mixture as eluent, to give the title compound as a black solid (0.5 g, 72%): ¹H NMR (DMSO-d₆, 400 MHz) δ 7.08 (d, J=6.4 Hz, 1H), 7.24 (d, J=6.8 Hz, 1H), 7.30 (s, 1H), 7.67 (s, 1H), 8.01 (s, 1H), 9.83 (s, 1H).

Step 4: 9-Amino-7-(trifluoromethyl)-10H-phenothiazine-3-carbonitrile

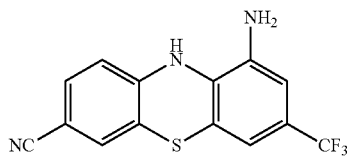

To a stirred solution of 9-nitro-7-(trifluoromethyl)-phenothiazine-3-carbonitrile (0.7 g, 2.07 mmol) in methanol (10 mL) were added zinc powder (0.13 g, 2.077 mmol), ammonium chloride (0.2 g, 4.154 mmol) and stirring continued for 4 h at RT. The reaction mixture was filtered through celite, concentrated, and the residue was purified by column chromatography over silica gel using ethyl acetate/hexane (1:2.3) mixture as eluent to give the title compound as a brown solid (0.4 g, 63%): MS (ESI) m/z 306.0 (M−H)⁺.

Step 5: Tert-butyl (2-(4-((7-cyano-3-(trifluoromethyl)-10H-phenothiazin-1-yl)amino) piperidin-1-yl)ethyl)carbamate

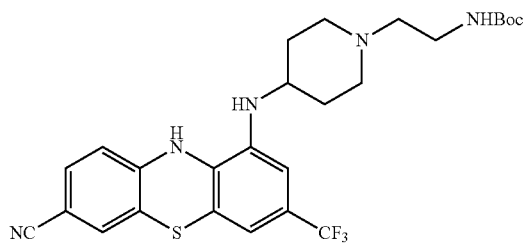 [SMILES: CC(C)(C)OC(=O)NCCN1CCC(Nc2cc(C(F)(F)F)cc3c2Nc2ccc(C#N)cc2S3)CC1]

To a stirred solution of 9-amino-7-(trifluoromethyl)-10H-phenothiazine-3-carbonitrile (3, 0.2 g, 0.65 mmol)) in dichloroethene (3 mL) at 0° C. were added tert-butyl (2-(4-oxopiperidin-1-yl)ethyl)carbamate (4, 0.31 g, 1.30 mmol), acetic acid (0.3 mL) and stirring continued for 5 min. To the reaction mixture was added sodium borohydride (0.05 g, 1.30 mmol) at 0° C. and stirring continued at room temperature for 2 h. The reaction mixture was washed with sodium bicarbonate solution, extracted with dichloromethane, the combined organic phase was dried over Na₂SO₄, concentrated, and the residue was purified by column chromatography over silica gel using methanol/dichloromethane (10%) mixture as eluent to give the title compound (0.07 g, 20%): ¹H NMR (DMSO-d₆, 400 MHz) δ 1.35 (s, 9H), 1.41 (s, 2H), 1.88 (bs, 4H), 2.07 (bs, 2H), 2.39 (m, 2H), 2.47 (bs, 2H), 2.81 (bs, 2H), 3.00 (bs, 1H), 5.25 (d, J=6.8 Hz, 1H), 6.54 (s, 1H), 6.59 (s, 1H), 6.90 (d, J=8.4 Hz, 1H), 7.39-7.43 (m, 2H), 8.45 (s, 1H).

Step 6: Tert-butyl (2-(4-((7-(aminomethyl)-3-(trifluoromethyl)-10H-phenothiazin-1-yl) amino) piperidin-1-yl)ethyl)carbamate

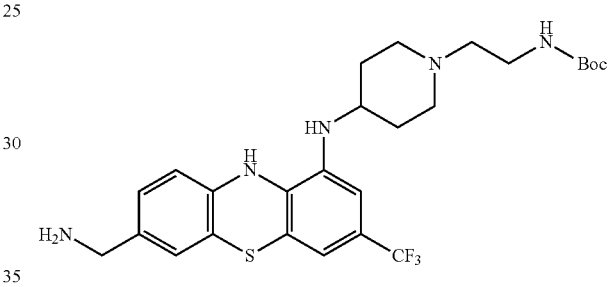

To a stirred solution of tert-butyl (2-(4-((7-cyano-3-(trifluoromethyl)-10H-phenothiazin-1-yl)amino)piperidin-1-yl)ethyl)carbamate (0.08 g, 0.15 mmol) in MeOH (15 mL) was added raney Ni (0.05 g) and hydrogenated under H₂atmosphere at 20 psi pressure & room temperature. The reaction mixture was filtered through celite and filtrate was evaporated to get title compound as an light brown solid (0.08 g, crude): MS (ESI) m/z 538 (M+H)⁺.

Step 7: N-(1-(2-Aminoethyl)piperidin-4-yl)-7-(aminomethyl)-3-(trifluoromethyl)-10H-phenothiazin-1-amine

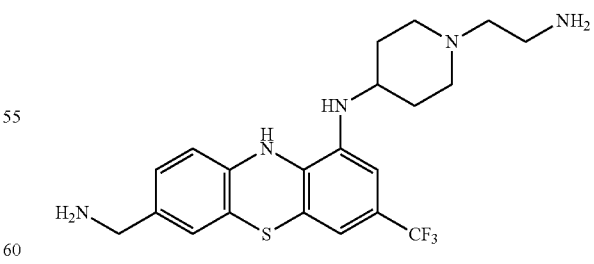

To a stirred solution of tert-butyl (2-(4-((7-(aminomethyl)-3-(trifluoromethyl)-10H-phenothiazin-1-yl)amino)piperidin-1-yl)ethyl)carbamate (0.08 g, 0.14 mmol) in dichloromethane (3 mL) at 0° C. was added HCl/dioxane (0.4 mL) and stirring continued for 4 h. The reaction mixture was evaporated, residue was washed with sodium bicarbonate solution, extracted with dichloromethane, the combined organic phase was dried over Na$_2$SO$_4$, and concentrated to gave the crude compound. Crude compound was purified by prep-HPLC to give title compound as an brown solid (0.002 g, 4%): $^1$H NMR (DMSO-d$_6$, 400 MHz) δ 1.63-1.72 (m, 2H), 1.94-1.98 (m, 2H), 2.07-2.18 (m, 2H), 3.12-3.33 (m, 4H), 3.63-3.73 (m, 2H), 3.83-3.84 (m, 2H), 5.42-5.47 (m, 1H), 6.89-6.63 (m, 2H), 6.85-6.87 (m, 1H), 7.04-7.07 (m, 2H), 7.97 (bs, 4H, salt); MS (ESI) m/z 436.4 (M−H)$^+$; HPLC purity: 97.03%.

Compound 217: 9-((1-(2-Aminoethyl)piperidin-4-yl)amino)-7-(trifluoromethyl)-10H-phenothiazine-3-carbonitrile

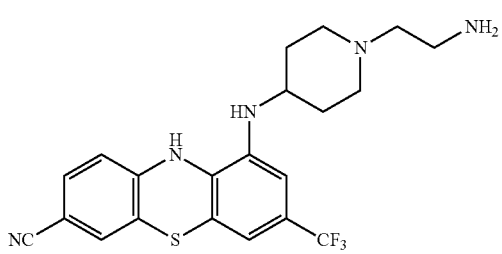 [SMILES: N#Cc1ccc2c(c1)Sc1cc(C(F)(F)F)cc(NC3CCN(CCN)CC3)c1N2]

To a stirred solution of tert-butyl (3-(((3-(trifluoromethyl)-10H-phenothiazin-1-yl)amino)methyl)cyclohexyl)carbamate (186, 0.06 g) in dichloromethane (5 mL) at 0° C. was added HCl/dioxane solution (0.3 mL) and stirring continued for 4 h. The reaction mixture was evaporated, residue was washed with sodium bicarbonate solution, extracted with dichloromethane, the combined organic phase was dried over Na$_2$SO$_4$, concentrated, to give the title compound as a light brown solid (0.03 g, 63%): $^1$H NMR (DMSO-d$_6$, 400 MHz) δ 1.42-1.45 (m, 2H), 1.88 (bs, 2H), 2.07 (d, J=11.2 Hz, 2H), 2.30-2.33 (m, 2H), 2.65 (d, J=8.0 Hz, 2H), 2.81 (bs, 2H), 5.32 (d, J=6.4 Hz, 1H), 6.54 (s, 1H), 6.59 (s, 1H), 6.93 (d, J=8.4 Hz, 1H), 7.39-7.43 (m, 2H), 8.51 (bs, 1H). MS (ESI) m/z 434.2 (M+H)$^+$; HPLC purity: 98.8%.

Figure 15:
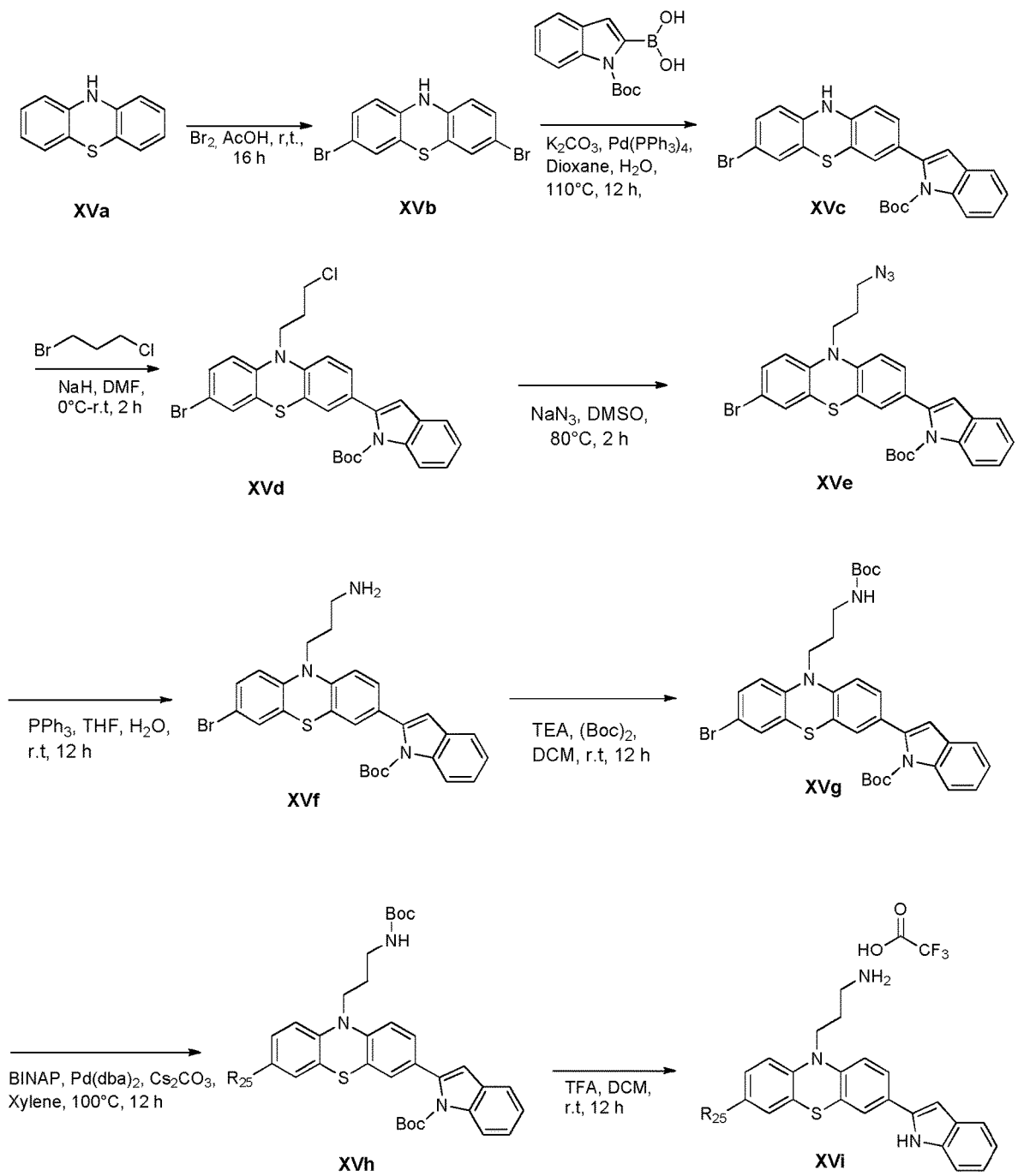
FIG. 15 shows general synthetic scheme XV for the synthesis of selected compounds according to the present invention.

FIG. 15 shows general synthetic scheme XV for the synthesis of selected trisubstituted phenothiazenes. Bromination of phenothiazene XVa with Br$_2$ gave the dibromo phenothiazene XVb which on Suzuki coupling with indole boronic acid gave compound XVc. N-10 alkylation of XVc with dihalide followed by azide formation gave compound XVe. Azide reduction followed by amine protection gave compound XVg. Palladium catalyzed amination/cayanation followed by deprotection gave the title compound XVi.

A detailed synthetic description of a compound synthesised by the method of Scheme XV is provided below.

Compound 244: 3-(3-(1H-indol-2-yl)-7-(piperazin-1-yl)-10H-phenothiazin-10-yl)propan-1-amine

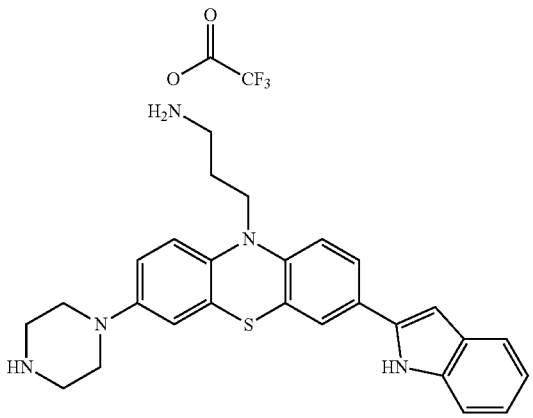

Step 1: 3,7-Dibromo-10H-phenothiazine

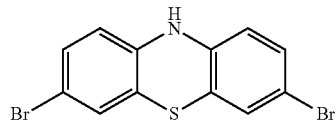 [SMILES: Brc1ccc2c(c1)Sc1cc(Br)ccc1N2]

To a stirred solution of 10H-phenothiazine (5 g, 25.1 mmol) in AcOH (50 mL) was added Br$_2$ (3.3 mL, 63 mmol) and stirring continued at room temperature for 16 h. The reaction mixture was filtered and dried to get the title compound as brown solid (7 g, quantitative): $^1$HNMR (DMSO, 400 MHz) δ 6.55-6.57 (m, 2H), 7.06-7.20 (m, 4H), 8.79 (s, 1H); MS (ESI) m/z 358 (M+2H)$^+$.

Step 2: Tert-butyl 2-(7-bromo-10H-phenothiazin-3-yl)-1H-indole-1-carboxylate

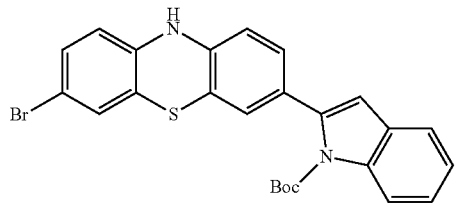 [SMILES: CC(C)(C)OC(=O)n1c(-c2ccc3c(c2)Sc2cc(Br)ccc2N3)cc2ccccc21]

To a stirred solution of 3,7-dibromo-10H-phenothiazine (3.5 g, 9.80 mmol) and (1-(tert-butoxycarbonyl)-1H-indol-2-yl)boronic acid (3.8 g, 14.7 mmol) in a mixture of 1,4-dioxane/water (55/5 mL) mixture was added potassium carbonate (4 g, 29.4 mmol) and was purged with nitrogen for 15 mins. To the reaction mixture was added tetrakis(triphenylphosphine)palladium(0)(1.1 g, 0.98 mmol), was purged with nitrogen for 10 mins, and heated at 100° C. for 12 h in a seal tube. The reaction mixture was filtered through celite, filtrate was diluted with EtOAc, and washed with water followed by brine. The organic layer was dried over sodium sulphate and concentrated. The crude was purified over silica gel using 12% EtOAc/hexane as eluant to give title compound as brown solid (1.5 g, 31%): MS (ESI) m/z 496 (M+2H)⁺.

Step 3: Tert-butyl 2-(7-bromo-10-(3-chloropropyl)-10H-phenothiazin-3-yl)-1H-indole-1-carboxylate

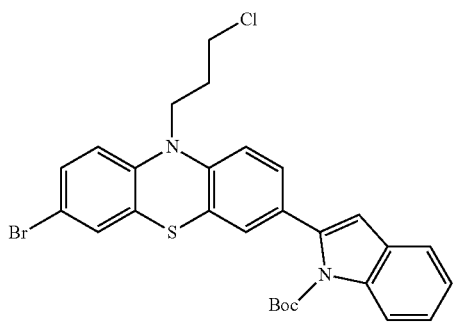

To a stirred solution of tert-butyl 2-(7-bromo-10H-phenothiazin-3-yl)-1H-indole-1-carboxylate (1.5 g, 3.04 mmol) in DMF (30 mL) was added sodium hydride (0.18 g, 4.56 mmol) at 0° C. in small portions and stirring continued at 0° C. for 15 mins. To the reaction mixture was added 3-bromo chloropropane (0.57 g, 3.64 mmol) at 0° C. and stirring continued at room temperature for 1 h. The reaction mixture was quenched with aq.NH₄Cl solution, extracted with EtOAc, the organic layer was washed with brine, dried over anhydrous sodium sulphate, and concentrated to gave the title compound as an pale yellow solid (1.5 g, crude). The crude product was as such taken to the next step without further purification. MS (ESI) m/z 370 (M+2H)⁺.

Step 4: Tert-butyl 2-(10-(3-azidopropyl)-7-bromo-10H-phenothiazin-3-yl)-1H-indole-1-carboxylate

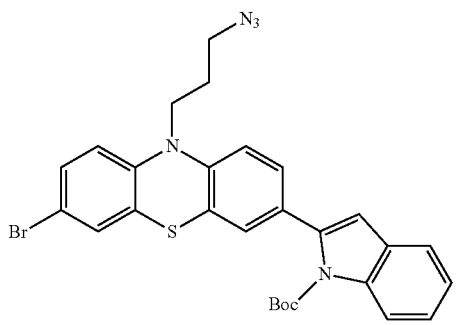 [SMILES: CC(C)(C)OC(=O)n1c(-c2ccc3c(c2)Sc2cc(Br)ccc2N3CCCN=[N+]=[N-])cc2ccccc21]

To a stirred solution of tert-butyl 2-(7-bromo-10-(3-chloropropyl)-10H-phenothiazin-3-yl)-1H-indole-1-carboxylate (1.5 g, 2.63 mmol) in DMSO (30 mL) was added sodium azide (0.51 g, 7.89 mmol) and the reaction mixture was heated at 80° C. for 2 h. The reaction mixture was quenched with ice, extracted with EtOAc, the organic layer was dried over sodium sulphate, and concentrated. The crude product was purified over silica gel using 5% EtOAc/hexane as eluant to give the title compound as brown solid (0.9 g, 59%): MS (ESI) m/z 576 (M+2H)⁺.

Step 5: Tert-butyl 2-(10-(3-aminopropyl)-7-bromo-10H-phenothiazin-3-yl)-1H-indole-1-carboxylate

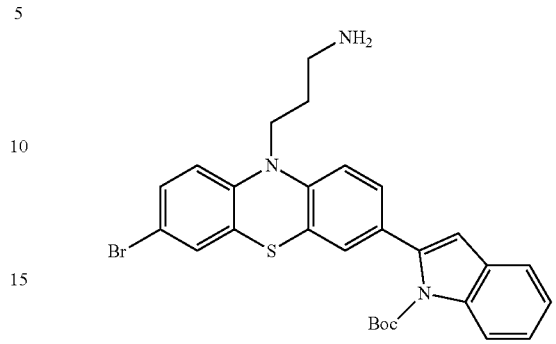

To a stirred solution of tert-butyl 2-(10-(3-azidopropyl)-7-bromo-10H-phenothiazin-3-yl)-1H-indole-1-carboxylate (0.9 g, 1.56 mmol) in a mixture of THF (20 mL) and H₂O (5 mL) was added triphenylphosphine (0.81 g, 3.12 mmol) and stirring continued at room temperature for 12 h. The reaction mixture was diluted with water, extracted with ethyl acetate, the organic layer is dried over sodium sulphate, and concentrated to get the title compound as an viscous solid (1 g, crude). Compound was taken to next step without further purification. MS (ESI) m/z 550 (M+2H)⁺.

Step 6: Tert-butyl 2-(7-bromo-10-(3-((tert-butoxycarbonyl)amino)propyl)-10H-phenothiazin-3-yl)-1H-indole-1-carboxylate

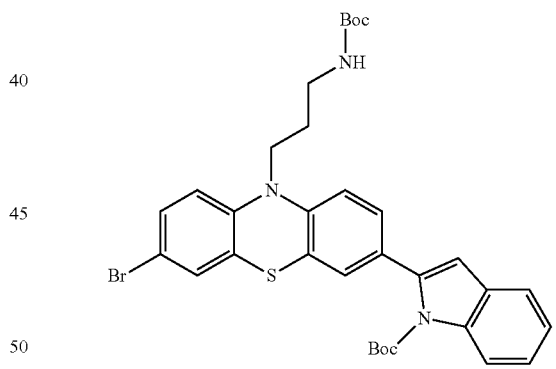

To a stirred solution of tert-butyl 2-(10-(3-aminopropyl)-7-bromo-10H-phenothiazin-3-yl)-1H-indole-1-carboxylate (0.9 g, 1.81 mmol) in dichloromethane (30 mL) were added Et₃N (0.5 mL, 3.63 mmol), (Boc)₂O (0.8 mL, 3.63 mmol) at 0° C. and stirring continued at room temperature for 2 h. The reaction mixture was concentrated and the crude product was purified over silica gel using 15% EtOAc in hexane as eluant to get the title compound as yellow solid (0.65 g, 55%): ¹HNMR (DMSO, 400 MHz) δ 1.28 (s, 9H), 1.33 (s, 9H), 1.78-1.81 (m, 2H), 3.02-3.03 (m, 2H), 3.87-3.89 (m, 2H), 6.67 (s, 1H), 6.85 (br s, 1H), 6.95 (d, J=8.4 Hz, 1H), 7.06 (d, J=8.4 Hz, 1H), 7.13-7.34 (m, 6H), 7.56 (d, J=7.6 Hz, 1H), 8.04 (d, J=8.4 Hz, 1H).

77

Step 7: Tert-butyl 2-(10-(3-((tert-butoxycarbonyl)amino)propyl)-7-(4-(tert-butoxycarbonyl)piperazin-1-yl)-10H-phenothiazin-3-yl)-1H-indole-1-carboxylate

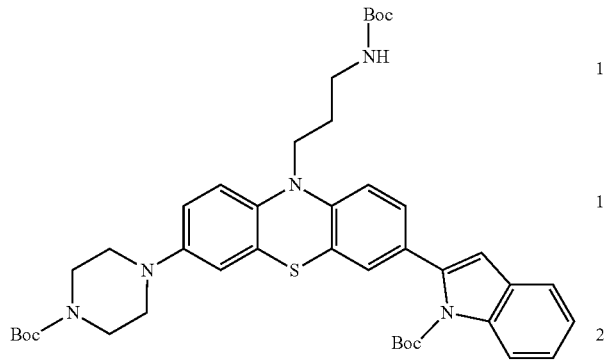

To a stirred solution of tert-butyl 2-(7-bromo-10-(3-((tert-butoxycarbonyl)amino)propyl)-10H-phenothiazin-3-yl)-1H-indole-1-carboxylate (0.23 g, 0.35 mmol) in a mixture of o-xylene (15 mL) were added tert-butyl piperazine-1-carboxylate (0.16 g, 0.88 mmol), cesium carbonate (0.57 g, 1.76 mmol), BINAP (0.0065 g, 0.01 mmol) and reaction mixture was purged with nitrogen for 15 mins. To the reaction mixture was added tris(dibenzylideneacetone)dipalladium (0.1 g, 0.17 mmol), was purged with nitrogen for 10 mins, and heated at 100° C. for 12 h in a seal tube. The reaction mixture was filtered through celite, filtrate was diluted with EtOAc, washed with water followed by brine. The organic layer was dried over sodium sulphate, and concentrated. The crude was purified over silica gel using 15% EtOAc/hexane as eluant to give title compound as brown solid (0.15 g, 56%): MS (ESI) m/z 756 (M+H)$^+$.

78

Step 8: 3-(3-(1H-Indol-2-yl)-7-(piperazin-1-yl)-10H-phenothiazin-10-yl)propan-1-amine

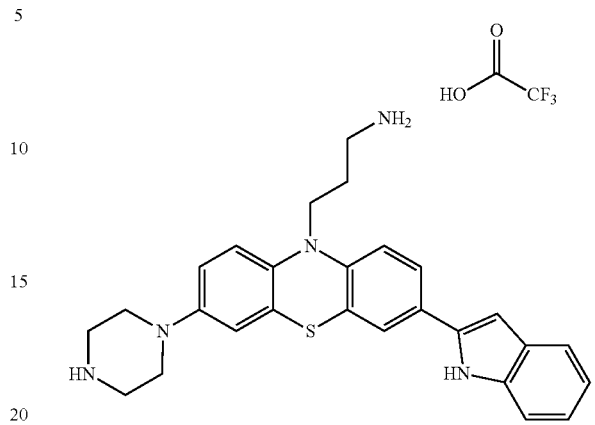

To a stirred solution of tert-butyl 2-(10-(3-((tert-butoxycarbonyl)amino)propyl)-7-(4-(tert-butoxycarbonyl)piperazin-1-yl)-10H-phenothiazin-3-yl)-1H-indole-1-carboxylate (0.15 g, 0.19 mmol) in dichloromethane (10 mL) was added TFA (2 mL) at 0° C. and stirring continued at room temperature for 12 h. The reaction mixture was concentrated, residue was basified with saturated sodium bicarbonate solution, extracted with dichloromethane, the organic layer was dried over sodium sulphate, and concentrated. Crude product was purified by prep. HPLC to give the title compound as brown solid (25 g, 22%): $^1$H NMR (DMSO-d$_6$, 400 MHz) δ 1.93-1.97 (m, 2H), 2.85-2.95 (m, 2H), 3.20-3.23 (m, 8H), 6.79 (s, 1H), 6.84-6.87 (m, 2H), 6.93-6.98 (m, 2H), 7.02-7.09 (m, 2H), 7.33-7.47 (m, 2H), 7.65-7.68 (m, 2H), 7.72 (bs, 3H, TFA salt), 8.78 (bs, 2H, TFA salt), 11.39 (s, 1H); MS (ESI) m/z 456.2 (M+H)$^+$; HPLC purity: 99.38%.

Some examples of compounds synthesised by the method of Scheme XV are provided in Table.

TABLE XV

| Cmpd # | R$^3$ | R$^1$ | R$^6$ |
|---|---|---|---|
| 286 | piperazine-CH$_2$CH$_2$NH$_2$ · HCl | propyl-NH$_2$ | 3,5-dimethylpiperidinyl |
| 291 | piperazine-CH$_2$CH$_2$NH$_2$ · HCl | propyl-NH$_2$ | pyrrolidinyl |

TABLE XV-continued

| Cmpd # | R³ | R¹ | R⁶ |
|---|---|---|---|
| 292 | 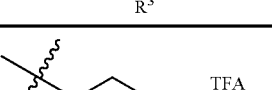 TFA | 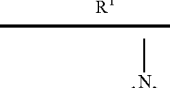 | CN |

Figure 16:
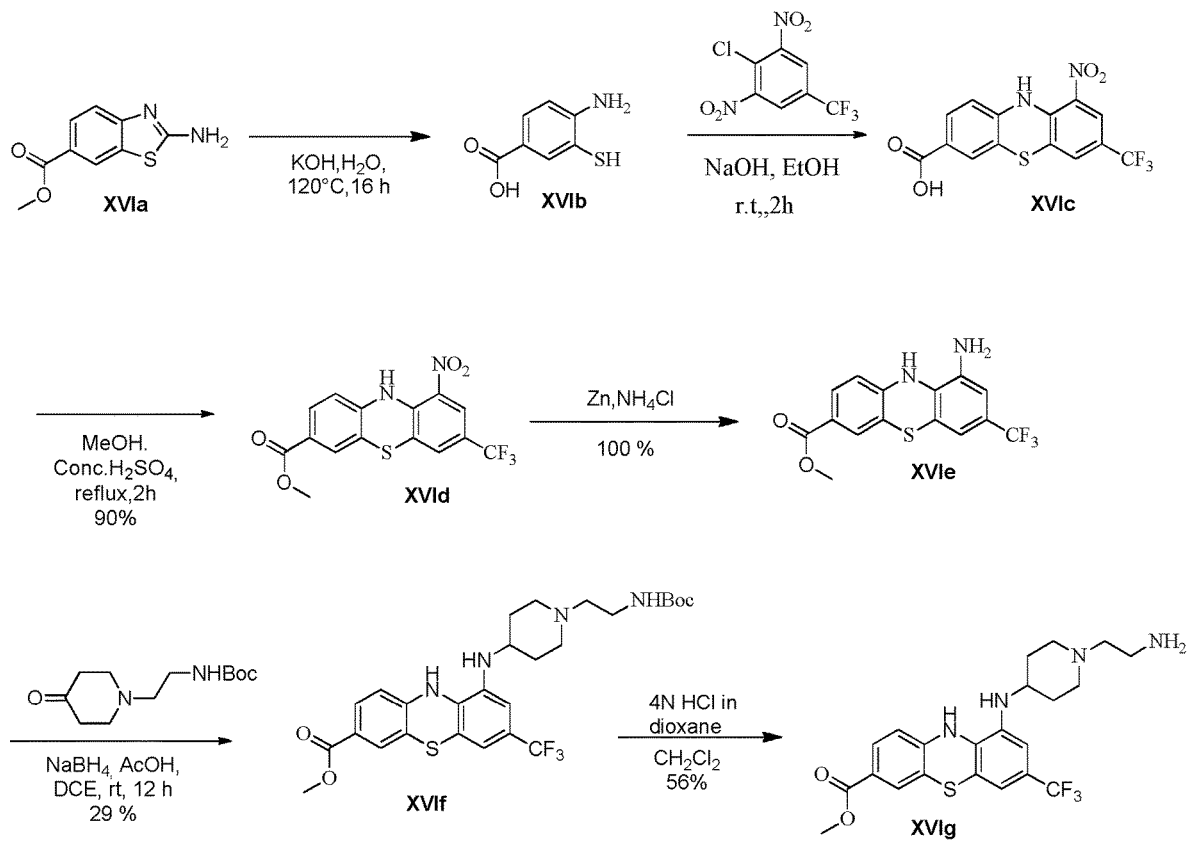
FIG. 16 shows general synthetic scheme XVI for the synthesis of selected compounds according to the present invention.

FIG. 16 shows general synthetic scheme XVI for the synthesis of selected trisubstituted phenothiazenes. Substituted benzothiazoles XVIa were hydrolysed with potassium hydroxide to the corresponding aminothiols XVIb, which on nucleophilic substitution with aryl halides followed by insituSmiles rearrangement gave the corresponding substituted phenothiazene XVIc. Esterification of XVIc followed by reduction of nitro group gave the corresponding amines XVIe, which on reductive amination with appropriate carbonyl compounds gave the compound XVIf, which is deprotected with acid to give the title compound XVIg.

A detailed synthetic description of a compound synthesised by the method of Scheme XVI is provided below.

Compound 247: Methyl 9-((1-(2-aminoethyl)piperidin-4-yl)amino)-7-(trifluoromethyl)-10H-phenothiazine-3-carboxylate

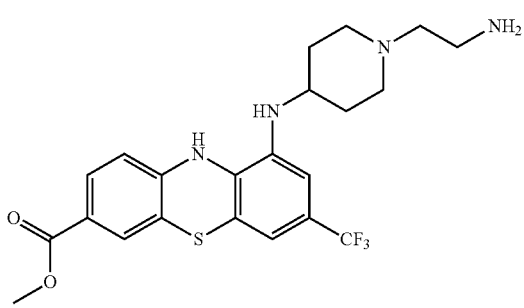 [SMILES: COC(=O)c1ccc2c(c1)Sc1cc(C(F)(F)F)cc(NC3CCN(CCN)CC3)c1N2]

Step 1: 4-Amino-3-mercaptobenzoic Acid

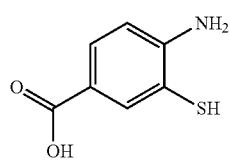 [SMILES: Nc1ccc(C(=O)O)cc1S]

A solution of methyl 2-aminobenzo[d]thiazole-6-carboxylate (2 g, 9.61 mmol)) in water (25 mL) was heated at 100° C. for 16 h. Reaction mixture was neutralized with citric acid, extracted with ethyl acetate, the combined organic phase was dried over Na₂SO₄, and concentrated to get the title compound as off white solid (1.625 g, 90%): MS (ESI) m/z 170 (M+H)⁺.

Step 2: 9-Nitro-7-(trifluoromethyl)-10H-phenothiazine-3-carboxylic Acid

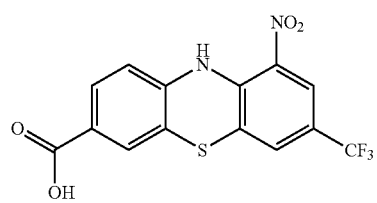 [SMILES: O=C(O)c1ccc2c(c1)Sc1cc(C(F)(F)F)cc([N+](=O)[O-])c1N2]

To a stirred solution of 4-amino-3-mercaptobenzoic acid (1.6 g, 9.31 mmol) and 2-chloro-1,3-dinitro-5-(trifluoromethyl)benzene (1.5 g, 7.57 mmol) in EtOH (30 mL) was added NaOH (1.1 g, 28.3 mmol) and stirring continued for 16 h. The reaction mixture was diluted with water, neutralized with citric acid solution, solid was filtered, and dried by azeotropic distillation using toluene to gave title compound as brown solid (1.6 g, crude). MS(ESI)355 (M–H)⁺.

Step 3: Methyl 9-nitro-7-(trifluoromethyl)-10H-phenothiazine-3-carboxylate

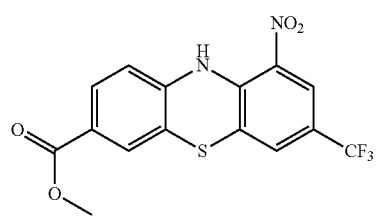 [SMILES: COC(=O)c1ccc2c(c1)Sc1cc(C(F)(F)F)cc([N+](=O)[O-])c1N2]

To a stirred solution of 9-nitro-7-(trifluoromethyl)-10H-phenothiazine-3-carboxylic acid (0.2 g, 0.561 mmol) in MeOH (10 mL) was added conc. H₂SO₄ (0.1 mL) and reaction mixture was refluxed for 2 h. The reaction mixture was concentrated, residue was diluted with EtOAc, and washed with sat. NaHCO₃ solution, dried over sodium sulphate, and concentrated to gave title compound as brown solid (0.18 g, 90%): MS(ESI)369 (M–H)⁺.

Step 4: Methyl 9-amino-7-(trifluoromethyl)-10H-phenothiazine-3-carboxylate

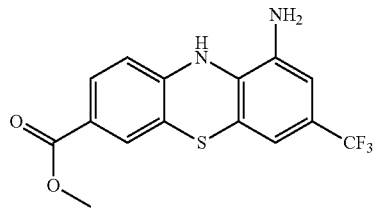 [SMILES: COC(=O)c1ccc2c(c1)Sc1cc(C(F)(F)F)cc(N)c1N2]

To a stirred solution of methyl 9-nitro-7-(trifluoromethyl)-10H-phenothiazine-3-carboxylate (0.18 g, 0.48 mmol) were added Zn dust (0.158 g, 2.43 mmol), NH$_4$Cl (0.128 g, 2.43 mmol) and stirring continued for 2 h. The reaction mixture was filtered and evaporated to gave title compound as yellow solid (0.165 g, quantitative): MS(ESI) 339 (M−H)$^+$.

Step 5: Methyl 9-((1-(2-((tert-butoxycarbonyl)amino)ethyl)piperidin-4-yl)amino)-7-(trifluoromethyl)-10H-phenothiazine-3-carboxylate

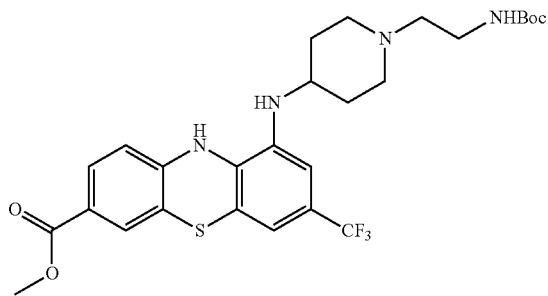 [SMILES: COC(=O)c1ccc2c(c1)Sc1cc(C(F)(F)F)cc(NC3CCN(CCNC(=O)OC(C)(C)C)CC3)c1N2]

To a stirred solution of methyl 9-amino-7-(trifluoromethyl)-10H-phenothiazine-3-carboxylate (0.25 g, 0.73 mmol)) in 1,2-dichloroethane (5 mL) were added tert-butyl (2-(4-oxopiperidin-1-yl)ethyl)carbamate (0.266 g, 1.10 mmol), AcOH (0.1 mL), sodium borohydride (0.28 g, 7.35 mmol) and stirring continued for 12 h. The reaction mixture was washed with sodium bicarbonate solution, extracted with ethyl acetate, the combined organic phase was dried over Na$_2$SO$_4$, concentrated, and the crude product was purified by column chromatography using 5-10% MeOH/DCM as eluent to give title compound as yellow solid (0.12 g, 29%): MS (ESI) m/z 567 (M+H)$^+$.

Step 6: Methyl 9-((1-(2-aminoethyl)piperidin-4-yl)amino)-7-(trifluoromethyl)-10H-phenothiazine-3-carboxylate

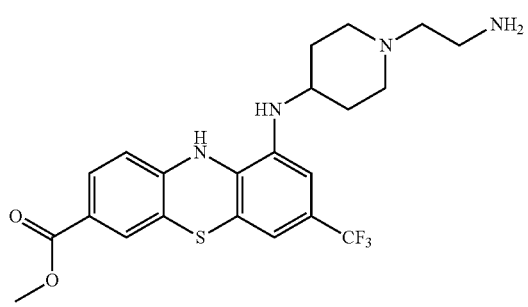 [SMILES: COC(=O)c1ccc2c(c1)Sc1cc(C(F)(F)F)cc(NC3CCN(CCN)CC3)c1N2]

To a stirred solution of methyl 9-((1-(2-((tert-butoxycarbonyl)amino)ethyl)piperidin-4-yl)amino)-7-(trifluoromethyl)-10H-phenothiazine-3-carboxylate (0.02 g, 0.035 mmol) in dichloromethane (5 mL) was added a solution of 4 N HCl in dioxane (1 mL) at 0° C. and stirring continued at room temperature for 1 h. The reaction mixture was concentrated, dissolved in saturated sodium bicarbonate solution, extracted with dichloromethane, and concentrated. The residue was washed with DCM/n-pentane (1:10) to gave the title compound as brown solid (0.009 g, 56%): $^1$H NMR (DMSO-d$_6$, 400 MHz) δ, 1.43-1.45 (m, 2H), 1.88-2.07 (m, 5H), 2.30-2.32 (m, 2H), 2.81 (s, 3H), 3.75 (s, 3H) 5.30 (s, 1H), 6.53 (s, 1H), 6.59 (s, 1H), 6.92 (d, J=8.4 Hz, 1H), 7.42 (s, 1H), 7.60 (d, J=8.4 Hz, 1H), 8.44 (bs, 1H); MS (ESI) 467 (M+H)$^+$; HPLC purity: 99.43%.

Figure 17:
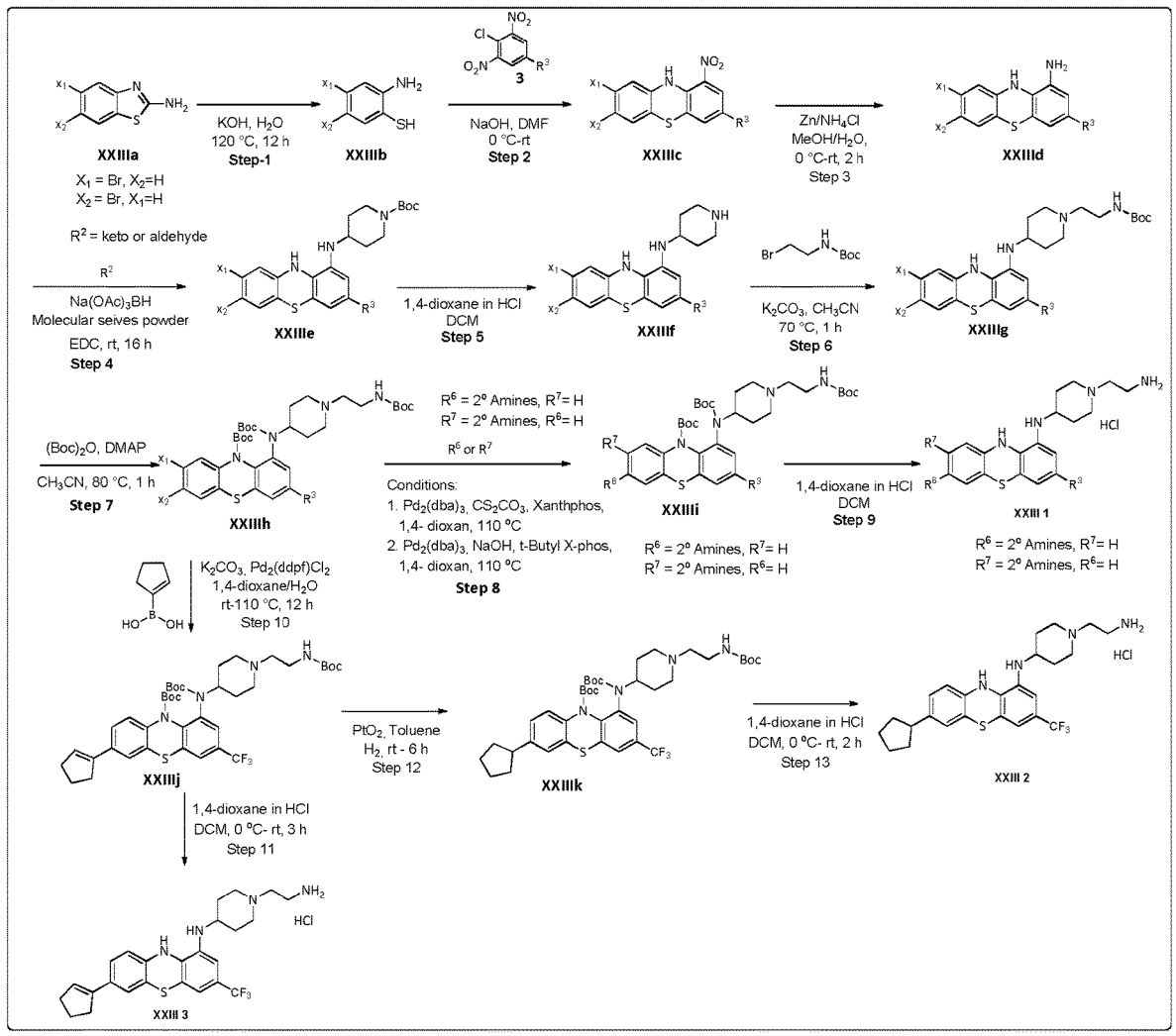
FIG. 17 shows general synthetic scheme XXIII for the synthesis of selected compounds according to the present invention.

FIG. 17 shows general reaction scheme XXIII for the synthesis of selected 1, 3, 6-trisubstituted phenothiazenes. 6-bromobenzo[d]thiazol-2-amine or 7-bromobenzo[d]thiazol-2-amine (XXIIIa)hydrolized with KOH then Nucleophilic substitution of 2-amino 5-bromo thiophenol or 2-amino 4-bromo thiophenol/2-amino 5-bromophenols or 2-amino 4-bromo thiophenol (XXIIIb) with substituted aryl halides (XXIIIb) followed by insituSmiles rearrangement yielded substituted phenothiazene/substituted phenoxazines (XXIIIc). Compounds XXIIIc were reduced using Zn/NH4Cl to yield the corresponding 1-amino 6-bromophenothiazenes or 1-amino 7-bromophenothiazenes/1-amino 6-bromo phenoxazines or 1-amino 7-bromophenothiazenes (XXIIId). Reductive amination of compound XXIIId with various aldehydes or ketones yielded corresponding n-alkylated phenothiazines XXIIIe, which were further deprotected to give the corresponding free amines XXIIIf. and alkylated to give XXIIIg. Further protection of the XXIIIg with boc anhydride to give tri protected compounds of XXIIIh. Further Buchwald coupling of compound XXIIIh with various amines, followed by deprotection gave XXIII 1 with corresponding salts. And Further Suzuki coupling of compound of XXVIIIh with boronic acids followed by deprotection gave XXIII 3 with corresponding salts and also with XXIIIj double bond reduction with platinum oxide and followed by deprotection gave XXIII 2

Compound 272: N-(1-(2-aminoethyl)piperidin-4-yl)-7-(4-aminopiperidin-1-yl)-3-(trifluoromethyl)-10H-phenothiazin-1-amine

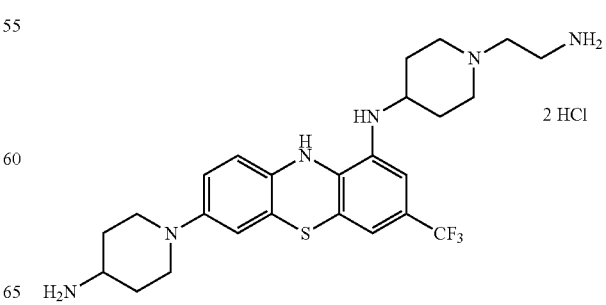

Step 1: 2-amino-5-bromobenzenethiol

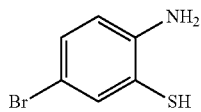

To a stirred solution of 6-bromobenzo[d]thiazol-2-amine (100 g, 436.68 mmol, compound-1) in H$_2$O (1000 mL) was added potassium hydroxide (500 g, 8928.57 mmol) portion wise for a period of 30 min at 0° C. and stirred the reaction mixture at 120° C. for 12 h. The Progress of the reaction was monitored by TLC. The reaction mixture was cooled to 0° C., neutralized with Acetic acid (pH~7) at 0° C. and stirred at rt. After stirring the reaction mixture for 10 min, was added toluene (2×500 mL), the combined organic layer was washed with water (500 mL), dried over anhydrous sodium sulphate and concentrated under reduced pressure below 50° C. The crude compound was purified by adding ethanol (400 mL), stirred at reflux temperature for 20 min. The compound was cooled to room temperature, solid was filtered and dried under vacuum to afford 2-amino-5-bromobenzenethiol (50 g, yield: 56%) as yellow solid. $^1$H NMR (400 MHz, DMSO-d$_6$) δ 5.7 (s, 2H), 6.85 (d, J=2.3 Hz, 1H), 7.2 (d, J=6.3 Hz, 1H), 7.2-7.3 (d, J=6.3 Hz 1H). LC-MS m/z (M+H): 204.0

Step 2: 7-bromo-1-nitro-3-(trifluoromethyl)-10H-phenothiazine

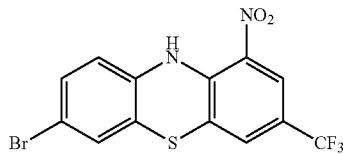

To a stirred solution of 2-amino-5-bromobenzenethiol (30 g, 147.05 mmol), 2-chloro-1,3-dinitro-5-(trifluoromethyl) benzene (39.9 g, 147.77 mmol) in DMF (150 mL) was added sodium hydroxide (188 g, 441.15 mmol) at 0° C. and stirred the reaction mixture at room temperature for 2 h. Progress of the reaction was monitored by TLC. The reaction mixture was quenched with ice-cold water (200 mL), extracted with ethyl acetate (2×300 mL). The combined organic layer was washed with water (500 mL), dried over anhydrous sodium sulphate filtered and concentrated under reduced pressure. The crude compound was diluted with ethanol (120 mL), stirred for 20 min solid was filtered and dried under vacuum to afford 7-bromo-1-nitro-3-(trifluoromethyl)-10H-phenothiazine (10 g, yield: 17%) as black solid. $^1$H NMR (400 MHz, DMSO-d$_6$) 7.0 (d, J=8.52 Hz, 1H), 7.2-7.3 (d, J=2.15 Hz, 2H), 7.7 (s, 1H), 8.0 (s, 1H), 9.8 (s, 1H).

Step 3: 7-bromo-3-(trifluoromethyl)-10H-phenothiazin-1-amine

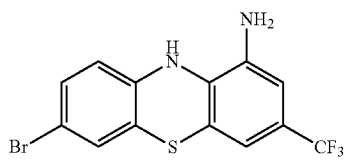

To a stirred solution of 7-bromo-1-nitro-3-(trifluoromethyl)-10H-phenothiazine (11 g, 28.13 mmol) in MeOH (110 ml) water (50 mL) was added Zn powder (9.13 g, 140.46 mmol), NH$_4$Cl (7.5 g, 140.44 mmol) at 0° C. and stirred the reaction mixture at room temperature for 2 h. The progress of the reaction was monitored by TLC. The reaction mixture was filtered through a pad of celite; the filtrate was evaporated under reduced pressure. The residue was diluted with EtOAc (500 mL), washed with water (500 mL). The organic layer was dried over anhydrous sodium sulphate and concentrated under reduced pressure. The crude compound was purified by gradient column chromatography (eluted with 20% EtOAc in Hexane) to afford 7-bromo-3-(trifluoromethyl)-10H-phenothiazin-1-amine (8 g, yield: 80%) as black solid. $^1$H NMR (400 MHz, DMSO-d$_6$) δ 5.4-5.6 (m, 2H), 6.5 (s, 1H), 6.7-6.8 (d, J=8.48 Hz, 2H), 7.2-7.3 (m, 21H), δ 7.9-8.0 (s, 1H). LC-MS m/z (M+H): 361.04

Step 4: tert-butyl 4-((7-bromo-3-(trifluoromethyl)-10H-phenothiazin-1-yl)amino)piperidine-1-carboxylate

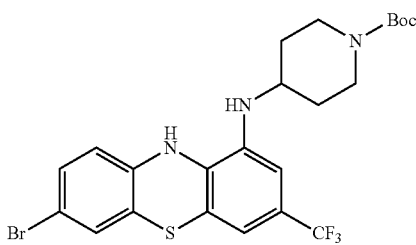 [SMILES: CC(C)(C)OC(=O)N1CCC(Nc2cc(C(F)(F)F)cc3c2Nc2ccc(Br)cc2S3)CC1]

To a stirred solution of 7-bromo-3-(trifluoromethyl)-phenothiazin-1-amine (4 g, 11.11 mmol), in 1,2-dichloroethane (100 mL) was added tert-butyl 4-oxopiperidine-1-carboxylate (4.42 g, 22.22 mmol,) and 4 A° Molecular sieves powder (10 g) at room temperature After stirring the reaction mixture for 1 h was added sodium triacetoxy borohydride (11.77 g, 56.03 mmol). Reaction mixture was stirred at room temperature for 16 h. The reaction mixture was quenched with sat NaHCO$_3$ solution, extracted with ethyl acetate (2×70 mL). The combined organic layer was dried over anhydrous sodium sulphate and concentrated under reduced pressure. The crude compound was purified by gradient column chromatography (eluted with 20% EtOAc in Hexane) to afford tert-butyl 4-((7-bromo-3-(trifluoromethyl)-10H-phenothiazin-1-yl)amino)piperidine-1-carboxylate (5 g, yield: 83%) as green solid. $^1$H NMR (400 MHz, DMSO-d$_6$) δ 1.2-1.3 (m, 2H), 1.4 (s, 9H), 1.9 (d, J=21.46 Hz, 2H), 2.9-3.0 (br, 2H), 3.5-3.6 (m, 1H), 3.8-3.9 (m, 2H), 5.2 (d, J=7.16 Hz, 1H), 6.5 (s, 1H), 6.6 (s, 1H), 6.7 (d, J=8.42 Hz, 2H), 7.2 (m, 2H), 8.0 (s, 1H). LC-MS m/z (M+H): 544.0.

Step 5: 7-bromo-N-(piperidin-4-yl)-3-(trifluoromethyl)-10H-phenothiazin-1-amine

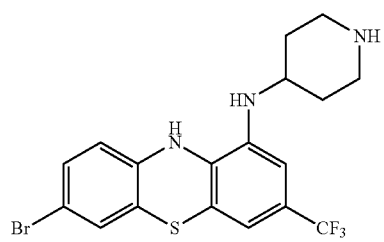

To a stirred solution of tert-butyl 4-((7-bromo-3-(trifluoromethyl)-10H-phenothiazin-1-yl)amino)piperidine-1-carboxylate (5 g, 9.19 mmol) in DCM (50 mL) was added 4M HCl in 1,4-dioxane (10 mL) at 0° C. and stirred the reaction mixture at room temperature for 1 h. Progress of the reaction was monitored by TLC. The reaction mixture was evaporated under reduced pressure. The residue was basified with saturated NaHCO$_3$ solution (PH-7 to 8), extracted with ethyl acetate (2×100 mL). The combined organic layer was dried over anhydrous sodium sulphate and concentrated under reduced pressure to afford 7-bromo-N-(piperidin-4-yl)-3-(trifluoromethyl)-10H-phenothiazin-1-amine (3.4 g, yield: 85%) as green solid. $^1$H NMR (400 MHz, DMSO-d$_6$) δ 1.2 (s, 2H), 1.3-1.4 (m, 2H), 1.9 (m, 2H), 2.6-2.7 (t, J=10.98 Hz, 2H), 3.0-3.07 (m, 2H), 3.4-3.43 (m, 1H), 5.2 (d, J=3.06 Hz, 1H), 6.5 (s, 1H), 6.6 (s, 1H), 6.8 (d, J=8.43 Hz, 1H), 7.2-7.23 (m, 2H), 8.1 (s, 1H). LC-MS m/z (M+H): 444.0.

Step 6: tert-butyl (2-(4-((7-bromo-3-(trifluoromethyl)-10H-phenothiazin-1-yl)amino)piperidin-1-yl)ethyl)carbamate

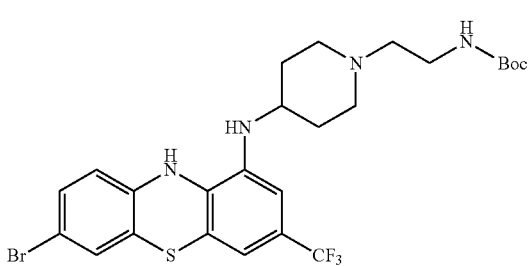

To a stirred solution of 7-bromo-N-(piperidin-4-yl)-3-(trifluoromethyl)-10H-phenothiazin-1-amine (3.4 g, 7.67 mmol) in Acetonitrile (34 mL) was added K$_2$CO$_3$ (3.17 g, 22.97 mmol) followed by tert-butyl (2-chloroethyl)carbamate (1.79 g, 9.97 mmol) at 0° C. and stirred the reaction mixture at 70° C. for 1 h. The progress of the reaction was monitored by TLC. The reaction mixture was cooled to room temperature, reaction mixture was diluted with water (20 mL), extracted with ethyl acetate (2×100 mL). The combined organic layer was dried over anhydrous sodium sulphate and concentrated under reduced pressure. The crude compound was purified by gradient column chromatography (eluted with 2-8% EtOAc in Hexane) to afford tert-butyl (2-(4-((7-bromo-3-(trifluoromethyl)-10H-phenothiazin-1-yl)amino)piperidin-1-yl)ethyl)carbamate (700 mg, yield: 16%) as yellow solid. $^1$H NMR (400 MHz, DMSO-d$_6$) δ 1.3 (s, 1H), 1.9-2.1 (m, 2H), 2.1-2.2 (m, 2H), 3.1-3.2 (m, 2H), 3.3-3.4 (m, 5H), 5.6 (s, 1H), 6.2 (s, 1H), 6.5 (s, 1H), 6.6 (d, J=27.67 Hz, 2H), 7.1 (d, J=24.63 Hz, 1H), 7.2 (m, 2H), 8.3-8.4 (m, 4H), 10.9 (s, 1H). LC-MS m/z (M+H): 587.19.

Step 7: tert-butyl 7-bromo-1-((tert-butoxycarbonyl)(1-(2-((tert-butoxycarbonyl) amino)ethyl) piperidin-4-yl) amino)-3-(trifluoromethyl)-10H-phenothiazine-10-carboxylate

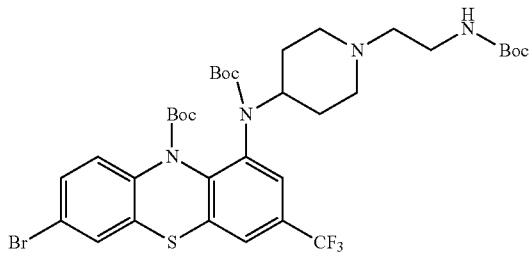 [SMILES: CC(C)(C)OC(=O)NCCN1CCC(N(C(=O)OC(C)(C)C)c2cc(C(F)(F)F)cc3c2N(C(=O)OC(C)(C)C)c2ccc(Br)cc2S3)CC1]

To a stirred solution of tert-butyl (2-(4-((7-bromo-3-(trifluoromethyl)-10H-phenothiazin-1-yl)amino)piperidin-1-yl)ethyl)carbamate (700 mg, 1.19 mmol) in Acetonitrile (10 mL) was added DMAP (364 mg, 2.98 mmol) followed by ditert-butyl dicarbonate (0.78 mL, 3.57 mmol) at 0° C. and stirred the reaction mixture at 80° C. for 1 h. The progress of the reaction was monitored by TLC. The reaction mixture was cooled to room temperature, reaction mixture was diluted with water (10 mL) and extracted with ethyl acetate (2×50 mL). The combined organic layer was dried over anhydrous sodium sulphate filtered and concentrated under reduced pressure. The crude compound was purified by gradient column chromatography (eluted with 2-8% EtOAc in Hexane) to afford tert-butyl 7-bromo-1-((tert-butoxycarbonyl)(1-(2-((tert-butoxycarbonyl) amino)ethyl) piperidin-4-yl) amino)-3-(trifluoromethyl)-10H-phenothiazine-10-carboxylate (700 mg, yield: 74%) as off white solid. $^1$H NMR (400 MHz, DMSO-d$_6$) δ 1.3 (s, 2H), 1.3 (s, 10H), 1.5 (s, 19H), 1.6-165 (m, 2H), 1.8-1.9 (m, 1H), 1.91-2.01 (m, 1H), 2.1-2.2 (m, 2H), 2.4-2.56 (m, 2H), 2.8-2.89 (m, 2H), 3.4-3.5 (m, 1H), 3.6 (1, J=6.63 Hz, 2H), 3.5-3.6 (br, 1H), 6.8 (s, 1H), 6.9 (s, 1H), 7.6 (d. J=2.17 Hz 1H), 7.8-7.9 (m, 1H). LC-MS m/z (M+H): 787.2.

Step 8: tert-butyl 1-((tert-butoxycarbonyl)(1-(2-((tert-butoxycarbonyl)amino)ethyl)piperidin-4-yl) amino)-7-(4-((tert-butoxycarbonyl)amino)piperidin-1-yl)-3-(trifluoromethyl)-10H-phenothiazine-10-carboxylate

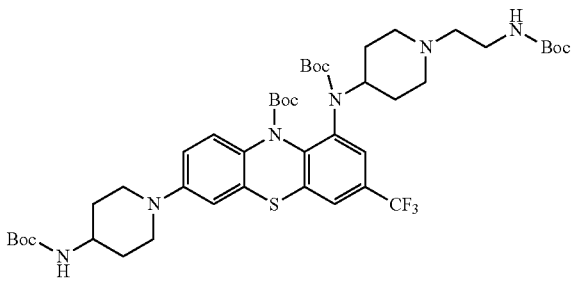 [SMILES: CC(C)(C)OC(=O)NCCN1CCC(N(C(=O)OC(C)(C)C)c2cc(C(F)(F)F)cc3c2N(C(=O)OC(C)(C)C)c2ccc(N4CCC(NC(=O)OC(C)(C)C)CC4)cc2S3)CC1]

To a stirred solution of tert-butyl 7-bromo-1-((tert-butoxycarbonyl)(1-(2-((tert-butoxycarbonyl) amino)ethyl) piperidin-4-yl) amino)-3-(trifluoromethyl)-10H-phenothiazine-10-carboxylate (190 mg, 0.24 mmol), tert-butyl piperidin-4-ylcarbamate (62.4 mg, 0.31 mmol) in 1 4 Dioxane (4 mL) was added cesium carbonate (195 mg, 0.6 mmol) at room temperature. After degassed with argon for 10 min was added Pd$_2$(dba)$_3$ (21.9 mg, 0.02 mmol), Xanthphos, (27.7 mg, 0.04 mmol) again degassed for 5 min and stirred the reaction mixture at 110° C. for 16 h. The progress of the reaction was monitored by TLC. The reaction mixture was diluted with water (10 mL), extracted with ethyl acetate (2×20 mL). The combined organic layer was dried over anhydrous sodium sulphate and concentrated under reduced pressure. The crude compound was purified by gradient column chromatography (eluted with 2-3% MeOH/DCM) to afford tert-butyl 1-((tert-butoxycarbonyl)(1-(2-((tert-butoxycarbonyl)amino)ethyl)piperidin-4-yl)amino)-7-(4-((tert-butoxycarbonyl)amino)piperidin-1-yl)-3-(trifluoromethyl)-10H-phenothiazine-10-carboxylate (30 mg, yield: 13%) as grey solid. $^1$H NMR (400 MHz, DMSO-d$_6$) δ 1.3 (s, 9H), 1.33 (s, 18H), 1.44-1.46 (m, 20H), 1.89-1.97 (m, 3H), 2.10-2.25 (m, 5H), 2.42-2.49 (m, 2H), 2.72-2.85 (m, 4H), 3.41 (brs, 2H), 3.56-3.64 (m, 4H), 6.81-6.90 (m, 2H), 6.93-6.98 (m, 3H), 7.51 (d, J=8.59 Hz, 1H), LC-MS m/z (M+H): 906.1

Step 9: N-(1-(2-aminoethyl)piperidin-4-yl)-7-(4-aminopiperidin-1-yl)-3-(trifluoromethyl)-10H-phenothiazin-1-amine

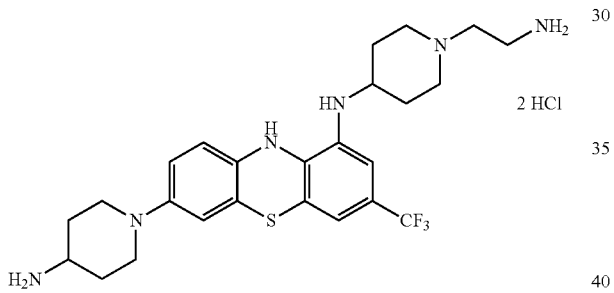

To a stirred solution of tert-butyl 1-((tert-butoxycarbonyl) (1-(2-((tert-butoxycarbonyl)amino)ethyl)piperidin-4-yl) amino)-7-(4-((tert-butoxycarbonyl)amino)piperidin-1-yl)-3-(trifluoromethyl)-10H-phenothiazine-10-carboxylate (45 mg, 0.04 mmol) in DCM (1 mL) was added 4M HCl in 1,4-dioxane (3 mL) at 0° C. and stirred the reaction mixture at room temperature for 2 h. The progress of the reaction was monitored by TLC. The reaction mixture was concentrated under reduced pressure. The crude compound was washed with ether (2×2 mL) and dried under reduced pressure to afford N-(1-(2-aminoethyl) piperidin-4-yl)-7-(4-aminopiperidin-1-yl)-3-(trifluoromethyl)-10H-phenothiazin-1-amine (20 mg, yield: 83%) as off white solid.

$^1$H NMR (400 MHz, DMSO-d$_6$) δ 1.93-1.99 (m, 4H), 2.11 (d, J=10.7 Hz, 4H), 2.91 (s, 2H), 3.11-3.19 (m, 2H), 3.31-3.39 (m, 8H), 3.61-3.68 (m, 5H), 6.61 (d, J=22.4 Hz, 2H), 7.09 (s, 1H), 7.20-7.43 (m, 2H), 8.32 (d, J=17.5 Hz, 6H), 8.61 (s, 1H), 10.89 (s, 1H). LC-MS m/z (M+H): 507.1

Compound 359: N-(1-(2-aminoethyl) piperidin-4-yl)-7-(cyclopent-1-en-1-yl)-3-(trifluoromethyl)-10H-phenothiazin-1-amine hydrochloride

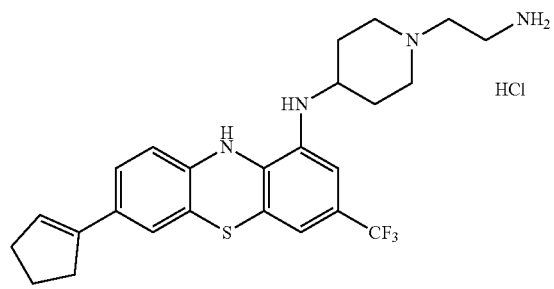 [SMILES: NCCN1CCC(Nc2cc(C(F)(F)F)cc3c2Nc2ccc(C4=CCCC4)cc2S3)CC1 ; Cl]

Step 10: tert-butyl 1-((tert-butoxycarbonyl)(1-(2-((tert-butoxycarbonyl)amino)ethyl)piperidin-4-yl) amino)-7-(cyclopent-1-en-1-yl)-3-(trifluoromethyl)-10H-phenothiazine-10-carboxylate

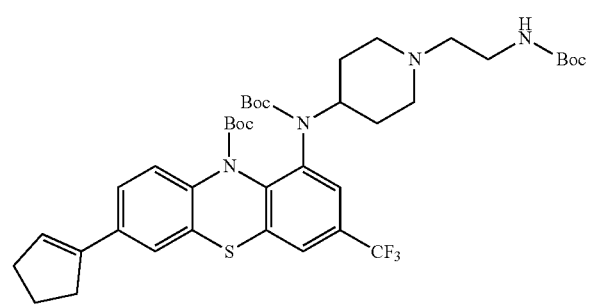 [SMILES: CC(C)(C)OC(=O)NCCN1CCC(N(C(=O)OC(C)(C)C)c2cc(C(F)(F)F)cc3c2N(C(=O)OC(C)(C)C)c2ccc(C4=CCCC4)cc2S3)CC1]

To a stirred solution of tert-butyl 7-bromo-1-((tert-butoxycarbonyl)(1-(2-((tert-butoxycarbonyl)amino)ethyl)piperidin-4-yl)amino)-3-(trifluoromethyl)-10H-phenothiazine-10-carboxylate (200 mg, 0.254 mmol) in 1 4 Dioxane/H$_2$O (8 mL) was added potassium carbonate (70 mg, 0.508 mmol) at room temperature. After degassed with argon for 10 min was added cyclopent-1-en-1-ylboronic acid (58 mg, 0.508 mmol,) and was added Pd2(dppf)Cl2 DCM complex. (11 mg, 0.05 mmol) again degassed for 5 min and stirred the reaction mixture at 110° C. for 12 h. Progress of the reaction was monitored by TLC. The reaction mixture was filtered through a pad of celite; the filtrate was concentrated under reduced pressure. The crude compound was purified by combi-flash chromatography (eluted with 2-3% EA in Pet Ether) followed by preparative TLC to afford tert-butyl 1-(1-(2-(tert-butoxycarbonylamino) ethyl) piperidin-4-ylamino)-7-cyclopentenyl-3-(trifluoromethyl)-10H-phenothiazine-10-carboxylate as sticky liquid (85 mg, yield: 62%). $^1$H NMR (400 MHz, DMSO-d$_6$) δ 1.22 (s, 9H), 1.3 (s, 18H), 1.5-1.6 (m, 3H), 1.81-1.9 (m, 1H), 1.97 (t, J=7.4 Hz, 3H), 2.17-2.2 (m, 2H), 2.31-2.39 (m, 1H), 2.43 (t, J=6.72 Hz, 2H), 2.6-2.7 (m, 2H), 2.84-2.89 (m, 2H), 3.29-3.43 (m, 1H), 3.56 (t, J=6.5 Hz, 2H), 5.42 (br, 1H), 6.34 (s, 1H), 6.84 (s, 1H), 6.96 (s, 1H), 7.46 (d, J=8.3 Hz, 1H), 7.51 (s, 1H), 7.71 (d, J=8.32 Hz, 1H). LC-MS m/z (M+H): 775

Step 11: N-(1-(2-aminoethyl) piperidin-4-yl)-7-(cyclopent-1-en-1-yl)-3-(trifluoromethyl)-10H-phenothiazin-1-amine hydrochloride

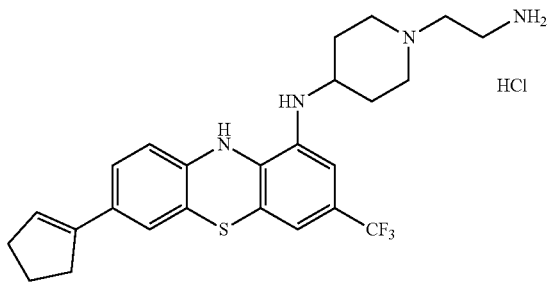 [SMILES: NCCN1CCC(Nc2cc(C(F)(F)F)cc3c2Nc2ccc(C4=CCCC4)cc2S3)CC1 ; Cl]

To a stirred solution of tert-butyl 1-(1-(2-(tert-butoxycarbonylamino) ethyl) piperidin-4-ylamino)-7-cyclopentenyl-3-(trifluoromethyl)-10H-phenothiazine-10-carboxylate (30 mg, 0.03870 mmol) in CH$_2$Cl$_2$ (1 mL) was added 1,4-dioxane HCl (2 mL) at 0° C. and stirred the reaction mixture at rt for 3 h. The progress of the reaction was monitored by TLC. The reaction mixture was concentrated under reduced pressure. The crude compound was triturated with n-pentane (2×2 mL) and dried n to afford N-(1-(2-aminoethyl) piperidin-4-yl)-7-(cyclopent-1-en-1-yl)-3-(trifluoromethyl)-10H-phenothiazin-1-amine hydrochloride as pale yellow solid. (14 mg, yield: 77%). $^1$H NMR (400 MHz, DMSO-d$_6$) δ1.8-1.9 (m, 3H), 2.1 (d, J=16.1 Hz, 2H), 2.4-2.5 (m, 2H), 2.5-2.6 (m, 2H), 3.1-3.2 (m, 2H), 3.3-3.4 (m, 4H), 3.6-3.7 (m, 3H), 6.1 (s, 1H), 6.5-6.6 (m, 2H), 7.01 (s, 2H), 7.2 (d, J=7.2 Hz 1H), 8.2 (br s, 4H). LC-MS m/z (M+H): 475.2

Compound 354: N-(1-(2-aminoethyl) piperidin-4-yl)-7-cyclopentyl-3-(trifluoromethyl)-10H-phenothiazin-1-amine hydrochloride

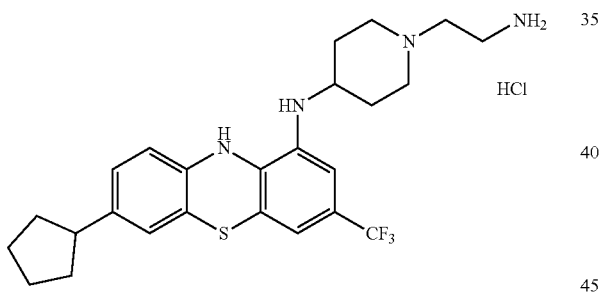

Step 12: tert-butyl 1-((tert-butoxycarbonyl)(1-(2-((tert-butoxycarbonyl)amino)ethyl)piperidin-4-yl)amino)-7-cyclopentyl-3-(trifluoromethyl)-10H-phenothiazine-10-carboxylate

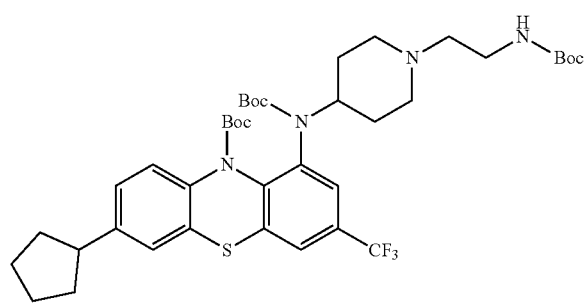 [SMILES: CC(C)(C)OC(=O)NCCN1CCC(N(C(=O)OC(C)(C)C)c2cc(C(F)(F)F)cc3c2N(C(=O)OC(C)(C)C)c2ccc(C4CCCC4)cc2S3)CC1]

To a stirred solution of tert-butyl 1-((tert-butoxycarbonyl)(1-(2-((tert-butoxycarbonyl)amino)ethyl)piperidin-4-yl)amino)-7-(cyclopent-1-en-1-yl)-3-(trifluoromethyl)-10H-phenothiazine-10-carboxylate (50 mg, 0.06459 mmol) in Toluene (5 mL) was added platinum oxide (30 mg) at room temperature under H$_2$ atmosphere for 6 h. The progress of the reaction was monitored by TLC. The reaction mixture was filtered through celite bed filtrate was concentrated under reduced pressure, crude product was purified by prep TLC (30% ethyl acetate/n-Hexane) to afford tert-butyl 1-((tert-butoxycarbonyl)(1-(2-((tert-butoxycarbonyl)amino)ethyl)piperidin-4-yl)amino)-7-cyclopentyl-3-(trifluoromethyl)-10H-phenothiazine-10-carboxylate as colorless sticky solid (21 mg, yield: 42%). LC-MS m/z (M+H): 777.1

Step 13: N-(1-(2-aminoethyl) piperidin-4-yl)-7-cyclopentyl-3-(trifluoromethyl)-10H-phenothiazin-1-amine hydrochloride

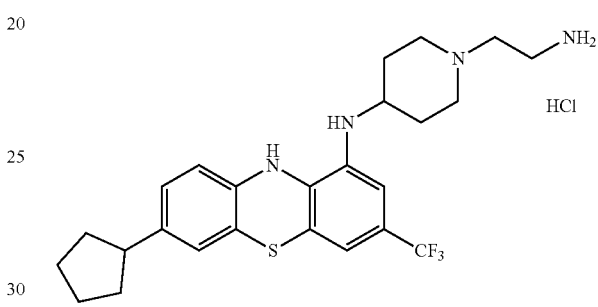

To a stirred solution of tert-butyl 1-((tert-butoxycarbonyl)(1-(2-((tert-butoxycarbonyl)amino)ethyl)piperidin-4-yl)amino)-7-cyclopentyl-3-(trifluoromethyl)-10H-phenothiazine-10-carboxylate (52 mg, 0.073 mmol) in DCM (1 mL) was added 1,4-dioxane HCl (2 mL) at 0° C. and stirred the reaction mixture at room temperature for 3 h. The progress of the reaction was monitored by TLC. The reaction mixture was concentrated under reduced pressure. The crude compound was triturated with n-pentane (2×2 mL) and dried to afford N-(1-(2-aminoethyl) piperidin-4-yl)-7-cyclopentyl-3-(trifluoromethyl)-10H-phenothiazin-1-amine hydrochloride as pale yellow solid (12 mg, yield: 100%). $^1$H NMR (400 MHz, DMSO-d$_6$) δ 1.4-1.49 (m, 2H), 1.6-1.7 (m, 2H), 1.7-1.8 (m, 2H), 1.9-2.0 (m, 4H), 2.1 (d, J=13.1 Hz, 2H), 2.8-2.9 (m, 1H), 3.1-3.2 (m, 2H), 3.27-3.33 (m, 4H), 3.6 (d, J=11.8 Hz, 3H), 5.6 (br s, 1H), 6.6 (s, 1H), 6.7 (s, 1H), 6.8 (s, 1H), 6.9 (d, J=8.4 Hz, 2H), 8.2 (br s, 4H), 10.94 (br s, 1H). LC-MS m/z (M+H): 477.2

Some examples of compounds synthesised by the method of Scheme XXIII are provided in Table XXIII

TABLE XXIII

| Cmpd # | R¹ | R³ | R⁶ | R⁷ |
|---|---|---|---|---|
| 269 | 4-piperidinyl (NH) | CF₃ | 4-(2-aminoethyl)piperazin-1-yl | H |
| 270 | 4-piperidinyl (NH) | CF₃ | piperazin-1-yl | H |
| 319 | 4-[2-(piperazin-1-yl)ethyl]piperidin-1-yl-amino | CF₃ | Br | H |
| 330 | 4-[2-(piperazin-1-yl)ethyl]piperidin-1-yl-amino | CF₃ | pyrrolidin-1-yl | H |
| 324 | HN-CH₂CH₂CH₂-NH₂ | CF₃ | pyrrolidin-1-yl | H |
| 333 | HN-CH₂CH₂CH₂-NH₂ | CF₃ | Br | H |
| 272 | 1-(2-aminoethyl)piperidin-4-yl-amino | CF₃ | 4-aminopiperidin-1-yl | H |
| 273 | 1-(2-aminoethyl)piperidin-4-yl-amino | CF₃ | 4-(2-aminoethyl)piperazin-1-yl | H |

TABLE XXIII-continued

| Cmpd # | R¹ | R³ | R⁶ | R⁷ |
|---|---|---|---|---|
| 274 | 4-(2-aminoethyl)amino-piperidinyl | CF₃ | 3,5-dimethylpiperidin-1-yl | H |
| 275 | 4-(2-aminoethyl)amino-piperidinyl | CF₃ | 2,6-dimethylmorpholin-4-yl | H |
| 282 | 4-(2-aminoethyl)amino-piperidinyl | CF₃ | Br | H |
| 283 | 4-(2-aminoethyl)amino-piperidinyl | CF₃ | 3,5-dimethylpiperazin-1-yl | H |
| 284 | 4-(2-aminoethyl)amino-piperidinyl | CF₃ | pyrrolidin-1-yl | H |
| 289 | 4-(2-aminoethyl)amino-piperidinyl | CF₃ | piperidin-1-yl | H |
| 295 | 4-(2-aminoethyl)amino-piperidinyl | CF₃ | 4-(dimethylamino)piperidin-1-yl | H |
| 296 | 4-(2-aminoethyl)amino-piperidinyl | CF₃ | azetidin-1-yl | H |

TABLE XXIII-continued

| Cmpd # | R¹ | R³ | R⁶ | R⁷ |
|---|---|---|---|---|
| 299 | 4-((2-aminoethyl)piperidin-1-yl)-NH- | CF₃ | 3-(dimethylamino)pyrrolidin-1-yl | H |
| 301 | 4-((2-aminoethyl)piperidin-1-yl)-NH- | CF₃ | 3-methylpiperidin-1-yl | H |
| 303 | 4-((2-aminoethyl)piperidin-1-yl)-NH- | CF₃ | 3,3-difluoropyrrolidin-1-yl | H |
| 305 | 4-((2-aminoethyl)piperidin-1-yl)-NH- | CF₃ | 3,3-dimethylpiperidin-1-yl | H |
| 306 | 4-((2-aminoethyl)piperidin-1-yl)-NH- | CF₃ | diethylamino | H |
| 307 | 4-((2-aminoethyl)piperidin-1-yl)-NH- | CF₃ | 4-methylpiperidin-1-yl | H |
| 310 | 4-((2-aminoethyl)piperidin-1-yl)-NH- | CF₃ | indolin-1-yl | H |

TABLE XXIII-continued

| Cmpd # | R¹ | R³ | R⁶ | R⁷ |
|---|---|---|---|---|
| 311 | piperidine-N-CH₂CH₂NH₂, 4-HN- | CF₃ | 3-methylpyrrolidin-1-yl | H |
| 342 | piperidine-N-CH₂CH₂NH₂, 4-HN- | CF₃ | 3-(trifluoromethyl)pyrrolidin-1-yl | H |
| 314 | piperidine-N-CH₂CH₂NH₂, 4-HN- | CF₃ | 2-methylpiperidin-1-yl | H |
| 316 | piperidine-N-CH₂CH₂NH₂, 4-HN- | CF₃ | 2-methylpyrrolidin-1-yl | H |
| 318 | piperidine-N-CH₂CH₂NH₂, 4-HN- | CF₃ | 3-fluoropiperidin-1-yl | H |
| 320 | piperidine-N-CH₂CH₂NH₂, 4-HN- | CF₃ | 3-isopropylpiperidin-1-yl | H |
| 321 | piperidine-N-CH₂CH₂NH₂, 4-HN- | CF₃ | 3-methoxypyrrolidin-1-yl | H |

TABLE XXIII-continued

| Cmpd # | R¹ | R³ | R⁶ | R⁷ |
|---|---|---|---|---|
| 322 | 4-(ethylamine)piperidinyl-NH- | $CF_3$ | 2-azaspiro[4.4]nonan-2-yl | H |
| 325 | 4-(ethylamine)piperidinyl-NH- | $CF_3$ | 2-azaspiro[3.3]heptan-2-yl | H |
| 326 | 4-(ethylamine)piperidinyl-NH- | $CF_3$ | 3-methoxypiperidin-1-yl | H |
| 327 | 4-(ethylamine)piperidinyl-NH- | $CF_3$ | 2-azabicyclo[2.2.1]heptan-2-yl | H |
| 330 | 4-(ethylamine)piperidinyl-NH- | $CF_3$ | 3,3-dimethylpyrrolidin-1-yl | H |
| 334 | 4-(ethylamine)piperidinyl-NH- | $CF_3$ | N,N-dimethylamino | H |
| 335 | 4-(ethylamine)piperidinyl-NH- | $CF_3$ | Br-CH< | H |

TABLE XXIII-continued

| Cmpd # | R¹ | R³ | R⁶ | R⁷ |
|---|---|---|---|---|
| 336 | piperidine-CH₂CH₂NH₂ with HN linker | CF₃ | 2,3-dimethylpyrrolidin-1-yl | H |
| 337 | piperidine-CH₂CH₂NH₂ with HN linker | CF₃ | 2,2-dimethylazetidin-1-yl | H |
| 338 | piperidine-CH₂CH₂NH₂ with HN linker | CF₃ | 3-carbamoylpyrrolidin-1-yl | H |
| 339 | piperidine-CH₂CH₂NH₂ with HN linker | CF₃ | N-methyl-N-ethylamino | H |
| 329 | piperidine-CH₂CH₂NH₂ with HN linker | CH₃ | Br | H |
| 340 | piperidine-CH₂CH₂NH₂ with HN linker | CF₃ | octahydrocyclopenta[b]pyrrol-1-yl | H |

TABLE XXIII-continued

| Cmpd # | R¹ | R³ | R⁶ | R⁷ |
|---|---|---|---|---|
| 341 | 4-(HN-)piperidine-N-CH₂CH₂NH₂ | CF₃ | 2,5-dimethylpyrrolidin-N-yl | H |
| 354 | 4-(HN-)piperidine-N-CH₂CH₂NH₂ | CF₃ | cyclopentyl | H |
| 359 | 4-(HN-)piperidine-N-CH₂CH₂NH₂ | CF₃ | cyclopentenyl | H |
| 352 | 4-(HN-)piperidine-N-CH₂CH₂NH₂ | CF₃ | H | Br |
| 356 | 4-(HN-)piperidine-N-CH₂CH₂NH₂ | CF₃ | H | pyrrolidin-N-yl |
| 357 | 4-(HN-)piperidine-N-CH₂CH₂NH₂ | CF₃ | H | 3,5-dimethylpiperazin-N-yl |

Figure 18:
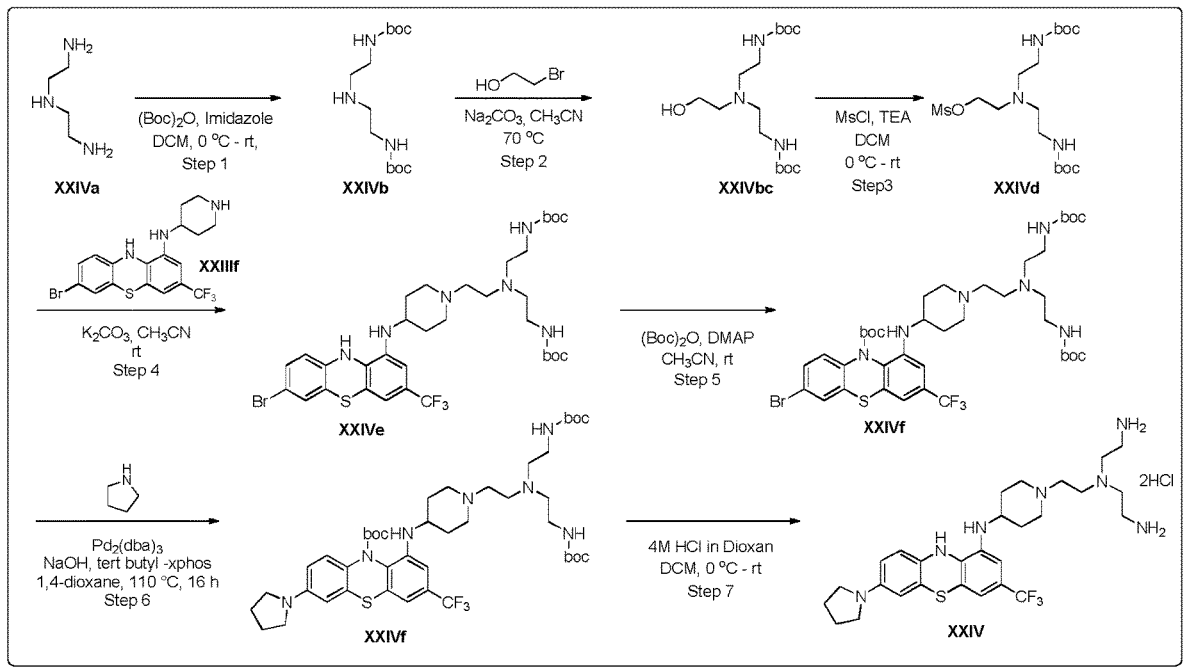
FIG. 18 shows general synthetic scheme XXIV for the synthesis of selected compounds according to the present invention.

FIG. 18 shows general reaction scheme XXIV for the synthesis of selected 1, 3, 6-trisubstituted phenothiazenes. Boc protection of 2-aminoethyl)ethane-1,2-diamine (XXIVa) with alkylation with bromo ethanol (XXIVb) followed by mestylation yielded diboc protected 2-(bis(2-aminoethyl)amino)ethyl methanesulfonate to yield XXIVd. Compound XXIVd were n-alkylated with XXIIIf yielded corresponding n-alkylated phenothiazines XXIVe. Further protection of the XXIVe with boc anhydride to give tri protected compounds of XXIVf. Further Buchwald coupling of compound XXIVg with various amine, followed by deprotection gave XXIV with corresponding salts.

Compound 335: N1-(2-aminoethyl)-N1-(2-(4-((7-(pyrrolidin-1-yl)-3-(trifluoromethyl)-10H-phenothiazin-1-yl)amino)piperidin-1-yl)ethyl)ethane-1,2-diamine hydrochloride

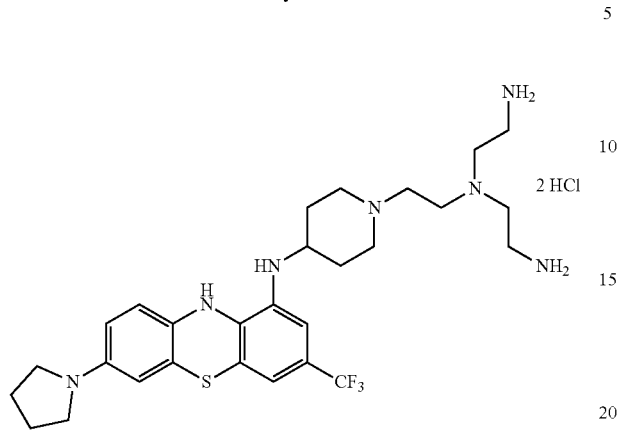

Step 1: di-tert-butyl (azanediylbis(ethane-2,1-diyl))dicarbamate

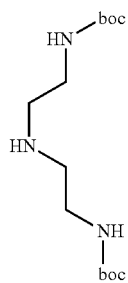

To a stirred solution of imidazole (5 g, 73.52 mmol) in DCM (5 mL) was added di tert-butyl dicarbonate (15.25 g, 69.95 mmol) at room temperature and stirred for 2 h. After completion of the reaction, diluted with 100 mL of DCM and washed with water (50 mL) and organic layer was dried over sodium sulfate, filtered and concentrated to give crude residue to this was added N1-(2-aminoethyl)ethane-1,2-diamine (3.5 mL, 33.98 mmol) and stirred for 1 h at room temperature. After completion of the reaction, diluted with water (10 mL) extracted with DCM (2×20 mL). Combined organic layers were dried over sodium sulfate, filtered and evoparted to give crude residue, which was purified by gradient chromatography (Product eluted with 5% MeOH/DCM) to afford di-tert-butyl (azanediylbis(ethane-2,1-diyl)) dicarbamate as a colorless liquid (4.3 g, 40%). $^1$H NMR (400 MHz, CDCl$_3$) δ 1.44 (s, 18H), 2.73 (t, J=5.79 Hz, 4H), 4.9 (s, 1H).

Step 2: di-tert-butyl (((2-hydroxyethyl)azanediyl)bis(ethane-2,1-diyl))dicarbamate

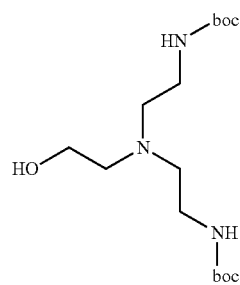

To a solution of di-tert-butyl (azanediylbis(ethane-2,1-diyl))dicarbamate (3.7 g, 12.19 mmol) in acetonitrile (40 mL) was added sodium carbonate (12.92 g, 122.88 mmol) at room temperature and stirred for 10 min., then 2-bromo ethanol (3.81 g) was added to the reaction mixture and stirred at 70° C. for 16 h. After completion of the reaction, diluted with water (10 mL) extracted with ethyl acetate (2×50 mL). The combined organic layers were dried over sodium sulfate, filtered and concentrated to give crude residue, which was purified by gradient chromatography (product eluted with 5% of Methanol/DCM) to give di-tert-butyl (((2-hydroxyethyl)azanediyl)bis(ethane-2,1-diyl))dicarbamate as colorless liquid (3.8 g, 90%). $^1$H NMR (400 MHz, DMSO-d$_6$) δ 1.28 (s, 18H), 2.41-2.49 (m, 6H), 2.90-2.95 (m, 4H), 3.34-3.38 (m, 2H)

Step 3: 2-(bis(2-((tert-butoxycarbonyl)amino)ethyl)amino)ethyl methanesulfonate

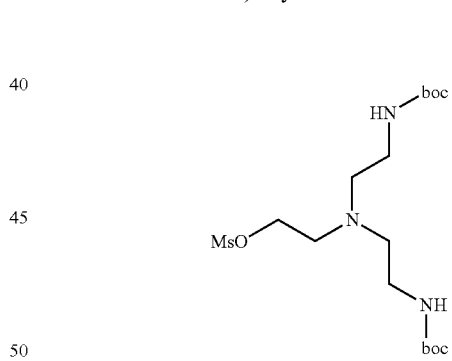

To a stirred solution of di-tert-butyl (((2-hydroxyethyl) azanediyl) bis (ethane-2, 1-diyl)) dicarbamate (0.75 g, 2.158 mmol) in DCM (15 mL) was added triethyl amine (0.45 g, 4.447 mmol) and mesyl chloride (0.3 g, 2.589 mmol) at 0° C. Reaction mixture was stirred at room temperature for 1 h. After completion of the reaction, diluted with ice water (15 mL) and extracted with DCM (2×20 mL). Combined organic layers was washed with saturated sodium bi carbonate (10 mL) and followed by water (10 mL). Organic layer was dried over sodium sulfate, filtered and evaporated to give 2-(bis (2-((tert-butoxycarbonyl) amino) ethyl) amino) ethyl methanesulfonate as brown liquid (crude, 0.8 g), which was used for the next without further purification.

Step 4: di-tert-butyl (((2-(4-((7-bromo-3-(trifluoromethyl)-10H-phenothiazin-1-yl)amino)piperidin-1-yl)ethyl)azanediyl)bis(ethane-2,1-diyl))dicarbamate

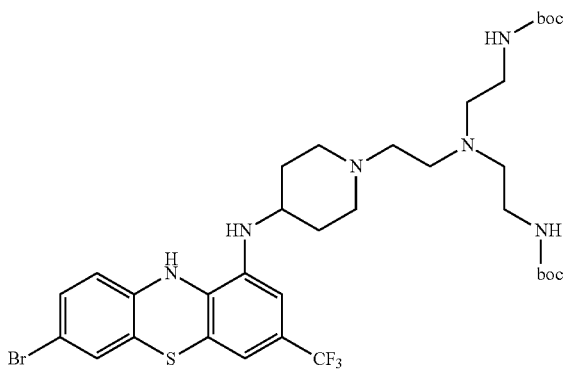

To a stirred solution of 7-bromo-N-(piperidin-4-yl)-3-(trifluoromethyl)-10H-phenothiazin-1-amine (0.2 g, 0.45 mmol) in Acetonitrile (12 mL) was added potassium carbonate (0.075 g, 0.542 mmol) stirred for 10 min., room temperature. To this 2-(bis (2-((tert-butoxycarbonyl) amino) ethyl) amino) ethyl methanesulfonate (0.235 g, 0.552 mmol) was added and stirred at room temperature for 16 h. After completion of the reaction, diluted with ethyl acetate (25 mL) and washed with water (10 mL). Organic layer was dried over sodium sulfate, filtered and evoparted to give crude residue, which was purified by gradient chromatography (product eluted with 4% methanol/DCM) to give di-tert-butyl (((2-(4-((7-bromo-3-(trifluoromethyl)-10H-phenothiazin-1-yl)amino)piperidin-1-yl)ethyl)azanediyl)bis (ethane-2,1-diyl))dicarbamate as blue solid (65 mg, 18.6%). $^1$H NMR (400 MHz, DMSO-d$_6$): δ 1.4 (s, 23H), 1.4-1.5 (m, 2H), 1.9 (m, 2H), 2.1 (m, 2H), 2.3 (m, 1H), 2.8-2.9 (m, 2H), 2.9-3.0 (m, 5H), 5.2 (br, 1H), 6.6 (m, 4H), 6.8 (db, J=8.29 Hz, 1H), 7.2 (m, 2H), 8.1 (s, 1H)

Step 5: tert-butyl 1-((1-(2-(bis(2-((tert-butoxycarbonyl)amino)ethyl)amino)ethyl)piperidin-4-yl)amino)-7-bromo-3-(trifluoromethyl)-10H-phenothiazine-10-carboxylate

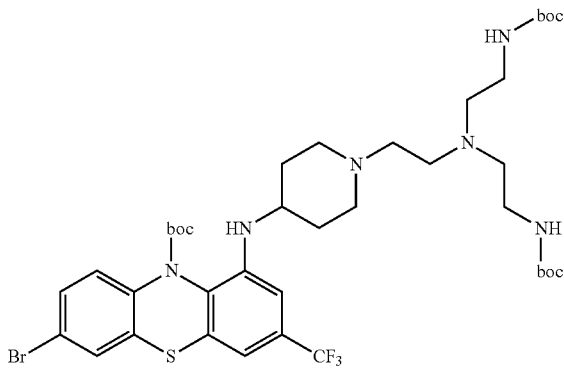

To stirred solution of di-tert-butyl (((2-(4-((7-bromo-3-(trifluoromethyl)-10H-phenothiazin-1-yl)amino)piperidin-1-yl)ethyl)azanediyl)bis(ethane-2,1-diyl))dicarbamate (0.3 g, 0.387 mmol) in Acetonitrile (15 mL) was added 4-dimethyl amine pyridine (0.165 g, 1.356 mmol) and di tert-butyl dicarbamate (0.422 g, 1.938 mmol). Reaction mixture was stirred at room temperature for 3 h. After completion of the reaction, diluted with ethyl acetate (25 mL) and washed with water (10 mL). Organic layer was dried over sodium sulfate, filtered and evaporated to give crude product, which was purified a by gradient chromatography (product eluted with 3% methanol/DCM) to give tert-butyl 1-((1-(2-(bis(2-((tert-butoxycarbonyl)amino)ethyl)amino)ethyl)piperidin-4-yl)amino)-7-bromo-3-(trifluoromethyl)-10H-phenothiazine-10-carboxylate as brown solid (0.104 g, 30%). $^1$H NMR (400 MHz, DMSO-d$_6$): δ 1.3 (s, 29H), 1.4 (d, J=3.29 Hz, 3H), 1.5-1-57 (m, 1H), 1.7-1.9 (m, 2H), 2.1-2.2 (m, 2H), 2.3-2.39 (m, 2H), 2.4-2.6 (m, 6H), 2.8-2.89 (m, 1H), 2.9-3.01 (m, 1H), 3.01-3.2 (m, 4H), 3.4-3.45 (m, 1H), 6.6-6.79 (m, 1H), 6.8 (s, 1H), 6.9 (s, 1H), 7.5-7.6 (dd, J=1.8 Hz, 1H), 7.8 (m, 2H)

Step 6: tert-butyl 1-((1-(2-(bis(2-((tert-butoxycarbonyl)amino)ethyl)amino)ethyl)piperidin-4-yl)amino)-7-(pyrrolidin-1-yl)-3-(trifluoromethyl)-10H-phenothiazine-10-carboxylate

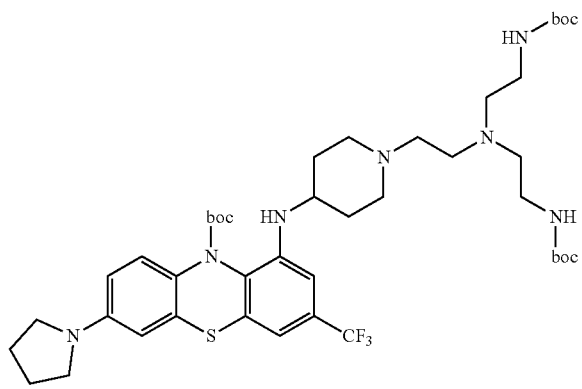

To a stirred solution of tert-butyl 1-((1-(2-(bis(2-((tert-butoxycarbonyl)amino)ethyl)amino)ethyl)piperidin-4-yl)amino)-7-bromo-3-(trifluoromethyl)-10H-phenothiazine-10-carboxylate (0.080 g, 0.0916 mmol), Pyrrolidine (13 mg, 0.183 mmol) in 1, 4 Dioxane (3 mL) was added sodium hydroxide (9.1 mg, 0.229 mmol) in water (0.5 mL) at room temperature. After degassed with argon for 10 min was added Pd$_2$(dba)$_3$ (8.39 mg, 0.009 mmol), tert butyl Xphos, (5.82 mg, 0.0137 mmol) again degassed for 5 min and stirred the reaction mixture at 110° C. for 16 h. The progress of the reaction was monitored by TLC. The reaction mixture was diluted with water (10 mL), extracted with ethyl acetate (2×20 mL). The combined organic layer was dried over anhydrous sodium sulfate and concentrated under reduced pressure. The crude compound was purified by gradient column chromatography (eluted with 6% MeOH/DCM) to afford tert-butyl 1-((1-(2-(bis(2-((tert-butoxycarbonyl)amino)ethyl)amino)ethyl)piperidin-4-yl)amino)-7-(pyrrolidin-1-yl)-3-(trifluoromethyl)-10H-phenothiazine-10-carboxylate (35 mg, yield: 43.75%) as brown solid. $^1$H NMR (400 MHz, DMSO-d$_6$): δ 1.3 (s, 28H), 1.5-1.59 (m, 1H), 1.6-1.7 (m, 1H), 1.8-2.0 (m, 6H), 2.1-2.2 (m, 2H), 2.3-2.39 (m, 1H), 2.4-2.6 (m, 5H), 2.7-2.9 (m, 2H), 2.9-3.0 (m, 4H), 3.2-3.3 (m, 4H), 3.4-3.45 (m, 1H), 5.2 (br, 1H), 6.5-6.61 (m, 2H), 6.62-6.65 (m, 2H), 6.8 (s, 1H), 6.9 (s, 1H), 7.4 (d, J=0.0216 Hz, 1H)

Step 7: N1-(2-aminoethyl)-N1-(2-(4-((7-(pyrrolidin-1-yl)-3-(trifluoromethyl)-10H-phenothiazin-1-yl)amino)piperidin-1-yl)ethyl)ethane-1,2-diamine hydrochloride

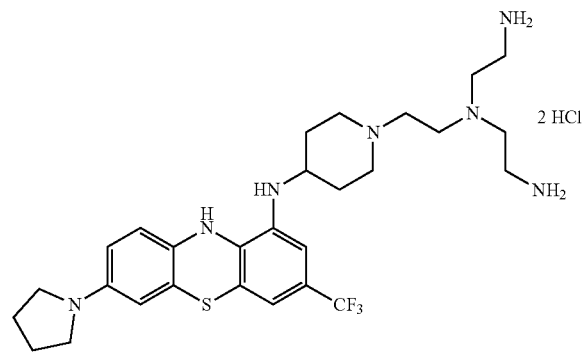 [SMILES: NCCN(CCN)CCN1CCC(Nc2cc(C(F)(F)F)cc3c2Nc2ccc(N4CCCC4)cc2S3)CC1]

To a stirred solution of tert-butyl 1-((1-(2-(bis(2-((tert-butoxycarbonyl)amino)ethyl)amino)ethyl)piperidin-4-yl)amino)-7-(pyrrolidin-1-yl)-3-(trifluoromethyl)-10H-phenothiazine-10-carboxylate (35 mg, 0.04 mmol) in DCM (0.3 mL) was added 4M HCl in 1,4-dioxane (1 mL) at 0° C. and stirred the reaction mixture at room temperature for 1 h. The progress of the reaction was monitored by TLC. The reaction mixture was concentrated under reduced pressure. The crude compound was washed with n-Pentane (5 mL) and dried under reduced pressure to afford N1-(2-aminoethyl)-N1-(2-(4-((7-(pyrrolidin-1-yl)-3-(trifluoromethyl)-10H-phenothiazin-1-yl)amino)piperidin-1-yl)ethyl)ethane-1,2-diamine hydrochloride (25 mg, yield: 100%) as grey solid. $^1$H NMR (400 MHz, DMSO-$d_6$): δ 1.8-2.2 (m, 6H), 2.7-2.79 (m, 3H), 2.8-2.9 (m, 2H), 3.0-3.09 (m, 4H), 3.1-3.2 (m, 1H), 3.3-3.5 (m, 4H), 3.6-3.7 (m, 2H), 6.5-7.4 (m, 2H), 8.2 (br, 5H), 10.3 (br, 1H)

Some examples of compounds synthesised by the method of Scheme XXIV are provided in Table XXIV

TABLE XXIV

| Cmpd # | R$^6$ |
|---|---|
| 331 | 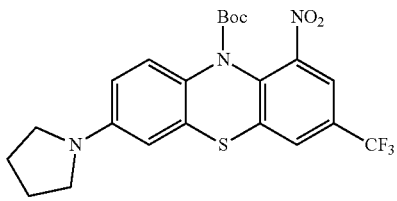 |
| 335 | |

Figure 19:
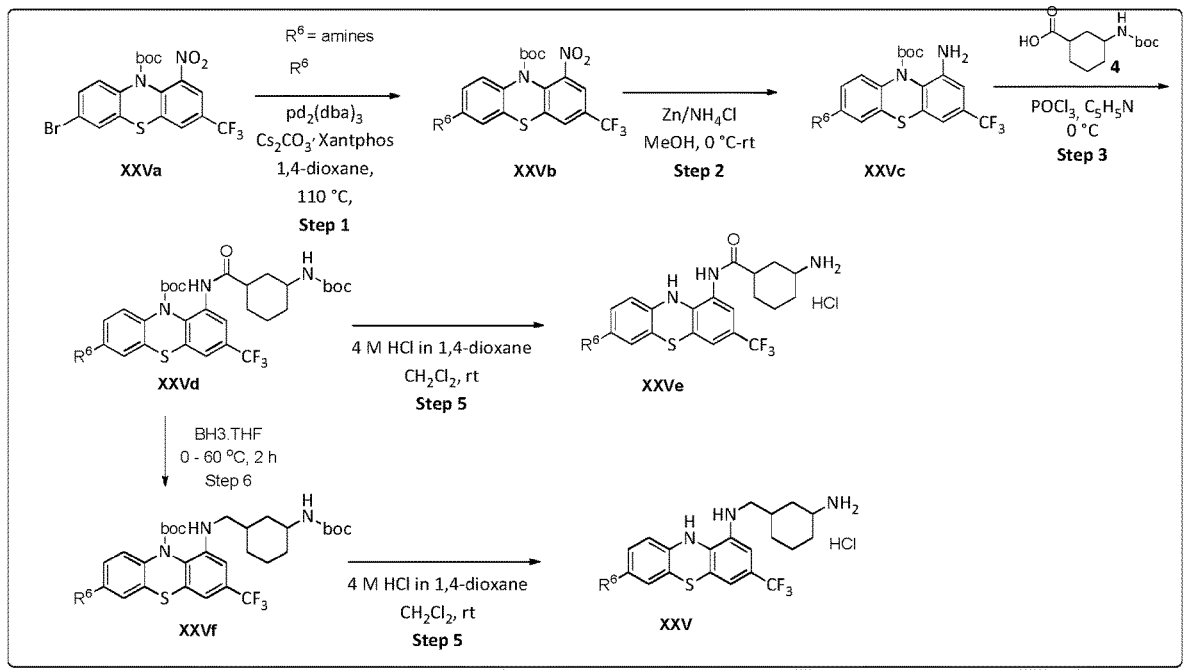

FIG. 19 shows general reaction scheme XXV for the synthesis of selected 1, 3, 6-trisubstituted phenothiazenes. Buchwald coupling of nitro bromo phenothiazines (XXVa) yielded substituted phenothiazene/substituted phenoxazines (XXVb). Compounds XXVb were redusing Zn/NH4Cl to yield the corresponding 1-amino 6-substituted phenothiazenes/1-amino 6-substituted phenoxazines (XXVc). Compounds XXVc were reacted with acid chlorides or acids to form corresponding amides XXVd, further deprotection gave XXVe with corresponding salts and XXVd reduction with boran DMS to give XXVf, further deprotection gave XXV with corresponding salts.

Compound 300: N-((3-aminocyclohexyl)methyl)-7-(pyrrolidin-1-yl)-3-(trifluoromethyl)-10H-phenothiazin-1-amine

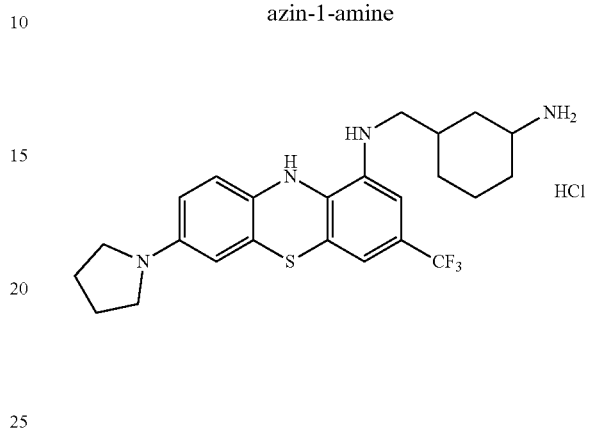

Step-1: Synthesis of tert-butyl 1-nitro-7-(pyrrolidin-1-yl)-3-(trifluoromethyl)-10H-phenothiazine-10-carboxylate To a stirred solution of tert-butyl 7-bromo-1-nitro-3-(trifluoromethyl)-10H-phenothiazine-10-carboxylate (1 g, 2.55 mmol) and pyrrolidine (907 mg, 12.78 mmol) in 1,4-Dioxan (20 mL) was added cessium carbonate (2.49 g, 7.67 mmol) at room temperature, then degassed with argon for 15 min. Then added xantphos (295 mg, 0.511 mmol) and Pd$_2$(dba)$_3$ (234 mg, 0.255 mmol) degassed for 5 min. The reaction mixture was stirred at 110° C. for 12 h. The progress of the reaction was monitored by TLC. Reaction mixture was cooled to room temperature, filtered through celite bed washed with ethyl acetate (100 mL). Filtrate was concentrated under reduced pressure. The crude compound was purified by column chromatography (silica gel 60-120 mesh, eluted with 2-3% EtOAc in pet ether) to afford tert-butyl 1-nitro-7-(pyrrolidin-1-yl)-3-(trifluoromethyl)-10H-phenothiazine-10-carboxylate (850 mg, yield: 87%) as brown solid.

1H NMR (400 MHz, DMSO-d6) δ 1.32 (s, 9H), 1.94-1.96 (m, 4H), 3.22-3.30 (m, 4H), 6.59-6.61 (m, 2H), 7.33-7.37 (m, 1H), 7.45-7.46 (m, 1H), 7.70-7.80 (m, 1H), 8.27 (brs, 1H), 8.32 (s, 1H). LC-MS m/z (M+H): 482.1

Step-2: Synthesis of tert-butyl 1-amino-7-(pyrrolidin-1-yl)-3-(trifluoromethyl)-10H-phenothiazine-10-carboxylate

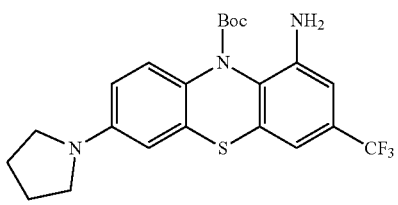 [SMILES: CC(C)(C)OC(=O)N1c2ccc(N3CCCC3)cc2Sc2cc(C(F)(F)F)cc(N)c21]

To a stirred solution of tert-butyl 1-nitro-7-(pyrrolidin-1-yl)-3-(trifluoromethyl)-10H-phenothiazine-10-carboxylate (850 mg, 1.76 mmol, step-1) in 1,4-Dioxan/H$_2$O (10 mL, 7:3) was added Zn (918 mg, 14.13 mmol) followed by ammonium chloride (791 mg, 14.13 mmol) at 0° C. Then reaction mixture was stirred at rt for 15 h. The progress of the reaction was monitored by TLC. The reaction mixture was filtered through a pad of celite, washed with ethyl acetate (100 mL). Filtrate was washed with brine solution (50 mL). The combined organic layer was dried over anhydrous sodium sulphate and concentrated under reduced pressure to afford tert-butyl 1-amino-7-(pyrrolidin-1-yl)-3-(trifluoromethyl)-10H-phenothiazine-10-carboxylate (700 mg, yield: 88%) as brown solid. 1H NMR (400 MHz, DMSO-d6) δ 1.34 (s, 9H), 1.94-1.97 (m, 4H), 3.20-3.30 (m, 4H), 5.73 (s, 2H), 6.47-6.57 (m, 2H), 6.88 (s, 1H), 6.93 (s, 1H), 7.37 (d, J=8.6 Hz, 1H) LC-MS (m/z) (M+1) 452.1

Step-3: Synthesis of tert-butyl 1-(3-(tert-butoxycarbonylamino)cyclohexanecarboxamido)-7-(pyrrolidin-1-yl)-3-(trifluoromethyl)-10H-phenothiazine-10-carboxylate

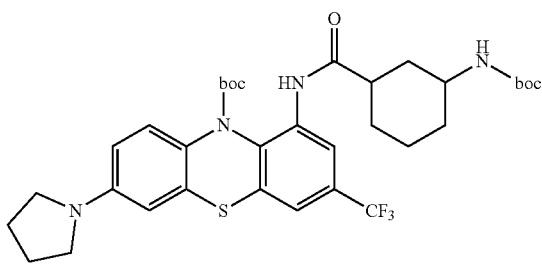

To a stirred solution of 3-(tert-butoxycarbonylamino) cyclohexanecarboxylic acid (65 mg, 0.266 mmol) in pyridine (2.5 mL) was cooled to 0° C., then added tert-butyl 1-amino-7-(pyrrolidin-1-yl)-3-(trifluoromethyl)-10H-phenothiazine-10-carboxylate (100 mg, 0.221 mmol) in pyridine (2.5 mL) was stirred at 0-10° C. for 1 h. The progress of the reaction was monitored by TLC. The reaction mixture was poured into ice-cold water (50 mL) slowly drop wise very carefully then extracted with ethyl acetate (2×40 mL). The combined organic layer was washed with saturated NaHCO$_3$ solution (100 mL) dried over anhydrous sodium sulphate and concentrated under reduced pressure. The crude compound was purified by column chromatography (silica gel 60-120 mesh, eluted with 2-3% EtOAc in DCM) to afford tert-butyl 1-(3-(tert-butoxycarbonylamino)cyclohexanecarboxamido)-7-(pyrrolidin-1-yl)-3-(trifluoromethyl)-10H-phenothiazine-10-carboxylate (30 mg, yield: 16%) as grey color solid. 1H NMR (400 MHz, DMSO-d6) δ 1.30-1.32 (m, 9H), 1.35-1.39 (m, 13H), 1.41-1.49 (m, 10H), 1.50-1.59 (m, 2H), 1.94-1.97 (m, 7H), 3.17-3.19 (s, 4H), 4.19-4.20 (m, 1H), 6.10-6.18 (m, 2H), 6.54 (d, J=7.43 Hz, 1H), 6.80-6.89 (m, 1H), 6.98-6.99 (m, 1H), 7.34-739 (m, 1H), 7.51-7.53 (m, 1H) 7.61-7.17 (m, 1H), 8.03-8.20 (m, 1H). LC-MS (m/z) (M+1): 677.2

Step-4: Synthesis of 3-amino-N-(7-(pyrrolidin-1-yl)-3-(trifluoromethyl)-10H-phenothiazin-1-yl)cyclohexanecarboxamide

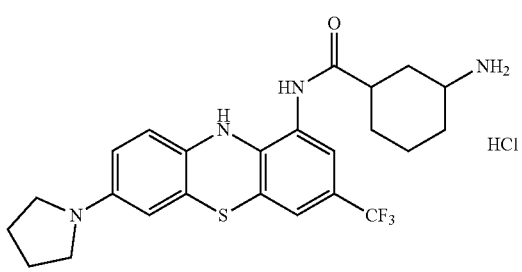 [SMILES: NC1CCCC(C(=O)Nc2cc(C(F)(F)F)cc3c2Nc2ccc(N4CCCC4)cc2S3)C1 ; Cl]

To a stirred solution of tert-butyl 1-(3-(tert-butoxycarbonylamino)cyclohexanecarboxamido)-7-(pyrrolidin-1-yl)-3-(trifluoromethyl)-10H-phenothiazine-10-carboxylate (12 mg, 0.017 mmol,) in DCM (0.5 mL) was added 4M HCl in 1,4-Dioxan (1 mL) at 0° C., then the reaction mixture was stirred at rt for 1 h. The progress of the reaction was monitored by TLC. The reaction mixture was concentrated under reduced pressure obtained solid was washed with diethyl ether (2×3 mL) and dried under reduced pressure to afford 3-amino-N-(7-(pyrrolidin-1-yl)-3-(trifluoromethyl)-10H-phenothiazin-1-yl)cyclohexanecarboxamide (5 mg, yield: 45%) as grey solid. $^1$H NMR (400 MHz, DMSO-d$_6$) δ 1.12-1.37 (m, 2H), 1.41-1.50 (m, 1H), 1.80-1.92 (m, 8H), 2.08 (d, J=12.1 Hz, 1H), 3.03-3.20 (m, 6H), 6.20-6.27 (m, 1H), 6.29-6.32 (m, 1H), 6.74 (s, 1H), 7.08 (s, 1H), 7.27 (s, 1H), 7.93 (s, 5H), 9.67 (brs, 1H) LC-MS (m/z) (M+1) 477.2

Step-5: Synthesis of tert-butyl 1-((3-(tert-butoxycarbonylamino)cyclohexyl)methylamino)-7-(pyrrolidin-1-yl)-3-(trifluoromethyl)-10H-phenothiazine-10-carboxylate

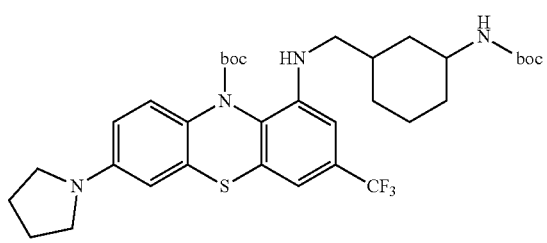

To a stirred solution of tert-butyl 1-(3-(tert-butoxycarbonylamino)cyclohexanecarboxamido)-7-(pyrrolidin-1-yl)-3-(trifluoromethyl)-10H-phenothiazine-10-carboxylate (130 mg, 0.19 mmol, step-3,) in THF (2 mL) was cooled to 0° C., then added BH$_3$.DMS (2.5 mL), reaction mixture was stirred at 60° C. for 1 h. The progress of the reaction was monitored by TLC. The reaction mixture was cooled to rt, quenched with 1N HCl (10 mL) slowly drop wise then extracted with ethyl acetate (2×30 mL) and washed with water (1×50 mL). The organic layer was dried over anhydrous sodium sulphate and concentrated under reduced pressure. The crude compound was purified by prepative TLC (eluted with 20% EtoAc in petether) to afford tert-butyl 1-((3-(tert-butoxycarbonylamino)cyclohexyl)methylamino)-7-(pyrrolidin-1-yl)-3-(trifluoromethyl)-10H-phenothiazine-10-carboxylate (20 mg, yield: 15.7%) as yellow solid. 1H NMR (400 MHz, DMSO-d6) δ 1.22-1.24 (m, 8H), 1.27 (s, 9H), 1.32 (s, 9H), 1.67-1.76 (m, 4H), 1.94-2.1 (m, 6H), 2.99-3.1 (m, 2H), 3.20-3.29 (m, 5H), 5.81 (d, J=6.92 Hz, 1H), 6.12-6.18 (m, 1H), 6.41-6.45 (m, 2H), 6.90 (s, 1H), 7.44 (d, J=8.81 Hz, 1H). LC-MS (m/z) (M+1) 663.2

Step-6: Synthesis of N-((3-aminocyclohexyl)methyl)-7-(pyrrolidin-1-yl)-3-(trifluoromethyl)-10H-phenothiazin-1-amine

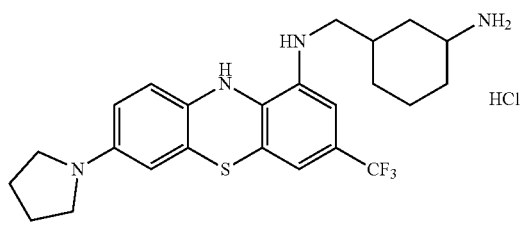 [SMILES: NC1CCCC(CNc2cc(C(F)(F)F)cc3c2Nc2ccc(N4CCCC4)cc2S3)C1 ; Cl]

To a stirred solution of tert-butyl 1-((3-(tert-butoxycarbonylamino)cyclohexyl)methylamino)-7-(pyrrolidin-1-yl)-3-(trifluoromethyl)-10H-phenothiazine-10-carboxylate (20 mg, 0.030 mmol, step-5) in DCM (1 mL) was added 1,4-Dioxan.HCl (1 mL, 4M) at 0° C., then the reaction mixture was stirred at rt for 1 h. The progress of the reaction was monitored by TLC. The reaction mixture was concentrated under reduced pressure obtained solid was washed with diethyl ether (2×3 mL) and dried under reduced pressure to afford N-((3-aminocyclohexyl)methyl)-7-(pyrrolidin-1-yl)-3-(trifluoromethyl)-10H-phenothiazin-1-amine hydrochloride (9 mg, yield: 56%) as yellow solid. $^1$H NMR (400 MHz, DMSO-d6) δ 0.82-0.90 (m, 1H), 0.95-1.05 (m, 1H), 1.10-1.35 (m, 3H), 1.68-1.88 (m, 4H), 1.89-2.0 (m, 3H), 2.05-2.15 (m, 2H), 2.95-3.05 (m, 2H), 3.10-3.25 (m, 2H), 3.85-4.10 (m, 3H), 6.02-6.90 (m, 2H), 7.93 (brs, 3H). LC-MS (M+1) m/z: 463.1

Some examples of compounds synthesised by the method of Scheme XXV are provided in Table XXV

TABLE XXV

| Cmpd # | R$^1$ | R$^6$ |
|---|---|---|
| 256 | ![amide-cyclohexyl-NH2] | piperazine |
| 294 | ![amide-cyclohexyl-NH2] | pyrrolidine |
| 312 | ![amide-cyclohexyl-NH2] | Br |
| 313 | ![amide-cyclohexyl-NH2] | 3-methylpiperidine |
| 300 | ![CH2NH-cyclohexyl-NH2] | pyrrolidine |

Figure 20:
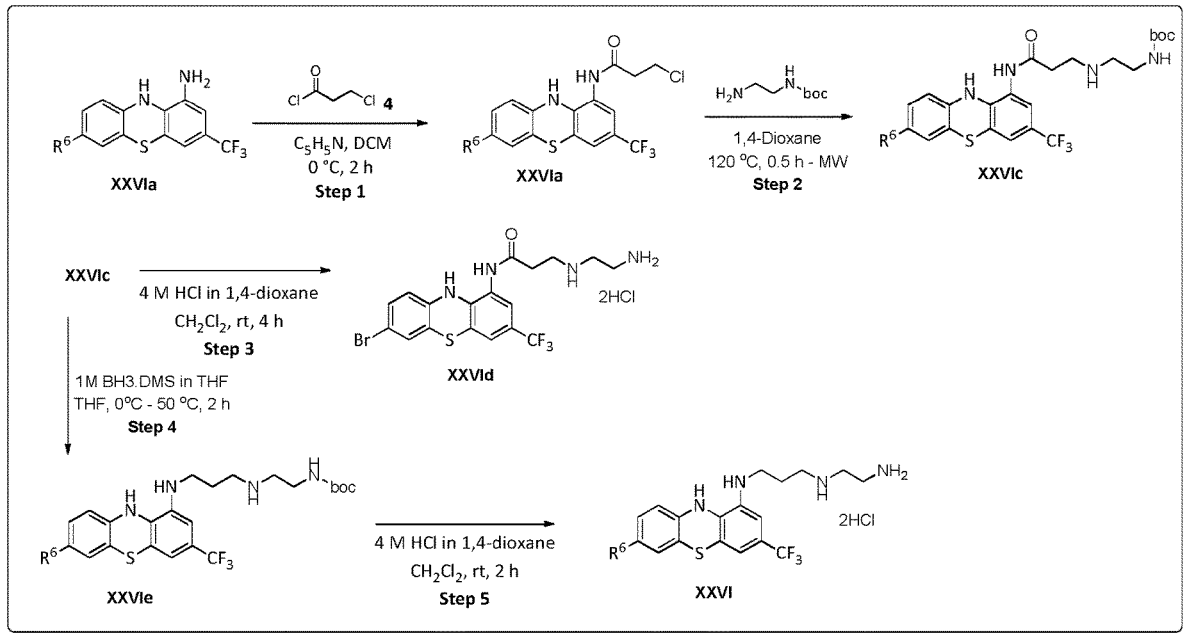
FIG. 20 shows general synthetic scheme XXVI for the synthesis of selected compounds according to the present invention

FIG. 20 shows general reaction scheme XXVI for the synthesis of selected 1, 3, 6-trisubstituted phenothiazenes. XXVIa reacted with acid chloride yielded corresponding amide of 1,3 6 tri substituted phenothiazene/substituted phenoxazines (XXVIb). Compounds XXVIb father undergoes alkylation in microwave gave XXVIc. Compounds XXVIc deprotection of Boc to give corresponding salt XXVId by using HCl in dioxane and XXVIc reduce the amide bond and followed by boc deprotections gave XXVIe with corresponding salts Compound 298: N1-(2-aminoethyl)-N3-(7-bromo-3-(trifluoromethyl)-10H-phenothiazin-1-yl)propane-1,3-diamine

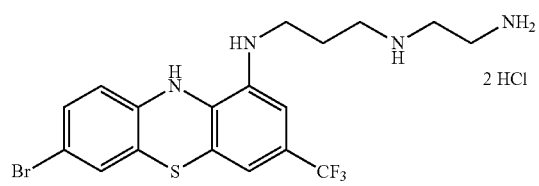 [SMILES: NCCNCCCNc1cc(C(F)(F)F)cc2c1Nc1ccc(Br)cc1S2 ; "2 HCl"]

Step 1: N-(7-bromo-3-(trifluoromethyl)-10H-phenothiazin-1-yl)-3-chloropropanamide

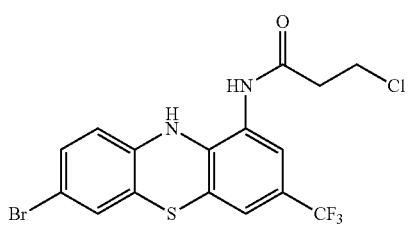 [SMILES: O=C(CCCl)Nc1cc(C(F)(F)F)cc2c1Nc1ccc(Br)cc1S2]

To a stirred solution of 7-bromo-3-(trifluoromethyl)-10H-phenothiazin-1-amine (2 g, 5.115 mmol) in DCM (20 mL) was added pyridine (5.2 mL) and 3-chloropropanoyl chloride (0.8 g, 6.138 mmol) at 0° C. Reaction mixture was stirred at room temperature for 2 h. After completion of the reaction, solvent was removed under vacuo to give crude residue, which was poured on to ice and stirred for 0.5 h, solid was collected from filtration and washed with water (10 mL) dried to give N-(7-bromo-3-(trifluoromethyl)-10H-phenothiazin-1-yl)-3-chloropropanamide as light green solid (1.1 g, 47%) 1H NMR (400 MHz, DMSO-d6) δ 2.89 (t, J=6.64 Hz, 3H), 3.38 (t, J=6.72 Hz, 2H), 6.83 (d, J=8.24 Hz, 1H), 7.19-7.25 (m, 3H), 7.31 (brs, 1H), 8.01 (s, 1H), 9.58 (s, 1H). LC-MS m/z (M+H): 452.11

Step 2: tert-butyl (2-((3-((7-bromo-3-(trifluoromethyl)-10H-phenothiazin-1-yl)amino)-3-oxopropyl)amino)ethyl)carbamate

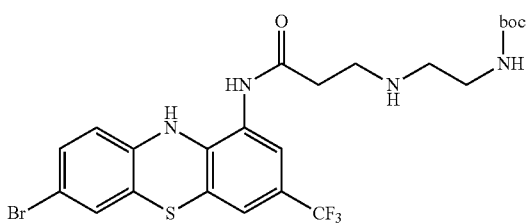

To a stirred solution of N-(7-bromo-3-(trifluoromethyl)-10H-phenothiazin-1-yl)-3-chloropropanamide (0.5 g, 1.108 mmol) in 1,4-Dioxan (5 mL) was added tert-butyl (2-aminoethyl)carbamate (0.212 g, 1.33 mmol). Reaction mixture was stirred at 120° C. in Microwave irradiation for 0.5 h. After completion of the reaction, solvent was removed under vacuo to give crude residue, which was poured on to DCM (5 mL), solid was filtered and dried to give tert-butyl (2-((3-((7-bromo-3-(trifluoromethyl)-10H-phenothiazin-1-yl)amino)-3-oxopropyl)amino)ethyl)carbamate as green solid (0.4 g, 63%). $^1$H NMR (400 MHz, DMSO-d6) δ 1.22 (m, 2H), 1.32 (s 9H), 2.55-2.64 (m, 2H), 2.82-2.88 (m, 2H), 2.97-3.05 (m, 2H), 6.72 (brs, 1H), 6.78 (d, J=8.19 Hz, 1H), 7.20 (d, J=8.1 Hz, 3H), 7.28 (s, 1H), 8.13 (brs, 1H). LC-MS m/z (M+H): 577

Step 3: 3-((2-aminoethyl)amino)-N-(7-bromo-3-(trifluoromethyl)-10H-phenothiazin-1-yl)propanamide

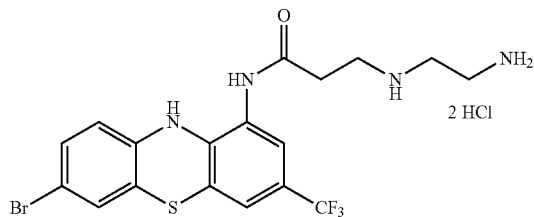 [SMILES: NCCNCCC(=O)Nc1cc(C(F)(F)F)cc2c1Nc1ccc(Br)cc1S2 ; "2 HCl"]

To a stirred solution of tert-butyl (2-((3-((7-bromo-3-(trifluoromethyl)-10H-phenothiazin-1-yl)amino)-3-oxopropyl)amino)ethyl)carbamate (100 mg, 0.21 mmol) in DCM (2 mL) was added 4M HCl in 1,4-Dioxan (0.5 mL) at 0° C., then the reaction mixture was stirred at room temperature for 2 h. After completion of the reaction, reaction mixture was concentrated under reduced pressure to give solid which was washed with diethyl ether (2×3 mL) and n-Pentane (2 mL), dried under reduced pressure to afford 3-((2-aminoethyl)amino)-N-(7-bromo-3-(trifluoromethyl)-10H-phenothiazin-1-yl)propanamide hydrochloride (50 mg, yield: 43%) as brown solid. $^1$H NMR (400 MHz, DMSO-d$_6$) δ 2.96-2.99 (m, 2H), 3.12-3.30 (m, 7H), 7.06 (d, J=8.19 Hz, 1H), 7.15-7.23 (m, 3H), 7.48 (s, 1H), 8.22 (brs, 3H), 8.67 (s, 1H), 9.35 (brs, 2H), 10.07 (s, 1H) LC-MS (M+1): 475.12

Step 4: tert-butyl (2-((3-((7-bromo-3-(trifluoromethyl)-10H-phenothiazin-1-yl)amino)propyl)amino)ethyl)carbamate (BI-001-0027-150)

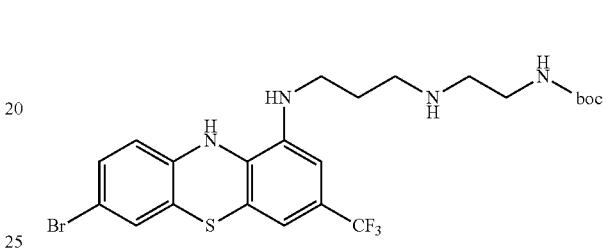

To a stirred solution of tert-butyl (2-((3-((7-bromo-3-(trifluoromethyl)-10H-phenothiazin-1-yl) amino)-3-oxopropyl) amino) ethyl) carbamate (400 mg, 0.695 mmol) in THF (5 mL) was added 2M borane. DMS in THF solution at 0° C. Reaction mixture was stirred at 50° C. for 2 h. After completion of the reaction quenched with ice and extracted with ethyl acetate (2×25 mL). The combined organic layers were dried over sodium sulfate, filtered and evaporated to give crude residue, which was purified by gradient column chromatography (product eluted with 3% methanol in DCM) to afford tert-butyl (2-((3-((7-bromo-3-(trifluoromethyl)-10H-phenothiazin-1-yl)amino)propyl)amino)ethyl)carbamate as Brown Solid (130 mg, 33%). $^1$H NMR (400 MHz, DMSO-d$_6$) δ 1.22 (s, 4H), 1.37 (s, 9H), 1.62-1.85 (m, 2H), 2.62-2.70 (m, 2H), 2.71-2.78 (m, 2H), 3.02-3.10 (m, 2H), 3.11-3.19 (m, 2H), 6.53 (m, 2H), 6.78-6.82 (m, 2H), 7.19-7.24 (m, 32H), 8.12 (s, 1H). LC-MS m/z (M+H): 563

Step 5: N1-(2-aminoethyl)-N3-(7-bromo-3-(trifluoromethyl)-10H-phenothiazin-1-yl)propane-1,3-diamine (BI-001-0027-167)

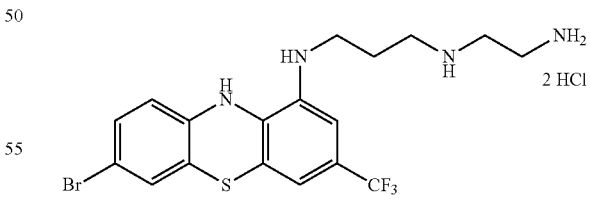

To a stirred solution of tert-butyl (2-((3-((7-bromo-3-(trifluoromethyl)-10H-phenothiazin-1-yl)amino)propyl)amino)ethyl)carbamate (50 mg, 0.089 mmol) in DCM (2 mL) was added 4M HCl in 1,4-Dioxan (1 mL) at 0° C., then the reaction mixture was stirred at room temperature for 2 h. After completion of the reaction, reaction mixture was concentrated under reduced pressure to give solid which was washed with diethyl ether (3 mL) and n-Pentane (3 mL), dried under reduced pressure to afford N1-(2-aminoethyl)-

N3-(7-bromo-3-(trifluoromethyl)-10H-phenothiazin-1-yl)propane-1,3-diamine hydrochloride (30 mg, yield: 68%) as yellow solid. $^1$H NMR (400 MHz, DMSO-d$_6$) δ 1.97-2.04 (m, 2H), 3.10-3.27 (m, 8H), 3.11-3.24 (m, 8H), 6.52-6.58 (m, 2H), 7.10-7.20 (m, 2H), 8.25 (brs, 3H), 8.67 (s, 1H) 9.22 (brs, 2H) LC-MS (M+1) 461.2

Some examples of compounds synthesised by the method of Scheme XXVI are provided in Table XXVI

TABLE XXVI

| Cmpd # | R$^1$ | R$^6$ |
|---|---|---|
| 297 | ![structure] | H |
| 298 | ![structure] | Br |
| 315 | ![structure] | Br |

Figure 21:
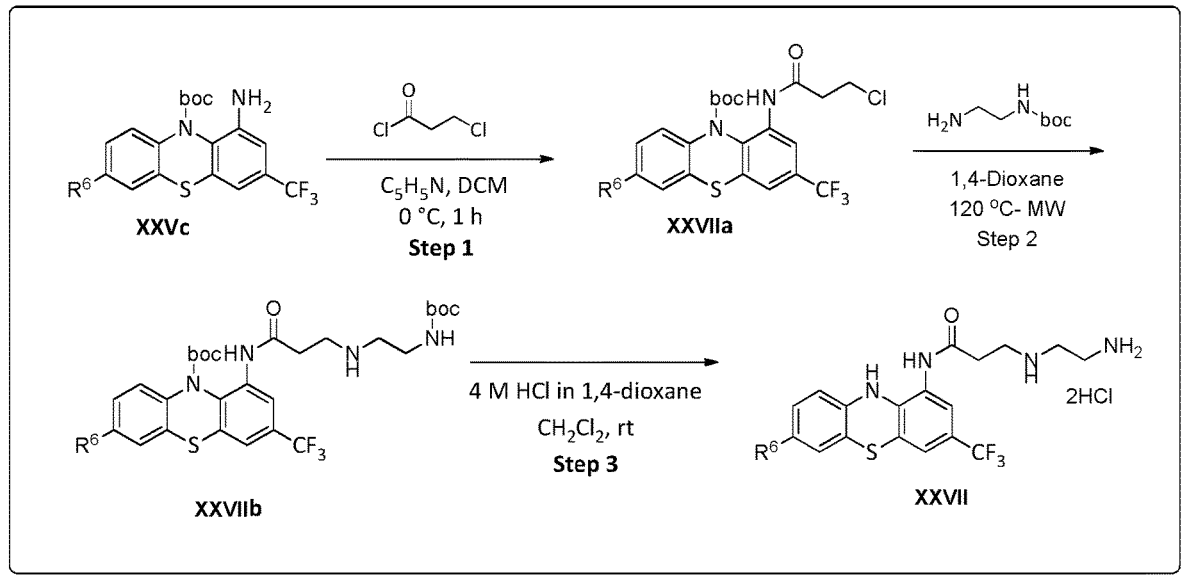
FIG. 21 shows general synthetic scheme XXVII for the synthesis of selected compounds according to the present invention

FIG. 21 shows general reaction scheme XXVII for the synthesis of selected 1, 3, 6-trisubstituted phenothiazenes. XXVc reacted with acid chloride yielded corresponding amide of 1,3 6 tri substituted phenothiazene/substituted phenoxazines (XXVIIa). Compounds XXVIIa futher undergoes alkylation in microwave gave XXVIIb. Compounds XXVIIb reduce the amide bond and followed by boc deprotections gave XXVII with corresponding salts Compound 315:-3-((2-aminoethyl)amino)-N-(7-(pyrrolidin-1-yl)-3-(trifluoromethyl)-10H-phenothiazin-1-yl)propanamide hydrochloride

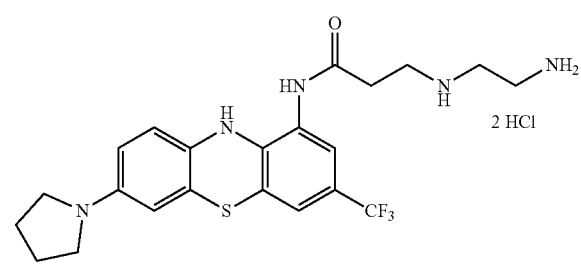 [SMILES: NCCNCCC(=O)Nc1cc(C(F)(F)F)cc2c1Nc1ccc(N3CCCC3)cc1S2]

Step 1: tert-butyl 1-(3-chloropropanamido)-7-(pyrrolidin-1-yl)-3-(trifluoromethyl)-10H-phenothiazine-10-carboxylate

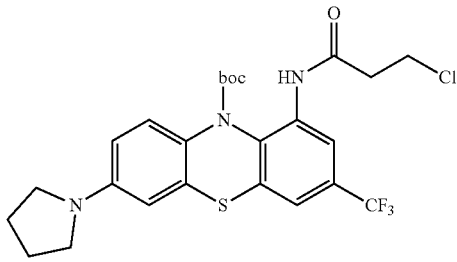

To a stirred solution of tert-butyl 1-amino-7-(pyrrolidin-1-yl)-3-(trifluoromethyl)-10H-phenothiazine-10-carboxylate (0.65 g, 1.441 mmol) in DCM (20 mL) was added pyridine (2 mL) and 3-chloropropanoyl chloride (0.218 g, 1.729 mmol) at 0° C. Reaction mixture was stirred at room temperature for 2 h. After completion of the reaction, solvent was removed under vacuo to give crude residue, diluted with ethyl acetate (50 mL) washed with water (50 mL). Organic layer was dried over sodium sulfate, filtered and evaporated to give crude product, which was purified by gradient column chromatography (20-30% ethyl acetate/Hexane) to give tert-butyl 1-(3-chloropropanamido)-7-(pyrrolidin-1-yl)-3-(trifluoromethyl)-10H-phenothiazine-10-carboxylate as off white solid (0.7 g, 89%) 1H NMR (400 MHz, DMSO-d6) δ 1.29 (s, 9H), 1.90-1.95 (m, 4H), 2.90-3.10 (m, 2H), 3.18-3.22 (m, 4H), 3.90 (t, J=6.72 Hz, 2H), 6.52-6.59 (m, 2H), 7.52 (d, J=8.24 Hz, 1H), 7.62 (s, 1H), 8.14 (brs, 1H), 9.77 (brs, 1H). LC-MS m/z (M+H): 542.11

Step 2: tert-butyl 1-(3-((2-((tert-butoxycarbonyl)amino)ethyl)amino)propanamido)-7-(pyrrolidin-1-yl)-3-(trifluoromethyl)-10H-phenothiazine-10-carboxylate

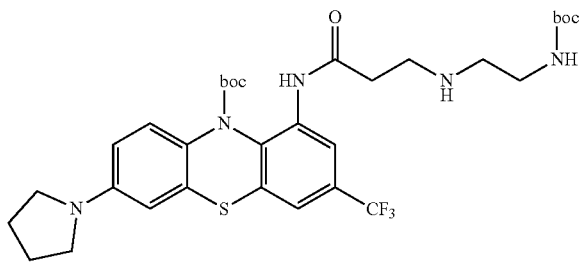

To a stirred solution of tert-butyl 1-(3-chloropropanamido)-7-(pyrrolidin-1-yl)-3-(trifluoromethyl)-10H-phenothiazine-10-carboxylate (0.7 g, 1.29 mmol) in 1,4-Dioxan (3 mL) was added tert-butyl (2-aminoethyl)carbamate (0.250 g, 1.549 mmol). Reaction mixture was stirred at 120° C. in Microwave irradiation for 0.5 h. After completion of the reaction, solvent was removed under vacuo to give crude residue, which was diluted with ethyl acetate (20 mL) and washed with water (20 mL). Organic layer was dried over sodium sulfate, filtered and evaporated to give crude product. Crude product was purified by gradient column chromatography (3-4% methanol/DCM) to give tert-butyl 1-(3-

((2-((tert-butoxycarbonyl) amino) ethyl) amino) propanamido)-7-(pyrrolidin-1-yl)-3-(trifluoromethyl)-10H-phenothiazine-10-carboxylate as off white solid (0.62 g, 72%). 1H NMR (400 MHz, DMSO-d6) δ 1.30 (s, 9H), 1.37 (s, 9H) 1.95 (m, 4H), 2.50-2.55 (m, 2H), 2.65-2.70 (m, 2H), 2.81-2.89 (m, 2H), 3.17-3.25 (m, 4H), 6.51-6.59 (m, 2H), 6.80 (brs, 1H), 7.45 (d, J=8.1 Hz, 1H), 7.58 (s, 1H), 8.45 (brs, 1H). LC-MS m/z (M+H): 666.30

Step 3: 3-((2-aminoethyl)amino)-N-(7-(pyrrolidin-1-yl)-3-(trifluoromethyl)-10H-phenothiazin-1-yl)propanamide hydrochloride

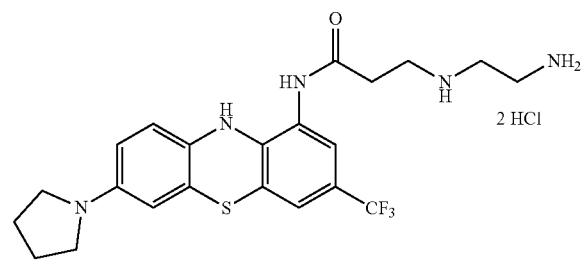 [SMILES: NCCNCCC(=O)Nc1cc(C(F)(F)F)cc2c1Nc1ccc(N3CCCC3)cc1S2]

To a stirred solution of tert-butyl 1-(3-((2-((tert-butoxycarbonyl) amino) ethyl) amino) propanamido)-7-(pyrrolidin-1-yl)-3-(trifluoromethyl)-10H-phenothiazine-10-carboxylate (100 mg, 0.15 mmol) in DCM (10 mL) was added 4M HCl in 1,4-Dioxan (2 mL) at 0° C., then the reaction mixture was stirred at room temperature for 2 h. After completion of the reaction, reaction mixture was concentrated under reduced pressure to give solid which was washed with diethyl ether (3 mL) and n-Pentane (3 mL), dried under reduced pressure to afford 3-((2-aminoethyl) amino)-N-(7-(pyrrolidin-1-yl)-3-(trifluoromethyl)-10H-phenothiazin-1-yl)propanamide hydrochloride (60 mg, 75%) as grey solid. $^1$H NMR (400 MHz, DMSO-d$_6$) δ 1.92 (brs, 4H), 3.02 (brs, 3H), 3.15-3.35 (m, 9H), 6.20-6.47 (m, 2H), 6.80-7.01 (m, 1H), 7.02-7.20 (m, 1H), 7.21-7.42 (m, 1H), 8.25 (s, 4H), 9.45 (s, 2H), 10.01 (brs, 1H) LC-MS (M+1): 466.38

Some examples of compounds synthesised by the method of Scheme XXVII are provided in Table XXVII

| Cmpd # | R¹ | R⁶ |
|---|---|---|
| 302 | ![structure] HN-C(O)-CH2-CH2-NH-CH2-CH2-NH-boc | pyrrolidine |
| 304 | HN-C(O)-CH2-CH2-NH-CH2-CH2-NH-boc | NC-CH< |
| 308 | HN-C(O)-CH2-CH2-NH-CH2-CH2-NH-boc | 3-methylpiperidine |
| 317 | HN-C(O)-CH2-CH2-NH-CH2-CH2-NH-boc | N(Et)2 |
| 323 | HN-C(O)-CH2-CH2-NH-CH2-CH2-N(Me)2 | pyrrolidine |

Figure 22:
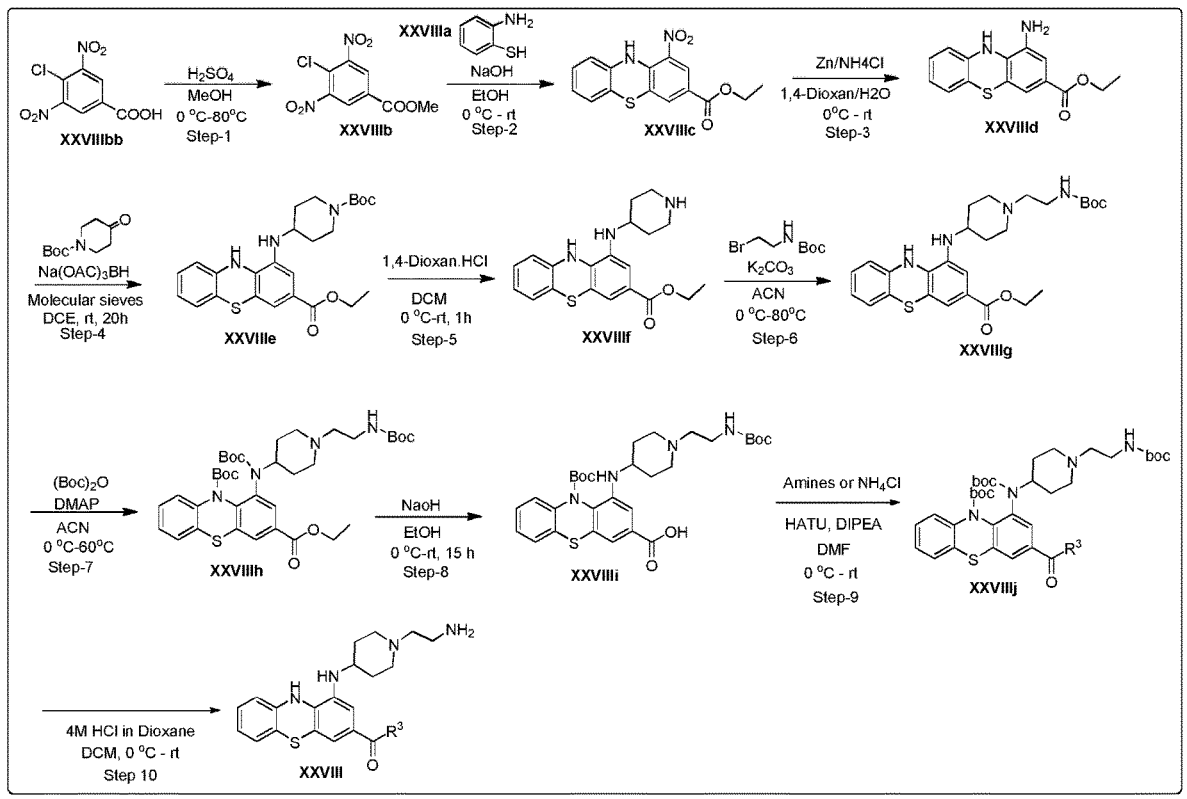
FIG. 22 shows general synthetic scheme XXVIII for the synthesis of selected compounds according to the present invention

FIG. 22 shows general synthetic scheme XXVIII for the synthesis of selected 1, 3, substituted phenothiazenes. Nucleophilic substitution of 2-amino thiophenol (XXVIIIa) with aryl halides (XXVIIIb) followed by insituSmiles rearrangement yielded 1,3-disubstituted phenothiazenes (XXVIIIc), which are reduce by Zn/NH4Cl to yield the corresponding 1-amino substituted phenothiazenes (XXVIIId). Reductive amination of compound XXVIIId with Keto yielded corresponding n-alkylated phenothiazines XXVIIIg, Compounds XXVIIIg protected with boc yielded tri boc of XXVIIIh was hydrolysed to gave acid (XXVIIIi), XXXVIIIi were reacted with acid chlorides or acids to form corresponding amides XXVIIIj, which further deprotected to yield corresponding title compounds XXVIII.

Compound 288: (1-(1-(2-aminoethyl)piperidin-4-ylamino)-10H-phenothiazin-3-yl)(pyrrolidin-1-yl) methanone

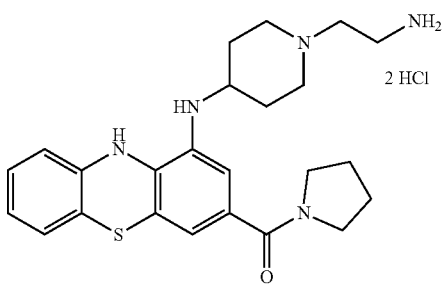 [SMILES: NCCN1CCC(Nc2cc(C(=O)N3CCCC3)cc3c2Nc2ccccc2S3)CC1]

Step-1: Synthesis of methyl 4-chloro-3,5-dinitrobenzoate

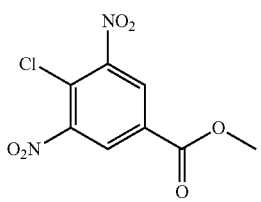 [SMILES: COC(=O)c1cc([N+](=O)[O-])c(Cl)c([N+](=O)[O-])c1]

To a stirred solution of 4-chloro-3,5-dinitrobenzoic acid (10 g, 40.5 mmol) in MeOH (100 mL) was added concentrated sulphuric acid (5 mL) at 0° C., then the reaction mixture was stirred at 80° C. for 8 h. The progress of the reaction was monitored by TLC. Reaction mixture was concentrated under reduced pressure remove the solvent, obtained residue was diluted with ice-water (200 mL). Then extracted with ethyl acetate (2×100 mL), the combined organic layer was washed with saturated. NaHCO₃ solution (2×100 mL). The organic layer was separated, dried over anhydrous sodium sulphate and concentrated under reduced pressure to afford methyl 4-chloro-3,5-dinitrobenzoate (9.5 g, yield: 90%) as light yellow solid. LC-MS m/z (M+H):

Step-2: Synthesis of ethyl 1-nitro-10H-phenothiazine-3-carboxylate

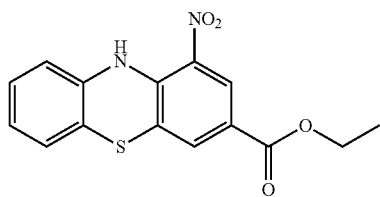 [SMILES: CCOC(=O)c1cc2c(c([N+](=O)[O-])c1)Nc1ccccc1S2]

To a stirred solution of methyl 4-chloro-3,5-dinitrobenzoate (1 g, 8 mmol, step-1) in ethanol (15 mL) was added 2-aminobenzenethiol (2.08 g, 8 mmol) followed by sodium hydroxide (960 mg, 24 mmol) at 0° C. Then reaction mixture was stirred at room temperature for 4 h. The progress of the reaction was monitored by TLC. Reaction mixture was filtered and washed with ethanol (10 mL) dried under vacuum to afford ethyl 1-nitro-10H-phenothiazine-3-carboxylate (1.3 g, yield: 52%) as brown color solid. LC-MS m/z (M+H): 317.1

Step-3: Synthesis of ethyl 1-amino-10H-phenothiazine-3-carboxylate

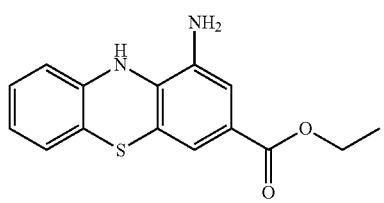

To a stirred solution of ethyl 1-nitro-10H-phenothiazine-3-carboxylate (800 mg, 2.53 mmol, step-2) in 1,4-Dioxan/H₂O (10:3 mL, 7:3) was added Zn (1.31 g, 20.25 mmol) followed by NH4Cl (1.09 g, 20.25 mmol) at 0° C. Then reaction mixture was stirred at room temperature for 5 h. The progress of the reaction was monitored by TLC. The reaction mixture was filtered through a pad of celite, washed with ethyl acetate (100 mL). Take filtrate washed with brine solution (1×100 mL). The combined organic layer was dried over anhydrous sodium sulphate and concentrated under reduced pressure to afford ethyl 1-amino-10H-phenothiazine-3-carboxylate (600 mg,) as yellow solid. LC-MS m/z (M+H): 286.1

Step-4: Synthesis of ethyl 1-(1-(tert-butoxycarbonyl)piperidin-4-ylamino)-10H-phenothiazine-3-carboxylate

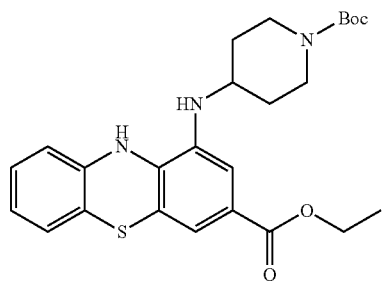 [SMILES: CCOC(=O)c1cc(NC2CCN(C(=O)OC(C)(C)C)CC2)c2c(c1)Sc1ccccc1N2]

To a stirred solution of ethyl 1-amino-10H-phenothiazine-3-carboxylate (250 mg, 0.70 mmol, step-3,) and tert-butyl 4-oxopiperidine-1-carboxylate (550 mg, 1.92 mmol) in 1,2-dichloroethane (50 mL) was added molecular sieves powder (10 g), stirred at room temperature for 1 h. Then added sodium tri acetoxy borohydride (4 g, 19.2 mmol) at room temperature, then the reaction mixture was stirred at rt for 16 h. The progress of the reaction was monitored by TLC. The reaction mixture was filtered through celite pad washed with DCM (100 mL). Take filtrate concentrated under reduced pressure. The crude compound was purified by column chromatography (silica gel 60-120 mesh, eluted with 10% EtOAc in DCM). The pure fractions were collected and concentrated under reduced pressure to afford ethyl 1-(1-(tert-butoxycarbonyl)piperidin-4-ylamino)-10H-phenothiazine-3-carboxylate (700 mg, yield: 70%) as yellow solid. LC-MS m/z (M+H): 470.2

Step-5: Synthesis of ethyl 1-(piperidin-4-ylamino)-10H-phenothiazine-3-carboxylate

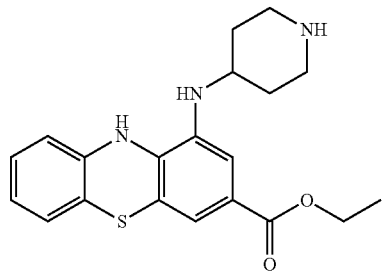 [SMILES: CCOC(=O)c1cc(NC2CCNCC2)c2c(c1)Sc1ccccc1N2]

To a stirred solution of ethyl 1-(1-(tert-butoxycarbonyl)piperidin-4-ylamino)-10H-phenothiazine-3-carboxylate (1.8 g, 3.83 mmol, step-4) in DCM (2 mL) was added 1,4-Dioxan.HCl (5 mL, 4M) at 0° C., then the reaction mixture was stirred at rt for 1 h. The progress of the reaction was monitored by TLC. The reaction mixture was concentrated under reduced pressure to obtained crude was basified with saturated NaHCO₃ solution up to pH~7 then extracted with 5% MeOH:DCM (2×100 mL). The combined organic layer was dried over anhydrous sodium sulphate and concentrated under reduced pressure to afford ethyl 1-(piperidin-4-ylamino)-10H-phenothiazine-3-carboxylate (1.2 g, yield: 85%) as yellow solid. LC-MS m/z (M+H): 370.1

Step-6: Synthesis of ethyl 1-(1-(2-(tert-butoxycarbonylamino)ethyl)piperidin-4-ylamino)-10H-phenothiazine-3-carboxylate

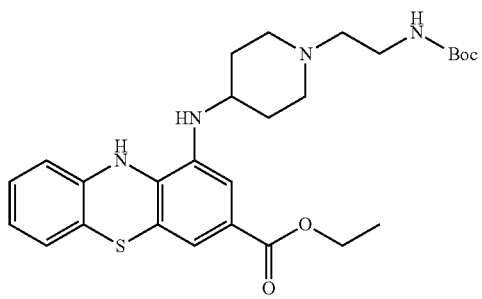 [SMILES: CCOC(=O)c1cc(NC2CCN(CCNC(=O)OC(C)(C)C)CC2)c2c(c1)Sc1ccccc1N2]

To a stirred solution of ethyl 1-(piperidin-4-ylamino)-10H-phenothiazine-3-carboxylate (1.2 g, 3.25 mmol, step-5) in acetonitrile (20 mL) was added potassium carbonate (1.34 g, 9.75 mmol) at 0° C., stirred for 5 min. Then added tert-butyl 2-bromoethylcarbamate (1.09 g, 4.87 mmol) at 0° C., reaction mixture was stirred at 80° C. for 2 h. The progress of the reaction was monitored by TLC. The reaction mixture was cooled to room temperature diluted with water (30 mL) and extracted with 5% MeoH:DCM (2×20 mL). The combined organic layer was dried over anhydrous sodium sulphate and concentrated under reduced pressure. The crude compound was purified by column chromatography (silica gel 60-120 mesh, eluted with 2-3% MeoH in DCM). The pure fractions were collected and concentrated under reduced pressure to afford ethyl 1-(1-(2-(tert-butoxycarbonylamino)ethyl)piperidin-4-ylamino)-10H-phenothiazine-3-carboxylate (1.1 g, yield: 66%) as yellow solid. LC-MS m/z (M+H): 513.2

Step-7: Synthesis of 10-tert-butyl 3-ethyl 1-(tert-butoxycarbonyl(1-(2-(tert-butoxycarbonylamino)ethyl)piperidin-4-yl)amino)-10H-phenothiazine-3,10-dicarboxylate

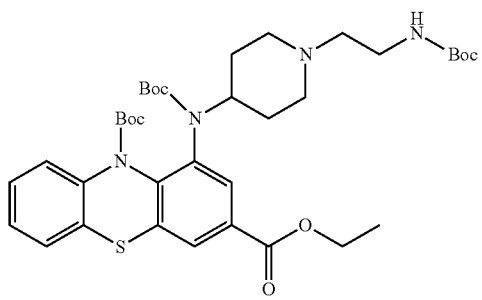 [SMILES: CCOC(=O)c1cc2c(c(N(C(=O)OC(C)(C)C)C3CCN(CCNC(=O)OC(C)(C)C)CC3)c1)N(C(=O)OC(C)(C)C)c1ccccc1S2]

To a stirred solution of ethyl 1-(1-(2-(tert-butoxycarbonylamino)ethyl)piperidin-4-ylamino)-10H-phenothiazine-3-carboxylate (800 mg, 1.56 mmol) in ACN (10 mL) was added DMAP (476 mg, 3.90 mmol) and followed by Di-tert-butyl dicarbonate (1.02 g, 4.68 mmol) at 0° C., reaction mixture was heated at 80° C. for 3 h. The progress of the reaction was monitored by TLC. Reaction mixture was cooled to room temperature, diluted with water (100 mL) then extracted with ethyl acetate (2×60 mL). The combined organic layer was dried over anhydrous sodium sulphate and concentrated under reduced pressure. The crude compound was purified by column chromatography (silica gel 60-120 mesh, eluted with 10% EtoAc in petether). The pure fractions were collected and concentrated under reduced pressure to afford and dried under reduced pressure to afford 10-tert-butyl 3-ethyl 1-(tert-butoxycarbonyl(1-(2-(tert-butoxycarbonylamino)ethyl)piperidin-4-yl)amino)-10H-phenothiazine-3,10-dicarboxylate (400 mg, yield: 36%) as grey solid. LC-MS m/z (M+H): 712.1

Step-8: Synthesis of 10-(tert-butoxycarbonyl)-1-(1-(2-(tert-butoxycarbonylamino)ethyl)piperidin-4-ylamino)-10H-phenothiazine-3-carboxylic Acid

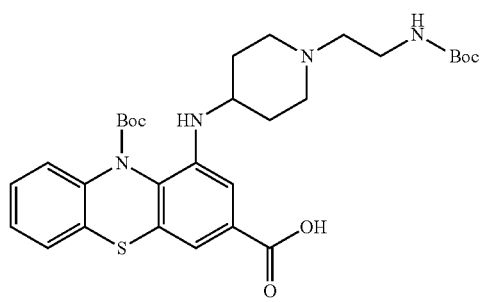 [SMILES: CC(C)(C)OC(=O)NCCN1CCC(Nc2cc(C(=O)O)cc3c2N(C(=O)OC(C)(C)C)c2ccccc2S3)CC1]

To a stirred solution of 10-tert-butyl 3-ethyl 1-(tert-butoxycarbonyl(1-(2-(tert-butoxycarbonylamino)ethyl)piperidin-4-yl)amino)-10H-phenothiazine-3,10-dicarboxylate (350 mg, 0.491 mmol) in ethanol (3.5 mL) was added sodium hydroxide (58.9 mg, 1.47 mmol) in $H_2O$ (0.7 mL) at 0° C., Then the reaction mixture was stirred at room temperature for 16 h. The progress of the reaction was monitored by TLC. The reaction mixture was concentrated under reduced pressure, to obtained crude was acidified with 10% citric acid solution (pH~4) solid was obtained. Filter The solid dried under vacuum to afford 10-tert-butyl 3-ethyl 1-(tert-butoxycarbonyl(1-(2-(tert-butoxycarbonylamino)ethyl)piperidin-4-yl)amino)-10H-phenothiazine-3,10-dicarboxylate (200 mg, yield: 69%) as off white solid. LC-MS m/z (M+H): 685.3

Step-9: Synthesis of tert-butyl 1-(1-(2-(tert-butoxycarbonylamino)ethyl)piperidin-4-ylamino)-3-(pyrrolidine-1-carbonyl)-10H-phenothiazine-10-carboxylate

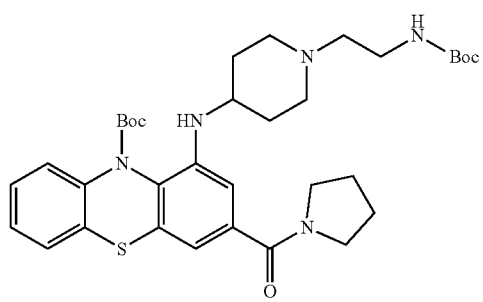 [SMILES: CC(C)(C)OC(=O)NCCN1CCC(Nc2cc(C(=O)N3CCCC3)cc3c2N(C(=O)OC(C)(C)C)c2ccccc2S3)CC1]

To a stirred solution of 10-tert-butyl 3-ethyl 1-(tert-butoxycarbonyl(1-(2-(tert-butoxycarbonylamino)ethyl)piperidin-4-yl)amino)-10H-phenothiazine-3,10-dicarboxylate (50 mg, 0.085 mmol) and pyrrolidine (9.1 mg, 0.12 mmol) in DMF (1 mL) was added DIPEA (33.1 mg, 0.25 mmol) at 0° C., stirred for 5 min. Then added HATU (48.7 mg, 0.12 mmol) at 0° C. Then the reaction mixture was stirred at room temperature for 2 h. The progress of the reaction was monitored by TLC. The reaction mixture was poured into ice-water (10 mL) stirred for 5 min solid is obtained. Filter the solid dried under vacuum. The solid was purified by preparative TLC (eluted with 3% MeOH/DCM) to afford tert-butyl 1-(1-(2-(tert-butoxycarbonylamino)ethyl)piperidin-4-ylamino)-3-(pyrrolidine-1-carbonyl)-10H-phenothiazine-10-carboxylate (20 mg, yield: 30%) as off white solid. 1H NMR (400 MHz, DMSO-d6) δ 1.36 (s, 9H), 1.38 (s, 9H), 1.52-1.61 (m, 1H), 1.72-1.92 (m, 4H), 2.05-2.15 (m, 2H), 2.29-2.36 (m, 2H), 2.71-2.89 (m, 2H), 2.97-3.07 (m, 2H), 3.30-3.33 (m, 2H), 3.37-3.43 (m, 2H), 5.74 (brs, 1H), 6.60-6.68 (m, 1H), 6.72 (d, J=3.12 Hz, 2H), 7.25 (t, J=7.72 Hz, 1H), 7.35 (t, J=7.71 Hz, 3H), 7.46 (d, J=7.70 Hz, 1H), 7.73 (d, J=7.79 Hz, 1H). LC-MS m/z (M+H): 638.3

Step-10: Synthesis of (1-(1-(2-aminoethyl)piperidin-4-ylamino)-10H-phenothiazin-3-yl)(pyrrolidin-1-yl) methanone

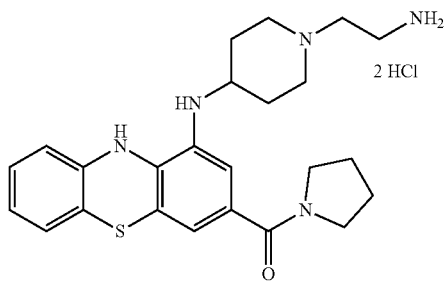 [SMILES: NCCN1CCC(Nc2cc(C(=O)N3CCCC3)cc3c2Nc2ccccc2S3)CC1]

To a stirred solution of tert-butyl 1-(1-(2-(tert-butoxycarbonylamino)ethyl)piperidin-4-ylamino)-3-(pyrrolidine-1-carbonyl)-10H-phenothiazine-10-carboxylate (20 mg, 0.031 mmol) in DCM (1.5 mL) was added 1,4-Dioxan.HCl (1 mL, 4M) at 0° C., then the reaction mixture was stirred at room temperature for 2 h. The progress of the reaction was monitored by TLC. The reaction mixture was concentrated under reduced pressure obtained solid was washed with diethyl ether (2×3 mL) and dried under reduced pressure to afford (1-(1-(2-aminoethyl)piperidin-4-ylamino)-10H-phenothiazin-3-yl)(pyrrolidin-1-yl)methanone (15 mg, yield: 78%) as yellow solid.
$^1$H NMR (400 MHz, DMSO-d$_6$) δ 1.79 (s, 4H), 1.92 (d, J=11.4 Hz, 2H), 2.12 (d, J=12.4 Hz, 2H), 3.13 (d, J=10.1 Hz, 2H), 3.30-3.39 (m, 9H), 3.61 (d, J=10.2 Hz, 4H), 6.40-6.47 (m, 1H), 6.58 (s, 1H), 6.78 (t, J=6.6 Hz, 1H), 6.91-7.02 (m, 3H), 8.11 (s, 1H), 8.31 (s, 3H), 8.59 (s, 1H), 10.94 (brs, 1H) LC-MS m/z (M+H): 438.2

Some examples of compounds synthesised by the method of Scheme XXVIII are provided in Table XXVIII

| Cmpd # | R³ |
|---|---|
| 280 | 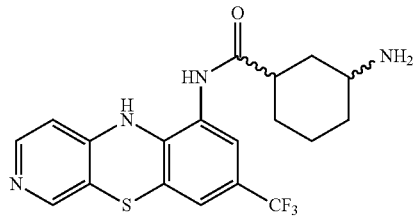 |
| 281 | |
| 287 | |
| 288 | |

-continued

| Cmpd # | R³ |
|---|---|
| 281 | |
| 287 | |
| 288 | |

Figure 23:
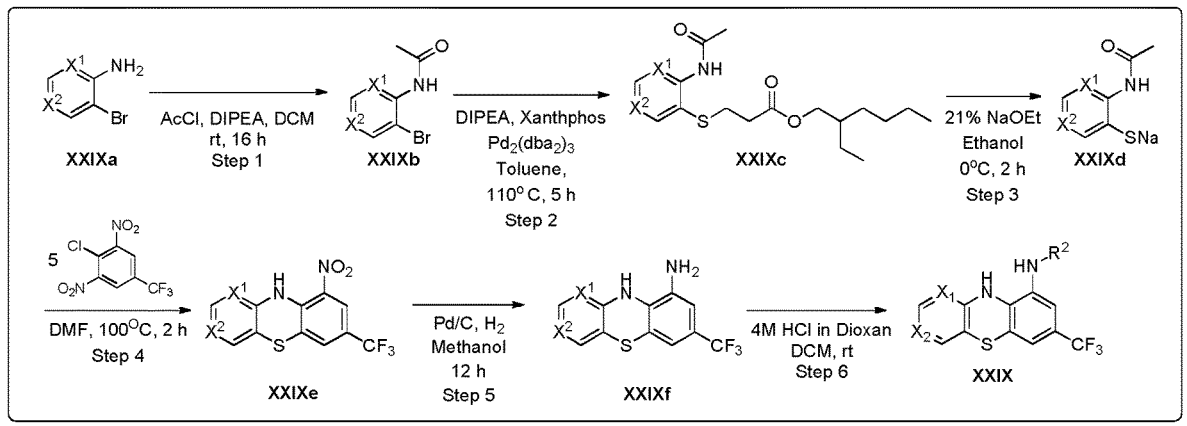
FIG. 23 shows general synthetic scheme XXVIX for the synthesis of selected compounds according to the present invention

FIG. 23 shows general synthetic scheme XXIX for the synthesis of a selected 1, 3, 8-trisubstituted phenothiazine. N-Acylation of 2-bromo-amino pyridines (XXIXa) followed by nucleophilic substitution reaction with a thiol surrogate yielded compound XXIXd. Deprotection of alkyl chain using NaOEt followed by nucleophilic substitution and Smiles rearrangement give compound XXIXe. Acid-amine coupling or reductive amination of XXIXe followed by deprotection using HCl yielded the corresponding salts.

Compound 257: 3-amino-N-(8-(trifluoromethyl)-5H-benzo[e]pyrido[3,4-b][1,4]thiazin-6-yl)cyclohexanecarboxamide Step 1: N-(3-bromopyridin-4-yl)acetamide

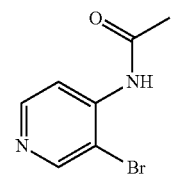

To a stirred solution of 3-bromopyridin-4-amine (1.0 g, 5.780 mmol) in dichloromethane (20 mL) was added di isopropyl ethylamine (1.5 mL, 8.678 mmol) followed by acetyl chloride (0.45 mL, 6.345 mmol) at 0° C. and starred at room temperature for 12 h. After completion of the reaction mixture was diluted with dichloromethane (20 mL) and washed with saturated sodium bicarbonate solution (20 mL), dried over sodium sulphate, and concentrated. The crude product obtained as N-(3-bromopyridin-4-yl)acetamide as off white solid. (1.24 g, 80%).

$^1$H NMR (400 MHz, DMSO-d$_6$) δ 3.62 (s, 3H), 6.43 (brs, 2H), 6.77 (d, J=8.16 Hz, 1H), 7.33 (d, J=2.05 Hz, 1H), 7.65 (dd, J=8.5 Hz, 1H)

LC-MS m/z (M+H): 215.0

Step 2: 3-ethylheptyl 3-(4-acetamidopyridin-3-ylthio)propanoate

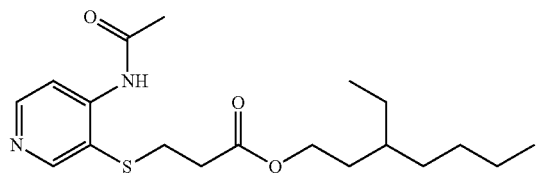 [SMILES: CCCCC(CC)CCOC(=O)CCSc1cnccc1NC(C)=O]

To a stirred solution of N-(3-bromopyridin-4-yl)acetamide (1.1 g, 0.086 mmol) and 2-ethylhexyl 3-mercaptopropanoate (1.4 mL, 6.138 mmol) in toluene (20 mL) was added DIPEA (4.85 mL 27.62 mmol,) followed by Xanthpos (0.061 g, 0.1023 mmol) at room temperature. Then purged with argon for 10 min, then added Pd$_2$(dba)$_3$ (0.046 g, 0.0511 mol), then purged with argon for 5 min. Reaction mixture was stirred at 110° C. for 4 h. The reaction mixture was filtered through celite, concentrated under reduced pressure. Obtained crude product was purified on gradient column with 30-40% Ethyl acetate/hexane as eluant to gives 3-ethylheptyl 3-(4-acetamidopyridin-3-ylthio)propanoate as colour less oil (1.4 g, 77%).

$^1$H NMR (400 MHz, CDCl$_3$) δ 0.87-0.95 (m, 6H), 1.25-1.40 (m, 9H), 1.55-1.65 (m, 1H), 2.35 (s, 3H), 2.57 (t, J=7.02 Hz, 2H), 2.95 (t, J=7.06 Hz, 2H), 4.07-4.09 (m, 2H), 8.43 (d, J=5.5 Hz, 1H), 8.47 (t, J=5.7 Hz, 1H), 8.68 (s, 1H), 8.98 (brs, 1H). LC-MS m/z (M+H): 353.48

Step 3: sodium 4-acetamidopyridine-3-thiolate

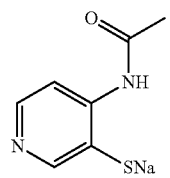

To a stirred solution of 3-ethylheptyl 3-(4-acetamidopyridin-3-ylthio)propanoate (1.5 g, 4.225 mmol) in ethanol (20 mL) was added 21% sodium ethoxide solution in ethanol (3 mL) at 0° C., then stirred at 0° C. for 1 h, evaporated the solvent under reduced pressure, to get sodium 4-acetamidopyridine-3-thiolate (0.75 g) obtained was forwarded to the next step.

Step 4: 6-nitro-8-(trifluoromethyl)-5H-benzo[e]pyrido[3,4-b][1,4]thiazine

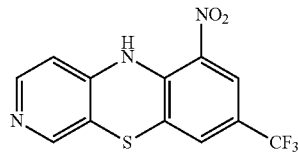 [SMILES: O=[N+]([O-])c1cc(C(F)(F)F)cc2c1Nc1ccncc1S2]

A stirred suspension of sodium 4-acetamidopyridine-3-thiolate (0.75 g, 3.94 mmol), 2-chloro-1,3-dinitro-5-(trifluoromethyl)benzene (1.2 g, 4.33 mmol), in DMF (7.5 mL) was heated at 100° C. for 12 h. To this added 50 mL of ice cold water, extracted the compound into EtOAc, dried the organic layer over sodium sulphate, filtered and concentrated. Obtained crude was purified on gradient column with 20-30% EtOAc/hexane as eluant to gives 6-nitro-8-(trifluoromethyl)-5H-benzo[e]pyrido[3,4-b][1,4]thiazine (0.8 g, 65%), as off Black solid. $^1$H NMR (400 MHz, DMSO-d$_6$) δ 7.13 (d, J=5.39 Hz, 1H), 7.79-7.80 (m, 1H), 8.05 (s, 1H), 8.14 (s, 1H), 8.18 (d, J=6.12 Hz, 1H), 9.85 (brs, 1H) LC-MS m/z (M+H): 314.2

Step 5: 8-(trifluoromethyl)-5H-benzo[e]pyrido[3,4-b][1,4]thiazin-6-amine

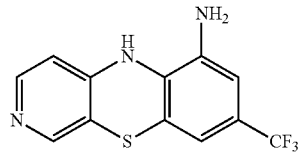 [SMILES: Nc1cc(C(F)(F)F)cc2c1Nc1ccncc1S2]

To a stirred solution of 6-nitro-8-(trifluoromethyl)-5H-benzo[e]pyrido[3,4-b][1,4]thiazine (0.3 g, 0.961 mmol) in methanol (10 mL) was added a solution of pd/C (10%, water wet, 0.04 g), and stirred at room temperature for 12 h. The reaction mixture was filtered through celite and concentrated to get 8-(trifluoromethyl)-5H-benzo[e]pyrido[3,4-b][1,4]thiazin-6-amine (0.200 g, 74%)) as a brown solid. $^1$H NMR (400 MHz, DMSO-d$_6$) δ 5.50 (brs, 2H) 6.52 (s, 1H), 6.73 (d, J=5.39 Hz, 1H), 6.77 (d, J=1.86 Hz, 1H), 7.93 (s, 1H), 8.03 (d, J=5.37 Hz, 1H), 8.29 (brs, 1H). LC-MS m/z (M+H): 284.1

Step 6: tert-butyl 3-(8-(trifluoromethyl)-5H-benzo[e]pyrido[3,4-b][1,4]thiazin-6-ylcarbamoyl)cyclohexylcarbamate

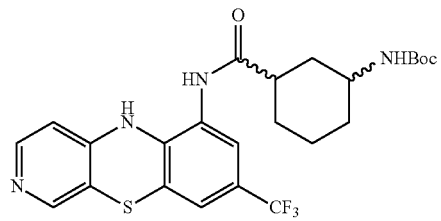

To a stirred solution of 3-((tert-butoxycarbonyl)amino) cyclohexanecarboxylic acid (0.21 g, 0.864 mmol) in pyridine (2 mL) was added a solution POCl₃ (0.8 mL) at 0° C. and starred at 0° C. for 10 min. and was added a solution of 8-(trifluoromethyl)-5H-benzo[e]pyrido[3,4-b][1,4]thiazin-6-amine in pyridine (2 ml) at 0° C. and starred at 0° C. for 1 h. After completion of the reaction mixture was poured in to ice, and basified with saturated sodium bi carbonate solution and extracted compound with EtOAc (3×25 ml), dried the organic layer over sodium sulphate filtered and concentrated. The crude was purified by gradient column chromatography (product eluted with 20% EtOAc/hexane) to give tert-butyl3-(8-(trifluoromethyl)-5H-benzo[e]pyrido[3,4-b][1,4]thiazin-6-ylcarbamoyl)cyclohexylcarbamate as off white solid (0.120 g, 35%). ¹H NMR (400 MHz, DMSO-d₆) δ1.29-1.33 (m, 4H), 1.35-1.42 (m, 12H), 1.62-1.89 (m, 4H), 2.01-2.09 (m, 1H), 6.84 (d, J=5.55 Hz, 1H), 7.21 (s, 1H), 7.34 (s, 1H), 7.99 (s, 1H), 8.08 (d, J=5.39 Hz, 1H), 8.49 (s, 1H), 9.38 (s, 1H). LC-MS m/z (M+H): 509.56

Step 7: 3-amino-N-(8-(trifluoromethyl)-5H-benzo[e]pyrido[3,4-b][1,4]thiazin-6-yl)cyclohexanecarboxamide

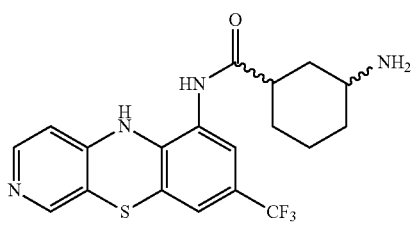 [SMILES: NC1CCCC(C(=O)Nc2cc(C(F)(F)F)cc3c2Nc2ccncc2S3)C1]

To a stirred solution of tert-butyl3-(8-(trifluoromethyl)-5H-benzo[e]pyrido[3,4-b][1,4]thiazin-6-ylcarbamoyl)cyclohexylcarbamate (0.1 g, 0.196 mmol) in dichloromethane (20 mL) was added a solution of HCl/dioxane (4M, 2.0 mL) at 0° C. and starred at room temperature for 1 h. The reaction mixture was concentrated under reduced pressure, neutralized with saturated sodium bicarbonate solution, extracted with dichloromethane (30 ml), and concentrated. The crude was purified by preparative TLC (3% MeOH in DCM) to get the 3-amino-N-(8-(trifluoromethyl)-5H-benzo[e]pyrido[3,4-b][1,4]thiazin-6-yl)cyclohexanecarboxamide (0.04 g, 50%). as off white solid ¹H NMR (400 MHz, DMSO-d₆) δ 1.01-1.07 (m, 1H), 1.22-1.34 (m, 4H), 1.77-1.83 (m, 2H), 1.89 (d, J=10.3 Hz, 1H), 2.05 (d, J=11.7 Hz, 1H), 2.52-2.59 (m, 1H), 2.69-2.75 (m, 1H), 6.91 (d, J=5.3 Hz, 1H), 7.19 (s, 1H), 7.43 (s, 1H), 7.98 (s, 1H), 8.07 (d, J=5.3 Hz, 1H)
LC-MS m/z (M+H): 409.1

Some examples of compounds synthesised by the method of Scheme XXIX are provided in Table XXIX

| Cmpd # | X¹ | X² | R² |
|---|---|---|---|
| 257 | H | N | (cyclohexyl-NH₂ with carbonyl linker) |
| 263 | N | H | (cyclohexyl-NH₂ with carbonyl linker) |
| 264 | N | H | (piperidin-4-yl NH) |
| 268 | N | H | (piperidinyl-CH₂CH₂-NH₂) |
| 285 | N | ethyl ester O-C(=O)-C(CH₃)- | (piperidinyl-CH₂CH₂-NH₂) |

Figure 24:
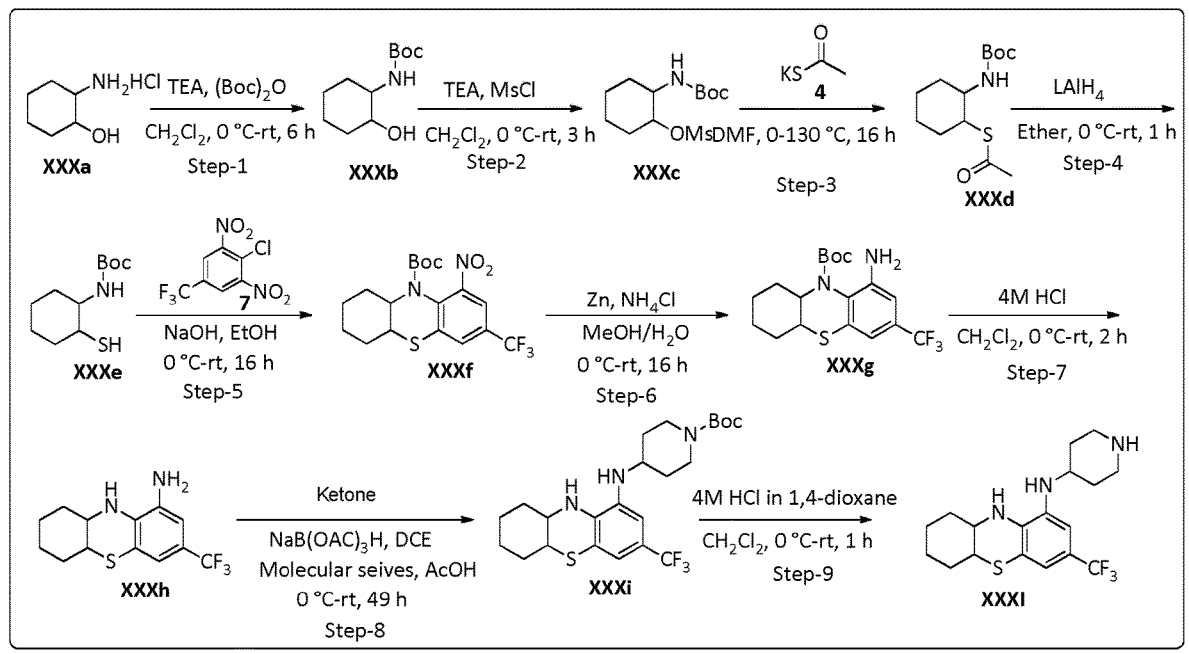
FIG. 24 shows general synthetic scheme XXX for the synthesis of selected compounds according to the present invention

FIG. 24 shows general synthetic scheme XXX for the synthesis of selected substituted phenothiazenes. 2-amino cyclo hexanol of XXXa were protected with boc and and nucleophilic substitution reaction with a thiol surrogate by using potassium thio acetate via., mesylation XXXd, followed bu insituSmiles rearrangement resulted in the formation of trisubstituted phemothiaxzenes XXXd. Nitro group reduction with Zn/NH4Cl gave compound XXXg, Reductive amination of XXXh with an appropriate ketone resulted in compound XXXi, followed by deprotection resulted compound XXX.

Compound 259: N-(piperidin-4-yl)-7-(trifluoromethyl)-2,3,4,4a,10,10a-hexahydro-1H-phenothiazin-9-amine

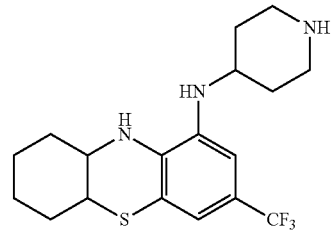 [SMILES: FC(F)(F)c1cc(NC2CCNCC2)c2c(c1)SC1CCCCC1N2]

Step-1: Synthesis of tert-butyl (2-hydroxycyclohexyl) carbamate

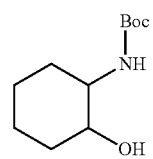

To a stirred solution of 2-aminocyclohexanol hydrochloride (6.5 g, 43.04 mmol) in DCM (120 mL) was added TEA (15 mL, 107.61 mmol) at 0° C. followed by di tert butyl carbamate (8.75 g, 40.89 mmol) and stirred the reaction mixture at room temperature for 16 h. The progress of the

131 reaction was monitored by TLC. The reaction mixture was diluted with DCM (100 mL), washed with water (200 mL), saturated NaHCO₃ solution (100 mL). The organic layer was separated, dried over anhydrous sodium sulphate and concentrated under reduced pressure to afford tert-butyl (2-hydroxycyclohexyl) carbamate (8.5 g, yield: 92%) as off white solid.

Step-2: Synthesis of 2-((tert-butoxycarbonyl)amino)cyclohexyl methanesulfonate

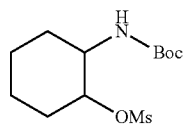 [SMILES: CC(C)(C)OC(=O)NC1CCCCC1OS(C)(=O)=O]

To a stirred solution of tert-butyl (2-hydroxycyclohexyl) carbamate (8.5 g, 39.53 mmol) in (100 mL) was DCM added tri ethyl amine (17 mL, 118.60 mmol) followed by mesyl chloride (4 mL, 51.39 mmol) at 0° C. After stirring the reaction mixture for 15 min allowed to stir at room temperature for 3 h. The progress of the reaction was monitored by TLC. The reaction mixture was diluted with DCM (100 mL), washed with brine (100 mL) and saturated NaHCO₃ solution (100 mL). The organic layer was separated dried over anhydrous sodium sulphate and concentrated under reduced pressure to afford 2-((tert-butoxycarbonyl)amino) cyclohexyl methanesulfonate (10.1 g, yield: 87%) as off white solid.

Step-3: Synthesis of 2-((tert-butoxycarbonyl)amino)cyclohexyl methanesulfonate

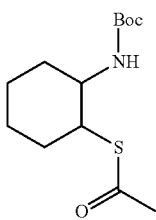 [SMILES: CC(=O)SC1CCCCC1NC(=O)OC(C)(C)C]

To a stirred solution of 2-((tert-butoxycarbonyl)amino) cyclohexyl methanesulfonate (10 g, 34.12 mmol,) in DMF (100 mL) was added potassiumthioacetate (11.6, 102.38 mmol) at 0° C. and stirred the reaction mixture at 130° C. for 16 h. The progress of the reaction was monitored by TLC. The reaction mixture was poured into ice-cold water (100 mL), extracted with ethyl acetate (3×100 mL). The combined organic layer was dried over anhydrous sodium sulphate and concentrated under reduced pressure. The crude compound was purified by gradient column chromatography (eluted with 4-5% EtOAc in Hexane). The pure fractions were collected and concentrated under reduced pressure to afford 2-((tert-butoxycarbonyl)amino)cyclohexyl methanesulfonate (2.4 g, yield: 26%) as off white solid.

132

Step-4: Synthesis of tert-butyl (2-mercaptocyclohexyl) carbamate

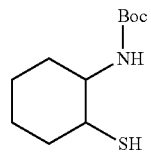

6

To a stirred solution of Lithium aluminium hydride (0.42 g, 10.98 mmol) in di ethyl ether (5 mL) was added 2-((tert-butoxy carbonyl) amino) cyclohexyl methanesulfonate (1 g, 3.66 mmol) in di ethyl ether (35 mL) at 0° C. drop wise over as period of 20 min and stirred the reaction mixture at room temperature for 1 h. The progress of the reaction was monitored by TLC. The reaction mixture was cooled to 0° C., added 2N NaOH solution (2.5 mL) and stirred for 10 min; solid formed was filtered through a pad of celite, washed with ethyl acetate (2×25 mL). The combined organic layer was dried over anhydrous sodium sulphate and concentrated (20-25° C.) under reduced pressure to afford tert-butyl (2-mercaptocyclohexyl)carbamate (380 mg, crude) as colorless solid. The crude compound was used in the next step without any purification.

Step-5: Synthesis of 2-((tert-butoxycarbonyl)amino)cyclohexyl methanesulfonate

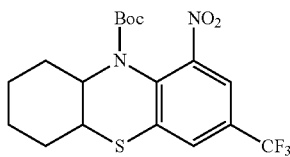 [SMILES: CC(C)(C)OC(=O)N1c2c(cc(C(F)(F)F)cc2[N+](=O)[O-])SC2CCCCC21]

To a stirred solution of tert-butyl (2-mercaptocyclohexyl) carbamate (700 mg, 3.03 mmol), 2-chloro-1,3-dinitro-5-(trifluoromethyl)benzene (818 mg, 2.42 mmol) in EtOH (10 mL) was added NaOH (364 mg, 9.09 mmol) at 0° C. and stirred the reaction mixture at room temperature for 16 h. The progress of the reaction was monitored by TLC. The reaction mixture was diluted with water (30 mL), extracted with ethyl acetate (3×25 mL). The combined organic layer was dried over anhydrous sodium sulphate and concentrated under reduced pressure. The crude compound was purified by gradient column chromatography (eluted with 4-5% EtOAc in Hexane). The pure fractions were collected and concentrated under reduced pressure to afford 2-((tert-butoxycarbonyl) amino)cyclohexyl methanesulfonate (180 mg, yield: 14%) as yellow oil. LC-MS m/z (M+H): 418.43

Step-6: Synthesis of tert-butyl 9-amino-7-(trifluoromethyl)-2,3,4,4a-tetrahydro-1H-phenothiazine-10(10aH)-carboxylate

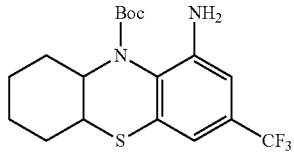 [SMILES: CC(C)(C)OC(=O)N1c2c(N)cc(C(F)(F)F)cc2SC2CCCCC21]

To a stirred solution of 2-((tert-butoxycarbonyl)amino) cyclohexyl methanesulfonate (35 mg, 0.08 mmol) in MeOH (1 mL), H$_2$O (1 mL) was added NH$_4$Cl (22 mg, 0.41 mmol) followed by Zn dust (27 mg, 0.41 mmol) at 0° C. and stirred the reaction mixture at room temperature for 16 h. The progress of the reaction was monitored by TLC. The reaction mixture was filtered through a pad of celite, washed with ethyl acetate (2×10 mL). The filtrate was dried over anhydrous sodium sulphate and concentrated under reduced pressure. The crude compound was purified by gradient column chromatography (eluted with EtOAc in Hexane) followed by preparative TLC (to afford tert-butyl 9-amino-7-(trifluoromethyl)-2,3,4,4a-tetrahydro-1H-phenothiazine-10(10aH)-carboxylate (25 mg, yield: 800) as yellow gummy liquid. LC-MS m/z (M+H): 389.33

Step-7: Synthesis of 7-(trifluoromethyl)-2,3,4,4a,10,10a-hexahydro-1H-phenothiazin-9-amine: (BI-001-0015-161)

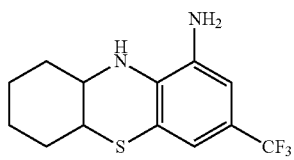 [SMILES: Nc1cc(C(F)(F)F)cc2c1NC1CCCCC1S2]

To a stirred solution of tert-butyl 9-amino-7-(trifluoromethyl)-2,3,4,4a-tetrahydro-1H-phenothiazine-10(10aH)-carboxylate (60 mg, 0.15 mmol) in DCM (2 mL) was added 4M HCl in Dioxane (2 mL) at 0° C. and stirred the reaction mixture at room temperature for 2 h. The progress of the reaction was monitored by TLC. The reaction mixture was concentrated under reduced pressure. The residue was basified by using aqueous saturated NaHCO$_3$, extracted with ethyl acetate (2×20 mL). The combined organic layer was dried over anhydrous sodium sulphate and concentrated under reduced pressure. The crude compound was purified by preparative HPLC (20% EtOAc in Hexane) to afford 7-(trifluoromethyl)-2,3,4,4a,10,10a-hexahydro-1H-phenothiazin-9-amine (35 mg, yield: 79%) as colorless liquid. $^1$H NMR (400 MHz, DMSO-d6) δ 1.30-1.44 (m, 2H), 1.55-1.68 (m, 4H), 1.70-1.81 (m, 1H), 1.90-1.99 (m, 1H), 3.26-3.31 (m, 1H), 3.73-3.74 (m, 1H), 5.03 (s, 1H), 5.15 (s, 1H), 6.48 (s, 1H), 6.58 (d, J=1.99 Hz, 1H). LC-MS m/z (M+H): 289.3

Step-8: Synthesis of tert-butyl 4-((7-(trifluoromethyl)-2,3,4,4a,10,10a-hexahydro-1H-phenothiazin-9-yl)amino) piperidine-1-carboxylate

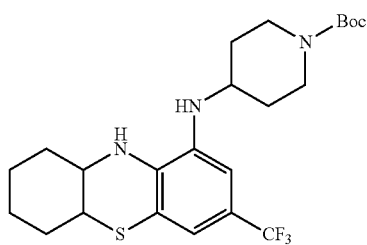

To a stirred solution of 7-(trifluoromethyl)-2,3,4,4a,10,10a-hexahydro-1H-phenothiazin-9-amine (30 mg, 0.10 mmol) in DCE (3 mL) was added molecular sieves (200 mg), tert-butyl 4-oxopiperidine-1-carboxylate (24 mg, 0.12 mmol), Acetic acid (0.01 mL) at 0° C. After stirring the reaction mixture for 1 h, was added sodium triacetoxy borohydride (177 mg, 0.83 mmol) and stirred the reaction mixture at room temperature for 48 h. The progress of the reaction was monitored by TLC. The reaction mixture was filtered through a pad of celite, washed with DCM (2×10 mL). The combined organic layer was washed with saturated NaHCO$_3$ (25 mL). The aq layer was extracted with DCM (2×10 mL), dried over anhydrous sodium sulphate and concentrated under reduced pressure to afford tert-butyl 4-((7-(trifluoromethyl)-2,3,4,4a,10,10a-hexahydro-1H-phenothiazin-9-yl)amino) piperidine-1-carboxylate (60 mg, crude) as brown color liquid. The crude compound was used in the next step without any purification.

Step-9: Synthesis of N-(piperidin-4-yl)-7-(trifluoromethyl)-2,3,4,4a,10,10a-hexahydro-1H-phenothiazin-9-amine

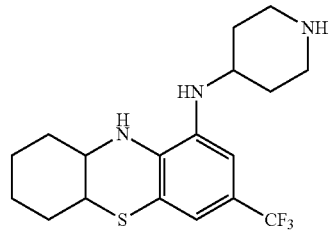

To a stirred solution of tert-butyl 4-((7-(trifluoromethyl)-2,3,4,4a,10,10a-hexahydro-1H-phenothiazin-9-yl) amino) piperidine-1-carboxylate (50 mg, 0.10 mmol) in DCM (2 mL) was added 4M HCl in 1,4-dioxane (2 mL) at 0° C. and stirred the reaction mixture at room temperature for 1 h. The progress of the reaction was monitored by TLC. The reaction mixture was concentrated under reduced pressure. The residue was diluted with ethyl acetate (20 mL), washed with saturated NaHCO$_3$ (20 mL). The organic layer was dried over anhydrous sodium sulphate and concentrated under reduced pressure. The crude compound was purified by preparative TLC (3% MeOH in DCM) to afford N-(piperidin-4-yl)-7-(trifluoromethyl)-2,3,4,4a,10,10a-hexahydro-1H-phenothiazin-9-amine (9 mg, yield: 24%) as grey solid.

¹H NMR (400 MHz, DMSO-d₆) δ 8.05 (s, 1H), 6.56 (s, 1H), 6.48 (s, 1H), 5.43 (s, 1H), 4.92 (d, J=6.8 Hz, 1H), 3.74 (s, 1H), 3.54-3.51 (m, 1H), 3.26-3.23 (m, 5H), 2.93 (t, J=11.6 Hz, 2H), 2.03-1.90 (m, 2H), 1.79-1.78 (m, 1H), 1.65-1.51 (m, 5H), 1.49-1.33 (m, 2H) LC-MS m/z (M+H): 372.1

Figure 25:
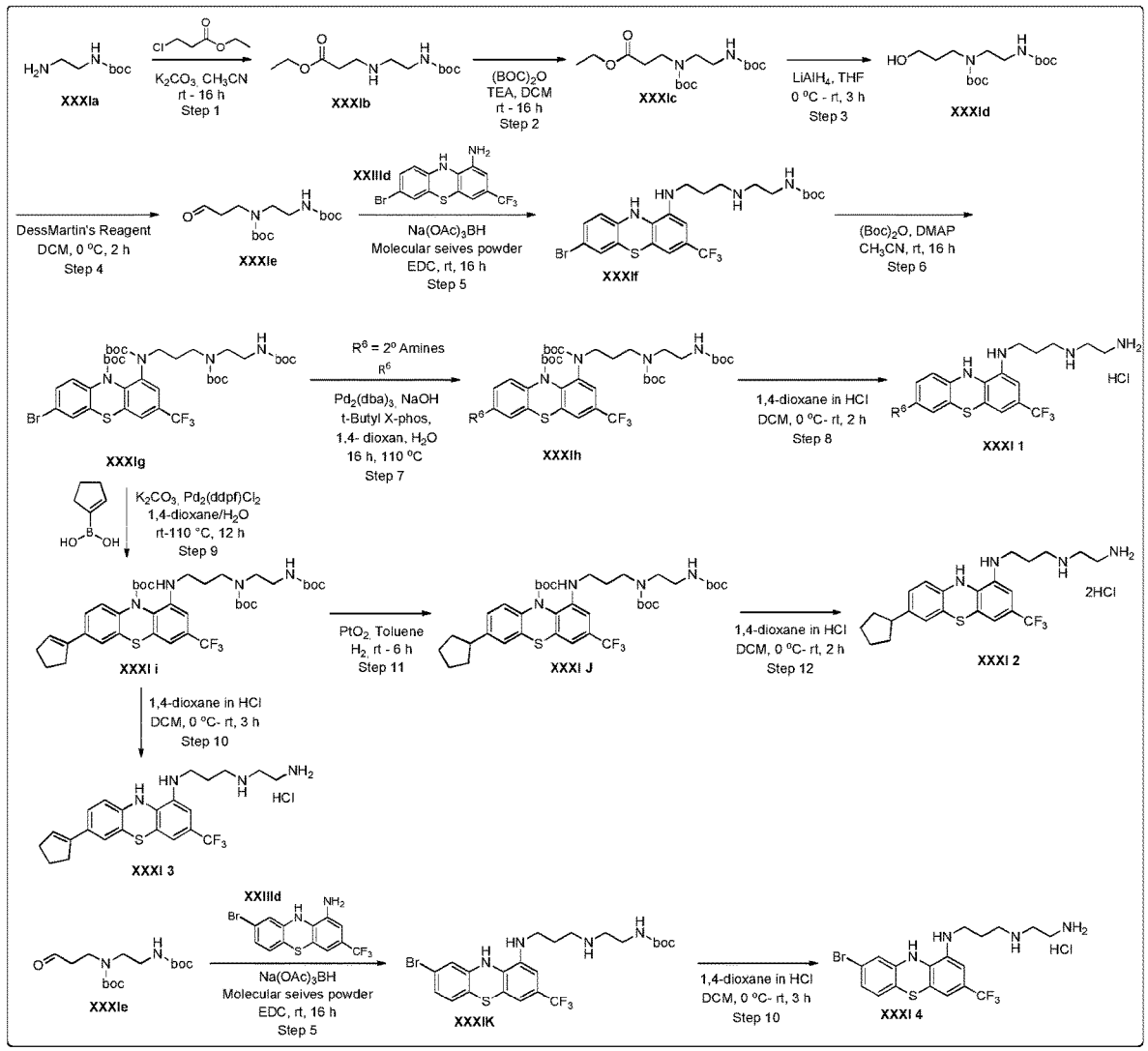
FIG. 25 shows general synthetic scheme XXXI for the synthesis of selected compounds according to the present invention

FIG. 25 shows general reaction scheme XXXI for the synthesis of selected tert-butyl (2-aminoethyl) carbamate alkylated with ethyl 3-chloropropanoate in the presence of base to gave XXXIb, which were further protected with boc anhydride to give N-protected ester XXXIc, XXXIc was ester reduction with lithium aluminum hydride to gave XXXId and followed by oxidation with martin's reagent to give corresponding aldehydes XXXIe. Reductive amination of compound XXXI e with various aldehydes or ketones yielded corresponding n-alkylated phenothiazines XXXIf, which were further deprotected to give the corresponding free amines XXXIg. And alkylated to give XXXIh, further protection of the XXXIh with boc anhydride to give tetra boc protected compounds of XXXIi. Further Buchwald coupling of compound XXXIi with various amines, followed by deprotection gave XXXI 1 with corresponding salts. And Further Suzuki coupling of compound of XXXIi with boronic acids followed by deprotection gave XXXI 3 with corresponding salts and also with XXXIj double bond reduction with platinum oxide and followed by deprotection gave XXXI 2

Compound 346: N1-(2-aminoethyl)-N3-(7-(3, 5-dimethylpiperidin-1-yl)-3-(trifluoromethyl)-10H-phenothiazin-1-yl) propane-1,3-diamine hydrochloride

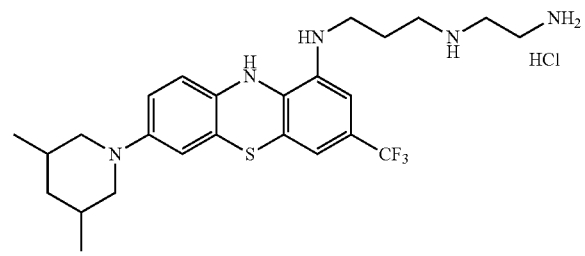 [SMILES: CC1CC(C)CN(c2ccc3c(c2)Sc2cc(C(F)(F)F)cc(NCCCNCCN)c2N3)C1 ; Cl]

Step 1: Ethyl 3-((2-((tert-butoxycarbonyl) amino) ethyl) amino) propanoate

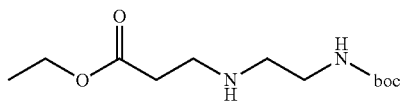

To a solution of tert-butyl (2-aminoethyl) carbamate (20 g, 124.843 mmol) in acetonitrile (200 mL) was added potassium carbonate (68.9 g, 499.275 mmol) and ethyl 3-chloro formate (18.9 g, 138.38 mmol) at room temperature. Reaction mixture was stirred at room temperature for 16 h. Progress of the reaction was followed by TLC (5% methanol/DCM). After completion of the reaction, diluted with water (400 mL) and extracted with ethyl acetate (150 mL×3). Organic layer was dried over sodium sulphate, filtered and concentrated to give crude product. This crude product purified by gradient column chromatography (product eluted with 100% DCM) to give ethyl 3-((2-((tert-butoxycarbonyl) amino) ethyl) amino) propanoate as colorless liquid (20 g, 61%). ¹H NMR (400 MHz, DMSO-d6) δ1.1 (t, J=7.16 Hz, 3H), 1.4 (s, 9H), 1.6 (br s, 1H), 2.3 (t, J=5.08 Hz, 2H), 2.4-2.5 (m, 2H), 2.7 (t, J=6.8 Hz, 2H), 2.9-3.0 (m, 2H), 4.0 (q, J=7.04 Hz 2H).

Step 2: Ethyl 3-((tert-butoxycarbonyl)(2-((tert-butoxycarbonyl)amino)ethyl)amino)propanoate

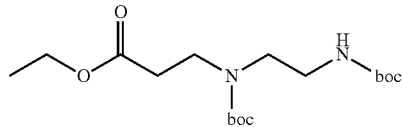

To a solution of ethyl 3-((2-((tert-butoxycarbonyl) amino) ethyl) amino) propanoate (20 g, 76.79 mmol) in DCM (200 mL) was added triethyl amine (31.1 g, 307.342 mmol) and followed by di tert butyl di carbonate (28.7 g, 131,651 mmol) at 0° C. Reaction mixture was stirred at room temperature for 16 h. After completion of the reaction, diluted with DCM (200 mL) and washed with water (100 mL×2). Organic layer was dried over sodium sulphate, filtered and evaporated to give crude product. This crude product purified by gradient column chromatography (product eluted with 10% ethyl acetate/n-hexane) to give ethyl 3-((tert-butoxycarbonyl)(2-((tert-butoxycarbonyl)amino) ethyl)amino)propanoate as colorless liquid (23 g, 83%). ¹H NMR (400 MHz, DMSO-d₆) δ1.1 (t, J=7.08 Hz, 3H), 1.4 (s, 19H), 2.4-2.5 (m, 1H), 2.9-3.0 (m, 2H), 3.1 (t, J=6.36 Hz, 2H), 3.2 (s, 1H), 3.3 (t, J=7.08 Hz, 2H), 4.0-4.1 (m, 2H), 6.8 (br s, 1H).

Step 3: Tert-butyl (2-((tert-butoxycarbonyl) amino) ethyl)(3-hydroxypropyl)carbamate

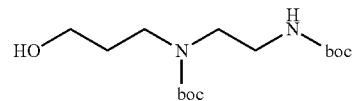

To a solution of ethyl 3-((tert-butoxycarbonyl)(2-((tert-butoxycarbonyl)amino)ethyl)amino)propanoate (12 g, 33.291 mmol) in THF (120 mL) was added lithium aluminum hydride (1.53 g, 40.326 mmol) at 0° C. Reaction mixture stirred at room temperature at room temperature for 3 h. After completion of the reaction, quenched with ice water and diluted with ethyl acetate, filtered through celite for remove inorganic salts. Organic layer was separated and dried over sodium sulphate, filtered and evaporated to give crude product. This crude product purified by gradient column chromatography (product eluted with 40% ethyl acetate/n-hexane) to give tert-butyl (2-((tert-butoxycarbonyl) amino) ethyl)(3-hydroxypropyl)carbamate (8 g, 75.5%). ¹H NMR (400 MHz, DMSO-d₆) δ1.4 (s, 18H), 1.5 (br s, 2H), 3.0-3.1 (m, 2H), 3.1-3.2 (m, 2H), 3.3 (q, J=5.88 Hz, 2H), 4.4 (br s, 1H), 6.8 (br s, 1H).

Step 4: Tert-butyl (2-((tert-butoxycarbonyl) amino) ethyl) (3-oxopropyl) carbamate

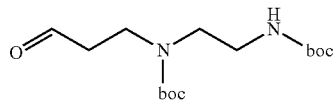

To a solution of tert-butyl (2-((tert-butoxycarbonyl) amino) ethyl)(3-hydroxypropyl)carbamate (8 g, 25.157 mmol) in DCM (160 mL) was added Dessmartin's reagent (16 g, 37.735 mmol) at 0° C. Reaction mixture stirred at room temperature at room temperature for 3 h. After completion of the reaction, diluted with DCM (100 mL) and filtered through celite, filtrate was washed with water (100 mL). Organic layer was separated and dried over sodium sulphate, filtered and evaporated to give crude residue, which was triturated with diethyl ether (100 mL) and filtered to remove the inorganic salts. Filtrate was concentrated to give crude product, which was used for the next step without further purification (8 g, crude).

Step 5: tert-butyl (2-((3-((7-bromo-3-(trifluoromethyl)-10H-phenothiazin-1-yl) amino) propyl) amino) ethyl) carbamate

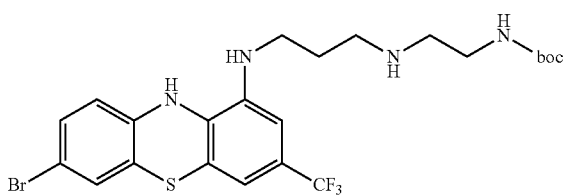

To a stirred solution of 7-bromo-3-(trifluoromethyl)-10H-phenothiazin-1-amine (5.2 g, 14.448 mmol) in dichloroethane (100 mL) was added tert-butyl (2-((tert-butoxycarbonyl) amino) ethyl) (3-oxopropyl) carbamate (5.485 g, 17.337 mmol) and 4A° Molecular sieves powder (10 g) at room temperature After stirring the reaction mixture for 1 h, was added sodium triacetoxy boro hydride (9.184 g, 43.344 mmol). Reaction mixture was stirred at room temperature for 16 h. The reaction mixture was quenched with saturated NaHCO₃ solution, extracted with DCM (2×100 mL). The combined organic layer was dried over anhydrous sodium sulphate and concentrated under reduced pressure. The crude compound was purified by gradient column chromatography (eluted with 20% EtOAc in Hexane) to afford tert-butyl (2-((3-((7-bromo-3-(trifluoromethyl)-10H-phenothiazin-1-yl) amino) propyl) amino) ethyl) carbamate as Off white solid (3 g, 31.4%). $^1$H NMR (400 MHz, DMSO-db) δ1.3-1.5 (m, 11H), 1.7-1.8 (m, 2H), 3.0-3.1 (m, 4H), 3.2 (t, J=6.4 Hz, 2H), 3.3 (t, J=9.64 Hz, 2H), 6.4 (s, 1H), 6.5 (s, 1H), 6.8 (d, J=8.7 Hz, 2H), 7.2 (m, 2H), 8.0 (s, 1H).

Step 6: tert-butyl 7-bromo-1-((tert-butoxycarbonyl) (3-((tert-butoxycarbonyl)(2-((tert-butoxycarbonyl) amino)ethyl)amino)propyl)amino)-3-(trifluoromethyl)-10H-phenothiazine-10-carboxylate

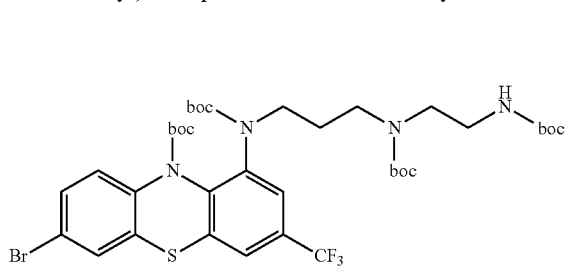

To a stirred solution of tert-butyl (2-((3-((7-bromo-3-(trifluoromethyl)-10H-phenothiazin-1-yl) amino) propyl) amino) ethyl) carbamate (3 g, 4.534 mmol) in Acetonitrile (50 mL) was added DMAP (1.9 g, 15.871 mmol) followed by ditert-butyl dicarbonate (5 g, 22.673 mmol) at 0° C. and stirred the reaction mixture at room temperature for 16 h. The progress of the reaction was monitored by TLC. After completion of the reaction, reaction mixture was diluted with ethyl acetate (100 mL) and washed with ethyl acetate (50 mL). The combined organic layer was dried over anhydrous sodium sulphate filtered and concentrated under reduced pressure. The crude compound was purified by gradient column chromatography (eluted with 15% EtOAc in Hexane) to afford tert-butyl 7-bromo-1-((tert-butoxycarbonyl) (3-((tert-butoxycarbonyl) (2-((tert-butoxycarbonyl) amino) ethyl)amino) propyl) amino)-3-(trifluoromethyl)-10H-phenothiazine-10-carboxylate as off white solid (2.1 g, 53.8%). $^1$H NMR (400 MHz, DMSO-d₆)) δ1.2 (s, 5H), 1.3-1.4 (m, 12H), 1.6-1.8 (m, 2H), 3.1-3.3 (m, 5H), 3.4 (s, 1H), 3.6 (s, 2H), 6.2 (br, 1H), 6.7-6.8 (m, 1H), 6.9 (m, 1H), 7.5 (d, J=7.68 Hz, 1H) 7.7 (d, J=8.48 Hz, 1H), 7.7 (s, 1H)

Step 7: tert-butyl 1-((tert-butoxycarbonyl)(3-((tert-butoxycarbonyl)(2-((tert-butoxycarbonyl)amino) ethyl)amino)propyl)amino)-7-(3,5-dimethylpiperidin-1-yl)-3-(trifluoromethyl)-10H-phenothiazine-10-carboxylate

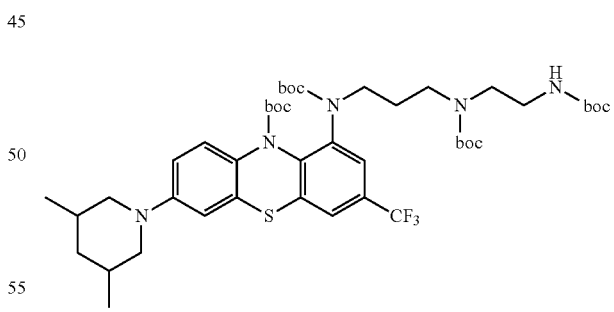

To a stirred solution of tert-butyl 7-bromo-1-((tert-butoxycarbonyl) (3-((tert-butoxycarbonyl) (2-((tert-butoxycarbonyl)amino) ethyl)amino) propyl) amino)-3-(trifluoromethyl)-10H-phenothiazine-10-carboxylate (120 mg, 0.139 mmol), 3,5-dimethylpiperidine (31.5 mg, 0.278 mmol) in 1 4 Dioxane (3 mL), water (1 mL) was added sodium hydroxide (13.92 mg, 0.348 mmol) at room temperature. After degassed with argon for 10 min was added Pd₂(dba)₃ (12.75 mg, 0.013 mmol), tert-butylX-phos (8.85 mg, 0.020 mmol) again degassed for 5 min and stirred the reaction mixture at 110° C. for 16 h. The progress of the reaction was monitored by TLC. The reaction mixture was diluted with water (10 mL), extracted with ethyl acetate (2×20 mL). The combined organic layer was dried over anhydrous sodium sulphate and concentrated under reduced pressure. The crude compound was purified by gradient column chromatography (eluted with 25% ethyl acetate/n-Hexane) to afford tert-butyl 1-((tert-butoxycarbonyl)(3-((tert-butoxycarbonyl)(2-((tert-butoxycarbonyl)amino)ethyl)amino)propyl)amino)-7-(3,5-dimethylpiperidin-1-yl)-3-(trifluoromethyl)-10H-phenothiazine-10-carboxylate as off white solid (30 mg, 24.19%). $^1$H NMR (400 MHz, DMSO-d$_6$) δ 0.6-0.8 (m, 1H), 0.9 (d, J=2.6 Hz, 6H), 1.2 (s, 4H), 1.3 (s, 9H), 1.4 (s, 18H), 1.5-1.6 (m, 5H), 1.7-1.9 (m, 1H), 3.6-3.7 (m, 4H), 5.4 (br, 1H), 6.7-6.8 (m, 2H), 6.9 (s, 1H), 7.2 (d, J=8.68 Hz, 1H), 7.3 (d, J=2.08 Hz, 1H).

Step 8: N1-(2-aminoethyl)-N3-(7-(3,5-dimethylpiperidin-1-yl)-3-(trifluoromethyl)-10H-phenothiazin-1-yl)propane-1,3-diamine hydrochloride

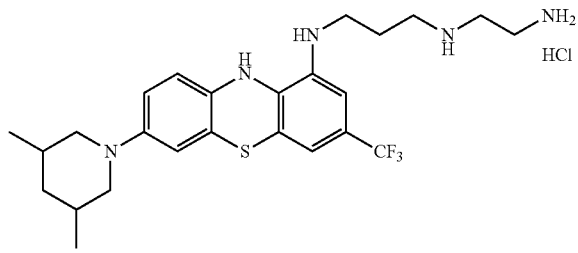 [SMILES: CC1CC(C)CN(c2ccc3c(c2)Sc2cc(C(F)(F)F)cc(NCCCNCCN)c2N3)C1 ; Cl]

To a stirred solution of tert-butyl 1-((tert-butoxycarbonyl) (3-((tert-butoxycarbonyl)(2-((tert-butoxycarbonyl)amino) ethyl)amino)propyl)amino)-7-(3,5-dimethylpiperidin-1-yl)-3-(trifluoromethyl)-10H-phenothiazine-10-carboxylate (30 mg, 0.003 mmol) in DCM (1 mL) was added 4M HCl in 1,4-dioxane (2 mL) at 0° C. and stirred the reaction mixture at room temperature for 2 h. The progress of the reaction was monitored by TLC. The reaction mixture was concentrated under reduced pressure. The crude compound was washed with n-pentane (2×2 mL) and dried under reduced pressure to afford N1-(2-aminoethyl)-N3-(7-(3,5-dimethylpiperidin-1-yl)-3-(trifluoromethyl)-10H-phenothiazin-1-yl)propane-1,3-diamine hydrochloride as grey solid (16 mg, 90.3%) $^1$H NMR (400 MHz, DMSO-d6) δ 0.8-0.9 (m, 7H), 1.1-1.3 (m, 1H), 1.7-1.8 (m, 1H), 2.0-2.1 (m, 2H), 2.2-2.3 (m, 2H), 3.0-3.2 (m, 9H), 3.3-3.4 (m, 4H), 6.5 (d, J=6 Hz 2H), 7.2-7.5 (m, 3H), 8.3 (br s, 3H), 9.3 (br s, 2H). MS m/z (M+H): 494.23

Compound 358: N1-(2-aminoethyl)-N3-(7-(cyclopent-1-en-1-yl)-3-(trifluoromethyl)-10H-phenothiazin-1-yl) propane-1, 3-diaminehydrochloride

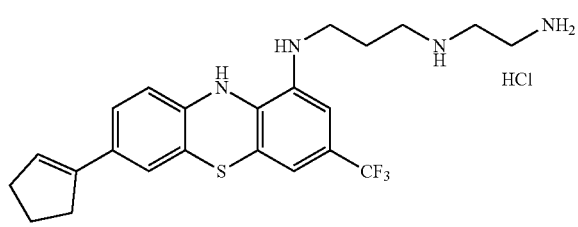 [SMILES: NCCNCCCNc1cc(C(F)(F)F)cc2c1Nc1ccc(C3=CCCC3)cc1S2 ; Cl]

Step 9: tert-butyl 1((3((tertbutoxycarbonyl)(2((tert-butoxycarbonyl)amino)ethyl)amino)propyl)amino)-7-(cyclopent-1-en-1-yl)-3-(trifluoromethyl)-10H-phenothiazine-10-carboxylate

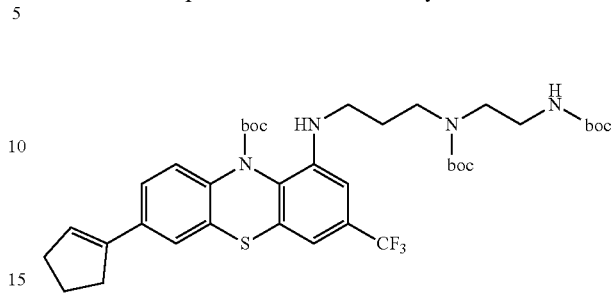

To a stirred solution (200 mg, 0.232 mmol, compound-1) in 1 4 Dioxane/H$_2$O (8 mL) was added potassium carbonate (76 mg, 0.696 mmol) at room temperature. After degassed with argon for 10 min was added boronic acid (52 mg, 0.464 mmol) and finally added Pd2(dppf)Cl2 DCM complex. (10 mg, 0.116 mmol) again degassed for 5 min and stirred the reaction mixture at 110° C. for 12 h. Progress of the reaction was monitored by TLC. The reaction mixture was filtered through a pad of celite; the filtrate was concentrated under reduced pressure. The crude compound was purified by combi-flash chromatography (eluted with 2-3% EA in Pet Ether) followed by preparative TLC to afford tert-butyl1((3 ((tertbutoxycarbonyl)(2((tertbutoxycarbonyl)amino)ethyl) amino)propyl)amino)-7-(cyclopent-1-en-1-yl)-3-(trifluoromethyl)-10H-phenothiazine-10-carboxylate as off white solid (82 mg, yield: 47%). 1H NMR (400 MHz, DMSO-d6) δ 1.2 (s, 18H), 1.31-1.35 (m, 4H), 1.4 (s, 18H), 1.7-1.8 (m, 2H), 1.91-1.92 (m, 2H), 2.6 (d, J=4.5 Hz, 2H), 3.19-3.25 (m, 4H), 3.29-3.33 (m, 1H), 3.61-3.69 (m, 2H), 6.11 (brs, 1H), 6.33 (s, 1H), 6.72 (s, 1H), 6.94 (s, 1H), 7.45 (d, J=16.4 Hz, 1H), 7.5 (s, 1H), 7.64 (d, J=8.2 Hz, 1H).
LC-MS m/z (M+H): 749.2

Step 10: N1-(2-aminoethyl)-N3-(7-(cyclopent-1-en-1-yl)-3-(trifluoromethyl)-10H-phenothiazin-1-yl) propane-1, 3-diamine hydrochloride

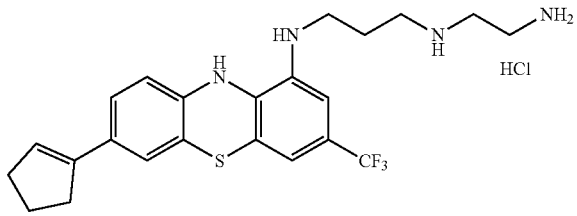 [SMILES: NCCNCCCNc1cc(C(F)(F)F)cc2c1Nc1ccc(C3=CCCC3)cc1S2 ; Cl]

To a stirred solution of tert-butyl1((3((tertbutoxycarbonyl)(2((tertbutoxycarbonyl)amino)ethyl)amino)propyl) amino)-7-(cyclopent-1-en-1-yl)-3-(trifluoromethyl)-10H-phenothiazine-10-carboxylate (25 mg, 0.0334 mmol) in DCM (1 mL) was added 1,4-dioxane HCl (2 mL) at 0° C. and stirred the reaction mixture at room temperature for 2 h. The progress of the reaction was monitored by TLC. The reaction mixture was concentrated under reduced pressure. The crude compound was triturated with n-pentane (2×2 mL) and dried to afford N1-(2-aminoethyl)-N3-(7-(cyclopent-1-en-1-yl)-3-(trifluoromethyl)-10H-phenothiazin-1-yl) propane-1, 3-diamine hydrochloride as pale yellow solid (12 mg, yield: 85%). ¹H NMR (400 MHz, DMSO-d₆) δ1.8-1.9 (m, 2H), 2.1-2.19 (m, 2H), 2.4-2.5 (m, 2H), 2.5-2.55 (m, 1H), 3.19-3.25 (m, 10H), 3.5-3.7 (m, 2H), 6.14 (s, 1H), 6.5 (d, J=6.8 Hz, 2H), 7.1 (s, 3H), 8.23 (br s, 3H), 8.4 (br s, 1H), 9.2 (br s, 2H). LC-MS m/z (M+H): 449.3

Compound 353: N1-(2-aminoethyl)-N3-(7-cyclopentyl-3-(trifluoromethyl)-10H-phenothiazin-1-yl) propane-1, 3-diamine hydrochloride

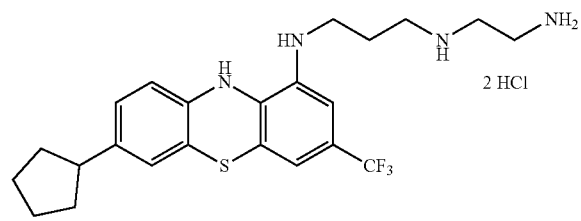 [SMILES: NCCNCCCNc1cc(C(F)(F)F)cc2c1Nc1ccc(C3CCCC3)cc1S2 ; "2 HCl"]

Step 11: tert-butyl 1-((3-((tert-butoxycarbonyl)(2-((tert-butoxycarbonyl)amino)ethyl)amino)propyl) amino)-7-cyclopentyl-3-(trifluoromethyl)-10H-phenothiazine-10-carboxylate

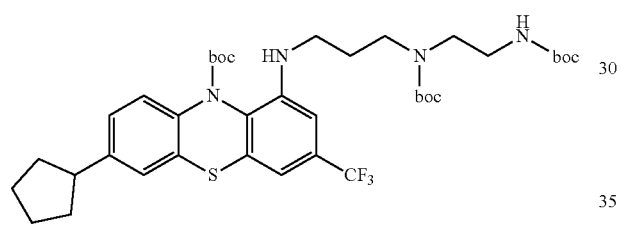

To a stirred solution of tert-butyl 1((3((tertbutoxycarbonyl)(2((tertbutoxycarbonyl)amino)ethyl)amino)propyl) amino)-7-(cyclopent-1-en-1-yl)-3-(trifluoromethyl)-10H-phenothiazine-10-carboxylate (60 mg, 0.0802 mmol) in Toluene (5 mL) was added platinum oxide (30 mg) at room temperature under hydrogen atmosphere for 6 h. The progress of the reaction was monitored by TLC. The reaction mixture was filtered through celite bed filtrate was concentrated under reduced pressure, crude product was purified by prep TLC (20% ethyl acetate/n-Hexane) to afford tert-butyl 1-((3-((tert-butoxycarbonyl)(2-((tert-butoxycarbonyl) amino)ethyl)amino)propyl)amino)-7-cyclopentyl-3-(trifluoromethyl)-10H-phenothiazine-10-carboxylate as colorless gel (42 mg, yield: 70%). LC-MS m/z (M+H): 751.2

Step 12: N1-(2-aminoethyl)-N3-(7-cyclopentyl-3-(trifluoromethyl)-10H-phenothiazin-1-yl) propane-1, 3-diamine hydrochloride

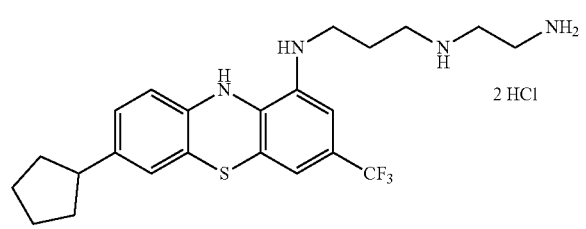 [SMILES: NCCNCCCNc1cc(C(F)(F)F)cc2c1Nc1ccc(C3CCCC3)cc1S2]

To a stirred solution of tert-butyl 1-((3-((tert-butoxycarbonyl)(2-((tert-butoxycarbonyl)amino)ethyl)amino)propyl) amino)-7-cyclopentyl-3-(trifluoromethyl)-10H-phenothiazine-10-carboxylate (42 mg, 0.056 mmol) in DCM (1 mL) was added 1,4-dioxane HCl (2 mL) at 0° C. and stirred the reaction mixture at room temperature for 3 h. The progress of the reaction was monitored by TLC. The reaction mixture was concentrated under reduced pressure. The crude compound was triturated with n-pentane (2×2 mL) and dried to afford N1-(2-aminoethyl)-N3-(7-cyclopentyl-3-(trifluoromethyl)-10H-phenothiazin-1-yl) propane-1, 3-diamine hydrochloride as pale yellow solid (24 mg, yield: 96%). ¹H NMR (400 MHz, DMSO-d₆) δ 1.4-1.5 (m, 2H), 1.5-1.6 (m, 2H), 1.7 (m, 2H), 1.9-2.0 (m, 2H), 2.01 (t, J=6.6 Hz, 2H), 2.71-2.81 (m, 1H), 3.1-3.2 (m, 8H), 6.54 (d, J=7.6 Hz, 2H), 6.8 (s, 1H), 6.9 (d, J=12.2 Hz, 1H), 7.03 (s, 1H), 8.2-8.3 (m, 4H), 9.2 (br s, 2H).

Some examples of compounds synthesized by the method of Scheme XXXI are provided in Table XXXI

TABLE XXXI

| Cmpd # | $R^3$ | $R^6$ | $R^7$ |
|---|---|---|---|
| 345 | $CF_3$ | pyrrolidinyl | H |
| 346 | $CF_3$ | 3,5-dimethylpiperidinyl | H |
| 347 | $CF_3$ | 2-azaspiro[3.3]heptyl | H |
| 348 | $CF_3$ | N-ethyl | H |
| 349 | $CF_3$ | 2,4-dimethylpyrrolidinyl | H |
| 350 | $CF_3$ | 8-azabicyclo[3.2.1] | H |

TABLE XXXI-continued

| Cmpd # | R³ | R⁶ | R⁷ |
|---|---|---|---|
| 351 | CF₃ | 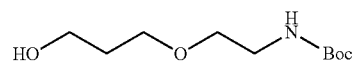 | H |
| 353 | CF₃ | (cyclopentyl) | H |
| 358 | CF₃ | (cyclopentenyl) | H |
| 355 | CF₃ | H | (Br-substituted group) |

Figure 26:
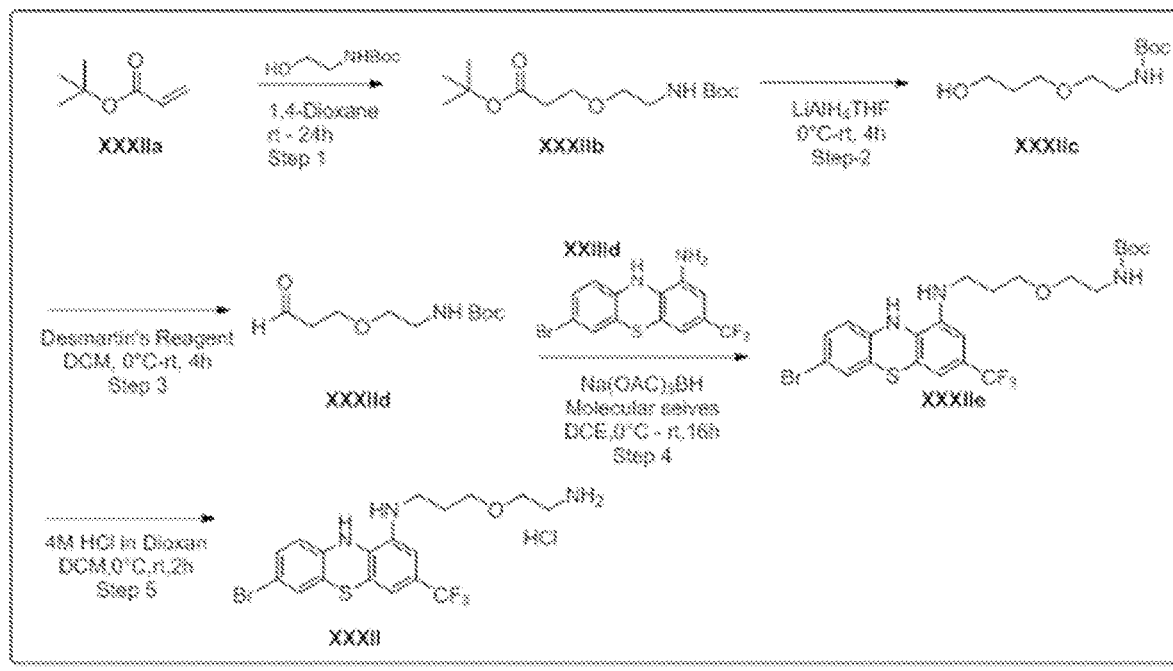
FIG. 26 shows general synthetic scheme XXXII for the synthesis of selected compounds according to the present invention

FIG. 26 shows general reaction scheme XXXII for the synthesis of selected 1, 3, 6-trisubstituted phenothiazines. Tert butyl acrylate was treated with protected 2-amine ethanol to gave XXXIIa, further reduction with lithium aluminum hydride and followed by oxidation with dessmartin' reagent to give corresponding aldehydes (XXXIId). Reductive amination of compound XXXIId with XXIIId yielded corresponding n-alkylated phenothiazines XXXIIe and further deprotection gave XXXII with corresponding salts.

Compound 343: N-(3-(2-aminoethoxy) propyl)-7-bromo-3-(trifluoromethyl)-10H-phenothiazin-1-amine hydrochloride

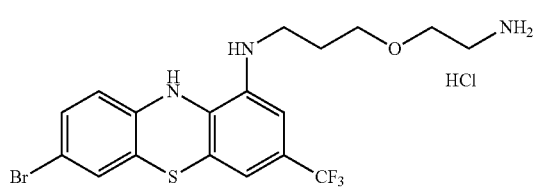

Step-1: tert-butyl 3-(2-(tert-butoxycarbonylamino)ethoxy)propanoate

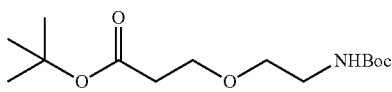 [SMILES: CC(C)(C)OC(=O)CCOCCNC(=O)OC(C)(C)C]

To a stirred solution of tert-butyl acrylate (16 g, 124.223 mmol), in 1, 4-dioxane (100 mL) was added 60% KOH in water at room temperature and stirred the reaction mixture at room temperature for 24 h. The progress of the reaction was monitored by TLC. Reaction mixture diluted with ethyl acetate (100 mL), washed with water (100 mL). The organic layer was dried over anhydrous sodium sulphate and concentrated under reduce pressure. The crude compound was purified by gradient column chromatography (eluted with 0-2 MeOH % in DCM) to afford tert-butyl 3-(2-(tert-butoxycarbonylamino)ethoxy)propanoate (12 g, yield: 66%) as colourless oil. ¹H NMR (400 MHz, DMSO-d₆) δ, 1.40-1.44 (s, 9H), 1.45-1.50 (s, 9H), 2.45-2.49 (m, 2H), 3.29-3.33 (m, 2H), 3.49-3.52 (m, 2H), 3.67-3.70 (m, 2H), 4.95 (br s, 1H)

Step-2: tert-butyl 2-(3-hydroxypropoxy) ethyl carbamate

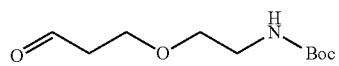 [SMILES: CC(C)(C)OC(=O)NCCOCCC=O]

To a stirred solution of tert-butyl 3-(2-(tert-butoxycarbonylamino)ethoxy)propanoate (5 g, 17.301 mmol) in dry THF (100 mL) was added lithium aluminium hydride at 0° C. and stirred the reaction mixture at room temperature for 4 h. The progress of the reaction was monitored by TLC. Reaction mixture was quenched with aqueous saturated sodium sulphate solution at 0° C. and stirred the reaction mixture at room temperature for 10 min, diluted with ethyl acetate (50 mL). The reaction mixture was filtered through a pad of celite and washed with ethyl acetate (20 mL). The filtrate was dried over anhydrous sodium sulphate and concentrated under reduce pressure. The crude compound was purified by gradient column chromatography (eluted with 30-50% in ethyl acetate/n-Hexane) to afford tert-butyl 2-(3-hydroxypropoxy) ethylcarbamate (2.5 g, yield: 67%) as colorless oil. ¹H NMR (400 MHz, DMSO-d₆) δ, 1.39 (s, 9H), 1.57-1.62 (m, 2H), 3.02-3.37 (m, 2H), 3.38-3.45 (m, 3H), 4.33 (m, 1H), 6.78 (brs, 1H)

Step-3: tert-butyl 2-(3-oxopropoxy) ethylcarbamate

To a stirred solution of tert-butyl 2-(3-hydroxypropoxy) ethylcarbamate (600 mg, 2.575 mmol) in DCM (10 mL) was added Desmartin's reagent (1.64 g, 3.86 mmol) at 0° C. and stirred the reaction mixture at room temperature for 4 h. The progress of the reaction was monitored by TLC. The reaction mixture was filtered through a pad of celite; the filtrate was extracted with ethyl acetate (2×20 mL). The combined organic layer was washed with water (15 mL), dried over anhydrous sodium sulphate and concentrated under reduce pressure to afford tert-butyl 2-(3-oxopropoxy) ethylcarbamate as colour less oil (340 mg, crude). The crude product was used for next step without further purification.

Step-4: tert-butyl 2-(3-(7-bromo-3-(trifluoromethyl)-10H-phenothiazin-1-ylamino) propoxy)ethylcarbamate

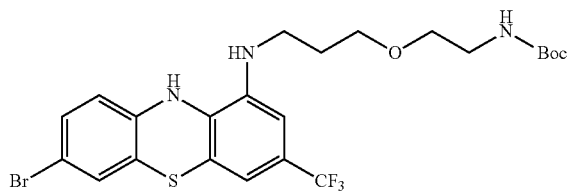 [SMILES: CC(C)(C)OC(=O)NCCOCCCNc1cc(C(F)(F)F)cc2c1Nc1ccc(Br)cc1S2]

To a stirred solution of 7-bromo-3-(trifluoromethyl)-10H-phenothiazin-1-amine (420 mg, 1.169 mmol) and tert-butyl 2-(3-oxopropoxy)ethylcarbamate (235 mg, 1.169 mmol), molecular sieves (3 g) in DCE (10 mL) was stirred at room temperature for 1 h. And was added sodium triacetoxyborohydride at 0° C. under nitrogen atmosphere and stirred the reaction mixture at room temperature for 16 h. The progress of the reaction was monitored by TLC. The reaction mixture was diluted with saturated sodium bicarbonate solution (20 mL), extracted with DCM (3×30 mL). The combined organic layer was washed with water (20 mL), brine (20 mL), dried over anhydrous sodium sulphate and concentrated under reduced pressure.

The crude compound was purified by gradient column chromatography (eluted with 20% ethyl acetate/n-Hexane) to afford tert-butyl 2-(3-(7-bromo-3-(trifluoromethyl)-10H-phenothiazin-1-ylamino)propoxy)ethylcarbamate (120 mg, yield: 18%) as brown oil. $^1$H NMR (400 MHz, DMSO-$d_6$) δ 1.30 (s, 9H) 1.83 (t, 2H), 3.07 (d, J=5.85 Hz, 2H), 3.12 (d, J=5.85 Hz, 2H), 3.31-3.37 (m, 3H), 3.52 (m, 2H), 6.5407 (d, J=5.39 Hz, 2H), 6.76-6.80 (m, 2H), 7.18-7.20 (m, 2H), 8.05 (s, 1H). LC-MS m/z (M+H): 561.9

Step-5: Synthesis of N-(3-(2-aminoethoxy)propyl)-7-bromo-3-(trifluoromethyl)-10H-phenothiazin-1-amine hydrochloride

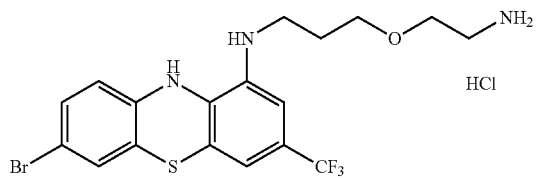 [SMILES: NCCOCCCNc1cc(C(F)(F)F)cc2c1Nc1ccc(Br)cc1S2 ; Cl]

To a stirred solution of tert tert-butyl 2-(3-(7-bromo-3-(trifluoromethyl)-10H-phenothiazin-1-ylamino)propoxy) ethylcarbamate (120 mg, 0.213 mmol) in 1,4-Dioxane (3 mL) was added 4M HCl in 1,4-Dioxane (3 mL) at 0° C., and stirred the reaction mixture at room temperature for 2 h. The progress of the reaction was monitored by TLC. The reaction mixture was concentrated under reduced pressure. The crude compound was washed with diethyl ether (2×3 mL), pentane (3 mL) and dried under reduced pressure to afford N-(3-(2-aminoethoxy)propyl)-7-bromo-3-(trifluoromethyl)-10H-phenothiazin-1-amine hydrochloride (90 mg, 84%) as pale green solid. $^1$H NMR (400 MHz, DMSO-$d_6$) δ 1.80-1.92 (m, 2H) 2.90-3.11 (m, 2H), 3.15-3.22 (m, 2H), 3.50-3.62 (m, 4H) 6.51 (s, 1H), 7.13 (d, 2H), 7.93 (br s, 3H), 8.73 (s, 1H). LC-MS m/z (M+H): 462

Figure 27:
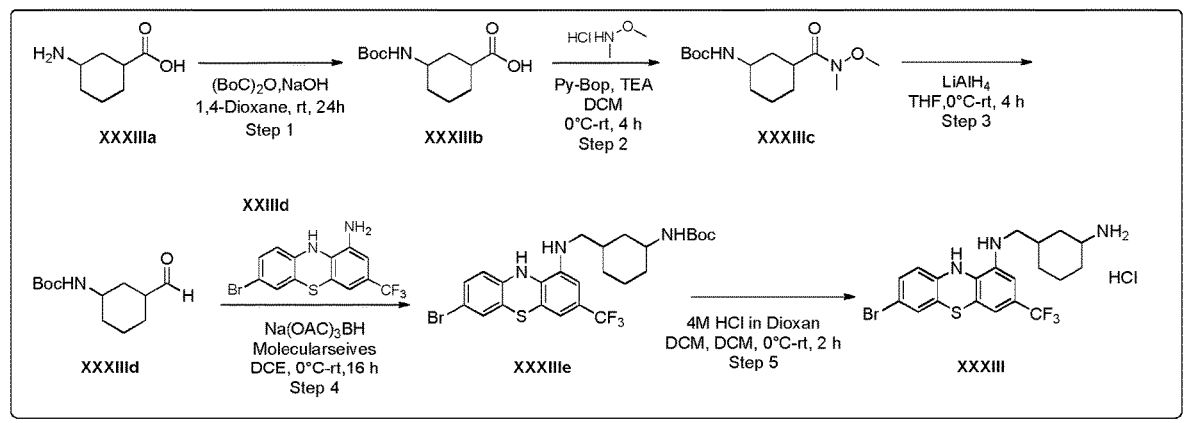
FIG. 27 shows general synthetic scheme XXXIII for the synthesis of selected compounds according to the present invention

FIG. 27 shows general reaction scheme XXXIII for the synthesis of selected 1, 3, 6-trisubstituted phenothiazines. 3 amino cyclo hexyl carboxylic was protected boc anhydride to gave XXXIIIa, and followed by acid amide coupling with weinreb amine to gave XXXIIIc further reduction with lithium aluminum hydride to give corresponding aldehydes (XXXIIId). Reductive amination of compound XXXIIId with XXIIId yielded corresponding n-alkylated phenothiazines XXXIIIe and further deprotection gave XXXIII with corresponding salts.

Compound 343: N-((3-aminocyclohexyl)methyl)-7-bromo-3-(trifluoromethyl)-10H-phenothiazin-1-amine hydrochloride

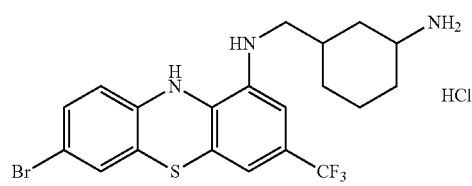 [SMILES: NC1CCCC(CNc2cc(C(F)(F)F)cc3c2Nc2ccc(Br)cc2S3)C1 ; Cl]

Step-1: 3-(tert-butoxycarbonylamino) cyclohexane carboxylic Acid

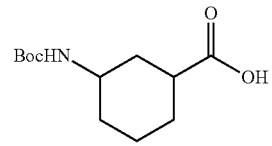 [SMILES: CC(C)(C)OC(=O)NC1CCCC(C(=O)O)C1]

To a stirred solution of 3-aminocyclohexanecarboxylic acid (5 g, 34.92 mmol), in 1, 4-dioxane (50 mL) was added sodium hydroxide and stirred the reaction mixture at room temperature for 24 h. The progress of the reaction was monitored by TLC. Reaction mixture was cooled to 0° C. then added 1N HCl to adjust the $P^H$ to 4, the solid precipitates were filtered and washed with water (100 mL) dried under vacuum to give 3-(tert-butoxycarbonylamino) cyclohexane carboxylic acid (7.0 g, 82%) as white colour solid. $^1$H NMR (400 MHz, DMSO-$d_6$) δ 0.985-1.3 (m, 4H), 1.39 (s, 9H), 1.6-1.8 (m, 3H), 1.9-2.0 (m, 1H), 2.2-2.4 (m, 1H), 3.15-3.3 (m, 1H), 6.73-6.75 (d, J=8.0 Hz, 1H), 12.04 (s, 1H). LC-MS m/z (M+H): 144.05

Step-2: tert-butyl3-(methoxy (methyl) carbamoyl) cyclohexylcarbamate

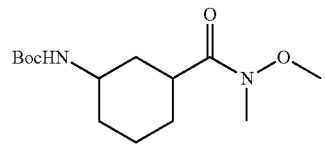 [SMILES: CON(C)C(=O)C1CCCC(NC(=O)OC(C)(C)C)C1]

To a stirred solution 3-(tert-butoxycarbonylamino)cyclohexane carboxylic acid (3.0 g, 12.341 mmol) in dry DCM (30 mL) was added TEA at 0° C. and stirred for 15 min then added N,O-dimethylhydroxylamine and Py-Bop then stirred at room temperature for 14 h. The progress of the reaction was monitored by TLC. Reaction mixture was quenched with saturated NaHCO$_3$ solution at 0° C. and stirred the reaction mixture at room temperature for 10 min, Organic layer was separated and dried over anhydrous sodium sulphate and concentrated under reduce pressure. The crude compound was purified by combi flash (eluted with 20 ethyl acetate/n-Hexane) to afford the title compound (3.2 g, yield: 91%) as brown color oil. $^1$H NMR (400 MHz, DMSO-$d_6$) δ, 1.1-1.3 (m, 4H), 1.39 (s, 9H), 1.57-1.62 (m, 1H), 1.7 (brs, 3H), 2.62-2.81 (m, 1H), 3.02 (s, 3H), 3.258-3.298 (m, 1H), 3.653 (s, 3H), 5.742 (s, 1H), 6.736-6.75 (d, J=7.6 Hz 1H), LC-MS m/z (M+H): 187.1

Step-3: tert-butyl 3-formylcyclohexylcarbamate

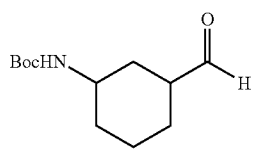 [SMILES: CC(C)(C)OC(=O)NC1CCCC(C=O)C1]

To a stirred solution of tert-butyl3-(methoxy (methyl) carbamoyl) cyclohexylcarbamate (3.5 g, 12.195 mmol) in THF (10 mL) was added lithium aluminum hydride (463 mg, 12.195 mmol) at 0° C. and stirred the reaction mixture at room temperature for 0.5 h. The progress of the reaction was monitored by TLC. The reaction mixture was quenched with saturated $Na_2SO_4$ then filtered the reaction mass, filtrate was dried over anhydrous sodium sulphate then concentrated under vacuum to get title compound tert-butyl 3-formylcyclohexylcarbamate (1.3 g, crude) as colorless oil, which was used for the next step without further purification. $^1$H NMR (400 MHz, DMSO-$d_6$) δ, 0.9-1.29 (m, 9H), 1.39 (s, 9H), 1.57-1.9 (m, 5H), 1.97-2.00 (m, 2H), 4.0 (m, 1H), 4.33 (m, 1H), 6.77-6.79 (d, J=8.0 Hz 1H), 9.59 (s, 1H).

Step-4: tert-butyl 3-((7-bromo-3-(trifluoromethyl)-10H-phenothiazin-1-ylamino) methyl) cyclohexyl-carbamate

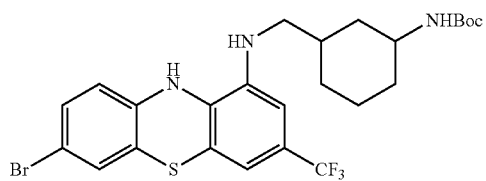 [SMILES: CC(C)(C)OC(=O)NC1CCCC(CNc2cc(C(F)(F)F)cc3c2Nc2ccc(Br)cc2S3)C1]

To a stirred solution of tert-butyl 3-formylcyclohexylcarbamate (1.062 g, 4.678 mmol) in DCE (10 mL) added 7-bromo-3-(trifluoromethyl)-10H-phenothiazin-1-amine (1.4 g, 3.899 mmol) molecular sieves (3 g) was stirred at room temperature for 1 h, then added sodium triacetoxyborohydride at 0° C. under nitrogen atmosphere and stirred the reaction mixture at same temperature for 16 h. The progress of the reaction was monitored by TLC. The reaction mixture was diluted with sat $NaHCO_3$ solution (20 mL), extracted with DCM (3×30 mL). The combined organic layer was washed with water (20 mL), brine (20 mL), dried over anhydrous sodium sulphate and concentrated under reduced pressure. The crude compound was purified by gradient column chromatography (eluted with 20% ethyl acetate/n-Hexane) to afford tert-butyl 3-((7-bromo-3-(trifluoromethyl)-10H-phenothiazin-1-ylamino) methyl) cyclohexylcarbamate (2.2 g, 22%) as brown oil. $^1$H NMR (400 MHz, DMSO-$d_6$) δ 1.33 (s, 9H), 1.751-1.957 (m, 5H), 1.977-2.02 (m, 1H), 2.50 (br s, 2H), 3.37 (s, 1H), 5.4 (s, 1H), 6.530-6.558 (d, J=11 Hz, 2H), 6.75-6.822 (m, 2H), 7.16-7.19 (m, 2H), 8.125 (s, 1H). LC-MS m/z (M+H): 572.1.

Step-5: N-((3-aminocyclohexyl)methyl)-7-bromo-3-(trifluoromethyl)-10H-phenothiazin-1-amine hydrochloride

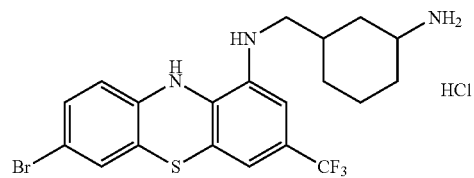 [SMILES: NC1CCCC(CNc2cc(C(F)(F)F)cc3c2Nc2ccc(Br)cc2S3)C1 ; Cl]

To a stirred solution of tert-butyl 3-((7-bromo-3-(trifluoromethyl)-10H-phenothiazin-1-ylamino)methyl)cyclohexylcarbamate (70 mg, 0.225 mmol) in 1,4-Dioxane (3 mL) was added 4M HCl in dioxane (3 mL) at 0° C., and stirred the reaction mixture at room temperature for 2 h. The progress of the reaction was monitored by TLC. The reaction mixture was concentrated under reduced pressure. The crude compound was washed with diethyl ether (2×3 mL), pentane (3 mL) and dried under reduced pressure to afford N-((3-aminocyclohexyl)methyl)-7-bromo-3-(trifluoromethyl)-10H-phenothiazin-1-amine hydrochloride (51 mg, yield: 82%) as pale yellow solid. $^1$H NMR (400 MHz, DMSO-$d_6$) δ 0.842-0.866 (m, 1H) 0.981-1.014 (m, 1H), 1.199-1.308 (m, 3H), 1.761-1.828 (m, 1H) 6.49-6.51 (d, J=11 Hz 2H), 7.07-7.09 (m, 3H), 7.901 (s, 3H), 8.660 (s, 1H). LC-MS m/z (M+H): 471.98

Characterisation of the Synthesised Compounds

Table 13 below provides LC-MS data on the compounds synthesised and indicates which general synthetic method (Scheme number) was used to obtain the compound.

TABLE 13

| Cmpd # | Structure | Name | Exact mass | LC-MS [M + H]+ (m/z) | Synthetic (Scheme no.) |
|---|---|---|---|---|---|
| 2 | 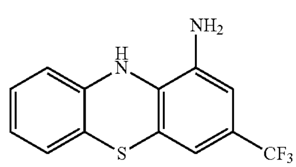 | 3-(trifluoromethyl)-10H-phenothiazin-1-amine | 282.04 | 283 | III |

TABLE 13-continued

| Cmpd # | Structure | Name | Exact mass | LC-MS [M + H]+ (m/z) | Synthetic (Scheme no.) |
|---|---|---|---|---|---|
| 30 | 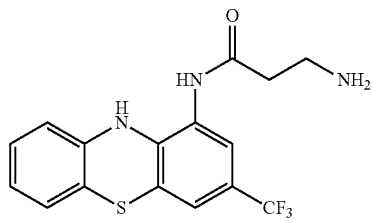 [SMILES: NCCC(=O)Nc1cc(C(F)(F)F)cc2c1Nc1ccccc1S2] | 3-amino-N-(3-(trifluoromethyl)-10H-phenothiazin-1-yl)propanamide | 353 | 354.1 | III |
| 39 | 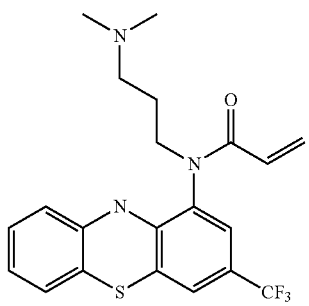 [SMILES: C=CC(=O)N(CCCN(C)C)c1cc(C(F)(F)F)cc2c1Nc1ccccc1S2] | N-(3-(dimethylamino)propyl)-N-(3-(trifluoromethyl)-10H-phenothiazin-1-yl)acrylamide | 421.48 | 422.5 | III |
| 42 | 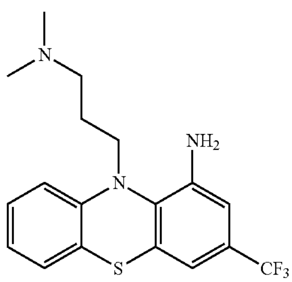 [SMILES: CN(C)CCCN1c2ccccc2Sc2cc(C(F)(F)F)cc(N)c21] | 10-(3-(dimethylamino)propyl)-3-(trifluoromethyl)-10H-phenothiazin-1-amine | 367.43 | 368.4 | II |
| 44 | 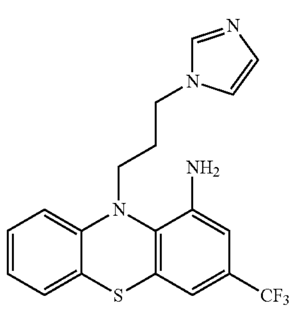 [SMILES: Nc1cc(C(F)(F)F)cc2c1N(CCCn1ccnc1)c1ccccc1S2] | 10-(3-(1H-imidazol-1-yl)propyl)-3-(trifluoromethyl)-10H-phenothiazin-1-amine | 390.43 | 391.1 | II |
| 67 | 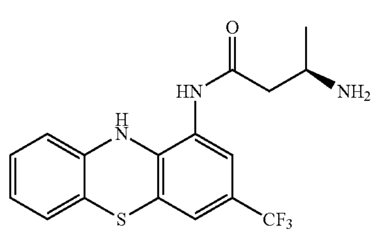 [SMILES: C[C@@H](N)CC(=O)Nc1cc(C(F)(F)F)cc2c1Nc1ccccc1S2] | (R)-3-amino-N-(3-(trifluoromethyl)-10H-phenothiazin-1-yl)butanamide | 367.39 | 368.0 | III |

TABLE 13-continued

| Cmpd # | Structure | Name | Exact mass | LC-MS [M + H]+ (m/z) | Synthetic (Scheme no.) |
|---|---|---|---|---|---|
| 83 | 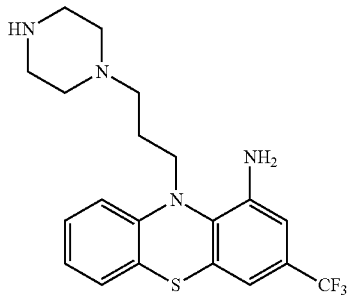 [SMILES: Nc1cc(C(F)(F)F)cc2c1N(CCCN1CCNCC1)c1ccccc1S2] | 10-(3-(piperazin-1-yl)propyl)-3-(trifluoromethyl)-10H-phenothiazin-1-amine | 408.48 | 409.1 | II |
| 87 | 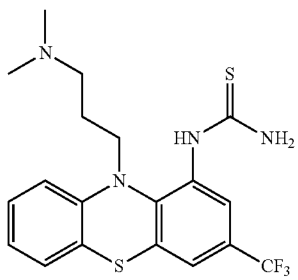 [SMILES: CN(C)CCCN1c2ccccc2Sc2cc(C(F)(F)F)cc(NC(N)=S)c21] | 1-(10-(3-(dimethylamino)propyl)-3-(trifluoromethyl)-10H-phenothiazin-1-yl)thiourea | 426.52 | 427.1 | II |
| 88 | 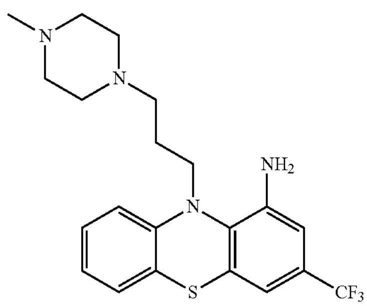 [SMILES: CN1CCN(CCCN2c3ccccc3Sc3cc(C(F)(F)F)cc(N)c32)CC1] | 10-(3-(4-methylpiperazin-1-yl)propyl)-3-(trifluoromethyl)-10H-phenothiazin-1-amine | 422.51 | 423.2 | II |
| 89 | 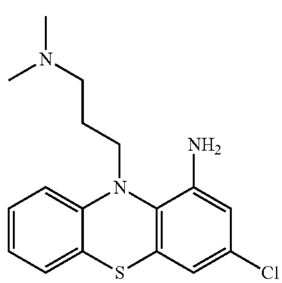 [SMILES: CN(C)CCCN1c2ccccc2Sc2cc(Cl)cc(N)c21] | 3-chloro-10-(3-(dimethylamino)propyl)-10H-phenothiazin-1-amine | 333.88 | 334.1 | II |
| 90 | 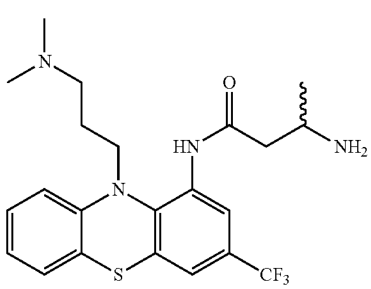 [SMILES: CC(N)CC(=O)Nc1cc(C(F)(F)F)cc2c1N(CCCN(C)C)c1ccccc1S2] | 3-amino-N-(10-(3-(dimethylamino)propyl)-3-(trifluoromethyl)-10H-phenothiazin-1-yl)butanamide | 452.54 | 453.2 | II |

TABLE 13-continued

| Cmpd # | Structure | Name | Exact mass | LC-MS [M + H]+ (m/z) | Synthetic (Scheme no.) |
|---|---|---|---|---|---|
| 91 | 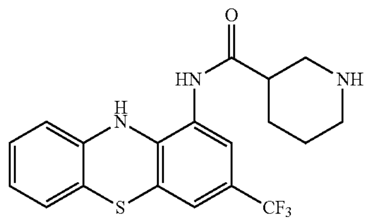 [SMILES: O=C(Nc1cc(C(F)(F)F)cc2c1Nc1ccccc1S2)C1CCCNC1] | N-(3-(trifluoromethyl)-10H-phenothiazin-1-yl)piperidine-3-carboxamide | 393.43 | 394.1 | III |
| 92 | 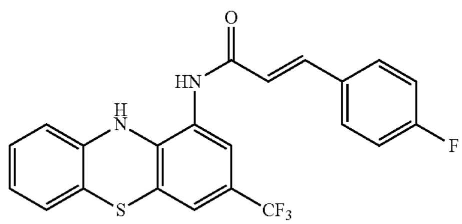 [SMILES: O=C(/C=C/c1ccc(F)cc1)Nc1cc(C(F)(F)F)cc2c1Nc1ccccc1S2] | E-3-(4-fluorophenyl)-N-(3-(trifluoromethyl)-10H-phenothiazin-1-yl)acrylamide | 430.42 | 431.1 | III |
| 94 | 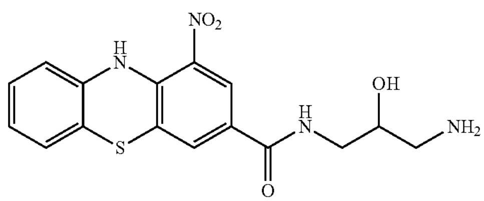 [SMILES: NCC(O)CNC(=O)c1cc2c(c([N+](=O)[O-])c1)Nc1ccccc1S2] | N-(3-amino-2-hydroxypropyl)-1-nitro-10H-phenothiazine-3-carboxamide | 360.09 | 361.1 | V |
| 95 | 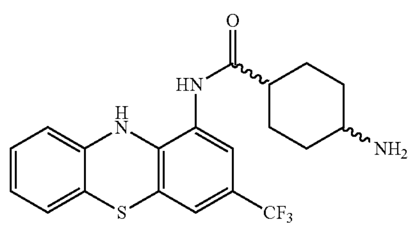 [SMILES: NC1CCC(C(=O)Nc2cc(C(F)(F)F)cc3c2Nc2ccccc2S3)CC1] | 4-amino-N-(3-(trifluoromethyl)-10H-phenothiazin-1-yl)cyclohexane-carboxamide | 407.45 | 408.1 | III |
| 97 | 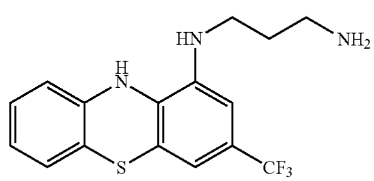 [SMILES: NCCCNc1cc(C(F)(F)F)cc2c1Nc1ccccc1S2] | N1-(3-(trifluoromethyl)-10H-phenothiazin-1-yl)propane-1,3-diamine | 339.38 | 340.1 | III |
| 98 | 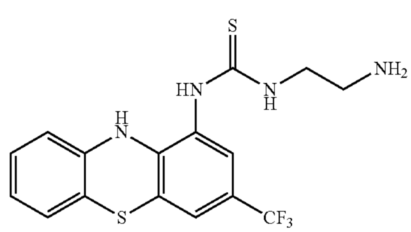 [SMILES: NCCNC(=S)Nc1cc(C(F)(F)F)cc2c1Nc1ccccc1S2] | 1-(2-aminoethyl)-3-(3-(trifluoromethyl)-10H-phenothiazin-1-yl)thiourea | 384.07 | 385.1 | III |
| 100 | 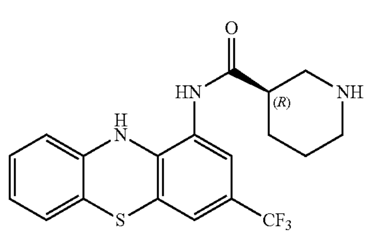 | (R)-N-(3-(trifluoromethyl)-10H-phenothiazin-1-yl)piperidine-3-carboxamide | 393.11 | 394.1 | III |

TABLE 13-continued

| Cmpd # | Structure | Name | Exact mass | LC-MS [M + H]+ (m/z) | Synthetic (Scheme no.) |
|---|---|---|---|---|---|
| 101 | 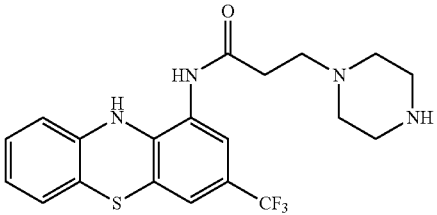 [SMILES: O=C(CCN1CCNCC1)Nc1cc(C(F)(F)F)cc2c1Nc1ccccc1S2] | 3-(piperazin-1-yl)-N-(3-(trifluoromethyl)-10H-phenothiazin-1-yl)propanamide | 422.47 | 423.1 | III |
| 105 | 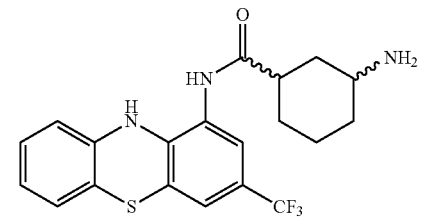 | 3-amino-N-(3-(trifluoromethyl)-10H-phenothiazin-1-yl)cyclohexane-carboxamide | 407.13 | 408.1 | III |
| 106 | 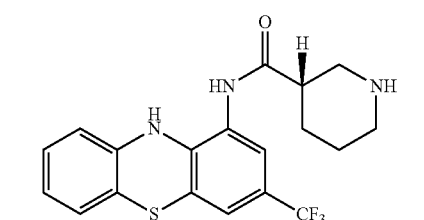 | N-(3-(trifluoromethyl)-10H-phenothiazin-1-yl)piperidine-3-carboxamide | 393.11 | 394.1 | III |
| 108 | 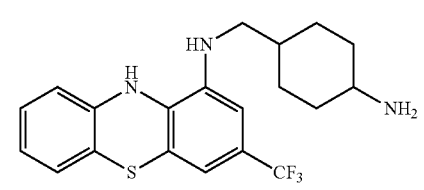 [SMILES: NC1CCC(CNc2cc(C(F)(F)F)cc3c2Nc2ccccc2S3)CC1] | N-((4-aminocyclohexyl)methyl)-3-(trifluoromethyl)-10H-phenothiazin-1-amine | 393.15 | 394.2 | III |
| 110 | 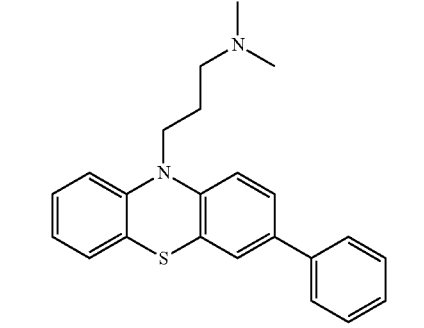 [SMILES: CN(C)CCCN1c2ccccc2Sc2cc(-c3ccccc3)ccc21] | N,N-dimethyl-3-(3-phenyl-10H-phenothiazin-10-yl)propan-1-amine | 360.17 | 361.5 | IV |
| 111 | 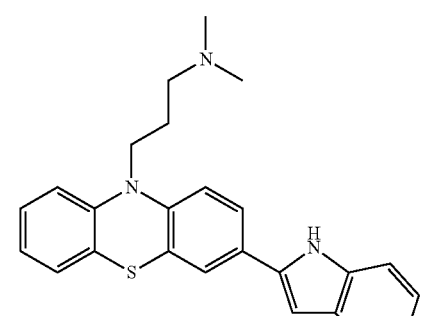 | 3-(3-(1H-indol-2-yl)-10H-phenothiazin-10-yl)-N,N-dimethylpropan-1-amine | 399.18 | 400.2 | IV |

TABLE 13-continued

| Cmpd # | Structure | Name | Exact mass | LC-MS [M + H]+ (m/z) | Synthetic (Scheme no.) |
|---|---|---|---|---|---|
| 113 | 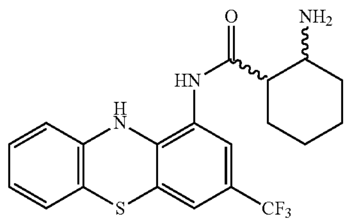 [SMILES: NC1CCCCC1C(=O)Nc1cc(C(F)(F)F)cc2c1Nc1ccccc1S2] | 2-amino-N-(3-(trifluoromethyl)-10H-phenothiazin-1-yl)cyclohexane-carboxamide | 407.13 | 408.1 | III |
| 115 | 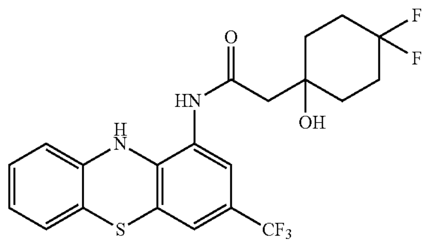 [SMILES: O=C(CC1(O)CCC(F)(F)CC1)Nc1cc(C(F)(F)F)cc2c1Nc1ccccc1S2] | 2-(4,4-difluoro-1-hydroxycyclo-hexyl)-N-(3-(trifluoromethyl)-10H-phenothiazin-1-yl)acetamide | 458.11 | 459.1 | III |
| 116 | 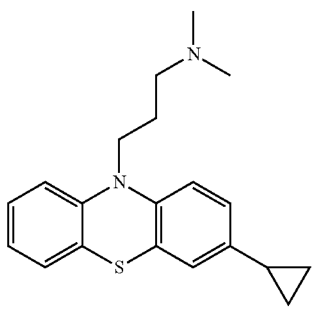 [SMILES: CN(C)CCCN1c2ccccc2Sc2cc(C3CC3)ccc21] | 3-(3-cyclopropyl-10H-phenothiazin-10-yl)-N,N-dimethylpropan-1-amine | 324.17 | 325.2 | IV |
| 117 | 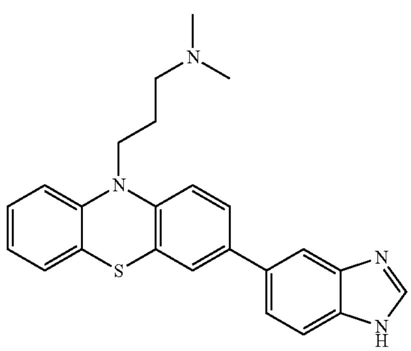 | 3-(3-(1H-benzo[d]imidazol-5-yl)-10H-phenothiazin-10-yl)-N,N-dimethylpropan-1-amine | 400.17 | 401.2 | IV |
| 118 | 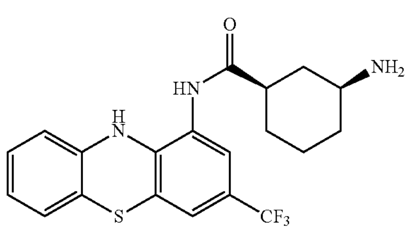 [SMILES: N[C@H]1CCC[C@@H](C(=O)Nc2cc(C(F)(F)F)cc3c2Nc2ccccc2S3)C1] | (1R,3S)-3-amino-N-(3-(trifluoromethyl)-10H-phenothiazin-1-yl)cyclohexane-carboxamide | 407.13 | 408.1 | III |

TABLE 13-continued

| Cmpd # | Structure | Name | Exact mass | LC-MS [M + H]+ (m/z) | Synthetic (Scheme no.) |
|---|---|---|---|---|---|
| 119 | 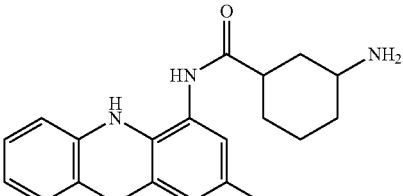 | 3-amino-N-(3-cyano-10H-phenothiazin-1-yl)cyclohexane-carboxamide | 364.14 | 365.2 | III |
| 120 | 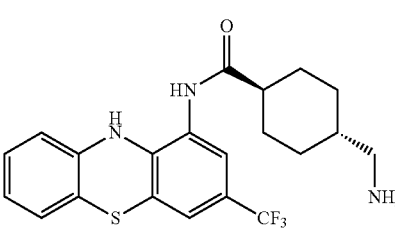 | (1R,4R)-4-(aminomethyl)-N-(3-(trifluoromethyl)-10H-phenothiazin-1-yl)cyclohexane-carboxamide | 421.14 | 422.2 | III |
| 121 | 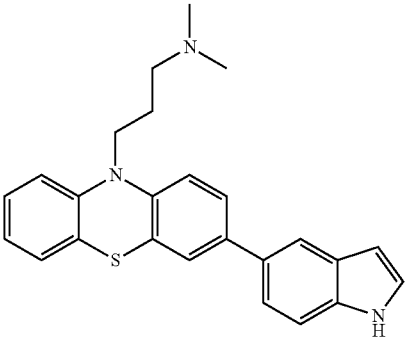 | 3-(3-(1H-indol-5-yl)-10H-phenothiazin-10-yl)-N,N-dimethylpropan-1-amine | 399.18 | 400.2 | IV |
| 122 | 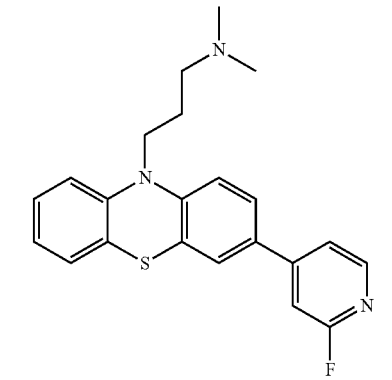 [SMILES: CN(C)CCCN1c2ccccc2Sc2cc(-c3ccnc(F)c3)ccc21] | 3-(3-(2-fluoropyridin-4-yl)-10H-phenothiazin-10-yl)-N,N-dimethylpropan-1-amine | 379.18 | 380.2 | IV |
| 123 | 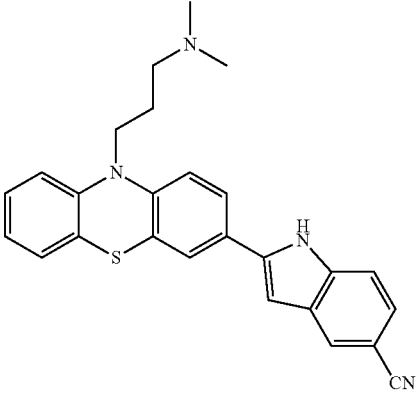 [SMILES: CN(C)CCCN1c2ccccc2Sc2cc(-c3cc4cc(C#N)ccc4[nH]3)ccc21] | 2-(10-(3-(dimethylamino)propyl)-10H-phenothiazin-3-yl)-1H-indole-5-carbonitrile | 424.17 | 425.2 | IV |

TABLE 13-continued

| Cmpd # | Structure | Name | Exact mass | LC-MS [M + H]+ (m/z) | Synthetic (Scheme no.) |
|---|---|---|---|---|---|
| 124 | 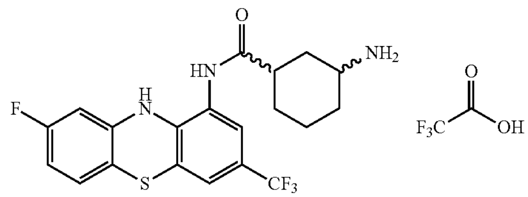 [SMILES: NC1CCCC(C(=O)Nc2cc(C(F)(F)F)cc3c2Nc2cc(F)ccc2S3)C1 ; O=C(O)C(F)(F)F] | 3-amino-N-(8-fluoro-3-(trifluoromethyl)-10H-phenothiazin-1-yl)cyclohexane-carboxamide 2,2,2-trifluoroacetate | 539.11 | 426.1 | XI |
| 125 | 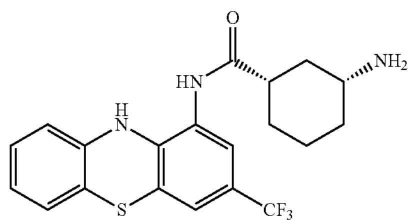 [SMILES: N[C@@H]1CCC[C@H](C(=O)Nc2cc(C(F)(F)F)cc3c2Nc2ccccc2S3)C1] | (1S,3R)-3-amino-N-(3-(trifluoromethyl)-10H-phenothiazin-1-yl)cyclohexane-carboxamide | 407.13 | 408.1 | III |
| 126 | 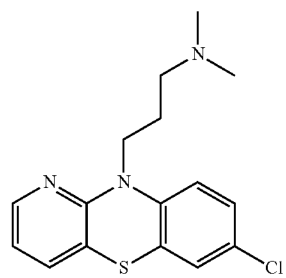 [SMILES: CN(C)CCCN1c2ccc(Cl)cc2Sc2cccnc21] | 3-(7-chloro-10H-benzo[b]pyrido[2,3-e][1,4]thiazin-10-yl)-N,N-dimethyl-propan-1-amine | 319.09 | 320.1 | VI |
| 129 | 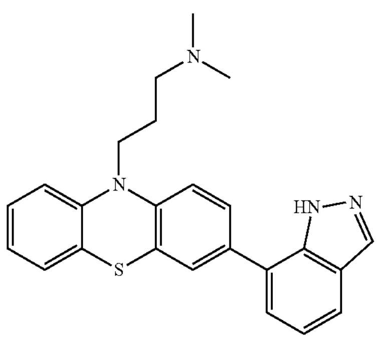 [SMILES: CN(C)CCCN1c2ccccc2Sc2cc(-c3cccc4cn[nH]c34)ccc21] | 3-(3-(1H-indazol-7-yl)-10H-phenothiazin-10-yl)-N,N-dimethylpropan-1-amine | 400.17 | 401.2 | IV |
| 130 | 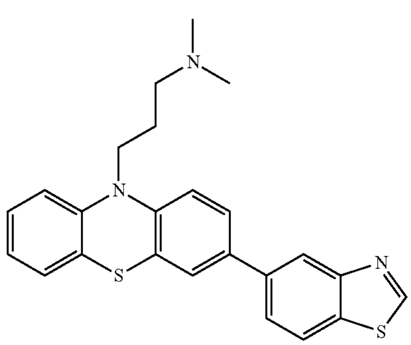 [SMILES: CN(C)CCCN1c2ccccc2Sc2cc(-c3ccc4scnc4c3)ccc21] | 3-(3-(benzo[d]thiazol-5-yl)-10H-phenothiazin-10-yl)-N,N-dimethylpropan-1-amine | 417.13 | 418.4 | IV |

TABLE 13-continued

| Cmpd # | Structure | Name | Exact mass | LC-MS [M + H]+ (m/z) | Synthetic (Scheme no.) |
|---|---|---|---|---|---|
| 132 | 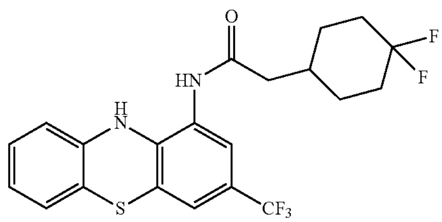 [SMILES: O=C(CC1CCC(F)(F)CC1)Nc1cc(C(F)(F)F)cc2c1Nc1ccccc1S2] | 2-(4,4-difluorocyclohexyl)-N-(3-(trifluoromethyl)-10H-phenothiazin-1-yl)acetamide | 442.11 | 443.4 | III |
| 133 | 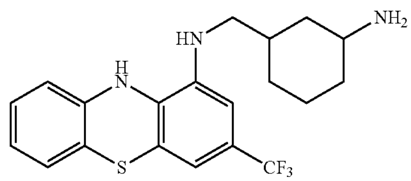 [SMILES: NC1CCCC(CNc2cc(C(F)(F)F)cc3c2Nc2ccccc2S3)C1] | N-((3-aminocyclohexyl)methyl)-3-(trifluoromethyl)-10H-phenothiazin-1-amine | 393.15 | 394.2 | III |
| 134 | 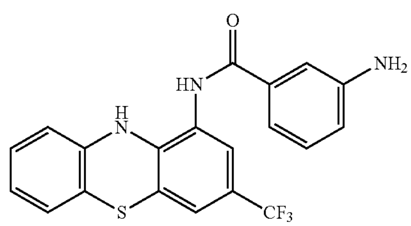 | 3-amino-N-(3-(trifluoromethyl)-10H-phenothiazin-1-yl)benzamide | 401.08 | 402.1 | III |
| 135 | 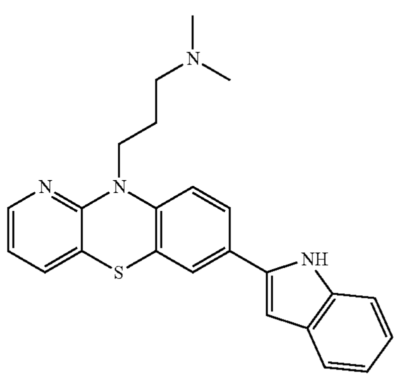 [SMILES: CN(C)CCCN1c2ccc(-c3cc4ccccc4[nH]3)cc2Sc2cccnc21] | 3-(7-(1H-indol-2-yl)-10H-benzo[b]pyrido[2,3-e][1,4]thiazin-10-yl)-N,N-dimethylpropan-1-amine | 400.17 | 401.2 | VI |
| 136 | 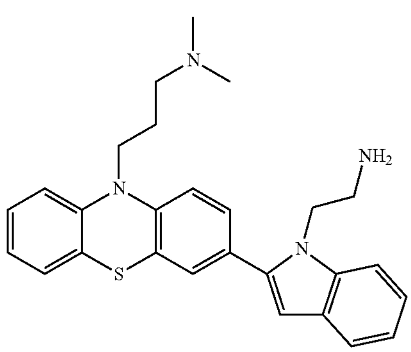 [SMILES: CN(C)CCCN1c2ccccc2Sc2cc(-c3cc4ccccc4n3CCN)ccc21] | 3-(3-(1-(2-aminoethyl)-1H-indol-2-yl)-10H-phenothiazin-10-yl)-N,N-dimethylpropan-1-amine | 442.22 | 443.2 | IV |

TABLE 13-continued

| Cmpd # | Structure | Name | Exact mass | LC-MS [M + H]+ (m/z) | Synthetic (Scheme no.) |
| --- | --- | --- | --- | --- | --- |
| 137 | 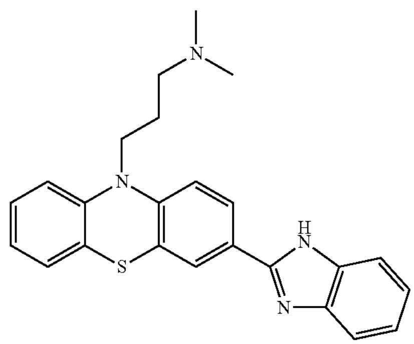 | 3-(3-(1H-benzo[d]imidazol-2-yl)-10H-phenothiazin-10-yl)-N,N-dimethylpropan-1-amine | 400.17 | 401.2 | VII |
| 139 | 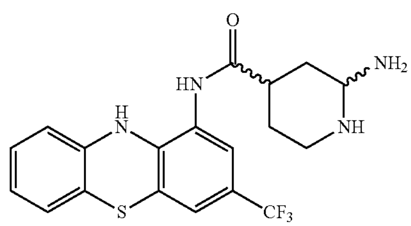 [SMILES: NC1CC(C(=O)Nc2cc(C(F)(F)F)cc3c2Nc2ccccc2S3)CCN1] | 2-amino-N-(3-(trifluoromethyl)-10H-phenothiazin-1-yl)piperidine-4-carboxamide | 408.12 | 408.1 | III |
| 140 | 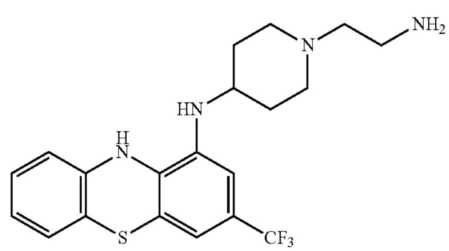 [SMILES: NCCN1CCC(Nc2cc(C(F)(F)F)cc3c2Nc2ccccc2S3)CC1] | N-(1-(2-aminoethyl)piperidin-4-yl)-3-(trifluoromethyl)-10H-phenothiazin-1-amine | 408.16 | 409.2 | III |
| 141 | 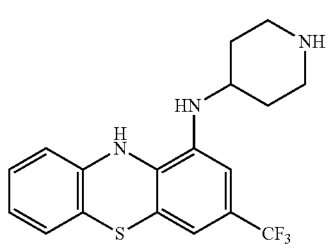 [SMILES: FC(F)(F)c1cc(NC2CCNCC2)c2c(c1)Sc1ccccc1N2] | N-(piperidin-4-yl)-3-(trifluoromethyl)-10H-phenothiazin-1-amine | 365.12 | 366.1 | III |
| 143 | 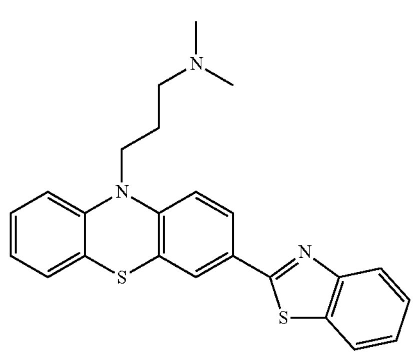 | 3-(3-(benzo[d]thiazol-2-yl)-10H-phenothiazin-10-yl)-N,N-dimethylpropan-1-amine | 419.15 | 418.2 | VII |

TABLE 13-continued

| Cmpd # | Name | Exact mass | LC-MS [M + H]+ (m/z) | Synthetic (Scheme no.) |
|---|---|---|---|---|
| 144 | 3-(3-(5-methoxy-1H-indol-2-yl)-10H-phenothiazin-10-yl)-N,N-dimethylpropan-1-amine | 429.19 | 430.2 | IV |
| 148 | 3-hydroxy-N-(3-(trifluoromethyl)-10H-phenothiazin-1-yl)cyclohexane-carboxamide | 408.11 | 409.0 | III |
| 149 | 3-(aminomethyl)-N-(3-(trifluoromethyl)-10H-phenothiazin-1-yl)cyclohexane-carboxamide | 421.14 | 422.2 | III |
| 150 | 3-(3-(1H-indol-2-yl)-10H-phenothiazin-10-yl)propan-1-amine | 371.15 | 372.1 | IV |
| 151 | 2-(10-(3-(dimethylamino)propyl)-10H-phenothiazin-3-yl)-1H-indole-5-carbonitrile 2,2,2-trifluoroacetate salt | 538.17 | 425.2 | IV |

TABLE 13-continued

| Cmpd # | Structure | Name | Exact mass | LC-MS [M + H]+ (m/z) | Synthetic (Scheme no.) |
|---|---|---|---|---|---|
| 152 | 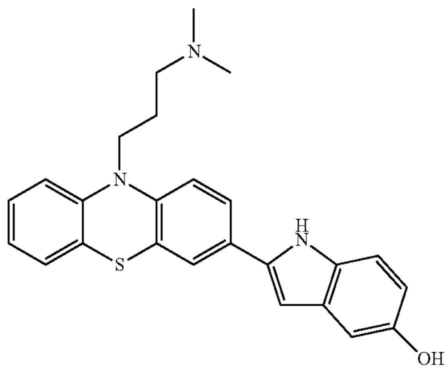 [SMILES: CN(C)CCCN1c2ccccc2Sc2cc(-c3cc4cc(O)ccc4[nH]3)ccc21] | 2-(10-(3-(dimethylamino) propyl)-10H-phenothiazin-3-yl)-1H-indol-5-ol | 415.17 | 416.2 | IV |
| 153 | 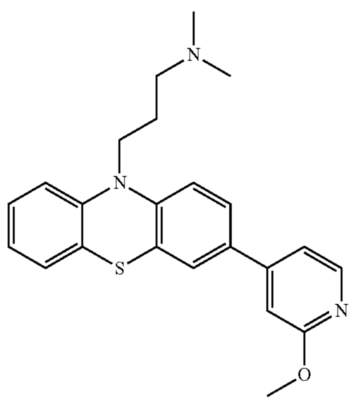 [SMILES: COc1cc(-c2ccc3c(c2)Sc2ccccc2N3CCCN(C)C)ccn1] | 3-(3-(2-methoxypyridin-4-yl)-10H-phenothiazin-10-yl)-N,N-dimethylpropan-1-amine | 391.53 | 392.2 | IV |
| 155 | 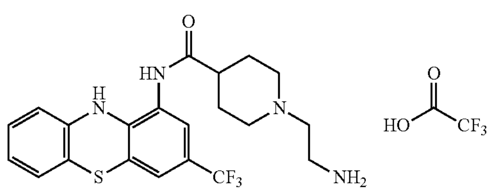 [SMILES: NCCN1CCC(C(=O)Nc2cc(C(F)(F)F)cc3c2Nc2ccccc2S3)CC1 ; O=C(O)C(F)(F)F] | 1-(2-aminoethyl)-N-(3-(trifluoromethyl)-10H-phenothiazin-1-yl)piperidine-4-carboxamide 2,2,2-trifluoroacetate | 550.15 | 437.2 | III |
| 156 | 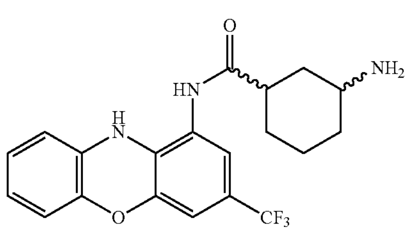 [SMILES: NC1CCCC(C(=O)Nc2cc(C(F)(F)F)cc3c2Nc2ccccc2O3)C1] | 3-amino-N-(3-(trifluoromethyl)-10H-phenoxazin-1-yl)cyclohexane-carboxamide | 391.15 | 392.2 | III |
| 157 | 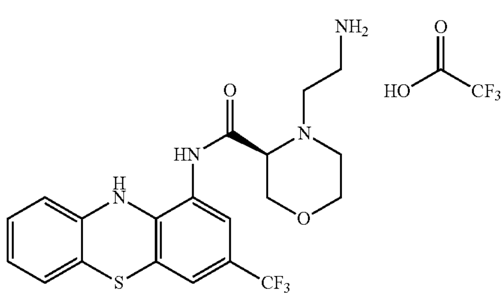 [SMILES: NCCN1CCOC[C@H]1C(=O)Nc1cc(C(F)(F)F)cc2c1Nc1ccccc1S2 ; O=C(O)C(F)(F)F] | (S)-4-(2-aminoethyl)-N-(3-(trifluoromethyl)-10H-phenothiazin-1-yl)morpholine-3-carboxamide 2,2,2-trifluoroacetate | 552.13 | 437.1 | III |

TABLE 13-continued

| Cmpd # | Structure | Name | Exact mass | LC-MS [M + H]+ (m/z) | Synthetic (Scheme no.) |
|---|---|---|---|---|---|
| 158 | 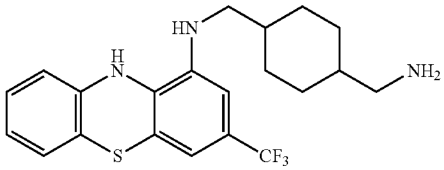 [SMILES: NCC1CCC(CNc2cc(C(F)(F)F)cc3c2Nc2ccccc2S3)CC1] | N-((4-(aminomethyl)cyclohexyl)methyl)-3-(trifluoromethyl)-10H-phenothiazin-1-amine | 407.16 | 408.2 | III |
| 159 | 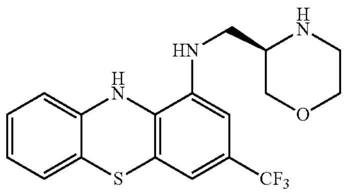 [SMILES: FC(F)(F)c1cc(NC[C@@H]2COCCN2)c2c(c1)Sc1ccccc1N2] | (R)-N-(morpholin-3-ylmethyl)-3-(trifluoromethyl)-10H-phenothiazin-1-amine | 381.11 | 382.0 | III |
| 160 | 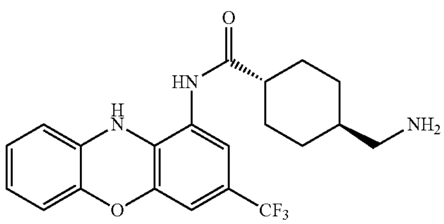 | (1r,4r)-4-(aminomethyl)-N-(3-(trifluoromethyl)-10H-phenoxazin-1-yl)cyclohexane-carboxamide | 405.17 | 404.5 | III |
| 161 | 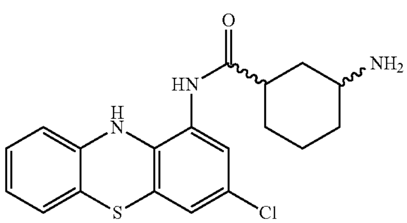 [SMILES: NC1CCCC(C(=O)Nc2cc(Cl)cc3c2Nc2ccccc2S3)C1] | 3-amino-N-(3-chloro-10H-phenothiazin-1-yl)cyclohexane-carboxamide | 373.1 | 374.1 | III |
| 162 | 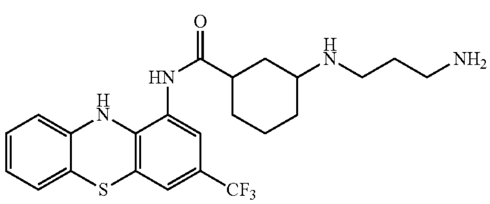 [SMILES: NCCCNC1CCCC(C(=O)Nc2cc(C(F)(F)F)cc3c2Nc2ccccc2S3)C1] | 3-((3-aminopropyl)amino)-N-(3-(trifluoromethyl)-10H-phenothiazin-1-yl)cyclohexane-carboxamide | 464.19 | 465.2 | III |
| 163 | 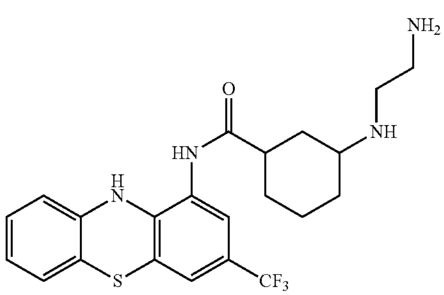 [SMILES: NCCNC1CCCC(C(=O)Nc2cc(C(F)(F)F)cc3c2Nc2ccccc2S3)C1] | 3-((2-aminoethyl)amino)-N-(3-(trifluoromethyl)-10H-phenothiazin-1-yl)cyclohexane-carboxamide | 450.17 | 451.2 | III |
| 164 | 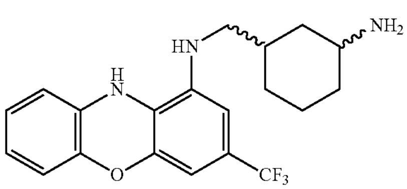 [SMILES: NC1CCCC(CNc2cc(C(F)(F)F)cc3c2Nc2ccccc2O3)C1] | N-((3-aminocyclohexyl)methyl)-3-(trifluoromethyl)-10H-phenoxazin-1-amine | 377.17 | 378.2 | III |

TABLE 13-continued

| Cmpd # | Structure | Name | Exact mass | LC-MS [M + H]+ (m/z) | Synthetic (Scheme no.) |
|---|---|---|---|---|---|
| 165 | 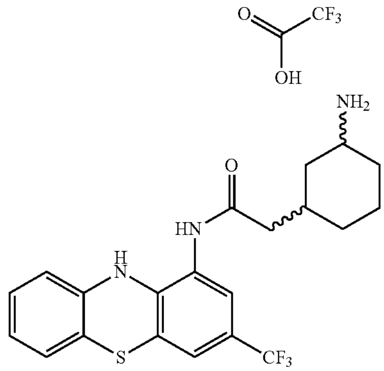 [SMILES: O=C(O)C(F)(F)F ; NC1CCCC(CC(=O)Nc2cc(C(F)(F)F)cc3c2Nc2ccccc2S3)C1] | 2-(3-aminocyclohexyl)-N-(3-(trifluoromethyl)-10H-phenothiazin-1-yl)acetamide 2,2,2-trifluoroacetate | 535.14 | 422.2 | III |
| 167 | 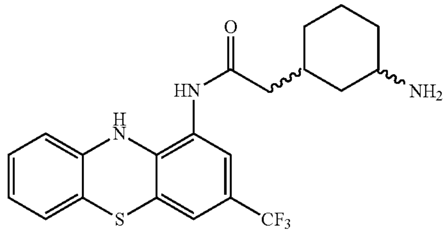 [SMILES: NC1CCCC(CC(=O)Nc2cc(C(F)(F)F)cc3c2Nc2ccccc2S3)C1] | 2-(3-aminocyclohexyl)-N-(3-(trifluoromethyl)-10H-phenothiazin-1-yl)acetamide | 421.14 | 422.4 | III |
| 169 | 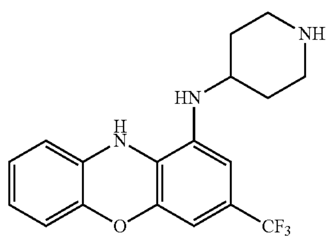 [SMILES: FC(F)(F)c1cc(NC2CCNCC2)c2c(c1)Oc1ccccc1N2] | N-(piperidin-4-yl)-3-(trifluoromethyl)-10H-phenoxazin-1-amine | 349.14 | 350.2 | III |
| 170 | 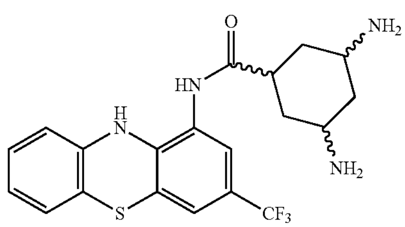 [SMILES: NC1CC(N)CC(C(=O)Nc2cc(C(F)(F)F)cc3c2Nc2ccccc2S3)C1] | 3,5-diamino-N-(3-(trifluoromethyl)-10H-phenothiazin-1-yl)cyclohexanecarboxamide | 422.14 | 423.2 | III |
| 171 | 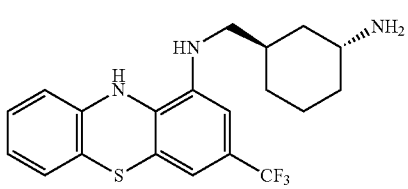 [SMILES: N[C@@H]1CCC[C@@H](CNc2cc(C(F)(F)F)cc3c2Nc2ccccc2S3)C1] | N-(((1R,3R)-3-aminocyclohexyl)methyl)-3-(trifluoromethyl)-10H-phenothiazin-1-amine | 393.15 | 394.1 | III |
| 172 | 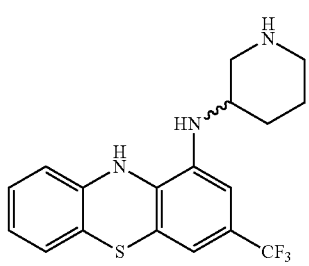 [SMILES: FC(F)(F)c1cc(NC2CCCNC2)c2c(c1)Sc1ccccc1N2] | N-(piperidin-3-yl)-3-(trifluoromethyl)-10H-phenothiazin-1-amine | 365.12 | 366.1 | III |

TABLE 13-continued

| Cmpd # | Structure | Name | Exact mass | LC-MS [M + H]+ (m/z) | Synthetic (Scheme no.) |
|---|---|---|---|---|---|
| 173 | 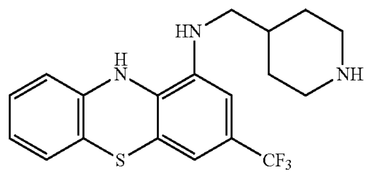 [SMILES: FC(F)(F)c1cc(NCC2CCNCC2)c2c(c1)Sc1ccccc1N2] | N-(piperidin-4-ylmethyl)-3-(trifluoromethyl)-10H-phenothiazin-1-amine | 379.13 | 380.1 | III |
| 174 | 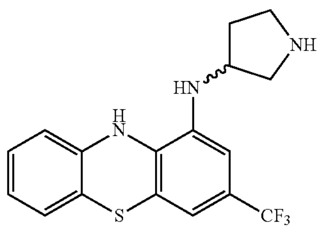 | N-(pyrrolidin-3-yl)-3-(trifluoromethyl)-10H-phenothiazin-1-amine | 351.10 | 352.1 | III |
| 175 | 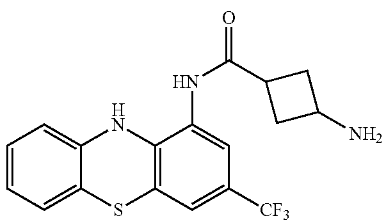 [SMILES: NC1CC(C(=O)Nc2cc(C(F)(F)F)cc3c2Nc2ccccc2S3)C1] | 3-amino-N-(3-(trifluoromethyl)-10H-phenothiazin-1-yl)cyclobutane-carboxamide | 379.10 | 380.1 | III |
| 178 | 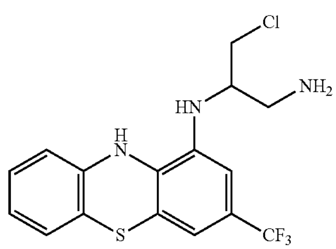 [SMILES: NCC(CCl)Nc1cc(C(F)(F)F)cc2c1Nc1ccccc1S2] | 3-chloro-N2-(3-(trifluoromethyl)-10H-phenothiazin-1-yl)propane-1,2-diamine | 373.06 | 374.1 | III |
| 179 | 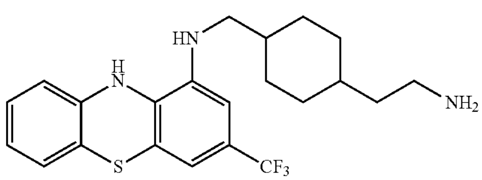 [SMILES: NCCC1CCC(CNc2cc(C(F)(F)F)cc3c2Nc2ccccc2S3)CC1] | N-((4-(2-aminoethyl)cyclohexyl)methyl)-3-(trifluoromethyl)-10H-phenothiazin-1-amine | 421.18 | 423.0 | III |
| 180 | 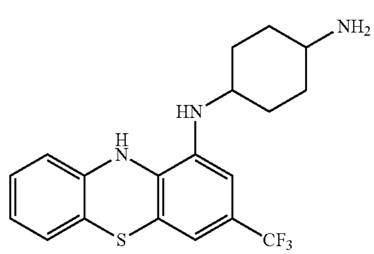 [SMILES: NC1CCC(Nc2cc(C(F)(F)F)cc3c2Nc2ccccc2S3)CC1] | N1-(3-(trifluoromethyl)-10H-phenothiazin-1-yl)cyclohexane-1,4-diamine | 379.13 | 380.0 | III |

TABLE 13-continued

| Cmpd # | Structure | Name | Exact mass | LC-MS [M + H]+ (m/z) | Synthetic (Scheme no.) |
|---|---|---|---|---|---|
| 181 | 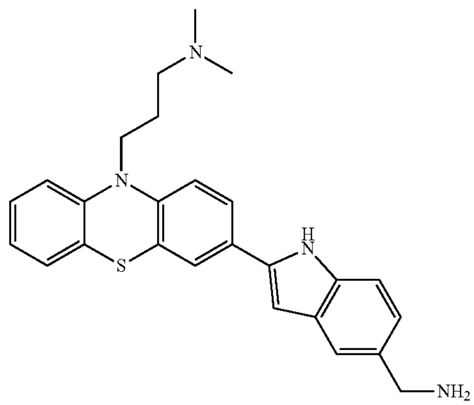 [SMILES: CN(C)CCCN1c2ccccc2Sc2cc(-c3cc4cc(CN)ccc4[nH]3)ccc21] | 3-(3-(5-(aminomethyl)-1H-indol-2-yl)-10H-phenothiazin-10-yl)-N,N-dimethylpropan-1-amine | 428.20 | 429.2 | IV |
| 182 | 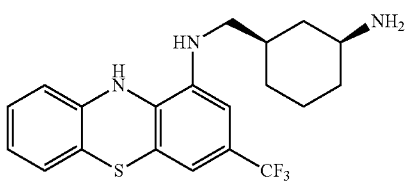 [SMILES: N[C@H]1CCC[C@@H](CNc2cc(C(F)(F)F)cc3c2Nc2ccccc2S3)C1] | N-(((1R,3S)-3-aminocyclohexyl)methyl)-3-(trifluoromethyl)-10H-phenothiazin-1-amine | 393.15 | 394.0 | III |
| 184 | 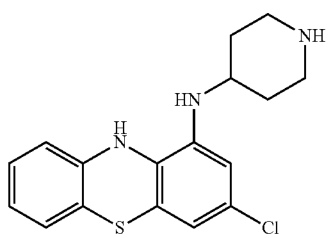 [SMILES: Clc1cc(NC2CCNCC2)c2c(c1)Sc1ccccc1N2] | 3-chloro-N-(piperidin-4-yl)-10H-phenothiazin-1-amine | 331.09 | 332.1 | III |
| 186 | 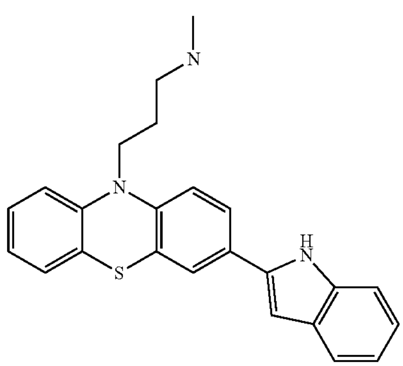 [SMILES: CNCCCN1c2ccccc2Sc2cc(-c3cc4ccccc4[nH]3)ccc21] | 3-(3-(1H-indol-2-yl)-10H-phenothiazin-10-yl)-N-methylpropan-1-amine | 385.16 | 386.2 | IV |
| 187 | 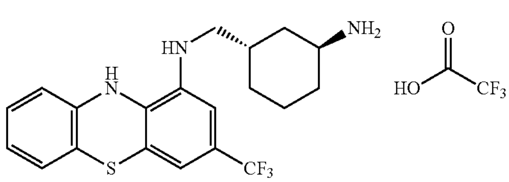 [SMILES: N[C@H]1CCC[C@H](CNc2cc(C(F)(F)F)cc3c2Nc2ccccc2S3)C1 ; O=C(O)C(F)(F)F] | N-(((1S,3S)-3-aminocyclohexyl)methyl)-3-(trifluoromethyl)-10H-phenothiazin-1-amine 2,2,2-trifluoroacetate | 507.14 | 394.0 | III |

TABLE 13-continued

| Cmpd # | Structure | Name | Exact mass | LC-MS [M + H]+ (m/z) | Synthetic (Scheme no.) |
|---|---|---|---|---|---|
| 188 | 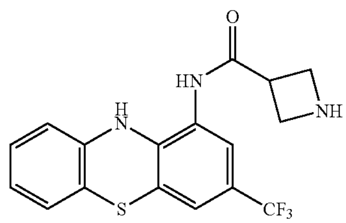 [SMILES: O=C(Nc1cc(C(F)(F)F)cc2c1Nc1ccccc1S2)C1CNC1] | N-(3-(trifluoromethyl)-10H-phenothiazin-1-yl)azetidine-3-carboxamide | 365.08 | 366.1 | III |
| 189 | 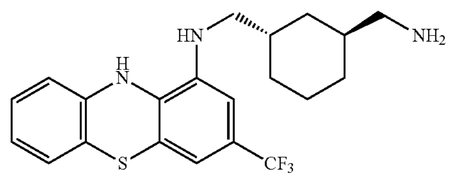 [SMILES: NC[C@H]1CCC[C@H](CNc2cc(C(F)(F)F)cc3c2Nc2ccccc2S3)C1] | N-(((1S,3S)-3-(aminomethyl)cyclohexyl)methyl)-3-(trifluoromethyl)-10H-phenothiazin-1-amine | 407.16 | 408.2 | III |
| 190 | 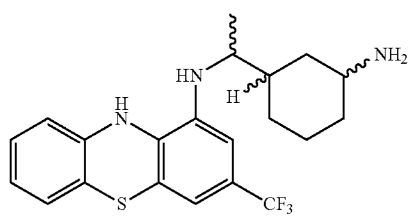 [SMILES: CC(Nc1cc(C(F)(F)F)cc2c1Nc1ccccc1S2)C1CCCC(N)C1] | N-(1-(3-aminocyclohexyl)ethyl)-3-(trifluoromethyl)-10H-phenothiazin-1-amine | 407.16 | 408.3 | III |
| 191 | 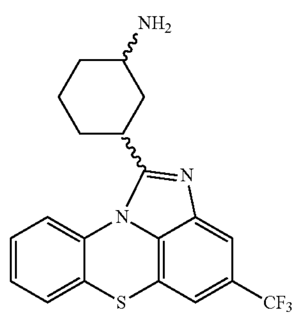 [SMILES: NC1CCCC(c2nc3cc(C(F)(F)F)cc4c3n2-c2ccccc2S4)C1] | 3-(4-(trifluoromethyl)imidazo[4,5,1-kl]phenothiazin-1-yl)cyclohexan-amine | 389.12 | 390.2 | XIII |
| 192 | 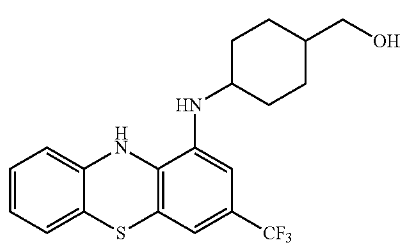 [SMILES: OCC1CCC(Nc2cc(C(F)(F)F)cc3c2Nc2ccccc2S3)CC1] | (4-((3-(trifluoromethyl)-10H-phenothiazin-1-yl)amino)cyclohexyl)methanol | 394.13 | 395.2 | III |
| 193 | 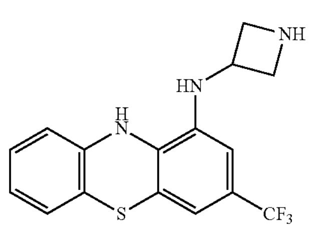 [SMILES: FC(F)(F)c1cc(NC2CNC2)c2c(c1)Sc1ccccc1N2] | N-(azetidin-3-yl)-3-(trifluoromethyl)-10H-phenothiazin-1-amine | 337.09 | 338.1 | III |

TABLE 13-continued

| Cmpd # | Structure | Name | Exact mass | LC-MS [M + H]+ (m/z) | Synthetic (Scheme no.) |
|---|---|---|---|---|---|
| 196 | 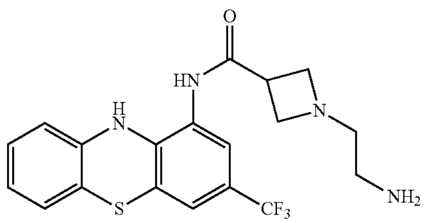 [SMILES: NCCN1CC(C(=O)Nc2cc(C(F)(F)F)cc3c2Nc2ccccc2S3)C1] | 1-(2-aminoethyl)-N-(3-(trifluoromethyl)-10H-phenothiazin-1-yl)azetidine-3-carboxamide | 408.12 | 409.4 | III |
| 197 | 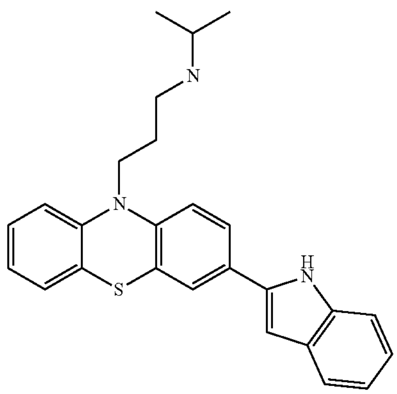 [SMILES: CC(C)NCCCN1c2ccccc2Sc2cc(-c3cc4ccccc4[nH]3)ccc21] | 3-(3-(1H-indol-2-yl)-10H-phenothiazin-10-yl)-N-isopropylpropan-1-amine | 413.19 | 414.2 | IV |
| 198 | 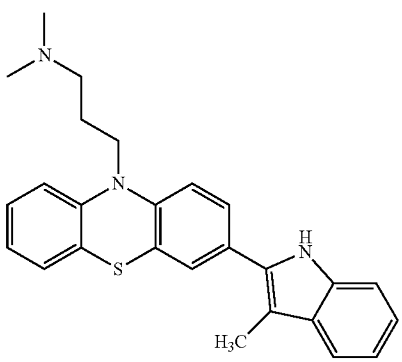 [SMILES: Cc1c(-c2ccc3c(c2)Sc2ccccc2N3CCCN(C)C)[nH]c2ccccc12] | N,N-dimethyl-3-(3-(3-methyl-1H-indol-2-yl)-10H-phenothiazin-10-yl)propan-1-amine | 413.19 | 414.0 | IV |
| 199 | 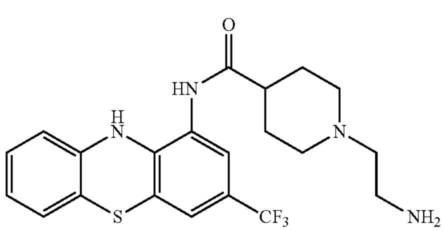 [SMILES: NCCN1CCC(C(=O)Nc2cc(C(F)(F)F)cc3c2Nc2ccccc2S3)CC1] | 1-(2-aminoethyl)-N-(3-(trifluoromethyl)-10H-phenothiazin-1-yl)piperidine-4-carboxamide | 436.15 | 437.2 | III |
| 203 | 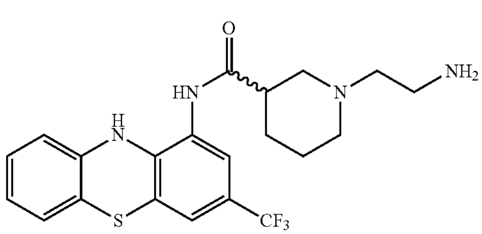 [SMILES: NCCN1CCCC(C(=O)Nc2cc(C(F)(F)F)cc3c2Nc2ccccc2S3)C1] | 1-(2-aminoethyl)-N-(3-(trifluoromethyl)-10H-phenothiazin-1-yl)piperidine-3-carboxamide | 436.15 | 437.2 | III |

TABLE 13-continued

| Cmpd # | Structure | Name | Exact mass | LC-MS [M + H]+ (m/z) | Synthetic (Scheme no.) |
|---|---|---|---|---|---|
| 204 | 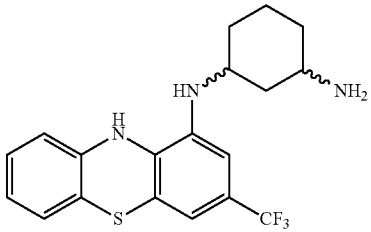 [SMILES: NC1CCCC(Nc2cc(C(F)(F)F)cc3c2Nc2ccccc2S3)C1] | N1-(3-(trifluoromethyl)-10H-phenothiazin-1-yl)cyclohexane-1,3-diamine | 379.13 | 380.2 | III |
| 205 | 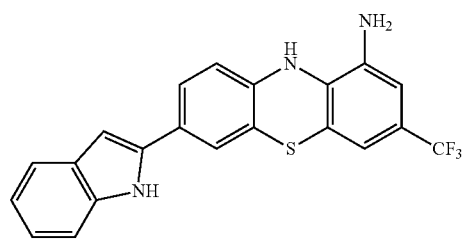 | 7-(1H-indol-2-yl)-3-(trifluoromethyl)-10H-phenothiazin-1-amine | 397.09 | 398.3 | VIII |
| 206 | 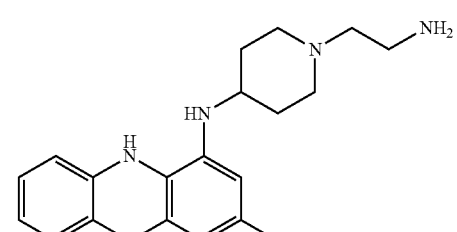 | N-(1-(2-aminoethyl)piperidin-4-yl)-3-(trifluoromethyl)-10H-phenoxazin-1-amine | 392.18 | 393.2 | III |
| 207 | 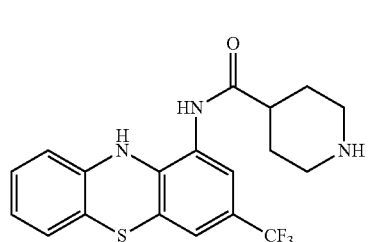 | N-(3-(trifluoromethyl)-10H-phenothiazin-1-yl)piperidine-4-carboxamide | 393.11 | 394.1 | III |
| 208 | 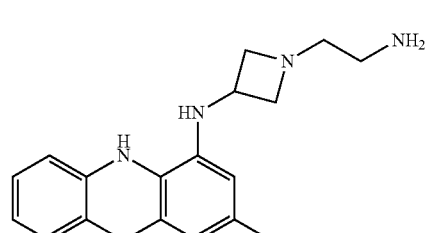 | N-(1-(2-aminoethyl)azetidin-3-yl)-3-(trifluoromethyl)-10H-phenothiazin-1-amine | 380.13 | 381.2 | III |
| 210 | 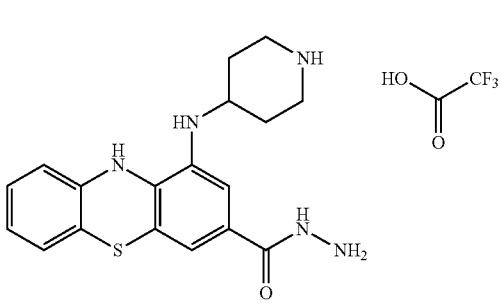 [SMILES: NNC(=O)c1cc(NC2CCNCC2)c2c(c1)Sc1ccccc1N2 ; O=C(O)C(F)(F)F] | 1-(piperidin-4-ylamino)-10H-phenothiazine-3-carbohydrazide 2,2,2-trifluoroacetate salt | 469.14 | 356.1 | V |

TABLE 13-continued

| Cmpd # | Structure | Name | Exact mass | LC-MS [M + H]+ (m/z) | Synthetic (Scheme no.) |
|---|---|---|---|---|---|
| 211 | 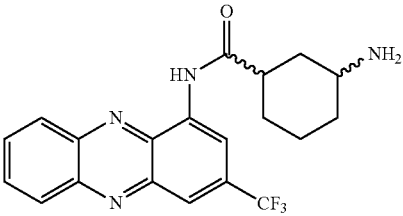 [SMILES: NC1CCCC(C(=O)Nc2cc(C(F)(F)F)cc3nc4ccccc4nc23)C1] | 3-amino-N-(3-(trifluoromethyl) phenazin-1-yl) cyclohexane-carboxamide | 388.15 | 389.3 | XII |
| 212 | 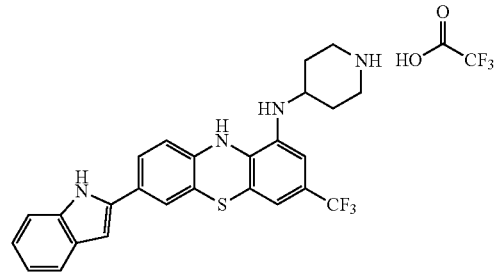 [SMILES: FC(F)(F)c1cc(NC2CCNCC2)c2c(c1)Sc1cc(-c3cc4ccccc4[nH]3)ccc1N2 ; O=C(O)C(F)(F)F] | 7-(1H-indol-2-yl)-N-(piperidin-4-yl)-3-(trifluoromethyl)-10H-phenothiazin-1-amine 2,2,2-trifluoroacetate salt | 594.15 | 481.2 | VIII |
| 213 | 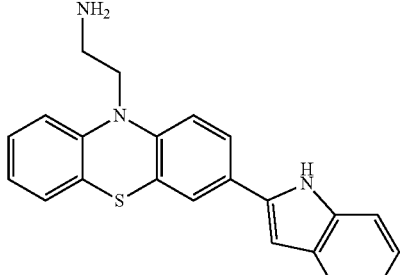 | 2-(3-(1H-indol-2-yl)-10H-phenothiazin-10-yl)ethanamine | 357.13 | 358.1 | IV |
| 214 | 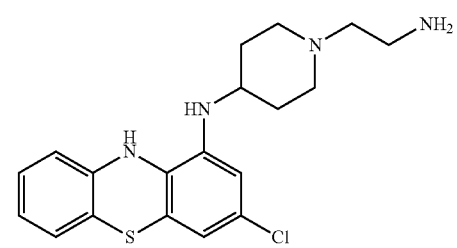 | N-(1-(2-aminoethyl) piperidin-4-yl)-3-chloro-10H-phenothiazin-1-amine | 374.13 | 375.0 | III |
| 215 | 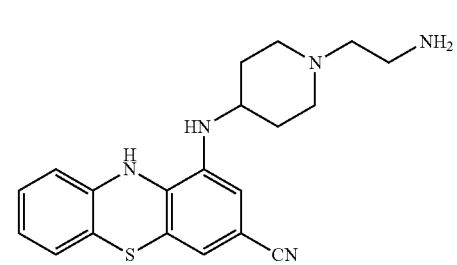 | 1-((1-(2-aminoethyl) piperidin-4-yl)amino)-10H-phenothiazine-3-carbonitrile | 365.17 | 366.3 | III |

TABLE 13-continued

| Cmpd # | Structure | Name | Exact mass | LC-MS [M + H]+ (m/z) | Synthetic (Scheme no.) |
|---|---|---|---|---|---|
| 216 | 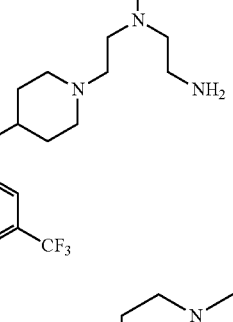 | N1-(2-aminoethyl)-N1-(2-(4-((3-(trifluoromethyl)-10H-phenothiazin-1-yl)amino)piperidin-1-yl)ethyl)ethane-1,2-diamine 2,2,2-trifluoroacetate salt | 608.24 | 495.2 | III |
| 217 | 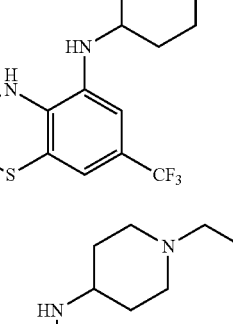 | 9-((1-(2-aminoethyl)piperidin-4-yl)amino)-7-(trifluoromethyl)-10H-phenothiazine-3-carbonitrile | 433.15 | 434.2 | XVII |
| 218 | 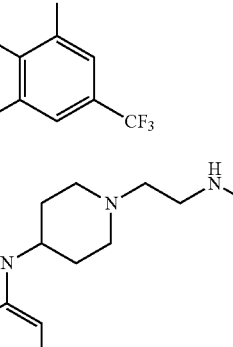 | N-(1-(2-aminoethyl)piperidin-4-yl)-10-methyl-3-(trifluoromethyl)-10H-phenothiazin-1-amine | 422.18 | 423.2 | III |
| 219 | 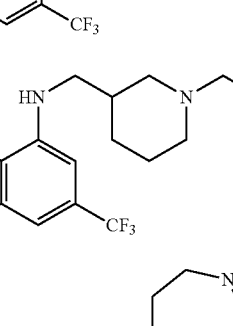 | N1-(2-(4-((3-(trifluoromethyl)-10H-phenothiazin-1-yl)amino)piperidin-1-yl)ethyl)ethane-1,2-diamine | 451.20 | 451.2 | III |
| 220 | 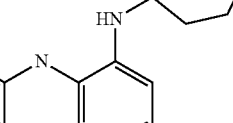 | N-((1-(2-aminoethyl)piperidin-3-yl)methyl)-3-(trifluoromethyl)-10H-phenothiazin-1-amine | 422.18 | 423.2 | III |
| 221 | 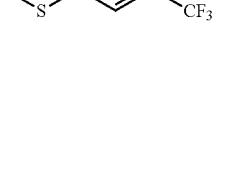 | N-(azepan-4-yl)-3-(trifluoromethyl)-10H-phenothiazin-1-amine | 379.13 | 380.1 | III |

TABLE 13-continued

| Cmpd # | Structure | Name | Exact mass | LC-MS [M + H]+ (m/z) | Synthetic (Scheme no.) |
|---|---|---|---|---|---|
| 222 | 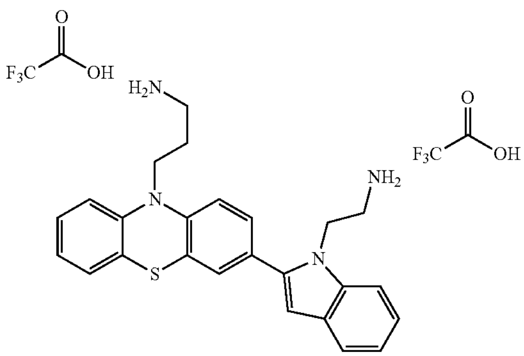 [SMILES: O=C(O)C(F)(F)F ; NCCCN1c2ccccc2Sc2cc(-c3cc4ccccc4n3CCN)ccc21 ; O=C(O)C(F)(F)F] | 3-(3-(1-(2-aminoethyl)-1H-indol-2-yl)-10H-phenothiazin-10-yl)propan-1-amine bis(2,2,2-trifluoroacetate) salt | 642.17 | 415.2 | IV |
| 223 | 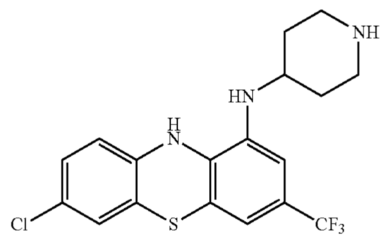 | 7-chloro-N-(piperidin-4-yl)-3-(trifluoromethyl)-10H-phenothiazin-1-amine | 399.08 | 400.2 | III |
| 224 | 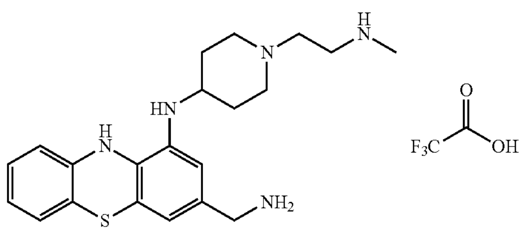 [SMILES: CNCCN1CCC(Nc2cc(CN)cc3c2Nc2ccccc2S3)CC1 ; O=C(O)C(F)(F)F] | 3-(aminomethyl)-N-(1-(2-(methylamino)ethyl)piperidin-4-yl)-10H-phenothiazin-1-amine 2,2,2-trifluoroacetate salt | 497.21 | 384.2 | XI |
| 225 | 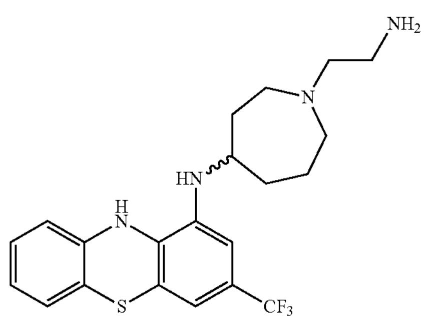 [SMILES: NCCN1CCCC(Nc2cc(C(F)(F)F)cc3c2Nc2ccccc2S3)CC1] | N-(1-(2-aminoethyl)azepan-4-yl)-3-(trifluoromethyl)-10H-phenothiazin-1-amine | 422.18 | 423.2 | III |
| 226 | 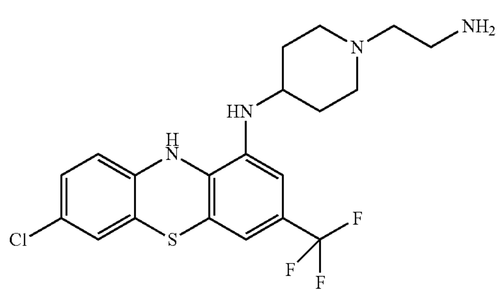 [SMILES: NCCN1CCC(Nc2cc(C(F)(F)F)cc3c2Nc2ccc(Cl)cc2S3)CC1] | N-(1-(2-aminoethyl)piperidin-4-yl)-7-chloro-3-(trifluoromethyl)-10H-phenothiazin-1-amine | 442.9 | 443.1 | III |

TABLE 13-continued

| Cmpd # | Structure | Name | Exact mass | LC-MS [M + H]+ (m/z) | Synthetic (Scheme no.) |
|---|---|---|---|---|---|
| 227 | 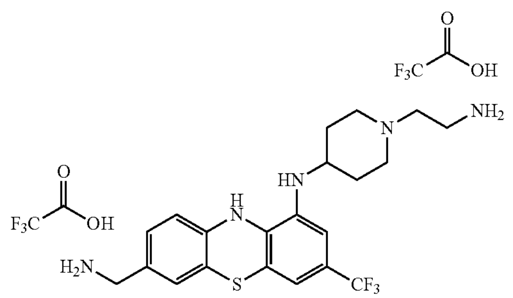 | N-(1-(2-aminoethyl) piperidin-4-yl)-7-(aminomethyl)-3-(trifluoromethyl)-10H-phenothiazin-1-amine 2,2,2-trifluoroacetate | 665.58 | 436.4 | XVIII |
| 228 | 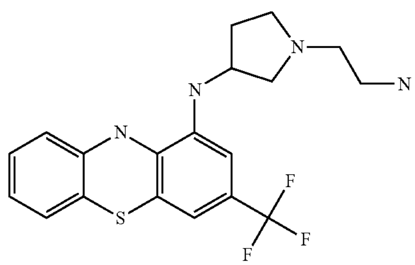 [SMILES: NCCN1CCC(Nc2cc(C(F)(F)F)cc3c2Nc2ccccc2S3)C1] | N-(1-(2-aminoethyl) pyrrolidin-3-yl)-3-(trifluoromethyl)-10H-phenothiazin-1-amine | 394.47 | 395.2 | III |
| 232 | 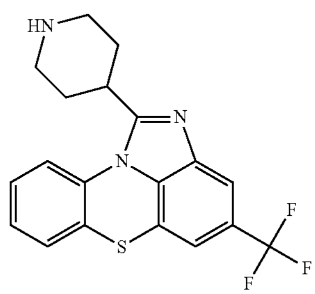 [SMILES: FC(F)(F)c1cc2c3c(c1)nc(C1CCNCC1)n3-c1ccccc1S2] | 1-(piperidin-4-yl)-4-(trifluoromethyl) imidazo[4,5,1-kl]phenothiazine | 375.42 | 376.1 | XIII |
| 234 | 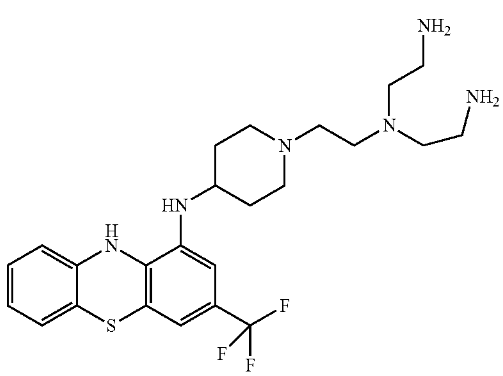 [SMILES: NCCN(CCN)CCN1CCC(Nc2cc(C(F)(F)F)cc3c2Nc2ccccc2S3)CC1] | N1-(2-aminoethyl)-N1-(2-(4-((3-(trifluoromethyl)-10H-phenothiazin-1-yl)amino) piperidin-1-yl) ethyl)ethane-1,2-diamine | 494.63 | 495.2 | III |

TABLE 13-continued

| Cmpd # | Structure | Name | Exact mass | LC-MS [M + H]+ (m/z) | Synthetic (Scheme no.) |
|---|---|---|---|---|---|
| 239 | 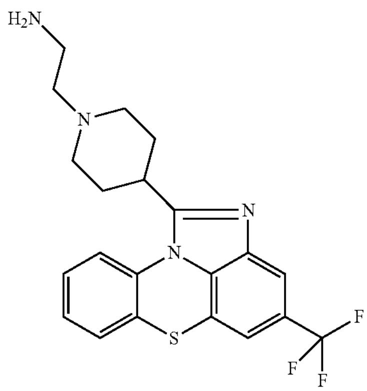 [SMILES: NCCN1CCC(c2nc3cc(C(F)(F)F)cc4c3n2-c2ccccc2S4)CC1] | 2-(4-(4-(trifluoromethyl)imidazo[4,5,1-kl]phenothiazin-1-yl)piperidin-1-yl)ethanamine | 418.49 | 419.2 | XIII |
| 240 | 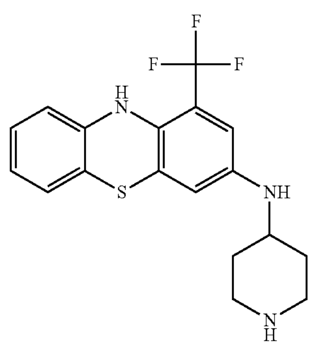 [SMILES: FC(F)(F)c1cc(NC2CCNCC2)cc2c1Nc1ccccc1S2] | N-(piperidin-4-yl)-1-(trifluoromethyl)-10H-phenothiazin-3-amine | 365.42 | 366.1 | III |
| 241 | 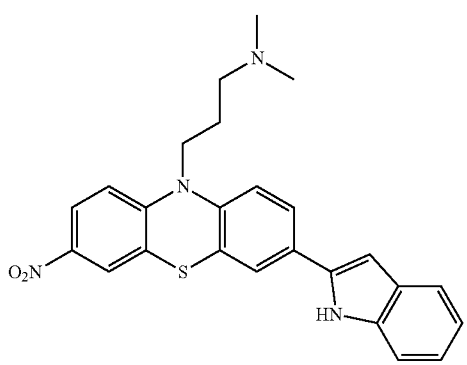 [SMILES: CN(C)CCCN1c2ccc(-c3cc4ccccc4[nH]3)cc2Sc2cc([N+](=O)[O-])ccc21] | 3-(3-(1H-indol-2-yl)-7-nitro-10H-phenothiazin-10-yl)-N,N-dimethylpropan-1-amine | 444.56 | 445.1 | IV |
| 242 | 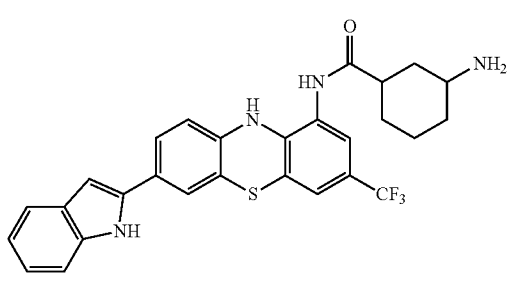 [SMILES: NC1CCCC(C(=O)Nc2cc(C(F)(F)F)cc3c2Nc2ccc(-c4cc5ccccc5[nH]4)cc2S3)C1] | N-(7-(1H-indol-2-yl)-3-(trifluoromethyl)-10H-phenothiazin-1-yl)-3-amino-cyclohexane-carboxamide | 522.6 | 523.2 | VIII |

TABLE 13-continued

| Cmpd # | Structure | Name | Exact mass | LC-MS [M + H]+ (m/z) | Synthetic (Scheme no.) |
|---|---|---|---|---|---|
| 243 | 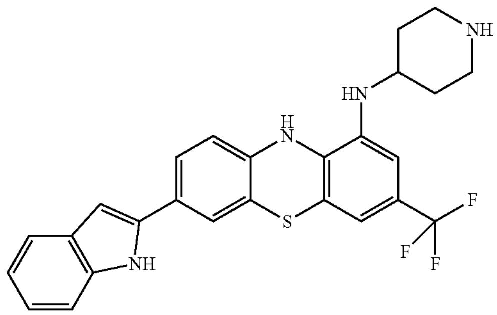 [SMILES: FC(F)(F)c1cc(NC2CCNCC2)c2c(c1)Sc1cc(-c3cc4ccccc4[nH]3)ccc1N2] | 7-(1H-indol-2-yl)-N-(piperidin-4-yl)-3-(trifluoromethyl)-10H-phenothiazin-1-amine | 480.56 | 481.1 | VIII |
| 244 | 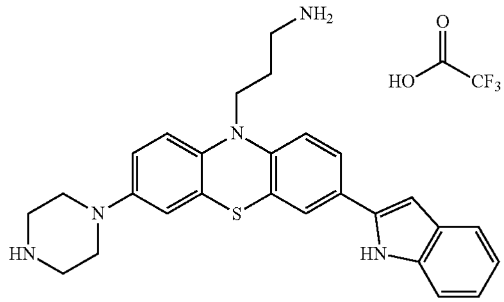 [SMILES: NCCCN1c2ccc(-c3cc4ccccc4[nH]3)cc2Sc2cc(N3CCNCC3)ccc21 ; O=C(O)C(F)(F)F] | 3-(3-(1H-indol-2-yl)-7-(piperazin-1-yl)-10H-phenothiazin-10-yl)propan-1-amine 2,2,2-trifluoroacetate | 569.65 | 456.2 | XX |
| 245 | 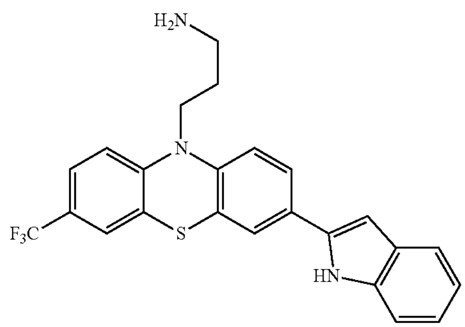 [SMILES: NCCCN1c2ccc(-c3cc4ccccc4[nH]3)cc2Sc2cc(C(F)(F)F)ccc21] | 3-(3-(1H-indol-2-yl)-7-(trifluoromethyl)-10H-phenothiazin-10-yl)propan-1-amine | 439.51 | 440.1 | IV |
| 247 | 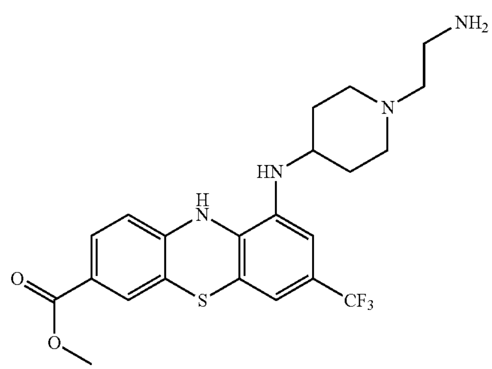 [SMILES: COC(=O)c1ccc2c(c1)Sc1cc(C(F)(F)F)cc(NC3CCN(CCN)CC3)c1N2] | methyl 9-((1-(2-aminoethyl)piperidin-4-yl)amino)-7-(trifluoromethyl)-10H-phenothiazine-3-carboxylate | 466.53 | 467.2 | XXII |
| 252 | 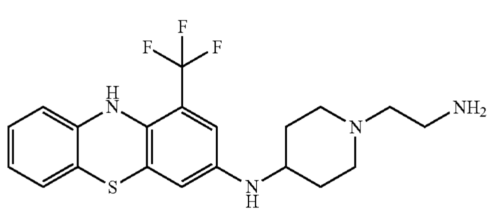 [SMILES: NCCN1CCC(Nc2cc3c(c(C(F)(F)F)c2)Nc2ccccc2S3)CC1] | N-(1-(2-aminoethyl)piperidin-4-yl)-1-(trifluoromethyl)-10H-phenothiazin-3-amine | 408.49 | 409.4 | III |

TABLE 13-continued

| Cmpd # | Structure | Name | Exact mass | LC-MS [M + H]+ (m/z) | Synthetic (Scheme no.) |
|---|---|---|---|---|---|
| 253 | 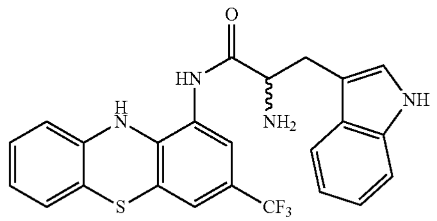 | 2-amino-3-(1H-indol-3-yl)-N-(3-(trifluoromethyl)-10H-phenothiazin-1-yl)propanamide | 468.5 | 469.2 | III |
| 254 | 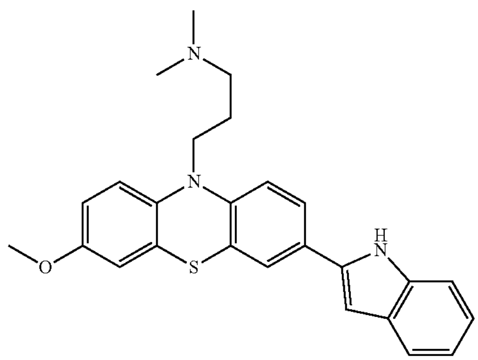 [SMILES: COc1ccc2c(c1)Sc1cc(-c3cc4ccccc4[nH]3)ccc1N2CCCN(C)C] | 3-(3-(1H-indol-2-yl)-7-methoxy-10H-phenothiazin-10-yl)-N,N-dimethylpropan-1-amine | 429.59 | 430.2 | IV |
| 255 | | N-(2-aminoethyl)-9-((1-(2-aminoethyl)piperidin-4-yl)amino)-7-(trifluoromethyl)-10H-phenothiazine-3-carboxamide trifluroroacetic acid | 608.20 | | XXII |
| 256 | 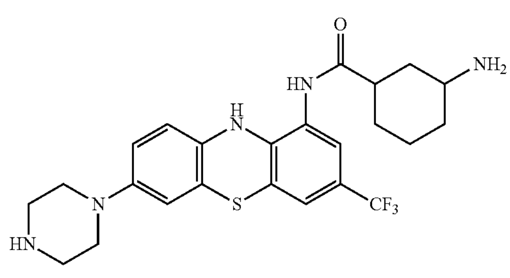 [SMILES: NC1CCCC(C(=O)Nc2cc(C(F)(F)F)cc3c2Nc2ccc(N4CCNCC4)cc2S3)C1] | 3-amino-N-(7-(piperazin-1-yl)-3-(trifluoromethyl)-10H-phenothiazin-1-yl)cyclohexane-1-carboxamide | 491.20 | 492.2 | XXV |
| 257 | 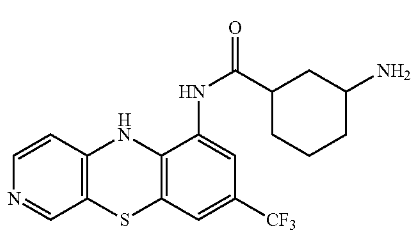 [SMILES: NC1CCCC(C(=O)Nc2cc(C(F)(F)F)cc3c2Nc2ccncc2S3)C1] | 3-amino-N-(8-(trifluoromethyl)-5H-benzo[b]pyrido[4,3-e][1,4]thiazin-6-yl)cyclohexane-2-carboxamide | 408.12 | 409.1 | XXIX |

TABLE 13-continued

| Cmpd # | Structure | Name | Exact mass | LC-MS [M + H]+ (m/z) | Synthetic (Scheme no.) |
|---|---|---|---|---|---|
| 258 | 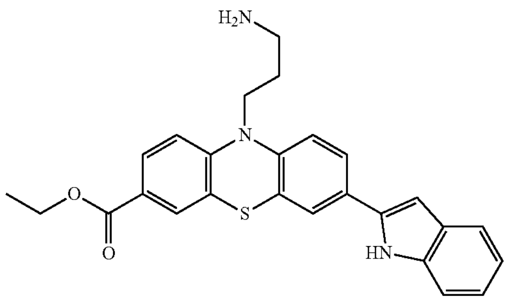 [SMILES: CCOC(=O)c1ccc2c(c1)Sc1cc(-c3cc4ccccc4[nH]3)ccc1N2CCCN] | ethyl 10-(3-aminopropyl)-7-(1H-indol-2-yl)-10H-phenothiazine-3-carboxylate | 443.17 | 444.2 | IV |
| 259 | 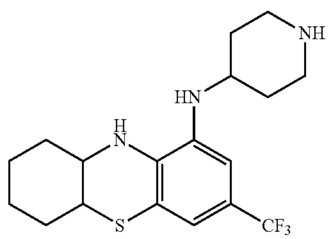 [SMILES: FC(F)(F)c1cc(NC2CCNCC2)c2c(c1)SC1CCCCC1N2] | N-(piperidin-4-yl)-7-(trifluoromethyl)-2,3,4,4a,10,10a-hexahydro-1H-phenothiazin-9-amine | 371.16 | 372.1 | XXX |
| 262 | 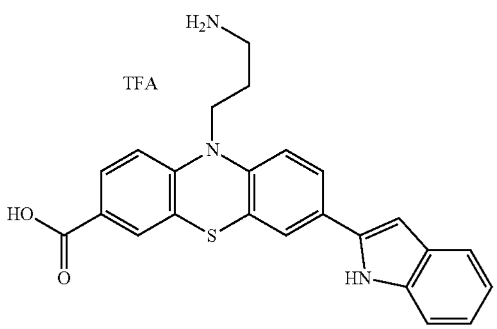 [SMILES: NCCCN1c2ccc(C(=O)O)cc2Sc2cc(-c3cc4ccccc4[nH]3)ccc21] | 10-(3-aminopropyl)-7-(1H-indol-2-yl)-10H-phenothiazine-3-carboxylic acid trifluoro acetic acid | 529.13 | 416.2 | IV |
| 263 | 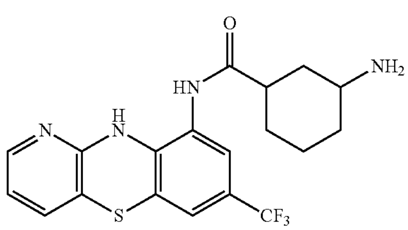 [SMILES: NC1CCCC(C(=O)Nc2cc(C(F)(F)F)cc3c2Nc2ncccc2S3)C1] | 3-amino-N-(7-(trifluoromethyl)-10H-benzo[b]pyrido[2,3-e][1,4]thiazin-9-yl)cyclohexane-1-carboxamide | 408.12 | 409.1 | XXIX |
| 264 | 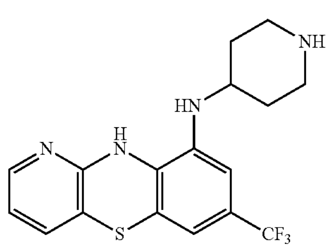 [SMILES: FC(F)(F)c1cc(NC2CCNCC2)c2c(c1)Sc1cccnc1N2] | N-(piperidin-4-yl)-7-(trifluoromethyl)-10H-benzo[b]pyrido[2,3-e][1,4]thiazin-9-amine | 366.11 | 367.1 | XXIX |

TABLE 13-continued

| Cmpd # | Structure | Name | Exact mass | LC-MS [M + H]+ (m/z) | Synthetic (Scheme no.) |
|---|---|---|---|---|---|
| 265 | 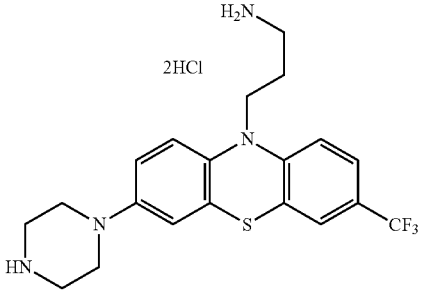 [SMILES: NCCCN1c2ccc(N3CCNCC3)cc2Sc2cc(C(F)(F)F)ccc21] | 3-(3-(piperazin-1-yl)-7-(trifluoromethyl)-10H-phenothiazin-10-yl)propan-1-amine hydrochloride | 480.11 | 409.1 | IV |
| 266 | 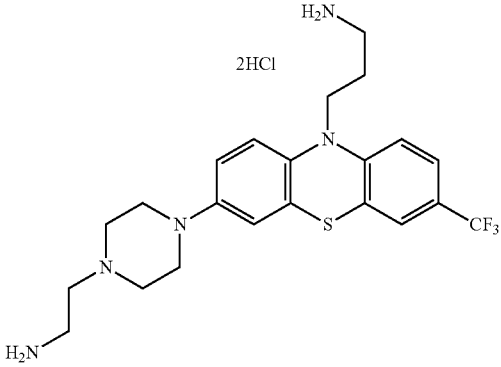 [SMILES: NCCCN1c2ccc(N3CCN(CCN)CC3)cc2Sc2cc(C(F)(F)F)ccc21] | 3-(3-(4-(2-aminoethyl)piperazin-1-yl)-7-(trifluoromethyl)-10H-phenothiazin-10-yl)propan-1-amine hydrochloride | 523.16 | 452.1 | IV |
| 267 | 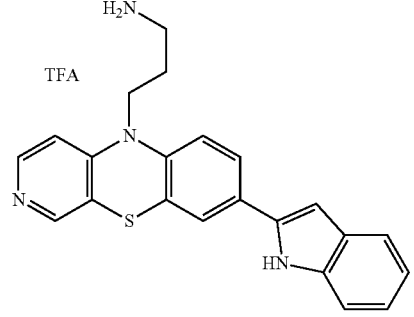 [SMILES: NCCCN1c2ccncc2Sc2cc(-c3cc4ccccc4[nH]3)ccc21] | 3-(8-(1H-indol-2-yl)-5H-benzo[b]pyrido[4,3-e][1,4]thiazin-5-yl)propan-1-amine trifluoro acetic acid | 486.13 | 374.1 | VI |
| 268 | 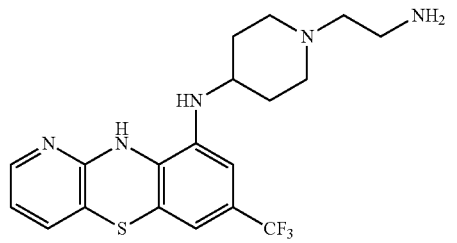 [SMILES: NCCN1CCC(Nc2cc(C(F)(F)F)cc3c2Nc2ncccc2S3)CC1] | N-(1-(2-aminoethyl)piperidin-4-yl)-7-(trifluoromethyl)-10H-benzo[b]pyrido[2,3-e][1,4]thiazin-9-amine | 409.15 | 410.1 | XXIX |

TABLE 13-continued

| Cmpd # | Structure | Name | Exact mass | LC-MS [M + H]+ (m/z) | Synthetic (Scheme no.) |
|---|---|---|---|---|---|
| 269 | 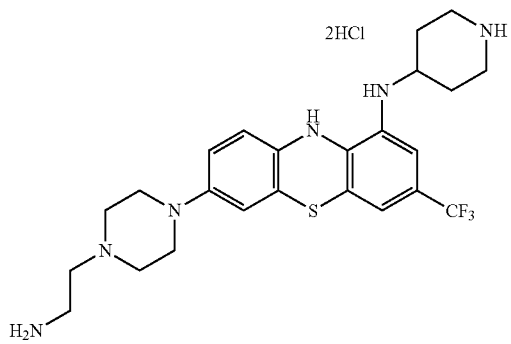 [SMILES: NCCN1CCN(c2ccc3c(c2)Sc2cc(C(F)(F)F)cc(NC4CCNCC4)c2N3)CC1] | 7-(4-(2-aminoethyl)piperazin-1-yl)-N-(piperidin-4-yl)-3-(trifluoromethyl)-10H-phenothiazin-1-amine hydrochloride | 492.23 | 493.2 | XXIII |
| 270 | 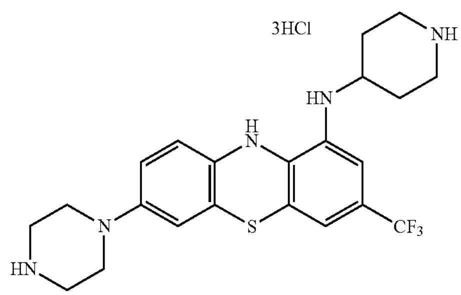 [SMILES: FC(F)(F)c1cc(NC2CCNCC2)c2c(c1)Sc1cc(N3CCNCC3)ccc1N2] | 7-(piperazin-1-yl)-N-(piperidin-4-yl)-3-(trifluoromethyl)-10H-phenothiazin-1-amine hydrochloride | 557.12 | 450.1 | XXIII |
| 271 | 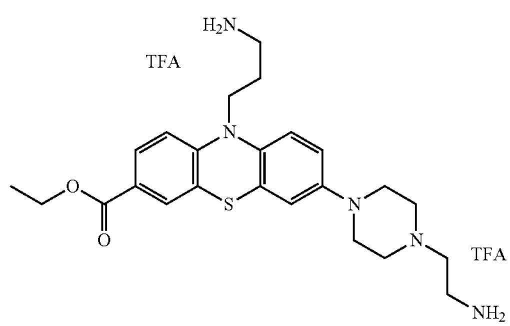 [SMILES: CCOC(=O)c1ccc2c(c1)Sc1cc(N3CCN(CCN)CC3)ccc1N2CCCN] | ethyl 7-(4-(2-aminoethyl)piperazin-1-yl)-10-(3-aminopropyl)-10H-phenothiazine-3-carboxylate trifluoro acetic acid | 683.22 | 456.2 | IV |
| 272 | 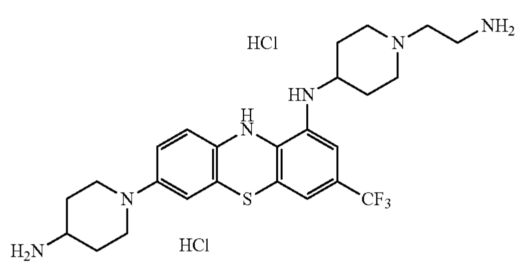 [SMILES: NCCN1CCC(Nc2cc(C(F)(F)F)cc3c2Nc2ccc(N4CCC(N)CC4)cc2S3)CC1 ; Cl ; Cl] | N-(1-(2-aminoethyl)piperidin-4-yl)-7-(4-aminopiperidin-1-yl)-3-(trifluoromethyl)-10H-phenothiazin-1-amine hydrochloride | 578.20 | 507.1 | XXIII |
| 273 | 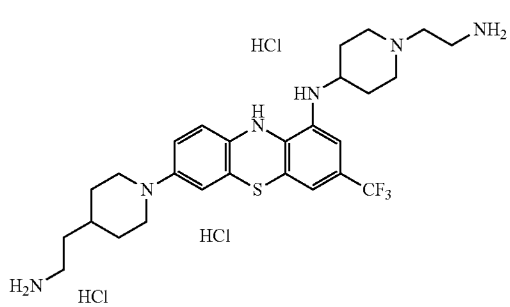 [SMILES: NCCC1CCN(c2ccc3c(c2)Sc2cc(C(F)(F)F)cc(NC4CCN(CCN)CC4)c2N3)CC1 ; Cl ; Cl ; Cl] | 7-(4-(2-aminoethyl)piperidin-1-yl)-N-(1-(2-aminoethyl)piperidin-4-yl)-3-(trifluoromethyl)-10H-phenothiazin-1-amine hydrochloride | 642.21 | 536.2 | XXIII |

TABLE 13-continued

| Cmpd # | Structure | Name | Exact mass | LC-MS [M + H]+ (m/z) | Synthetic (Scheme no.) |
|---|---|---|---|---|---|
| 274 | 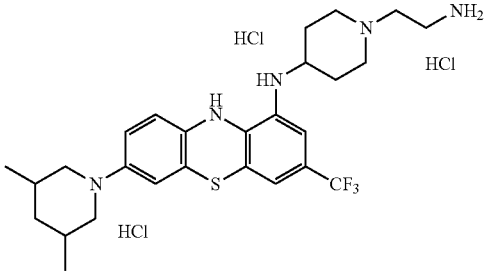 [SMILES: CC1CC(C)CN(c2ccc3c(c2)Sc2cc(C(F)(F)F)cc(NC4CCN(CCN)CC4)c2N3)C1 ; Cl ; Cl ; Cl] | N-(1-(2-aminoethyl)piperidin-4-yl)-7-(3,5-dimethyl-piperidin-1-yl)-3-(trifluoromethyl)-10H-phenothiazin-1-amine hydrochloride | 627.19 | 520.2 | XXIII |
| 275 | 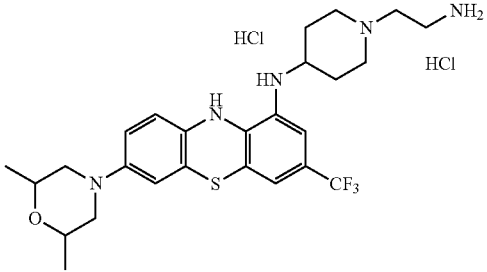 [SMILES: CC1CN(c2ccc3c(c2)Sc2cc(C(F)(F)F)cc(NC4CCN(CCN)CC4)c2N3)CC(C)O1 ; Cl ; Cl] | N-(1-(2-aminoethyl)piperidin-4-yl)-7-(2,6-dimethyl-morpholino)-3-(trifluoromethyl)-10H-phenothiazin-1-amine hydrochloride | 593.20 | 522.1 | XXIII |
| 275 | 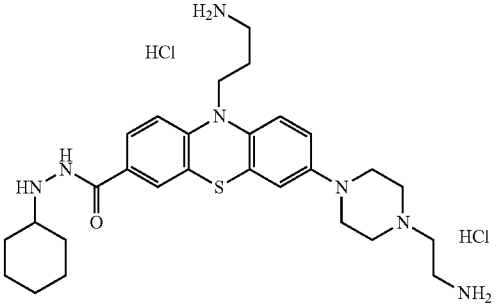 [SMILES: NCCCN1c2ccc(C(=O)NNC3CCCCC3)cc2Sc2cc(N3CCN(CCN)CC3)ccc21 ; Cl ; Cl] | 7-(4-(2-aminoethyl)piperazin-1-yl)-10-(3-aminopropyl)-N'-cyclohexyl-10H-phenothiazine-3-carbohydrazide hydrochloride | 595.26 | 524.2 | IV |
| 276 | 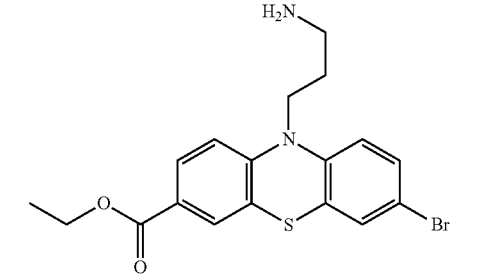 [SMILES: CCOC(=O)c1ccc2c(c1)Sc1cc(Br)ccc1N2CCCN] | ethyl 10-(3-aminopropyl)-7-bromo-10H-phenothiazine-3-carboxylate | 406.04 | 407 | IV |
| 277 | 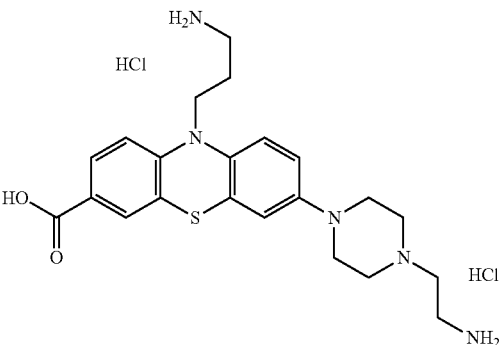 | 7-(4-(2-aminoethyl)piperazin-1-yl)-10-(3-aminopropyl)-10H-phenothiazine-3-carboxylic acid hydrochloride | 499.16 | 428.2 | IV |

TABLE 13-continued

| Cmpd # | Structure | Name | Exact mass | LC-MS [M + H]+ (m/z) | Synthetic (Scheme no.) |
|---|---|---|---|---|---|
| 278 | 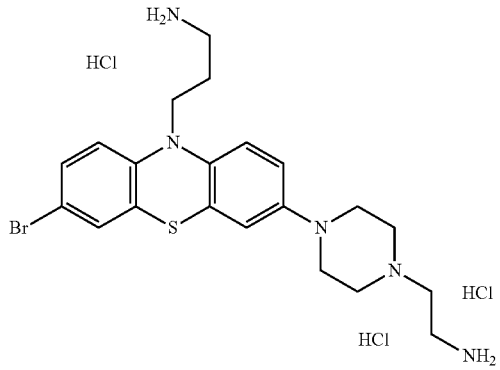 [SMILES: NCCCN1c2ccc(Br)cc2Sc2cc(N3CCN(CCN)CC3)ccc21 ; Cl ; Cl ; Cl] | 3-(3-(4-(2-aminoethyl)piperazin-1-yl)-7-bromo-10H-phenothiazin-10-yl)propan-1-amine hydrochloride | 569.05 | 462.1 | IV |
| 279 | 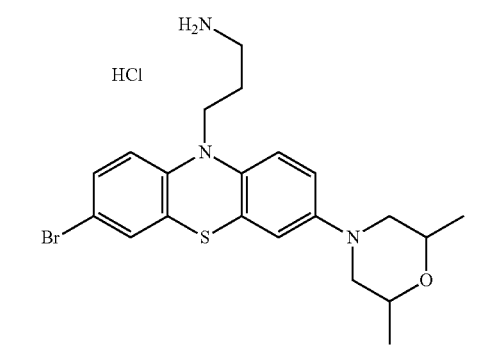 | 3-(3-bromo-7-(2,6-dimethyl-morpholino)-10H-phenothiazin-10-yl)propan-1-amine hydrochloride | 483.07 | 449.1 | IV |
| 280 | 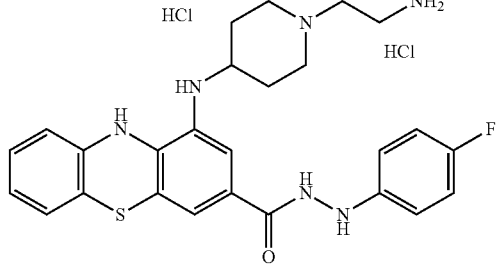 | 1-((1-(2-aminoethyl)piperidin-4-yl)amino)-N'-(4-fluorophenyl)-10H-phenothiazine-3-carbohydrazide hydrochloride | 564.16 | 493.2 | XXVII |
| 281 | 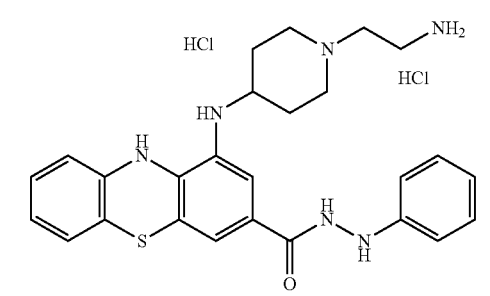 [SMILES: NCCN1CCC(Nc2cc(C(=O)NNc3ccccc3)cc3c2Nc2ccccc2S3)CC1 ; Cl ; Cl] | 1-((1-(2-aminoethyl)piperidin-4-yl)amino)-N'-phenyl-10H-phenothiazine-3-carbohydrazide hydrochloride | 546.17 | 475.2 | XXVII |
| 282 | 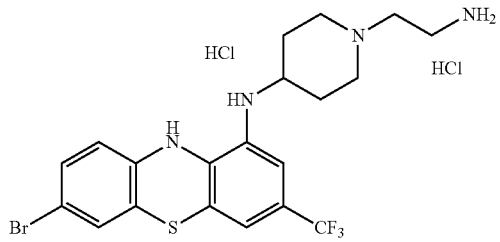 [SMILES: NCCN1CCC(Nc2cc(C(F)(F)F)cc3c2Nc2ccc(Br)cc2S3)CC1 ; Cl ; Cl] | N-(1-(2-aminoethyl)piperidin-4-yl)-7-bromo-3-(trifluoromethyl)-10H-phenothiazin-1-amine hydrochloride | 558.02 | 488.1 | XXIII |

TABLE 13-continued

| Cmpd # | Structure | Name | Exact mass | LC-MS [M + H]+ (m/z) | Synthetic (Scheme no.) |
|---|---|---|---|---|---|
| 283 | 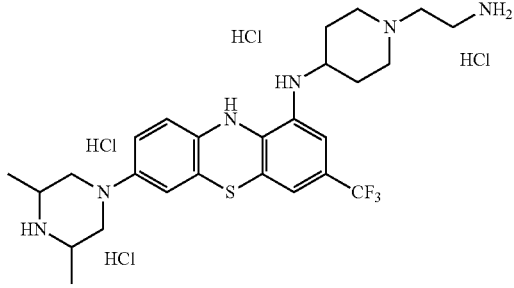 [SMILES: CC1CN(c2ccc3c(c2)Sc2cc(C(F)(F)F)cc(NC4CCN(CCN)CC4)c2N3)CC(C)N1 ; Cl ; Cl ; Cl ; Cl] | N-(1-(2-aminoethyl)piperidin-4-yl)-7-(3,5-dimethyl-piperazin-1-yl)-3-(trifluoromethyl)10H-phenothiazin-1-amine hydrochloride | 664.17 | 521.2 | XXIII |
| 284 | 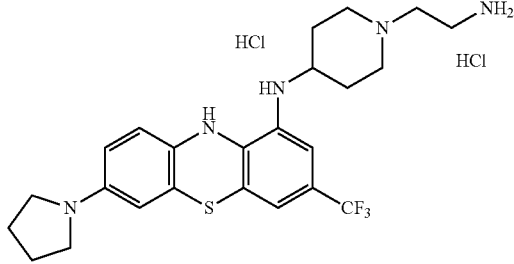 [SMILES: NCCN1CCC(Nc2cc(C(F)(F)F)cc3c2Nc2ccc(N4CCCC4)cc2S3)CC1 ; Cl ; Cl] | N-(1-(2-aminoethyl)piperidin-4-yl)-7-(pyrrolidin-1-yl)-3-(trifluoromethyl)-10H-phenothiazin-1-amine hydrochloride | 549.17 | 478.2 | XXIII |
| 285 | 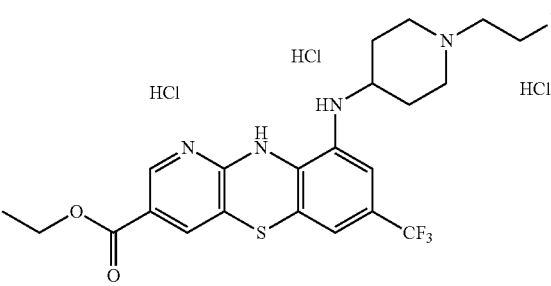 | ethyl 9-((1-(2-aminoethyl)piperidin-4-yl)amino)-7-(trifluoromethyl)-10H-benzo[b]pyrido[2,3-e][1,4]thiazine-3-carboxylate hydrochloride | 589.11 | 482.1 | XXIX |
| 286 | 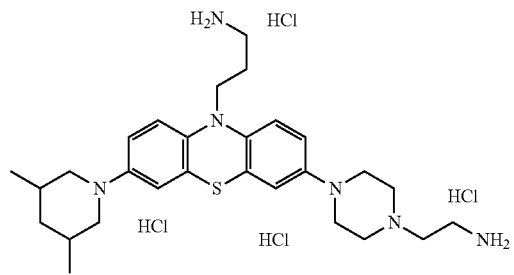 [SMILES: CC1CC(C)CN(c2ccc3c(c2)Sc2cc(N4CCN(CCN)CC4)ccc2N3CCCN)C1 ; Cl ; Cl ; Cl ; Cl] | 3-(3-(4-(2-aminoethyl)piperazin-1-yl)-7-(3,5-dimethyl-piperidin-1-yl)-10H-phenothiazin-10-yl)propan-1-amine hydrochloride | 638.23 | 495.4 | XV |
| 287 | 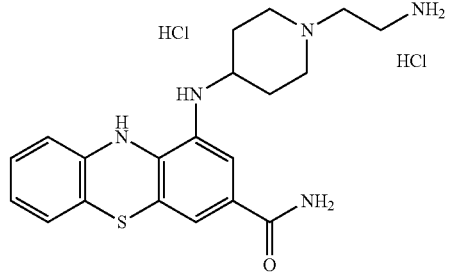 [SMILES: NCCN1CCC(Nc2cc(C(N)=O)cc3c2Nc2ccccc2S3)CC1 ; Cl ; Cl] | 1-((1-(2-aminoethyl)piperidin-4-yl)amino)-10H-phenothiazine-3-carboxamide hydrochloride | 455.13 | 384.2 | XXVII |

TABLE 13-continued

| Cmpd # | Structure | Name | Exact mass | LC-MS [M + H]+ (m/z) | Synthetic (Scheme no.) |
|---|---|---|---|---|---|
| 288 | 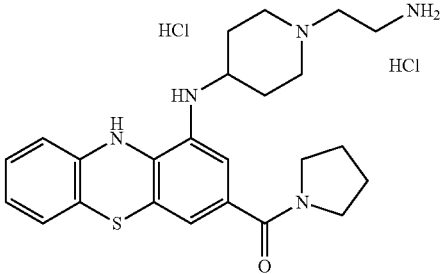 [SMILES: NCCN1CCC(Nc2cc(C(=O)N3CCCC3)cc3c2Nc2ccccc2S3)CC1 ; Cl ; Cl] | (1-((1-(2-aminoethyl)piperidin-4-yl)amino)-10H-phenothiazin-3-yl)(pyrrolidin-1-yl)methanone hydrochloride | 509.18 | 438.2 | XXVII |
| 289 | 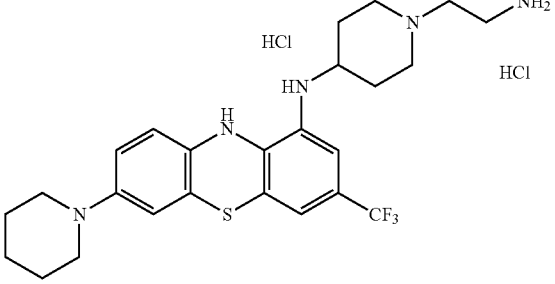 | N-(1-(2-aminoethyl)piperidin-4-yl)-7-(piperidin-1-yl)-3-(trifluoromethyl)-10H-phenothiazin-1-amine hydrochloride | 563.19 | 490.2 | XXIII |
| 290 | 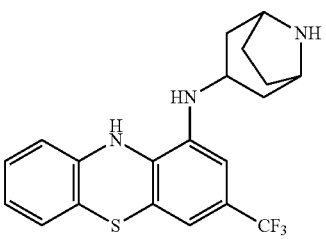 | N-(8-azabicyclo[3.2.1]octan-3-yl)-3-(trifluoromethyl)-10H-phenothiazin-1-amine | 391.13 | 392.2 | XXIII |
| 291 | 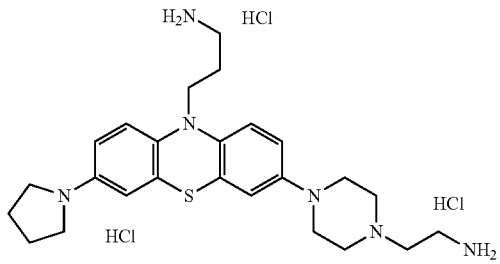 [SMILES: NCCCN1c2ccc(N3CCCC3)cc2Sc2cc(N3CCN(CCN)CC3)ccc21 ; Cl ; Cl ; Cl] | 3-(3-(4-(2-aminoethyl)piperazin-1-yl)-7-(pyrrolidin-1-yl)-10H-phenothiazin-10-yl)propan-1-amine hydrochloride | 560.2 | 451.3 | XV |
| 292 | 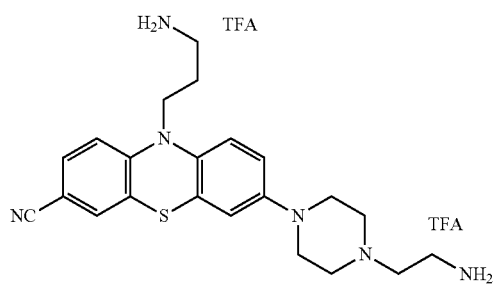 [SMILES: N#Cc1ccc2c(c1)Sc1cc(N3CCN(CCN)CC3)ccc1N2CCCN ; "TFA" ; "TFA"] | 7-(4-(2-aminoethyl)piperazin-1-yl)-10-(3-aminopropyl)-10H-phenothiazine-3-carbonitrile trifluoro acetic acid | 636.2 | 409.3 | XV |

TABLE 13-continued

| Cmpd # | Structure | Name | Exact mass | LC-MS [M + H]+ (m/z) | Synthetic (Scheme no.) |
|---|---|---|---|---|---|
| 293 | 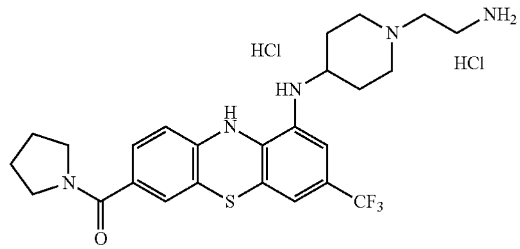 [SMILES: NCCN1CCC(Nc2cc(C(F)(F)F)cc3c2Nc2ccc(C(=O)N4CCCC4)cc2S3)CC1 ; Cl ; Cl] | (9-((1-(2-aminoethyl)piperidin-4-yl)amino)-7-(trifluoromethyl)-10H-phenothiazin-3-yl)(pyrrolidin-1-yl)methanone hydrochloride | 577.17 | 506.2 | XXVIII |
| 294 | 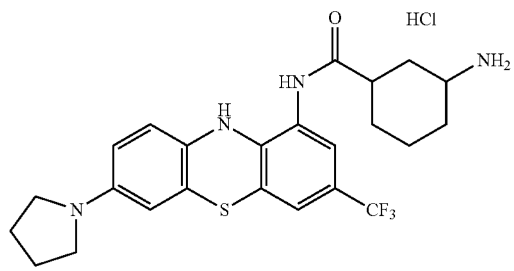 [SMILES: NC1CCCC(C(=O)Nc2cc(C(F)(F)F)cc3c2Nc2ccc(N4CCCC4)cc2S3)C1 ; Cl] | 3-amino-N-(7-(pyrrolidin-1-yl)-3-(trifluoromethyl)-10H-phenothiazin-1-yl)cyclohexane-1-carboxamide hydrochloride | 512.16 | 477.2 | XXV |
| 295 | 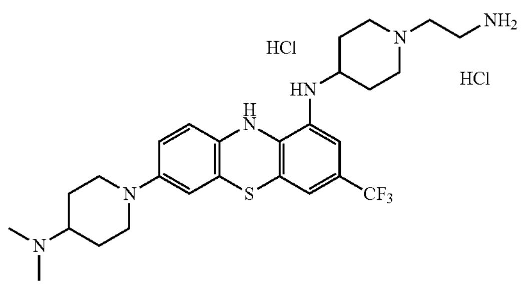 [SMILES: CN(C)C1CCN(c2ccc3c(c2)Sc2cc(C(F)(F)F)cc(NC4CCN(CCN)CC4)c2N3)CC1 ; Cl ; Cl] | N-(1-(2-aminoethyl)piperidin-4-yl)-7-(4-(dimethylamino)piperidin-1-yl)-3-(trifluoromethyl)-10H-phenothiazin-1-amine hydrochloride | 606.23 | 535.2 | XXIII |
| 296 | 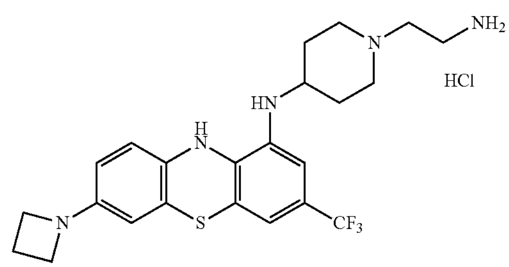 [SMILES: NCCN1CCC(Nc2cc(C(F)(F)F)cc3c2Nc2ccc(N4CCC4)cc2S3)CC1 ; Cl] | N-(1-(2-aminoethyl)piperidin-4-yl)-7-(azetidin-1-yl)-3-(trifluoromethyl)-10H-phenothiazin-1-amine hydrochloride | 499.18 | 502.2 | XXIII |
| 297 | 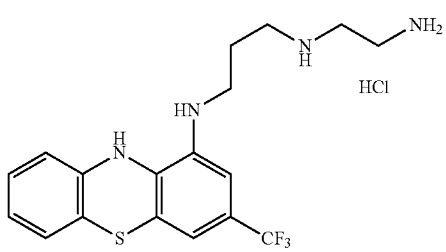 [SMILES: NCCNCCCNc1cc(C(F)(F)F)cc2c1Nc1ccccc1S2 ; Cl] | N1-(2-aminoethyl)-N3-(3-(trifluoromethyl)-10H-phenothiazin-1-yl)propane-1,3-diamine hydrochloride | 418.12 | 383.22 | XXVI |
| 298 | 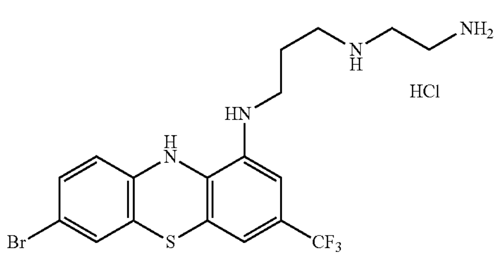 [SMILES: NCCNCCCNc1cc(C(F)(F)F)cc2c1Nc1ccc(Br)cc1S2 ; Cl] | N1-(2-aminoethyl)-N3-(7-bromo-3-(trifluoromethyl)-10H-phenothiazin-1-yl)propane-1,3-diamine hydrochloride | 496.03 | 461.20 | XXVI |

TABLE 13-continued

| Cmpd # | Structure | Name | Exact mass | LC-MS [M + H]+ (m/z) | Synthetic (Scheme no.) |
|---|---|---|---|---|---|
| 299 | 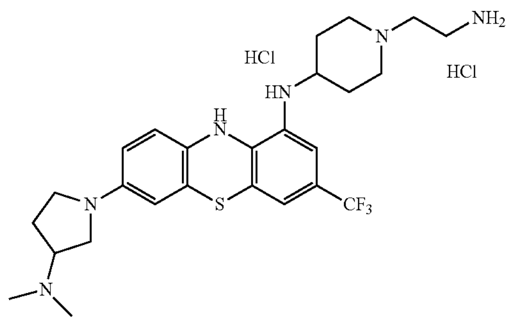 [SMILES: CN(C)C1CCN(c2ccc3c(c2)Sc2cc(C(F)(F)F)cc(NC4CCN(CCN)CC4)c2N3)C1 ; Cl ; Cl] | N-(1-(2-aminoethyl)piperidin-4-yl)-7-(3-(dimethylamino)pyrrolidin-1-yl)-3-(trifluoromethyl)-10H-phenothiazin-1-amine hydrochloride | 592.21 | 521.22 | XXIII |
| 300 | 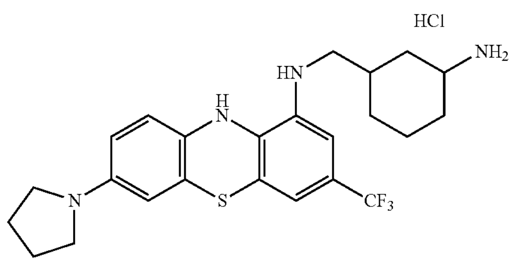 [SMILES: Cl ; NC1CCCC(CNc2cc(C(F)(F)F)cc3c2Nc2ccc(N4CCCC4)cc2S3)C1] | N-((3-aminocyclohexyl)methyl)-7-(pyrrolidin-1-yl)-3-(trifluoromethyl)-10H-phenothiazin-1-amine hydrochloride | 498.18 | 463.1 | XXV |
| 301 | 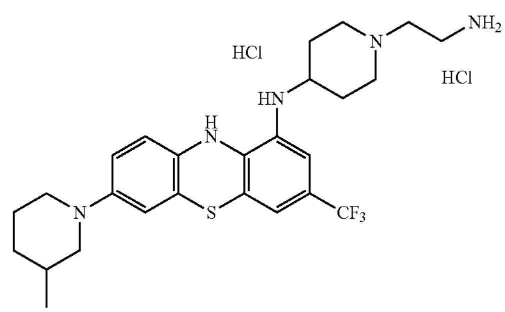 [SMILES: CC1CCCN(c2ccc3c(c2)Sc2cc(C(F)(F)F)cc(NC4CCN(CCN)CC4)c2N3)C1 ; Cl ; Cl] | N-(1-(2-aminoethyl)piperidin-4-yl)-7-(3-methylpiperidin-1-yl)-3-(trifluoromethyl)-10H-phenothiazin-1-amine hydrochloride | 577.2 | 506.2 | XXIII |
| 302 | 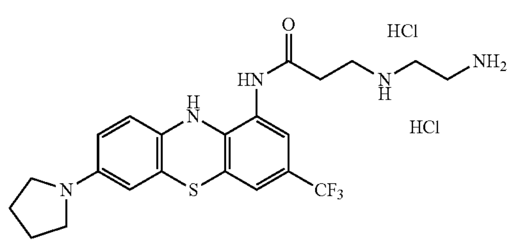 [SMILES: NCCNCCC(=O)Nc1cc(C(F)(F)F)cc2c1Nc1ccc(N3CCCC3)cc1S2 ; Cl ; Cl] | 3-((2-aminoethyl)amino)-N-(7-(pyrrolidin-1-yl)-3-(trifluoromethyl)-10H-phenothiazin-1-yl)propanamide hydrochloride | 537.13 | 466.38 | XXVII |
| 303 | 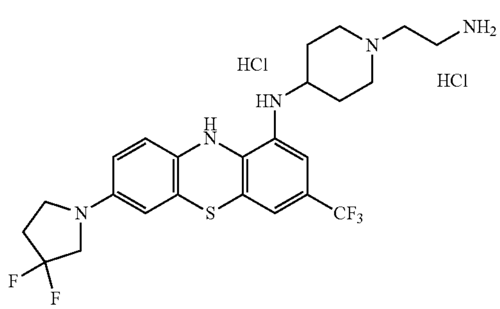 [SMILES: NCCN1CCC(Nc2cc(C(F)(F)F)cc3c2Nc2ccc(N4CCC(F)(F)C4)cc2S3)CC1 ; Cl ; Cl] | N-(1-(2-aminoethyl)piperidin-4-yl)-7-(3,3-difluoropyrrolidin-1-yl)-3-(trifluoromethyl)-10H-phenothiazin-1-amine hydrochloride | 585.15 | 514.4 | XXIII |

TABLE 13-continued

| Cmpd # | Structure | Name | Exact mass | LC-MS [M + H]+ (m/z) | Synthetic (Scheme no.) |
|---|---|---|---|---|---|
| 304 | 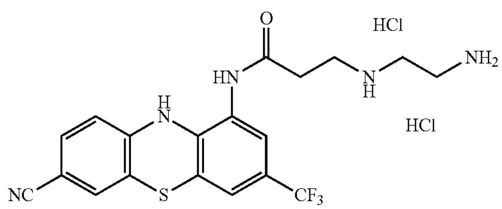 [SMILES: N#Cc1ccc2c(c1)Sc1cc(C(F)(F)F)cc(NC(=O)CCNCCN)c1N2 ; Cl ; Cl] | 3-((2-aminoethyl)amino)-N-(7-cyano-3-(trifluoromethyl)-10H-phenothiazin-1-yl)propanamide hydrochloride | 493.07 | 422.32 | XXVII |
| 305 | 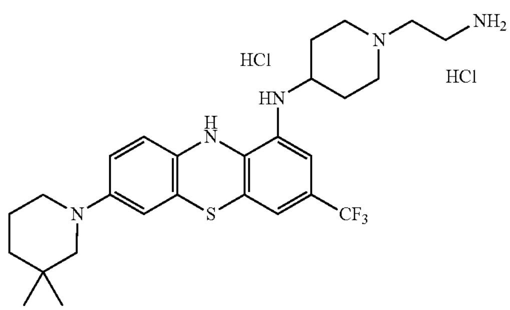 [SMILES: CC1(C)CCCN(c2ccc3c(c2)Sc2cc(C(F)(F)F)cc(NC4CCN(CCN)CC4)c2N3)C1 ; Cl ; Cl] | N-(1-(2-aminoethyl)piperidin-4-yl)-7-(3,3-dimethyl-piperidin-1-yl)-3-(trifluoromethyl)-10H-phenothiazin-1-amine hydrochloride | 591.22 | 520.3 | XXIII |
| 306 | 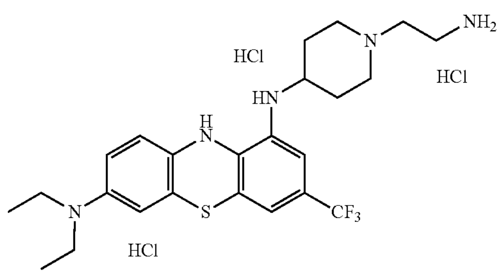 [SMILES: CCN(CC)c1ccc2c(c1)Sc1cc(C(F)(F)F)cc(NC3CCN(CCN)CC3)c1N2 ; Cl ; Cl ; Cl] | N1-(1-(2-aminoethyl)piperidin-4-yl)-N7,N7-diethyl-3-(trifluoromethyl)-10H-phenothiazine-1,7-diamine hydrochloride | 587.16 | 480.2 | XXIII |
| 307 | 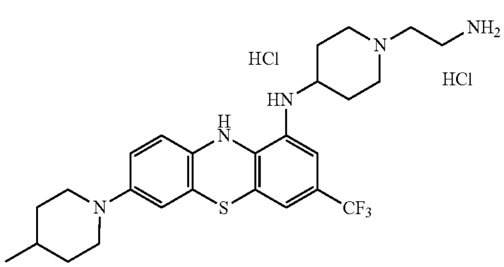 [SMILES: CC1CCN(c2ccc3c(c2)Sc2cc(C(F)(F)F)cc(NC4CCN(CCN)CC4)c2N3)CC1 ; Cl ; Cl] | N-(1-(2-aminoethyl)piperidin-4-yl)-7-(4-methyl-piperidin-1-yl)-3-(trifluoromethyl)-10H-phenothiazin-1-amine hydrochloride | 577.20 | 506.3 | XXIII |
| 308 | 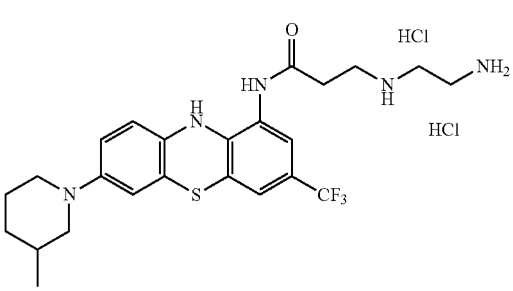 [SMILES: CC1CCCN(c2ccc3c(c2)Sc2cc(C(F)(F)F)cc(NC(=O)CCNCCN)c2N3)C1 ; Cl ; Cl] | 3-((2-aminoethyl)amino)-N-(7-(3-methyl-piperidin-1-yl)-3-(trifluoromethyl)-10H-phenothiazin-1-yl)propanamide hydrochloride | 565.17 | 494.2 | XXVII |

TABLE 13-continued

| Cmpd # | Structure | Name | Exact mass | LC-MS [M + H]+ (m/z) | Synthetic (Scheme no.) |
|---|---|---|---|---|---|
| 309 | 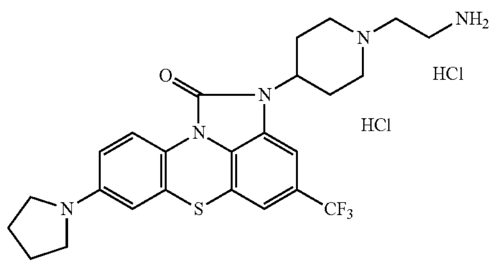 [SMILES: NCCN1CCC(n2c(=O)n3c4c(cc(C(F)(F)F)cc42)Sc2cc(N4CCCC4)ccc2-3)CC1 ; Cl ; Cl] | 2-(1-(2-aminoethyl)piperidin-4-yl)-8-(pyrrolidin-1-yl)-4-(trifluoromethyl)imidazo[4,5,1-kl]phenothiazin-1(2H)-one hydrochloride | 575.15 | 504.43 | XXIII |
| 310 | 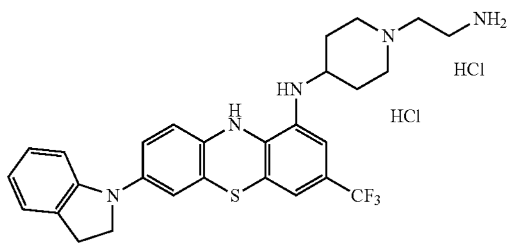 [SMILES: NCCN1CCC(Nc2cc(C(F)(F)F)cc3c2Nc2ccc(N4CCc5ccccc54)cc2S3)CC1 ; Cl ; Cl] | N-(1-(2-aminoethyl)piperidin-4-yl)-7-(indolin-1-yl)-3-(trifluoromethyl)-10H-phenothiazin-1-amine hydrochloride | 597.17 | 526.2 | XXIII |
| 311 | 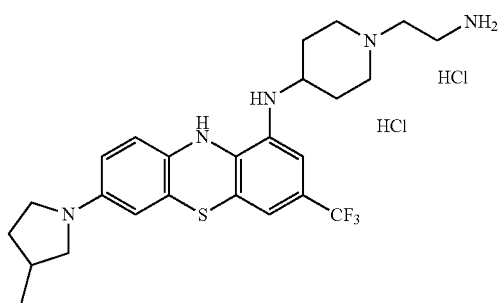 [SMILES: CC1CCN(c2ccc3c(c2)Sc2cc(C(F)(F)F)cc(NC4CCN(CCN)CC4)c2N3)C1 ; Cl ; Cl] | N-(1-(2-aminoethyl)piperidin-4-yl)-7-(3-methyl-pyrrolidin-1-yl)-3-(trifluoromethyl)-10H-phenothiazin-1-amine hydrochloride | 563.19 | 492.22 | XXIII |
| 312 | 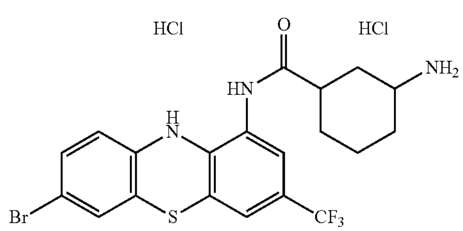 [SMILES: NC1CCCC(C(=O)Nc2cc(C(F)(F)F)cc3c2Nc2ccc(Br)cc2S3)C1 ; Cl ; Cl] | 3-amino-N-(7-bromo-3-(trifluoromethyl)-10H-phenothiazin-1-yl)cyclohexane-1-carboxamide hydrochloride | 556.99 | 488.0 | XXV |
| 313 | 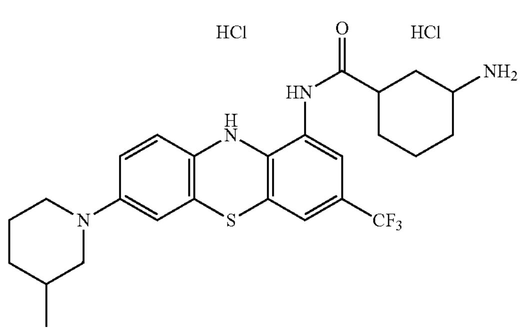 [SMILES: CC1CCCN(c2ccc3c(c2)Sc2cc(C(F)(F)F)cc(NC(=O)C4CCCC(N)C4)c2N3)C1 ; Cl ; Cl] | 3-amino-N-(7-(3-methyl-piperidin-1-yl)-3-(trifluoromethyl)-10H-phenothiazin-1-yl)cyclohexane-1-carboxamide hydrochloride | 576.17 | 505.2 | XXV |

TABLE 13-continued

| Cmpd # | Structure | Name | Exact mass | LC-MS [M + H]+ (m/z) | Synthetic (Scheme no.) |
|---|---|---|---|---|---|
| 314 | 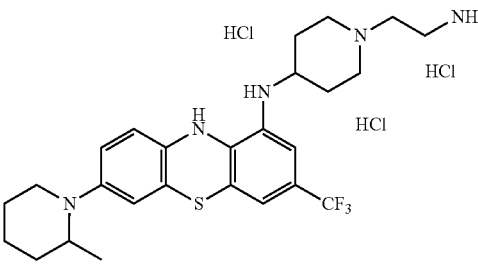 | N-(1-(2-aminoethyl)piperidin-4-yl)-7-(2-methyl-piperidin-1-yl)-3-(trifluoromethyl)-10H-phenothiazin-1-amine hydrochloride | 613.18 | 506.3 | XXIII |
| 315 | 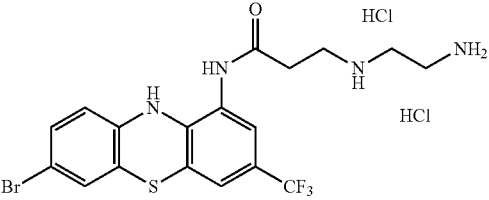 [SMILES: NCCNCCC(=O)Nc1cc(C(F)(F)F)cc2c1Nc1ccc(Br)cc1S2 ; Cl ; Cl] | 3-((2-aminoethyl)amino)-N-(7-bromo-3-(trifluoromethyl)-10H-phenothiazin-1-yl)propanamide hydrochloride | 545.99 | 475.12 | XXVI |
| 316 | 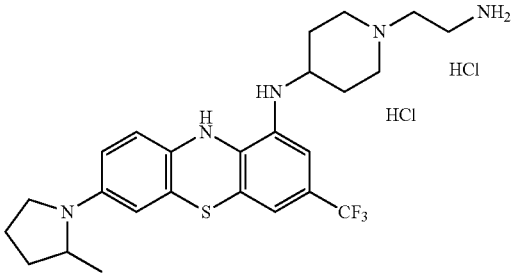 [SMILES: CC1CCCN1c1ccc2c(c1)Sc1cc(C(F)(F)F)cc(NC3CCN(CCN)CC3)c1N2 ; Cl ; Cl] | N-(1-(2-aminoethyl)piperidin-4-yl)-7-(2-methyl-pyrrolidin-1-yl)-3-(trifluoromethyl)-10H-phenothiazin-1-amine hydrochloride | 563.19 | 492.2 | XXIII |
| 317 | 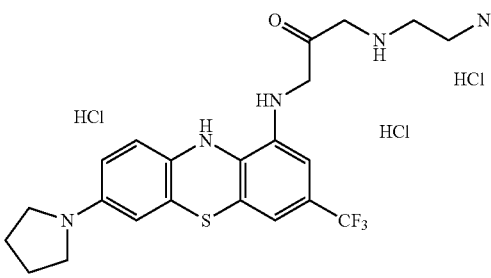 | 1-((2-aminoethyl)amino)-3-((7-(pyrrolidin-1-yl)-3-(trifluoromethyl)-10H-phenothiazin-1-yl)amino)propan-2-one hydrochloride | 573.11 | 468.22 | XXVII |
| 318 | 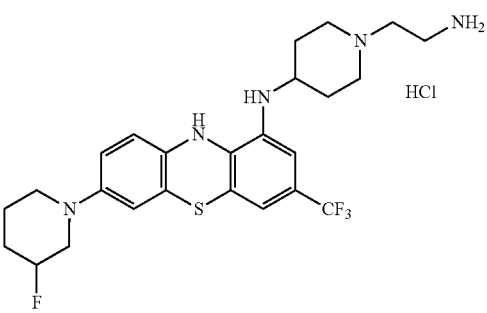 [SMILES: NCCN1CCC(Nc2cc(C(F)(F)F)cc3c2Nc2ccc(N4CCCC(F)C4)cc2S3)CC1 ; Cl] | N-(1-(2-aminoethyl)piperidin-4-yl)-7-(3-fluoro-piperidin-1-yl)-3-(trifluoromethyl)-10H-phenothiazin-1-amine hydrochloride | 545.20 | 510.23 | XXIII |

TABLE 13-continued

| Cmpd # | Structure | Name | Exact mass | LC-MS [M + H]+ (m/z) | Synthetic (Scheme no.) |
|---|---|---|---|---|---|
| 319 | 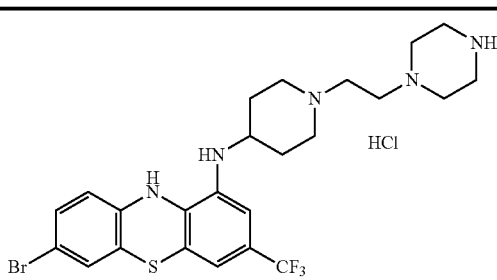 | 7-bromo-N-(1-(2-(piperazin-1-yl)ethyl)piperidin-4-yl)-3-(trifluoromethyl)-10H-phenothiazin-1-amine hydrochloride | 591.10 | 556.17 | XXIII |
| 320 | 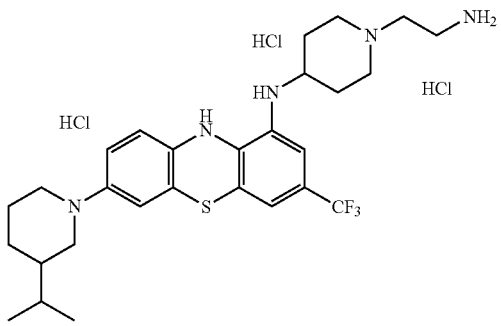 [SMILES: CC(C)C1CCCN(c2ccc3c(c2)Sc2cc(C(F)(F)F)cc(NC4CCN(CCN)CC4)c2N3)C1 ; Cl ; Cl ; Cl] | N-(1-(2-aminoethyl)piperidin-4-yl)-7-(3-isopropyl-piperidin-1-yl)-3-(trifluoromethyl)-10H-phenothiazin-1-amine hydrochloride | 641.21 | 534.28 | XXIII |
| 321 | 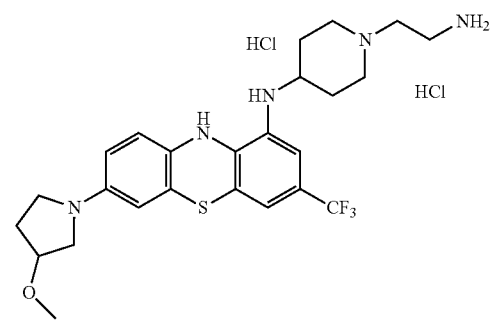 [SMILES: COC1CCN(c2ccc3c(c2)Sc2cc(C(F)(F)F)cc(NC4CCN(CCN)CC4)c2N3)C1 ; Cl ; Cl] | N-(1-(2-aminoethyl)piperidin-4-yl)-7-(3-methoxy-pyrrolidin-1-yl)-3-(trifluoromethyl)-10H-phenothiazin-1-amine hydrochloride | 579.18 | 508.21 | XXIII |
| 322 | 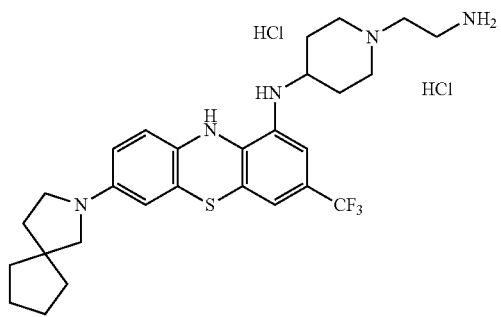 [SMILES: NCCN1CCC(Nc2cc(C(F)(F)F)cc3c2Nc2ccc(N4CCC5(CCCC5)C4)cc2S3)CC1 ; Cl ; Cl] | N-(1-(2-aminoethyl)piperidin-4-yl)-7-(2-azaspiro[4.4]nonan-2-yl)-3-(trifluoromethyl)-10H-phenothiazin-1-amine hydrochloride | 603.22 | 557.22 | XXIII |
| 323 | 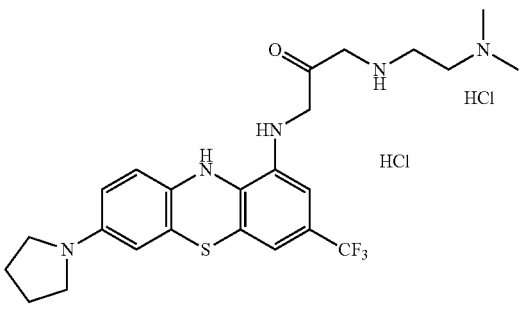 [SMILES: CN(C)CCNCC(=O)CNc1cc(C(F)(F)F)cc2c1Nc1ccc(N3CCCC3)cc1S2 ; Cl ; Cl] | 1-((2-(dimethyl-amino)ethyl)amino)-3-((7-(pyrrolidin-1-yl)-3-(trifluoromethyl)-10H-phenothiazin-1-yl)amino)propan-2-one hydrochloride | 565.15 | 494.21 | XXVII |

TABLE 13-continued

| Cmpd # | Structure | Name | Exact mass | LC-MS [M + H]+ (m/z) | Synthetic (Scheme no.) |
|---|---|---|---|---|---|
| 324 | 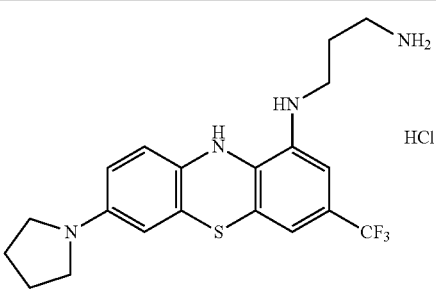 [SMILES: NCCCNc1cc(C(F)(F)F)cc2c1Nc1ccc(N3CCCC3)cc1S2 ; Cl] | N1-(7-(pyrrolidin-1-yl)-3-(trifluoromethyl)-10H-phenothiazin-1-yl)propane-1,3-diamine hydrochloride | 444.14 | 409.12 | XXIII |
| 325 | 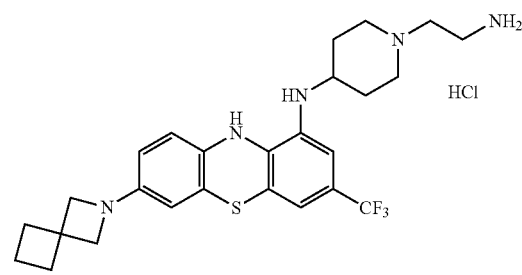 [SMILES: NCCN1CCC(Nc2cc(C(F)(F)F)cc3c2Nc2ccc(N4CC5(CCC5)C4)cc2S3)CC1 ; Cl] | N-(1-(2-aminoethyl)piperidin-4-yl)-7-(2-azaspiro[3.3]heptan-2-yl)-3-(trifluoromethyl)-10H-phenothiazin-1-amine hydrochloride | 539.21 | 504.2 | XXIII |
| 326 | 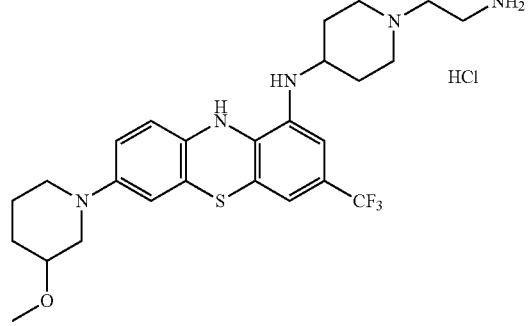 | N-(1-(2-aminoethyl)piperidin-4-yl)-7-(3-methoxy-piperidin-1-yl)-3-(trifluoromethyl)-10H-phenothiazin-1-amine hydrochloride | 557.22 | 422.2 | XXIII |
| 327 | 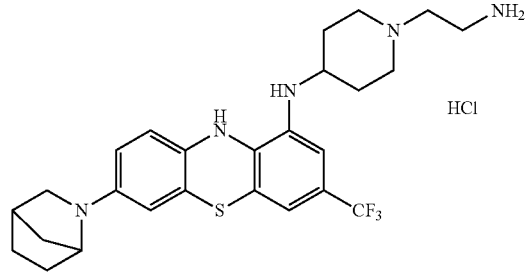 [SMILES: NCCN1CCC(Nc2cc(C(F)(F)F)cc3c2Nc2ccc(N4CC5CCC4C5)cc2S3)CC1 ; Cl] | N-(1-(2-aminoethyl)piperidin-4-yl)-7-(2-azabicyclo[2.2.1]heptan-2-yl)-3-(trifluoromethyl)-10H-phenothiazin-1-amine hydrochloride | 539.21 | 504.2 | XXIII |
| 328 | 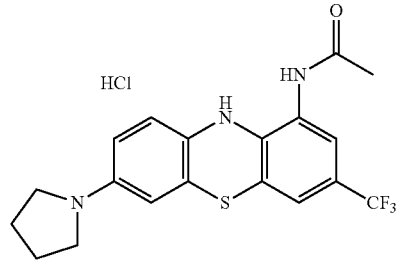 [SMILES: CC(=O)Nc1cc(C(F)(F)F)cc2c1Nc1ccc(N3CCCC3)cc1S2 ; Cl] | N-(7-(pyrrolidin-1-yl)-3-(trifluoromethyl)-10H-phenothiazin-1-yl)acetamide hydrochloride | 429.09 | 394.2 | XXVII |

TABLE 13-continued

| Cmpd # | Structure | Name | Exact mass | LC-MS [M + H]+ (m/z) | Synthetic (Scheme no.) |
|---|---|---|---|---|---|
| 329 | 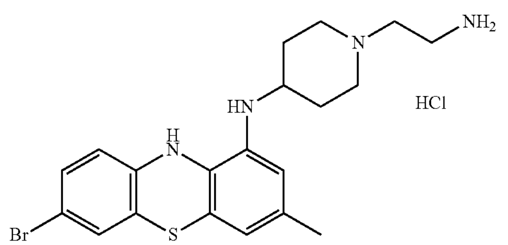 [SMILES: Cc1cc(NC2CCN(CCN)CC2)c2c(c1)Sc1cc(Br)ccc1N2 ; Cl] | N-(1-(2-aminoethyl)piperidin-4-yl)-7-bromo-3-methyl-10H-phenothiazin-1-amine hydrochloride | 468.08 | 433.15 | XXIII |
| 330 | 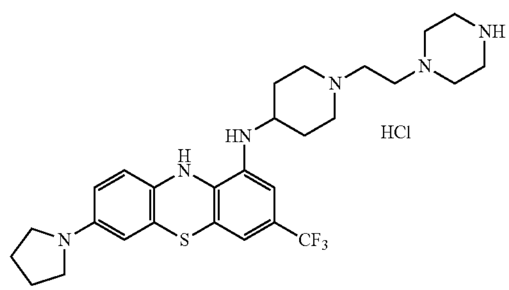 [SMILES: FC(F)(F)c1cc(NC2CCN(CCN3CCNCC3)CC2)c2c(c1)Sc1cc(N3CCCC3)ccc1N2 ; Cl] | N-(1-(2-(piperazin-1-yl)ethyl)piperidin-4-yl)-7-(pyrrolidin-1-yl)-3-(trifluoromethyl)-10H-phenothiazin-1-amine hydrochloride | 582.25 | 545.2 | XXIII |
| 331 | 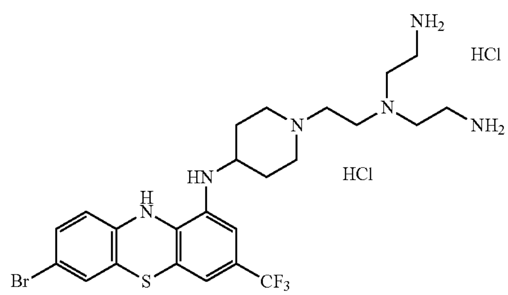 [SMILES: NCCN(CCN)CCN1CCC(Nc2cc(C(F)(F)F)cc3c2Nc2ccc(Br)cc2S3)CC1 ; Cl ; Cl] | N1-(2-aminoethyl)-N1-(2-(4-((7-bromo-3-(trifluoromethyl)-10H-phenothiazin-1-yl)amino)piperidin-1-yl)ethyl)ethane-1,2-diamine hydrochloride | 644.11 | 573.26 | XXIV |
| 332 | 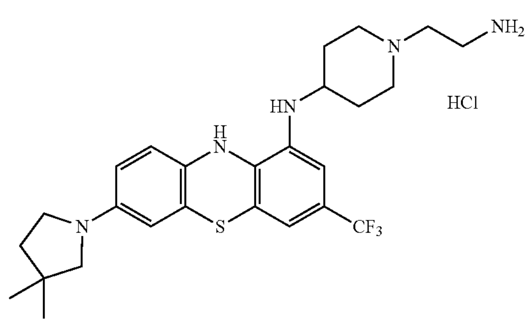 [SMILES: CC1(C)CCN(c2ccc3c(c2)Sc2cc(C(F)(F)F)cc(NC4CCN(CCN)CC4)c2N3)C1 ; Cl] | N-(1-(2-aminoethyl)piperidin-4-yl)-7-(3,3-dimethylpyrrolidin-1-yl)-3-(trifluoromethyl)-10H-phenothiazin-1-amine hydrochloride | 541.23 | 506.27 | XXIII |
| 333 | 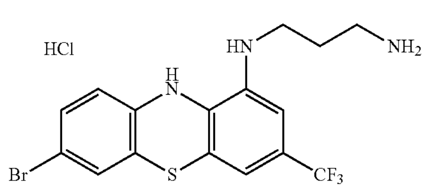 [SMILES: NCCCNc1cc(C(F)(F)F)cc2c1Nc1ccc(Br)cc1S2 ; Cl] | N1-(7-bromo-3-(trifluoromethyl)-10H-phenothiazin-1-yl)propane-1,3-diamine hydrochloride | 452.99 | 417.9 | XXIII |

TABLE 13-continued

| Cmpd # | Structure | Name | Exact mass | LC-MS [M + H]+ (m/z) | Synthetic (Scheme no.) |
|---|---|---|---|---|---|
| 334 | 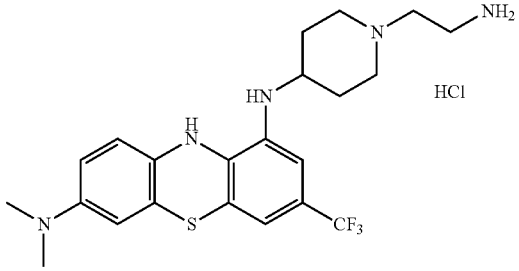 [SMILES: CN(C)c1ccc2c(c1)Sc1cc(C(F)(F)F)cc(NC3CCN(CCN)CC3)c1N2 ; Cl] | N1-(7-bromo-3-(trifluoromethyl)-10H-phenothiazin-1-yl)propane-1,3-diamine hydrochloride | 487.18 | 452.2 | XXIII |
| 335 | 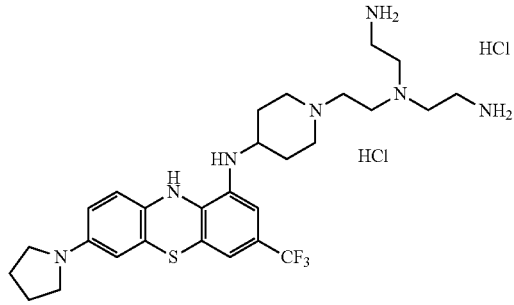 [SMILES: NCCN(CCN)CCN1CCC(Nc2cc(C(F)(F)F)cc3c2Nc2ccc(N4CCCC4)cc2S3)CC1 ; Cl ; Cl] | N1-(2-aminoethyl)-N1-(2-(4-((7-(pyrrolidin-1-yl)-3-(trifluoromethyl)-10H-phenothiazin-1-yl)amino) piperidin-1-yl) ethyl)ethane-1,2-diamine hydrochloride | 635.26 | 564.3 | XXIV |
| 336 | 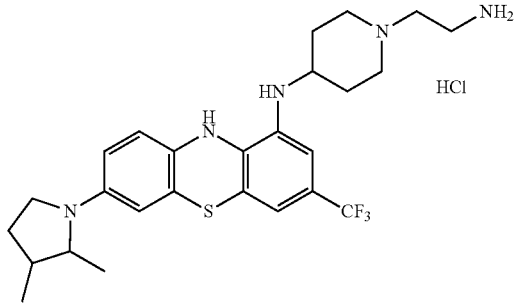 [SMILES: CC1CCN(c2ccc3c(c2)Sc2cc(C(F)(F)F)cc(NC4CCN(CCN)CC4)c2N3)C1C ; Cl] | N-(1-(2-aminoethyl) piperidin-4-yl)-7-(2,3-dimethyl-pyrrolidin-1-yl)-3-(trifluoromethyl)-10H-phenothiazin-1-amine hydrochloride | 541.23 | 506.31 | XXIII |
| 337 | 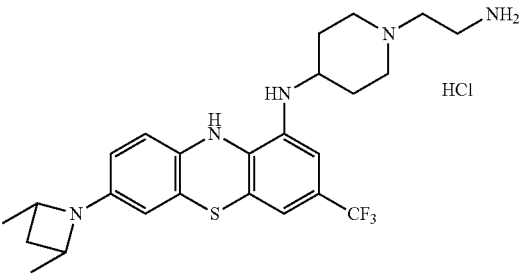 [SMILES: CC1CC(C)N1c1ccc2c(c1)Sc1cc(C(F)(F)F)cc(NC3CCN(CCN)CC3)c1N2 ; Cl] | N-(1-(2-aminoethyl) piperidin-4-yl)-7-(2,4-dimethyl-azetidin-1-yl)-3-(trifluoromethyl)-10H-phenothiazin-1-amine hydrochloride | 527.17 | 491.97 | XXIII |
| 338 | 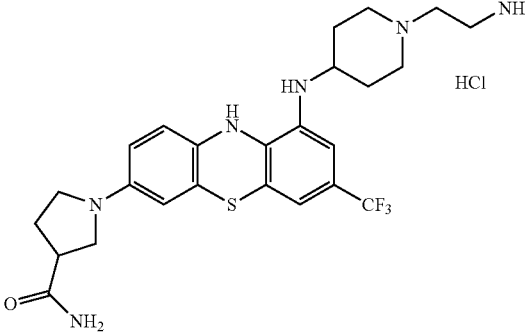 | 1-(9-((1-(2-aminoethyl) piperidin-4-yl) amino)-7-(trifluoromethyl)-10H-phenothiazin-3-yl)pyrrolidine-3-carboxamide hydrochloride | 556.20 | 521.2 | XXIII |

TABLE 13-continued

| Cmpd # | Structure | Name | Exact mass | LC-MS [M + H]+ (m/z) | Synthetic (Scheme no.) |
|---|---|---|---|---|---|
| 339 | 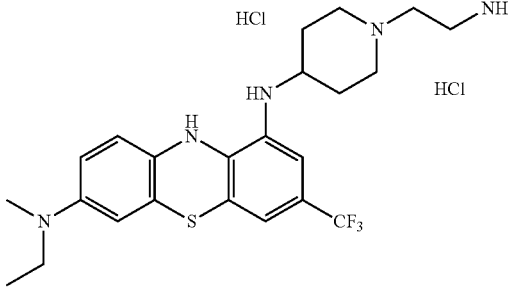 | N1-(1-(2-aminoethyl)piperidin-4-yl)-N7-ethyl-N7-methyl-3-(trifluoromethyl)-10H-phenothiazine-1,7-diamine hydrochloride | 537.17 | 466.1 | XXIII |
| 340 | 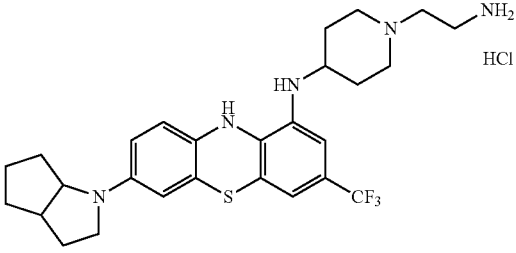 [SMILES: NCCN1CCC(Nc2cc(C(F)(F)F)cc3c2Nc2ccc(N4CCC5CCCC54)cc2S3)CC1 ; Cl] | N-(1-(2-aminoethyl)piperidin-4-yl)-7-(hexahydrocyclopenta[b]pyrrol-1(2H)-yl)-3-(trifluoromethyl)-10H-phenothiazin-1-amine hydrochloride | 553.23 | 516.3 | XXIII |
| 341 | 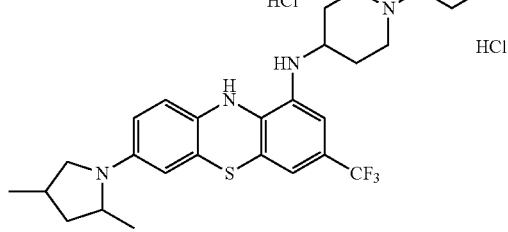 | N-(1-(2-aminoethyl)piperidin-4-yl)-7-(2,4-dimethylpyrrolidin-1-yl)-3-(trifluoromethyl)-10H-phenothiazin-1-amine hydrochloride | 577.2 | 506.2 | XXIII |
| 342 | 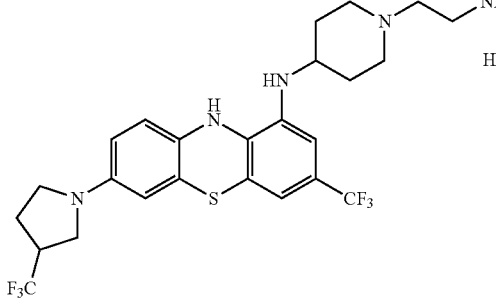 | N-(1-(2-aminoethyl)piperidin-4-yl)-3-methyl-7-(3-(trifluoromethyl)pyrrolidin-1-yl)-10H-phenothiazin-1-amine hydrochloride | 527.21 | 544.1 | XXIII |
| 343 | 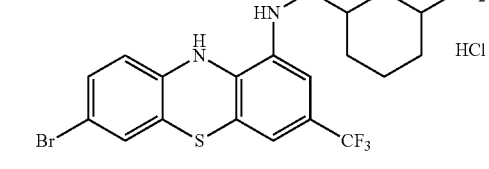 | N-((3-aminocyclohexyl)methyl)-7-bromo-3-(trifluoromethyl)-10H-phenothiazin-1-amine hydrochloride | 507.04 | 471.98 | XXXIII |
| 344 | 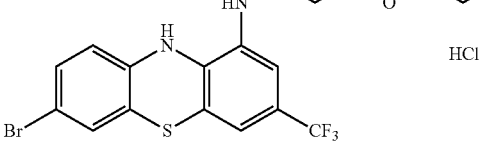 | N-(3-(2-aminoethoxy)propyl)-7-bromo-3-(trifluoromethyl)-10H-phenothiazin-1-amine hydrochloride | 497.02 | 462.0 | XXXII |

TABLE 13-continued

| Cmpd # | Structure | Name | Exact mass | LC-MS [M + H]+ (m/z) | Synthetic (Scheme no.) |
|---|---|---|---|---|---|
| 345 | 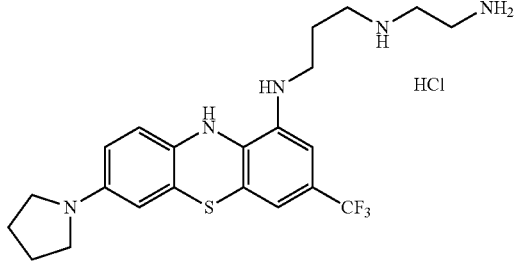 [SMILES: NCCNCCCNc1cc(C(F)(F)F)cc2c1Nc1ccc(N3CCCC3)cc1S2 ; Cl] | N1-(2-aminoethyl)-N3-(7-(pyrrolidin-1-yl)-3-(trifluoromethyl)-10H-phenothiazin-1-yl)propane-1,3-diamine hydrochloride | 487.18 | 452.16 | XXXI |
| 346 | 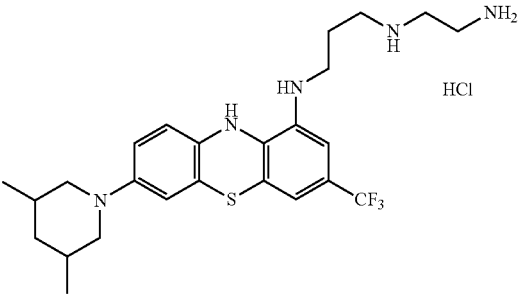 [SMILES: CC1CC(C)CN(c2ccc3c(c2)Sc2cc(C(F)(F)F)cc(NCCCNCCN)c2N3)C1 ; Cl] | N1-(2-aminoethyl)-N3-(7-(3,5-dimethyl-piperidin-1-yl)-3-(trifluoromethyl)-10H-phenothiazin-1-yl)propane-1,3-diamine hydrochloride | 529.13 | 494.23 | XXXI |
| 347 | 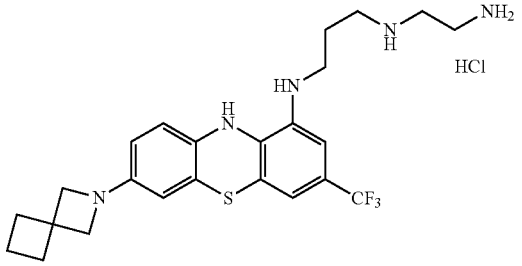 [SMILES: NCCNCCCNc1cc(C(F)(F)F)cc2c1Nc1ccc(N3CC4(CCC4)C3)cc1S2 ; Cl] | N1-(7-(2-azaspiro[3.3]heptan-2-yl)-3-(trifluoromethyl)-10H-phenothiazin-1-yl)-N3-(2-aminoethyl)propane-1,3-diamine hydrochloride | 513.19 | 476.23 | XXXI |
| 348 | 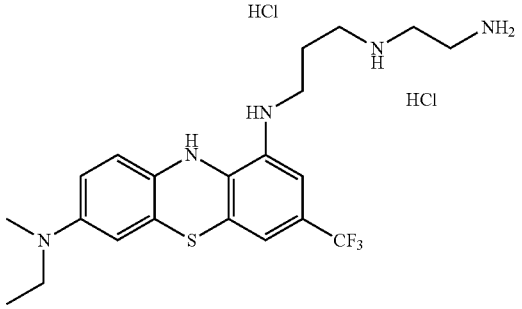 [SMILES: Cl ; CCN(C)c1ccc2c(c1)Sc1cc(C(F)(F)F)cc(NCCCNCCN)c1N2 ; Cl] | N1-(3-((2-aminoethyl)amino)propyl)-N7-ethyl-N7-methyl-3-(trifluoromethyl)-10H-phenothiazine-1,7-diamine hydrochloride | 511.16 | 440.18 | XXXI |
| 349 | 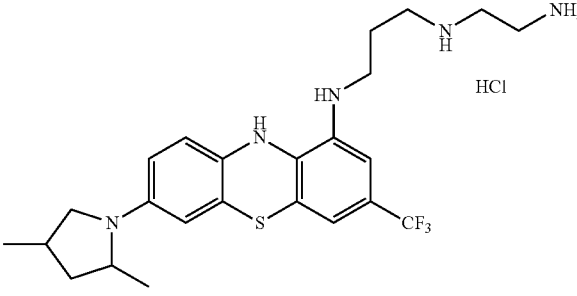 | N1-(2-aminoethyl)-N3-(7-(2,4-dimethyl-pyrrolidin-1-yl)-3-(trifluoromethyl)-10H-phenothiazin-1-yl)propane-1,3-diamine hydrochloride | 515.21 | 480.24 | XXXI |

TABLE 13-continued

| Cmpd # | Structure | Name | Exact mass | LC-MS [M + H]+ (m/z) | Synthetic (Scheme no.) |
|---|---|---|---|---|---|
| 350 | 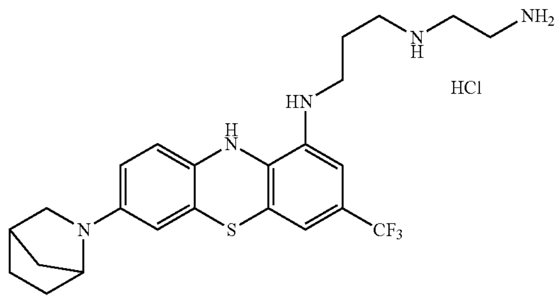 [SMILES: NCCNCCCNc1cc(C(F)(F)F)cc2c1Nc1ccc(N3CC4CCC3C4)cc1S2 ; Cl] | N1-(7-(2-azabicyclo[2.2.1]heptan-2-yl)-3-(trifluoromethyl)-10H-phenothiazin-1-yl)-N3-(2-aminoethyl)propane-1,3-diamine hydrochloride | 513.19 | 478.23 | XXXI |
| 351 | 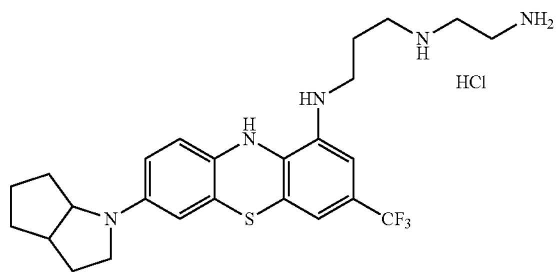 [SMILES: NCCNCCCNc1cc(C(F)(F)F)cc2c1Nc1ccc(N3CCC4CCCC43)cc1S2 ; Cl] | N1-(2-aminoethyl)-N3-(7-(hexahydrocyclopenta[b]pyrrol-1(2H)-yl)-3-(trifluoromethyl)-10H-phenothiazin-1-yl)propane-1,3-diamine hydrochloride | 527.21 | 492.22 | XXXI |
| 352 | 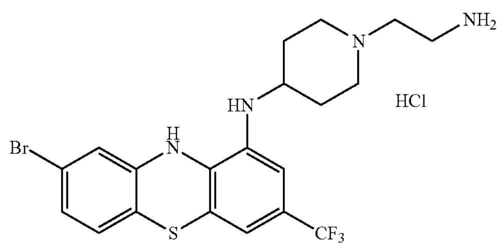 [SMILES: NCCN1CCC(Nc2cc(C(F)(F)F)cc3c2Nc2cc(Br)ccc2S3)CC1 ; Cl] | N-(1-(2-aminoethyl)piperidin-4-yl)-8-bromo-3-(trifluoromethyl)-10H-phenothiazin-1-amine hydrochloride | 522.05 | 487.2 | XXIII |
| 353 | 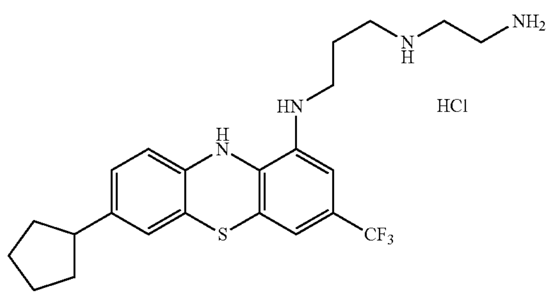 [SMILES: NCCNCCCNc1cc(C(F)(F)F)cc2c1Nc1ccc(C3CCCC3)cc1S2 ; Cl] | N1-(2-aminoethyl)-N3-(7-cyclopentyl-3-(trifluoromethyl)-10H-phenothiazin-1-yl)propane-1,3-diamine hydrochloride | 486.18 | 451.2 | XXXI |
| 354 | 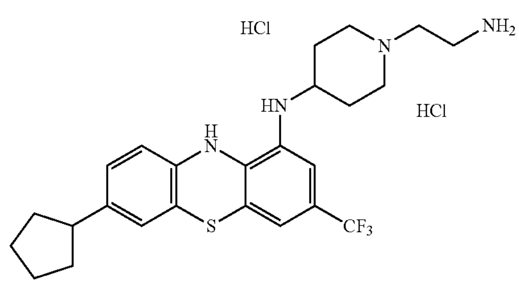 [SMILES: NCCN1CCC(Nc2cc(C(F)(F)F)cc3c2Nc2ccc(C4CCCC4)cc2S3)CC1 ; Cl ; Cl] | N-(1-(2-aminoethyl)piperidin-4-yl)-7-cyclopentyl-3-(trifluoromethyl)-10H-phenothiazin-1-amine hydrochloride | 548.16 | 477.2 | XXIII |

TABLE 13-continued

| Cmpd # | Structure | Name | Exact mass | LC-MS [M + H]+ (m/z) | Synthetic (Scheme no.) |
|---|---|---|---|---|---|
| 355 | 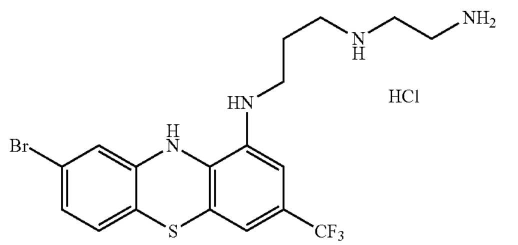 [SMILES: NCCNCCCNc1cc(C(F)(F)F)cc2c1Nc1cc(Br)ccc1S2 ; Cl] | N1-(2-aminoethyl)-N3-(8-bromo-3-(trifluoromethyl)-10H-phenothiazin-1-yl)propane-1,3-diamine hydrochloride | 496.03 | 461.1 | XXXI |
| 356 | 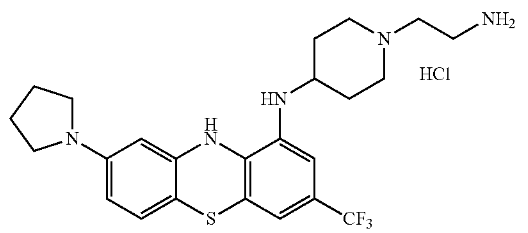 [SMILES: NCCN1CCC(Nc2cc(C(F)(F)F)cc3c2Nc2cc(N4CCCC4)ccc2S3)CC1 ; Cl] | N-(1-(2-aminoethyl)piperidin-4-yl)-8-(pyrrolidin-1-yl)-3-(trifluoromethyl)-10H-phenothiazin-1-amine hydrochloride | 513.19 | 478.24 | XXIII |
| 357 | 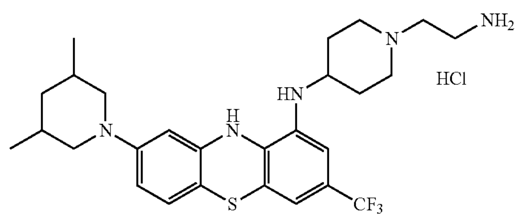 [SMILES: CC1CC(C)CN(c2ccc3c(c2)Nc2c(NC4CCN(CCN)CC4)cc(C(F)(F)F)cc2S3)C1 ; Cl] | N-(1-(2-aminoethyl)piperidin-4-yl)-8-(3,5-dimethyl-piperidin-1-yl)-3-(trifluoromethyl)-10H-phenothiazin-1-amine hydrochloride | 555.24 | 520.2 | XXIII |
| 358 | 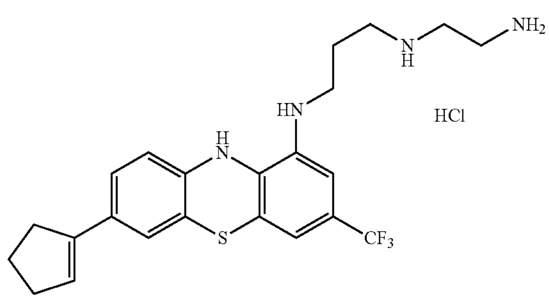 [SMILES: NCCNCCCNc1cc(C(F)(F)F)cc2c1Nc1ccc(C3=CCCC3)cc1S2 ; Cl] | N1-(2-aminoethyl)-N3-(7-(cyclopent-1-en-1-yl)-3-(trifluoromethyl)-10H-phenothiazin-1-yl)propane-1,3-diamine hydrochloride | 484.17 | 449.3 | XXXI |
| 359 | 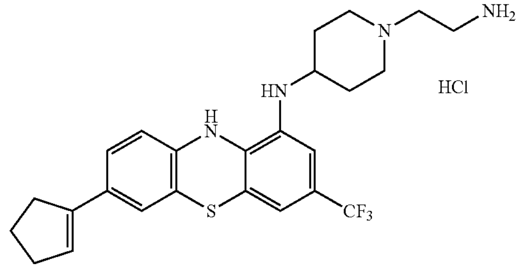 [SMILES: NCCN1CCC(Nc2cc(C(F)(F)F)cc3c2Nc2ccc(C4=CCCC4)cc2S3)CC1 ; Cl] | N-(1-(2-aminoethyl)piperidin-4-yl)-7-(cyclopent-1-en-1-yl)-3-(trifluoromethyl)-10H-phenothiazin-1-amine hydrochloride | 510.18 | 475.2 | XXXI |

Table 14 provides a summary of NMR data for the compounds synthesised.

TABLE 14

| Cmpd # | Structure | NMR data |
|---|---|---|
| 2 | (phenothiazine with NH₂ and CF₃ substituents) | $^1$H NMR (DMSO-$d_6$, 400 MHz) δ 5.44 (s, 2H), 6.49 (s, 1H), 6.73 (s, 1H), 6.81 (t, J = 7.2 Hz, 1H), 6.92 (d, J = 8 Hz, 1H), 6.92 (d, J = 7.6 Hz, 1H), 7.01 (t, J = 7.6 Hz, 1H), 7.81 (s, 1H) |
| 30 | (phenothiazine with propanamide-NH₂ and CF₃ substituents) | $^1$H NMR (DMSO-$d_6$, 400 MHz) δ 2.31-2.39 (m, 2H), 2.93-2.90 (m, 2H), 4.41 (bs, 3H), 6.20-6.38 (m, 2H), 6.95- 6.99 (m, 3H), 7.16 (s, 1H), 7.25 (s, 1H), 8.50 (br s, 1H) |
| 39 | (phenothiazine with N-(3-dimethylaminopropyl)acrylamide and CF₃ substituents) | $^1$H NMR (DMSO-$d_6$, 400 MHz) δ 1.56-1.63 (m, 2H), 2.05 (s, 6H), 2.15-2.19 (m, 2H), 3.23-3.34 (m, 2H), 3.90-3.94 (m, 1H), 5.59 (d, J = 10.8 Hz, 1H), 5.92-5.98 (m, 1H), 6.17 (d, J = 16.4 Hz, 1H), 6.85 (t, J = 7.6 Hz, 1H), 6.95 (d, J = 7.2 Hz, 1H), 6.99-7.07 (m, 2H), 7.19 (s, 1H), 7.32 (s, 1H), 8.51 (s, 1H) |
| 42 | (N-(3-dimethylaminopropyl)phenothiazine with NH₂ and CF₃) | $^1$H NMR (DMSO-$d_6$, 400 MHz) δ 1.60-1.61 (m, 2H), 2.07 (s, 6H), 2.32 (s, 2H), 3.67-3.71 (m, 2H), 5.49 (s, 2H), 6.65 (s, 1H), 6.89 (s, 1H), 7.01 (t, J = 6.8 Hz, 1H), 7.18-7.21 (m, 3H) |
| 44 | (N-(3-imidazolylpropyl)phenothiazine with NH₂ and CF₃) | $^1$H NMR (DMSO-$d_6$, 400 MHz) δ 1.90-1.88 (m, 2H), 3.69 (t, J = 6.4 Hz, 2H), 4.01 (t, J = 6.8 Hz, 2H), 5.51 (s, 2H), 6.73 (s, 1H), 6.90-6.91 (m, 2H), 7.03-7.05 (m, 2H), 7.19-7.23 (m, 3H), 7.56 (s, 1H) |
| 67 | (phenothiazine with 3-aminobutanamide and CF₃) | $^1$H NMR (DMSO-$d_6$, 400 MHz) δ 1.14 (d, 3H), 2.20-2.23 (m, 1H), 2.49 (bs, 1H), 4.66 (bs, 2H), 6.85 (d, J = 8.9 Hz, 2H), 6.98 (d, J = 8.0 Hz, 1H), 7.02 (t, J = 7.6 Hz, 1H), 7.16 (s, 1H), 7.21 (s, 1H), 8.85 (bs, 1H) |

TABLE 14-continued

| Cmpd # | Structure | NMR data |
|---|---|---|
| 83 | 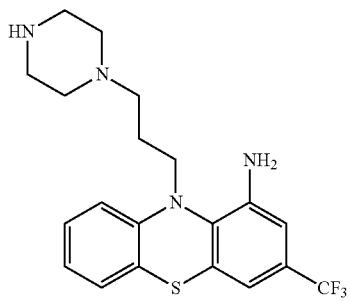 | $^1$H NMR (DMSO-d$_6$, 400 MHz) δ 1.57 (t, J = 6.4 Hz, 2H), 2.06 (bs, 4H), 2.21 (t, J = 6.4 Hz, 2H), 2.52-2.53 (m, 4H), 3.71 (t, J = 6.8 Hz, 2H), 5.47 (s, 2H), 6.66 (s, 1H), 6.88 (s, 1H), 6.99 (t, J = 7.2 Hz, 1H), 7.15 (d, J = 7.6 Hz, 1H), 7.18-7.23 (m, 2H) |
| 87 | 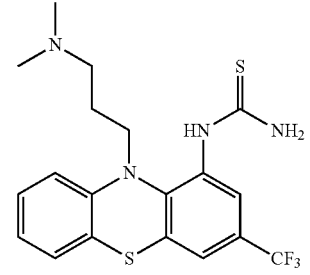 [SMILES: CN(C)CCCN1c2ccccc2Sc2cc(C(F)(F)F)cc(NC(N)=S)c21] | $^1$H NMR (DMSO-d$_6$, 400 MHz) δ 1.59-1.64 (m, 2H), 2.00-2.04 (m, 4H), 2.80-2.31 (m, 2H), 3.86 (t, J = 6.8 Hz, 2H), 7.03 (t, J = 7.6 Hz, 1H), 7.09 (d, J = 8 Hz, 1H), 7.19 (d, J = 7.2 Hz, 1H), 7.27 (t, J = 7.2 Hz, 1H), 7.37 (s, 1H), 7.54 (s, 1H), 9.41 (s, 1H) |
| 88 | 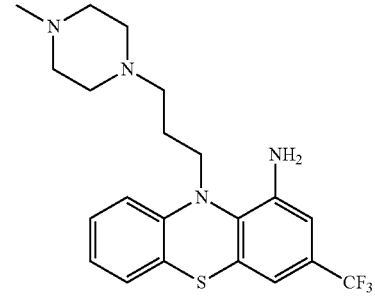 [SMILES: CN1CCN(CCCN2c3ccccc3Sc3cc(C(F)(F)F)cc(N)c32)CC1] | $^1$H NMR (DMSO-d$_6$, 400 MHz) δ 1.57 (t, J = 6.4 Hz, 2H), 2.08 (s, 3H), 2.16 (bs, 8H), 2.25 (t, J = 7.2 Hz, 2H), 3.70 (t, J = 6.8 Hz, 2H), 5.47 (s, 2H), 6.66 (s, 1H), 6.88 (s, 1H), 6.97-7.01 (m, 1H), 7.13-7.23 (m, 3H) |
| 89 | 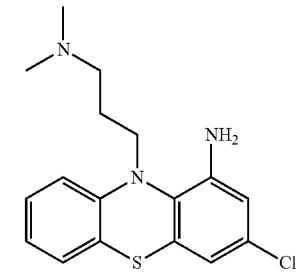 [SMILES: CN(C)CCCN1c2ccccc2Sc2cc(Cl)cc(N)c21] | $^1$H NMR (DMSO-d$_6$, 400 MHz) δ 1.77 (t, J = 6.4 Hz, 2H), 2.15 (s, 6H), 2.36 (t, J = 5.6 Hz, 2H), 3.83 (t, J = 7.2 Hz, 2H), 6.31 (s, 1H), 6.43 (s, 1H), 6.95 (t, J = 7.2 Hz, 1H), 7.02 (d, J = 8 Hz, 1H), 7.17 (d, J = 6.4 Hz, 1H), 7.20 (t, J = 7.6 Hz, 1H) |
| 90 | 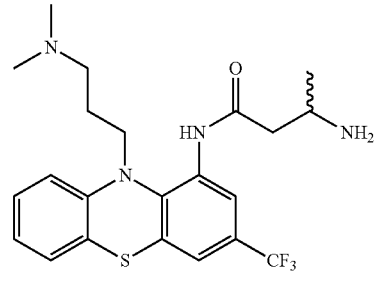 [SMILES: CC(N)CC(=O)Nc1cc(C(F)(F)F)cc2c1N(CCCN(C)C)c1ccccc1S2] | $^1$H NMR (DMSO-d$_6$, 400 MHz) δ 1.12 (d, J = 6.8 Hz, 3H), 1.54-1.57 (m, 2H), 1.93 (s, 6H), 1.97 (s, 1H), 2.16 (t, J = 5.6 Hz, 2H), 2.33-2.37 (m, 2H), 3.28 (s, 1H), 3.75 (s, 2H), 7.04 (t, J = 6.8 Hz, 1H), 7.18-7.29 (m, 4H), 8.12 (s, 1H) |

TABLE 14-continued

| Cmpd # | Structure | NMR data |
|---|---|---|
| 91 | 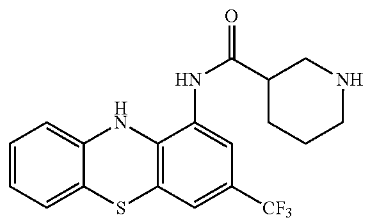 [SMILES: O=C(Nc1cc(C(F)(F)F)cc2c1Nc1ccccc1S2)C1CCCNC1] | ¹H NMR (DMSO-d₆, 400 MHz) δ 1.37-1.40 (m, 1H), 1.59-1.64 (m, 2H), 1.90-1.92 (m, 1H), 2.49 (br s, 2H), 2.65-2.70 (m, 1H), 2.84 (d, J = 10 Hz, 1H), 6.83-6.89 (m, 2H), 6.98 (d, J = 6.4 Hz, 1H), 7.06 (t, J = 6.8 Hz, 1H), 7.13 (s, 1H), 7.37 (s, 1H), 7.99 (s, 1H), 9.37 (s, 1H) |
| 92 | 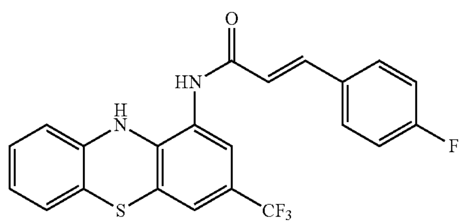 [SMILES: O=C(/C=C/c1ccc(F)cc1)Nc1cc(C(F)(F)F)cc2c1Nc1ccccc1S2] | ¹H NMR (DMSO-d₆, 400 MHz) δ 6.77 (s, 1H), 6.85 (t, J = 8.4 Hz, 1H), 6.97 (t, J = 8.4 Hz, 2H), 7.04 (t, J = 7.2 Hz, 1H), 7.16 (s, 1H), 7.30 (t, J = 8.8 Hz, 2H), 7.46 (s, 1H), 7.58 (s, 1H), 7.71 (t, J = 6 Hz, 2H), 8.20 (s, 1H), 9.65 (s, 1H) |
| 94 | 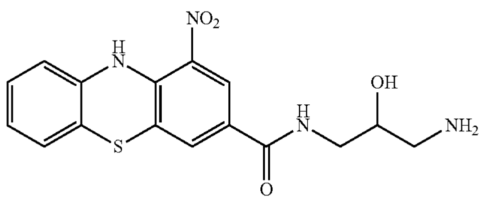 [SMILES: NCC(O)CNC(=O)c1cc2c(c([N+](=O)[O-])c1)Nc1ccccc1S2] | ¹H NMR (400 MHz, DMSO-d₆): δ 1.96 (s, 4H), 2.65 (d, J = 6.4 Hz, 1 H), 2.73 (d, J = 4.4 Hz, 1 H), 3.46-3.25 (m, 7 H), 3.68 (s, 1H), 6.85 (d, J = 8 Hz, 1 H), 6.95 (t, J = 7.6 Hz, 2H), 7.06 (t, J = 6.4 Hz, 2H), 7.74 (s, 1H), 8.39 (s, 1H), 8.46 (s, 1H), 9.91 (s, 1H) |
| 95 | 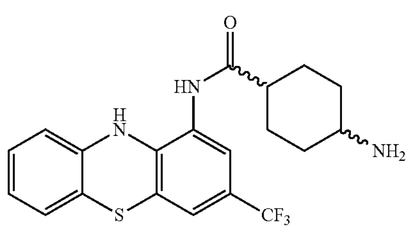 [SMILES: NC1CCC(C(=O)Nc2cc(C(F)(F)F)cc3c2Nc2ccccc2S3)CC1] | ¹H NMR (DMSO-d₆, 400 MHz) δ 1.68-1.76 (m, 6H), 1.99-2.01 (m, 2H), 2.78 (s, 1H), 3.04-3.06 (m, 1H), 6.85 (t, J = 8.4 Hz, 1H), 6.98 (t, J = 7.6 Hz, 2H), 7.03 (d, J = 9.8 Hz, 1H), 7.13 (s, 1H), 7.40 (s, 1H), 7.81 (bs, 2H), 8.25 (s, 1H) |
| 97 | 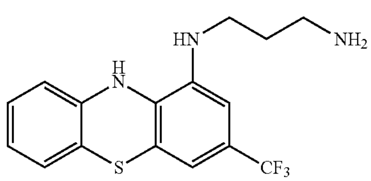 [SMILES: NCCCNc1cc(C(F)(F)F)cc2c1Nc1ccccc1S2] | ¹H NMR (DMSO-d₆, 400 MHz) δ 1.22 (s, 2H), 1.74 (t, J = 6.8 Hz, 2H), 1.85 (s, 1H), 2.73 (t, J = 6.8 Hz, 2H), 3.41 (br s, 3H), 5.62 (br s, 1H), 6.55 (s, 1H), 6.79-6.83 (m, 1H), 6.89-6.95 (m, 2H), 7.04 (t, J = 6.8 Hz, 1H), 8.11 (bs, 1H) |
| 98 | 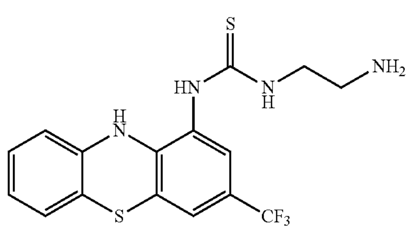 | ¹H NMR (DMSO-d₆, 400 MHz) δ 1.91 (s, 2H), 3.33 (s, 2H), 3.64 (s, 2H), 6.83 (t, J = 8.0 Hz, 1H), 6.94-7.01 (m, 3H), 7.15 (s, 2H), 7.81 (s, 1H), 8.00 (s, 1H), 8.94 (s, 1H) |
| 100 | 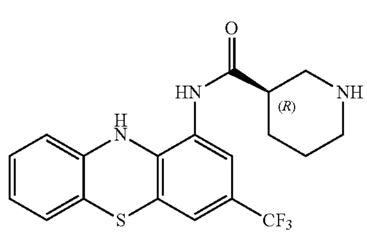 | ¹H NMR (DMSO-d₆, 400 MHz) δ 1.37-1.45 (m, 1H), 1.58-1.64 (m, 2H), 1.96 (d, J = 9.6 Hz, 1H), 2.57-2.65 (m, 2H), 2.78 (t, J = 10 Hz, 1H), 2.90 (d, J = 12 Hz, 1H), 3.15 (d, J = 10.8 Hz, 1H), 6.83-6.89 (m, 2H), 6.98 (d, J = 7.6 Hz, 1H), 7.07 (d, J = 7.6 Hz, 1H), 7.13 (s, 1H), 7.36 (s, 1H), 8.00 (s, 1H), 9.42 (s, 1H) |

TABLE 14-continued

| Cmpd # | Structure | NMR data |
|---|---|---|
| 101 | (phenothiazine with NH-C(O)-CH2CH2-piperazine at position 1 and CF3 at position 3) | ¹H NMR (DMSO-d₆, 400 MHz) δ 2.49-2.56 (m, 4H), 2.66-2.72 (m, 3H), 2.82 (s, 4H), 5.65 (bs, 1H), 6.85-6.90 (m, 2H), 6.98-7.00 (d, J = 6.8 Hz, 1H), 7.04-7.07 (t, J = 6.8 Hz, 1H), 7.16 (s, 1H), 7.34 (s, 1H), 8.03 (s, 1H), 9.66 (s, 1H) |
| 105 | (phenothiazine with NH-C(O)-(3-aminocyclohexyl) and CF3) | ¹H NMR (DMSO-d₆, 400 MHz) δ1.18- 1.22 (m, 4H), 1.75-1.78 (m, 2H), 1.84-1.86 (m, 1H), 1.98- 2.07 (d, J = 12.4 Hz, 1H), 2.59 (s, 1H), 3.45-3.48 (m, 1H), 6.83-6.91 (m, 2H), 6.96 (d, J = 6.8 Hz, 1H), 7.02 (t, J = 7.6 Hz, 1H), 7.12 (s, 1H), 8.13 (s, 1H), 7.38 (s, 1H), 8.03 (s, 1H) |
| 106 | (phenothiazine with NH-C(O)-(3-piperidinyl) and CF3) | ¹H NMR (DMSO-d₆, 400 MHz) δ 1.47 (s, 1H), 1.62 (s, 2H), 1.97 (d, J = 12 Hz, 1H), 2.66 (t, J = 11.2 Hz 1H), 2.80 (t, J = 10 Hz, 1H), 2.92 (d, J = 10 Hz, 1H), 3.17 (d, J = 12 Hz, 1H), 6.84- 6.90 (m, 2H), 6.98 (d, J = 7.6 Hz, 1H), 7.02 (t,, J = 7.6 Hz, 1H), 7.14 (s, 1H), 7.37 (s, 1H), 8.02 (s, 1H), 9.45 (s, 1H) |
| 108 | (phenothiazine with NH-CH2-(4-aminocyclohexyl) and CF3) | ¹H NMR (DMSO-d₆, 400 MHz) δ 1.43 (d, J = 9.6 Hz, 3H), 1.41-1.49 (m, 5H), 1.68 (d, J = 5.6 Hz, 3H), 2.65 (s, 1H), 3.01 (t, J = 6 Hz, 2H), 6.54 (d, J = 8 Hz, 2H), 6.84 (t, J = 7.2 Hz, 1H), 6.90 (d, J = 8 Hz, 1H), 6.96 (d, J = 7.2 Hz, 1H), 7.05 (t, J = 7.2 Hz, 1H), 8.01 (s, 1H) |
| 110 | (10-(3-dimethylaminopropyl)-3-phenylphenothiazine) | ¹H NMR (DMSO-d₆, 400 MHz) δ 1.83 (t, J = 8.0 Hz, 2H), 2.16 (s, 6H), 2.40 (s, 2H), 3.93 (t, J = 7.2 Hz, 2H), 6.94 (t, J = 7.2 Hz, 1H), 7.04 (d, J = 8.0 Hz, 1H), 7.09 (d, J = 8.0 Hz, 1H), 7.15-7.22 (m, 2H), 7.30 (t, J = 7.6 Hz, 1H), 7.39-7.43 (m, 3H), 7.49 (d, J = 8.0 Hz, 1H), 7.61 (d, J = 7.6 Hz, 2H) |
| 111 | (10-(3-dimethylaminopropyl)-3-(1H-indol-2-yl)phenothiazine) | ¹H NMR (DMSO-d₆, 400 MHz) δ 1.94 (s, 6H), 2.31 (s, 2H), 2.66 (s, 2H), 3.96 (s, 2H), 6.80 (s, 1H), 6.96-6.97 (m, 2H), 7.04-7.08 (m, 2H), 7.12 (d, J = 8.0 Hz, 1H), 7.19-7.24 (m, 2H), 7.35 (d, J = 8.0 Hz, 1H), 7.48 (d, J = 8.0 Hz, 1H), 7.66-7.69 (m, 2H), 11.40 9s, 1H) |

TABLE 14-continued

| Cmpd # | Structure | NMR data |
|---|---|---|
| 113 | 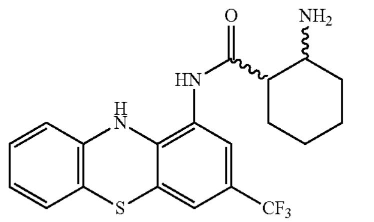 [SMILES: NC1CCCCC1C(=O)Nc1cc(C(F)(F)F)cc2c1Nc1ccccc1S2] | ¹H NMR (DMSO-d₆, 400 MHz) δ 1.22-1.24 (m, 1H), 1.31-1.35 (m, 1H), 1.50-1.53 (m, 1H), 1.60 (s, 3H), 1.73-1.81 (m, 2H), 2.48-2.57 (m, 1H), 3.35 (s, 1H), 4.66 (bs, 2H), 6.80-6.86 (m, 2H), 6.93-6.98 (m, 2H), 7.13-7.14 (d, J = 5.2 Hz, 1H), 8.8 (s, 1H) |
| 115 | 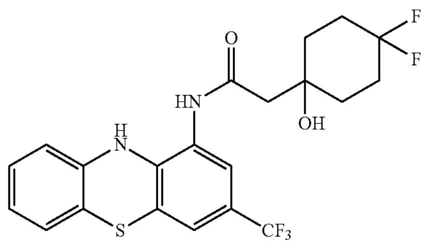 [SMILES: O=C(CC1(O)CCC(F)(F)CC1)Nc1cc(C(F)(F)F)cc2c1Nc1ccccc1S2] | ¹H NMR (DMSO-d₆, 400 MHz) δ 1.70-1.75 (m, 2H), 1.83-1.97 (m, 4H), 1.97-2.15 (m, 2H), 2.53 (s, 2H), 5.15 (s, 1H), 6.82-6.87 (m, 2H), 6.98 (d, J = 7.6 Hz, 1H), 7.05 (t, J = 7.6 Hz, 1H), 7.18 (s, 1H), 7.26 (s, 1H), 7.89 (s, 1H), 9.39 (s, 1H) |
| 116 | 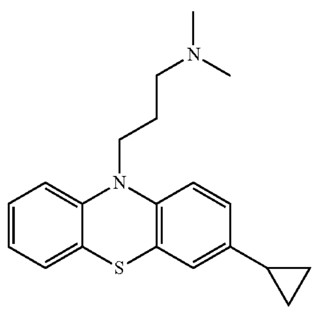 [SMILES: CN(C)CCCN1c2ccccc2Sc2cc(C3CC3)ccc21] | ¹H NMR (DMSO-d₆, 400 MHz) δ 0.58 (d, J = 4.0 Hz, 2H), 0.85 (d, J = 6.0 Hz, 2H), 1.73-1.81 (m, 3H), 2.09 (s, 6H), 2.30 (t, J = 6.0 Hz, 2H), 3.84 (t, J = 6.8 Hz, 2H), 6.83 (s, 1H), 6.86-6.91 (m, 3H), 6.97 (d, J = 8.0 Hz, 1H), 7.11 (d, J = 8.0 Hz, 1H), 7.16 (t, J = 8.0 Hz, 1H) |
| 117 | 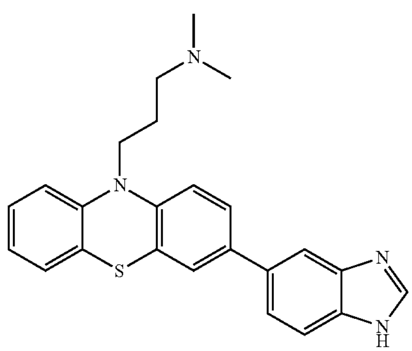 [SMILES: CN(C)CCCN1c2ccccc2Sc2cc(-c3ccc4[nH]cnc4c3)ccc21] | ¹H NMR (DMSO-d₆, 400 MHz) δ 1.81-1.83 (m, 2H), 2.11 (s, 6H), 2.33 (d, J = 7.6 Hz, 2H), 3.90-3.92 (m, 2H), 6.94 (t, J = 8.0 Hz, 1H), 7.04 (d, J = 8.0 Hz, 1H), 7.09 (d, J = 8.0 Hz, 1H), 7.15-7.22 (m, 2H), 7.40-7.55 (m, 3H), 7.65-7.68 (m, 2H), 8.20 (s, 1H), 12.44 (s, 1H) |
| 118 | Isomer-1 | ¹H NMR (DMSO-d₆, 400 MHz) δ 0.97-1.00 (m, 2H), 1.18-1.25 (m, 2H), 1.29-1.38 (m, 3H), 1.78 (d, J = 10.4 Hz, 2H), 1.86 (d, J = 7.6 Hz, 1H), 2.01 (d, J = 12 Hz, 1H), 2.59 (d, J = 11.2 Hz, 1H), 6.87 (d, J = 7.2 Hz, 1H), 6.91 (d, J = 8 Hz, 1H), 6.98 (d, J = 7.2 Hz, 1H), 7.07 (t, J = 7.6 Hz, 1H), 7.12 (s, 1H); 7.38 (s, 1H), 8.03 (s, 1H) |

TABLE 14-continued

| Cmpd # | Structure | NMR data |
|---|---|---|
| 119 | 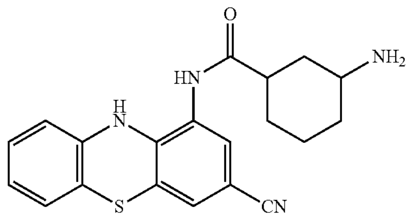 [SMILES: N#Cc1cc(NC(=O)C2CCCC(N)C2)c2c(c1)Sc1ccccc1N2] | $^1$H NMR (DMSO-$d_6$, 400 MHz) δ 1.33-1.37 (m, 2H), 1.49-1.61 (m, 1H), 1.61-1.74 (m, 1H), 1.77-1.99 (m, 4H), 2.31-2.57 (m, 1H), 6.84-6.89 (m, 2H), 6.95-6.97 (d, J = 7.2 Hz, 1H), 7.02-7.06 (t, J = 7.2 Hz, 1H), 7.24 (s, 1H), 7.43 (s, 1H), 7.67-7.68 (m, 1H) |
| 120 | 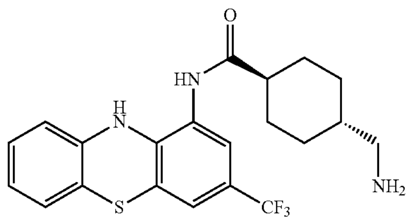 [SMILES: NC[C@H]1CC[C@H](C(=O)Nc2cc(C(F)(F)F)cc3c2Nc2ccccc2S3)CC1] | $^1$H NMR (DMSO-$d_6$, 400 MHz) δ, 0.90-0.96 (m, 2H), 1.39 (q, J = 12.4 Hz, 2H), 1.85 (d, J = 12.0 Hz, 2H), 1.95 (d, J = 11.6 Hz, 2H), 2.38-6.2.49 (m, 4 H), 6.83-6.91 (m, 1H), 6.97 (d, J = 7.6 Hz, 1H), 7.05 (t, J = 7.2 Hz, 1H), 7.12 (s, 1H), 7.39 (s, 1H), 8.00 (bs, 1H) |
| 121 | 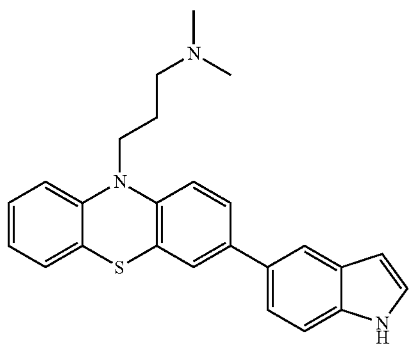 [SMILES: CN(C)CCCN1c2ccccc2Sc2cc(-c3ccc4[nH]ccc4c3)ccc21] | $^1$H NMR (DMSO-$d_6$, 400 MHz) δ 1.81-1.83 (m, 2H), 2.10 (s, 6H), 2.33 (d, J = 6.0 Hz, 2H), 3.91-3.93 (m, 2H), 6.44 (s, 1H), 6.93 (t, J = 7.2 Hz, 1H), 7.05 (q, J = 8.0 Hz, 2H), 7.15-7.21 (m, 2H), 7.33 (d, J = 8.0 Hz, 2H), 7.40-7.42 (m, 2H), 7.47 (d, J = 8.0 Hz, 1H), 7.74 (s, 1H), 11.07 (s, 1H) |
| 122 | 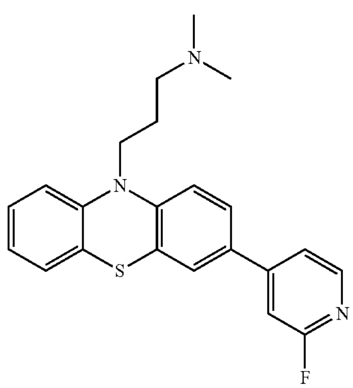 [SMILES: CN(C)CCCN1c2ccccc2Sc2cc(-c3ccnc(F)c3)ccc21] | $^1$H NMR (DMSO-$d_6$, 400 MHz) δ 1.80 (t, J = 6.0 Hz, 2H), 2.09 (s, 6H), 2.31 (t, J = 7.20 Hz, 2H), 3.95 (t, J = 6.0 Hz, 2H), 6.96 (t, J = 8.0 Hz, 1H), 7.06 (d, J = 8.0 Hz, 1H), 7.11-7.17 (m, 2H), 7.21 (t, J = 8.0 Hz, 1H), 7.48 (s, 1H), 7.66 (s, 2H), 7.71 (d, J = 8.0 Hz, 1H), 8.22 (d, J = 6.0 Hz, 1H) |
| 123 | 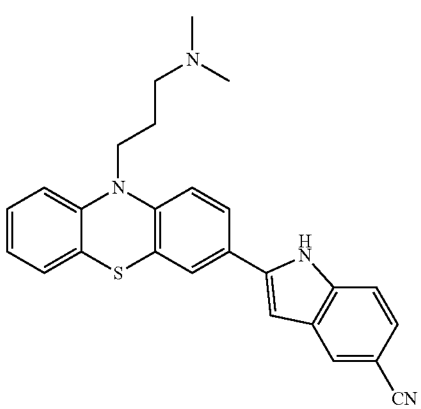 [SMILES: CN(C)CCCN1c2ccccc2Sc2cc(-c3cc4cc(C#N)ccc4[nH]3)ccc21] | $^1$H NMR (DMSO-$d_6$, 400 MHz) δ 1.81 (t, J = 6.0 Hz, 2H), 2.10 (s, 6H), 2.33 (t, J = 7.2 Hz, 2H), 3.94 (t, J = 7.2 Hz, 2H), 6.95 (s, 2H), 7.05 (d, J = 8.0 Hz, 1H), 7.12 (d, J = 8.0 Hz, 1H), 7.18-7.23 (m, 2H), 7.40 (d, J = 8.0 Hz, 1H), 7.50 (d, J = 8.0 Hz, 1H), 7.67 (s, 1H), 7.70 (d, J = 8.4 Hz, 1H), 8.00 (s, 1H), 11.99 (s, 1H) |

TABLE 14-continued

| Cmpd # | Structure | NMR data |
|---|---|---|
| 124 | 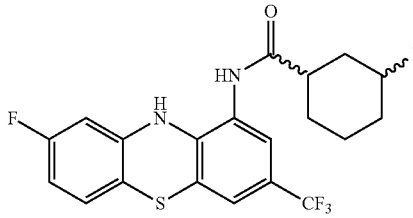 | $^1$H NMR (DMSO-$d_6$, 400 MHz) δ1.36-1.49 (m, 3 H), 1.80-2.01 (m, 5H), 2.11-2.31 (m, 1H), 3.089 (bs, 1H), 6.70-6.77 (m, 2 H), 7.00-7.04 (m, 1H), 7.20 (s, 1H), 7.30 (s, 1H), 7.77 (bs, 3H), 8.18 (s, 1H), 9.04 (s, 1H) |
| 125 | 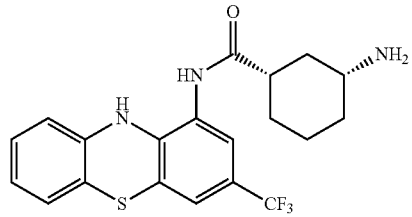  Isomer 2 | $^1$H NMR (DMSO-$d_6$, 400 MHz) δ 1.16 (s, 1H), 1.24 (d, J = 10.8 Hz, 2H), 1.34 (d, J = 5.6 Hz, 2H), 1.83 (s, 2H), 1.86 (d, J = 8.4 Hz, 1H), 2.02 (d, J = 12 Hz, 1H), 2.65 (s, 2H), 6.87 (t, J = 6.8 Hz, 1H), 6.92 (d, J = 8 Hz, 1H), 6.98 (d, J = 7.6 Hz, 1H), 7.07 (t, J = 7.6 Hz, 1H), 7.12 (s, 1H); 7.38 (s, 1H), 8.04 (s, 1H) |
| 126 | 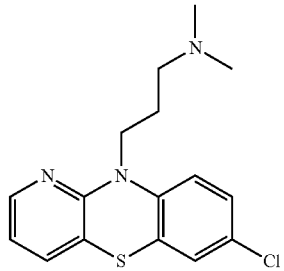 [SMILES: CN(C)CCCN1c2ccc(Cl)cc2Sc2cccnc21] | $^1$H NMR (DMSO-$d_6$, 400 MHz) δ 1.27-1.32 (m, 2H), 1.76-1.82 (m, 2H), 2.14 (s, 7H), 2.34 (t, J = 6.8 Hz, 2H), 4.02 (t, J = 8.0 Hz, 2H), 6.86-6.89 (m, 1H), 6.99 (d, J = 8.4 Hz, 1 H), 7.21 (d, J = 8.4 Hz, 2H), 7.43 (d, J = 7.6 Hz, 1H), 7.67-7.69 (m, 1H), 8.01 (d, J = 4.0 Hz, 1H) |
| 129 | 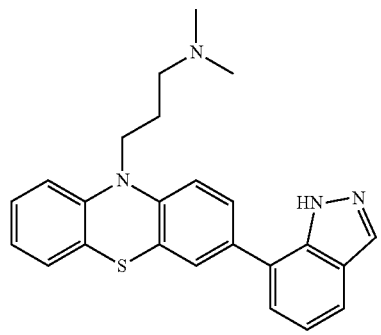 [SMILES: CN(C)CCCN1c2ccccc2Sc2cc(-c3cccc4cn[nH]c34)ccc21] | $^1$H NMR (DMSO-$d_6$, 400 MHz) δ 1.81-1.83 (m, 2H), 2.11 (s, 6H), 2.33-2.35 (m, 2H), 3.95-3.97 (m, 2H), 6.95 (t, J = 7.2 Hz, 1H), 7.06 (d, J = 8.0 Hz, 1H), 7.13-7.23 (m, 4H), 7.35 (d, J = 8.0 Hz, 1H), 7.44 (s, 1H), 7.50 (d, J = 8.0 Hz, 1H), 7.71 (d, J = 8.0 Hz, 1H), 8.14 (s, 1H), 13.16 (s, 1H) |
| 130 | 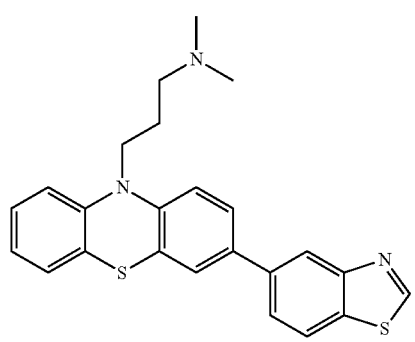 [SMILES: CN(C)CCCN1c2ccccc2Sc2cc(-c3ccc4scnc4c3)ccc21] | $^1$H NMR (DMSO-$d_6$, 400 MHz) δ 1.82 (t, J = 7.2 Hz, 2H), 2.11 (s, 6H), 2.34 (t, J = 7.2 Hz, 2H), 3.94 (t, J = 7.2 Hz, 2H), 6.95 (t, J = 7.2 Hz, 1H), 7.05 (d, J = 8.0 Hz, 1H), 7.12 (d, J = 8.0 Hz, 1H), 7.16-7.23 (m, 2H), 7.57 (s, 1H), 7.62 (d, J = 7.6 Hz, 1H), 8.19 (t, J = 8.4 Hz, 2H), 8.30 (s, 1H), 9.40 (s, 1H) |

TABLE 14-continued

| Cmpd # | Structure | NMR data |
|---|---|---|
| 132 | 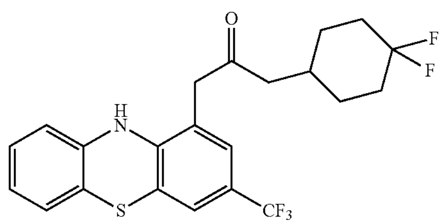 [SMILES: O=C(Cc1cc(C(F)(F)F)cc2c1Nc1ccccc1S2)CC1CCC(F)(F)CC1] | $^1$H NMR (DMSO-d$_6$, 400 MHz) δ 1.22 (s, 1H), 1.29 (d, J = 12.8 Hz, 2H), 1.84 (d, J = 12.8 Hz, 6H), 1.99 (bs, 2H), 2.36 (d, J = 7.2 Hz, 2H), 6.85-6.90 (m, 2 H), 6.98 (d, J = 7.6 Hz, 1H), 7.05 (d, J = 6.8 Hz, 1H), 7.14 (s, 1H), 7.36 (s, 1H), 8.00 (s, 1H), 9.36 (s, 1H) |
| 133 | 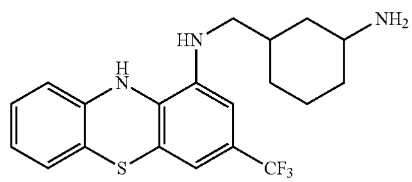 [SMILES: NC1CCCC(CNc2cc(C(F)(F)F)cc3c2Nc2ccccc2S3)C1] | $^1$H NMR (DMSO-d$_6$, 400 MHz) δ 0.85-0.97 (m, 1H), 1.13 (d, J = 11.6 Hz, 1H), 1.30-1.39 (m, 2H), 1.85 (t, J = 16.8 Hz, 3 H), 2.07 (s, 2H), 3.02 (t, J = 6 Hz, 2H), 3.26 (s, 1H), 5.58 (s, 1H), 6.55 (d, J = 12 Hz, 2H), 6.84 (t, J = 7.6 Hz, 1H), 6.90-6.96 (m, 2H), 7.05 (t, J = 6.8 Hz, 1H), 7.74 (s, 1H), 8.06 (s, 1H) |
| 134 | 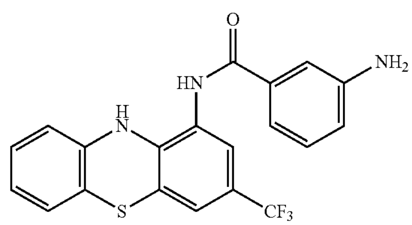 [SMILES: Nc1cccc(C(=O)Nc2cc(C(F)(F)F)cc3c2Nc2ccccc2S3)c1] | $^1$H NMR (DMSO-d$_6$, 400 MHz) δ 5.27 (s, 2H), 6.75-6.77 (d, J = 6.8 Hz, 1H), 6.82-6.85 (t, J = 7.6 Hz, 1H), 6.94-7.03 (m, 3H), 7.13-7.17 (m, 4H), 7.31 (s, 1H), 8.18 (s, 1H), 9.65 (s, 1H) |
| 135 | 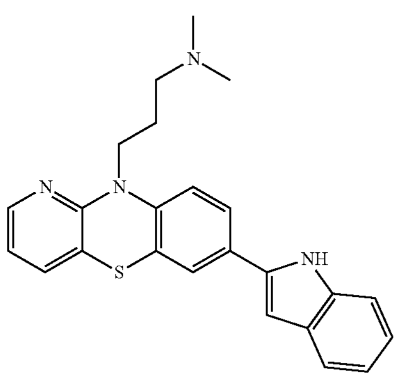 [SMILES: CN(C)CCCN1c2ccc(-c3cc4ccccc4[nH]3)cc2Sc2cccnc21] | $^1$H NMR (DMSO-d$_6$, 400 MHz) δ 0.84 (bs, H), 1.22 (s, 2H), 1.85-1.89 (m, 2H), 2.18 (s, 6H), 2.31-2.49 (m, 2H), 4.08 (t, J = 7.2 Hz, 2H), 6.81 (s, 1H), 6.86-6.89 (m, 1H), 6.96 (t, J = 7.6 Hz, 1H), 7.04-7.12 (m, 2 H), 7.35 (d, J = 8.4 Hz, 1H), 7.47 (t, J = 8.0 Hz, 2H), 7.58 (s, 1H). |
| 136 | 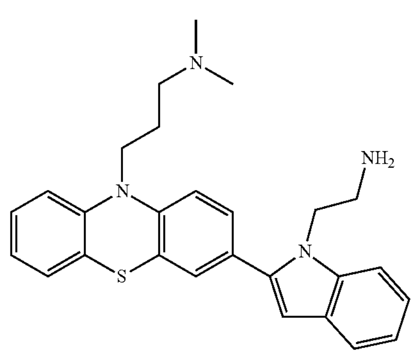 [SMILES: CN(C)CCCN1c2ccccc2Sc2cc(-c3cc4ccccc4n3CCN)ccc21] | $^1$H NMR (DMSO-d$_6$, 400 MHz) δ 1.83 (t, J = 6.0 Hz, 2H), 2.06 (s, 6H), 2.33 (t, J = 7.2 Hz, 2H), 2.72 (t, J = 7.2 Hz, 2H), 3.95 (t, J = 6.8 Hz, 2H), 4.12 (t, J = 7.2 Hz, 2H), 6.44 (s, 1H), 6.96 (t, J = 7.6 Hz, 1H), 7.01-7.07 (m, 2H), 7.12-7.20 (m, 3H), 7.22 (t, J = 8.0 Hz, 1H), 7.33 (s, 1H), 7.38 (d, J = 8.0 Hz, 1H), 7.51 (d, J = 7.2 Hz, 2H) |

TABLE 14-continued

| Cmpd # | Structure | NMR data |
|---|---|---|
| 137 | 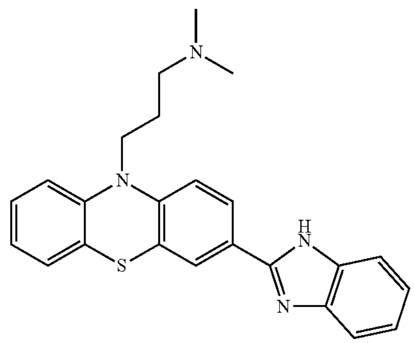 [SMILES: CN(C)CCCN1c2ccccc2Sc2cc(-c3nc4ccccc4[nH]3)ccc21] | $^1$H NMR (DMSO-d$_6$, 400 MHz) δ 1.78-1.89 (m, 2H), 2.10 (s, 6H), 2.33 (t, J = 7.2 Hz, 2H), 3.96 (t, J = 7.2 Hz, 2H), 6.97 (t, J = 7.2 Hz, 1H), 7.07 (d, J = 8.0 Hz, 1H), 7.12-7.24 (m, 5H), 7.47 (d, J = 6.8 Hz, 2H), 7.60 (d, J = 7.2 Hz, 1H), 7.90 (s, 1H), 7.60-7.99 (m, 1H), 12.72 (s, 1H) |
| 139 | 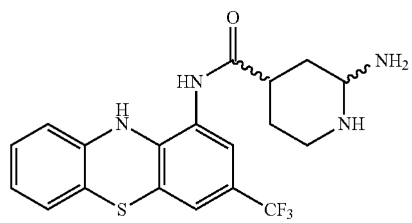 [SMILES: NC1CC(C(=O)Nc2cc(C(F)(F)F)cc3c2Nc2ccccc2S3)CCN1] | $^1$H NMR (DMSO-d$_6$, 400 MHz) δ 1.78 (d, J = 8 Hz, 1H), 2.06 (s, 2H), 2.42 (s, 3H), 2.94 (s, 2H), 3.29 (s, 2H), 6.87-6.84 (m, 1H), 6.90 (d, J = 8.6 Hz, 1H), 6.97 (d, J = 7.2 Hz, 1H), 7.06 (t, J = 8 Hz, 1H), 7.15 (s, 1H), 7.36 (s, 1H), 7.48 (s, 1H), 8.0 (s, 1H), 9.44 (s, 1H) |
| 140 | 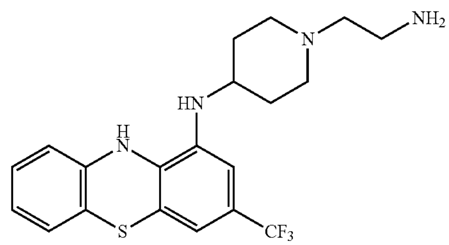 [SMILES: NCCN1CCC(Nc2cc(C(F)(F)F)cc3c2Nc2ccccc2S3)CC1] | $^1$H NMR (DMSO-d$_6$, 400 MHz) δ 1.41-1.48 (m, 4H), 1.90-1.93 (d, J = 12 Hz, 2H), 2.063 (t, J = 12 Hz, 2H), 2.30 (t, J = 4 Hz, 2H), 2.58-2.61 (m, 2H), 2, 82-2.84 (d, J = 8 Hz, 2H), 5.26-5.28 (d, J = 8 Hz, 1H), 6.54 (s, 1H), 6.58 (s, 1H), 6.80-6.82 (m, 1H), 6.84-6.88 (m, 1H), 6.90-6.95 (m, 1H), 7.01-7.05 (m, 1H), 8.02 (s, 1H) |
| 141 | 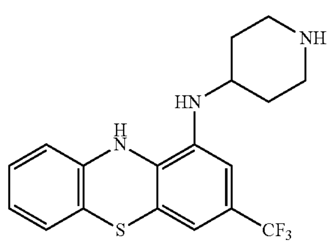 [SMILES: FC(F)(F)c1cc(NC2CCNCC2)c2c(c1)Sc1ccccc1N2] | $^1$H NMR (DMSO-d$_6$, 400 MHz) δ 1.25-1.32 (m, 2H), 1.89 (d, J = 11.2 Hz, 2H), 2.01-2.02 (m, 1H), 2.49-2.57 (m, 2H), 2.97 (d, J = 12 Hz, 2H), 3.29-3.33 (m, 1H), 6.53 (s, 2H), 6.58 (s, 2H), 6.82 (t, J = 7.2 Hz, 1H), 6.90 (d, J = 8 Hz, 1H), 6.95 (d, J = 7.6 Hz, 1H), 7.03 (t, J = 7.2 Hz, 1H), 8.02 (s, 1H) |
| 143 | 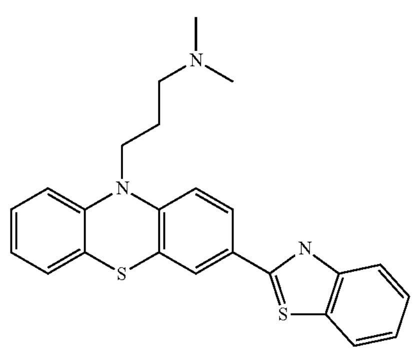 | $^1$H NMR (DMSO-d$_6$, 400 MHz) δ 1.78-1.85 (m, 2H), 2.08 (s, 6H), 2.32 (t, J = 7.2 Hz, 2H), 3.97 (t, J = 6.8 Hz, 2H), 6.98 (t, J = 7.6 Hz, 1H), 7.08 (d, J = 8.0 Hz, 1H), 7.16-7.18 (m, 2H), 7.23 (t, J = 7.6 Hz, 1H), 7.42 (t, J = 7.6 Hz, 1H), 7.51 (d, J = 7.2 Hz, 1H), 7.79 (d, J = 2.4 Hz, 1H), 7.87-7.89 (m, 1H), 7.99 (d, J = 8.0 Hz, 1H), 8.09 (d, J = 8.0 Hz, 2H) |

TABLE 14-continued

| Cmpd # | Structure | NMR data |
|---|---|---|
| 144 | 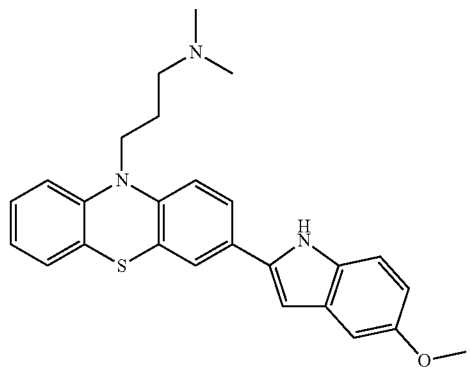 [SMILES: COc1ccc2[nH]c(-c3ccc4c(c3)Sc3ccccc3N4CCCN(C)C)cc2c1] | ¹H NMR (DMSO-d₆, 400 MHz) δ 1.80 (t, J = 7.2 Hz, 2H), 2.10 (s, 6H), 2.33 (t, J = 7.2 Hz, 2H), 3.74 (s, 3H), 3.93 (t, J = 6.8 Hz, 2H), 6.70 (d, J = 6.0 Hz, 2H), 6.92-6.97 (m, 2H), 7.03-7.09 (m, 2H), 7.15-7.24 (m, 3H), 7.59 (s, 1H), 7.63 (d, J = 7.6 Hz, 1H), 11.22 (s, 1H) |
| 148 | 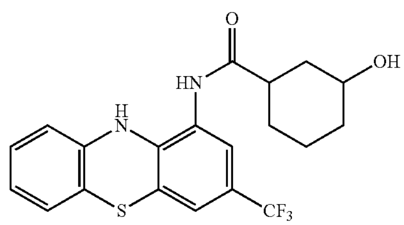 [SMILES: O=C(Nc1cc(C(F)(F)F)cc2c1Nc1ccccc1S2)C1CCCC(O)C1] | ¹H NMR (DMSO-d₆, 400 MHz) δ 1.22-1.44 (m, 3H), 1.50-1.61 (m, 2H), 1.65-1.69 (m, 1H), 1.77-1.85 (m, 2H), 2.86-2.92 (m, 1H), 3.98 (s, 1H), 4.45 (s, 1H), 6.83-6.90 (m, 2H), 6.96-6.98 (d, J = 7.6 Hz, 1H) 7.03-7.07 (t, J = 7.6 Hz, 1H), 7.11 (s, 1H), 7.42 (s, 1H), 8.02 (s, 1H), 9.25 (s, 1H) |
| 149 | 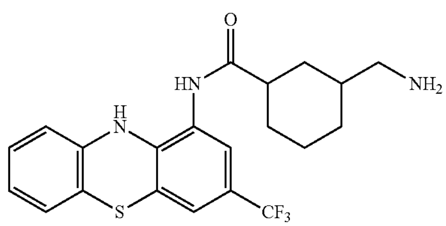 [SMILES: NCC1CCCC(C(=O)Nc2cc(C(F)(F)F)cc3c2Nc2ccccc2S3)C1] | ¹H NMR (DMSO-d₆, 400 MHz) δ 1.23-1.30 (m, 5H), 1.77-1.82 (m, 3H), 1.90-1.98 (m, 2H), 2.08-2.13 (m, 1H), 3.49-3.55 (m, 3H), 6.85 (s, 1H), 6.95-6.97 (m, 1H), 7.03 (s, 2H), 7.09 (s, 1H), 7.51 (s, 1H), 8.43 (s, 1H), 9.71 (bs, 1H) |
| 150 | 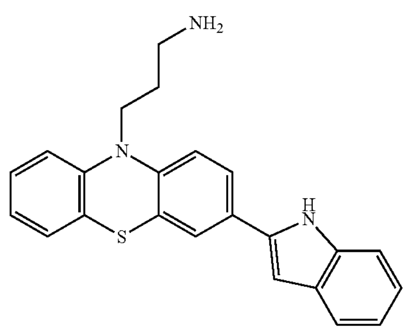 [SMILES: NCCCN1c2ccccc2Sc2cc(-c3cc4ccccc4[nH]3)ccc21] | ¹H NMR (DMSO-d₆, 400 MHz) δ 1.78-1.81 (m, 2H), 2.67-2.71 (m, 2H), 3.93-3.96 (m, 2H), 6.77 (s, 1H), 6.93-6.98 (m, 3H), 7.02-7.21 (m, 6H), 7.33 (d, J = 8 Hz, 1H), 7.56 (d, J = 7.6 Hz, 1H), 7.62-7.66 (m, 2H), 11.37 (s, 1H) |
| 151 | 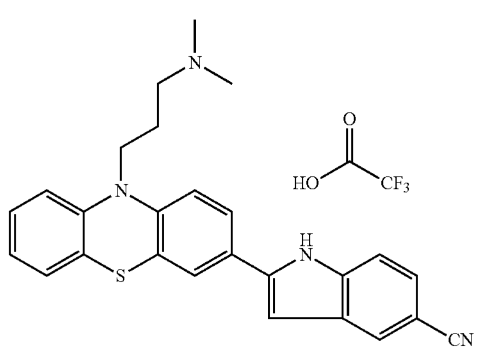 [SMILES: CN(C)CCCN1c2ccccc2Sc2cc(-c3cc4cc(C#N)ccc4[nH]3)ccc21 ; O=C(O)C(F)(F)F] | ¹H NMR (DMSO-d₆, 400 MHz) δ 2.05-2.07 (m, 2H), 2.75 (s, 6H), 3.15-3.17 (m, 2H), 4.00 (t, J = 6.8 Hz, 2H), 6.98 (s, 1H), 7.02 (d, J = 8.0 Hz, 1H), 7.10 (d, J = 8.4 Hz, 1H), 7.17 (d, J = 8.4 Hz, 1H), 7.22-7.27 (m, 2H), 7.41 (d, J = 8.1 Hz, 1H), 7.51 (d, J = 8.4 Hz, 1H), 7.69-7.75 (m, 2H), 8.01 (s, 1H), 9.29 (s, 1H), 12.02 (s, 1H). |

TABLE 14-continued

| Cmpd # | Structure | NMR data |
|---|---|---|
| 152 | 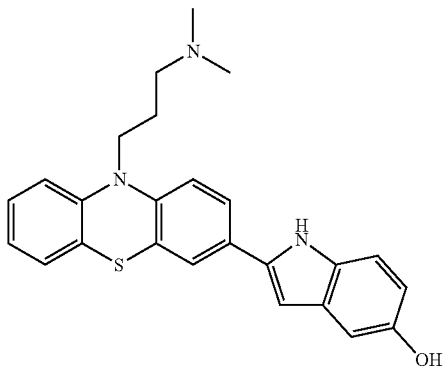 [SMILES: CN(C)CCCN1c2ccccc2Sc2cc(-c3cc4cc(O)ccc4[nH]3)ccc21] | $^1$H NMR (DMSO-d$_6$, 400 MHz) δ 1.82-1.84 (m, 2H), 1.97-1.99 (m, 1H), 2.06 (s, 6H), 2.48 (t, J = 7.2 Hz, 2H), 3.93 (t, J = 7.2 Hz, 2H), 6.55-6.60 (m, 2H), 6.78 (t, J = 2.0 Hz, 2H), 6.94 (t, J = 7.2 Hz, 1H), 7.03-7.22 (m, 5H), 7.57 (s, 1H), 7.61 (d, J = 7.6 Hz, 1H), 11.06 (s, 1H) |
| 153 | 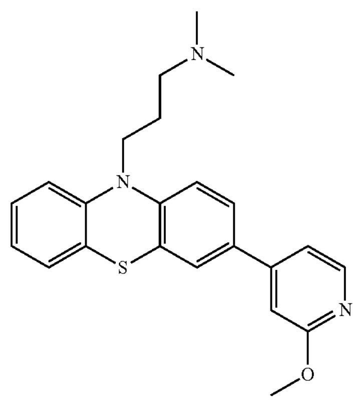 [SMILES: COc1cc(-c2ccc3c(c2)Sc2ccccc2N3CCCN(C)C)ccn1] | $^1$H NMR (DMSO-d$_6$, 400 MHz) δ 1.22 (s, 6H), 1.89 (s, 2H), 3.87 (s, 3H), 3.94 (t, J = 6.0, 2H), 6.86 (d, J = 8.8, 1H), 6.96 (t, J = 6.2, 2H), 7.108-7.042 (m, 2H), 7.215-7.162 (m, 2H), 7.449 (s, 1H), 7.48 (d, J = 8.4 Hz, 1H), 7.96 (d, J = 6 Hz, 1H), 8.43 (d, J = 2.8 Hz, 1H). |
| 155 | 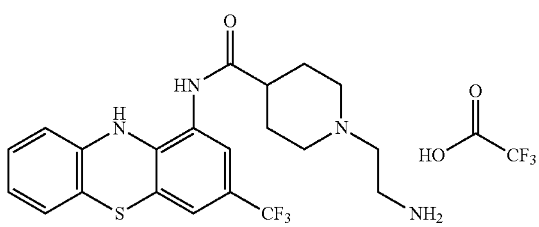 [SMILES: NCCN1CCC(C(=O)Nc2cc(C(F)(F)F)cc3c2Nc2ccccc2S3)CC1 ; O=C(O)C(F)(F)F] | $^1$H NMR (DMSO-d$_6$, 400 MHz) δ 0.1.82-1.85 (m, 1H), 2.10-2.15 (m, 2H), 2.99-3.22 (m, 7H), 6.84-6.89 (m, 2H), 6.98 (d, J = 7.6 Hz, 1H), 7.05 (t, J = 7.6 Hz, 1H), 7.17 (s, 1H), 7.34 (s, 1H), 7.91-8.04 (m, 4H). |
| 156 | 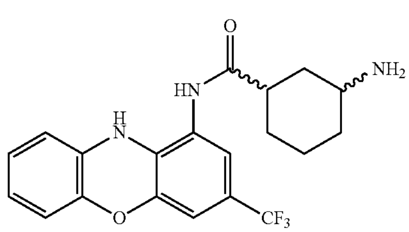 [SMILES: NC1CCCC(C(=O)Nc2cc(C(F)(F)F)cc3c2Nc2ccccc2O3)C1] | $^1$H NMR (DMSO-d$_6$, 400 MHz) δ 0.94-0.97 (m, 1H), 1.18-1.26 (m, 3H), 1.74-1.83 (m, 4H), 1.96 (d, J = 11.2 Hz, 1H), 2.49-2.65 (m, 4H), 6.65-6.67 (m, 3H), 6.73 (s, 1H), 6.77-6.81 (m, 1H), 7.26 (s, 1H), 7.87 (s, 1H). |
| 157 | 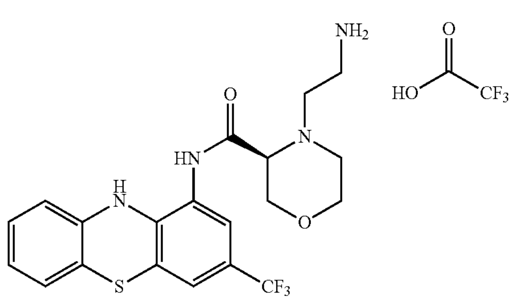 [SMILES: NCCN1CCOC[C@H]1C(=O)Nc1cc(C(F)(F)F)cc2c1Nc1ccccc1S2 ; O=C(O)C(F)(F)F] | $^1$H NMR (DMSO-d$_6$, 400 MHz) δ 2.49-2.62 (m, 2H), 2.81-2.92 (m, 2H), 3.43 (s, 2H), 3.59 (d, J = 8.8 Hz, 1 H), 3.69-3.74 (m, 3H), 4.03 (d, J = 10 Hz, 2H), 6.90 (d, J = 6.4 Hz, 2H), 7.01 (d, J = 7.2 Hz, 1H), 7.09 (t, J = 7.2 Hz, 1H), 7.20 (s, 1H), 7.40 (S, 1H), 7.56 (br s, 2 H), 7.97 (s, 1H) |

TABLE 14-continued

| Cmpd # | Structure | NMR data |
|---|---|---|
| 158 | 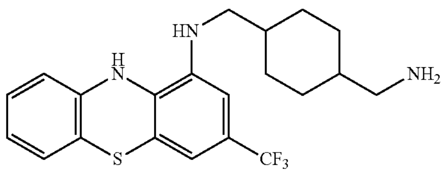 [SMILES: NCC1CCC(CNc2cc(C(F)(F)F)cc3c2Nc2ccccc2S3)CC1] | $^1$H NMR (DMSO-d$_6$, 400 MHz) δ 1.22-1.32 (m, 4H), 1.45-1.55 (m, 2H), 1.55 (bs, 1H), 1.78 (m, 2H), 1.88-1.91 (m, 2H), 2.95 (s, 2H), 5.50 (s, 1H), 6.50 (s, 1H), 6.55 (s, 1H), 6.81-6.84 (t, J = 7.2 Hz, 1H), 6.89-6.91 (d, J = 7.6 Hz, 1H), 6.94-6.96 (d, J = 7.6 Hz, 2H), 7.02-7.05 (t, J = 7.2 Hz, 1H), 8.03 (s, 1H) |
| 159 | 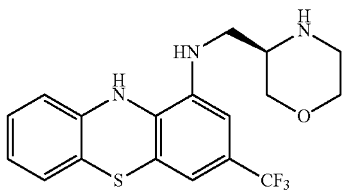 [SMILES: FC(F)(F)c1cc(NC[C@@H]2COCCN2)c2c(c1)Sc1ccccc1N2] | $^1$H NMR (DMSO-d$_6$, 400 MHz) δ 2.73-2.81 (m, 2H), 2.73-2.81 (m, 2H), 2.92-2.94 (m, 1H), 2.97-2.02 (m, 2H), 3.35 (t, J = 10.4 Hz, 1H), 3.67 (d, J = 7.2 Hz, 1H), 3.83 (d, J = 10.4 Hz, 1H), 5.39 (br s, 1H), 6.58 (s, 2H), 6.82 (t, J = 7.2 Hz, 1H), 6.89 (d, J = 7.6 Hz, 1H), 6.95 (d, J = 7.2 Hz, 1H), 7.04 (t, J = 6.8 Hz, 1H), 7.97 (s, 1H) |
| 160 | 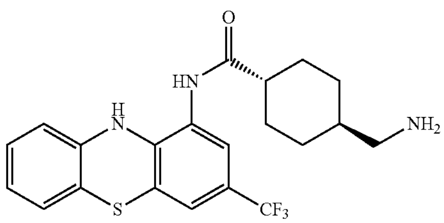 [SMILES: NC[C@H]1CC[C@H](C(=O)Nc2cc(C(F)(F)F)cc3c2Nc2ccccc2S3)CC1] | $^1$H NMR (DMSO-d$_6$, 400 MHz) δ 0.99 (d, J = 12.4 Hz, 2H), 1.22 (s, 2H), 1.4 (d, J = 13.2 Hz, 2H), 1.543 (s, 1H), 1.8 (d, J = 12.4 Hz, 2H), 1.96 (d, J = 9.6 Hz, 2H), 2.65 (s, 1H), 6.66 (d, J = 7.2 Hz, 2H), 6.744 (s, 1H), 6.67 (d, J = 5.6 Hz, 1H), 7.24 (s, 1H), 7.65 (bs, 2H), 7.82 (s, 1H), 9.11 (s, 1H) |
| 161 | 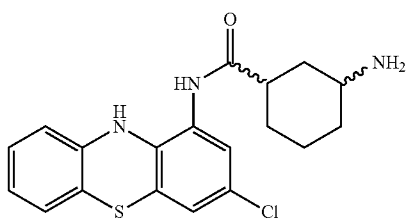 [SMILES: NC1CCCC(C(=O)Nc2cc(Cl)cc3c2Nc2ccccc2S3)C1] | $^1$H NMR (DMSO-d$_6$, 400 MHz) δ 0.95-0.98 (m, 1H), 1.62-1.32 (m, 4H), 1.75-1.99 (m, 3H), 2.60 (s, 1H), 3.46 (t, J = 4.0 Hz, 1H), 3.68 (d, J = 7.2 Hz, 1H), 6.80-6.90 (m, 3H), 6.96 (d, J = 7.6 Hz, 1H), 7.04 (t, J = 8.0 Hz, 1H), 7.14 (s, 1H), 7.71 (s, 1H), 9.14 (s, 1H) |
| 162 | 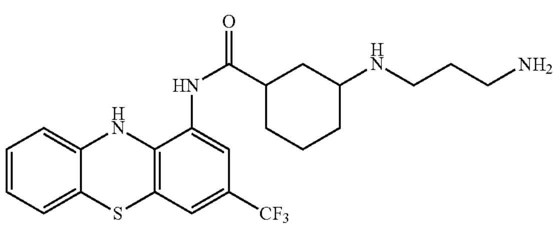 [SMILES: NCCCNC1CCCC(C(=O)Nc2cc(C(F)(F)F)cc3c2Nc2ccccc2S3)C1] | $^1$H NMR (DMSO-d$_6$, 400 MHz) δ 1.12 (s, 2H), 1.30 (s, 2H), 1.46 (s, 1H), 1.62 (s, 3H), 1.77 (s, 2H), 1.88 (s, 2H), 2.16 (d, J = 7.6 Hz, 2H), 2.66 (s, 1H), 2.79 (s, 2H), 6.83 (s, 2H), 7.01-6.93 (m, 4H), 7.09 (s, 1H), 7.41 (s, 1H) |
| 163 | 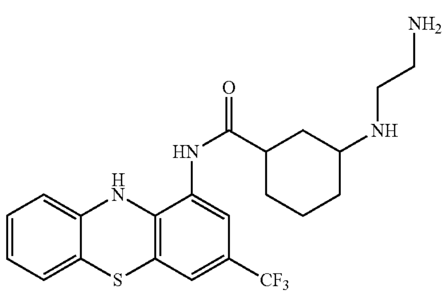 [SMILES: NCCNC1CCCC(C(=O)Nc2cc(C(F)(F)F)cc3c2Nc2ccccc2S3)C1] | $^1$H NMR (DMSO-d$_6$, 400 MHz) δ, 0.92-1.10 (m, 2H), 1.44-1.59 (m, 2H), 1.71-1.98 (m, 3H), 2.11-2.14 (m, 2H), 2.49-2.95 (m, 8 H), 6.84-7.10 (m, 5H), 7.41 (s, 1H), 8.17 (bs, 1H), 9.15 (bs, 1 H) |
| 164 | 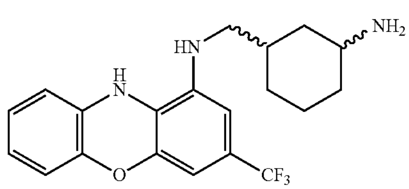 [SMILES: NC1CCCC(CNc2cc(C(F)(F)F)cc3c2Nc2ccccc2O3)C1] | $^1$H NMR (DMSO-d$_6$, 400 MHz) δ 0.73-0.76 (m, 2H), 1.27-1.34 (m, 3H), 1.60-1.69 (m, 1H), 1.75-1.78 (m, 3H), 1.93-1.96 (m, 1H), 2.66 (b, 2H), 2.91-2.92 (m, 2H), 4.13 (s, 1H), 5.01 (s, 1H), 6.25 (s, 1H), 6.31 (s, 1H), 6.56-6.62 (m, 2H), 6.74-6.76 (m, 1H), 7.67 (m, 1H) |

TABLE 14-continued

| Cmpd # | Structure | NMR data |
|---|---|---|
| 165 | [Structure: phenothiazine with CF3, NH-C(O)-CH2-cyclohexyl-NH2, and TFA salt] | ¹H NMR (400 MHz, DMSO-d6): δ 1.34-1.16 (m, 2 H), 1.60-1.54 (m, 2 H), 1.79-1.69 (m, 2 H), 1.88 (s, 2 H), 2.03 (d, J = 11.2 Hz, 1 H), 2.49-2.25 (m, 3 H), 3.02 (s, 1H), 6.88 (q, J = 8.4 Hz, 2 H), 6.98 (d, J = 7.2 Hz, 2 H), 7.05 (t, J = 7.2 Hz, 1 H), 7.15 (s, 1H), 7.36 (s, 1H), 7.70 (bs, 3 H), 8.03 (s, 1H), 9.39 (s, 1H) |
| 167 | [Structure: phenothiazine with CF3, NH-C(O)-CH2-cyclohexyl-NH2] | ¹H NMR (400 MHz, DMSO-d6): δ 1.80-1.13 (m, 11 H), 2.30 (d, J = 10 Hz, 2 H), 2.99 (s, 1H), 6.97-6.83 (m, 3 H), 7.04 (t, J = 7.6 Hz, 1 H), 7.11 (s, 1H), 7.39 (s, 1H), 8.3 (bs, 1H), 9.4 (bs, 1H) |
| 169 | [Structure: phenoxazine with CF3, NH-piperidine] | ¹H NMR (DMSO-d6, 400 MHz) δ 1.27-1.36 (m, 2H), 1.88 (d, J = 11.6 Hz, 2H), 2.56-2.66 (m, 2H), 2.98 (d, J = 12 Hz, 2H), 3.28 (b, 1H), 4.13 (s, 1H), 4.84 (d, J = 6.8 Hz, 1H), 6.24 (s, 1H), 6.39 (s, 1H), 6.55-6.64 (m, 3H), 6.74-6.78 (m, 1H), 7.66 (s, 1H) |
| 170 | [Structure: phenothiazine with CF3, NH-C(O)-cyclohexyl-(NH2)2] | ¹H NMR (DMSO-d6, 400 MHz) δ: 0.80-0.83 (m, 1H), 0.95 (d, J = 11.6 Hz, 1H), 1.05-1.14 (m, 2H), 1.22 (s, 1H), 1.94-1.97 (m, 4H), 2.65 (s, 1H), 6.65 (bs, 1H), 6.83-6.87 (m, 1H), 6.91 (s, 1H), 6.97 (d, J = 6.8 Hz, 1H), 7.03-7.05 (m, 1H), 7.12 (s, 1H), 7.37 (s, 1H), 8.03 (bs, 1H) |
| 171 | [Structure: phenothiazine with CF3, NH-CH2-cyclohexyl-NH2] | ¹H NMR (DMSO-d6, 400 MHz) δ: 0.68-0.77 (m, 1H), 0.81-0.87 (m, 1H), 0.90-0.96 (m, 1H), 1.25 (bs, 2H), 1.63-1.79 (m, 6H), 1.94 (d, J = 12.4 Hz, 1H), 2.95 (d, J = 6.0 Hz, 2H), 3.16 (d, J = 4.8 Hz, 1H), 5.49 (s, 1H), 6.50 (s, 1H), 6.54 (s, 1H), 6.80-6.84 (m, 1H), 6.88-6.90 (m, 1H), 7.02-7.05 (m, 1H), 8.01 (s, 1H) |
| 172 | [Structure: phenothiazine with CF3, NH-piperidin-3-yl] | ¹H NMR (DMSO-d6, 400 MHz) δ 1.65 (t, J = 8.4 Hz, 2H), 1.96 (s, 3H), 2.77 (t, 1H), 2.88 (s, 1H), 3.19 (s, 1H), 3.73 (s, 1H), 5.22 (s, 1H), 6.65 (d, J = 13.2 Hz, 2H), 6.85-6.81 (m, 1H), 6.95 (s, J = 7.2 Hz, 1H), 7.02 (d, J = 6 Hz, 1H), 8.22 (s, 1H) |

TABLE 14-continued

| Cmpd # | Structure | NMR data |
|---|---|---|
| 173 | 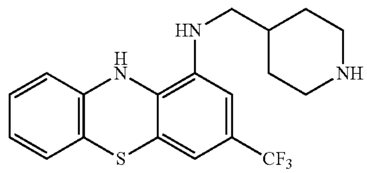 [SMILES: FC(F)(F)c1cc(NCC2CCNCC2)c2c(c1)Sc1ccccc1N2] | $^1$H NMR (DMSO-d$_6$, 400 MHz) δ 1.08-1.22 (m, 2H), 1.74 (d, J = 12 Hz, 2H), 2.95-3.15 (m, 4H), 3.46-3.50 (m, 2H), 3.67-3.70 (m, 2H), 5.47 (br s, 1H), 6.55 (d, J = 12 Hz, 2H), 6.82 (t, J = 7.6 Hz, 1H), 6.90 (d, J = 8 Hz, 1H), 6.96 (d, J = 6.8 Hz, 1H), 7.03 (t, J = 7.02 Hz, 1H), 8.020 (s, 1H) |
| 174 | 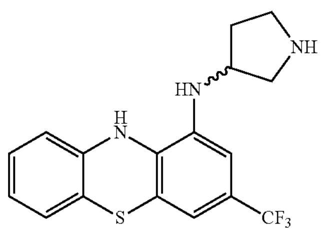 [SMILES: FC(F)(F)c1cc(NC2CCNC2)c2c(c1)Sc1ccccc1N2] | $^1$H NMR (DMSO-d$_6$, 400 MHz) δ 1.59-1.63 (m, 1H), 2.00-2.06 (m, 1H), 2.67 (t, J = 8 Hz, 1H), 2.75-2.78 (m, 1 H), 2.88-2.90 (m, 1H), 2.93-3.05 (m, 1H), 3.84 (br s, 1H), 5.46 (d, J = 5.6 Hz, 2H), 6.57 (d, J = 11.2 Hz, 1H), 6.83 (t, J = 7.6 Hz, 1H), 6.89 (d, J = 7.6 Hz, 1H), 6.95 (d, J = 7.2 Hz, 1H), 7.01-7.05 (m, 1H), 7.20 (s, 1H), 8.01 (s, 1H) |
| 175 | 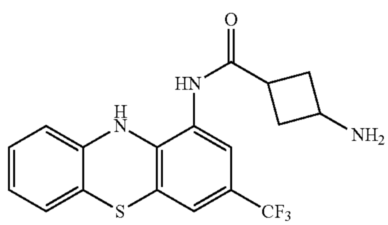 [SMILES: NC1CC(C(=O)Nc2cc(C(F)(F)F)cc3c2Nc2ccccc2S3)C1] | $^1$H NMR (DMSO-d$_6$, 400 MHz) δ 1.88 (d, J = 8.8 Hz, 2H), 2.38 (d, J = 7.2 Hz, 2H), 2.82 (t, J = 8 Hz, 1H), 3.26 (s, 1H), 6.83-6.90 (m, 1H), 6.97 (d, J = 7.6 Hz, 1H), 7.06 (t, J = 7.2 Hz, 1H), 7.11 (s, 1H), 7.39 (s, 1H), 8.07 (s, 1H), 9.40 (s, 1H) |
| 178 | 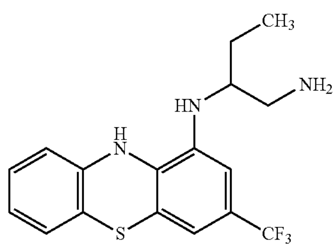 | $^1$H NMR (DMSO-d$_6$, 400 MHz) δ 2.77-2.88 (m, 2H), 3.65-3.72 (m, 2H), 3.77-3.81 (m, 1H), 5.29-5.31 (m, 1H), 6.64 (s, 1H), 6.69 (s, 1H), 6.81-6.85 (t, J = 7.6 Hz, 1H), 6.90 (d, J = 8 Hz, 1H), ), 6.96 (d, J = 7.6 Hz, 1H), 7.02-7.06 (t, J = 7.6 Hz, 1H), 8.26 (bs, 1H) |
| 179 | 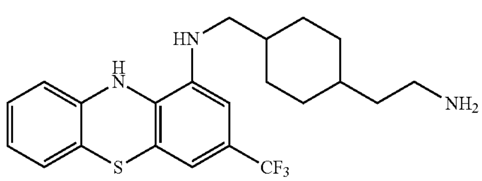 [SMILES: NCCC1CCC(CNc2cc(C(F)(F)F)cc3c2Nc2ccccc2S3)CC1] | $^1$H NMR (DMSO-d$_6$, 400 MHz) δ 1.23-1.25 (m, 3H), 1.59 (br s, 1H), 1.79 (d, J = 11.2 Hz, 2H), 1.91 (t, J = 10.8 Hz, 2H), 2.34 (br s, 2H), 2.71 (br s, 2H), 2.87 (d, J = 10.8 Hz, 2H), 2.98 (br s, 2H), 4.48 (br s, 1H), 5.48 (br s, 1H), 6.56 (d, J = 13.2 Hz, 2H), 6.83 (t, J = 7.2 Hz, 1H), 6.91 (d, J = 7.6 Hz, 1H), 6.96 (d, J = 7.6 Hz, 1H), 7.04 (t, J = 7.2 Hz, 1H), 8.03 (s, 1H) |
| 180 | 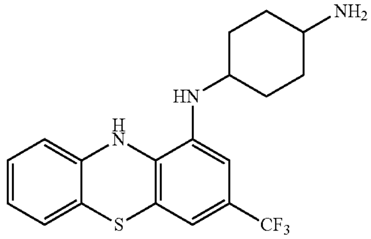 [SMILES: NC1CCC(Nc2cc(C(F)(F)F)cc3c2Nc2ccccc2S3)CC1] | $^1$H NMR (DMSO-d$_6$, 400 MHz) δ 1.63 (d, J = 11.2 Hz, 6H), 1.72 (d, J = 8.4 Hz, 2H), 1.871 (s, 2H), 1.543 (s, 1H), 2.99 (bs, 1H), 3.423 (bs, 1H), 5.2 (d, J = 6.4 Hz, 1H), 6.54 (d, J = 5.2 Hz, 2H), 6.840 (t, J = 7.6 Hz, 1H), 6.900-6.956 (m, 2H), 7.053 (t, J = 7.2 Hz, 1H), 8.213 (s, 1H), 9.117 (s, 1H) |

TABLE 14-continued

| Cmpd # | Structure | NMR data |
|---|---|---|
| 181 | 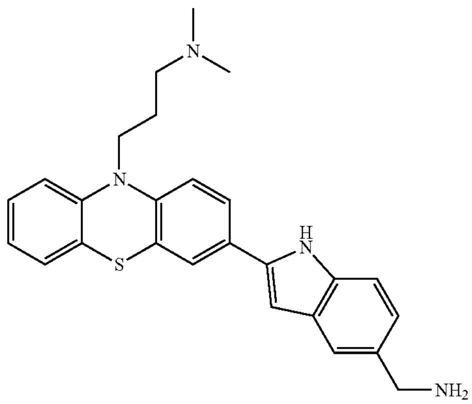 [SMILES: CN(C)CCCN1c2ccccc2Sc2cc(-c3cc4cc(CN)ccc4[nH]3)ccc21] | $^1$H NMR (DMSO-$d_6$, 400 MHz) δ 1.81 (t, J = 6.8 Hz, 2H), 2.11 (s, 6H), 2.34 (t, J = 6.8 Hz, 2H), 3.94 (t, J = 6.8 Hz, 2H), 4.04 (s, 2H), 6.85 (s, 1H), 6.95 (t, J = 7.6 Hz, 1H), 7.05 (d, J = 8.0 Hz, 1H), 7.09-7.23 (m, 4H), 7.38 (d, J = 8.0 Hz, 1H), 7.57 (s, 1H), 7.65-7.95 (m, 4H), 11.51 (s, 1H) |
| 182 | 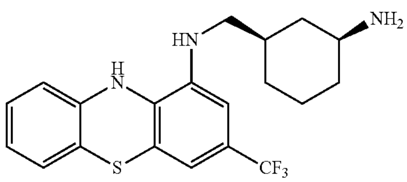 [SMILES: N[C@H]1CCC[C@@H](CNc2cc(C(F)(F)F)cc3c2Nc2ccccc2S3)C1] | $^1$H NMR (DMSO-$d_6$, 400 MHz) δ 0.75-0.97 (m, 1H), 1.01 (d, J = 10.8 Hz, 1H), 1.25 (br s, 2H), 1.63-1.79 (m, 4H), 1.96 (d, J = 11.6 Hz, 1 H), 2.64 (br s, 1H), 2.96 (d, J = 5.6 Hz, 2H), 5.50 (s, 1H), 6.53 (d, J = 14 Hz, 2H), 6.83 (t, J = 7.2 Hz, 1H), 6.88 (d, J = 7.6 Hz, 1H), 6.94 (d, J = 6.8 Hz, 1H), 7.02 (t, J = 7.2 Hz, 1H), 7.98 (s, 1H), 8.06 (s, 1H) |
| 184 | 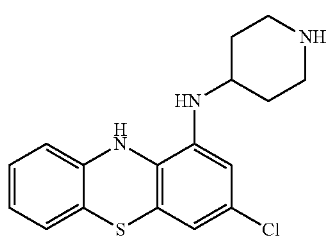 [SMILES: Clc1cc(NC2CCNCC2)c2c(c1)Sc1ccccc1N2] | $^1$H NMR (DMSO-$d_6$, 400 MHz) δ 1.13-1.31 (m, 3H), 1.87 (d, J = 12.0 Hz, 2H), 2.53-2.64 (m, 2H), 2.96 (d, J = 12.0 Hz, 2H), 5.19 (d, J = 7.6 Hz, 1H), 6.27 (s, 1H), 6.37 (s, 1H), 6.77 (t, J = 7.6 Hz, 1H), 6.84 (t, J = 8.0 Hz, 1H), 6.91 (t, J = 7.2 Hz, 1H), 6.99 (t, J = 7.6 Hz, 1H), 7.77 (s, 1H) |
| 186 | 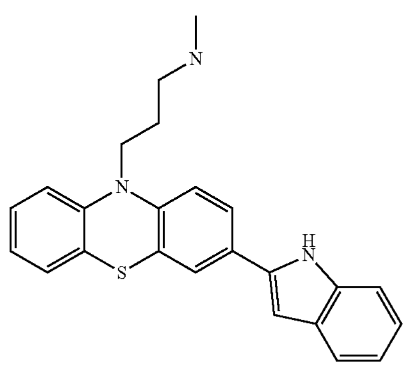 [SMILES: CNCCCN1c2ccccc2Sc2cc(-c3cc4ccccc4[nH]3)ccc21] | $^1$H NMR (DMSO-$d_6$, 400 MHz) δ, 1.81 (t, J = 6.8 Hz, 2H), 2.23 (s, 3H), 2.54-2.64 (m, 2H), 3.93 (t, J = 7.2 Hz, 2H), 6.77 (bs, 1H), 6.93 (q, J = 7.2 Hz, 2H), 7.03 (t, J = 6.0 Hz, 2H)7.08 (d, J = 8.4 Hz, 1 H), 7.14-7.20 (m, 2H), 7.33 (d, J = 8.0 Hz, 1H), 7.46 (d, J = 7.6 Hz, 1H), 7.60-7.65 (m, 2H) |
| 187 | 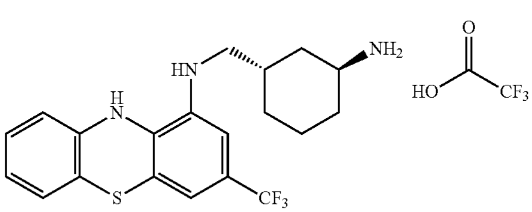 [SMILES: N[C@H]1CCC[C@H](CNc2cc(C(F)(F)F)cc3c2Nc2ccccc2S3)C1 ; O=C(O)C(F)(F)F] | $^1$H NMR (DMSO-$d_6$, 400 MHz) δ: 0.84-087 (m, 1H), 0.93-0.96 (m, 1H), 1.02-1.28 (m, 2H), 1.68 (bs, 1H), 1.76-1.83 (m, 2H), 1.88-1.90 (m, 1H), 3.02 (bs, 4H), 5.64 (s, 1H), 6.52-6.54 (d, J = 6.0 Hz, 2H), 6.80 (t, J = 7.6 Hz, 1H), 6.88 (d, J = 7.6 Hz, 1H), 6.94 (d, J = 6.8 Hz, 1H), 7.00-7.04 (t, J = 6.8 Hz, 1H), 7.73 (bs, 3H), 7.99 (s, 1H) |

TABLE 14-continued

| Cmpd # | Structure | NMR data |
|---|---|---|
| 188 | 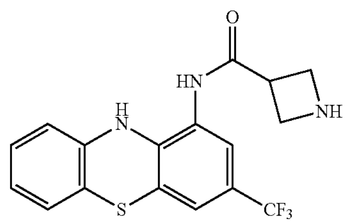 [SMILES: O=C(Nc1cc(C(F)(F)F)cc2c1Nc1ccccc1S2)C1CNC1] | $^1$H NMR (DMSO-d$_6$, 400 MHz) δ 3.54 (t, J = 7.2 Hz, 2H), 3.61-3.66 (m, 1H), 3.78 (t, J = 7.6 Hz, 2H), 3.91-3.99 (m, 1H), 6.82 (d, J = 7.6 Hz, 1H), 6.86 (d, J = 6.0 Hz, 1H), 6.95 (d, J = 7.2 Hz, 1H), 7.03 (d, J = 8.0 Hz, 1H), 7.13 (s, 3H), 7.34 (s, 1H), 8.00 (s, 1H), 9.30 (s, 1H) |
| 189 | 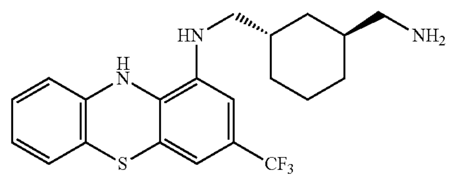 [SMILES: NC[C@H]1CCC[C@H](CNc2cc(C(F)(F)F)cc3c2Nc2ccccc2S3)C1] | $^1$H NMR (DMSO-d$_6$, 400 MHz) δ 0.78-.084 (m, 3H), 1.26-1.33 (m, 4H), 1.40 (bs, 1H), 1.75 (d, J = 11.2 Hz, 2H), 1.83-1.92 (m, 3H), 3.27 (s, 2H), 4.11 (s, 1H), 5.51 (s, 1H), 6.48 (s, 1H), 6.53 (s, 1H), 6.81 (t, J = 7.2 Hz, 1H), 6.89 (d, J = 7.6 Hz, 1H), 6.94 (d, J = 7.2 Hz, 1H), 7.02 (t, J = 7.2 Hz, 1H), 8.01 (s, 1H) |
| 190 | 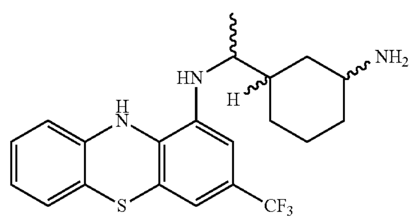 [SMILES: CC(Nc1cc(C(F)(F)F)cc2c1Nc1ccccc1S2)C1CCCC(N)C1] | $^1$H NMR (DMSO-d$_6$, 400 MHz) δ 1.10 (d, J = 6.4 Hz, 3H), 1.48 (s, 2H), 1.72 (d, J = 14.0 Hz, 4H), 1.86 (s, 1H), 1.96 (s, 1H), 3.4 (s, 2H), 5.21 (d, J = 8 Hz, 1H), 6.52 (d, J = 10 Hz, 2H), 6.81 (d, J = 7.6 Hz, 1H), 6.89 (d, J = 7.2 Hz, 1H), 6.94 (d, J = 7.6 Hz, 1H), 7.03 (t, J = 7.6 Hz, 1H), 8.04 (s, 1H) |
| 191 | 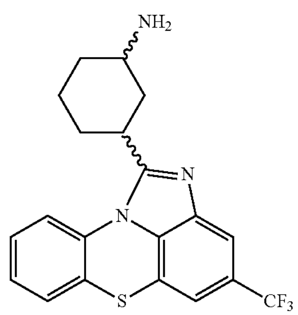 [SMILES: NC1CCCC(c2nc3cc(C(F)(F)F)cc4c3n2-c2ccccc2S4)C1] | $^1$H NMR (DMSO-d$_6$, 400 MHz) δ 1.07 (d, J = 12.0 Hz, 1H), 1.52-1.45 (m, 3H), 1.78 (s, 1H), 1.87 (s, J = 12.8 Hz, 1H), 2.06 (s, 1H), 2.20 (d, J = 12.4 Hz, 1H), 2.85 (s, 1H), 3.46 (s, 1H), 7.18 (t, J = 7.6 Hz, 1H), 7.23 (s, 1H), 7.31 (t, J = 7.6 Hz, 2H), 7.54 (s, 1H), 7.63 (d, J = 8.4 Hz, 1H) |
| 192 | 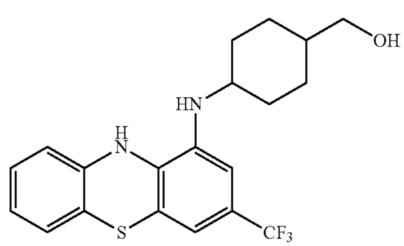 [SMILES: OCC1CCC(Nc2cc(C(F)(F)F)cc3c2Nc2ccccc2S3)CC1] | $^1$H NMR (DMSO-d$_6$, 400 MHz) δ 0.99-1.08 (m, 2H), 1.15-1.21 (m, 3H), 1.27 (br s, 1H), 1.76 (d, J = 12 Hz, 2 H), 2.01 (d, J = 11.2 Hz, 2 H), 3.21-3.27 (m, 2H), 6.51 (s, 1 H), 6.55 (s, 1 H), 6.82 (t, J = 6.8 Hz, 1H), 6.88 (d, J = 8 Hz, 1H), 6.94 (d, J = 7.2 Hz, 1H), 7.03 (t, J = 7.2 Hz, 1H), 7.97 (s, 1H) |
| 193 | 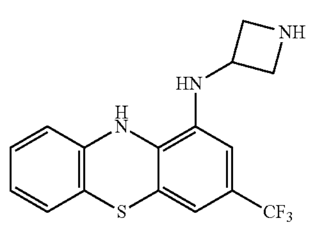 [SMILES: FC(F)(F)c1cc(NC2CNC2)c2c(c1)Sc1ccccc1N2] | $^1$H NMR (DMSO-d$_6$, 400 MHz) δ 3.53-3.57 (m, 2H), 3.91-3.97 (m, 2H), 4.26-4.27 (m, 1H), 5.93-5.94 (m, 1H), 6.30 (s, 1H), 6.61 (s, 1H), 6.72-6.86 (m, 2H), 6.93 (d, J = 7.6 Hz, 1H), 7.01-7.05 (t, J = 7.6 Hz, 1H), 7.96 (s, 1H) |

TABLE 14-continued

| Cmpd # | Structure | NMR data |
|---|---|---|
| 196 | 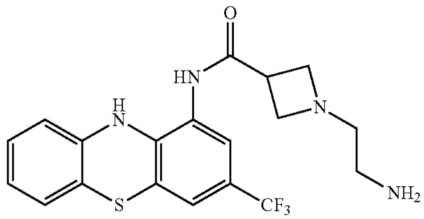 [SMILES: NCCN1CC(C(=O)Nc2cc(C(F)(F)F)cc3c2Nc2ccccc2S3)C1] | $^1$H NMR (DMSO-d$_6$, 400 MHz) δ 1.21-1.36 (m, 2H), 2.30-2.38 (m, 2H), 3.20-3.26 (m, 3H), 3.43-3.48 (m, 3H), 4.10-4.12 (m, 1H), 6.81-6.89 (m, 2H), 6.95 (t, J = 6.0 Hz, 1H), 7.03 (t, J = 8.0 Hz, 1H), 7.12 (s, 1H), 7.33 (s, 1H), 7.63-7.70 (m, 1H), 9.30-9.45 (m, 1H) |
| 197 | 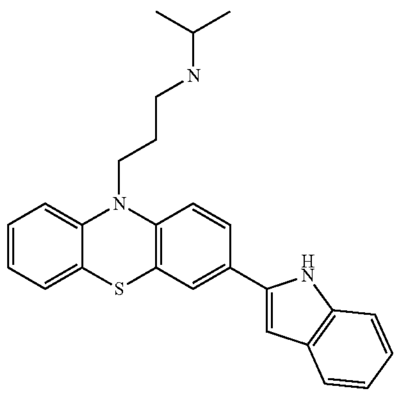 [SMILES: CC(C)NCCCN1c2ccccc2Sc2cc(-c3cc4ccccc4[nH]3)ccc21] | $^1$H NMR (DMSO-d$_6$, 400 MHz) δ 0.90 (d, J = 6.0 Hz, 6H), 1.45 (bs, 1H), 1.75-1.82 (m, 2H), 2.60-2.65 (m, 2H), 3.95 (t, J = 7.2 Hz, 2H), 6.77 (s, 1H), 6.90-6.96 (m, 2H), 7.02-7.06 (m, 2H), 7.13 (d, J = 12.0 Hz, 1H), 7.16-7.20 (m, 2H), 7.33 (t, J = 8.0 Hz, 1H), 7.46 (t, J = 8.0 Hz, 1H), 7.60 (s, 1H), 7.61-7.66 (m, 1H), 11.37 (s, 1H) |
| 198 | 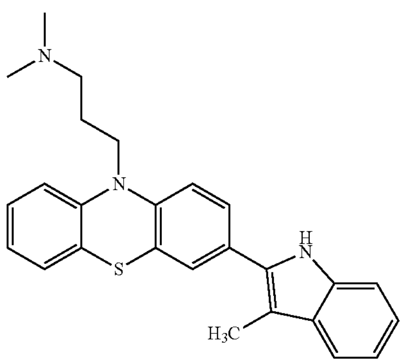 [SMILES: Cc1c(-c2ccc3c(c2)Sc2ccccc2N3CCCN(C)C)[nH]c2ccccc12] | $^1$H NMR (DMSO-d$_6$, 400 MHz) δ 1.80 (t,, J = 6.8 Hz, 2H), 2.09 (s, 6H), 2.32 (t, J = 7.2 Hz, 2H), 2.47 (s, 3H), 3.93 (t, J = 6.8 Hz, 2H), 6.94 (q, J = 7.6 Hz, 2 H), 7.05 (t, J = 8.0 Hz, 2H), 7.21-7.11 (m, 3H), 7.28 (d, J = 8.0 Hz, 2H), 7.40 (d, , J = 1.6 Hz, 1H), 7.47 (t, J = 6.8 Hz, 2H), 11.02 (s, 1H); |
| 199 | 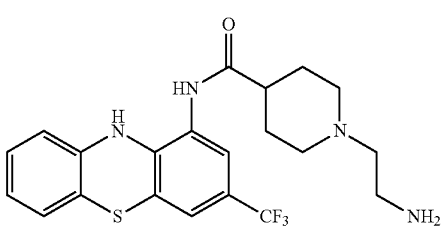 | $^1$H NMR (DMSO-d$_6$, 400 MHz) δ 1.79-1.84 (m, 2H), 2.09 (s, 6H), 2.26-2.35 (m, 5H), 3.92 (q, J = 6.8 Hz, 2H), 6.92-6.98 (m, 2 H), 7.03-7.06 (m, 2H), 7.11-7.21 (m, 3H), 7.28 (d, J = 8.0 Hz, 2H), 7.40-7.41 (m, 1H), 7.47 (t, J = 6.8 Hz, 2H), 11.02 (s, 1H); |
| 203 | 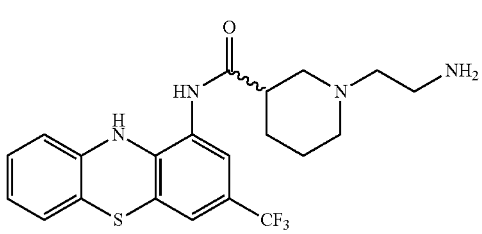 [SMILES: NCCN1CCCC(C(=O)Nc2cc(C(F)(F)F)cc3c2Nc2ccccc2S3)C1] | $^1$H NMR (DMSO-d$_6$, 400 MHz) δ 1.21-1.25 (m, 1H), 1.48 (d, J = 8.4 Hz, 2 H), 1.66 (br s, 1H), 1.87 (br s, 1H), 1.98 (br s, 1H), 2.18 (d, J = 10 Hz, 1H), 2.33 (br s, 1H), 2.64-2.67 (m, 3H), 2.94 (d, J = 10 Hz, 1H), 3.07 (br s, 1H), 6.82-6.88 (m, 2H), 6.96 (d, J = 7.6 Hz, 1 H), ), 7.04 (t, J = 7.2 Hz, 1 H), 7.11 (s, 1 H), 7.34 (s, 1 H) |

TABLE 14-continued

| Cmpd # | Structure | NMR data |
|---|---|---|
| 204 | 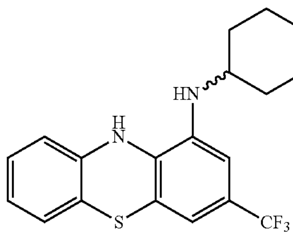 | $^1$H NMR (DMSO-d$_6$, 400 MHz) δ, 0.92-1.07 (m, 2H), 1.31-1.35 (m, 2H), 1.52-1.75 (m, 4H), 1.91 (d, J = 12.4 Hz, 1H), 2.06 (d, J = 11.6 Hz, 1H), 3.13-3.72 (m, 0.5H, m, 0.5 H), 5.10 (d, J = 6.0 Hz,0.5 H), 5.23 (d, J = 6.0 Hz,0.5 H), 6.52 (s, 1H), 6.56 (d, J = 11.6 Hz, 1 H), 6.80 (t, J = 7.2 Hz, 1H), 6.86 (d, J = 8.0 Hz, 1H), 6.93 (d, J = 7.6 Hz, 1H), 7.04 (t, J = 7.6 Hz, 1H), 7.97 (s,0.5 H), 8.05 (s, 1H) |
| 205 | 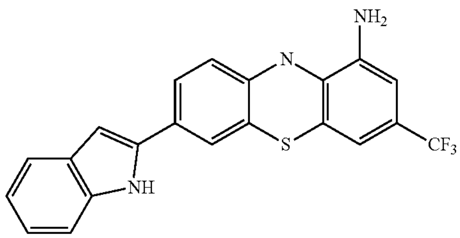 [SMILES: Nc1cc(C(F)(F)F)cc2c1Nc1ccc(-c3cc4ccccc4[nH]3)cc1S2] | $^1$H NMR (DMSO-d$_6$, 400 MHz) δ 5.43 (s, 2H), 6.52 (s, 1H), 6.72 (d, J = 5.2 Hz, 2H), 6.88 (d, J = 8.4 Hz, 1H), 6.94 (t, J = 7.6 Hz, 1H), 7.02 (t, J = 7.6 Hz, 1H), 7.31 (d, J = 8.0 Hz, 1H), 7.43 (d, J = 4 H, 1H), 7.45 (s, 1H), 7.49 (d, J = 8.4 Hz, 1H), 7.92 (s, 1H), 11.3 (s, 1H) |
| 206 | 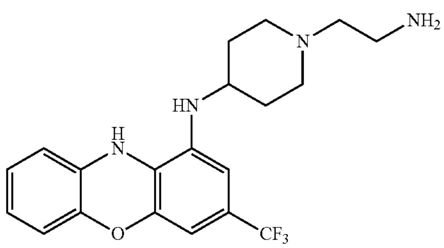 | $^1$H NMR (DMSO-d$_6$, 400 MHz) δ 1.35-1.40 (m, 3H), 1.87-1.90 (m, 3H), 2.01-2.07 (m, 3H), 2.28-2.29 (m, 2H), 2.57-2.60 (m, 2H), 20.8 (d, J = 11.2 Hz, 2H), 4.83 (d, J = 6.8 Hz, 1H), 6.22 (s, 1H), 6.36 (s, 1H), 6.54-6.62 (m, 3H), 6.72-6.76 (m, 1H), 7.66 (s, 1H) |
| 207 | 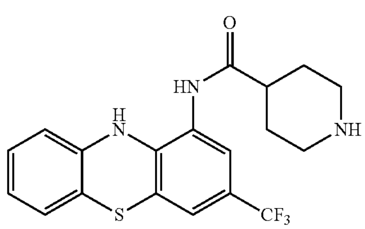 [SMILES: O=C(Nc1cc(C(F)(F)F)cc2c1Nc1ccccc1S2)C1CCNCC1] | $^1$H NMR (DMSO-d$_6$, 400 MHz) δ1.44-1.54 ( m, 2H), 1.77 (d, J = 12.0 Hz, 2H), 2.47 (bs, 2H), 2.98 (d, J = 12.0 Hz, 2H), 6.82-6.95 (m, 1 H), 6.96 (d, J = 22.8 Hz, 1 H), 7.05 (t, J = 7.2 Hz, 1H), 7.11 (s, 1H), 7.37 (s, 1H), 7.97 (s, 1H), 9.26 (s, 1H), MS (ESI) m/z 394.1 (M + H)$^-$; HPLC purity: 99.04%. |
| 208 | 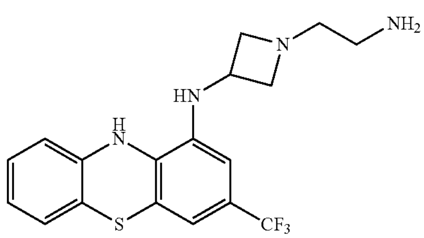 [SMILES: NCCN1CC(Nc2cc(C(F)(F)F)cc3c2Nc2ccccc2S3)C1] | $^1$H NMR (DMSO-d$_6$, 400 MHz) δ 2.47-2.57 (m, 4H), 2.90-2.94 (t, J = 6 Hz, 2H), 3.64-3.68 (t, J = 6.8 Hz, 2H), 3.96-4.00 (m, 1H), 5.89 (bs, 1H), 6.30 (s, 1H), 6.59 (s, 1H), 6.79-6.83 (t, J = 7.2 Hz, 1H), 6.86 (d, J = 7.6 Hz, 1H), 6.93 (d, J = 7.2 Hz, 1H), 7.00-7.04 (t, J = 7.2 Hz, 1H), 7.98 (s, 1H) |
| 210 | 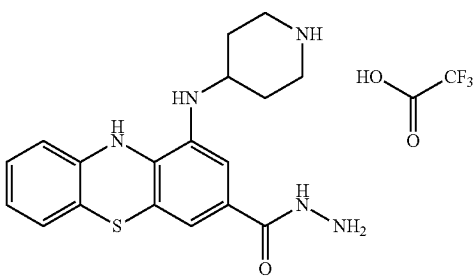 [SMILES: NNC(=O)c1cc(NC2CCNCC2)c2c(c1)Sc1ccccc1N2 ; O=C(O)C(F)(F)F] | $^1$H NMR (DMSO-d$_6$, 400 MHz) δ 1.21 (s, 1H), 1.59 (d, J = 11.6 Hz, 2H), 2.14 (d, J = 11.6 Hz, 2H) 3.02 (d, J = 9.6 Hz, 2H), 5.16 (bs, 1H), 6.85 (t, J = 15.2 Hz, 2H), 6.95 (t, J = 7.2 Hz, 2H), 7.04 (t, J = 7.6 Hz, 1H), 7.989 (s, 1H), 8.329 (bs, 1H), 8.502 (bs, 1H) |

TABLE 14-continued

| Cmpd # | Structure | NMR data |
| --- | --- | --- |
| 211 | 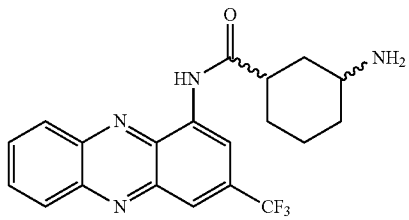 [SMILES: NC1CCCC(C(=O)Nc2cc(C(F)(F)F)cc3nc4ccccc4nc23)C1] | ¹H NMR (DMSO-d₆, 400 MHz) δ 1.20-1.25 (m, 1H), 1.33-1.37 (m, 2H), 1.77-1.80 (m, 2H), 1.91 (s, 1H), 2.03-2.06 (d, J = 12 Hz, 1H), 2.64-2.69 (m, 1H), 2.89-291 (m, 1H), 8.05-8.12 (m, 2H), 8.28 (s, 1H), 8.31-8.34 (dd, 1H), 8.40-8.42 (dd, 1H), 8.91 (s, 1H) |
| 212 | 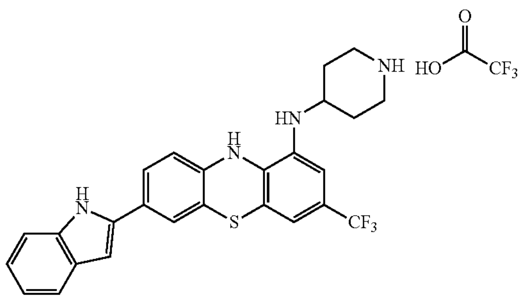 [SMILES: FC(F)(F)c1cc(NC2CCNCC2)c2c(c1)Sc1cc(-c3cc4ccccc4[nH]3)ccc1N2 ; O=C(O)C(F)(F)F] | ¹H NMR (400 MHz, DMSO-d₆): δ 1.58 (q, J = 10 Hz, 2 H), 2.00-1.96 (m, 1 H), 2.08 (d, J = 13.6 Hz, 2 H), 3.05 (d, J = 10.8 Hz, 2 H), 3.37 (bs, 2H), 3.66 (s, 1H), 5.33 (s, 1H), 6.64 (s, 1H), δ 6.71 (d, J = 17.6 Hz, 2 H), 6.96-6.90 (m, 2 H), 7.03 (t, J = 7.2 Hz, 1 H), 7.32 (d, J = 8 Hz, 1 H), 7.45 (s, 2 H), 7.52 (d, J = 8.4 Hz, 1 H), 8.10 (s, 1 H), 8.29 (bs, 1 H), 8.47 (bs, 1 H) |
| 213 | 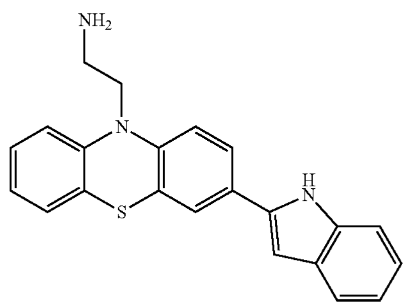 [SMILES: NCCN1c2ccccc2Sc2cc(-c3cc4ccccc4[nH]3)ccc21] | ¹H NMR (DMSO-d₆, 400 MHz) δ 1.31-1.33 (m, 2H), 2.89 (t, J = 6.4 Hz, 2H), 3.92 (t, J = 6.4 Hz, 2H), 6.78 (s, 1H), 6.94 (t, J = 7.6 Hz, 2H), 7.02-7.21 (m, 5H), 7.33 (d, J = 7.6 Hz, 1H), 7.46 (d, J = 7.2 Hz, 1H), 7.62-7.68 (m, 2H), 11.3 (s, 1H) |
| 214 | 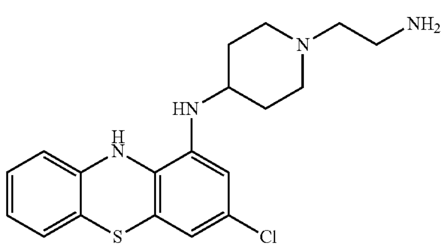 [SMILES: NCCN1CCC(Nc2cc(Cl)cc3c2Nc2ccccc2S3)CC1] | ¹H NMR (DMSO-d₆, 400 MHz) δ 1.37-1.45 (m, 2H), 1.77-1.90 (m, 2H), 2.03-2.06 (m, 2H), 2.26-2.29 (m, 2H), 2.58-2.64 (m, 2H), 2.82 (d, J = 12.0 Hz, 2H), 3.20-3.27 (m, 1H), 5.23 (d, J = 6.4 Hz, 1H), 6.22 (s, 1H), 6.38 (s, 1H), 6.76 (t, J = 8.4 Hz, 1H), 6.85 (d, J = 8.0 Hz, 1H), 6.91 (d, J = 8.0 Hz, 1H), 6.99 (t, J = 8.0 Hz, 1H), 7.82 (s, 1H) |
| 215 | 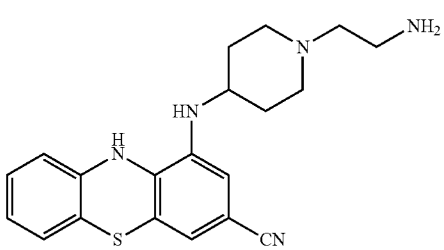 [SMILES: N#Cc1cc(NC2CCN(CCN)CC2)c2c(c1)Sc1ccccc1N2] | ¹H NMR (DMSO-d₆, 400 MHz) δ 1.31 (m, 2H), 1.39-1.44 (m, 2H), 1.65 (s, 1H), 1.77-1.91 (m, 2H), 2.04-2.20 (m, 2H), 2.30 (s, 2H), 2.57-2.64 (m, 2H), 2.82 (d, J = 9.6 Hz, 2H), 5.31 (d, J = 5.6 Hz, 1H), 6.67 (s, 1H), 6.74 9s, 1H), 6.79-6.83 (m, 1H), 6.87-6.91 (m, 2H), 6.92-7.03 (m, 1H), 8.19 (s, 1H) |

TABLE 14-continued

| Cmpd # | Structure | NMR data |
|---|---|---|
| 216 | 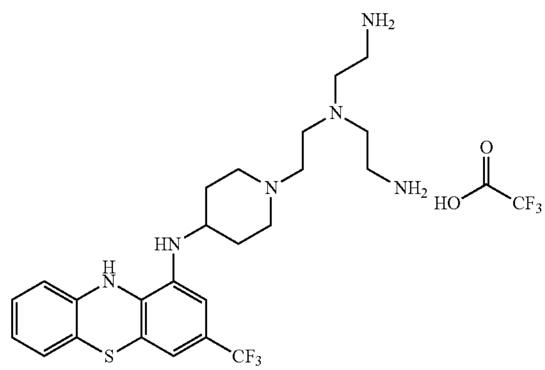 [SMILES: NCCN(CCN)CCN1CCC(Nc2cc(C(F)(F)F)cc3c2Nc2ccccc2S3)CC1 ; O=C(O)C(F)(F)F] | $^1$H NMR (DMSO-d$_6$, 400 MHz) δ, 1.52 (d, J = 11.6 Hz, 2H), 1.88-1.92 (m, 2H), 2.10 (t, J = 11.2 Hz, 2H), 2.37-2.64 (m, 10H), 2.80 (bs, 3H) 2.89 (d, , J = 12.0 Hz, 3H), 5.49 (d, J = 6.4 Hz, 1H), 6.53 (s,, 1H), 6.58 (s, 1 H), 6.80-6.82 (m, 1H), 6.92 (d, J = 7.6 Hz, 1H), 7.01 (d, J = 3.6 Hz, 1H), 8.19 (s, 1H) |
| 217 | 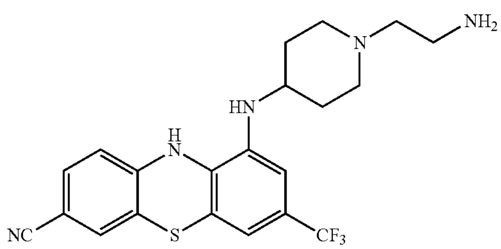 [SMILES: N#Cc1ccc2c(c1)Sc1cc(C(F)(F)F)cc(NC3CCN(CCN)CC3)c1N2] | $^1$H NMR (DMSO-d$_6$, 400 MHz) δ 1.42-1.45 (m, 2H), 1.88 (bs, 2H), 2.07 (d, J = 11.2 Hz, 2H), 2.30-2.33 (m, 2H), 2.65 (d, J = 8 Hz, 2H), 2.81 (bs, 2H), 5.32 (d, J = 6.4 Hz, 1H), 6.54 (s, 1H), 6.59 (s, 1H), 6.93 (d, J = 8.4 Hz, 1H), 7.39-7.43 (m, 2H), 8.51 (bs, 1H) |
| 218 | 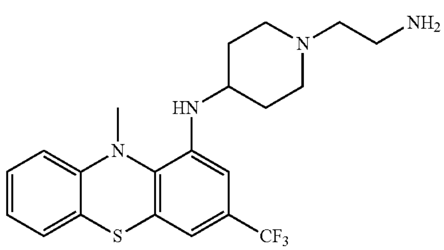 [SMILES: CN1c2ccccc2Sc2cc(C(F)(F)F)cc(NC3CCN(CCN)CC3)c21] | $^1$H NMR (DMSO-d$_6$, 400 MHz) δ 1.5 (d, J = 10.8 Hz, 2H), 1.85 (d, J = 9.2 Hz, 2H), 2.107 (t, J = 10 Hz, 2H), 2.2 (t, J = 5.6 Hz, 2H), 2.5 (d, J = 6 Hz, 2H), 2.77 (d, J = 10 Hz, 2H), 2.970 (s, 1H), 3.122 (s, 3H), 3.272 (s, 2H), 5.144 (d, J = 8.4 Hz, 1H), 6.715 (s, 1H), 6.744 (s, 1H), 7.044 (t, J = 7.6 Hz, 1H), 7.171 (d, J = 7.6 Hz, 1H), 7.23 (t, J = 7.2 Hz, 1H), 7.3015 (d, J = 7.6 Hz, 1H) |
| 219 | 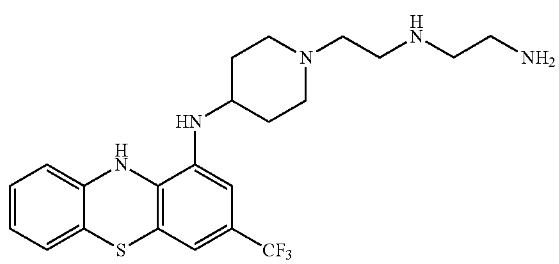 [SMILES: NCCNCCN1CCC(Nc2cc(C(F)(F)F)cc3c2Nc2ccccc2S3)CC1] | $^1$H NMR (DMSO-d$_6$, 400 MHz) δ, 0.95 (d, J = 6.4 Hz, 2H), 1.42 (d, J = 10.0 Hz, 2H), 1.90 (d, J = 11.6 Hz, 2H), 2.37-2.70 (m, 10H), 2.83 (d, J = 11.6 Hz, 2H), 5.23 (d, J = 6.4 Hz, 1H), 6.53 (s, 1H), 6.57 (s, 1 H), 6.81 (t, J = 7.6 Hz, 1H), 6.86 (d, J = 7.6 Hz, 1H), 6.93 (d, J = 7.6 Hz, 1H), 7.02 (t, J = 7.6 Hz), 7.97 (s, 1H) |
| 220 | 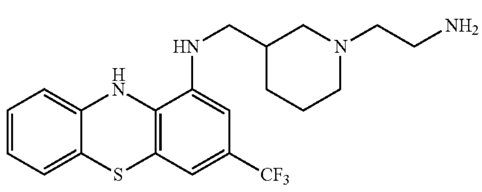 [SMILES: NCCN1CCCC(CNc2cc(C(F)(F)F)cc3c2Nc2ccccc2S3)C1] | $^1$H NMR (DMSO-d$_6$, 400 MHz) δ 1.01 (d, J = 11.6 Hz, 1 H), 1.40-1.45 (m, 2H), 1.77 (d, J = 10.8 Hz, 2H), 1.93-1.98 (m, 2H), 2.11-2.23 (m, 2H), 2.60-2.64 (m, 1H), 2.68 (br s, 1H), 2.71 (br s, 1H), 2.86 (br s, 2H), 5.47 (br s, 1H), 6.50 (s, 1H), 6.54 (s, 1H), 6.81 (t, J = 7.2 Hz, 1 H), 6.88 (d, J = 7.2 Hz, 1 H), 6.94 (d, J = 6.8 Hz, 1 H), 7.02 (t, J = 7.2 Hz, 1 H), 8.02 (s, 1 H) |
| 221 | 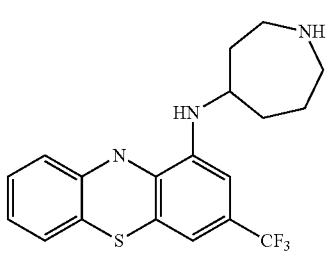 [SMILES: FC(F)(F)c1cc(NC2CCCNCC2)c2c(c1)Sc1ccccc1N2] | $^1$H NMR (DMSO-d$_6$, 400 MHz) δ 1.21 (br s, 2H), 1.63-1.69 (m, 2H), 1.74-1.84 (m, 2H), 1.98-2.01 (m, 2H), 3.06 (t, J = 11.2 Hz, 2H), 3.08-3.18 (m, 2H), 3.66 (br s, 1H), 6.55 (d, J = 12.4 Hz, 2H), 6.80 (t, J = 7.2 Hz, 1H), 6.92-7.03 (m, 3H), 8.20 (s, 1H) |

TABLE 14-continued

| Cmpd # | Structure | NMR data |
|---|---|---|
| 222 | 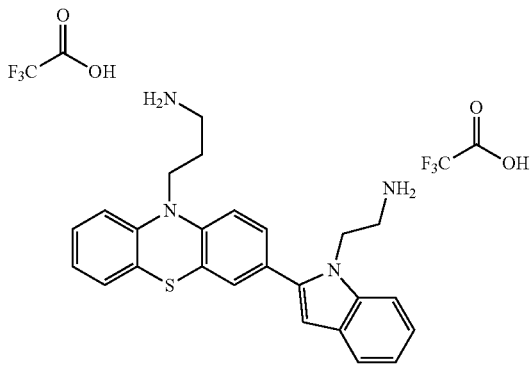 [SMILES: O=C(O)C(F)(F)F ; NCCCN1c2ccccc2Sc2cc(-c3cc4ccccc4n3CCN)ccc21 ; O=C(O)C(F)(F)F] | ¹H NMR (DMSO-d₆, 400 MHz) δ 1.99 (t, J = 7.2 Hz, 2H), 2.91 (m, 4H), 4.02 (t, J = 7.2 Hz, 2H), 4.35 (t, J = 7.6 Hz, 2H), 6.47 (s, 1H), 7.00 (t, J = 7.2 Hz, 1H), 7.08 (t, J = 8.0 Hz, 2H), 7.16-7.27 (m, 4H), 7.36 (d, J = 9.6 Hz, 2H), 7.55 (d, J = 8.0 Hz, 2H), 7.70-7.76 (m, 6H). |
| 223 | 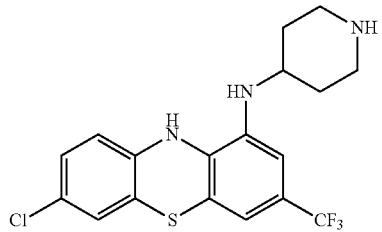 [SMILES: FC(F)(F)c1cc(NC2CCNCC2)c2c(c1)Sc1cc(Cl)ccc1N2] | NMR (DMSO-d₆, 400 MHz) δ 1.26-1.31 (m, 2H), 1.85-1.88 (m, 2H), 2.48-2.58 (m, 2H), 2.93-2.96 (m, 2H), 2.31-2.39 (m, 1H), 5.22 (d, J = 6.8 Hz, 1H), 6.53 (s, 1H), 6.58 (s, 1H), 6.85 (d, J = 8 Hz, 1H), 7.04-7.06 (m, 2H), 8.11 (bs, 1H). |
| 224 | 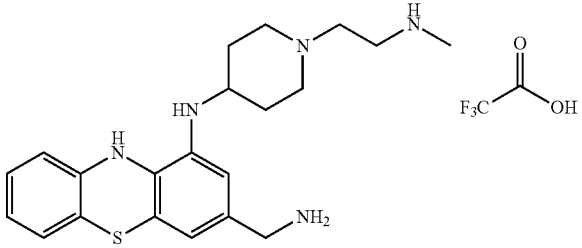 [SMILES: CNCCN1CCC(Nc2cc(CN)cc3c2Nc2ccccc2S3)CC1 ; O=C(O)C(F)(F)F] | ¹H NMR (DMSO-d₆, 400 MHz) δ 1.31-1.34 (m, 2H), 1.40-1.43 (m, 2H), 1.87-2.07 (m, 5H), 2.30-2.47 (m, 5H), 2.64 (s, 2H), 2.87-2.95 (m, 2H), 3.54-3.59 (m, 3H), 4.89 (d, J = 6.8 Hz, 1H), 6.26 (s, 1H), 6.44 (s, 1H), 6.71 (t, J = 7.2 Hz, 1H), 6.83 (d, J = 8 Hz, 1H), 6.90 (d, J = 6.8 Hz, 1H), 6.96 (t, J = 7.2 Hz, 1H), 7.68 (s, 1H) |
| 225 | 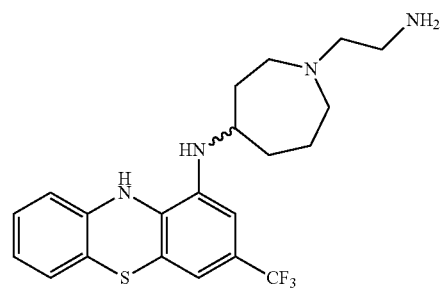 [SMILES: NCCN1CCCC(Nc2cc(C(F)(F)F)cc3c2Nc2ccccc2S3)CC1] | ¹H NMR (DMSO-d₆, 400 MHz) δ 1.64-1.72 (m, 4H), 1.87-1.96 (m, 3H), 2.42-2.64 (m, 7H), 3.55 (s, 1 H), 5.31 (d, J = 7.2 Hz, 1H), 6.45 (s, 1H), 6.52 (s, 1H), 6.80 (t, J = 7.6 Hz, 1H), 6.88 (d, J = 7.2 Hz, 1H), 6.94 (d, J = 6.8 Hz, 1H), 7.03 (t, J = 7.6 Hz, 1H), 8.01 (s, 1H) |
| 226 | 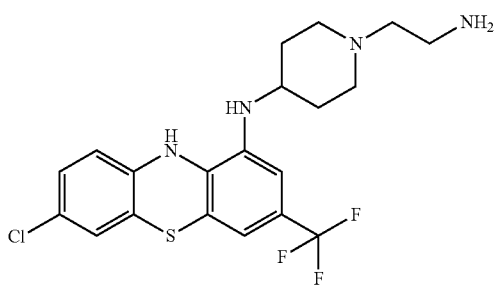 [SMILES: NCCN1CCC(Nc2cc(C(F)(F)F)cc3c2Nc2ccc(Cl)cc2S3)CC1] | NMR (DMSO-d₆, 400 MHz) δ 1.39-1.47 (m, 2H), 1.88-1.91 (m, 2H), 1.96-1.98 (m, 2H), 2.06-2.09 (m, 2H), 2.23-2.27 (m, 2H), 2.61-2.65 (m, 2H), 2.81-2.84 (m, 2H), 6.56 (d, J = 15.2 Hz, 2H), 6.86 (d, J = 8.4 Hz, 1H), 7.04 (s, 1H), 8.11 (s, 1H) |

TABLE 14-continued
| Cmpd # | Structure | NMR data |
|---|---|---|
| 227 | 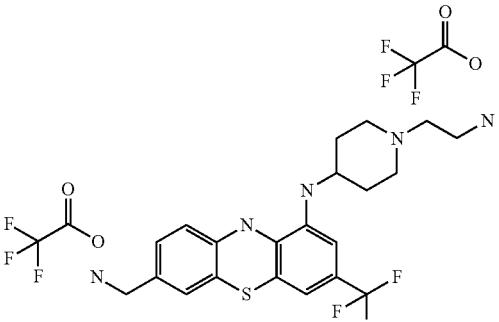 | $^1$H NMR (DMSO-d$_6$, 400 MHz) δ 1.63-1.72 (m, 2H), 1.94-1.98 (m, 2H), 2.07-2.18 (m, 2H), 3.12-3.33 (m, 4H), 3.63-3.73 (m, 2H), 3.83-3.84 (m, 2H), 5.42-5.47 (m, 1H), 6.89-6.63 (m, 2H), 6.85-6.87 (m, 1H), 7.04-7.07 (m, 2H), 7.97 (brs, 4H). |
| 228 | 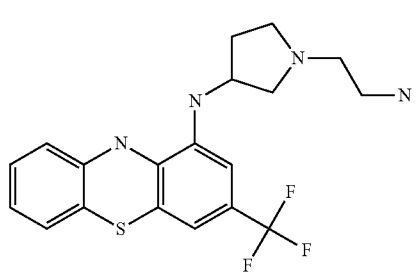 [SMILES: NCCN1CCC(Nc2cc(C(F)(F)F)cc3c2Nc2ccccc2S3)C1] | $^1$H NMR (DMSO-d$_6$, 400 MHz) δ, 1.64-1.76 (m, 2H), 2.18-2.24 (m, 1H), 2.26-2.37 (m, 3H), 2.47-2.53 (m, 2H) 2.62-2.74 (m, 4H), 3.92 (bs, 1H), 5.53 (d, J = 6.8 Hz, 1H), 6.48 (s, 1H), 6.55 (s, 1H), 6.78 (t, J = 10.4 Hz, 1H), 6.81 (d, J = 7.6 Hz, 1H), 6.93 (d, J = 6.8 Hz, 1H), 7.01 (t, J = 6.8 Hz, 1H), 8.03 (s, 1H). |
| 232 | 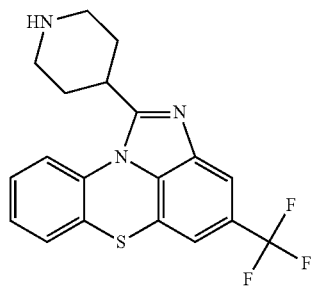 [SMILES: FC(F)(F)c1cc2c3c(c1)nc(C1CCNCC1)n3-c1ccccc1S2] | $^1$H NMR (DMSO-d$_6$, 400 MHz) δ 1.76 (t, J = 10.8 Hz, 2H), 1.99 (d, J = 12.8 Hz, 2H), 2.71 (t, J = 12 Hz, 2H), 3.02 (d, J = 11.6 Hz, 2H), 3.51 (s, 1H), 7.17 (t, J = 7.6 Hz, 1H), 7.23 (s, 1H), 7.31 (s, 2H), 7.56 (s, 1H), 7.66 (s, J = 8.4 Hz, 1H). |
| 234 | 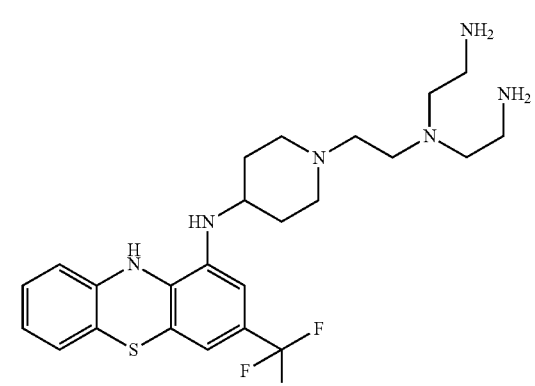 | %); $^1$H NMR (DMSO-d$_6$, 400 MHz) δ, 1.46 (d, J = 10.0 Hz, 2H), 1.89 (d, J = 11.2 Hz, 2H), 2.07 (t, J = 10.8 Hz, 2H), 2.35 (s, 2H), 2.64 (bs, 4H) 2.86 (d, J = 10.4 Hz, 2H), 5.35 (bs, 1H), 6.54 (d, J = 12.8 Hz, 2H), 6.80 (t, J = 7.6 Hz 1 H), 6.92 (t, J = 7.2 Hz, 2H), 7.01 (t, J = 6.8 Hz, 1H), 8.10 (s, 1H). |

TABLE 14-continued

| Cmpd # | Structure | NMR data |
|---|---|---|
| 239 | 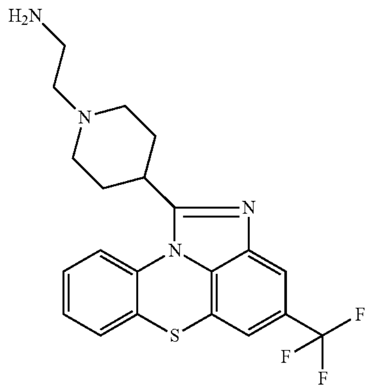 [SMILES: NCCN1CCC(c2nc3cc(C(F)(F)F)cc4c3n2-c2ccccc2S4)CC1] | $^1$H NMR (DMSO-d$_6$, 400 MHz) δ 1.91-1.83 (m, 2H), 2.05 (d, J = 11.6 Hz, 2H), 2.16 (t, J = 11.2 Hz, 2H), 2.35-2.30 (m, 2H), 3.51 (s, 1H), 2.62 (t, J = 6.8 Hz, 2H), 2.92 (d, J = 11.2 Hz, 2H), 3.39 (d, J = 11.6 Hz, 1H), 7.17 (t, J = 7.2 Hz, 1H), 7.23 (s, 1H), 7.31 (t, J = 7.6 Hz, 2H), 7.56 (s, 1H), 7.64 (d, J = 8.4 Hz, 1H). |
| 240 | 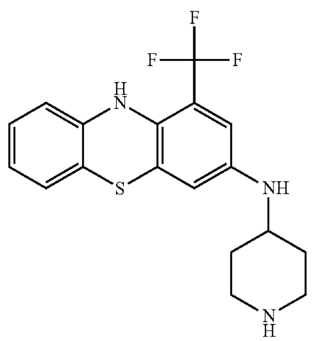 [SMILES: FC(F)(F)c1cc(NC2CCNCC2)cc2c1Nc1ccccc1S2] | $^1$H NMR (DMSO-d$_6$, 400 MHz) δ 1.21 (s, 2H), 1.80-1.86 (m, 2H), 2.57 (t, J = 11.5 Hz, 2H), 2.95 (t, J = 12 Hz, 2H), 5.52 (d, J = 8 Hz, 1H), 6.58 (s, 1H), 6.79 (t, J = 7.2 Hz, 1H), 7.0-7.05 (m, 3H), 7.36 (s, 1H), 8.31 (s, 1H). |
| 241 | 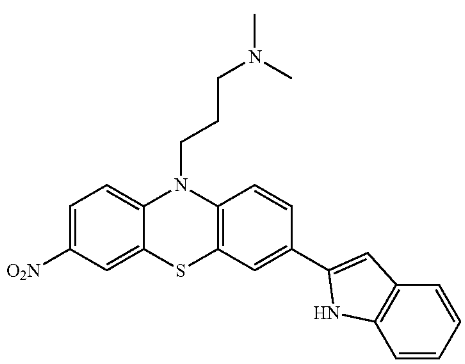 [SMILES: CN(C)CCCN1c2ccc(-c3cc4ccccc4[nH]3)cc2Sc2cc([N+](=O)[O-])ccc21] | $^1$H NMR (DMSO-d$_6$, 400 MHz) δ1.81 (t, J = 6.8 Hz, 2H), 2.10 (s, 6H), 2.30-2.34 (m, 2H), 4.02 (t, J = 6.8 Hz, 2H), 6.84 (s, 1H), 6.95 (t, J = 6.8 Hz, 1H), 7.05 (t, J = 7.6 Hz, H), 7.18 (t, J = 9.2 Hz, 2H), 7.34 (d, J = 8.4 Hz, 1H), 7.47 (d, J = 8.0 Hz, 1H), 7.65 (s, 1H), 7.65-7.71 (m, 1H), 7.95 (d, J = 2.8 Hz, 1H), 8.02-8.05 (m, 1H), 11.42 (s, 1H). |
| 242 | 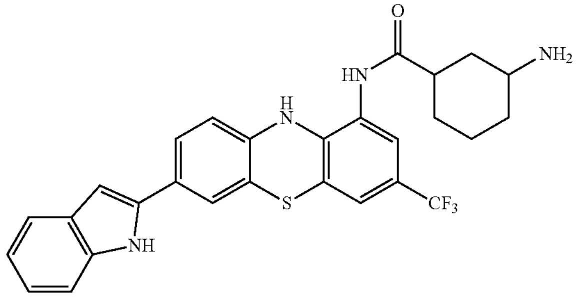 [SMILES: NC1CCCC(C(=O)Nc2cc(C(F)(F)F)cc3c2Nc2ccc(-c4cc5ccccc5[nH]4)cc2S3)C1] | $^1$H NMR (DMSO-d$_6$, 400 MHz) δ 1.21 (s, 2H), 1.75 (s, 4H), 1.87 (s, 2H), 1.98 (s, 2H), 6.75 (s, 1H), 6.94 (t, J = 7.2 Hz, 1H), 6.95 (d, J = 7.6 Hz, 2H), 7.05-7.02 (m, 1H), 7.48-7.42 (m, 2H), 7.16 (s, 1H), 7.32 (d, J = 8 Hz, 1H), 7.36 (s, 1H), 7.45 (d, J = 8 Hz, 2H), 7.52 (d, J = 8.4 Hz, 1H), 8.09 (s, 1H), 11.33 (s, 1H). |

TABLE 14-continued

| Cmpd # | Structure | NMR data |
|---|---|---|
| 243 | 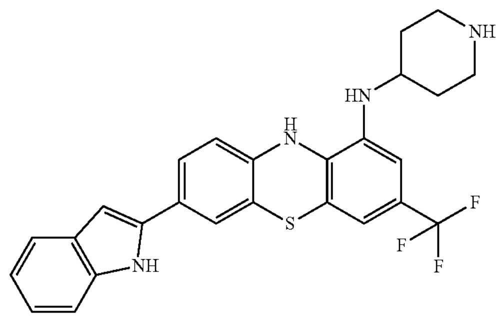 [SMILES: FC(F)(F)c1cc(NC2CCNCC2)c2c(c1)Sc1cc(-c3cc4ccccc4[nH]3)ccc1N2] | %) ¹H NMR (DMSO-d₆, 400 MHz) δ 1.45 (d, J = 10.8 Hz, 2H), 2.19 (d, J = 10.8 Hz, 2H), 2.82 (t, J = 11.2 Hz, 2H), 3.16 (d, J = 11.6 Hz, 2H), 3.52 (s, 1H), 5.29 (d, J = 6.4 Hz, 1H), 6.60 (s, 1H), 6.64 (s, 1H), 6.73 (s, 1H), 6.96-6.90 (m, 2H), 7.03 (t, J = 7.2 Hz, 1H), 7.32 (d, J = 8 Hz, 1H), 7.45 (d, J = 6 Hz, 2H), 7.51 (d, J = 8 Hz, 1H), 8.11 (s, 1H), 11.32 (s, 1H). |
| 244 | 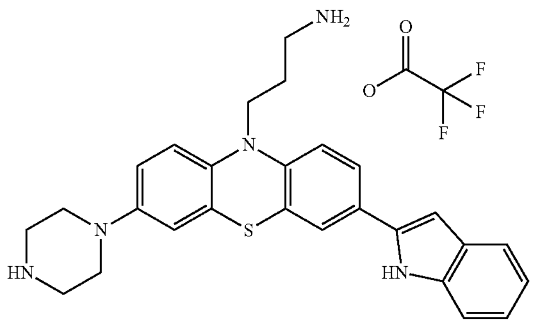 [SMILES: NCCCN1c2ccc(-c3cc4ccccc4[nH]3)cc2Sc2cc(N3CCNCC3)ccc21 ; O=C(O)C(F)(F)F] | ¹H NMR (DMSO-d₆, 400 MHz) δ 1.93-1.97 (m, 2H), 2.85-2.95 (m, 2H), 3.20-3.23 (m, 8H), 6.79 (s, 1H), 6.84-6.87 (m, 2H), 6.93-6.98 (m, 2H), 7.02-7.09 (m, 2H), 7.33-7.47 (m, 2H), 7.65-7.68 (m, 2H), 7.72 (br s, 3H, TFA salt), 8.78 (br s, 2H). |
| 245 | 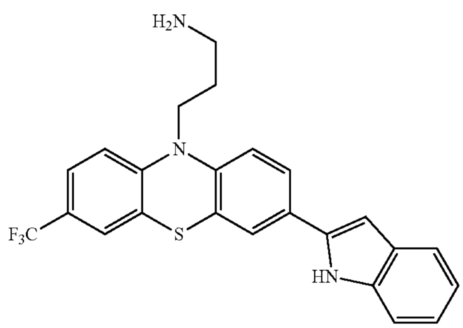 [SMILES: NCCCN1c2ccc(-c3cc4ccccc4[nH]3)cc2Sc2cc(C(F)(F)F)ccc21] | ¹H NMR (DMSO-d₆, 400 MHz) δ 1.78 (t, J = 6.8 Hz, 2H), 1.80-2.06 (m, 2H), 2.68 (t, J = 6.4 Hz, 2H), 4.0 (t, J = 6.8 Hz, 2H), 6.81 (s, 1H), 6.96 (t, J = 8 Hz, 1H), 7.05 (t, J = 7.6 Hz, 1H), 7.15-7.21 (m, 2H), 7.34 (t, J = 8 Hz, 1H), 7.46-7.51 (m, 3H), 7.63-7.69 (m, 2H), 11.40 (s, 1H). |
| 247 | 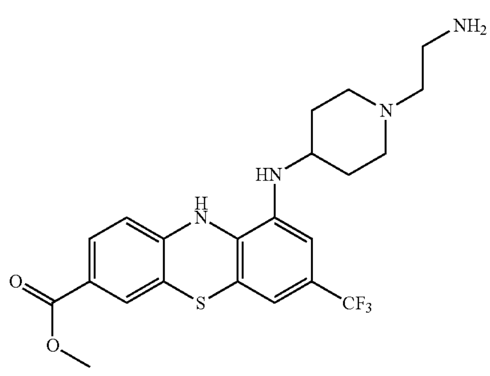 [SMILES: COC(=O)c1ccc2c(c1)Sc1cc(C(F)(F)F)cc(NC3CCN(CCN)CC3)c1N2] | ¹H NMR (DMSO-d₆, 400 MHz) δ 1.51-1.46 (m, 3H), 2.10 (d, J = 12 Hz, 2H), 2.93 (t, J = 11.2 Hz, 2H), 4.18 (s, 1H), 5.67 (s, 1H), 6.50 (s, 1H), 7.19-7.19-7.12 (m, 3H), 7.58-7.52 (m, 2H). |
| 252 | 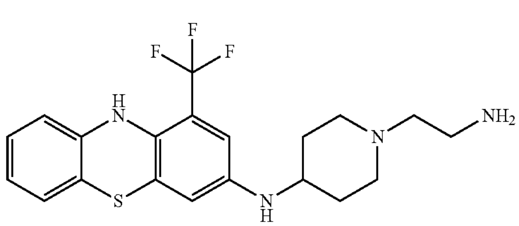 [SMILES: NCCN1CCC(Nc2cc3c(c(C(F)(F)F)c2)Nc2ccccc2S3)CC1] | ¹H NMR (DMSO-d₆, 400 MHz) δ 1.27-1.32 (m, 2H), 1.64 (bs, 1H), 1.78 (d, J = 11.2 Hz, 3H), 1.93 (t, J = 11.2 Hz, 2H), 2.24-2.30 (m, 2H), 2.55 (t, J = 6.8 Hz, 2H), 2.71 (t, J = 11.2 Hz, 2H), 6.75 (s, 2H), 6.79 (t, J = 7.2 Hz, 2H), 6.98-7.05 (m, 3H), 7.36 (s, 1H). |

TABLE 14-continued

| Cmpd # | Structure | NMR data |
| --- | --- | --- |
| 253 | 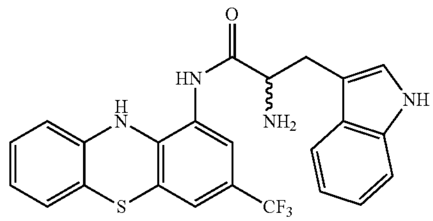 [SMILES: NC(Cc1c[nH]c2ccccc12)C(=O)Nc1cc(C(F)(F)F)cc2c1Nc1ccccc1S2] | $^1$H NMR (DMSO-d$_6$, 400 MHz) δ 2.97-3.09 (m, 1H), 3.10-3.3.14 (m, 1H), 3.70 (t, J = 6 Hz, 1H), 4.49 (bs, 1H), 6.70 (d, J = 7.6 Hz 1H), 6.81 (t, J = 8 Hz, 1H), 6.91 (m, 2H), 7.0 (m, 3H), 7.16 (s, 1H), 7.22 (s, 1H), 7.31 (d, J = 8 Hz, 1H), 7.55 (d, J = 8 Hz, 1H), 7.74 (s, 1H), 10.85 (s, 1H). |
| 254 | 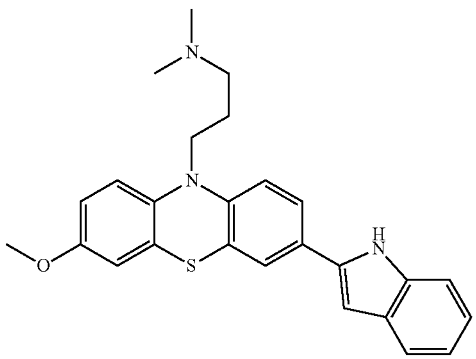 [SMILES: COc1ccc2c(c1)Sc1cc(-c3cc4ccccc4[nH]3)ccc1N2CCCN(C)C] | $^1$H NMR (DMSO-d$_6$, 400 MHz) δ 1.77 (s, 2H), 2.10 (s, 6H), 2.30 (b, 2H), 3.69 (s, 3H), 3.85-3.86 (m, 2H), 6.77 (d, J = 9.2 Hz, 3H), 6.92-6.95 (m, 2H), 7.01-7.05 (m, 2H), 7.33 (d, J = 8 Hz, 1H), 7.45 (d, J = 7.6 Hz, 1H), 7.60-7.65 (m, 2H), 11.35 (s, 1H). |
| 255 | 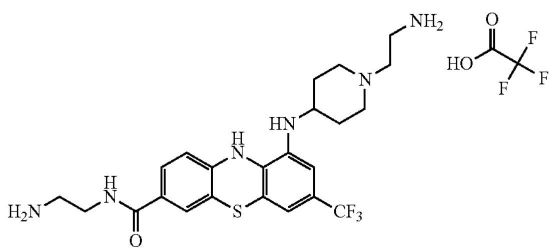 [SMILES: NCCNC(=O)c1ccc2c(c1)Sc1cc(C(F)(F)F)cc(NC3CCN(CCN)CC3)c1N2 ; O=C(O)C(F)(F)F] | |
| 256 | 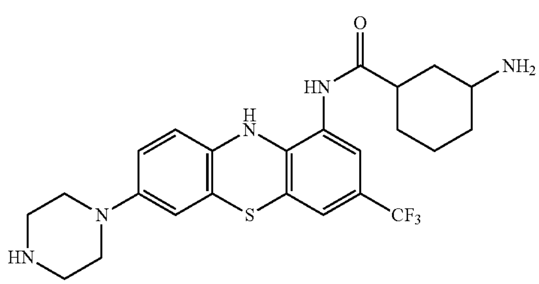 [SMILES: NC1CCCC(C(=O)Nc2cc(C(F)(F)F)cc3c2Nc2ccc(N4CCNCC4)cc2S3)C1] | $^1$H NMR (400 MHz, DMSO-d6) δ 0.95-1.03 (m, 1H), 1.15-1.33 (m, 4H), 1.73-1.79 (m, 1H), 1.85-1.87 (m, 1H), 2.01 (d, J = 11.9 Hz, 1H), 2.50-2.67 (m, 2H), 2.77-2.79 (m, 4H), 2.89-2.91 (m, 4H), 6.54 (d, J = 2.5 Hz, 1H), 6.64-6.67 (m, 1H), 6.80 (d, J = 6.7 Hz, 1H), 7.09 (s, 1H), 7.35 (s, 1H), 7.79 (s, 1H) |
| 257 | 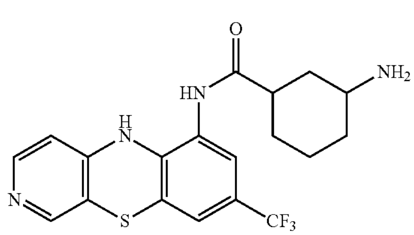 [SMILES: NC1CCCC(C(=O)Nc2cc(C(F)(F)F)cc3c2Nc2ccncc2S3)C1] | 1H NMR (400 MHz, DMSO-d6) δ 1.01-1.07 (m, 1H), 1.22-1.34 (m, 4H), 1.77-1.83 (m, 2H), 1.89 (d, J = 10.3 Hz, 1H), 2.05 (d, J = 11.7 Hz, 1H), 2.52-2.59 (m, 1H), 2.69-2.75 (m, 1H), 6.91 (d, J = 5.3 Hz, 1H), 7.19 (s, 1H), 7.43 (s, 1H), 7.98 (s, 1H), 8.07 (d, J = 5.3 Hz, 1H) |

TABLE 14-continued

| Cmpd # | Structure | NMR data |
|---|---|---|
| 258 | (ethyl phenothiazine-indole with aminopropyl, carboxylate) | 1H NMR (400 MHz, DMSO-d6) δ 1.22-1.28 (m, 2H), 1.32 (t, J = 5 Hz, 3H), 1.81 (t, J = 6.7 Hz, 2H), 2.71 (t, J = 6.6 Hz, 2H), 4.02 (t, J = 6.9 Hz, 2H), 4.27 (dd, J = 7 Hz, J = 7 Hz, 2H), 6.84 (s, 1H), 6.97 (t, J = 7.3 Hz, 1H), 7.07 (t, J = 7.7 Hz, 1H), 7.18 (t, J = 9.5 Hz, 2H), 7.36 (d, J = 8 Hz, 1H), 7.49 (d, J = 7.6 Hz, 1H), 7.65-7.71 (m, 3H), 7.80 (dd, J = 2 Hz, J = 8.6 Hz, 1H) |
| 259 | (octahydrophenothiazine with piperidinylamino, CF3) | 1H NMR (400 MHz, DMSO-d6) δ 1.23 (s, 1H), 1.41 (s, 2H), 1.60-1.63 (m, 6H), 1.80 (s, 1H), 1.92 (s, 1H), 2.05 (d, J = 11.9 Hz, 2H), 2.96 (t, J = 11.9 Hz, 2H), 3.27 (d, J = 3.6 Hz, 3H), 3.53 (s, 1H), 3.81 (s, 2H), 4.92 (d, J = 6.8 Hz, 1H), 5.41-5.44 (m, 1H), 6.48 (s, 1H), 6.56 (s, 1H) |
| 262 | (carboxy phenothiazine-indole with aminopropyl, TFA) | 1H NMR (400 MHz, DMSO-d6) δ 1.98-2.01 (m, 2H), 2.90-2.95 (m, 2H), 4.07 (t, J = 6.6 Hz, 2H), 6.86 (s, 1H), 6.97 (t, J = 7.6 Hz, 1H), 7.07 (t, J = 7.6 Hz, 1H), 7.15 (dd, J = 8.4 Hz, J = 11.3 Hz, 2H), 7.36 (d, J = 8 Hz, 1H), 7.49 (d, J = 7.8 Hz, 1H), 7.69-7.73 (m, 5H), 7.78 (dd, J = 1.6 Hz, J = 8.4 Hz, 1H), 11.46 (s, 1H), 12.49 (s, 1H) |
| 263 | (pyrido-phenothiazine with aminocyclohexylcarboxamide, CF3) | 1H NMR (400 MHz, DMSO-d6) δ 1.14-1.41 (m, 4H), 1.81-1.89 (m, 3H), 2.03 (d, J = 10.5 Hz, 1H), 2.55 (s, 1H), 2.95 (s, 1H), 6.85 (dd, J = 4.8 Hz, J = 7.4 Hz, 1H), 7.19 (s, 1H), 7.40 (d, J = 7.5 Hz, 1H), 7.53 (s, 1H), 7.88 (d, J = 4.6 Hz, 1H) |
| 264 | (pyrido-phenothiazine with piperidinylamino, CF3) | 1H NMR (400 MHz, DMSO-d6) δ 1.22 (s, 1H), 1.33-1.41 (m, 2H), 1.89-1.91 (m, 2H), 2.658-2.70 (m, 1H), 3.05 (d, J = 12.7 Hz, 2H), 3.44 (d, J = 5.4 Hz, 1H), 6.65 (s, 1H), 6.61 (s, 1H), 6.82 (dd, J = 5 Hz, J = 7.5 Hz, 1H), 7.34 (d, J = 7.4 Hz, 1H), 7.86 (d, J = 4.9 Hz, 1H), 8.36 (s, 1H), 8.74 (s, 1H) |

TABLE 14-continued

| Cmpd # | Structure | NMR data |
|---|---|---|
| 265 | 2HCl; phenothiazine with N-(CH₂)₃NH₂, 3-piperazinyl, 7-CF₃ | 1H NMR (400 MHz, DMSO-d6) δ 1.93-1.95 (m, 2H), 2.85-2.88 (m, 2H), 3.18 (s, 4H), 3.26 (s, 4H), 3.97 (t, J = 7.2 Hz, 2H), 6.87 (s, 2H), 7.00-7.02 (m, 1H), 7.15 (d, J = 8.4 Hz, 1H), 7.49-7.53 (m, 2H), 7.77 (s, 2H), 8.89 (s, 2H) |
| 266 | 2HCl; phenothiazine with N-(CH₂)₃NH₂, 3-[4-(2-aminoethyl)piperazin-1-yl], 7-CF₃ | 1H NMR (400 MHz, DMSO-d6) δ 1.93-1.96 (m, 2H), 2.86 (d, J = 5.1 Hz, 2H), 3.10-3.19 (m, 4H), 3.36 (d, J = 12.1 Hz, 4H), 3.63-3.69 (m, 2H), 3.82 (s, 2H), 3.96 (t, J = 6.5 Hz, 2H), 6.91 (s, 2H), 7.02 (d, J = 8.5 Hz, 1H), 7.16 (d, J = 8.2 Hz, 1H), 7.43-7.59 (m, 2H), 7.87 (s, 2H), 8.30 (s, 2H) |
| 267 | TFA; azaphenothiazine with N-(CH₂)₃NH₂ and indol-2-yl substituent | 1H NMR (400 MHz, DMSO-d6) δ 1.97-2.00 (m, 2H), 2.95-2.96 (m, 2H), 4.08 (t, J = 6.7 Hz, 2H), 6.90 (s, 1H), 6.98 (t, J = 7.4 Hz, 1H), 7.09 (t, J = 7.4 Hz, 1H), 7.16 (d, J = 6.1 Hz, 1H), 7.24 (d, J = 8.4 Hz, 1H), 7.37 (d, J = 8 Hz, 1H), 7.50 (d, J = 7.8 Hz, 1H), 7.71-7.74 (m, 4H), 8.31 (s, 1H), 8.36 (d, J = 5.7 Hz, 1H), 11.49 (s, 1H) |
| 268 | azaphenothiazine with NH-piperidin-4-yl-N-(2-aminoethyl) and CF₃ | 1H NMR (400 MHz, DMSO-d6) δ 1.42-1.50 (m, 2H), 1.87 (d, J = 10.8 Hz, 2H), 2.08 (t, J = 11 Hz, 2H), 2.33 (t, J = 6.2 Hz, 2H), 2.66 (t, J = 6.3 Hz, 2H), 2.83 (d, J = 11.8 Hz, 2H), 5.69 (d, J = 6.7 Hz, 1H), 6.57 (d, J = 11 Hz, 2H), 6.81 (dd, J = 5 Hz, J = 7.4 Hz, 1H), 7.33 (d, J = 7.4 Hz, 1H), 7.86 (d, v = 4.8 Hz, 1H) |

TABLE 14-continued

| Cmpd # | Structure | NMR data |
| --- | --- | --- |
| 269 | 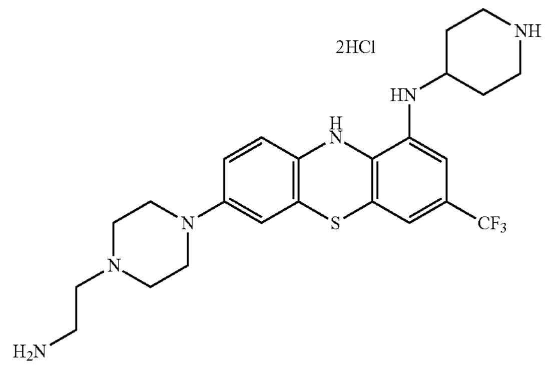 [SMILES: NCCN1CCN(c2ccc3c(c2)Sc2cc(C(F)(F)F)cc(NC4CCNCC4)c2N3)CC1] | 1H NMR (400 MHz, DMSO-d6) δ 1.05 (t, J = 7 Hz, 1H), 1.19 (s, 1H), 1.63 (d, J = 12.4 Hz, 2H), 2.05 (d, J = 13 Hz, 2H), 3.01 (t, J = 13.9 Hz, 2H), 3.13-3.48 (m, 16H), 6.58 (s, 1H), 6.66 (s, 2H), 6.71 (dd, J = 2.4 Hz, J = 8.7 Hz, 1H), 6.82-6.89 (m, 1H), 8.33-8.39 (m, 5H), 8.76 (s, 2H) |
| 270 | 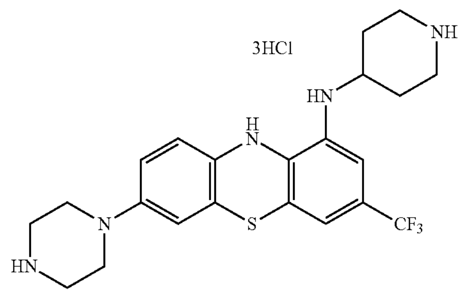 [SMILES: FC(F)(F)c1cc(NC2CCNCC2)c2c(c1)Sc1cc(N3CCNCC3)ccc1N2] | 1H NMR (400 MHz, DMSO-d6) δ 1.57-1.60 (m, 2H), 2.05 (d, J = 12.3 Hz, 1H), 3.04-3.07 (m, 3H), 3.19 (s, 8H), 3.33-3.36 (m, 2H), 3.66 (s, 1H), 6.59 (s, 1H), 6.66-6.78 (m, 3H), 6.79 (d, J = 8.4 Hz, 1H), 7.87 (s, 1H), 8.46 (d, J = 8.2 Hz, 1H), 8.61 (s, 1H), 8.75 (s, 2H) |
| 271 | 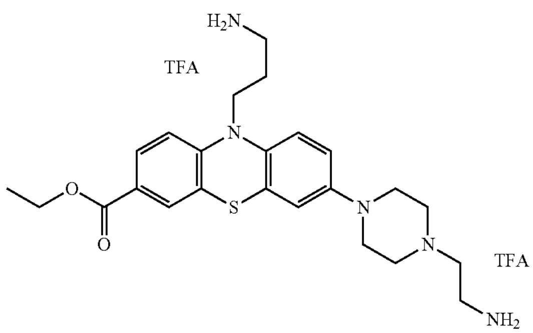 [SMILES: CCOC(=O)c1ccc2c(c1)Sc1cc(N3CCN(CCN)CC3)ccc1N2CCCN] | 1H NMR (400 MHz, DMSO-d6) δ 1.20 (d, J = 12.6 Hz, 2H), 1.28 (t, J = 7.1 Hz, 3H), 1.93 (s, 2H), 2.88 (d, J 5.6 Hz, 4H), 3.07 (s, 2H), 3.17 (s, 4H), 3.96 (s, 2H), 4.25 (dd, J = 7 Hz, J = 14.1 Hz, 2H), 4.75-4.79 (m, 1H), 6.87 (s, 1H), 6.99 (d, J = 9 Hz, 1H), 7.08 (d, J = 8.6 Hz, 1H), 7.63 (s, 1H), 7.72-7.81 (m, 5H), 7.95 (s, 2H) |
| 272 | 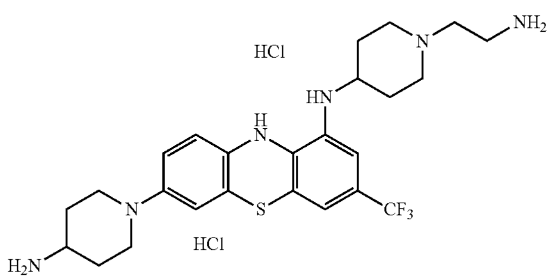 [SMILES: NCCN1CCC(Nc2cc(C(F)(F)F)cc3c2Nc2ccc(N4CCC(N)CC4)cc2S3)CC1 ; Cl ; Cl] | 1H NMR (400 MHz, DMSO-d6) δ 1.93-1.99 (m, 4H), 2.11 (d, J = 10.7 Hz, 4H), 2.91 (s, 2H), 3.11-3.19 (m, 2H), 3.31-3.39 (m, 8H), 3.61-3.68 (m, 5H), 6.61 (d, J = 22.4 Hz, 2H), 7.09 (s, 1H), 7.20-7.43 (m, 2H), 8.32 (d, J = 17.5 Hz, 6H), 8.61 (s, 1H), 10.89 (s, 1H) |
| 273 | 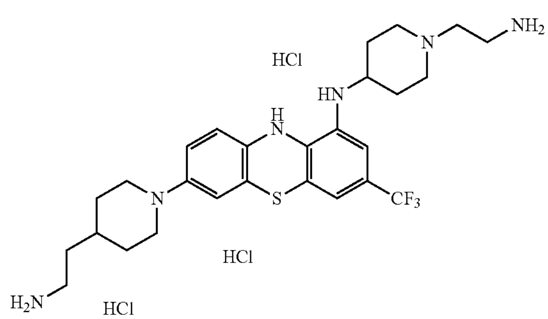 [SMILES: NCCC1CCN(c2ccc3c(c2)Sc2cc(C(F)(F)F)cc(NC4CCN(CCN)CC4)c2N3)CC1 ; Cl ; Cl ; Cl] | 1H NMR (400 MHz, DMSO-d6) δ 1.22 (s, 1H), 1.95 (s, 2H), 2.10 (s, 2H), 3.16 (d, J = 9.8 Hz, 5H), 3.32-3.39 (m, 10H), 3.63 (s, 7H), 6.61-6.65 (m, 3H), 6.95 (d, J = 15.4 Hz, 1H), 8.24 (s, 1H), 8.39 (s, 6H), 10.97 (s, 1H), 11.28 (s, 1H) |

TABLE 14-continued

| Cmpd # | Structure | NMR data |
|---|---|---|
| 274 | 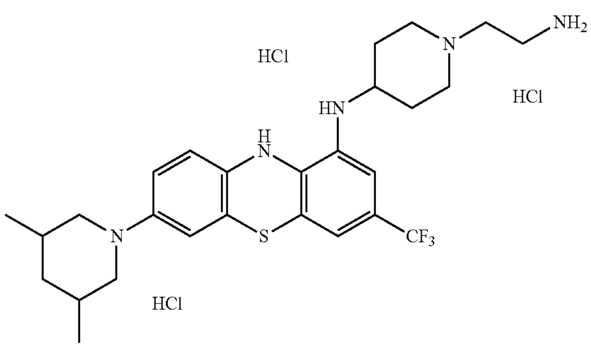 [SMILES: CC1CC(C)CN(c2ccc3c(c2)Sc2cc(C(F)(F)F)cc(NC4CCN(CCN)CC4)c2N3)C1 ; Cl ; Cl ; Cl] | 1H NMR (400 MHz, DMSO-d6) δ 0.83-0.86 (m, 1H), 0.89 (d, J = 6.4 Hz, 6H), 1.22-1.26 (m, 1H), 1.74-1.78 (m, 1H), 1.94-1.97 (m, 2H), 2.11 (d, J = 11.9 Hz, 4H), 2.95 (s, 4H), 3.10-3.18 (m, 2H), 3.30-3.39 (m, 7H), 6.63 (d, J = 21.3 Hz, 2H), 7.02 (s, 1H), 7.42 (s, 2H), 8.26 (s, 3H) |
| 275 | | 1H NMR (400 MHz, DMSO-d6) δ 1.22 (s, 7H), 1.94 (s, 2H), 2.10 (s, 2H), 3.18 (d, J = 10.3 Hz, 2H), 3.31-3.45 (m, 7H), 3.63 (s, 4H), 3.83 (s, 1H), 4.27 (t, J = 7.6 Hz, 2H), 6.58-7.12 (m, 4H), 8.34 (s, 4H), 10.93 (s, 1H) |
| 275 | | 1H NMR (400 MHz, DMSO-d6) δ 0.82 (d, J = 6.7 Hz, 1H), 1.06-1.09 (m, 1H), 1.22 (s, 4H), 1.34-1.37 (m, 2H), 1.58 (d, J = 13.5 Hz, 1H), 1.75 (d, J = 15 Hz, 2H), 1.98-2.05 (m, 3H), 2.87 (t, J = 6.5 Hz, 2H), 3.08-3.13 (m, 2H), 3.21 (s, 2H), 3.34 (s, 4H), 3.63 (s, 2H), 3.75 (s, 1H), 3.99 (t, J = 5.5 Hz, 2H), 6.88 (d, J = 8 Hz, 1H), 7.03 (d, J = 8.7 Hz, 1H), 7.13 (d, J = 8.8 Hz, 1H), 7.76 (s, 1H), 8.42 (d, J = 8.3 Hz, 1H) |
| 276 | 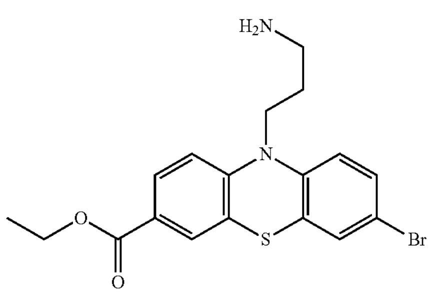 [SMILES: CCOC(=O)c1ccc2c(c1)Sc1cc(Br)ccc1N2CCCN] | 1H NMR (400 MHz, DMSO-d6) δ 1.26 (t, J = 7 Hz, 3H), 1.89-1.91 (m, 2H), 2.79 (t, J = 7.1 Hz, 2H), 3.98 (t, J = 6.8 Hz, 2H), 4.24 (dd, J = 7 Hz, J = 14.1 Hz, 2H), 7.04 (d, J = 9.1 Hz, 1H), 7.15 (d, J = 8.7 Hz, 1H), 7.38-7.40 (m, 2H), 7.14 (d, J = 1.9 Hz, 1H), 7.75 (dd, J = 1.9 Hz, J = 8.5 Hz, 1H) |

TABLE 14-continued

| Cmpd # | Structure | NMR data |
|---|---|---|
| 277 | 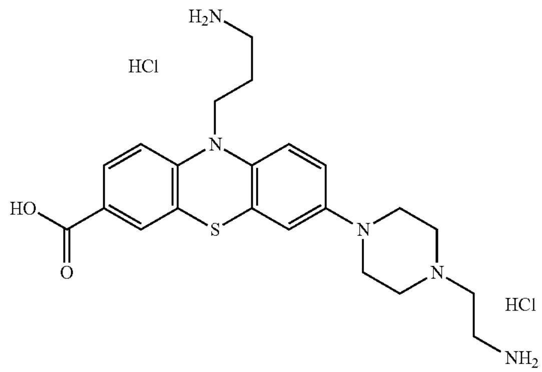 [SMILES: NCCCN1c2ccc(C(=O)O)cc2Sc2cc(N3CCN(CCN)CC3)ccc21 ; Cl ; Cl] | 1H NMR (400 MHz, DMSO-d6) δ 1.91-1.94 (m, 2H), 2.85 (t, J = 6.6 Hz, 2H), 3.22-3.29 (m, 3H), 3.30-3.36 (m, 7H), 3.93 (t, J = 6.3 Hz, 2H), 6.86-6.90 (m, 2H), 7.01 (d, J = 8.4 Hz, 1H), 7.08 (d, J = 8.7 Hz, 1H), 7.61 (s, 1H), 7.74 (d, J = 8.3 Hz, 1H), 7.86 (s, 3H), 8.29 (s, 3H)11.24 (brs, 1H) |
| 278 | 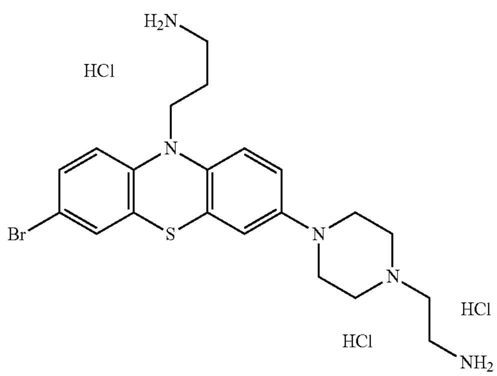 [SMILES: NCCCN1c2ccc(Br)cc2Sc2cc(N3CCN(CCN)CC3)ccc21 ; Cl ; Cl ; Cl] | 1H NMR (400 MHz, DMSO-d6) δ 8.36 (s, 2H), 7.92 (s, 2H), 7.36-7.34 (m, 2H), 6.97 (t, J = 8.1 Hz, 1H), 6.89 (d, J = 10 Hz, 2H), 3.90 (t, J = 6.5 Hz, 2H), 3.75 (d, J = 11.5 Hz, 2H), 3.65-3.56 (m, 2H), 3.48-3.35 (m, 4H), 3.19-3.11 (m, 3H), 2.85 (s, 2H), 1.95-1.91 (m, 2H), 1.28-1.22 (m, 2H) |
| 279 | 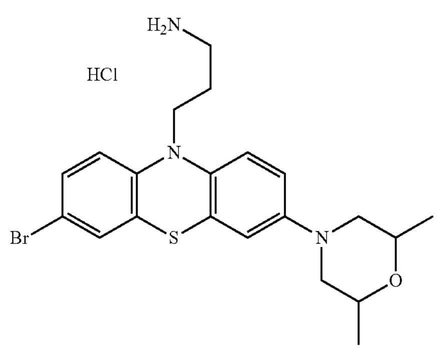 [SMILES: CC1CN(c2ccc3c(c2)Sc2cc(Br)ccc2N3CCCN)CC(C)O1 ; Cl] | 1H NMR (400 MHz, DMSO-d6) δ 1.08 (d, J = 6.1 Hz, 6H), 1.91 (s, 2H), 2.22 (s, 2H), 2.85 (s, 2H), 3.47 (d, J = 10.9 Hz, 2H), 3.69 (s, 4H), 6.86 (s, 1H), 6.95 (d, J = 6.7 Hz, 2H), 7.35 (s, 2H), 7.81 (s, 3H) |
| 280 | 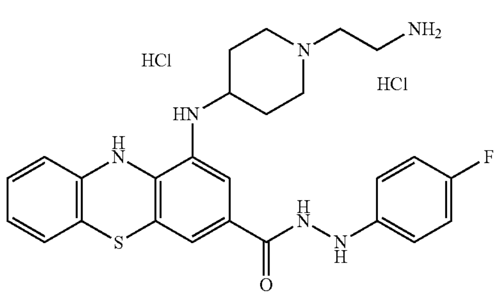 [SMILES: NCCN1CCC(Nc2cc(C(=O)NNc3ccc(F)cc3)cc3c2Nc2ccccc2S3)CC1 ; Cl ; Cl] | 11H NMR (400 MHz, DMSO-d6) δ 1.92-1.95 (m, 2H), 2.19 (d, J = 12.7 Hz, 2H), 3.12-3.15 (m, 2H), 3.32-3.48 (m, 5H), 3.66 (d, J = 10.8 Hz, 2H), 6.72-6.79 (m, 2H), 6.80 (t, J = 7 Hz, 1H), 6.92-7.01 (m, 7H), 8.23 (s, 4H), 10.11 (bs, 1H), 10.95 (bs, 1H) |

TABLE 14-continued

| Cmpd # | Structure | NMR data |
|---|---|---|
| 281 | 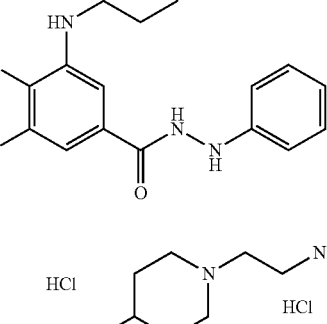 | 1H NMR (400 MHz, DMSO-d6) δ 1.90-1.96 (m, 2H), 2.19 (d, J = 12.5 Hz, 2H), 2.81-2.87 (m, 2H), 3.11-3.14 (m, 2H), 3.37 (s, 5H), 3.55-3.57 (m, 2H), 6.64-6.74 (m, 3H), 6.80 (d, J = 6.7 Hz, 1H), 6.93-6.99 (m, 3H), 7.01-7.14 (m, 1H), 7.12 (t, J = 7.8 Hz, 2H), 8.17-8.20 (m, 3H), 10.06 (brs, 1H), 10.86 (brs, 1H) |
| 282 | 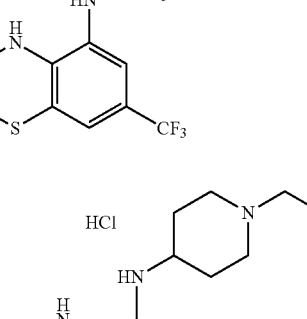 | 1H NMR (400 MHz, DMSO-d6) δ 1.91-1.94 (m, 2H), 2.11 (d, J = 13.5 Hz, 2H), 3.13-3.16 (m, 2H), 3.30-3.37 (m, 4H), 3.61-3.68 (m, 4H), 6.58-6.64 (m, 2H), 6.969 (d, J = 8.3 Hz, 1H), 7.12-7.18 (m, 2H), 8.28 (s, 3H), 8.53 (s, 1H), 10.84 (brs, 1H) |
| 283 | 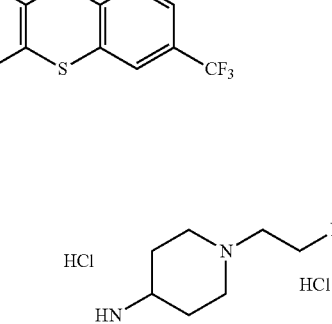 | 1H NMR (400 MHz, DMSO-d6) δ 10.98 (s, 1H), 9.61 (s, 1H), 8.95 (s, 1H), 8.41 (s, 2H), 6.94 (d, J = 8 Hz, 1H), 6.72-6.56 (m, 3H), 6.36 (d, J = 10 Hz, 4H), 3.39-3.31 (m, 6H), 3.15 (s, 2H), 2.61 (t, J = 12.7 Hz, 2H), 2.10 (d, J = 12.2 Hz, 2H), 1.93 (d, J = 11.2 Hz, 2H), 1.27 (d, J = 5.9 Hz, 6H) |
| 284 | 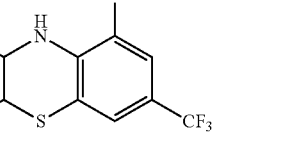 | 1H NMR (400 MHz, DMSO-d6) δ 10.91 (s, 1H), 8.24 (s, 2H), 6.83 (s, 1H), 6.60 (s, 1H), 6.57-6.29 (m, 2H), 3.62 (d, J = 9.8 Hz, 3H), 3.40-3.30 (m, 5H), 3.16-3.14 (m, 5H), 2.12 (d, J = 12.4 Hz, 2H), 1.92 (s, 5H), 1.22 (s, 2H) |
| 285 | 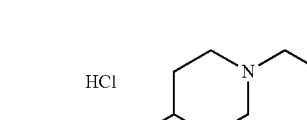 | 1H NMR (400 MHz, DMSO-d6) δ 1.26 (t, J = 7 Hz, 3H), 1.88-1.94 (m, 2H), 2.08 (d, J = 13.4 Hz, 2H), 3.13 (q, J = 11.1 Hz, 2H), 3.30 (s, 5H), 3.60-3.67 (m, 3H), 4.25 (dd, J = 7 Hz, J = 14 Hz, 2H), 6.59-6.64 (m, 2H), 7.68 (d, J = 1.7 Hz, 1H), 8.10-8.38 (m, 4H), 9.30 (s, 1H), 11.11 (brs, 1H) |

TABLE 14-continued

| Cmpd # | Structure | NMR data |
|---|---|---|
| 286 | 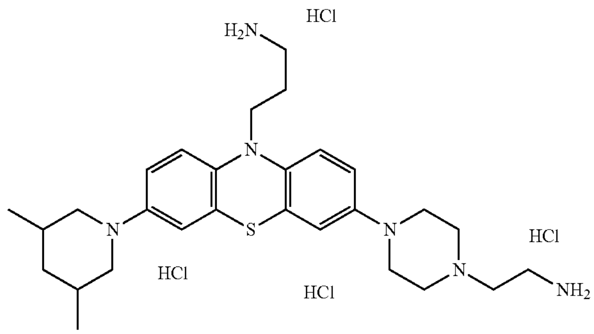 [SMILES: Cl ; CC1CC(C)CN(c2ccc3c(c2)Sc2cc(N4CCN(CCN)CC4)ccc2N3CCCN)C1 ; Cl ; Cl ; Cl] | 1H NMR (400 MHz, DMSO-d6) δ 8.39 (s, 2H), 8.00 (s, 2H), 7.73-7.55 (m, 2H), 7.33-7.64 (m, 4H), 3.88 (s, 2H), 3.35-3.12 (m, 13H), 2.85 (s, 4H), 1.94 (s, 2H), 1.77 (s, 1H), 0.89 (s, 6H) |
| 287 | 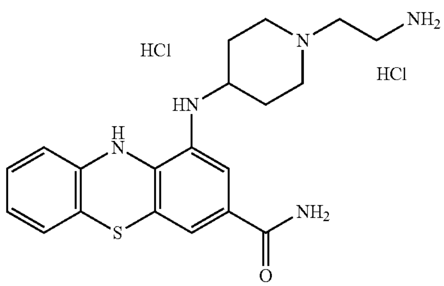 [SMILES: NCCN1CCC(Nc2cc(C(N)=O)cc3c2Nc2ccccc2S3)CC1 ; Cl ; Cl] | 1H NMR (400 MHz, DMSO-d6) δ 1.89-1.96 (m, 2H), 2.16 (d, J = 12.2 Hz, 2H), 3.14 (d, J = 10.5 Hz, 2H), 3.31-3.37 (m, 5H), 3.65 (d, J = 10.5 Hz, 3H), 6.78 (d, J = 6.7 Hz, 1H), 6.80-6.98 (m, 3H), 7.00-709 (m, 1H), 7.70 (brs, 1H), 8.14 (s, 1H), 8.27 (s, 3H), 10.93 (brs, 1H) |
| 288 | 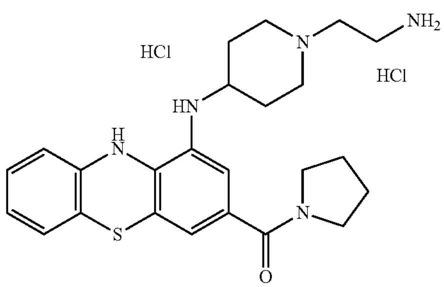 [SMILES: NCCN1CCC(Nc2cc(C(=O)N3CCCC3)cc3c2Nc2ccccc2S3)CC1 ; Cl ; Cl] | 1H NMR (400 MHz, DMSO-d6) δ 1.79 (s, 4H), 1.92 (d, J = 11.4 Hz, 2H), 2.12 (d, J = 12.4 Hz, 2H), 3.13 (d, J = 10.1 Hz, 2H), 3.30-3.39 (m, 9H), 3.61 (d, J = 10.2 Hz, 4H), 6.40-6.47 (m, 1H), 6.58 (s, 1H), 6.78 (t, J = 6.6 Hz, 1H), 6.91-7.02 (m, 3H), 8.11 (s, 1H), 8.31 (s, 3H), 8.59 (s, 1H), 10.94 (brs, 1H) |
| 289 | 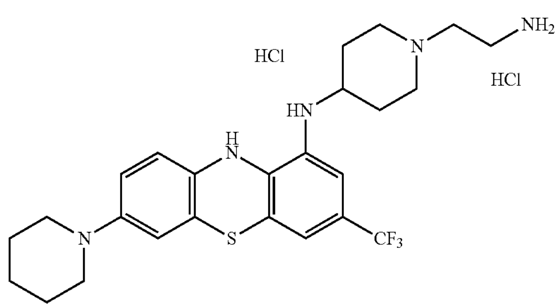 [SMILES: NCCN1CCC(Nc2cc(C(F)(F)F)cc3c2Nc2ccc(N4CCCCC4)cc2S3)CC1 ; Cl ; Cl] | 1H NMR (400 MHz, DMSO-d6) δ 8.20 (s, 2H), 7.40 (s, 2H), 7.15 (s, 1H), 6.62 (d, J = 20 Hz, 2H), 3.64-3.61 (m, 5H), 3.47-3.37 (m, 9H), 3.14 (d, J = 9.5 Hz, 3H), 2.11 (d, J = 11.7 Hz, 2H), 1.93-1.90 (m, 3H), 1.22 (s, 1H) |
| 290 | 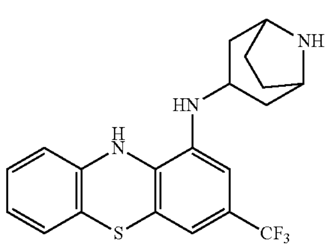 [SMILES: FC(F)(F)c1cc(NC2CC3CCC(C2)N3)c2c(c1)Sc1ccccc1N2] | 1H NMR (400 MHz, DMSO-d6) δ 1.22 (s, 1H), 1.72-1.85 (m, 4H), 2.05-2.22 (m, 4H), 3.15 (s, 1H), 3.65-3.75 (m, 3H), 5.20-5.30 (m, 1H), 6.47 (brs, 1H), 6.65 (brs, 1H), 6.82-6.88 (m, 2H), 6.96 (d, J = 7.53, 1H), 7.04 (t, J = 7.97 Hz, 1H), 7.95-8.02 (m, 1H) |

TABLE 14-continued

| Cmpd # | Structure | NMR data |
| --- | --- | --- |
| 291 | 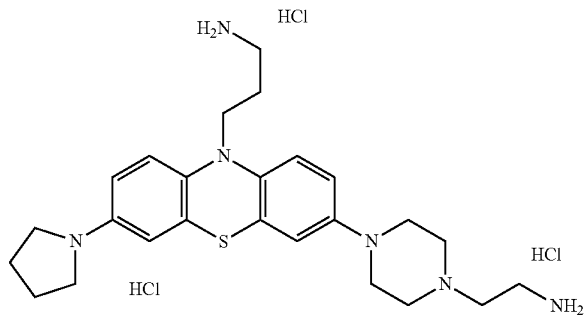 [SMILES: Cl ; NCCCN1c2ccc(N3CCCC3)cc2Sc2cc(N3CCN(CCN)CC3)ccc21 ; Cl ; Cl] | 1H NMR (400 MHz, DMSO-d6) δ 1.92-2.21 (m, 6H), 3.11-3.21 (m, 4H), 3.34-3.37 (m, 8H), 3.65 (s, 4H), 6.68-7.32 (m, 5H), 7.91 (s, 3H), 8.36 (s, 4H), 11.38 (brs, 1H) |
| 292 | 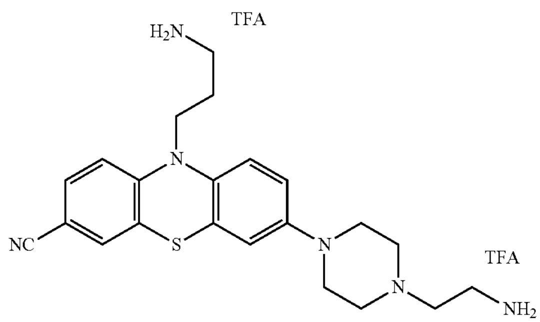 [SMILES: N#Cc1ccc2c(c1)Sc1cc(N3CCN(CCN)CC3)ccc1N2CCCN ; "TFA" ; "TFA"] | 1H NMR (400 MHz, DMSO-d6) δ 1.90-1.93 (m, 2H), 2.85 (t, J = 7.9 Hz, 2H), 3.10-3.14 (m, 9H), 3.18-3.22 (m, 3H), 6.84 (t, J = 6.6 Hz, 2H), 6.82-6.86 (m, 2H), 6.97 (d, J = 9 Hz, 1H), 7.07 (d, J = 8.5 Hz, 1H), 7.56-7.61 (m, 2H), 7.53-7.80 (m, 5H) |
| 293 | 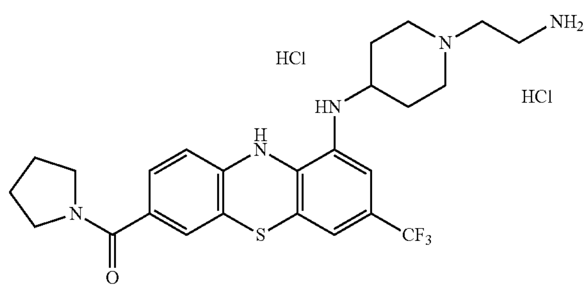 [SMILES: NCCN1CCC(Nc2cc(C(F)(F)F)cc3c2Nc2ccc(C(=O)N4CCCC4)cc2S3)CC1 ; Cl ; Cl] | 1H NMR (400 MHz, DMSO-d6) δ 1.75-1.85 (m, 4H), 1.87-1.98 (m, 2H), 2.08-2.17 (m, 2H), 3.12-3.21 (m, 2H), 3.23-3.35 (m, 4H), 3.35-3.42 (m, 5H), 6.59-6.65 (brs, 1H), 6.61 (s, 1H), 6.99 (d, J = 8.24 Hz, 1H), 7.05-7.12 (m, 1H), 7.18-7.22 (m, 1H), 8.22 (brs, 3H), 8.55 (s, 1H), 10.82 (brs, 1H) |
| 294 | 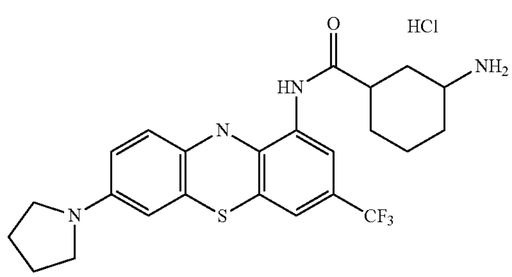 [SMILES: NC1CCCC(C(=O)Nc2cc(C(F)(F)F)cc3c2Nc2ccc(N4CCCC4)cc2S3)C1 ; Cl] | 1H NMR (400 MHz, DMSO-d6) δ 1.12-1.37 (m, 2H), 1.41-1.50 (m, 1H), 1.80-1.92 (m, 8H), 2.08 (d, J = 12.1 Hz, 1H), 3.03-3.20 (m, 6H), 6.20-6.27 (m, 1H), 6.29-6.32 (m, 1H), 6.74 (s, 1H), 7.08 (s, 1H), 7.27 (s, 1H), 7.93 (s, 5H), 9.67 (brs, 1H) |
| 295 | 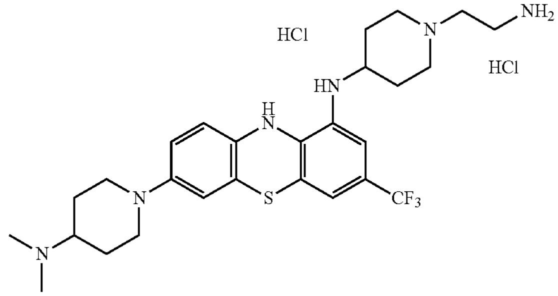 [SMILES: CN(C)C1CCN(c2ccc3c(c2)Sc2cc(C(F)(F)F)cc(NC4CCN(CCN)CC4)c2N3)CC1 ; Cl ; Cl] | 1H NMR (400 MHz, DMSO-d6) δ 1.90-2.0 (m, 4H), 2.12-2.20 (m, 2H), 2.71 (d, J = 4.68 Hz, 6H), 2.80-3.0 (m, 2H), 3.10-3.19 (m, 2H), 3.28-3.42 (m, 6H), 3.60-3.7 (m, 5H), 6.59 (d, J = 21.13, 2H), 6.85-7.0 (m, 2H), 8.34 (brs, 3H), 10.70-10.82 (m, 1H), 10.92 (brs, 1H). |

TABLE 14-continued
| Cmpd # | Structure | NMR data |
|---|---|---|
| 296 | 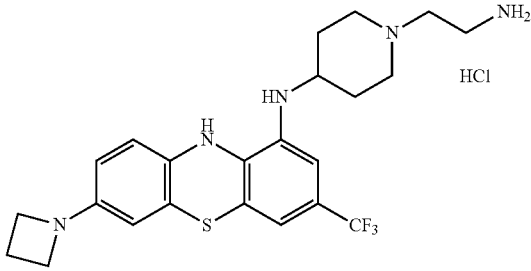 [SMILES: NCCN1CCC(Nc2cc(C(F)(F)F)cc3c2Nc2ccc(N4CCC4)cc2S3)CC1 ; Cl] | 1H NMR (400 MHz, DMSO-d6) δ 1.89-1.95 (m, 2H), 2.01-2.21 (m, 4H), 3.14-3.39 (m, 8H), 3.61-3.63 (m, 5H), 6.56 (d, J = 21.16 Hz, 2H), 6.95-7.08 (m, 2H), 8.36 (ms, 3H), 8.61 (brs, 1H), 10.89 (s, 1H). |
| 297 | 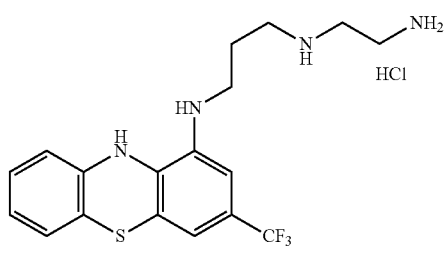 [SMILES: NCCNCCCNc1cc(C(F)(F)F)cc2c1Nc1ccccc1S2 ; Cl] | 1H NMR (400 MHz, DMSO-d6) δ 2.08-2.09 (m, 2H), 3.10-3.27 (m, 8H), 3.21-3.30 (m, 7H), 6.55 (d, J = 7.2 Hz, 2H), 6.82 (t, J = 7.2 Hz, 1H), 6.93 (d, J = 7.7 Hz, 1H), 7.00 (t, J = 7.59 Hz, 1H), 7.15 (d, J = 7.0 Hz, 1H), 8.25 (brs, 3H), 8.45 (s, 1H) 9.27 (brs, 1H) |
| 298 | 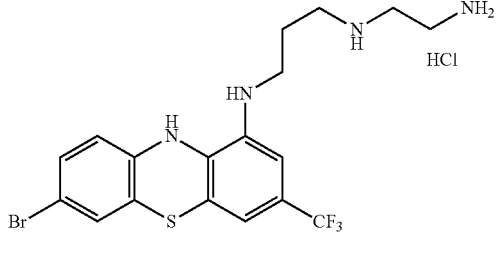 [SMILES: NCCNCCCNc1cc(C(F)(F)F)cc2c1Nc1ccc(Br)cc1S2 ; Cl] | 1H NMR (400 MHz, DMSO-d6) δ 1.97-2.04 (m, 2H), 3.10-3.27 (m, 8H), 3.11-3.24 (m, 8H), 6.52-6.58 (m, 2H), 7.10-7.20 (3, 2H), 8.25 (brs, 3H), 8.67 (s, 1H) 9.22 (brs, 2H) |
| 299 | 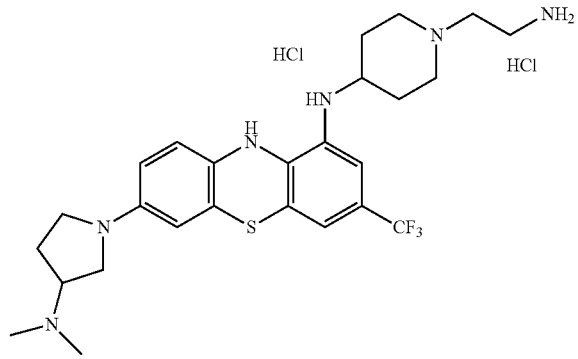 [SMILES: CN(C)C1CCN(c2ccc3c(c2)Sc2cc(C(F)(F)F)cc(NC4CCN(CCN)CC4)c2N3)C1 ; Cl ; Cl] | 1H NMR (400 MHz, DMSO-d6) δ 1.93 (s, 1H), 2.11 (s, 1H), 2.77 (s, 1H), 3.14-3.17 (m, 2H), 3.27-3.39 (m, 6H), 3.51-3.62 (m, 3H), 6.21-6.2 (m, 1H), 6.19-6.29 (m, 1H), 6.88-7.1 (m, 1H), 8.47 (s, 3H), 10.98 (s, 1H) |
| 300 | 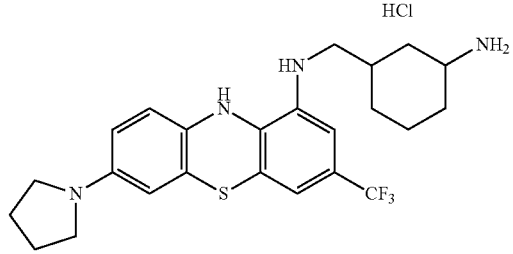 [SMILES: Cl ; NC1CCCC(CNc2cc(C(F)(F)F)cc3c2Nc2ccc(N4CCCC4)cc2S3)C1] | 1H NMR (400 MHz, DMSO-d6) δ 0.82-0.90 (m, 1H), 0.95-1.05 (m, 1H), 1.10-1.35 (m, 3H), 1.68-1.88 (m, 4H), 1.89-2.0 (m, 3H), 2.05-2.15 (m, 2H), 2.95-3.05 (m, 2H), 3.10-3.25 (m, 2H), 3.85-4.10 (m, 3H), 6.02-6.90 (m, 2H), 7.93 (brs, 3H) |

TABLE 14-continued

| Cmpd # | Structure | NMR data |
|---|---|---|
| 301 | 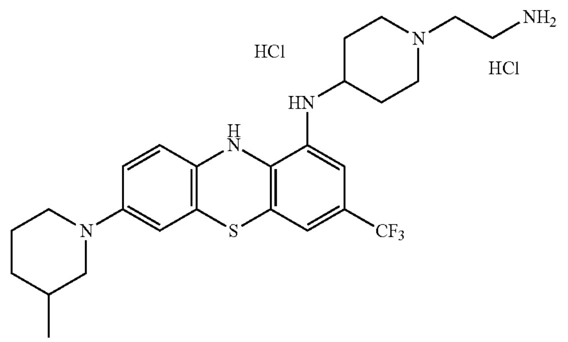 [SMILES: CC1CCCN(c2ccc3c(c2)Sc2cc(C(F)(F)F)cc(NC4CCN(CCN)CC4)c2N3)C1 ; Cl ; Cl] | 1H NMR (400 MHz, DMSO-d6) δ 0.84 ((t, J = 6.89 Hz, 2H), 1.72-1.85 (m, 2H), 1.88-2.0 (m, 2H), 3.10-3.13 (m, 2H), 3.28-3.42 (m, 7H), 3.6-3.75 (m, 4H), 6.62 (d, J = 22.87 Hz, 2H), 8.32 (s, 3H), 8.76 (s, 1H) |
| 302 | 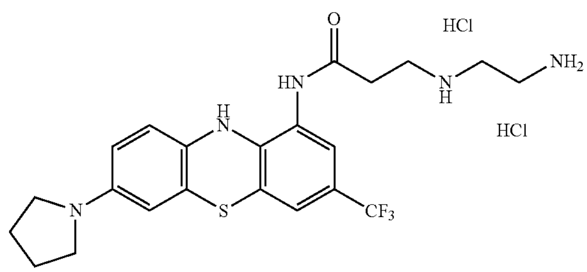 [SMILES: NCCNCCC(=O)Nc1cc(C(F)(F)F)cc2c1Nc1ccc(N3CCCC3)cc1S2 ; Cl ; Cl] | 1H NMR (400 MHz, DMSO-d6) δ 1.92 (brs, 4H), 3.02 (brs, 3H), 3.15-3.35 (m, 9H), 6.20-6.47 (m, 2H), 6.80-7.01 (m, 1H), 7.02-7.20 (m, 1H), 7.21-7.42 (m, 1H), 8.25 (s, 4H), 9.45 (s, 2H), 10.01 (brs, 1H) |
| 303 | 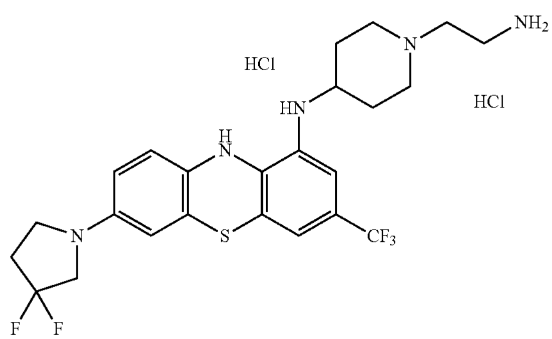 [SMILES: NCCN1CCC(Nc2cc(C(F)(F)F)cc3c2Nc2ccc(N4CCC(F)(F)C4)cc2S3)CC1 ; Cl ; Cl] | 1H NMR (400 MHz, DMSO-d6) δ 1.92 (s, 2H), 2.10 (s, 2H), 3.13-3.19 (m, 2H), 3.29-3.37 (m, 7H), 3.61 (s, 5H), 6.28-6.37 (m, 2H), 6.60 (s, 2H), 6.85-6.87 (m, 1H), 7.94 (brs, 1H), 8.22 (s, 3H), 10.89 (brs, 1H) |
| 304 | 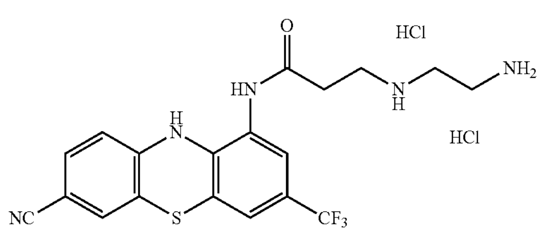 [SMILES: N#Cc1ccc2c(c1)Sc1cc(C(F)(F)F)cc(NC(=O)CCNCCN)c1N2 ; Cl ; Cl] | 1H NMR (400 MHz, DMSO-d6) δ 2.95 (t, J = 1.62 Hz, 2H), 2.98 (t, J = 6.31 Hz, 2H), 3.12-3.22 (m, 4H), 3.22-3.30 (m, 2H), 7.15-7.25 (m, 2H), 7.45-7.55 (m, 3H), 8.15 (brs, 3H), 9.04 (s, 1H), 9.25 (brs, 2H), 10.12 (s, 1H) |
| 305 | 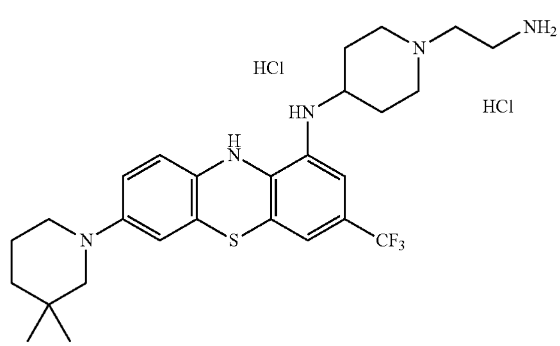 [SMILES: CC1(C)CCCN(c2ccc3c(c2)Sc2cc(C(F)(F)F)cc(NC4CCN(CCN)CC4)c2N3)C1 ; Cl ; Cl] | 1H NMR (400 MHz, DMSO-d6) δ 0.93-0.95 (m, 6H), 1.62-169 (m, 2H), 1.88-1.91 (m, 2H), 2.10-2.13 (m, 2H), 2.89-2.94 (m, 2H), 3.10-3.13 (m, 2H) 3.37-3.41 (m, 5H), 6.61 (d, J = 17.94 Hz, 3H), 6.8 (s, 1H), 7.1 (s, 1H), 8.18 (brs, 1H) |

TABLE 14-continued
| Cmpd # | Structure | NMR data |
|---|---|---|
| 306 | 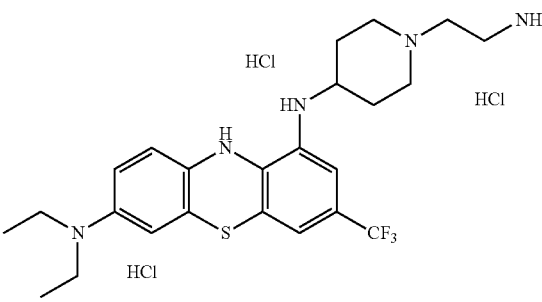 | 1H NMR (400 MHz, DMSO-d6) δ 0.99-1.03 (t, J = 14.2 Hz, 6H), 1.97 (d, J = 11.28 Hz, 2H), 2.13 (d, J = 14 Hz, 2H), 2.49 (s, 1H), 3.16-3.29 (m, 2H), 3.35-3.37 (m, 4H), 3.39-3.41 (m, 4H), 3.5-3.6 (m, 2H), 5.9 (brs, 1H), 6.67 (d, J = 19.4 Hz, 2H), ), 7.36 (d, J = 8.14 Hz, 1H), 7.45 (d, J = 20.4 Hz, 2H), 8.21 (brs, 3H), 8.75 (brs, 1H) |
| 307 | 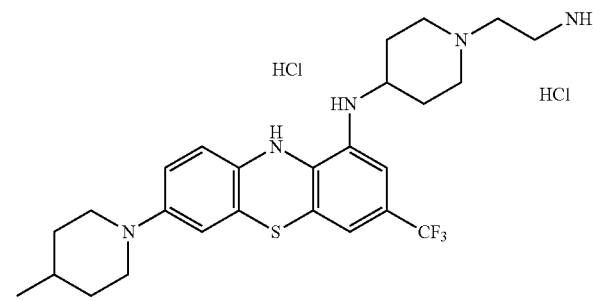 | 1H NMR (400 MHz, DMSO-d6) δ 0.93 (d, J = 6.39 Hz, 3H), 1.28-1.32 (m, 1H), 1.93-2.01 (m, 2H), 2.09-2.13 (m, 2H), 3.12-3.28 (m, 2H), 3.28-3.37 (m, 4H), 3.40-3.46 (m, 3H), 3.61-3.70 (m, 4H), 6.61 s, 1H), 6.67 (s, 1H), 7.00 (brs, 1H)7.16 (s, 1H) 7.41 (s, 1H), 8.12 (s, 3H), 10.76 (s, 1H). |
| 308 | 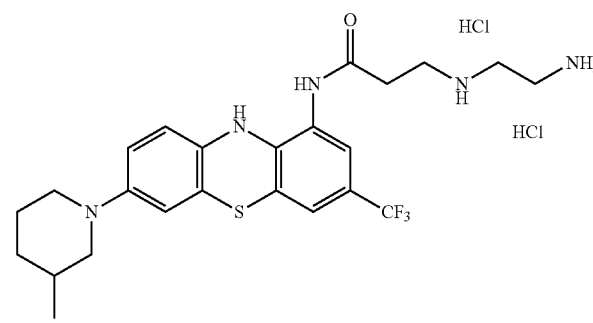 | 1H NMR (400 MHz, DMSO-d6) δ 0.88-0.90 (m, 3H), 1.15-1.21 (m, 1H), 1.74-1.84 (m, 2H), 1.82-2.23 (m, 2H), 2.98-3.07 (m, 2H), 3.22-3.33 (m, 6H), 3.33-3.55 (m, 2H), 7.18-7.34 (m, 2H), 7.42-7.52 (m, 2H), 8.32 (brs, 3H), 8.87 (brs, 1H), 9.52 (brs, 2H), 10.21 (brs, 1H) |
| 310 | 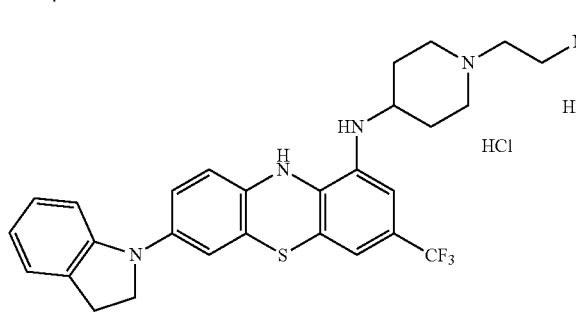 | 1H NMR (400 MHz, DMSO-d6) δ 1.90-1.98 (m, 2H), 2.10-2.19 (m, 2H), 3.02 (t, J = 8.17 Hz, 2H), 3.10-3.20 (m, 2H), 3.25-3.35 (m, 3H), 3.78-3.85 (m, 4H), 6.60-6.70 (m, 3H), 6.82 (s, 1H), 6.86 (d, J = 7.05 Hz, 1H), 6.97-7.04 (m, 3H), 7.12 (d, J = 7.04 Hz, 1H), 8.15-8.25 (m, 4H), 10.9 (brs, 1H) |
| 311 | 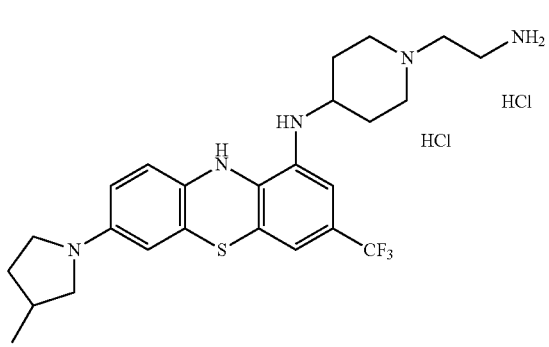 [SMILES: CC1CCN(c2ccc3c(c2)Sc2cc(C(F)(F)F)cc(NC4CCN(CCN)CC4)c2N3)C1 ; Cl ; Cl] | 1H NMR (400 MHz, DMSO-d6) δ 1.04 (d, J = 6.43 Hz, 3H), 1.22-1.54 (m, 1H), 1.88-1.91 (m, 2H), 2.10-2.13 (m, 3H) 3.13-3.2 (m, 5H), 3.58-3.69 (m, 3H), 5.12-5.32 (m, 1H), 6.51-6.69 (m, 2H) 6.81-6.98 (m, 1H), 8.19 (brs, 3H), 10.91 (s, 1H). |

TABLE 14-continued

| Cmpd # | Structure | NMR data |
|---|---|---|
| 312 | (structure: 7-bromo-3-(trifluoromethyl)-10H-phenothiazine with N-(3-aminocyclohexyl)carboxamide substituent, 2 HCl) | 1H NMR (400 MHz, DMSO-d6) δ 1.15-1.40 (m, 4H), 1.45-1.52 (m, 1H), 1.55-1.72 (m, 1H), 1.80-1.88 (m, 1H), 1.90-2.0 (m, 2H), 2.10-2.18 (m, 1H), 2.72-2.85 (m, 1H), 3.02-3.20 (m, 1H), 3.48-3.58 (m, 1H), 7.02-7.08 (m, 1H), 7.11 (s, 1H), 7.18-7.25 (m, 3H), 7.55 (s, 1H), 7.86 (brs, 1H), 8.0 (brs, 1H), 9.92 (s, 1H) |
| 313 | (structure: 7-(3-methylpiperidin-1-yl)-3-(trifluoromethyl)-10H-phenothiazine with N-(3-aminocyclohexyl)carboxamide, 2 HCl) | 1H NMR (400 MHz, DMSO-d6) δ 0.85-0.95 (m, 3H), 1.11-1.22 (m, 1H), 1.32-1.45 (m, 3H), 1.45-1.59 (m, 1H), 1.62-1.70 (m, 2H), 1.71-2.02 (m, 5H), 2.05-2.15 (m, 2H), 3.04-3.11 (m, 2H), 3.31-3.42 (m, 3H), 3.49-3.59 (m, 4H), 6.53-6.75 (m, 1H), 6.76-6.85 (m, 1H), 6.91-7.05 (m, 1H), 7.31-7.71 (m, 2H), 8.01-8.07 (m, 3H), 9.3 (brs, 1H), 9.80 (s, 1H), 12.60 (brs, 1H) |
| 314 | (structure: phenothiazine with 2-methylpiperidinyl and 4-(2-aminoethyl)piperidinylamino, CF3, 3 HCl) | 1H NMR (400 MHz, DMSO-d6) δ 0.99 (d, J = 5.04 Hz, 2H), 1.16-1.21 (m, 2H), 1.57-1.58 (m, 1H), 1.62-1.79 (m, 3H), 1.93-1.97 (m, 4H), 2.03-2.09 (m, 4H), 3.13-3.15 (m, 2H), 3.29-3.41 (m, 4H), 3.61-3.72 (m, 5H), 6.01 (s, 1H), 6.64 (d, J = 20.45 Hz, 2H), 7.14-7.16 (m, 1H), 7.51-7.53 (m, 2H), 8.24 (brs, 1H), 8.78 (s, 1H) 10.77 (s, 1H), 11.87 (s, 1H). |
| 315 | (structure: 7-bromo-3-(trifluoromethyl)phenothiazine with N-acyl ethylenediamine chain, 2 HCl) | 1H NMR (400 MHz, DMSO-d6) δ 2.96-2.99 (m, 2H), 3.12-3.30 (m, 7H), 7.06 (d, J = 8.19 Hz, 1H), 7.15-7.23 (m, 3H), 7.48 (s, 1H), 8.22 (brs, 3H), 8.67 (s, 1H), 9.35 (brs, 2H), 10.07 (s, 1H) |
| 316 | (structure: phenothiazine with 2-methylpyrrolidinyl and 4-(2-aminoethyl)piperidinylamino, CF3, 3 HCl) | 1H NMR (400 MHz, DMSO-d6) δ 1.74-1.98 (m, 4H), 2.04-2.18 (m, 4H), 3.11-3.19 (m, 2H), 3.31-3.45 (m, 6H), 3.61-3.69 (m, 4H), 3.79-3.84 (m, 2H), 3.90-3.92 (m, 1H), 6.59 (s, 1H), 6.64 (s, 1H), 7.10-7.16 (m, 1H), 7.35-7.56 (m, 2H), 8.30-8.40 (m, 3H), 10.89 (brs, 1H), 12.65 (brs, 1H) |

TABLE 14-continued
| Cmpd # | Structure | NMR data |
|---|---|---|
| 317 | 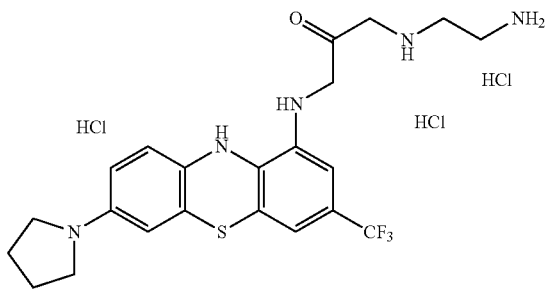 [SMILES: NCCNCC(=O)CNc1cc(C(F)(F)F)cc2c1Nc1ccc(N3CCCC3)cc1S2 ; Cl ; Cl ; Cl] | 1H NMR (400 MHz, DMSO-d6) δ 1.02 (t, J = 7.01 Hz, 6H), 2.98 (t, J = 6.31 Hz, 2H), 3.21-3.30 (m, 7H), 3.32-3.49 (m, 3H), 7.31-7.50 (m, 2H), 7.55-7.65 (m, 3H), 8.22 (s, 3H), 8.95 (s, 1H), 9.42 (s, 2H), 10.17 (s, 1H) 12.47 (brs, 1H) |
| 318 | 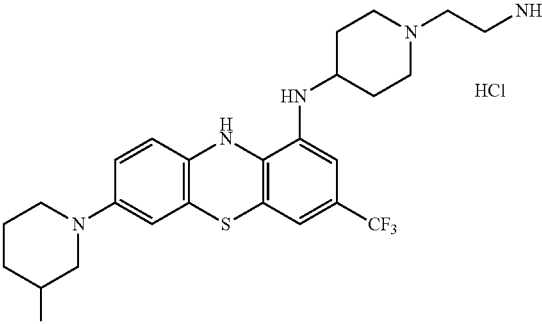 | 1H NMR (400 MHz, DMSO-d6) δ 1.69-1.73 (m, 2H), 1.91-2.00 (s, 4H), 2.09-2.12 (m, 2H), 3.13-3.19 (m, 3H), 3.31-3.38 (m, 6H), 3.61-3.64 (m, 3H), 4.82-4.94 (m, 2H), 6.57 (s, 1H), 6.62 (s, 1H), 6.87-6.97 (m, 3H), 8.35 (brs, 4H), 10.92 (s, 1H) |
| 319 | 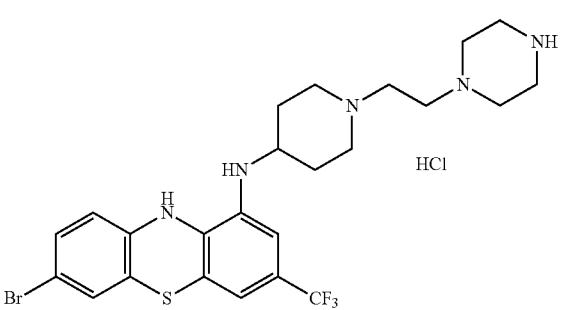 [SMILES: FC(F)(F)c1cc(NC2CCN(CCN3CCNCC3)CC2)c2c(c1)Sc1cc(Br)ccc1N2 ; Cl] | 1H NMR (400 MHz, DMSO-d6): δ 1.92-1.97 (m, 2H), 2.08-2.11 (m, 2H), 2.86-2.91 (m, 5H), 3.11-3.30 (m, 8H), 3.60-3.66 (m, 4H), 6.57 (s, 1H), 6.63 (s, 1H), 7.08 (s, 1H), 7.14-7.18 (m, 2H), 8.74 (brs, 1H), 9.06 (brs, 2H), 10.16 (brs, 1H) |
| 320 | 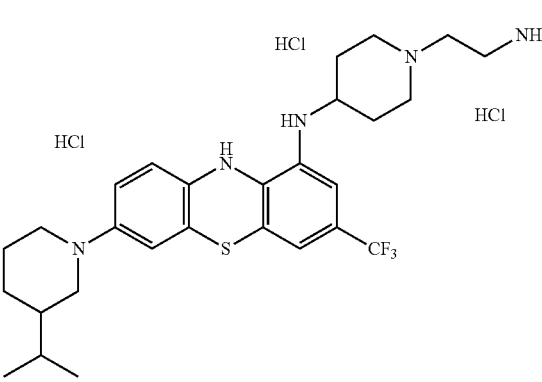 | 1H NMR (400 MHz, DMSO-d6) δ 0.85 (s, 3H), 0.87 (s, 3H), 1.19-1.29 (m, 2H), 1.51-1.55 (m, 1H), 1.74-1.77 (m, 1H), 1.89-2.13 (m, 7H), 3.12-3.18 (m, 3H), 3.21-3.40 (m, 7H), 3.51-3.68 (m, 2H), 6.62 (s, J = 7.97 Hz, 1H), 6.67 (s, 1H), 7.13-7.15 (d, J = 8.33 Hz, 1H), 7.44-7.60 (m, 2H), 8.30-8.40 (m, 3H), 8.80 (s, 1H), 10.85 (brs, 1H), 12.40 (brs, 1H) |

TABLE 14-continued
| Cmpd # | Structure | NMR data |
|---|---|---|
| 321 | 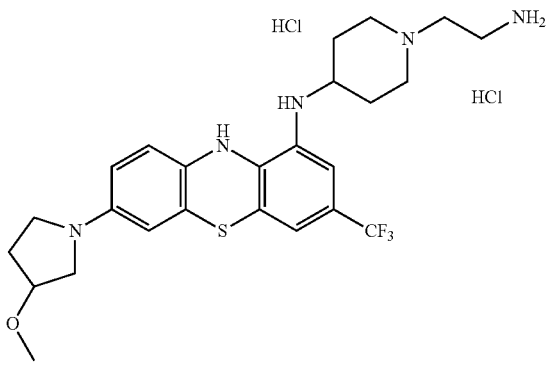 [SMILES: COC1CCN(c2ccc3c(c2)Sc2cc(C(F)(F)F)cc(NC4CCN(CCN)CC4)c2N3)C1 ; Cl ; Cl] | 1H NMR (400 MHz, DMSO-d6) δ 1.94-2.20 (m, 4H), 3.15-3.39 (m, 11H), 3.50-3.80 (m, 2H), 8.40 (s, 3H), 11.00 (brs, 1H) |
| 322 | 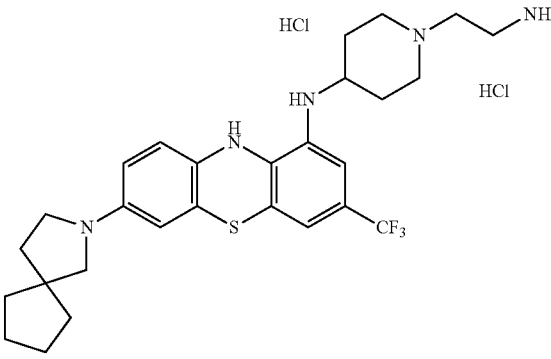 | 1H NMR (400 MHz, DMSO-d6) δ 1.55-1.16 (m, 10H), 1.92-1.97 (m, 2H), 2.10 (brs, 2H), 3.13-3.19 (m, 4H), 3.30-3.38 (m, 4H), 3.62 (m, 4H), 5.80-7.40 (m, 5H), 8.29 (s, 4H), 10.95 (s, 1H) |
| 323 | 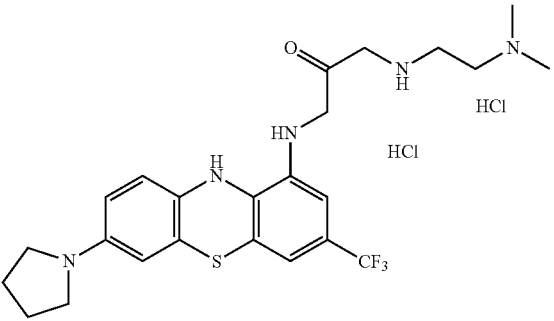 [SMILES: CN(C)CCNCC(=O)CNc1cc(C(F)(F)F)cc2c1Nc1ccc(N3CCCC3)cc1S2 ; Cl ; Cl] | 1H NMR (400 MHz, DMSO-d6) δ 2.83 (s, 8H), 3.247 (s, 2H), 3.43 (s, 4H), 9.45 (brs, 1H), 10.77 (brs, 1H) |
| 324 | 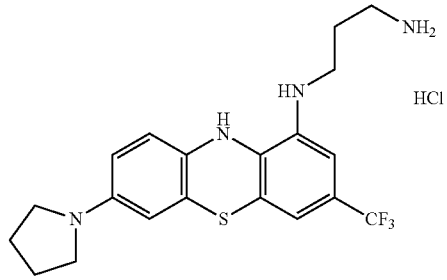 [SMILES: NCCCNc1cc(C(F)(F)F)cc2c1Nc1ccc(N3CCCC3)cc1S2 ; Cl] | 1H NMR (400 MHz, DMSO-d6): δ 0.80-0.90 (m, 1H), 0.91-1.05 (m, 4H), 1.15-1.40 (m, 5H), 1.47-1.60 (m, 2H), 1.62-1.80 (m, 5H), 1.87-1.95 (m, 2H), 1.97-2.09 (m, 2H), 2.90-3.10 (m, 3H), 3.30-3.40 (brs, 1H), 6.30-6.80 (m, 5H), 7.90 (brs, 5H) |

TABLE 14-continued
| Cmpd # | Structure | NMR data |
| --- | --- | --- |
| 325 | 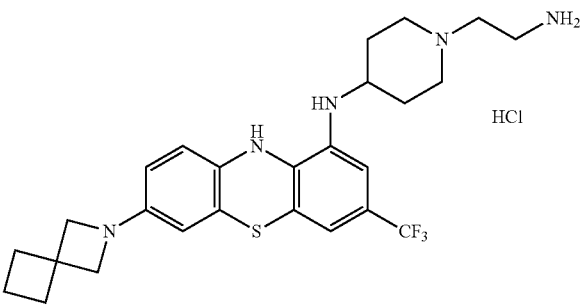 [SMILES: NCCN1CCC(Nc2cc(C(F)(F)F)cc3c2Nc2ccc(N4CC5(CCC5)C4)cc2S3)CC1 ; Cl] | 1H NMR (400 MHz, DMSO-d6) δ 1.76-1.82 (m, 7H), 2.13 (t, J = 7.1 Hz, 4H), 3.13 (s, 3H), 3.25-3.27 (m, 5H), 3.58 (s, 3H), 3.86 (s, 2H), 6.44-6.49 (m, 2H), 6.51-6.57 (m, 2H), 6.81-6.89 (m, 1H), 8.28 (s, 3H), 10.29 (brs, 1H) |
| 326 | 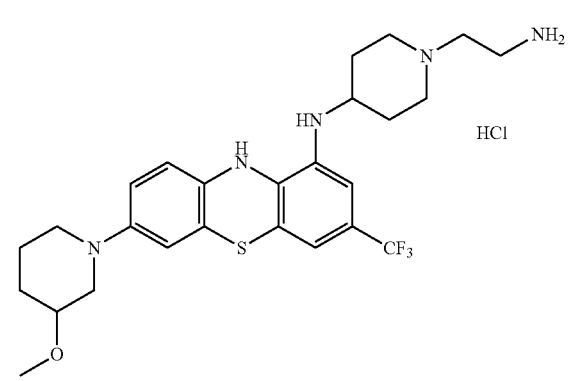 [SMILES: COC1CCCN(c2ccc3c(c2)Sc2cc(C(F)(F)F)cc(NC4CCN(CCN)CC4)c2N3)C1 ; Cl] | 1H NMR (400 MHz, DMSO-d6) δ 1.93-2.06 (m, 5H), 2.08-2.12 (m, 2H), 3.13-3.19 (m, 3H), 3.31-3.39 (m, 9H), 3.57-3.74 (m, 6H), 6.59 (s, 1H), 6.64 (s, 1H), 7.15 (brs, 1H), 7.34-7.48 (m, 2H), 8.39 (brs, 3H), 8.74 (brs, 1H), 10.87 (brs, 1H) |
| 327 | 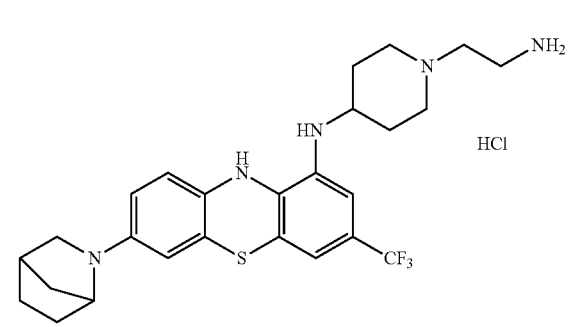 [SMILES: NCCN1CCC(Nc2cc(C(F)(F)F)cc3c2Nc2ccc(N4CC5CCC4C5)cc2S3)CC1 ; Cl] | 1H NMR (400 MHz, DMSO-d6) δ 1.33-1.34 (m, 2H), 1.52-1.62 (m, 4H), 1.93 (d, J = 10.2 Hz, 2H), 2.11 (d, J = 11.8 Hz, 2H), 3.14-3.16 (m, 2H), 3.30 (s, 4H), 3.38 (s, 1H), 3.62 (d, J = 8.9 Hz, 3H), 6.57 (d, J = 6.2 Hz, 3H), 8.33 (s, 3H), 10.94 (brs, 1H) |
| 328 | 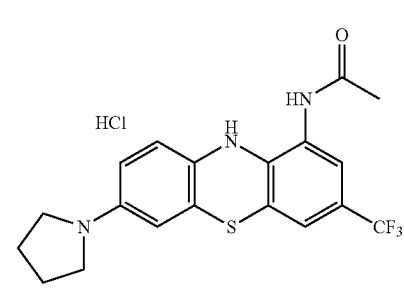 [SMILES: CC(=O)Nc1cc(C(F)(F)F)cc2c1Nc1ccc(N3CCCC3)cc1S2 ; Cl] | 1H NMR (400 MHz, DMSO-d6): δ 9.52 (brs, 1H), 7.99 (brs, 1H), 7.60-6.80 (m, 3H), 3.20 (brs, 3H), 2.1 (brs, 3H), 1.93 (brs, 4H) |
| 329 | 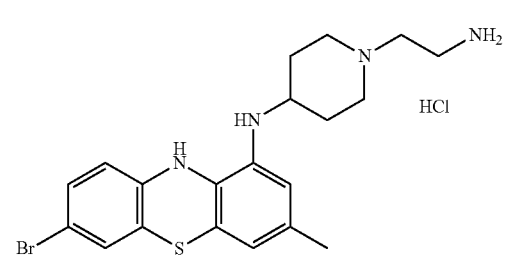 [SMILES: Cc1cc(NC2CCN(CCN)CC2)c2c(c1)Sc1cc(Br)ccc1N2 ; Cl] | 1H NMR (400 MHz, DMSO-d6): δ 10.90-10.81 (m, 1H), 8.41 (brs, 3H), 8.06 (s, 1H), 7.18-7.05 (m, 2H), 6.86 (d, J = 8.53 Hz, 1H), 6.32 (s, 1H), 6.13 (s, 1H), 3.70-3.58 (m, 3H), 3.37-3.31 (m, 4H), 3.12-3.09 (m, 2H), 2.14-2.09 (m, 5H), 1.94-1.88 (m, 2H) |

TABLE 14-continued
| Cmpd # | Structure | NMR data |
|---|---|---|
| 330 | 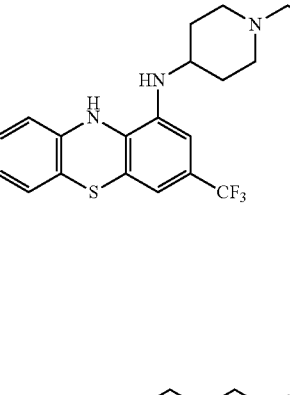 | 1H NMR (400 MHz, DMSO-d6) δ 1.21 (s, 2H), 1.89-1.93 (m, 4H), 2.09 (s, 2H), 3.07 (s, 4H), 3.14-3.17 (m, 4H), 3.27 (s, 4H), 3.36 (s, 2H), 3.56 (s, 8H), 3.62-3.68 (m, 3H), 6.56 (brs, 2H), 9.62 (brs, 1H) |
| 331 | 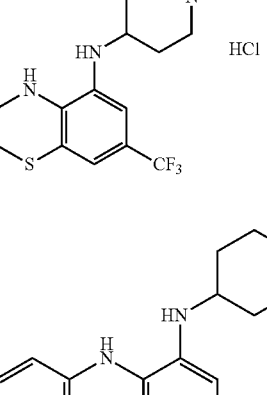 | 1H NMR (400 MHz, DMSO-d6): δ 10.23 (brs, 1H), 8.52 (brs, 1H), 8.08 (brs, 6H), 7.18-7.15 (m, 2H), 6.95 (brs, 1H), 6.65 (s, 1H), 6.58 (s, 1H), 3.65-3.63 (m, 4H), 3.28 (brs, 2H) 3.11 (brs, 2H), 2.98 (s, 4H), 2.84 (s, 2H), 2.69-2.65 (m, 4H), 2.20-1.90 (m, 4H) |
| 332 | 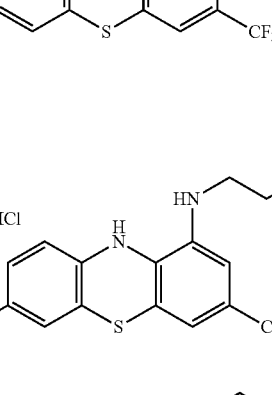 | 1H NMR (400 MHz, DMSO-d6) δ 0.99-1.21 (m, 9H), 1.85-1.96 (m, 4H), 2.10-2.21 (m, 2H), 3.14-3.21 (m, 3H), 3.28-3.34 (m, 5H), 3.37-3.47 (m, 5H), 3.64-3.73 (m, 3H), 5.3-7.3 (m, 2H), |
| 333 | 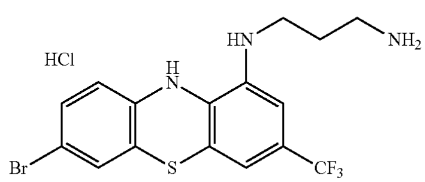 [SMILES: NCCCNc1cc(C(F)(F)F)cc2c1Nc1ccc(Br)cc1S2 ; Cl] | 1H NMR (400 MHz, DMSO-d6): δ 8.54 (s, 1H), 7.78 (s, 3H), 7.19-7.15 (m, 2H), 7.03 (d, J = 8.42 Hz, 1H), 6.56 (d, J = 8.82 Hz, 1H), 3.17 (t, J = 6.80 Hz, 2H), 2.97-2.93 (m, 2H), 1.93-1.86 (m, 2H) |
| 334 | 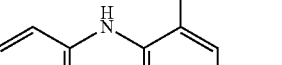 | 1H NMR (400 MHz, DMSO-d6) δ 1.23-1.28 (m, 1H), 1.93 (d, J = 9.7 Hz, 2H), 2.11 (d, J = 10.5 Hz, 2H), 2.98 (d, J = 5.2 Hz, 4H), 3.10-3.18 (m, 2H), 3.30-3.45 (m, 5H), 6.62 (d, J = 15.4 Hz, 2H), 7.04-7.17 (m, 2H), 8.29 (s, 3H), 10.86 (brs, 1H) |

TABLE 14-continued

| Cmpd # | Structure | NMR data |
|---|---|---|
| 335 | 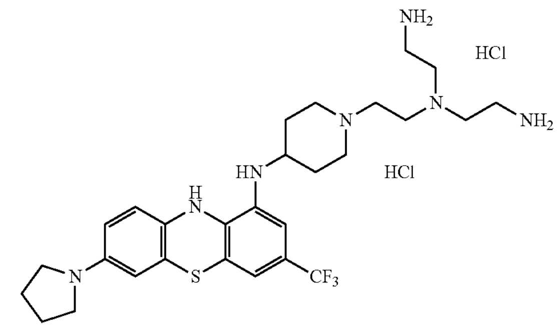 [SMILES: NCCN(CCN)CCN1CCC(Nc2cc(C(F)(F)F)cc3c2Nc2ccc(N4CCCC4)cc2S3)CC1 ; Cl ; Cl] | 1H NMR (400 MHz, DMSO-d6) δ 1.70-2.08 (m, 8H), 2.68 (s, 6H), 2.83 (s, 3H), 2.95 (s, 5H), 3.09 (t, J = 11.9 Hz, 3H), 3.16 (s, 4H), 3.36-3.43 (m, 4H), 3.44-3.47 (m, 2H), 6.22-7.33 (m, 2H), 8.19 (s, 5H) |
| 336 | 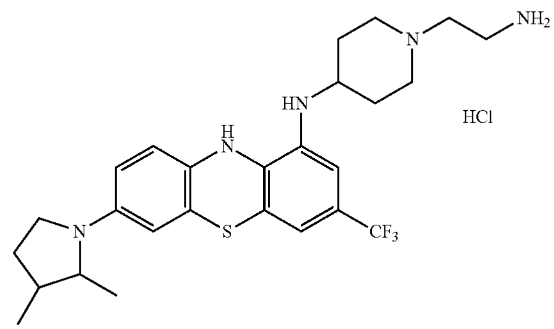 [SMILES: CC1CCN(c2ccc3c(c2)Sc2cc(C(F)(F)F)cc(NC4CCN(CCN)CC4)c2N3)C1C ; Cl] | 1H NMR (400 MHz, DMSO-d6) δ 0.99-1.11 (m, 6H), 1.72-1.92 (m, 2H), 2.10-2.19 (m, 3H), 3.16 (t, J = 8.3 Hz, 3H), 3.21-3.34 (m, 6H), 3.63-3.71 (m, 4H), 6.51-6.71 (m, 2H), 7.4-7.5 (m, 1H), 8.3 (brs, 3H), 10.99 (s, 1H). |
| 337 | 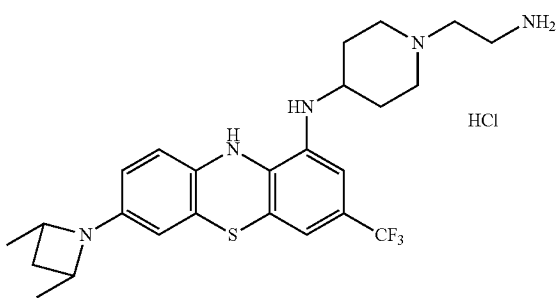 [SMILES: CC1CC(C)N1c1ccc2c(c1)Sc1cc(C(F)(F)F)cc(NC3CCN(CCN)CC3)c1N2 ; Cl] | 1H NMR (400 MHz, DMSO-d6) δ 1.04-1.22 (m, 2H), 1.32-1.48 (m, 6H), 1.75-1.93 (m, 3H), 2.10-2.13 (m, 3H), 2.51-2.60 (m, 1H) 3.13-3.17 (m, 3H), 3.28-3.29 (m, 6H), 3.37-3.42 (m, 1H), 4.40-4.42 (m, 2H), 6.65-6.67 (m, 2H), 6.94-7.07 (m, 2H), 8.34-8.38 (m, 3H), 10.89 (brs, 1H) |
| 338 | 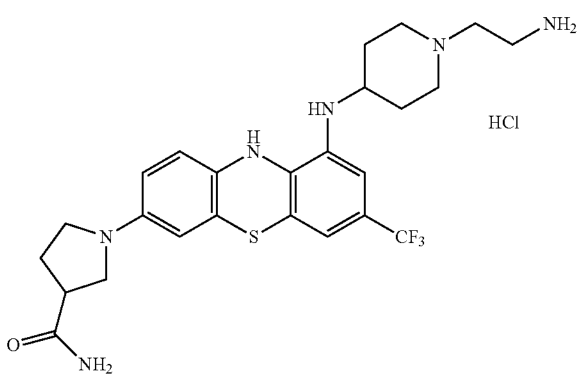 [SMILES: NCCN1CCC(Nc2cc(C(F)(F)F)cc3c2Nc2ccc(N4CCC(C(N)=O)C4)cc2S3)CC1 ; Cl] | 1H NMR (400 MHz, DMSO-d6) δ 1.11-1.24 (m, 1H), 1.74-2.11 (m, 3H), 3.05-3.17 (m, 3H), 3.31-3.49 (m, 9H), 3.56-3.72 (m, 4H), 6.93 (s, 1H), 7.08-7.34 (m, 3H), 7.45 (s, 1H), 8.35 (s, 4H), 10.98 (brs, 1H) |

TABLE 14-continued
| Cmpd # | Structure | NMR data |
|---|---|---|
| 339 | 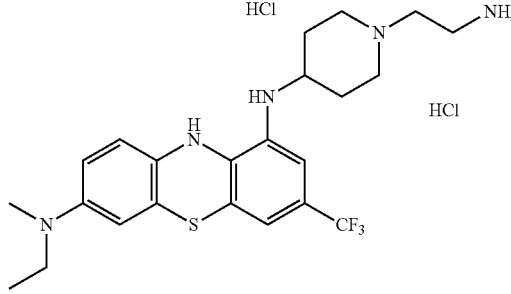 | 1H NMR (400 MHz, DMSO-d6) δ 1.03 (t, J = 6.9 Hz, 3H), 1.92-1.98 (m, 2H), 2.12 (d, J = 13.2 Hz, 2H), 3.00 (s, 3H), 3.11-3.18 (m, 2H), 3.30 (s, 3H), 3.37-3.48 (m, 3H), 3.55-3.68 (m, 4H), 6.63 (d, J = 22.1 Hz, 2H), 7.14 (d, J = 7.4 Hz, 1H), 7.36-7.47 (m, 1H), 8.30 (s, 3H), 10.85 (s, 1H), 12.61 (brs, 1H) |
| 340 | 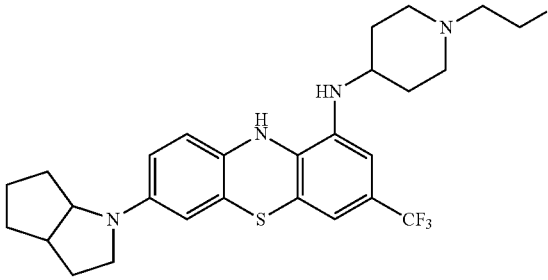 | 1H NMR (400 MHz, DMSO-d6) δ 1.44 (s, 4H), 2.11-2.13 (m, 5H), 3.14 (t, J = 11.9 Hz, 2H), 3.29-3.36 (m, 4H), 3.65 (s, 8H), 7.21 (br s, 1H), 8.40 (s, 3H), 10.96 (s, 1H) |
| 341 | 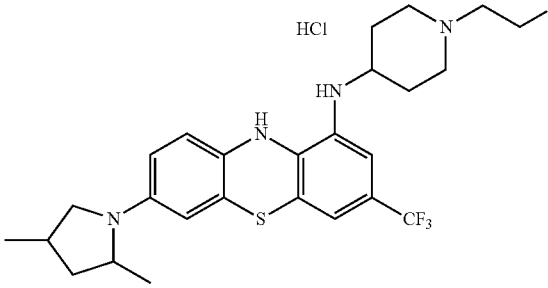 | $^1$H NMR (400 MHz, DMSO-d6) δ 1.11-1.21 (m, 8H), 1.54 (s, 1H), 1.74-2.10 (m, 2H), 3.03-3.19 (m, 2H), 3.31-3.48 (m, 6H), 3.64-3.68 (m, 3H), 6.52-6.75 (m, 2H), 7.07-7.65 (m, 2H), 8.34 s, 3H), 10.81-10.97 (m, 1H) |
| 342 | 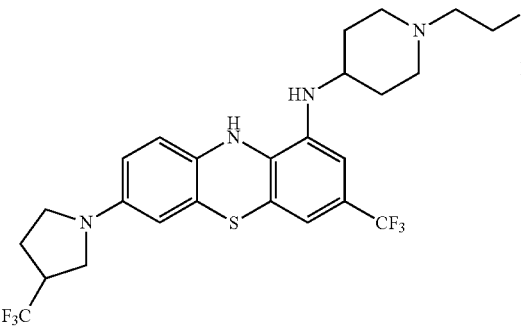 | $^1$H NMR (400 MHz, DMSO-d6) δ 1.16-1.22 m, 2H), 1.74-2.11 (m, 6H), 3.04-3.17 (m, 3H), 3.32-3.47 (m, 7H), 3.55-3.68 (m, 2H), 8.40 (m, 4H), 11.0 (br s, 1H) |
| 343 | 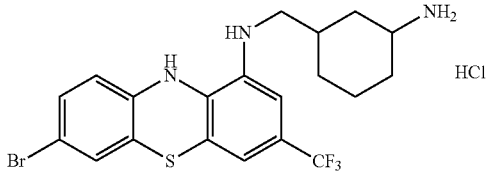 [SMILES: NC1CCCC(CNc2cc(C(F)(F)F)cc3c2Nc2ccc(Br)cc2S3)C1 ; Cl] | (400 MHz, DMSO-d6) δ 0.842-0.866 (m, 1H) 0.1 1H), 1.199-1.308 (m, 3H), 1.761-1.828 (m, 1H) 11 Hz 2H), 7.07-7.09 (m, 3H), 7.901 (s, 3H), 8.6 1H). |

TABLE 14-continued

| Cmpd # | Structure | NMR data |
|---|---|---|
| 344 | 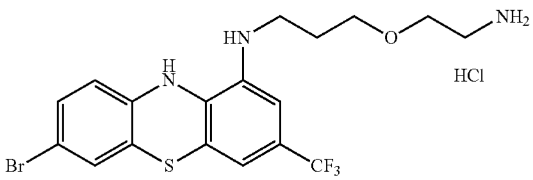 [SMILES: NCCOCCCNc1cc(C(F)(F)F)cc2c1Nc1ccc(Br)cc1S2 ; Cl] | (400 MHz, DMSO-d6) δ 1.80-1.92 (m, 2H) 2.90 1.15-3.22 (m, 2H), 3.50-3.62 (m, 4H) 6.51 (s, 1H), 23 (brs, 3H), 8.73 (s, 1H) |
| 345 | 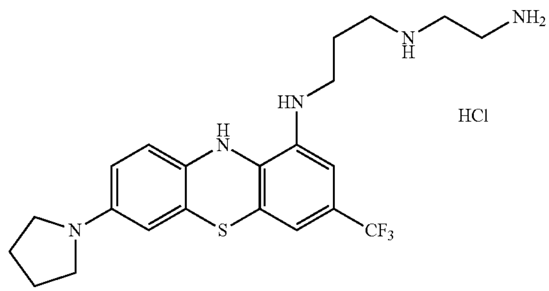 [SMILES: NCCNCCCNc1cc(C(F)(F)F)cc2c1Nc1ccc(N3CCCC3)cc1S2 ; Cl] | ¹H NMR (400 MHz, DMSO-d₆) δ 1.8-2.2 (m, 1H), 3.0-3.1 (m, 1H), 3.2-3.3 (m, 7H), 8.3 (s, 3H), 8.9 (s, 2H), 9.3 (br, S, 2H) |
| 346 | 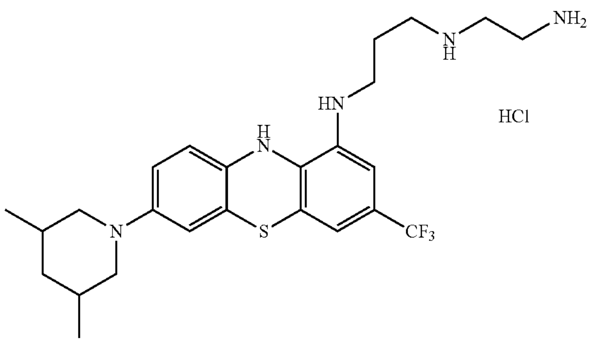 [SMILES: CC1CC(C)CN(c2ccc3c(c2)Sc2cc(C(F)(F)F)cc(NCCCNCCN)c2N3)C1 ; Cl] | ¹H NMR (400 MHz, DMSO-d₆) δ 0.8-0.9 (m, 7H), 1.1-1.3 (m, 1H), 1.7-1.8 (m, 1H), 2.0-2.1 (m, 2H), 2.2-2.3 (m, 2H), 3.0-3.2 (m, 9H), 3.3-3.4 (m, 4H), 6.5 (d, J = 6 Hz 2H), 7.2-7.5 (m, 3H), 8.3 (s, 3H), 9.3 (s, 2H). |
| 347 | 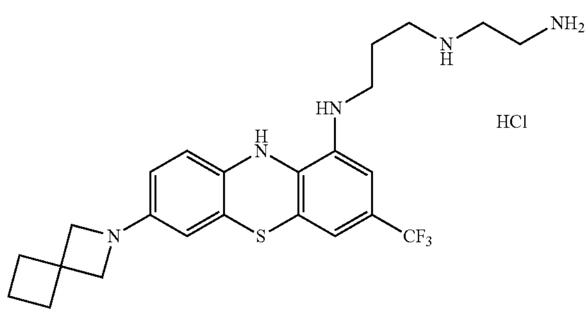 [SMILES: NCCNCCCNc1cc(C(F)(F)F)cc2c1Nc1ccc(N3CC4(CCC4)C3)cc1S2 ; Cl] | ¹H NMR (400 MHz, DMSO-d₆) δ 1.1-1.3 (m, 6 H), 1.7-2.0 (m, 7H), 2.1 (t, J = 6.88 Hz, 2H), 3.0-3.1 (m, 11H), 6.2-6.6 (m, 2H), 8.3 (br s, 4 H), 9.3 (br s, 2H). |
| 348 | 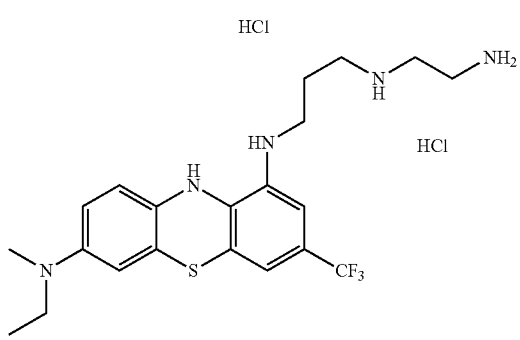 [SMILES: Cl ; CCN(C)c1ccc2c(c1)Sc1cc(C(F)(F)F)cc(NCCCNCCN)c1N2 ; Cl] | ¹H NMR (400 MHz, DMSO-d₆) δ 1.0 (s, 3H), 2.0 (s, 2H), 3.0 (s, 3H), 3.1-3.3 (m, 8H), 3.3-3.4 (m, 2H), 6.5 (br, 2H), 7.3 (br, 3H), 8.3 (s, 3H), 8.9 (s, 1H), 9.3 (br, 2H). |

TABLE 14-continued

| Cmpd # | Structure | NMR data |
|---|---|---|
| 349 | 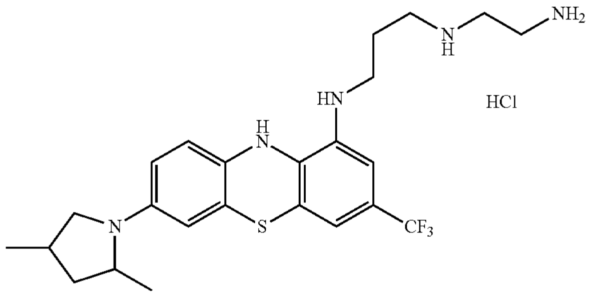 [SMILES: CC1CC(C)N(c2ccc3c(c2)Sc2cc(C(F)(F)F)cc(NCCCNCCN)c2N3)C1 ; Cl] | $^1$H NMR (400 MHz, DMSO-d$_6$) δ1.1 (d, J = 4.5 Hz, 6H), 2.0-2.1 (m, 2H), 2.4 (m, 1H), 3.1-3.3 (m, 10H), 6.5-6.6 (m, 2H), 7.5-7.6 (m, 2H), 8.3 (br, 3H). |
| 350 | 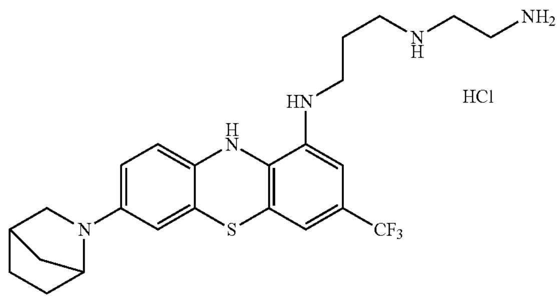 [SMILES: NCCNCCCNc1cc(C(F)(F)F)cc2c1Nc1ccc(N3CC4CCC3C4)cc1S2 ; Cl] | $^1$H NMR (400 MHz, DMSO-d$_6$) δ 1.2 (t, J = 7.28, 1H), 1.3-1.4 (m, 1H), 1.6 (br, 2H), 2.0 (br, 2H), 3.1-3.3 (m, 8H), 8.3 (br, 3H), 9.3 (br, 2H). |
| 351 | 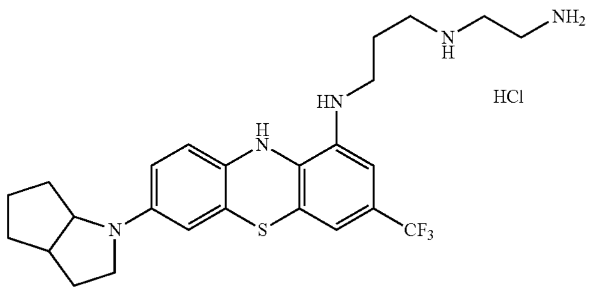 [SMILES: NCCNCCCNc1cc(C(F)(F)F)cc2c1Nc1ccc(N3CCC4CCCC43)cc1S2 ; Cl] | $^1$H NMR (400 MHz, DMSO-d$_6$) δ 1.3-1.4 (m, 13H), 1.4-1.6 (m, 15H), 1.7-1.9 (m, 2H), 3.1-3.3 (m, 2H), 3.3-3.4 (m, 5H), 3.5-3.9 (m, 2H), 6.1 (br, 1H), 6.6-6.7 (m, 4H), 6.9 (s, 1H), 7.4 (d, J = 7.2 Hz, 1H). |
| 352 | 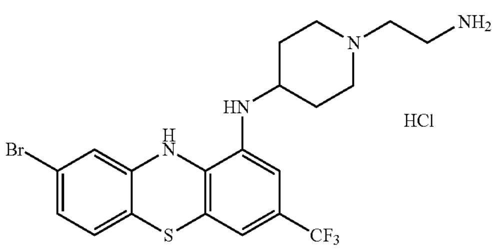 [SMILES: NCCN1CCC(Nc2cc(C(F)(F)F)cc3c2Nc2cc(Br)ccc2S3)CC1 ; Cl] | $^1$H NMR (400 MHz, DMSO-d$_6$) δ 1.95 (d, J = 11.6 Hz, 2H), 2.1 (d, J = 12.8 Hz, 2H), 3.1-3.2 (m, 1H), 3.39 (m, 4H), 3.61 (d, J = 11.48 Hz, 3H), 3.89-4.0 (m, 1H), 6.57 (s, 1H), 6.64 (s, 1H), 6.88 (d, J = 8.1 Hz, 1H), 6.97 (d, J = 1.8 Hz, 1H), 7.29 (S, 1H), 7.6 (s, 1H), 8.32 (br s, 3H), 8.63 (s, 1H), 9.22 (s, 1H). |
| 353 | 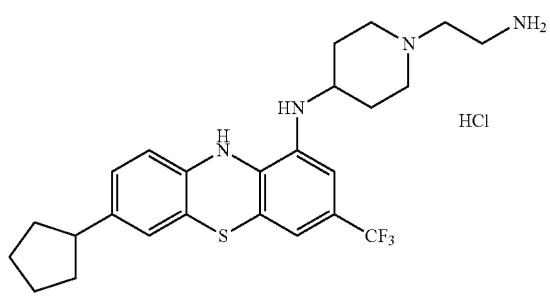 [SMILES: NCCN1CCC(Nc2cc(C(F)(F)F)cc3c2Nc2ccc(C4CCCC4)cc2S3)CC1 ; Cl] | $^1$H NMR (400 MHz, DMSO-d$_6$) δ 1.4-1.5 (m, 2H), 1.5-1.6 (m, 2H), 1.7 (m, 2H), 1.9-2.0 (m, 2H), 2.01 (t, J = 6.6 Hz, 2H), 2.71-2.81 (m, 1H), 3.1-3.2 (m, 8H), 6.54 (d, J = 7.6 Hz, 2H), 6.8 (s, 1H), 6.9 (d, J = 12.2 Hz, 1H), 7.03 (S, 1H), 8.2-8.3 (m, 4H), 9.2 (br s, 2H). |

TABLE 14-continued
| Cmpd # | Structure | NMR data |
|---|---|---|
| 354 | 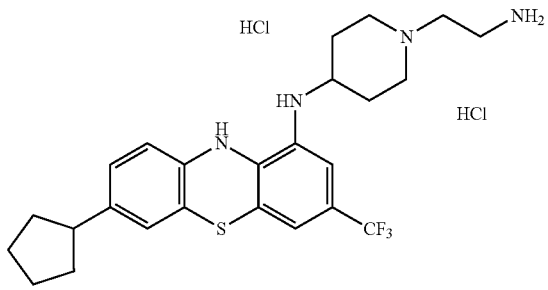 [SMILES: NCCN1CCC(Nc2cc(C(F)(F)F)cc3c2Nc2ccc(C4CCCC4)cc2S3)CC1 ; Cl ; Cl] | $^1$H NMR (400 MHz, DMSO-d$_6$) δ 1.4-1.49 (m, 2H), 1.6-1.7 (m, 2H), 1.7-1.8 (m, 2H), 1.9-2.0 (m. 4H), 2.1 (d, J = 13.1 Hz, 2H), 2.8-2.9 (m, 1H), 3.1-3.2 (m, 2H), 3.27-3.33 (m, 4H), 3.6 (d, J = 11.8 Hz, 3H), 5.6 (brs, 1H), 6.6 (s, 1H), 6.7 (s, 1H), 6.8 (s, 1H), 6.9 (d, J = 8.4 Hz, 2H), 8.2 (br, 4H), 10.94 (brs, 1H). |
| 355 | 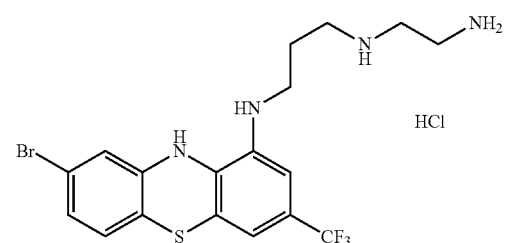 | $^1$H NMR (400 MHz, DMSO-d$_6$) δ 1.1-1.2 (m, 2H), 1.9-2.1 (m, 2H), 3.2 (br s, 8H), 6.5 (br s, 1H), 6.8-6.9 (m, 2H), 7.5 (s, 1H), 8.1-8.3 (m, 3H), 8.8 (br s, 1H), 9.3 (br s, 1H). |
| 356 | 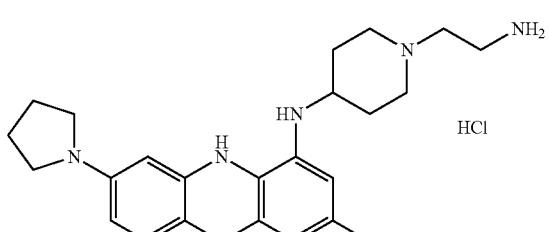 | $^1$H NMR (400 MHz, DMSO-d$_6$) δ 1.9-2.0 (m, 6H), 2.1-2.2 (m, 2H), 3.1-3.2 (m, 5H), 3.3-3.4 (m, 5H), 3.6 (d, J = 11.28 Hz, 3H), 6.1 (br, 1H), 6.3 (s, 1H), 6.5 (s, 2H), 6.6 (s, 1H), 6.7-6.8 (m, 1H), 8.1 (br, 1H), 8.3 (br s, 3H). |
| 357 | 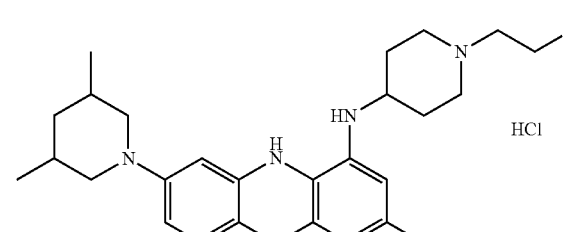 | $^1$H NMR (400 MHz, DMSO-d$_6$) δ 0.8 (d, J = 6.44, 6H), 1.1-1.3 (m, 2H), 1.6-1.7 (m, 1H), 1.9-2.0 (m, 3H), 2.0-2.1 (m, 3H), 3.3 (s, 4H), 3.4-3.5 (m, 6H), 6.5 (s, 1H), 6.6 (s, 1H), 6.7-6.9 (m, 2H), 8.3 (br s, 3H). |
| 358 | 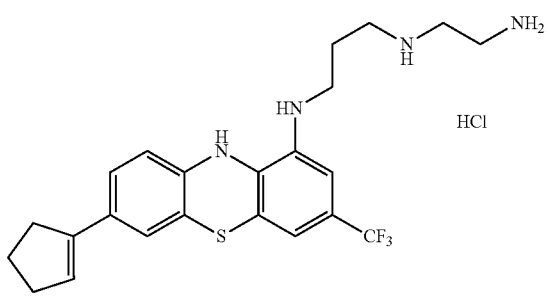 [SMILES: NCCNCCCNc1cc(C(F)(F)F)cc2c1Nc1ccc(C3=CCCC3)cc1S2 ; Cl] | $^1$H NMR (400 MHz, DMSO-d$_6$) δ1.8-1.9 (m, 2H), 2.1-2.19 (m, 2H), 2.4-2.5 (m, 2H), 2.5-2.55 (m, 1H), 3.19-3.25 (m, 10H), 3.5-3.7 (m, 2H), 6.14 (S, 1H), 6.5 (d, J = 6.8 Hz, 2H), 7.1 (s, 3H), 8.23 (brs, 3H), 8.4 (brs, 1H), 9.2 (brs, 2H). |

TABLE 14-continued

| Cmpd # | Structure | NMR data |
|---|---|---|
| 359 | 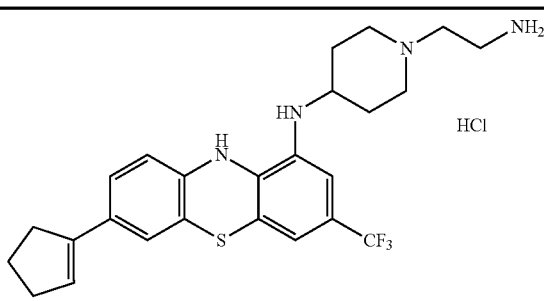 HCl | $^1$H NMR (400 MHz, DMSO-d$_6$) δ 1.22 (s, 9H), 1.3 (s, 18H), 1.5-1.6 (m, 3H), 1.81-1.9 (m, 1H), 1.97 (t, J = 7.4 Hz, 3H), 2.17-2.2 (m, 2H), 2.31-2.39 (m, 1H), 2.43 (t, J = 6.72 Hz, 2H), 2.6-2.7 (n, 2H), 2.84-2.89 (m, 2H), 3.29-3.43 (m, 1H), 3.56 (t, J = 6.5 Hz, 2H), 5.42 (br, 1H), 6.34 (s, 1H) 6.84 (s, 1H), 6.96 (s, 1H), 7.46 (d, J = 8.3 Hz, 1H) 7.51 (s, 1H), 7.716 (d, J = 8.32, 1H). |

Anti-Infective Activity of the Synthesised Compounds

The compounds as disclosed by the present application have anti-infective activity.

Initial minimal inhibitory concentration (MIC) tests were made on two bacterial strains:
 Escherichia coli (ATCC25922)
 Staphylococcus aureus (ATCC25923).

The results of these tests are shown in Table 15.

The MIC of selected compounds was determined against a number of further strains:
 Enterococcus faecalis (ATCC29212)
 Pseudomonas aeruginosa (ATCC27853)
 Staphylococcus aureus subsp. aureus (ATCC29213)
 Klebsiella pneumoniae subsp. pneumoniae (ATCC13883)
 Streptococcus pneumoniae (ATCC33400)
 Haemophilus influenzae (ATCC49766)
 Neisseria meningitidis (ATCC13077)
 Listeria monocytogenes (ATCC15313)
 Legionella pneumophila subsp. pneumophila (ATCC33152)
 Mycobacterium bovis BCG (ATCC19210)

The results of these tests are shown in Table 16.

Minimal Inhibitory Concentration (MIC)

MIC values were determined using the standard broth microdilution procedure based on the guidelines by the Clinical and Laboratory Standards Institute (CLSI). Briefly, the compounds were dissolved in DMSO to 10 mM. They were diluted in cation-adjusted Mueller-Hinton broth (CAMHB) to four times the highest concentration tested. A serial 2-fold dilution in CAMHB was done in microdilution plates. The inoculum of bacterial strain to be tested was prepared by making a suspension of colonies from an 18 to 24 hours old plate in CAMHB. The inoculum was diluted so that, after inoculation, each well contained approximately 5×10$^5$ CFU/mL. To a volume of 50 µl compound in CAMHB an equal volume of inoculum was added. The tray was sealed in a plastic bag and incubated at 35° C. for 16 to 20 hours. To aid in the detection of growth the dye resazurin was added to a final concentration 0.001% and incubated at room temperature for 1 h. Reduction of resazurin, and therefore bacterial growth, was seen as a change from blue to pink. The MIC is the lowest concentration of compound that completely inhibits growth of the organism.

The method used is described in detail in: Methods for Dilution Antimicrobial Susceptibility Tests for Bacteria That Grow Aerobically; Approved Standard-Ninth Edition. CLSI document M07-A9. Wayne, Pa.: Clinical and Laboratory Standards Institute; 2012.

Inhibition of bacterial RNaseP activity.

The assay is based on how much the cleavage of the substrate pATSerUG by E. coli RNase P RNA, M1 RNA, is inhibited by the compound.

The substrate pATSerUG is a 45 nt long model substrate that maintains T-stem/loop structure of the tRNA$^{ser}$ precursor. It was purchased from Dharmacon/GE Healthcare, and labelled with $^{32}$P at the 5' end with [γ-$^{32}$P]ATP according to standard procedures, and purified by electrophoresis on a denaturing polyacrylamide gel.

The M1 RNA was generated by T7 in vitro transcription using a PCR product with the M1 RNA gene as template.

The compound to be tested was dissolved in assay buffer (see below). Assay buffer was added to a theoretical concentration of up to 10 mM. After vortexing and incubation at room temperature for 30 minutes the undissolved compound was removed by centrifugation (17,000×g 10 min). The concentration of compound in the supernatant was determined spectroscopically by measuring the absorbance at a wavelength where the compound had an absorbance maximum. The calibration curve was made from known concentrations of the compound dissolved in DMSO.

The cleavage reaction was performed in assay buffer (50 mM Tris-HCl, pH 7.9, 1 mM NH$_4$Cl, 10 mM MgCl$_2$, 5% PEG6000, 10 mM spermidine).

M1 RNA was diluted to 10 times the concentration to be used in assay buffer and preincubated at 37° C. for 10 min to allow proper folding. The final concentration of M1 RNA was determined for each batch of enzyme, and was the concentration that gave approximately 50% cleavage of the substrate in a 10 min reaction. The folded M1 RNA was mixed with the compound to be tested in a total volume of 9 µl and incubated for an additional 10 min at 37° C. The substrate was preheated separately for 5 min at 37° C. The reaction was started by the addition of 1 µl substrate to the M1 RNA-compound mixture. After 10 min incubation at 37° C. the reaction was stopped by the addition of 20 µl stop solution (10 M urea, 100 mM EDTA, 0.05% bromophenol blue, 0.05% xylene cyanol). The reactions were then heated to 95° C. for 3 min, chilled on ice, then resolved on 20% polyacrylamide/7 M urea/TBE gels and detected using a Phosphoimager. The signals were quantitated using the softwares QuantityOne or ImageLab.

Initial Inhibition of RNase P Activity

To test if any inhibition could be detected for the compound an initial inhibition of RNase P activity was determined. The maximum amount of compound was used, ie. 8 µl of the supernatant from freshly dissolved compound in assay buffer in a 10 µl cleavage reaction. The degree of inhibition was judged from the normalised cleavage (the ratio between cleavage with compound divided by cleavage without compound). If this ratio was <0.5, the IC50 value was determined.

IC50 Determination.

About 8 different concentrations, generally ranging from maximum concentration for the compound down to 8000 times diluted, were tested for cleavage. The IC50 values and Hill slopes were calculated using the software GraphPad Prism. The determined IC50 values are listed in Table 15.

TABLE 15

RNase P inhibition and Antibacterial Efficacy Results

| Cmpd#. | RNAse P Inhibition at 10 µM | at 8 µM | RNAse P Inhibition IC$_{50}$ (µM) | E. coli MIC (µg/ml) | S. aureus ("Clinical") MIC (µg/ml) | S. aureus ("wound") (MIC) (µg/ml) |
|---|---|---|---|---|---|---|
| 2 | 0.84 | 0.42 | | >100 | 4 | |
| 30 | | 0.49 | >100 | 16 | 8 | |
| 39 | | 0.58 | 76 | >100 | 27 | |
| 42 | | 1.02 | | >100 | 47 | |
| 44 | | 1.06 | | >100 | 2 | |
| 67 | | 0.19 | >100 | 13 | 13 | |
| 83 | | | >100 | >100 | 32 | |
| 87 | | | >100 | >100 | 55 | |
| 88 | | | >100 | >100 | 27 | |
| 89 | | | >100 | >100 | 85 | |
| 90 | | | >100 | >100 | 64 | |
| 91 | | | >100 | 32 | 8 | |
| 92 | | | >100 | >100 | 1 | 1 |
| 94 | | | 202 | >100 | 64 | 94 |
| 95 | | | 94 | 64 | 32 | |
| 97 | | | >100 | 8 | 4 | |
| 98 | | | >100 | 16 | 8 | |
| 100 | | | >100 | 32 | 16 | |
| 101 | | | >100 | 64 | 32 | |
| 105 | | | 15 | 52 | 26 | 32 |
| 106 | | | >100 | 64 | 32 | |
| 108 | | | >100 | 32 | 8 | |
| 110 | | | >100 | >100 | 6 | |
| 111 | | | 20 (est) | >100 | 3 | 3 |
| 113 | | | NI | >100 | 7 | |
| 115 | | | >100 | >100 | 7 | |
| 116 | | | >100 | >100 | 42 | |
| 117 | | | >100 | >100 | 26 | |
| 118 | | | 17 | 26 | 13 | |
| 119 | | | >100 | >100 | 93 | |
| 120 | | | 12 | >100 | 27 | |
| 121 | | | >100 | >100 | 6 | |
| 122 | | | >100 | >100 | 24 | |
| 123 | | | >100 | >100 | 2 | 2 |
| 124 | | | 59 | 35 | 17 | |
| 125 | | | 20 | 26 | 13 | |
| 126 | | | >100 | >100 | 82 | |
| 129 | | | >100 | >100 | 6 | |
| 130 | | | 57 | >100 | 7 | |
| 132 | | | >100 | >100 | 4 | |
| 133 | | | 19 | 13 | 3 | 81 |
| 134 | | | >100 | >100 | 6 | |
| 135 | | | 24-32 | >100 | 6 | 8 |
| 136 | | | 37 | 7 | 7 | 16 |
| 137 | | | 160 | >100 | 13 | |
| 139 | | | >100 | >100 | 52 | |
| 140 | | | 8 | 7 | 3 | 8 |
| 141 | | | 12 | 12 | 3 | 6 |
| 143 | | | >100 | >100 | 3 | |
| 144 | | | >100 | >100 | 3 | |
| 148 | | | >100 | >100 | 26 | |
| 149 | | | 15 | 54 | 13 | |
| 150 | | | 14 | 12 | 1 | |
| 151 | | | >100 | >100 | 3 | |
| 152 | | | >100 | >100 | 13 | |
| 153 | | | >100 | >100 | 25 | |
| 155 | | | 53 | 35 | 35 | |
| 156 | | | >100 | 25 | 13 | |
| 157 | | | >100 | >100 | 71 | |
| 158 | | | 53 | 52 | 3 | |
| 159 | | | >100 | >100 | 12 | |
| 160 | | | 60 | 52 | 26 | |
| 161 | | | 68 | 96 | 24 | |

TABLE 15-continued

RNase P inhibition and Antibacterial Efficacy Results

| Cmpd#. | RNAse P Inhibition at 10 µM | at 8 µM | RNAse P Inhibition IC$_{50}$ (µM) | E. coli MIC (µg/ml) | S. aureus ("Clinical") MIC (µg/ml) | S. aureus ("wound") (MIC) (µg/ml) |
|---|---|---|---|---|---|---|
| 162 | | | 50 | >100 | 30 | |
| 163 | | | 72 | 14 | 14 | |
| 164 | | | | 97 | 24 | |
| 165 | | | | 34 | 17 | |
| 167 | | | >100 | 27 | 13 | |
| 169 | | | 36 | 45 | 11 | |
| 170 | | | 59 | 7 | 3 | |
| 171 | | | 42 | 13 | 3 | |
| 172 | | | 27 | 23 | 6 | |
| 173 | | | 59 | >100 | 24 | |
| 174 | | | 50 | 11 | 3 | |
| 175 | | | 80 | 49 | 24 | |
| 178 | | | | 48 | 6 | |
| 179 | | | >100 | 12 | 3 | |
| 180 | | | 87 | 14 | 7 | |
| 181 | | | >100 | 27 | 7 | |
| 182 | | | 61 | 25 | 3 | |
| 184 | | | 11 | 21 | 5 | |
| 186 | | | 30 | 99 | 2 | |
| 187 | | | 53 | 16 | 4 | |
| 188 | | | >100 | 23 | 12 | |
| 189 | | | >100 | 52 | 3 | |
| 190 | | | 82 | 26 | 3 | |
| 191 | | | 19 | 50 | 6 | |
| 192 | | | NI | NI | 6 | |
| 193 | | | 180 | 22 | 5 | |
| 196 | | | >100 | 52 | 26 | |
| 197 | | | 25 | NI | 6 | 4 |
| 198 | | | NI | NI | 3 | |
| 199 | | | 65 | 28 | 28 | |
| 203 | | | 4 | 14 | 14 | |
| 204 | | | 8 | 12 | 3 | |
| 205 | | | 364 | NI | 25 | |
| 206 | | | 89 | 50 | 25 | |
| 207 | | | 109 | 50 | 25 | |
| 208 | | | 258 | 24 | 12 | |
| 210 | | | 95 | >100 | 60 | |
| 211 | | | 258 | NI | 25 | 211 |
| 212 | | | 5 | >100 | 19 | |
| 213 | | | NI | 23 | 3 | |
| 214 | | | >100 | 24 | 12 | |
| 215 | | | >100 | 47 | 23 | |
| 216 | | | 5 | 19 | 5 | |
| 217 | | | 10 | 3 | 2 | 4 |
| 218 | | | 68 | 7 | 7 | |
| 219 | | | >100 | 14 | 7 | |
| 220 | | | >100 | 7 | 7 | |
| 221 | | | >100 | 24 | 6 | |
| 222 | | | 18 | 5 | 3 | |
| 223 | | | 24 | 6 | 3 | |
| 224 | | | 68 | 64 | 64 | |
| 225 | | | >100 | 7 | 3 | |
| 226 | | | 23 | 14 | 4 | |
| 227 | | | 7 | 43 | 5 | |
| 228 | | | NI | 13 | 6 | |
| 232 | | | 29 | 24 | 6 | |
| 234 | | | 5 | 8 | 4 | 8 |
| 239 | | | 17 | 13 | 7 | |
| 240 | | | 62 | >100 | 23 | |
| 241 | | | NI | NI | 4 | |
| 242 | | | 3 | NI | 4 | 8 |
| 243 | | | 39 | NI | 15 | |
| 244 | | | 4 | 36 | 9 | 4 |
| 245 | | | 1 | 7 | 2 | 1 |
| 247 | | | 16 | 4 | 4 | 8 |
| 252 | | | 9 | 26 | 7 | |
| 253 | | | NI | NI | 2 | |
| 254 | | | NI | NI | 2 | |
| 255 | | | | 39 | 2 | 8 |
| 256 | | | | 32 | | 16 |
| 257 | | | | 128 | | 64 |
| 258 | | | 24 | 128 | | 2 |

TABLE 15-continued

RNase P inhibition and Antibacterial Efficacy Results

| Cmpd#. | RNAse P Inhibition at 10 µM | at 8 µM | RNAse P Inhibition IC$_{50}$ (µM) | E. coli MIC (µg/ml) | S. aureus ("Clinical") MIC (µg/ml) | S. aureus ("wound") (MIC) (µg/ml) |
|---|---|---|---|---|---|---|
| 259 | | | | 64 | | 16 |
| 262 | | | | >128 | | 32 |
| 263 | | | | 64 | | 64 |
| 264 | | | | 16 | | 8 |
| 265 | | | | 64 | | 16 |
| 266 | | | 31 | 64 | | 16 |
| 267 | | | 27 | 16 | | 2 |
| 268 | | | 31 | 4 | | 8 |
| 269 | | | | 64 | | 16 |
| 270 | | | | 128 | | 32 |
| 271 | | | | >128 | | 128 |
| 272 | | | | 32 | | 16 |
| 273 | | | | 32 | | 8 |
| 274 | | | 24 | 8 | | 1 |
| 275 | | | | 32 | | 8 |
| 275 | | | | >128 | | >128 |
| 276 | | | | 32 | | 4 |
| 277 | | | | >128 | | >128 |
| 278 | | | | 128 | | 32 |
| 279 | | | | 128 | | 16 |
| 280 | | | | 64 | | 16 |
| 281 | | | | 64 | | 32 |
| 282 | | | | 8 | | 4 |
| 283 | | | | 64 | | 16 |
| 284 | | | 0.89 | 8 | | 2 |
| 283 | | | | 4 | | 4 |
| 286 | | | | 128 | | 32 |
| 287 | | | | >128 | | 128 |
| 288 | | | | 128 | | 128 |
| 289 | | | 33 | 8 | | 4 |
| 290 | | | | 32 | | 8 |
| 291 | | | | 128 | | 16 |
| 292 | | | 140 | >128 | | 128 |
| 293 | | | 62 | 16 | | 8 |
| 294 | | | 2.4 | 64 | | 8 |
| 295 | | | 21 | 128 | | 32 |
| 296 | | | 21 | 8 | | 4 |
| 297 | | | 43 | 32 | | 16 |
| 298 | | | 14 | 8 | | 8 |
| 299 | | | 6.8 | 32 | | 8 |
| 300 | | | 1.9 | 16 | | 1 |
| 301 | | | 27 | 4 | | 2 |
| 302 | | | 3.6 | 128 | | 32 |
| 303 | | | 9.7 | 32 | | 8 |
| 304 | | | | 32 | | 16 |
| 305 | | | 2.9 | 4 | | 2 |
| 306 | | | 50 | 4 | | 2 |
| 307 | | | 16 | 4 | | 2 |
| 308 | | | | 64 | | 16 |
| 310 | | | | 128 | | 8 |
| 311 | | | 2.5 | 8 | | 2 |
| 312 | | | 12 | 16 | | 2 |
| 313 | | | | >128 | | 16 |
| 314 | | | 30 | 8 | | 4 |
| 315 | | | 19 | 16 | | 8 |
| 316 | | | | 8 | | 2 |
| 317 | | | | 128 | | 64 |
| 318 | | | | 16 | | 8 |
| 319 | | | | 8 | | 8 |
| 320 | | | | 32 | | 4 |
| 321 | | | | 32 | | 8 |
| 322 | | | 4.1 | 4 | | 1 |
| 323 | | | | >128 | | 128 |
| 324 | | | | 32 | | 4 |
| 325 | | | 6.4 | 8 | | 2 |
| 326 | | | | 16 | | 8 |
| 327 | | | | 4 | | 1 |
| 328 | | | | >128 | | 16 |
| 329 | | | | 64 | | 16 |
| 330 | | | | >128 | | 128 |
| 331 | | | 5.1 | 8 | | 4 |
| 332 | | | 4.1 | 8 | | 1 |
| 333 | | | | 16 | | 8 |
| 334 | | | | 16 | | 4 |
| 335 | | | | 64 | | 4 |
| 336 | | | 19 | 4 | | 1 |
| 337 | | | 26 | 4 | | 2 |
| 338 | | | | 64 | | 4 |
| 339 | | | | 8 | | 4 |
| 340 | | | | 16 | | 4 |
| 341 | | | | 8 | | 1 |
| 342 | | | | 8 | | 4 |
| 343 | | | | 64 | | 16 |
| 344 | | | | 16 | | 8 |
| 345 | | | | 32 | | 4 |
| 346 | | | | 16 | | 4 |
| 347 | | | | 8 | | 4 |
| 348 | | | | 32 | | 4 |
| 349 | | | | 16 | | 4 |
| 350 | | | | 8 | | 4 |
| 351 | | | | 16 | | 4 |
| 352 | | | | 8 | | 4 |
| 353 | | | | 8 | | 2 |
| 354 | | | | 8 | | 1 |
| 355 | | | | 8 | | 4 |
| 356 | | | | 32 | | 16 |
| 357 | | | | 64 | | 16 |
| 358 | | | | 16 | | 16 |
| 359 | | | | 64 | | 16 |

NA: Not available
NI: No inhibition

TABLE 16

MIC of selected compounds against a range of bacteria

| Cmpd # | H. influenzae ATCC 49247 MIC (µg/ml) | A. baumannii ATCC 17978 MIC (µg/ml) | P. aeruginosa ATCC 27853 MIC (µg/ml) | P. aeruginosa NTUH-974 (MDR) MIC (µg/ml) | N. gonorrhoeae 612501 MIC (µg/ml) | H. pylori ATCC 43504 MIC (µg/ml) |
|---|---|---|---|---|---|---|
| 44 | 16 | >128 | >128 | >128 | 2 | |
| 92 | >128 | >128 | >128 | >128 | 0.25 | |
| 1050 | 32 | 128 | 128 | 128 | 8 | |

TABLE 16-continued

MIC of selected compounds against a range of bacteria

| 111 | 16 | 64 | >128 | >128 | 2 | |
|---|---|---|---|---|---|---|
| 123 | 16 | 64 | >128 | >128 | 1 | |
| 133 | 16 | 16 | 128 | 128 | 2 | |
| 140 | 8 | 8 | 64 | 32 | 2 | |
| 150 | 8 | 16 | >128 | >128 | 2 | |
| 186 | 16 | 16 | >128 | >128 | 4 | |
| 197 | 16 | 64 | >128 | >128 | 1 | |
| 242 | 16 | 16 | >128 | 64 | 2 | |
| 245 | 4 | 16 | >128 | 64 | 2 | |
| 255 | 64 | 128 | 128 | 64 | 16 | |
| 274 | 1 | 4 | 16 | 16 | 1 | 16 |
| 284 | 8 | 8 | 32 | 32 | 2 | 32 |
| 300 | 2 | 8 | >32 | >32 | 1 | 16 |
| 301 | 2 | 4 | 16 | 16 | 1 | 8 |
| 302 | 16 | 32 | 32 | 32 | 8 | 32 |
| 305 | 1 | 4 | 16 | 16 | 1 | 16 |
| 306 | 8 | 8 | 32 | 32 | 2 | 32 |
| 307 | 2 | 8 | 16 | 16 | 1 | 16 |

| | Organism: | | | | | |
|---|---|---|---|---|---|---|
| | E. faecalis | E. faecium | E. coli | E. coli | K. pneumoniae | M. phlei |
| | | | | Strain: | | |
| Cmpd # | ATCC 29212 MIC (µg/ml) | ATCC 700221 MIC (µg/ml) | ATCC 25922 MIC (µg/ml) | JW5503 MIC (µg/ml) | ATCC 43816 MIC (µg/ml) | ATCC 11758 MIC (µg/ml) |
| 44 | 16 | 8 | >128 | 8 | >128 | |
| 92 | 2 | 0.5 | >128 | >128 | >128 | |
| 1050 | 32 | 16 | 32 | 16 | 32 | |
| 111 | 4 | 2 | 64 | 4 | >128 | |
| 123 | 2 | 2 | >128 | 4 | >128 | |
| 133 | 8 | 4 | 32 | 8 | 32 | |
| 140 | 4 | 4 | 32 | 8 | 8 | |
| 150 | 2 | 2 | 16 | 4 | 16 | |
| 186 | 4 | 4 | 16 | 4 | 128 | |
| 197 | 2 | 2 | 64 | 4 | >128 | |
| 24239 | 4 | 2 | 64 | 64 | 128 | |
| 245 | 2 | 1 | 8 | 8 | 32 | |
| 255 | 16 | 32 | 64 | 16 | 128 | |
| 274 | 2 | 1 | 4 | 8 | 4 | 4 |
| 284 | 2 | 2 | 4 | 4 | 4 | 4 |
| 300 | 1 | 1 | 4 | 2 | 8 | 4 |
| 301 | 2 | 2 | 4 | 2 | 4 | 8 |
| 302 | 8 | 4 | 16 | 16 | 16 | 16 |
| 305 | 1 | 1 | 4 | 4 | 4 | 2 |
| 306 | 4 | 2 | 4 | 2 | 4 | 8 |
| 307 | 2 | 2 | 4 | 2 | 4 | 8 |

| | Organism: | | | | | |
|---|---|---|---|---|---|---|
| | S. aureus | S. aureus + 50% HS | S. aureus MRSA | S. pneumoniae | S. aureus USA300 MRSA | M. fortuitum |
| | | | | Strain: | | |
| Cmpd # | ATCC 29213 MIC (µg/ml) | ATCC 29213 MIC (µg/ml) | ATCC 33591 MIC (µg/ml) | ATCC 49619 MIC (µg/ml) | BAA 1717 MIC (µg/ml) | ATCC 110 MIC (µg/ml) |
| 44 | 4 | >128 | 64 | 16 | | |
| 92 | 0.5 | 128 | 2 | 8 | | |
| 1050 | 16 | 128 | 32 | 32 | | |
| 111 | 2 | 128 | 4 | 8 | | |
| 123 | 2 | 64 | 8 | 8 | | |
| 133 | 4 | 128 | 4 | 32 | | |
| 140 | 4 | 128 | 4 | 32 | | |
| 150 | 2 | 64 | 2 | 8 | | |
| 186 | 4 | 64 | 8 | 32 | | |
| 197 | 2 | 128 | 16 | 4 | | |
| 242 | 2 | 128 | 2 | 16 | | |
| 245 | 2 | 128 | 2 | 16 | | |
| 255 | 8 | 64 | 16 | 64 | | |
| 274 | 1 | 16 | 1 | 4 | 1 | 4 |

TABLE 16-continued

MIC of selected compounds against a range of bacteria

| | | | | | | |
|---|---|---|---|---|---|---|
| 284 | 2 | 32 | 2 | 8 | 2 | 8 |
| 300 | 1 | 16 | 1 | 4 | 1 | 2 |
| 301 | 4 | 16 | 2 | 4 | 2 | 4 |
| 302 | 8 | 64 | 8 | 64 | 8 | 8 |
| 305 | 1 | 32 | 1 | 2 | 1 | 4 |
| 306 | 2 | 8 | 2 | 4 | 2 | 4 |
| 307 | 2 | 32 | 2 | 8 | 2 | 4 |

The invention claimed is:

1. A compound of formula I:

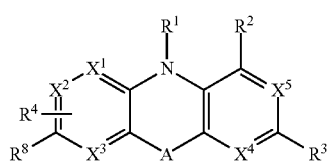

(I)

or a pharmaceutically acceptable salt thereof,
wherein
A is S;
$X^1$ is selected from CH and N;
each of $X^2$, $X^3$, $X^4$ and $X^5$ is CH;
$R^1$ is selected from the group consisting of
—H,
—$C_{1-6}$ alkyl,
—$C_{1-6}$ alkyl-amino wherein the amino group is optionally substituted with one or two $C_{1-6}$acyl or $C_{1-6}$alkyl groups,
and
—$C_{1-6}$ alkyl-heterocyclyl wherein the heterocyclyl group is a 5- or 6-membered aliphatic or aromatic heterocycle, optionally benzo-fused, and is optionally substituted with one or more $R^6$ groups;
$R^2$ is selected from the group consisting of —$N(R^5)_2$, —$NHR^5$, —$N(R^5)C(O)R^5$, and —$N(R^5)C(S)N(R^5)_2$;
$R^3$ is selected from —$CF_3$, —CN, —Cl, —$C_{1-6}$ alkyl, —$C_{3-6}$ cycloalkyl, —$C(O)NH_2$, —$C(O)NH$—$C_{1-6}$ alkyl, —NH-heterocyclyl, -phenyl, and -heterocyclyl, wherein the heterocyclyl group is a 5- or 6-membered aliphatic or aromatic optionally benzo-fused heterocycle, and wherein $R^3$ is optionally substituted with one of more $R^6$ groups;
each of $R^4$ and $R^8$ is selected from H, —CN, -halo, —$CF_3$, —$C_{1-6}$ alkoxy, —$CO_2$—$C_{1-6}$ alkyl, —$NO_2$, —$C_{1-6}$ alkyl-$NH_2$, -heterocyclyl, and —$CONH_m[(CH_2)_n NH_2]_{2-m}$, wherein the heterocyclyl group is a 5- or 6-membered aliphatic or aromatic optionally benzo-fused heterocycle;
each instance of $R^5$ is independently selected from the group consisting of
—H,
—$C_{1-6}$ alkyl optionally substituted with one or more $R^6$ groups,
—$C_{2-6}$ alkenyl optionally substituted with one or more $R^6$ groups,
—$C_{0-3}$ alkyl-$C_{3-6}$ cycloalkyl-$C_{0-3}$ alkyl optionally substituted with one or more $R^6$ groups,
-phenyl optionally substituted with one or more $R^6$ groups,
—C═C-Ph optionally substituted with one or more $R^6$ groups,
and
—$C_{0-3}$ alkyl-heterocyclyl-$C_{0-3}$ alkyl optionally substituted with one or more $R^6$ groups, wherein the heterocyclyl group is a 5-, 6- or 7-membered aliphatic or aromatic optionally benzo-fused heterocycle;
each instance of $R^6$ is independently selected from the group consisting of -halo, —CN, —$C_{1-6}$ alkyl, —OH, —$C_{1-6}$ alkoxy, —$C_{1-6}$ alkyl-$NH_2$, —$NH_m[(CH_2)_n NH_2]_{2-m}$, —$NH_2$, —NH—$C_{1-6}$ alkyl, and —N—$C_{1-6}$dialkyl;
n and m are integers, wherein each instance of n is independently chosen from 2 or 3, and each instance of m is independently chosen from 0 or 1.

2. A compound according to claim 1, having a formula II:

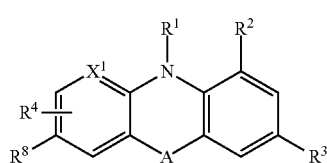

(II)

or a pharmaceutically acceptable salt thereof,
wherein
A is S;
$X^1$ is CH;
$R^1$ is selected from the group consisting of
—H,
—$C_{1-3}$ alkyl,
—$C_{1-3}$ alkyl-amino wherein the amino group is optionally substituted with one or two acetyl or $C_{1-3}$ alkyl groups,
and
—$C_{1-3}$ alkyl-heterocyclyl wherein the heterocyclyl group is selected from imidazolyl, piperazinyl and thiomorpholinyl and is optionally substituted with one or more $R^6$ groups;
$R^2$ is selected from the group consisting of —$N(R^5)_2$, —$NHR^5$, —$N(R^5)C(O)R^5$, and —$N(R^5)C(S)N(R^5)_2$;
$R^3$ is selected from —$CF_3$, —CN, —Cl, —$C_{1-3}$ alkyl, —$C_{1-3}$ cycloalkyl, —$C(O)NH_2$, —$C(O)NH$—$C_{1-3}$ alkyl, —NH-piperazinyl, -phenyl, -pyridinyl, -indolyl, -benzimidazolyl, -benzothiazolyl, and -benzopyrazolyl, wherein $R^3$ is optionally substituted with one of more $R^6$ groups;
each of $R^4$ and $R^8$ is selected from H, —CN, —Cl, —F, —$CF_3$, —$C_{1-3}$ alkoxy, —$CO_2Me$, —$NO_2$, —$C_{1-3}$ alkyl-$NH_2$, -piperazinyl, -indolyl, and —$CONH_m[(CH_2)_nNH_2]_{2-m}$;

each instance of $R^5$ is independently selected from the group consisting of
- —H,
- —$C_{1-3}$ alkyl optionally substituted with one or more $R^6$ groups,
- —$C_{2-3}$ alkenyl optionally substituted with one or more $R^6$ groups,
- —$C_{0-3}$ alkyl-$C_{3-6}$ cycloalkyl-$C_{0-3}$ alkyl optionally substituted with one or more $R^6$ groups,
- -phenyl optionally substituted with one or more $R^6$ groups,
- —C≡C-Ph optionally substituted with one or more $R^6$ groups, and
- —$C_{0-3}$ alkyl-heterocyclyl-$C_{0-3}$ alkyl optionally substituted with one or more $R^6$ groups, wherein the heterocyclyl group is selected from azetidinyl, pyrrolidinyl, piperidinyl, piperazinyl, morpholinyl, azepanyl and indolyl;

each instance of $R^6$ is independently selected from the group consisting of —F, —Cl, —CN, —$C_{1-3}$ alkyl, —OH, —$C_{1-3}$ alkoxy, —$C_{1-3}$ alkyl-$NH_2$, —$NH_m[(CH_2)_nNH_2]_{2-m}$, —$NH_2$, —NHMe, and —$NMe_2$;

n and m are integers, wherein each instance of n is independently chosen from 2 or 3, and each instance of m is independently chosen from 0 or 1.

3. A compound or salt according to claim 1, wherein $R^8$ is not H.

4. A compound or salt according to claim 1, wherein $X^1$, $X^2$, $X^3$, $X^4$ and $X^5$ are CH.

5. A compound or salt according to claim 1, wherein $R^1$ is H.

6. A compound or salt according to claim 1, wherein $R^2$ is selected from the group consisting of —$NH_2$ and —$NHR^5$.

7. A compound or salt according to claim 1, wherein $R^2$ is —$NHC(O)R^5$.

8. A compound or salt according to claim 1, wherein $R^4$ is H.

9. A compound or salt according to claim 1, wherein $R^3$ is selected from the group consisting of —$CF_3$ and -indolyl.

10. A method of treating a bacterial infection which comprises administering to a patient in need thereof a therapeutically effective amount of a compound or salt according to claim 1, or a pharmaceutically acceptable salt thereof.

11. The method according to claim 10, wherein the infection is a bacterial infection caused or complicated by bacteria of a genus selected from *Staphylococcus, Enterococcus, Streptococcus, Pseudomonas, Legionella, Klebsiella, Haemophilus, Neisseria, Listeria, Escherichia* and *Mycobacterium*.

12. The method according to claim 10, wherein the bacterial infection is caused or complicated by a bacterial species selected from the group: *S. aureus, E. faecalis, E. faecium, S. pneumoniae, E. coli, K. pneumoniae, H. influenza, A. baumannii, P. aeruginosa, N. gonorrhoeae*.

13. A method of inhibiting bacterial RNase P activity, comprising contacting a bacterial RNase P with the compound or salt of claim 1.

14. A method of inhibiting growth of a bacterium, comprising contacting a bacterium with the compound or salt of claim 1.

15. A pharmaceutical composition comprising a compound according to claim 1, or a pharmaceutically acceptable salt thereof, in association with a pharmaceutically acceptable excipient, adjuvant, diluent and/or carrier.

16. A compound selected from the group consisting of

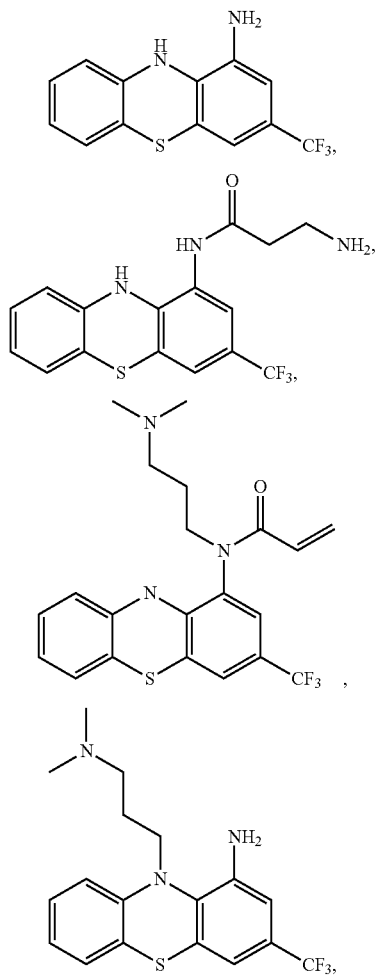

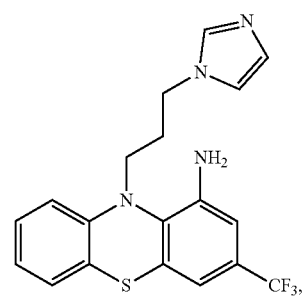

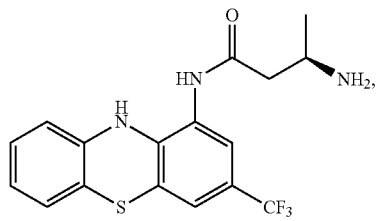

343
-continued
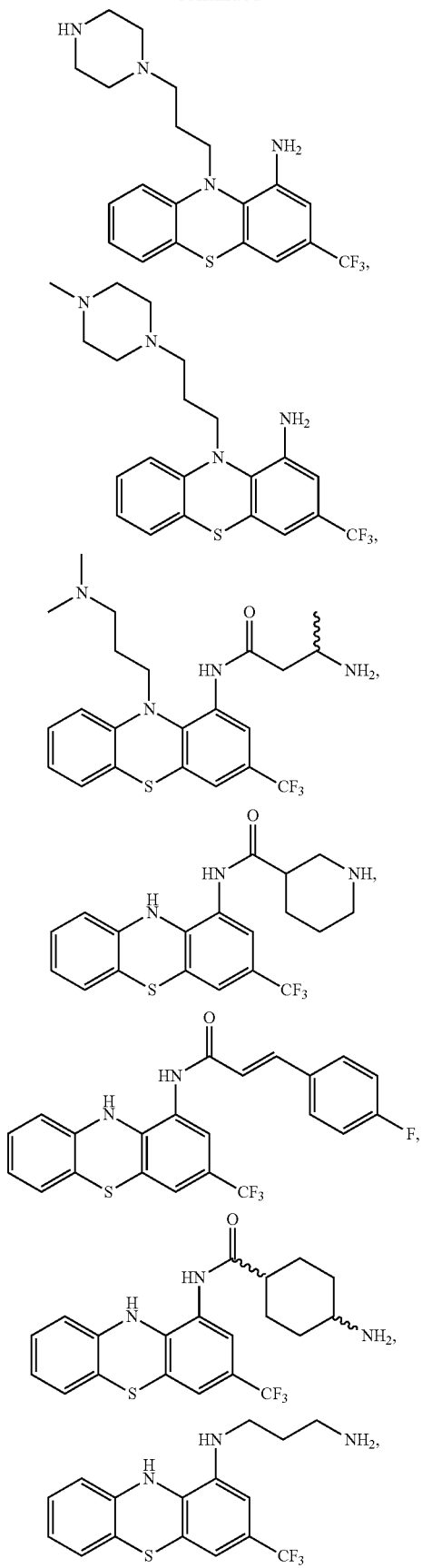
344
-continued
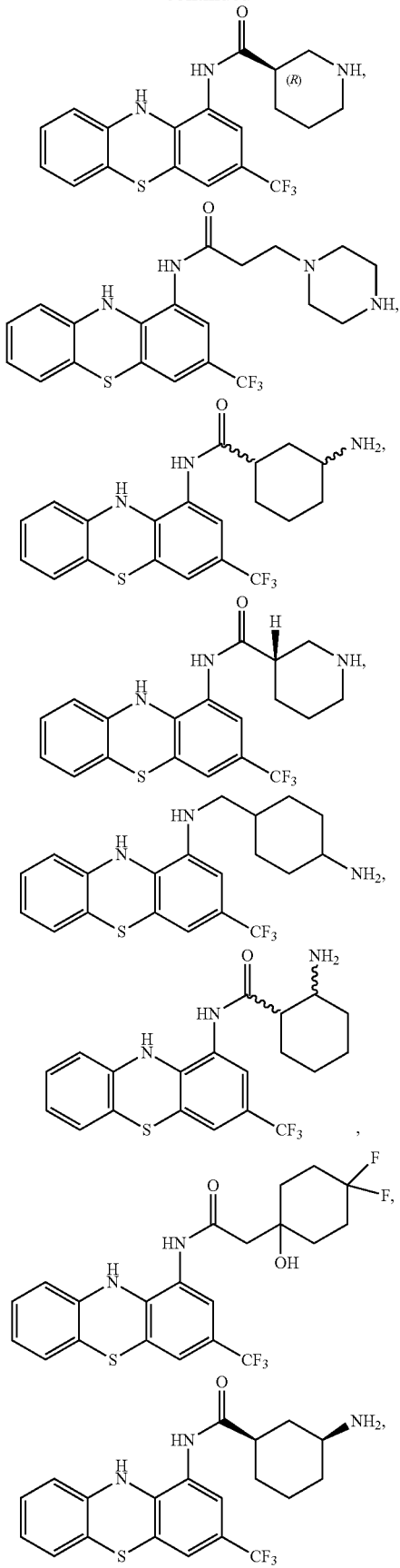

-continued
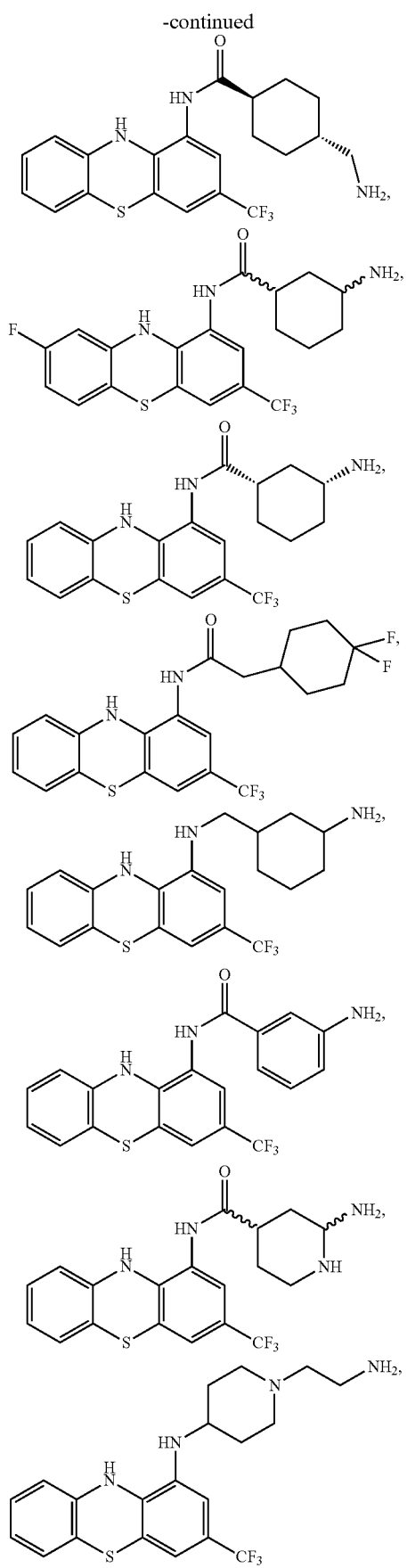
-continued
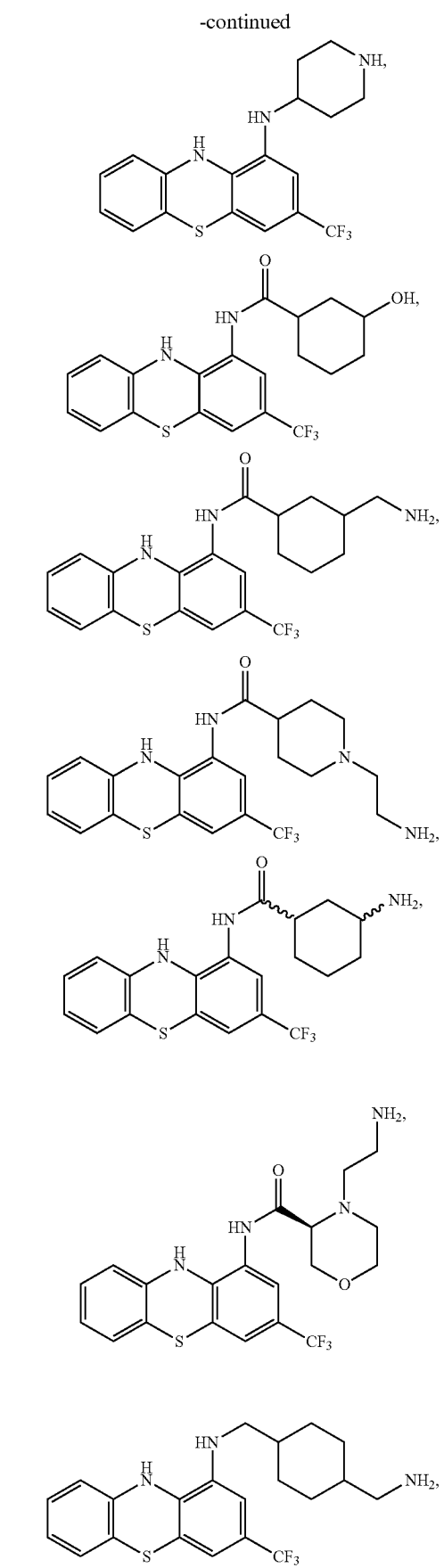

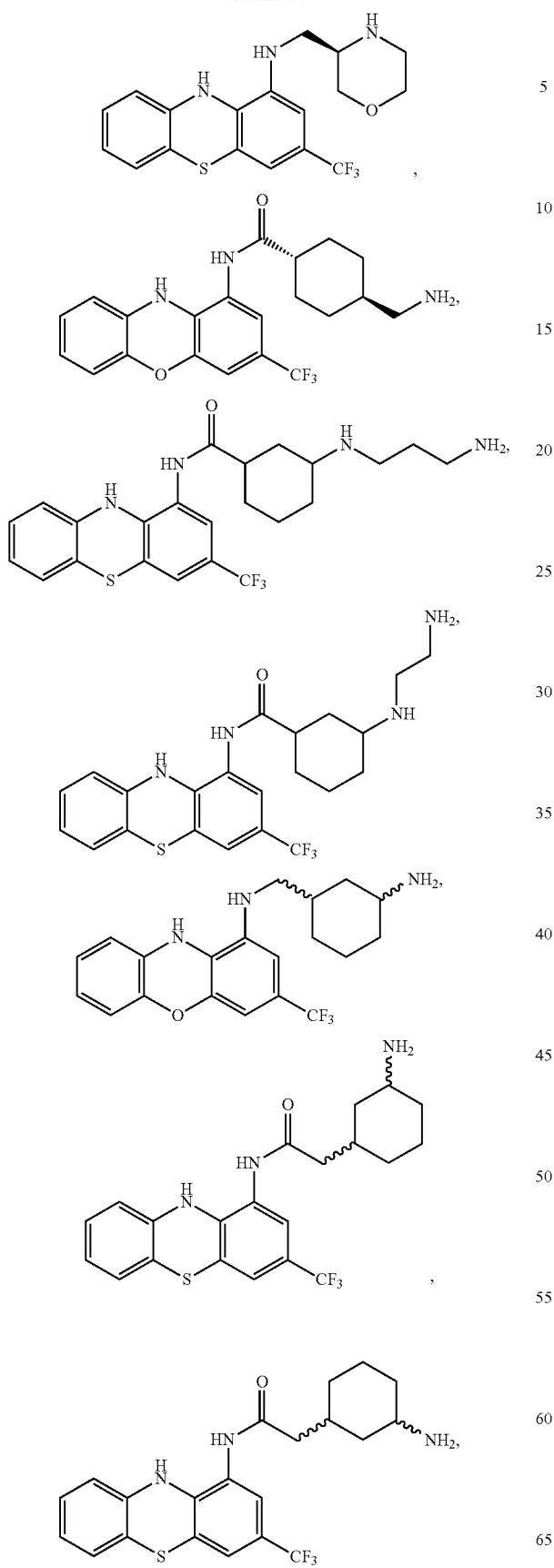
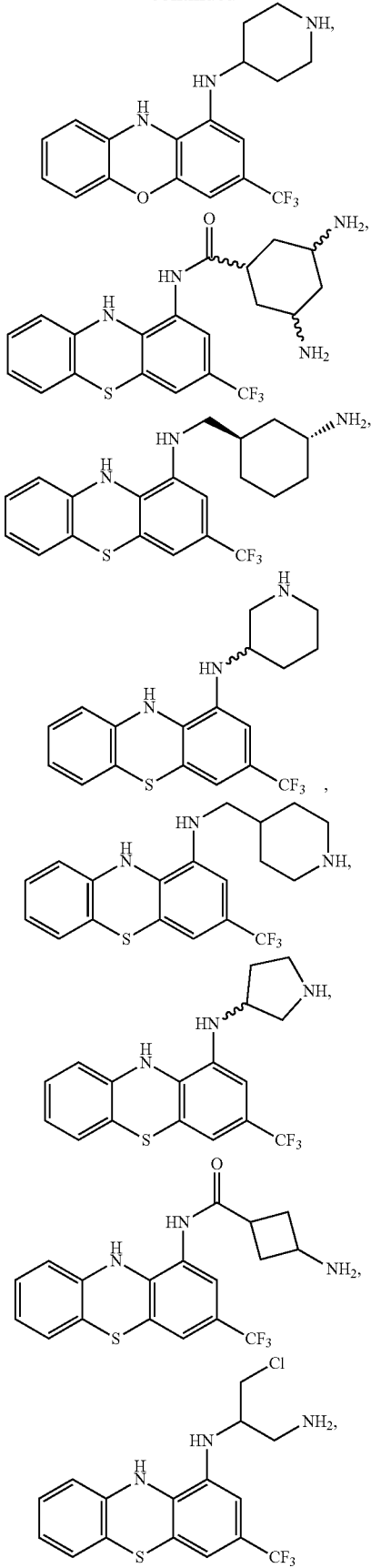

-continued
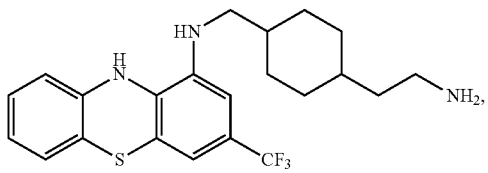
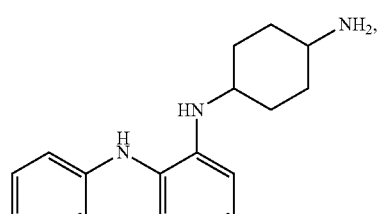
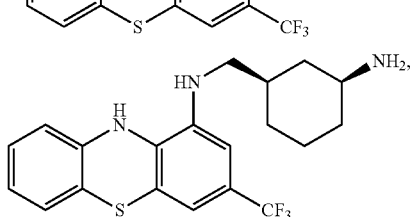
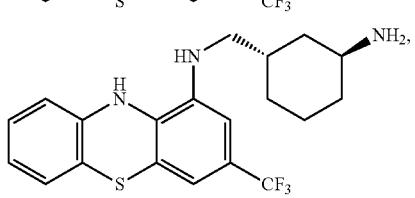
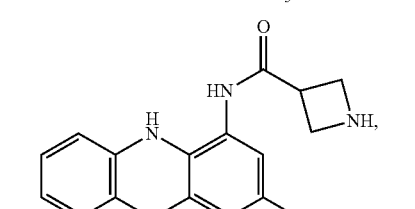
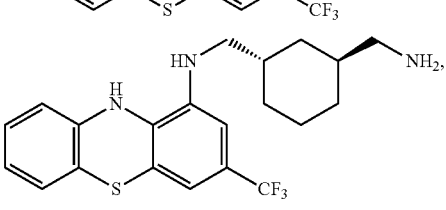
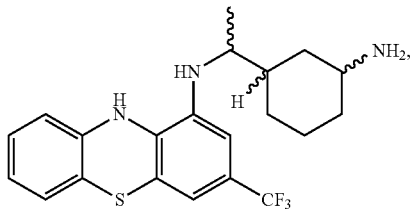
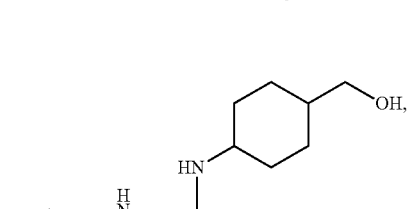
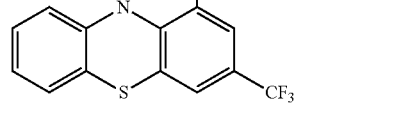
-continued
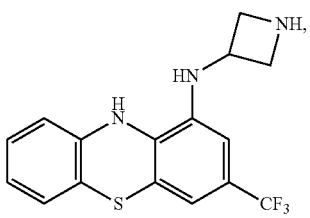
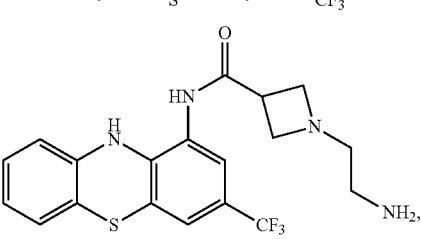
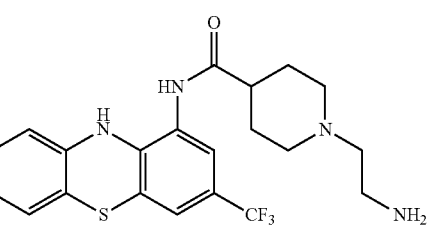
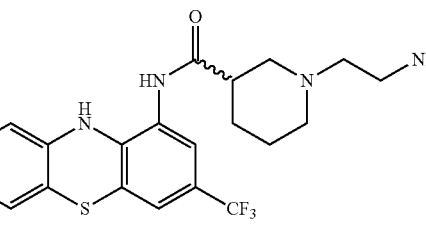
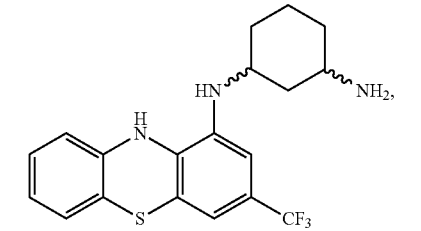
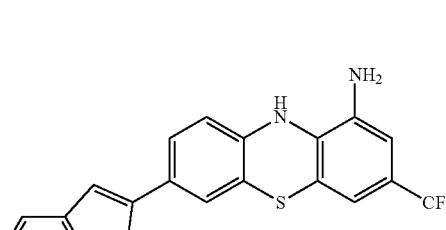
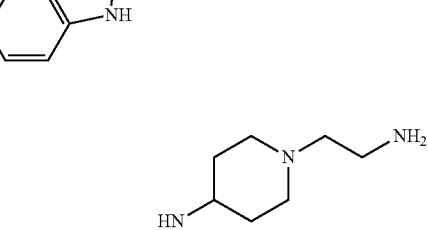
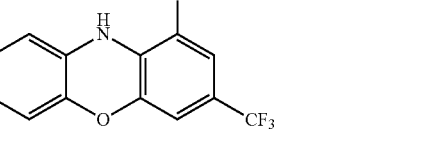

351
-continued
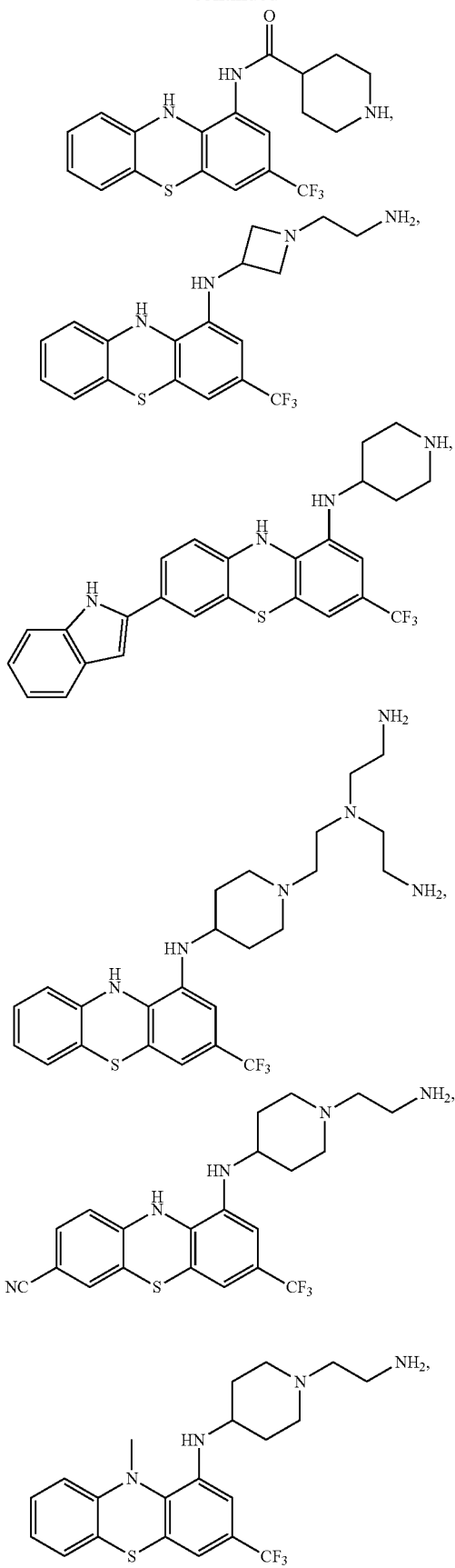
352
-continued
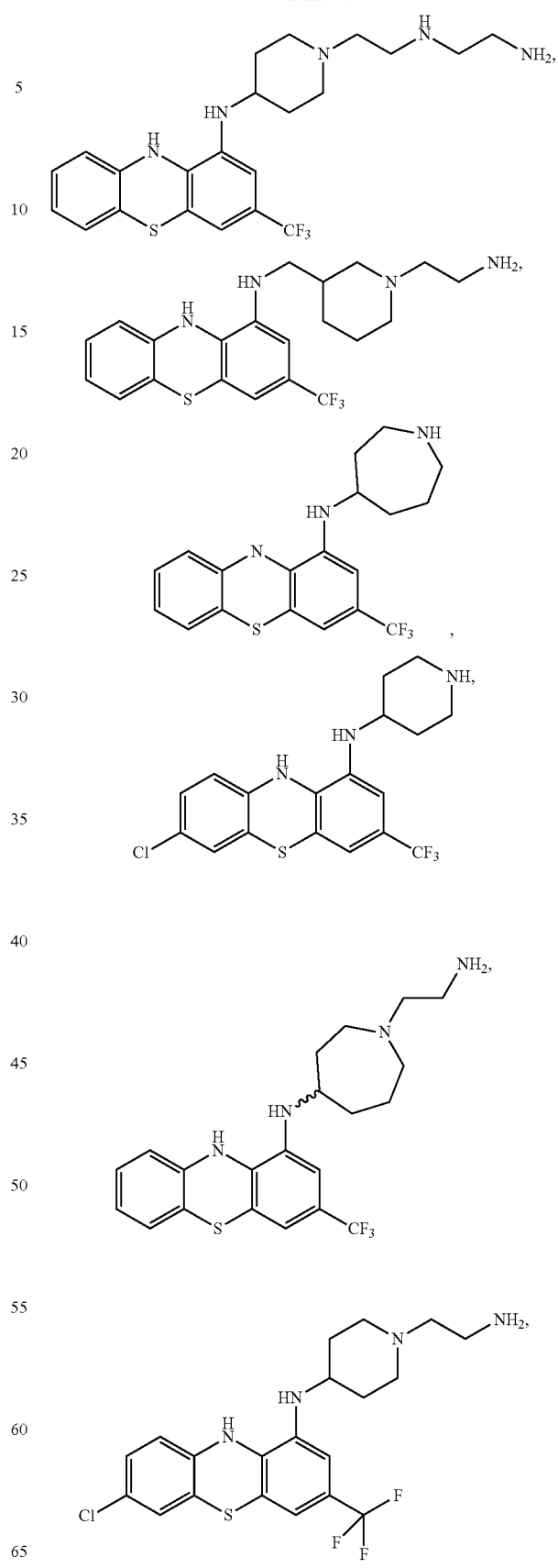

353
-continued
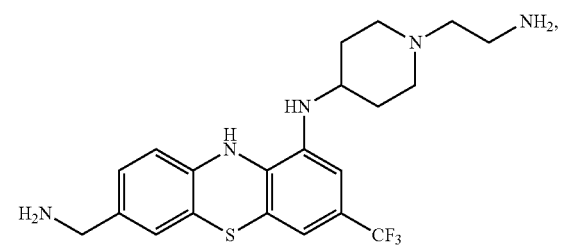
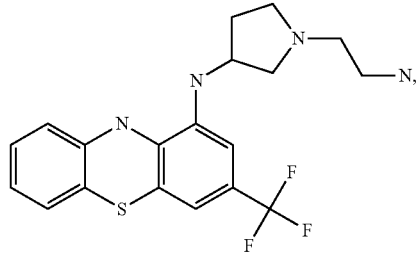
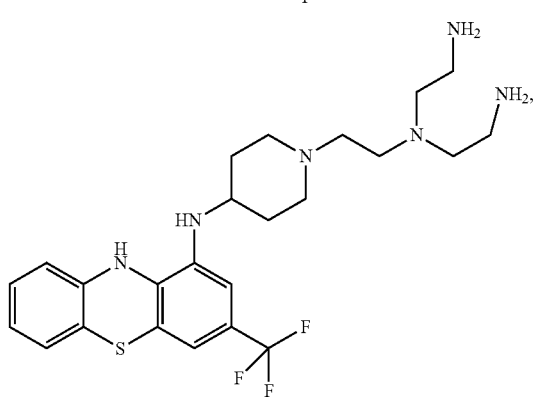
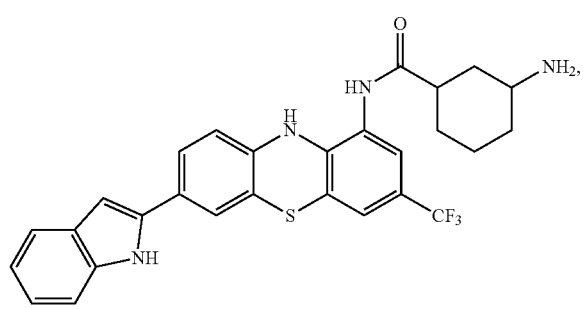
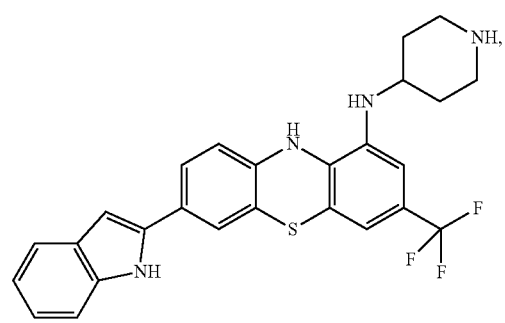
354
-continued
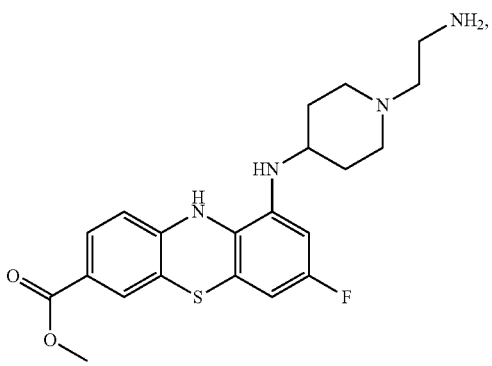
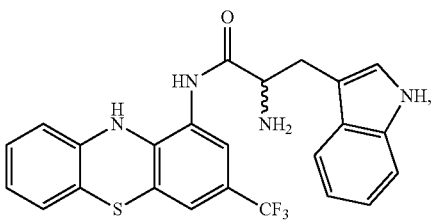
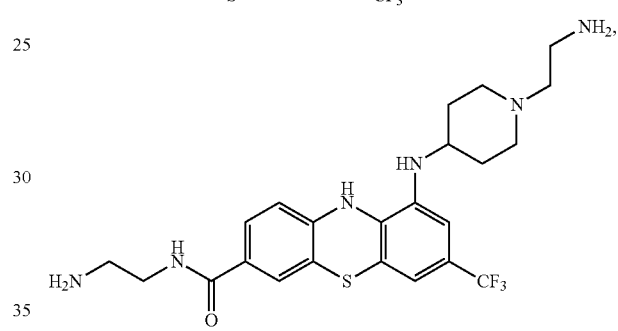
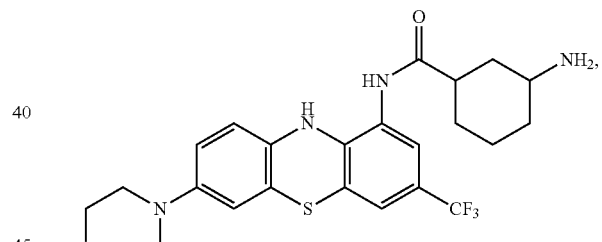
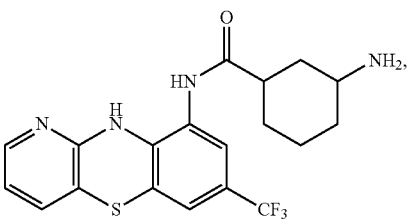
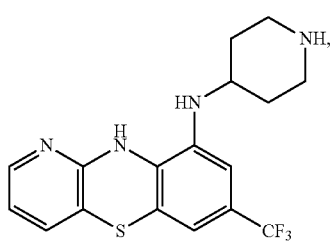

355
-continued
356
-continued
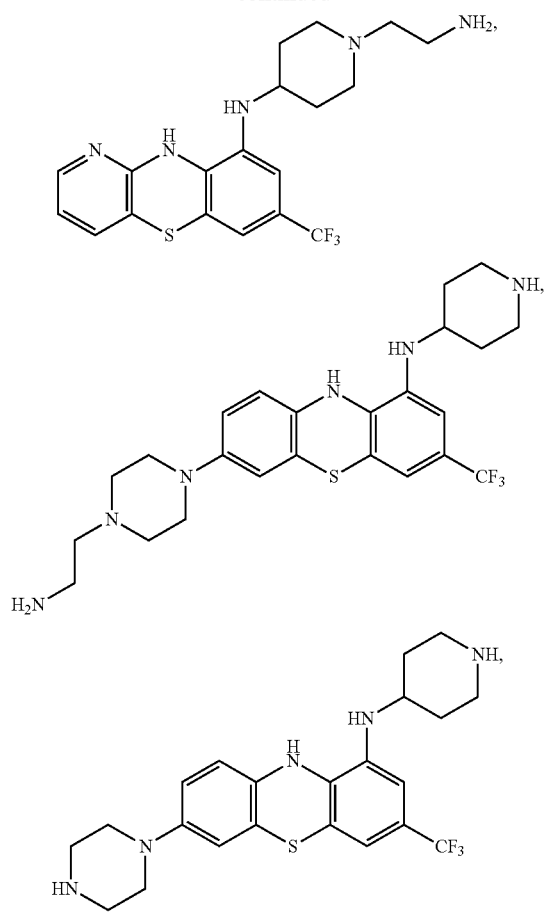
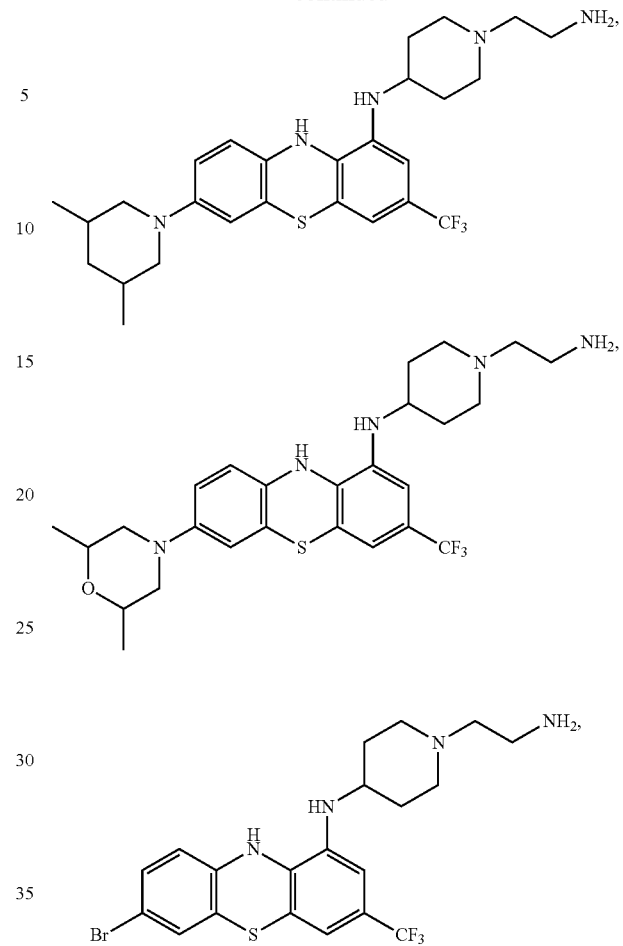
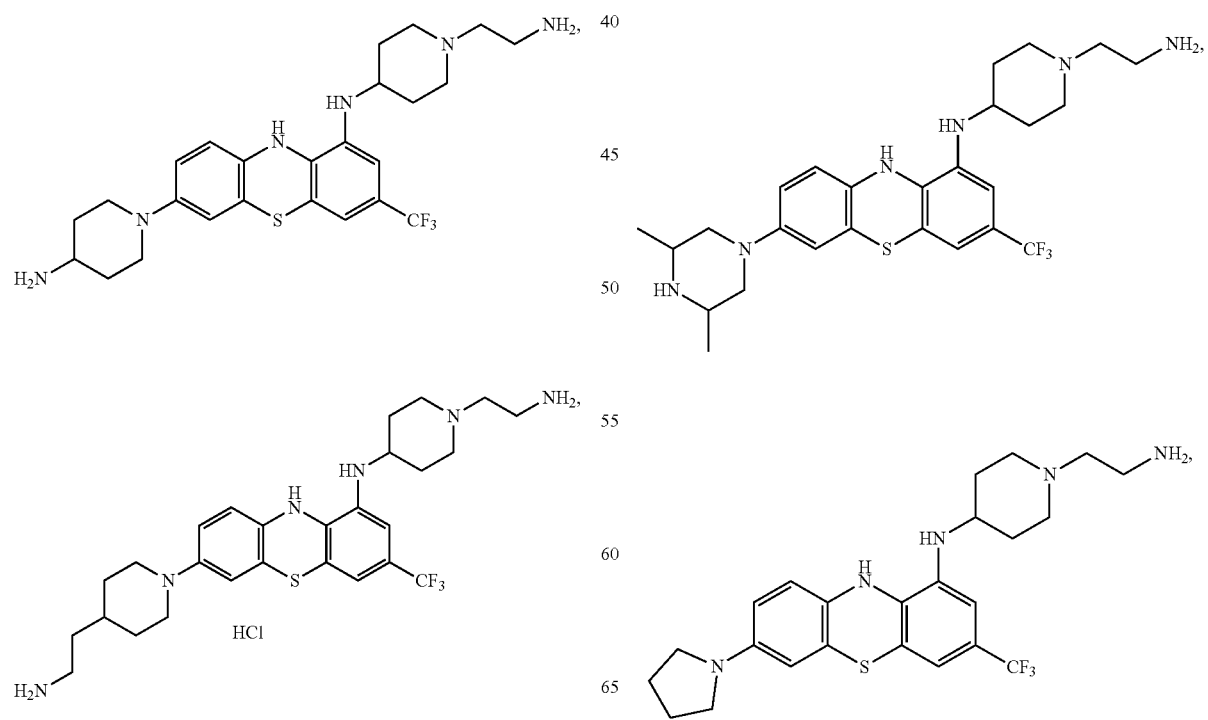

357
-continued
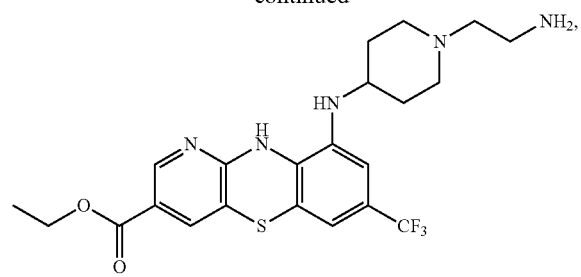
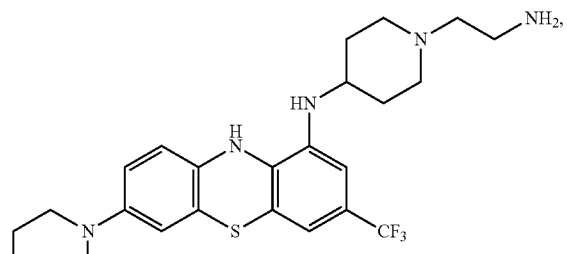
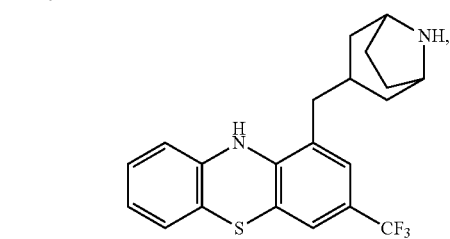
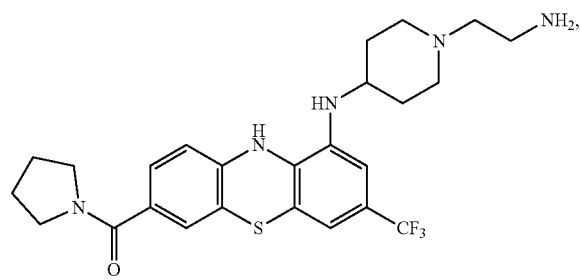
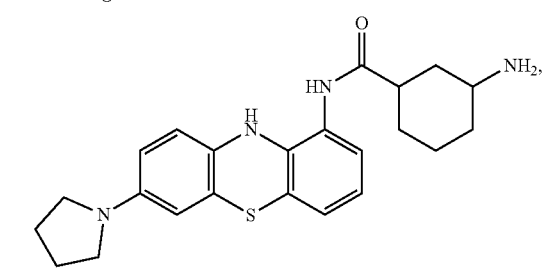
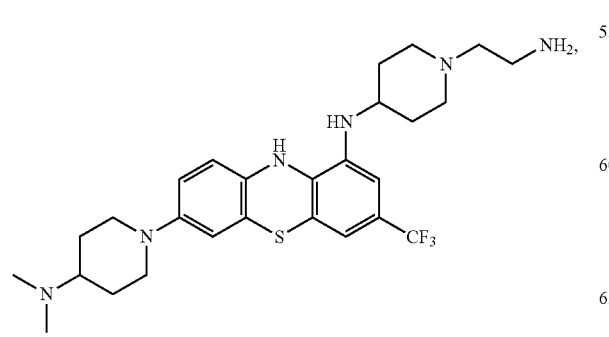
358
-continued
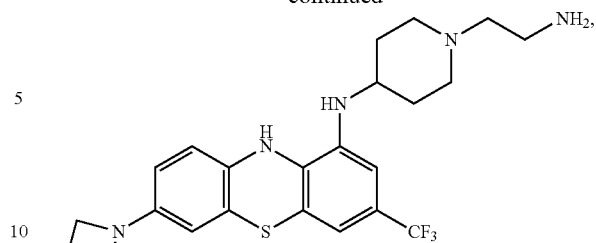
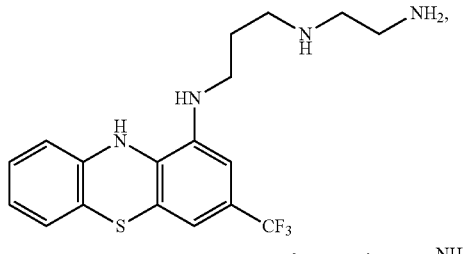
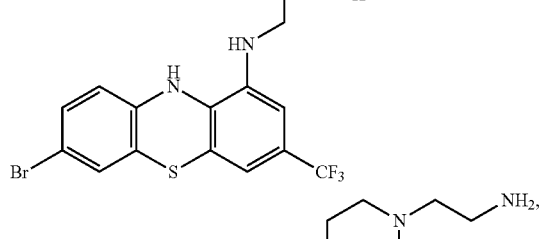
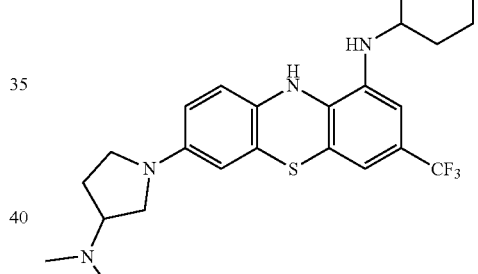
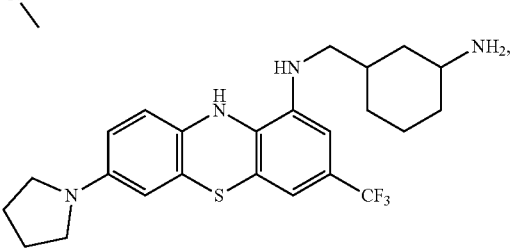
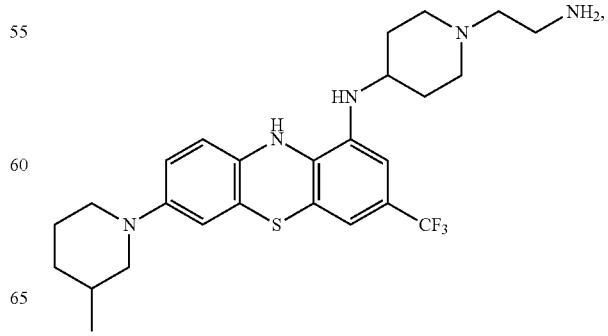

359
-continued
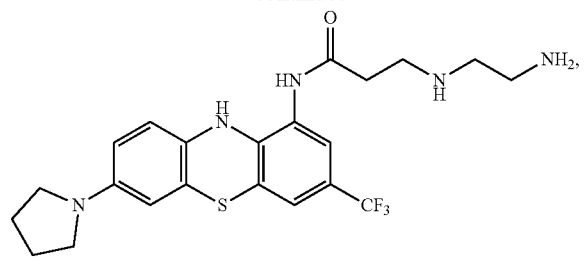
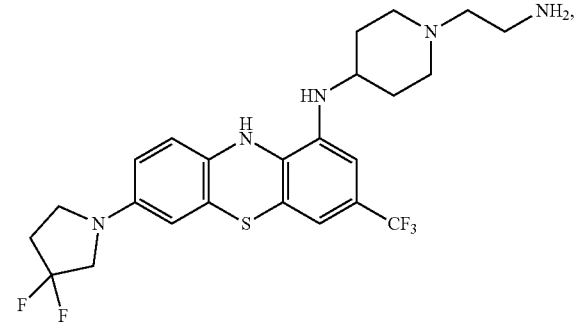
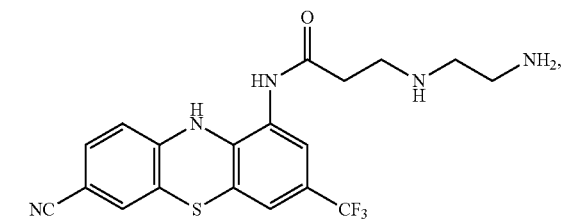
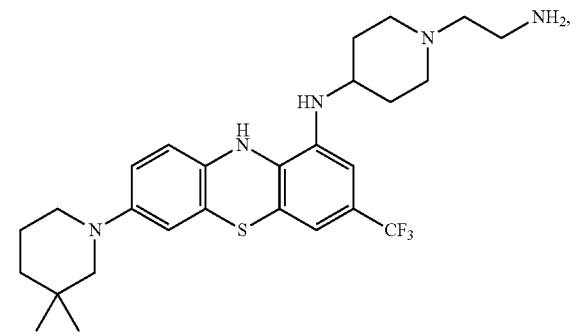
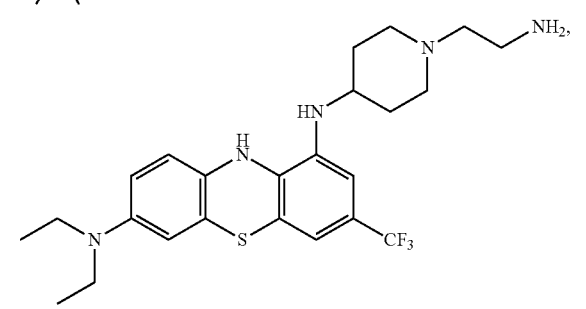
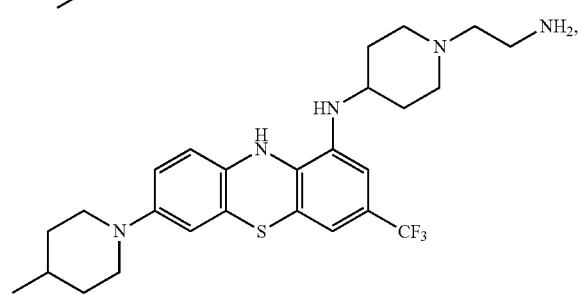
360
-continued
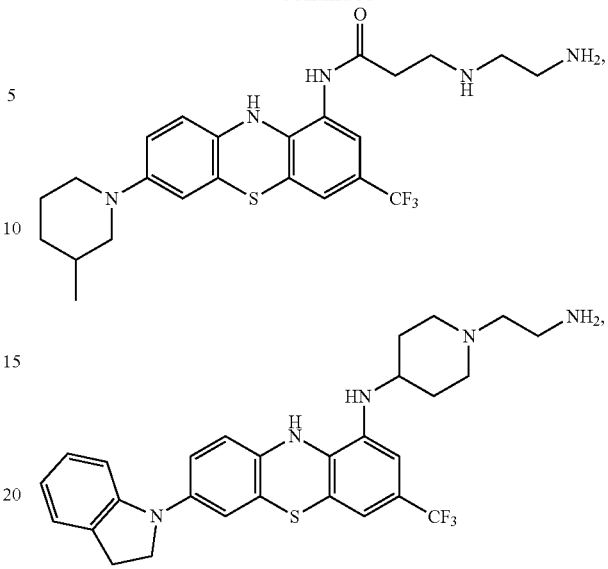
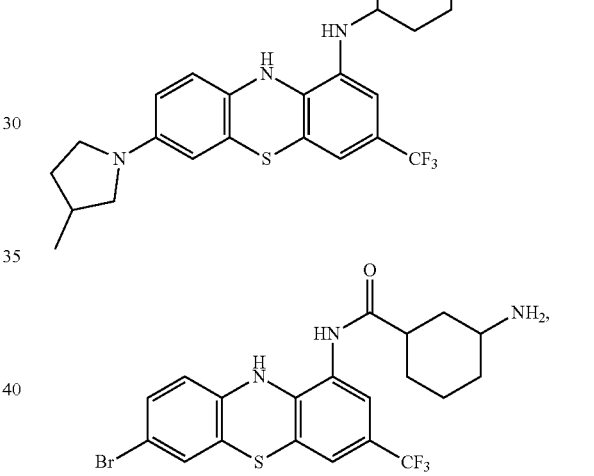
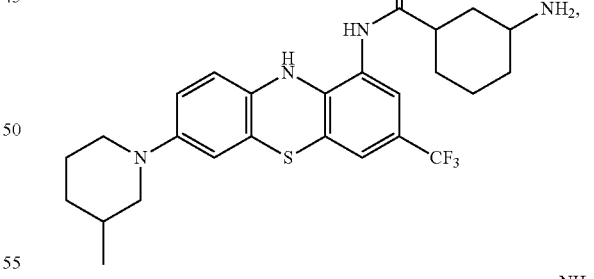
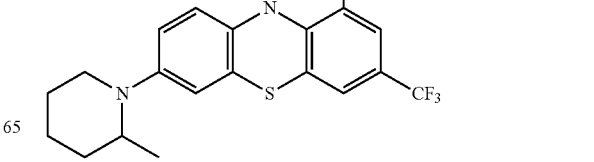

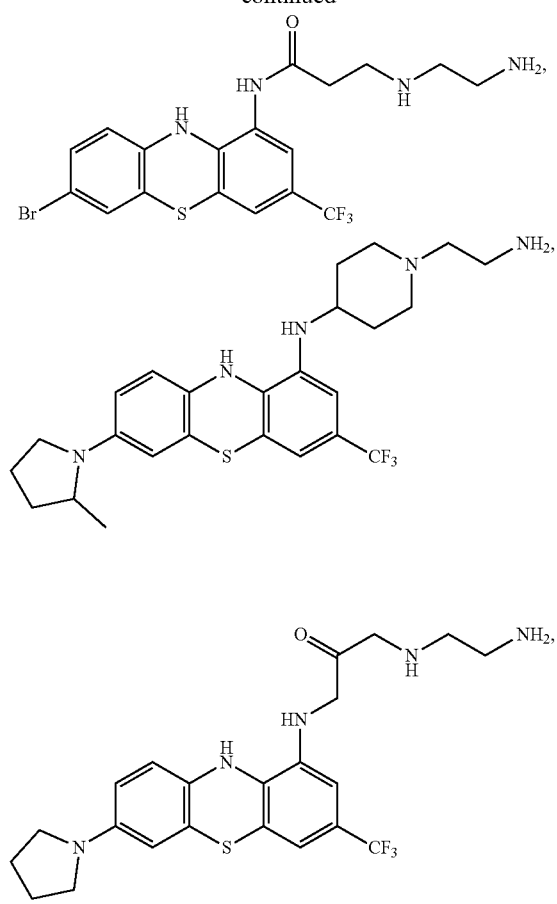
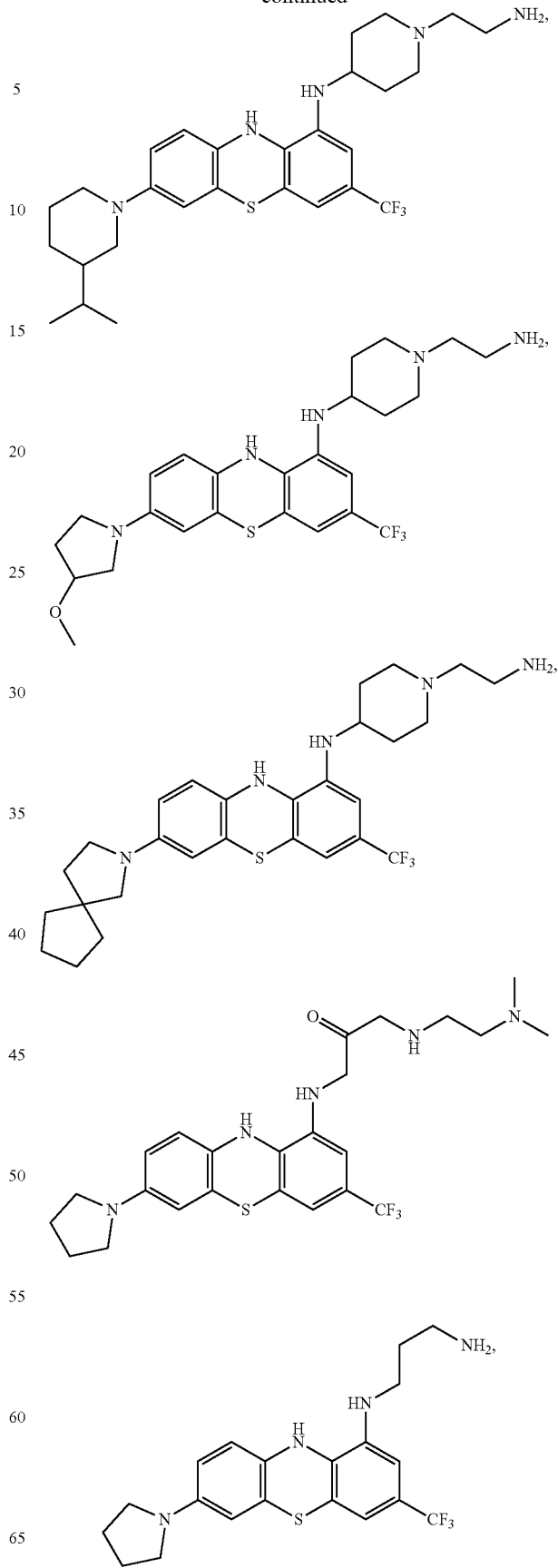

363
-continued
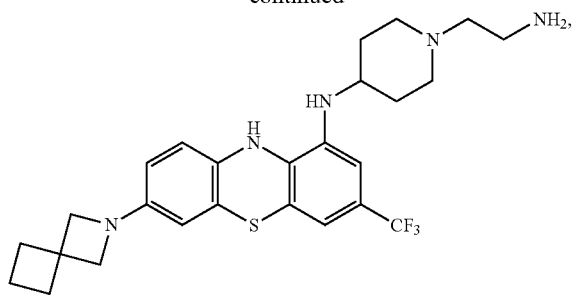
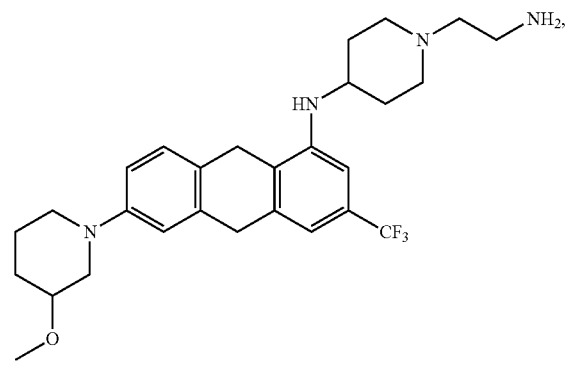
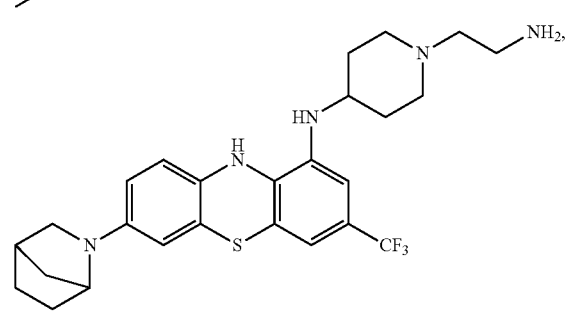
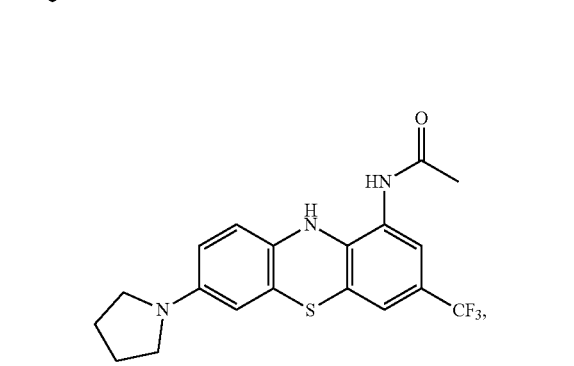
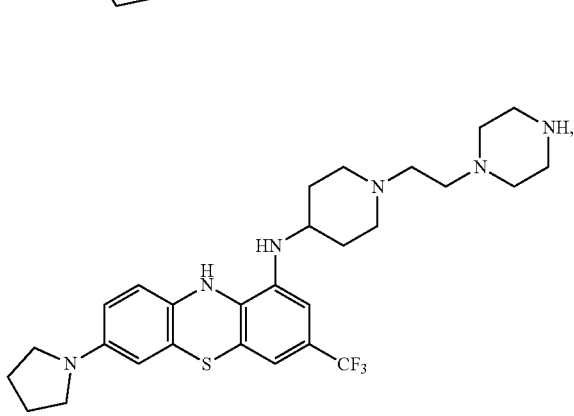
364
-continued
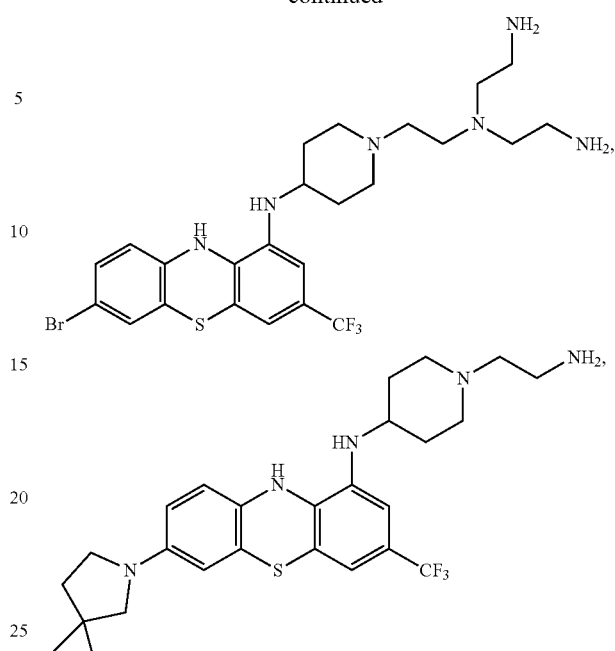
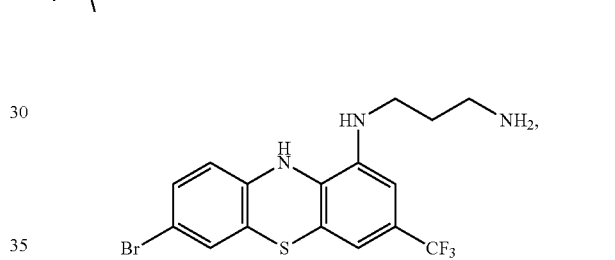
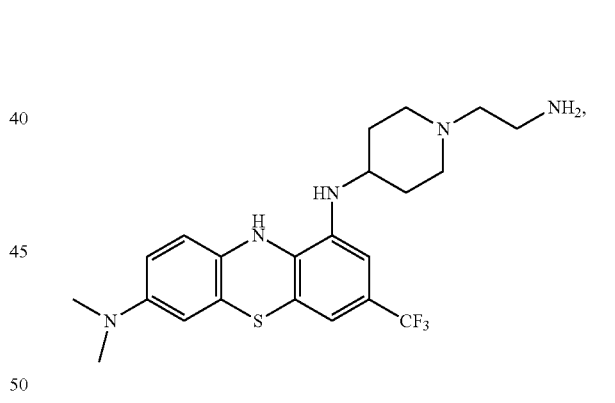
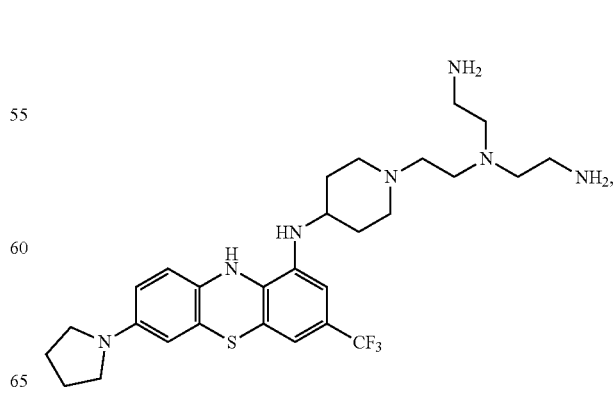

365
-continued
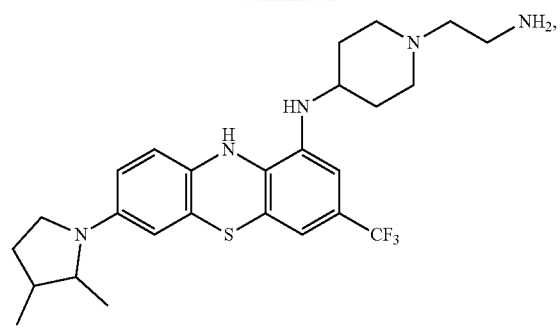
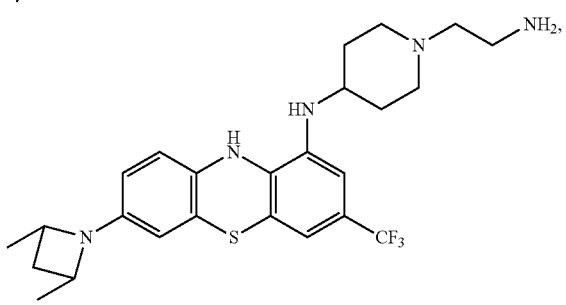
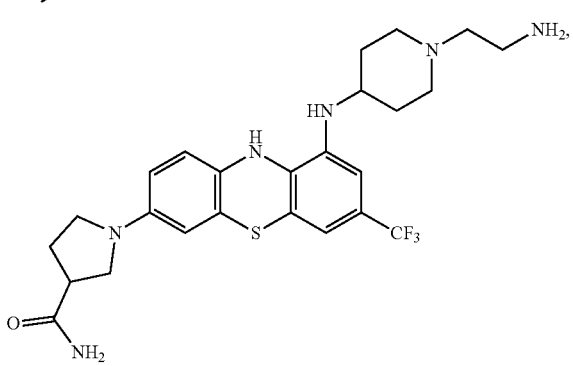
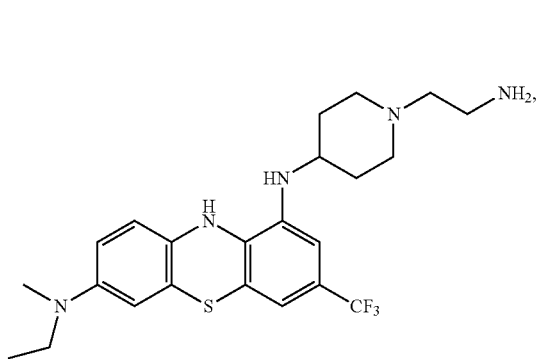
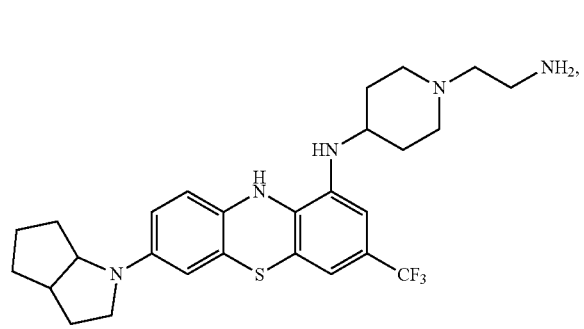
366
-continued
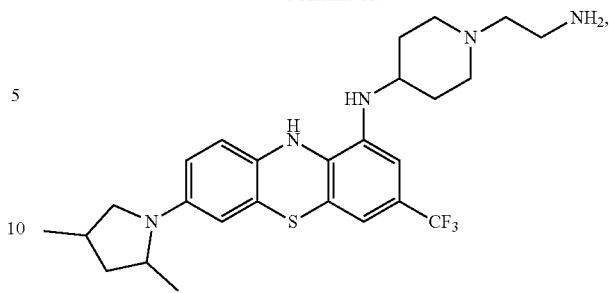
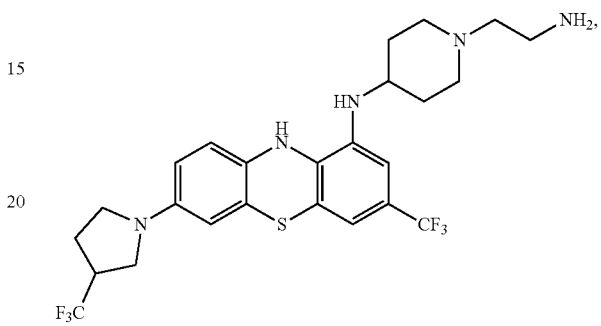
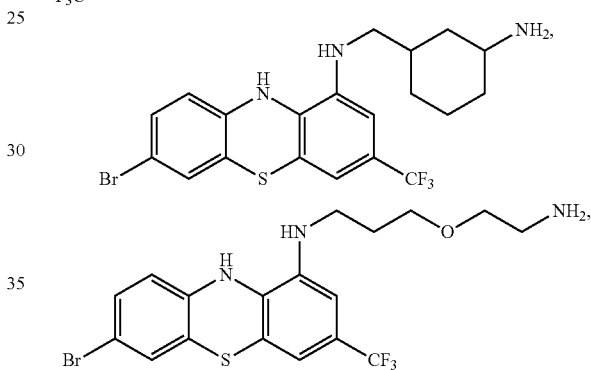
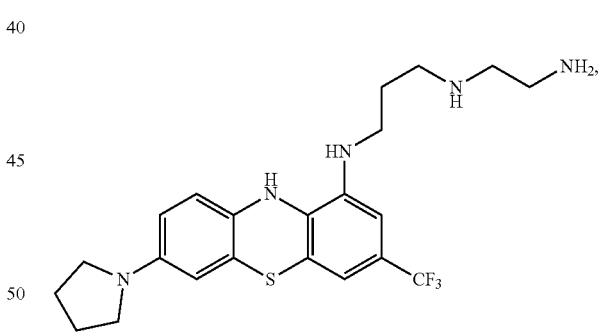
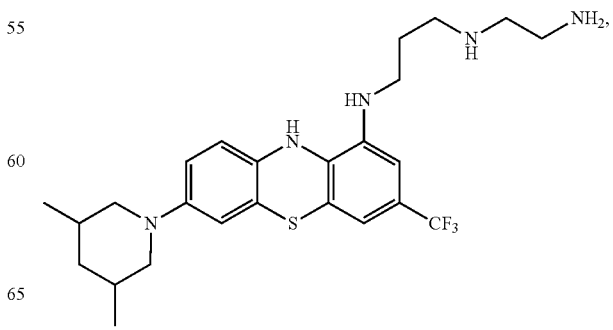

367
-continued
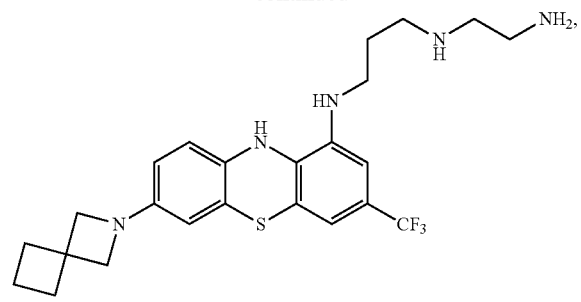
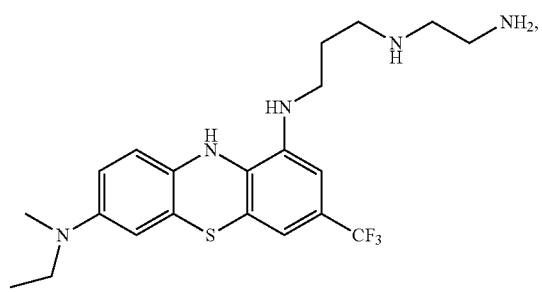
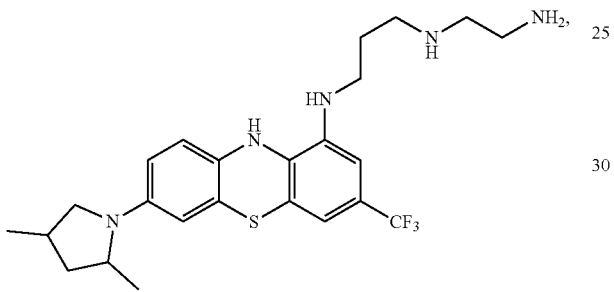
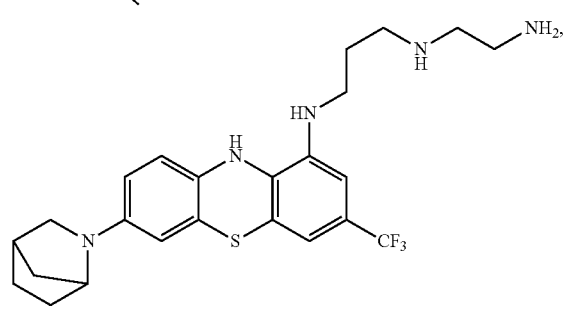
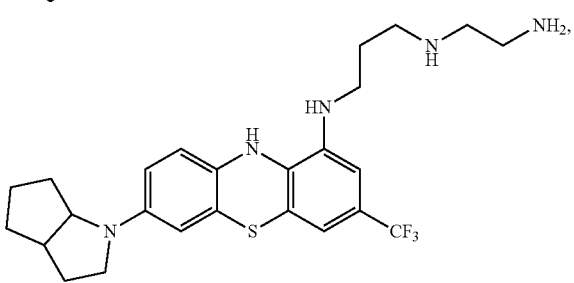
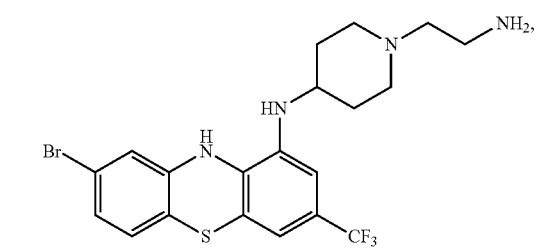
368
-continued
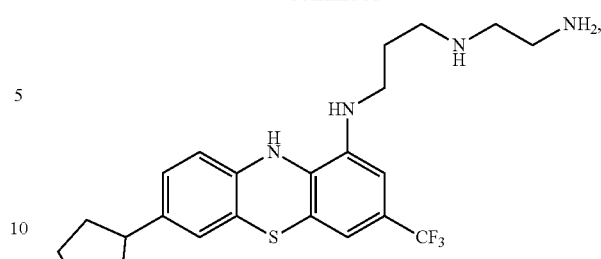
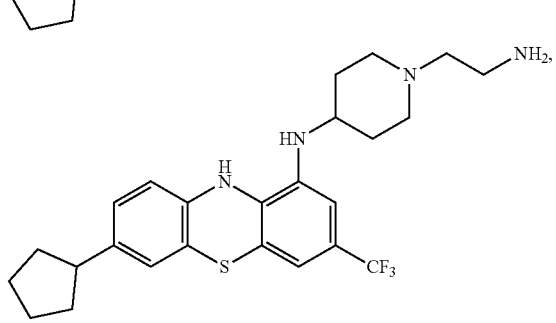
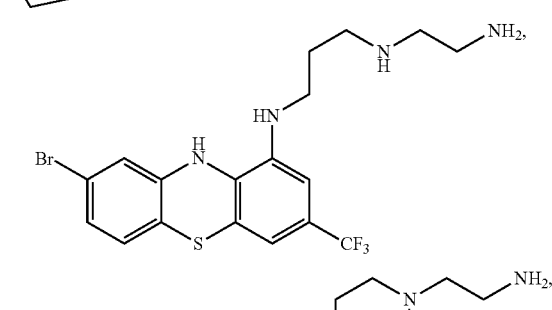
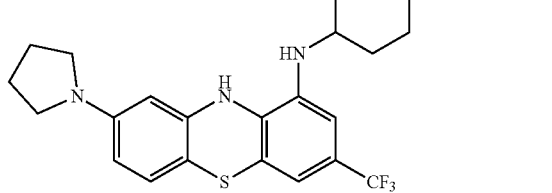
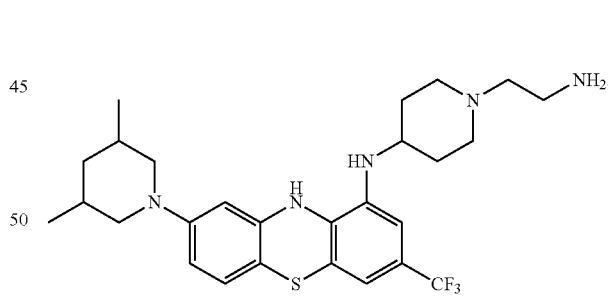
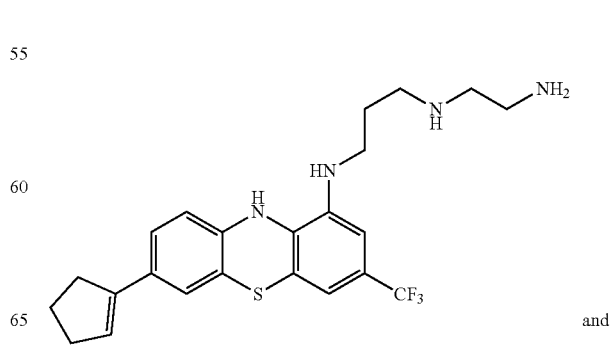
and -continued

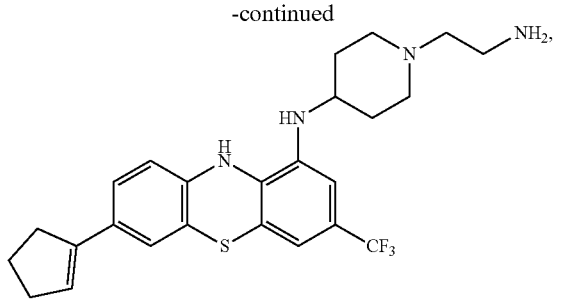

or a pharmaceutically acceptable salt thereof.

17. A method of treating a bacterial infection which comprises administering to a patient in need thereof a therapeutically effective amount of a compound or salt according to claim 16, or a pharmaceutically acceptable salt thereof.

18. A method of inhibiting bacterial RNase P activity, comprising contacting a bacterial RNase P with the compound or salt of claim 16.

19. A method of inhibiting growth of a bacterium, comprising contacting a bacterium with the compound or salt of claim 16.

20. A pharmaceutical composition comprising a compound according to claim 16, or a pharmaceutically acceptable salt thereof, in association with a pharmaceutically acceptable excipient, adjuvant, diluent and/or carrier.

* * * * *